United States Patent
Arora et al.

(10) Patent No.: US 10,717,745 B2
(45) Date of Patent: Jul. 21, 2020

(54) INHIBITORS OF BRUTON'S TYROSINE KINASE AND METHOD OF THEIR USE

(71) Applicant: JANSSEN PHARMACEUTICA NV, Beerse (BE)

(72) Inventors: Nidhi Arora, San Diego, CA (US); Genesis M. Bacani, San Diego, CA (US); Joseph Kent Barbay, Flourtown, PA (US); Scott D. Bembenek, San Diego, CA (US); Min Cai, Shanghai (CN); Wei Chen, Shanghai (CN); Charlotte Pooley Deckhut, San Diego, CA (US); James P. Edwards, Ambler, PA (US); Brahmananda Ghosh, Spring House, PA (US); Kevin D. Kreutter, Arlington, MA (US); Gang Li, Shanghai (CN); Mark S. Tichenor, San Diego, CA (US); Jennifer D. Venable, Solana Beach, CA (US); Jianmei Wei, San Diego, CA (US); John J. M. Wiener, San Diego, CA (US); Yao Wu, Shanghai (CN); Kun Xiao, Shanghai (CN); Feihuang Zhang, Shanghai (CN); Yaoping Zhu, Shanghai (CN)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/374,905

(22) Filed: Dec. 9, 2016

(65) Prior Publication Data

US 2017/0283430 A1 Oct. 5, 2017

Related U.S. Application Data

(60) Provisional application No. 62/265,836, filed on Dec. 10, 2015.

(51) Int. Cl.
C07D 495/16 (2006.01)
C07D 519/00 (2006.01)

(52) U.S. Cl.
CPC ......... *C07D 495/16* (2013.01); *C07D 519/00* (2013.01)

(58) Field of Classification Search
CPC ................ C07D 495/16; C07D 519/00
See application file for complete search history.

(56) References Cited

U.S. PATENT DOCUMENTS

| | | | |
|---|---|---|---|
| 5,300,478 A | 4/1994 | Michaely et al. | |
| 7,579,356 B2 | 8/2009 | Battista et al. | |
| 2006/0058341 A1 | 3/2006 | Connolly et al. | |
| 2008/0076921 A1 | 3/2008 | Honigberg et al. | |
| 2014/0249105 A1 | 9/2014 | Diverchim | |
| 2017/0283431 A1 | 10/2017 | Arora et al. | |

FOREIGN PATENT DOCUMENTS

| | | |
|---|---|---|
| EP | 0061588 A1 | 10/1982 |
| EP | 0602306 A1 | 6/1994 |
| WO | 2006031929 A2 | 3/2006 |
| WO | 2006118749 A1 | 11/2006 |
| WO | 2007019191 A2 | 2/2007 |
| WO | 2007092879 A2 | 8/2007 |
| WO | 2010056875 A1 | 5/2010 |
| WO | 2011133609 A3 | 3/2014 |
| WO | 2014139970 A1 | 9/2014 |
| WO | WO 2017/100662 A1 | 6/2017 |
| WO | WO 2017/100668 A1 | 6/2017 |
| WO | WO 2018/103058 A1 | 6/2018 |
| WO | WO 2018/103060 A1 | 6/2018 |

OTHER PUBLICATIONS

Svensson, et al., B Cell-deficient Mice Do Not Develop Type II Collagen-induced Arthritis (CIA), Clin. Exp. Immunol., 111, 521-526 (1998).*
Corneth et al., "BTK Signaling in B Cell Differentiation and Autoimmunity", Current Topics in Microbiology and Immunology, 2016, pp. 67-105, vol. 393.
Svensson, et al., "B cell-deficient mice do not develop type II collagen-induced arthritis (CIA)", Clin Exp Immunol, vol. 111: pp. 521-526 (1998).
International Search Report with Written Opinion Corresponding to International Patent Application No. PCT/US2016/065954, dated Feb. 9, 2017.
Di Paolo, et al., "Specific BTK Inhibition Suppresses B-Cell and Myeloid Cell-Mediated Arthritis", Natre Chemical Biology, vol. 7: pp. 41-50 (Jan. 2011).
Evan, et al., "Inhibition of BTK with CC-292 Provides Early Pharmacodynamic Assessment of Activity in Mice and Humans", The Journal of Pharmacology and Experimental Therapeutics, vol. 346: pp. 219-228 (Aug. 2013).
Hendriks, et al., "Targeting Bruton's Tyrosine Kinase in B Cell Malignancies", Nature Reviews Cancer, vol. 14: pp. 219-232 (Apr. 2014).
Honigberg, et al., "The Bruton Tyrosine Kinase Inhibitor PCI-32765 Blocks B-Cell Activation and is Efficacious in Models of Autoimmune Disease and B-cell Malignancy", PNAS, vol. 107 (29): pp. 13075-13080 (Jul. 20, 2010).

(Continued)

*Primary Examiner* — Erich A Leeser

(57) ABSTRACT

The present disclosure is directed to compounds of Formula (I) and methods of their use and preparation, as well as compositions comprising compounds of Formula (I).

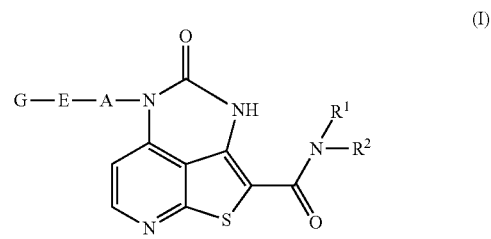

26 Claims, No Drawings

(56) References Cited

OTHER PUBLICATIONS

Kenny, et al., "Bruton's Tyrosine Kinase Mediates the Syngergistic Signalling between TLR9 and the B Cell Receptor by Regulating Calcium and Calmodulin", PLOS One, vol. 8 (8) e74103: pp. 1-14, (Aug. 2013).

Liu, et al., "Antiarthritis Effect of a Novel Bruton's Trosine Kinase (BTK) Inhibitor in Rat Collagen-Induced Arthritis and Mechanism-Based Pharmacokinetic/Pharmacodynamic Modeling: Relationships Between Inhibition of BTK Phosphorylation and Efficacy", The Journal of Pharmacolocy and Experimental Therapeutics, vol. 338 (1): pp. 154-163 (2011).

R. West Anthony, Chapter 10. Solid Solutions, Solid State Chemistry and its applications, 1988, pp. 358-365, page No.

T.P. Selby, "Synthesis of a Novel Thiadiazacyclazine", Journal of Organic Chemistry, vol. 53 (10): pp. 2386-2388 (1988).

Pan, et al., "Discovery of Selective Irreverisible Inhibitors for Bruton's Tyrosine Kinase", Chem Med Chem, vol. 2; pp. 58-61 (2007).

Rocca, P. et al., "First Metalation of Aryl Iodides: Directed Ortho-Lithiation of Iodopyridines, Halogen-Dance, and Application to Synthesis", J. Org. Chem. 58 (1993) pp. 7832-7838.

International Search Report with Written Opinion Corresponding to PCT/US2016/065964, dated Mar. 1, 2017.

International Search Report with Written Opinion Corresponding to PCT/CN2016/109134, dated Aug. 2, 2017.

International Search Report with Written Opinion Corresponding to PCT/CN2016/109143, dated Sep. 14, 2017.

Kametani, Tetsuji and Sato, Minoru, "Syntheses of heterocyclic compounds. LXXVI. Synthesis of 4-methylpyridine derivatives" *Yakugaku Kenkyu* (1962) 34, 117-24 (English language translation of Abstract only).

Magidson, O. Yu and Menshikov, G. P., "Iodization of α-aminopyridine" *Trudy Nauchnogo Khimiko-Farmatsevticheskogo Instituta* , (1926) (No. 16), 23-31 (English language translation of Abstract only).

Kong, W. et al., Increased Expression of Bruton Tyrosine Kinase in Patients with Lupus Nephritis and Its Clinic Significance, 2015 ACR/ARHP Annual Meeting, Sep. 29, 2015, Abstract Number: 1848.

Whang, J., et al., Bruton's tyrosine kinase inhibitors for the treatment of rheumatoid arthritis, Drug Discovery Today, vol. 19/No. 8, Aug. 2014, pp. 1200-1201.

Woyach, J., et al., Bruton's tyrosine kinase (BTK) function is important to the development and expansion of chronic lymphocytic leukemia (CLL), Blood, vol. 123/No. 8, Feb. 2014, pp. 1207-1213. < https://rarediseases.org/rare-diseases/pemphigus/>, accessed Jun. 4, 2019.

U.S. Appl. No. 16/413,317, dated May 15, 2019, Nidhi Arora et al.
U.S. Appl. No. 16/413,417, dated May 15, 2019, Nidhi Arora et al.

\* cited by examiner

INHIBITORS OF BRUTON'S TYROSINE KINASE AND METHOD OF THEIR USE

CROSS REFERENCE TO RELATED APPLICATION

This application claims the benefit of U.S. Provisional Application No. 62/265,836, filed on Dec. 10, 2015, which is incorporated herein by reference in its entirety.

TECHNICAL FIELD

The present disclosure is directed to small molecule tyrosine kinase inhibitors.

BACKGROUND

Rheumatoid arthritis ("RA") is a chronic, autoimmune, inflammatory disorder that affects the lining of the joints, causing painful swelling that can result in bone erosion and joint deformation. RA presents a significant societal impact—it has a relatively high prevalence (about 1% of the United States population suffers from RA), produces irreversible joint damage, and has a widespread occurrence of co-morbities. While many patients benefit from currently marketed biologic and small molecule medicines, most patients still suffered from the chronic pain and inflammation of the disease.

Cancer, in particular mantle cell lymphoma, chronic lymphocytic leukemia, macroglobulinemia, and multiple myeloma, continues to afflict patients. Alternative, effective treatments of cancer are still needed.

Human Bruton's tyrosine kinase ("Btk") is a ~76 kDa protein belonging to the Tec family of non-receptor tyrosine kinases. Tec kinases form the second largest family of cytoplasmic tyrosine kinases in mammalian cells, which consists of four other members in addition to BTK: the eponymous kinase TEC, ITK, TXK/RLK and BMX. Tec kinases are evolutionarily conserved throughout vertebrates. They are related to, but structurally distinct from, the larger Src and Syk kinase families. Tec family proteins are abundantly expressed in hematopoietic tissues and play important roles in the growth and differentiation of blood and endothelial cells in mammals.

Based upon Btk expression from IHC studies described in the art, Btk inhibition has the potential to modulate biology associated with B cells, macrophages, mast cells, osteoclasts, and platelet microparticles. Corneth, O. B., et al. Curr. Top. Microbiol. Immunol. *BTK Signaling in B Cell Differentiation and Autoimmunity.* 2015 Sep. 5. The role of B cells in RA is supported by the therapeutic benefit exhibited in the clinic upon B cell depletion with Rituximab™. Since autoreactive antibodies play such a critical role in synovial inflammation, therapeutic modulation of the B cell compartment is an attractive mechanism to treat early RA and potentially modulate disease at the earliest stages. B cell depletion in murine models such as collagen-induced arthritis (CIA) prevents arthritis development. Svensson, et al. (1998) B cell-deficient mice do not develop type II collagen-induced arthritis (CIA). *Clin Exp Immunol* 111, 521-526.

SUMMARY

The present disclosure is directed to compounds of Formula (I):

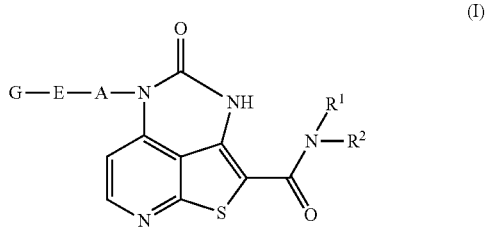

wherein
$R^1$ is H or $C_{1-6}$alkyl;
$R^2$ is selected from the group consisting of: $C_{0-6}$alk-cycloalkyl optionally substituted with 1, 2, or 3 substituents each independently selected from the group consisting of: $NR^8$—C(O)—$C(R^3)$=$CR^4(R^5)$; $NR^6R^7$; OH; CN; oxo; O—$C_{1-6}$alkyl; halogen; $C_{1-6}$alkyl; $C_{1-6}$haloalkyl; $C_{1-6}$alk-OH; $C_{3-6}$cycloalkyl; $C_{1-6}$alkaryl; $SO_2C_{1-6}$alkyl; $SO_2C_{2-6}$alkenyl; $NR^8$—C(O)—$C_{1-6}$ alk-$NR^6R^7$; $NR^8$—C(O)—$C_{1-6}$alkyl; $NR^8$—C(O)—O—$C_{1-6}$alkyl; $NR^8$—C(O)—$C_{3-6}$cycloalkyl; $NR^8$—C(O)H; $NR^8$—C(O)—$C_{3-6}$cycloalkyl; $NR^8$—C(O)—$C_{1-6}$haloalkyl; $NR^8$—C(O)-alkynyl; $NR^8$—C(O)—$C_{6-10}$aryl; $NR^8$—C(O)-heteroaryl; $NR^8$—C(O)—$C_{1-6}$alk-CN; $NR^8$—C(O)—$C_{1-6}$alk-OH; $NR^8$—C(O)—$C_{1-6}$alk-$SO_2$—$C_{1-6}$alkyl; $NR^8$—C(O)—$C_{1-6}$alk-$NR^6R^7$; $NR^8$—C(O)—$C_{1-6}$alk-O—$C_{1-6}$alkyl wherein the
$C_{1-6}$alk is optionally substituted with OH, $OC_{1-6}$alkyl, or $NR^6R^7$; and
$NR^8$—C(O)—$C_{0-6}$alk-heterocycloalkyl wherein the $C_{0-6}$alk is optionally substituted with oxo and the heterocycloalkyl is optionally substituted with $C_{1-6}$alkyl;
wherein $R^6$ and $R^7$ are each independently selected from the group consisting of:
H; $C_{1-6}$alkyl; $C_{3-6}$cycloalkyl; C(O)H; and CN;
$R^3$ is selected from the group consisting of: H, CN, halogen, $C_{1-6}$haloalkyl, and $C_{1-6}$alkyl;
$R^4$ and $R^5$ are each independently selected from the group consisting of: H; $C_{0-6}$alk-$NR^6R^7$; $C_{1-6}$alk-OH; $C_{0-6}$alk-$C_{3-6}$cycloalkyl optionally substituted with $C_{1-6}$alkyl; halogen; $C_{1-6}$alkyl; $OC_{1-6}$alkyl; $C_{1-6}$alk-O—$C_{1-6}$ alkyl; $C_{1-6}$alk-NH—$C_{0-6}$alk-O—$C_{1-6}$alkyl; $C_{0-6}$alk-heterocycloalkyl optionally substituted with $C(O)C_{1-6}$alkyl or $C_{1-6}$alkyl; $C_{1-6}$alk-$NHSO_2$—$C_{1-6}$alkyl; $C_{1-6}$alk-$SO_2$—$C_{1-6}$alkyl; —NHC(O)—$C_{1-6}$alkyl; and -linker-PEG-Biotin;
$R^8$ is H or $C_{1-6}$alkyl;
or $R^1$ and $R^2$, together with the nitrogen atom to which they are attached, form a pyrrolidinyl ring optionally substituted with $NR^6R^7$, wherein $R^6$ and $R^7$ are each independently selected from the group consisting of H; $C_{1-6}$alkyl; $NR^8$—C(O)—$C_{1-6}$alkyl; and $NR^8$—C(O)—$C(R^3)$=$CR^4(R^5)$, wherein $R^8$ is H; $R^3$ is H or CN; $R^4$ is H; and $R^5$ is H or cyclopropyl
A is selected from the group consisting of: a bond; pyridyl; phenyl; napthalenyl; pyrimidinyl; pyrazinyl; pyridazinyl; benzo[d][1,3]dioxolyl optionally substituted with halogen; benzothiophenyl; and pyrazolyl; wherein the A is optionally substituted with 1, 2, or 3 substituents each independently selected from the group consisting of: $C_{1-6}$ alkyl; halogen; $SF_5$; $OC_{1-6}$alkyl; $C(O)-C_{1-6}$alkyl; and $C_{1-6}$haloalkyl;

E is selected from the group consisting of: O, a bond, $C(O)-NH$, $CH_2$, and $CH_2-O$;

G is selected from the group consisting of: H; $C_{3-6}$cycloalkyl; phenyl; thiophenyl; $C_{1-6}$alkyl; pyrimidinyl; pyridyl; pyridazinyl; benzofuranyl; $C_{1-6}$haloalkyl; heterocycloalkyl that contains an oxygen heteroatom; phenyl-$CH_2-O$-phenyl; $C_{1-6}$alk-$O-C_{1-6}$alkyl; $NR^6R^7$; $SO_2C_{1-6}$ alkyl; and OH; wherein the phenyl; pyridyl; pyridazinyl; benzofuranyl; or thiophenyl is optionally substituted with 1, 2, or 3 substituents each independently selected from the group consisting of: halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-$O-C_{1-6}$alkyl; $C(O)-NR^6R^7$; and $C(O)-C_{1-6}$alkyl; and stereoisomers and isotopic variants thereof; and
pharmaceutically acceptable salts thereof.

Compositions comprising compounds of Formula (I) are also described. Methods of using compounds of Formula (I) are also within the scope of the disclosure.

DETAILED DESCRIPTION OF ILLUSTRATIVE EMBODIMENTS

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect. Conversely, various features of the disclosed compositions and methods that are, for brevity, described in the context of a single aspect, may also be provided separately or in any subcombination.

The term "alkyl," when used alone or as part of a substituent group, refers to a straight- or branched-chain alkyl group having from 1 to 12 carbon atoms ("$C_{1-12}$"), preferably 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples.

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The term "$C_{1-6}$alk" refers to an aliphatic linker having 1, 2, 3, 4, 5, or 6 carbon atoms and includes, for example, $CH_2$, $CH(CH_3)$, $CH(CH_3)-CH_2$, and $C(CH_3)_2-$. The term "—$C_0$alk-" refers to a bond. In some aspects, the $C_{1-6}$alk can be substituted with an oxo group or an OH group.

The term "alkenyl," when used alone or as part of a substituent group, refers to straight and branched carbon chains having from 2 to 12 carbon atoms ("$C_{2-12}$"), preferably 2 to 6 carbon atoms ("$C_{2-6}$"), wherein the carbon chain contains at least one, preferably one to two, more preferably one double bond. For example, alkenyl moieties include, but are not limited to, allyl, 1-propen-3-yl, 1-buten-4-yl, propa-1,2-dien-3-yl, and the like.

The term "alkynyl," when used alone or as part of a substituent group, refers to straight and branched carbon chains having from 2 to 12 carbon atoms ("$C_{2-12}$"), preferably 2 to 6 carbon atoms ("$C_{2-6}$"), wherein the carbon chain contains at least one, preferably one to two, more preferably one triple bond. For example, alkynyl moieties include, but are not limited to vinyl, 1-propyn-3-yl, 2-butyn-4-yl, and the like.

The term "aryl" refers to carbocylic aromatic groups having from 6 to 10 carbon atoms ("$C_{6-10}$") such as phenyl, naphthyl, and the like.

The term "cycloalkyl" refers to monocyclic, non-aromatic hydrocarbon groups having from 3 to 10 carbon atoms ("$C_{3-10}$"), preferably from 3 to 6 carbon atoms ("$C_{3-6}$"). Examples of cycloalkyl groups include, for example, cyclopropyl ($C_3$), cyclobutyl ($C_4$), cyclopentyl ($C_5$), cyclohexyl ($C_6$), 1-methylcyclopropyl ($C_4$), 2-methylcyclopentyl ($C_4$), adamantanyl ($C_{10}$) and the like.

The term "heterocycloalkyl" refers to any five to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahyofuranyl, tetrahydropyranyl, piperazinyl, hexahydro-5H-[1,4]dioxino[2,3-c]pyrrolyl, benzo[d][1,3]dioxolyl, and the like.

The term "heteroaryl" refers to a mono- or bicyclic aromatoic ring structure including carbon atoms as well as up to four heteroatoms selected from nitrogen, oxygen, and sulfur. Heteroaryl rings can include a total of 5, 6, 9, or 10 ring atoms ("$C_{5-10}$"). Examples of heteroaryl groups include but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The term "halogen" represents chlorine, fluorine, bromine, or iodine. The term "halo" represents chloro, fluoro, bromo, or iodo.

The term "haloalkyl" refers to an alkyl moiety wherein one or more of the hydrogen atoms has been replaced with one or more halogen atoms. One exemplary substitutent is fluoro. Preferred haloalkyl groups of the disclosure include trihalogenated alkyl groups such as trifluoromethyl groups.

The term "oxo" refers to a =O moiety, wherein two hydrogens from the same carbon atom have be replaced with a carbonyl. For example, an oxo-substituted pyrrolidinyl moiety could be a pyrrolidin-2-one moiety or a pyrrolidin-3-one moiety.

The term "benzofuranyl" represents the following moiety:

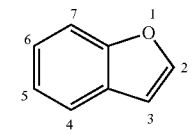

The benzofuranyl moiety can be attached through any one of the 2-, 3-, 4-, 5-, or 7-carbon atoms.

The term "benzo[d][1,3]dioxolyl" represents the following moiety:

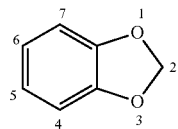

The benzo[d][1,3]dioxolyl moiety can be attached through any one of the 2-, 4-, 5-, 6-, or 7-carbon atoms. In those aspects wherein the "benzo[d][1,3]dioxolyl moiety is substituted with halogen," the following moieties are preferred:

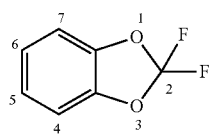 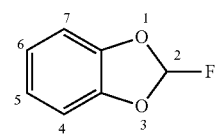

The term "benzothiophenyl" represents the following moiety:

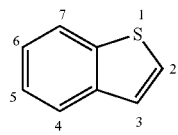

The benzothiophenyl moiety can be attached through any one of the 2-, 3-, 4-, 5-, 6-, or 7-carbon atoms.

The term "phenyl" represents the following moiety:

The phenyl moiety can be attached through any of the carbon atoms.

The term "napthalenyl" (i.e., naphthyl) represents the following moiety:

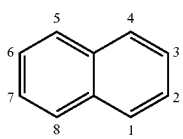

The naphthalenyl moiety can be attached through any one of the 1-, 2-, 3-, 4-, 5-, 6-, 7-, or 8-position carbon atoms.

The term "pyridyl" represents the following moiety:

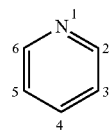

The pyridyl moiety can be attached through any one of the 2-, 3-, 4-, 5-, or 6-position carbon atoms.

The term "pyrimidinyl" represents the following moiety:

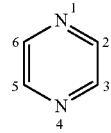

The pyrimidinyl moiety can be attached through any one of the 2-, 4-, 5-, or 6-position carbon atoms.

The term "pyrazinyl" represents the following moiety:

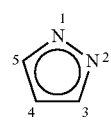

The pyrazinyl moiety can be attached through any one of the 2-, 3-, 5-, or 6-position carbon atoms.

The term "pyridazinyl" represents the following moiety:

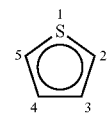

The pyridazinyl moiety can be attached through any one of the 3-, 4-, 5-, or 6-position carbon atoms.

The term "pyrazolyl" represents the following moiety:

The pyrazolyl moiety can be attached through any one of the 1-, 2-, 3-, 4-, or 5-position carbon atoms.

The term "thiophenyl" represents the following moiety:

The thiophenyl moiety can be attached through any one of the 2-, 3-, 4-, or 5-position carbon atoms.

The term "linker-PEG-Biotin" refers to a moiety comprising linker-PEG-CH$_2$—NH-biotinyl. Compounds of the disclosure that include a linker-PEG-Biotin moiety can be used according to any of the methods described herein. Alternatively, compounds of the disclosure that include a linker-PEG-Biotin moiety can be used as diagnostic probes according to methods known in the art. Preferred linkers are known in the art, with the linker CH$_2$—NHC(O)—(CH$_2$)$_3$—C(O)—NH—CH$_2$— being particularly preferred. Preferred PEG moieties include at least two or three repeating CH$_2$—CH$_2$—O— moieties. A preferred linker-PEG-Biotin moiety is The term "aziridinyl" represents a 3-membered heterocycloalkyl moiety having one ring nitrogen. When the aziridinyl moiety is a substituent, it can be attached through any ring carbon atom or through the nitrogen atom, as permitted.

The term "azetidinyl" represents a 4-membered heterocycloalkyl moiety having one ring nitrogen. When the azetidinyl moiety is a substituent, it can be attached through any carbon atom or through the nitrogen atom, as permitted.

The term "azepanyl" represents a 7-membered heterocycloalkyl moiety having one ring nitrogen. When the azepanyl moiety is a substitutent, it can be attached through any carbon atom or through the nitrogen atom, as permitted

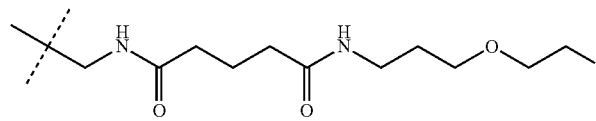

The term "piperidinyl" represents the following moiety:

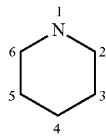

When the piperidinyl moiety is a substituent, it can be attached through any one of the 1-, 2-, 3-, 4-, 5-, or 6-position atoms, as permitted.

The term "pyrrolidinyl" represents the following moiety:

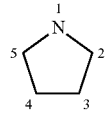

When the piperidinyl moiety is a substituent, it can be attached through any one of the 1-, 2-, 3-, 4-, or 5-position atoms, as permitted.

The term "oxazepanyl" refers to a 7-membered heterocycloalkyl moiety having one ring nitrogen atom and one ring oxygen atom. Examples include 1,3-oxazepanyl and 1,4-oxazepanyl moieties

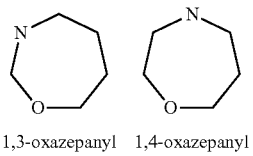

1,3-oxazepanyl  1,4-oxazepanyl

When the oxazepanyl moiety is a substituent, it can be attached through any ring carbon atom or through the nitrogen atom, as permitted The term "quinuclidinyl" represents the following moiety:

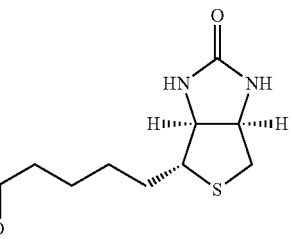

Within the disclosure, when the quinuclidinyl moiety is a substituent, it can be attached to the compound of Formula (I) through any one of the ring carbon atoms.

The term "imidazolidinyl" represents the following moiety:

When the imidazolidinyl moiety is a substituent, it can be attached through any one of the 1-, 2-, 3-, 4-, or 5-position atoms, as permitted The term "piperazinyl" represents the following moiety:

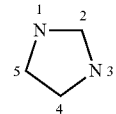

When the piperazinyl moiety is a substituent, it can be attached through any one of the 1-, 2-, 3-, 4-, 5-, or 6-position atoms, as permitted The term "morpholinyl" represents the following moiety:

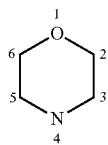

When the morpholinyl moiety is a substituent, it can be attached through any one of the 2-, 3-, 4-, 5-, or 6-position atoms, as permitted.

The term "tetrahydropyranyl" represents a 6-membered heterocycloalkyl moiety having one ring oxygen. The tetrahydropyranyl moiety can be attached through any carbon atom on the ring.

The term "tetrahydrofuranyl" represents a 5-membered heterocycloalkyl moiety having one ring oxygen. The tetrahydrofuranyl moiety can be attached through any carbon atom on the ring.

As used herein, the term "compound(s) of Formula (I)" includes those compounds of "Formula (I)," as well as compounds of any of the Formula (I) subgenera.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the disclosure may include the preparation of isotopic variants with radioisotopes, in the instance for example, where the resulting compounds may be used for drug and/or substrate tissue distribution studies. Radiolabeled compounds of the disclosure can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the disclosure, radioactive or not, are intended to be encompassed within the scope of the disclosure.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers.

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Atropisomers" refer to stereoisomers that arise because of hindered rotation around a single bond.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

The present disclosure is directed to compounds of Formula (I):

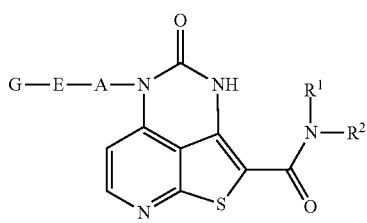

(I)

wherein
R$^1$ is H or C$_{1-6}$alkyl;
R$^2$ is selected from the group consisting of: C$_{0-6}$alk-cycloalkyl optionally substituted with 1, 2, or 3 substituents each independently selected from the group consisting of: NR$^8$—C(O)—C(R$^3$)=CR$^4$(R$^5$); NR$^6$R$^7$; OH; CN; oxo; O—C$_{1-6}$alkyl; halogen; C$_{1-6}$alkyl; C$_{1-6}$haloalkyl; C$_{1-6}$alk-OH; C$_{3-6}$cycloalkyl; C$_{1-6}$alkaryl; SO$_2$C$_{1-6}$alkyl; SO$_2$C$_{2-6}$alkenyl; NR$^8$—C(O)—C$_{1-6}$alk-NR$^6$R$^7$; NR$^8$—C(O)—C$_{1-6}$alkyl; NR$^8$—C(O)—O—C$_{1-6}$alkyl; NR$^8$—C(O)—C$_{3-6}$cycloalkyl; NR$^8$—C(O)H; NR$^8$—C(O)—C$_{3-6}$cycloalkyl; NR$^8$—C(O)—C$_{1-6}$haloalkyl; NR$^8$—C(O)-alkynyl; NR$^8$—C(O)—C$_{6-10}$aryl; NR$^8$—C(O)-heteroaryl; NR$^8$—C(O)—C$_{1-6}$alk-CN; NR$^8$—C(O)—C$_{1-6}$ alk-OH; NR$^8$—C(O)—C$_{1-6}$alk-SO$_2$—C$_{1-6}$alkyl; NR$^8$—C(O)—O—C$_{1-6}$alkyl; NR$^8$—C(O)—C$_{1-6}$alk-NR$^6$R$^7$; NR$^8$—C(O)—C$_{1-6}$alk-O—C$_{1-6}$alkyl, wherein the C$_{1-6}$alk- is optionally substituted with a member selected from the group consisting of: OH, OC$_{1-6}$alkyl, and NR$^6$R$^7$; and NR$^8$—C(O)—C$_{0-6}$alk-heterocycloalkyl wherein the C$_{0-6}$alk is optionally substituted with oxo and the heterocycloalkyl is optionally substituted with C$_{1-6}$alkyl;

wherein R$^6$ and R$^7$ are each independently selected from the group consisting of:
H; C$_{1-6}$alkyl, C$_{3-6}$cycloalkyl, C(O)H, and CN;

R$^3$ is selected from the group consisting of: H, CN, halogen, C$_{1-6}$haloalkyl, and C$_{1-6}$alkyl;

R$^4$ and R$^5$ are each independently selected from the group consisting of: H; C$_{0-6}$alk-NR$^6$R$^7$; C$_{1-6}$alk-OH; C$_{0-6}$alk-C$_{3-6}$cycloalkyl optionally substituted with C$_{1-6}$alkyl; halogen; C$_{1-6}$alkyl; OC$_{1-6}$alkyl; NR$^6$R$^7$; C$_{1-6}$alk-O—C$_{1-6}$ alkyl; C$_{1-6}$alk-NH—C$_{0-6}$alk-O—C$_{1-6}$alkyl; C$_{0-6}$alk-heterocycloalkyl optionally substituted with C(O)C$_{1-6}$alkyl or C$_{1-6}$alkyl; C$_{1-6}$alk-NHSO$_2$—C$_{1-6}$ alkyl; C$_{1-6}$alk-SO$_2$—C$_{1-6}$alkyl; NHC(O)—C$_{1-6}$alkyl; and linker-PEG-Biotin;

R$^8$ is H or C$_{1-6}$alkyl;

A is selected from the group consisting of: a bond; pyridyl; phenyl; napthalenyl; pyrimidinyl; pyrazinyl; pyridazinyl; benzo[d][1,3]dioxolyl optionally substituted with halogen; benzothiophenyl; and pyrazolyl; optionally substituted with 1, 2, or 3 substituents each independently selected from the group consisting of: C$_{1-6}$alkyl; halogen; SF$_5$; OC$_{1-6}$alkyl; C(O)—C$_{1-6}$alkyl; and C$_{1-6}$haloalkyl;

E is selected from the group consisting of: O, a bond, C(O)—NH, CH$_2$, and CH$_2$—O;

G is selected from the group consisting of: H; C$_{3-6}$cycloalkyl; phenyl; thiophenyl; C$_{1-6}$alkyl; pyrimidinyl; pyridyl; pyridazinyl; benzofuranyl; C$_{1-6}$haloalkyl; heterocycloalkyl that contains an oxygen heteroatom; phenyl-CH$_2$—O-phenyl; C$_{1-6}$alk-O—C$_{1-6}$alkyl; NR$^6$R$^7$; SO$_2$C$_{1-6}$ alkyl; and OH; wherein the phenyl, pyridyl, pyridazinyl, benzofuranyl, or thiophenyl is optionally substituted with 1, 2, or 3 substituents each independently selected from the group consisting of: halogen; C$_{1-6}$alkyl, C$_{1-6}$haloalkyl, OC$_{1-6}$haloalkyl, C$_{3-6}$cycloalkyl, OC$_{1-6}$alkyl, CN, OH, C$_{1-6}$alk-O—C$_{1-6}$alkyl, C(O)—NR$^6$R$^7$, and C(O)—C$_{1-6}$ alkyl; and stereoisomers and isotopic variants thereof; and
pharmaceutically acceptable salts thereof.

The present disclosure is also directed to compounds of Formula (I):

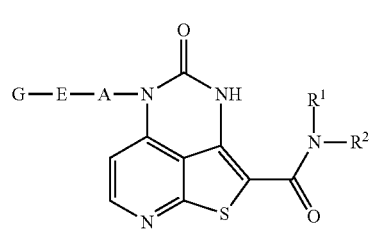

(I)

wherein

R¹ is H or C₁₋₆alkyl;

R¹ and R², together with the nitrogen atom to which they are attached, form an optionally substituted ring that is a pyrrolidinyl ring or a piperidinyl ring;

wherein the pyrrolidinyl ring or piperidinyl ring formed from the joining of R¹ and R² are optionally substituted with 1, 2, or 3 substituents each independently selected from the group consisting of: NR⁸—C(O)—C(R³)=CR⁴ (R⁵); NR⁶R⁷; OH; CN; oxo; O—C₁₋₆alkyl; halogen; C₁₋₆alkyl; C₁₋₆haloalkyl; C₁₋₆alk-OH; C₃₋₆cycloalkyl; C₁₋₆alkaryl; SO₂C₁₋₆alkyl; SO₂C₂₋₆alkenyl; —NR⁸—C(O)—C₁₋₆alk-NR⁶R⁷; NR⁸—C(O)—C₁₋₆alkyl; NR⁸—C(O)—O—C₁₋₆alkyl; NR⁸—C(O)—C₃₋₆cycloalkyl; NR⁸—C(O)H; NR⁸—C(O)—C₁₋₆alkyl; NR⁸—C(O)—C₃₋₆-cycloalkyl; NR⁸—C(O)—C₁₋₆haloalkyl; NR⁸—C(O)-alkynyl; NR⁸—C(O)—C₆₋₁₀aryl; NR⁸—C(O)-heteroaryl; NR⁸—C(O)—C₁₋₆alk-CN; NR⁸—C(O)—C₁₋₆alk-OH; NR⁸—C(O)—C₁₋₆alk-SO₂—C₁₋₆alkyl; NR⁸—C(O)—O—C₁₋₆alkyl; NR⁸—C(O)—C₁₋₆alk-NR⁶R⁷; NR⁸—C(O)—C₁₋₆alk-O—C₁₋₆alkyl wherein the C₁₋₆alk- is optionally substituted with OH, OC₁₋₆alkyl, or NR⁶R⁷; and NR⁸—C(O)—C₀₋₆alk-heterocycloalkyl wherein the C₀₋₆alk is optionally substituted with oxo and the heterocycloalkyl is optionally substituted with C₁₋₆alkyl;

wherein R⁶ and R⁷ are each independently selected from the group consisting of: H, C₁₋₆alkyl, C₃₋₆cycloalkyl, C(O)H, and —CN;

R³ is selected from the group consisting of: H, CN, halogen, C₁₋₆haloalkyl, and C₁₋₆alkyl;

R⁴ and R⁵ are each independently selected from the group consisting of: H; C₀₋₆ alk-NR⁶R⁷; C₁₋₆alk-OH; C₀₋₆alk-C₃₋₆cycloalkyl optionally substituted with C₁₋₆alkyl; halogen; C₁₋₆alkyl; —OC₁₋₆alkyl; NR⁶R⁷; C₁₋₆alk-O—C₁₋₆alkyl; C₁₋₆alk-NH—C₀₋₆alk-O—C₁₋₆alkyl; C₀₋₆alk-heterocycloalkyl optionally substituted with C(O)C₁₋₆alkyl or C₁₋₆alkyl; C₁₋₆alk-NHSO₂—C₁₋₆alkyl; C₁₋₆alk-SO₂—C₁₋₆alkyl; NHC(O)—C₁₋₆alkyl; or linker-PEG-Biotin;

R⁸ is H or C₁₋₆alkyl;

A is selected from the group consisting of: a bond; pyridyl; phenyl; napthalenyl; pyrimidinyl; pyrazinyl; pyridazinyl; benzo[d][1,3]dioxolyl optionally substituted with halogen; benzothiophenyl; or pyrazolyl; optionally substituted with 1, 2, or 3 substituents independently selected from the group consisting of C₁₋₆alkyl, halogen, SF₅, OC₁₋₆alkyl, C(O)—C₁₋₆alkyl, and C₁₋₆haloalkyl;

E is selected from the group consisting of: O, a bond, C(O)—NH, CH₂, and CH₂—O;

G is selected from the group consisting of: H; C₃₋₆cycloalkyl; phenyl; thiophenyl; C₁₋₆alkyl; pyrimidinyl; pyridyl; pyridazinyl; benzofuranyl; —C₁₋₆haloalkyl; heterocycloalkyl that contains an oxygen heteroatom; phenyl-CH₂—O-phenyl; C₁₋₆alk-O—C₁₋₆alkyl; NR⁶R⁷; SO₂C₁₋₆alkyl; or OH; wherein the phenyl, pyridyl, pyridazinyl, benzofuranyl, or thiophenyl is optionally substituted with 1, 2, or 3 substituents each independently selected from the group consisting of: halogen, C₁₋₆alkyl, C₁₋₆haloalkyl, OC₁₋₆haloalkyl, C₃₋₆cycloalkyl, OC₁₋₆alkyl, CN, OH, C₁₋₆alk-O—C₁₋₆alkyl, C(O)—NR⁶R⁷, and C(O)—C₁₋₆alkyl; and stereoisomers and isotopic variants thereof; and pharmaceutically acceptable salts thereof.

The present disclosure is also directed to compounds of Formula (I):

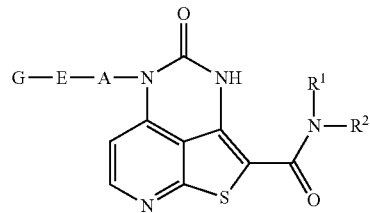

(I)

wherein

R¹ is H;

R² is selected from the group consisting of: CH₂-cyclohexyl, wherein the cyclohexyl is optionally substituted with OH; 3-hydroxyadamantan-1-yl; and C₃₋₆cycloalkyl optionally substituted with 1, 2, or 3 substituents each independently selected from the group consisting of: OH, halogen, C₁₋₆alkyl, C₁₋₆haloalkyl, OC₁₋₆alkyl, CN, NR⁶R⁷, NR⁸—C(O)H, NR⁸—C(O)—C₁₋₆alkyl, NR⁸—C(O)—C₁₋₆haloalkyl, NR⁸—C(O)—O—C₁₋₆alkyl, NR⁸—C(O)—C₁₋₆alk-OH, NR⁸—C(O)—C₁₋₆alk-NR⁶R⁷, and NR⁸—C(O)—C(R³)=CR⁴(R⁵); wherein R³ is selected from the group consisting of: H, CN, halogen, C₁₋₆haloalkyl, and C₁₋₆alkyl;

R⁴ and R⁵ are each independently selected from the group consisting of: H; C₀₋₆ alk-NR⁶R⁷; C₁₋₆alk-O—C₁₋₆alkyl; C₃₋₆cycloalkyl; heterocycloalkyl optionally substituted with C₁₋₆alkyl; and -linker-PEG-Biotin;

R⁶ and R⁷ are each independently selected from the group consisting of: H, C₁₋₆alkyl, C(O)H, and CN; and R⁸ is H;

or R¹ and R², together with the nitrogen atom to which they are attached, form a pyrrolidinyl ring optionally substituted with NR⁶R⁷, where R⁶ and R⁷ are each independently selected from the group consisting of H; C₁₋₆alkyl; NR⁸—C(O)—C₁₋₆alkyl; and NR⁸—C(O)—C(R³)=CR⁴(R⁵), wherein R³ is H or CN, R⁴ is H and R⁵ is H or cyclopropyl;

A is selected from the group consisting of: pyridyl; phenyl; pyrimidinyl; pyrazinyl; pyridin-2(1H)-one; and pyridazinyl; wherein the A is optionally substituted with 1, 2, or 3 substituents each independently selected from the group consisting of: halogen, C₁₋₆alkyl, C₁₋₆haloalkyl, and OC₁₋₆ alkyl;

E is selected from the group consisting of: O, a bond, and CH₂;

G is selected from the group consisting of: H; halogen; C₁₋₆alkyl; C₁₋₆haloalkyl; NH(C₁₋₆alkyl); C₃₋₆cycloalkyl; phenyl; pyrimidinyl; pyridyl; pyridazinyl; pyridin-2(1H)-one; heterocycloalkyl that contains an oxygen heteroatom; and phenyl-CH₂—O-phenyl, wherein the —O-phenyl is substituted with CN; wherein the phenyl, pyridyl, pyridazinyl, and pyridin-2(1H)-one is optionally substituted with 1, 2, or 3 substituents each independently selected from the group consisting of: halogen, C₁₋₆alkyl, C₁₋₆haloalkyl, OC₁₋₆haloalkyl, and OC₁₋₆alkyl; and stereoisomers or isotopic variant thereof; and pharmaceutically acceptable salts thereof.

According to the disclosure, R¹ is H or C₁₋₆alkyl. In some aspects, R¹ is C₁₋₆alkyl, for example, methyl, ethyl, n-propyl, isopropyl, n-butyl, s-butyl, or t-butyl. In preferred aspects, R¹ is H.

According to the disclosure, R² is a C₀₋₆ alk-cycloalkyl moiety that can be unsubstituted. In other aspects of the disclosure, R² is a C₀₋₆ alk-cycloalkyl moiety substituted with 1, 2, or 3 substituents, preferably 1 or 2 substituents, more preferably 1 substituent. In those embodiments wherein $R^2$ is $C_0$ alk-cycloalkyl, the cycloalkyl is directly attached to the compound of Formula (I) through a bond. In those aspects wherein $R^2$ is a $C_{1-6}$ alk-cycloalkyl moiety, the cycloalkyl moiety is attached to the compound of Formula (I) through an aliphatic linker having 1, 2, 3, 4, 5, or 6 carbon atoms, wherein the $C_{1-6}$ alk includes, for example, $CH_2$—, $CH(CH_3)$—, $CH(CH_3)$—$CH_2$—, and $C(CH_3)_2$—. In preferred aspects, $R^2$ is $C_{0-1}$ alk-cycloalkyl, for example $C_0$ alk-cycloalkyl (i.e., cycloalkyl) or $C_1$ alk-cycloalkyl (i.e., $CH_2$-cycloalkyl).

In preferred aspects, the $R^2$ cycloalkyl moiety is a 3-, 4-, 5-, 6-, or 10-membered cycloalkyl, preferably a 5- or 6-membered cycloalkyl, with a 5-membered cycloalkyl being most preferred.

In some aspects of the disclosure, $R^2$ is $C_{0-6}$alk-cylopropyl, preferably $C_0$ alk-cylopropyl or $C_1$ alk-cylopropyl, optionally substituted with 1, 2, or 3 substituents as recited herein. In more preferred aspects, $R^2$ is $C_{0-6}$alk-cylopropyl, preferably $C_0$ alk-cylopropyl or $C_1$ alk-cylopropyl, substituted with 1 or 2 substituents as recited herein. The substituents can be attached through any position on the cylopropyl ring.

In some aspects of the disclosure, $R^2$ is $C_{0-6}$alk-cylobutyl, preferably $C_0$ alk-cylobutyl or $C_1$ alk-cylobutyl, optionally substituted with 1, 2, or 3 substituents as recited herein. In more preferred aspects, $R^2$ is $C_{0-6}$alk-cylobutyl, preferably $C_0$ alk-cylobutyl or $C_1$ alk-cylobutyl, substituted with 1 or 2 substituents as recited herein. The substituents can be attached through any position on the cylobutyl ring.

In preferred aspects of the disclosure, $R^2$ is $C_{0-6}$alk-cyclopentyl, preferably $C_0$ alk-cyclopentyl or $C_1$ alk-cyclopentyl, optionally substituted with 1, 2, or 3 substituents as recited herein. In more preferred aspects, $R^2$ is $C_{0-6}$alk-cyclopentyl, preferably $C_0$ alk-cyclopentyl or $C_1$ alk-cyclopentyl, substituted with 1 or 2 substituents as recited herein. The substituents can be attached through any position on the cyclopentyl ring.

In some aspects of the disclosure, $R^2$ is $C_{0-6}$alk-cyclohexyl, preferably $C_0$ alk-cyclohexyl or $C_1$ alk-cyclohexyl, optionally substituted with 1, 2, or 3 substituents as recited herein. In more preferred aspects, $R^2$ is $C_{0-6}$alk-cyclohexyl, preferably $C_0$ alk-cyclohexyl or $C_1$ alk-cyclohexyl, substituted with 1 or 2 substituents as recited herein. The substituents can be attached through any position on the cyclohexyl ring.

In some aspects of the disclosure, $R^2$ is $C_{0-6}$alk-adamantanyl, preferably $C_0$ alk-adamantanyl or $C_1$ alk-adamantanyl, optionally substituted with 1, 2, or 3 substituents as recited herein. In more preferred aspects, $R^2$ is $C_{0-6}$alk-adamantanyl, preferably $C_0$ alk-adamantanyl or $C_1$ alk-adamantanyl, substituted with 1 or 2 substituents as recited herein. The substituents can be attached through any position on the adamantanyl ring.

According to the disclosure, the $R^2$ cycloalkyl can be unsubstituted. In some aspects, the $R^2$ cycloalkyl is substituted with 1, 2, or 3 substituents. In preferred aspects, the $R^2$ cycloalkyl is substituted with 1 or 2 substituents, more preferably 1 substituent. In those aspects wherein the $R^2$ cycloalkyl is substituted, the substituents may be independently selected from the group consisting of $NR^8$—C(O)—$C(R^3)$=$CR^4(R^5)$; $NR^6R^7$; OH; CN; oxo; O—$C_{1-6}$alkyl; halogen; $C_{1-6}$alkyl; $C_{1-6}$haloalkyl; $C_{1-6}$alk-OH; $C_{3-6}$cycloalkyl; $C_{1-6}$alkaryl; $SO_2C_{1-6}$alkyl; $SO_2C_{2-6}$alkenyl; $NR^8$—C(O)—$C_{1-6}$alk-$NR^6R^7$; $NR^8$—C(O)—$C_{1-6}$alkyl; $NR^8$—C(O)—O—$C_{1-6}$alkyl; $NR^8$—C(O)—$C_{3-6}$cycloalkyl; $NR^8$—C(O)H; $NR^8$—C(O)—$C_{3-6}$cycloalkyl; $NR^8$—C(O)—$C_{1-6}$haloalkyl; $NR^8$—C(O)-alkynyl; $NR^8$—C(O)—$C_{6-10}$aryl; $NR^8$—C(O)-heteroaryl; $NR^8$—C(O)—$C_{1-6}$alk-CN; $NR^8$—C(O)—$C_{1-6}$alk-OH; $NR^8$—C(O)—$C_{1-6}$alk-$SO_2$—$C_{1-6}$alkyl; $NR^8$—C(O)—$C_{1-6}$alk-$NR^6R^7$; $NR^8$—C(O)—$C_{1-6}$alk-O—$C_{1-6}$alkyl wherein the $C_{1-6}$alk- is optionally substituted with OH, $OC_{1-6}$alkyl, or $NR^6R^7$; $NR^8$—C(O)—$C_{0-6}$alk-heterocycloalkyl wherein the alk- is optionally substituted with oxo and the heterocycloalkyl is optionally substituted with $C_{1-6}$alkyl; and wherein $R^3$, $R^4$, $R^5$, $R^6$, $R^7$, and $R^8$ are as defined herein.

In some aspects, the $R^2$ cycloalkyl is substituted with an oxo moiety, for example one oxo moiety. In those aspects wherein the $R^2$ cycloalkyl is substituted with an oxo moiety, the cycloalkyl ring may optionally be substituted with one or two additional substituents as defined herein for the $R^2$ substituents.

In some aspects, the $R^2$ cycloalkyl is substituted with a halogen, for example a fluorine or chlorine or bromine. In some aspects, the $R^2$ cycloalkyl is substituted with one or two halogens, preferably one halogen. In those aspects wherein the $R^2$ cycloalkyl is substituted with a halogen, the cycloalkyl ring may optionally be substituted with one or two additional substituents as defined herein for the $R^2$ substituents.

In some aspects, the $R^2$ cycloalkyl is substituted with CN. In some aspects, the $R^2$ cycloalkyl is substituted with one or two CN, preferably one CN. In those aspects wherein the $R^2$ cycloalkyl is substituted with CN, the cycloalkyl ring may optionally be substituted with one or two additional substituents as defined herein for the $R^2$ substituents.

In some aspects, the $R^2$ cycloalkyl is substituted with OH. In some aspects, the $R^2$ cycloalkyl is substituted with one or two OH, preferably one OH. In those aspects wherein the $R^2$ cycloalkyl is substituted with OH, the cycloalkyl ring may optionally be substituted with one or two additional substituents as defined herein for the $R^2$ substituents.

In some aspects, the $R^2$ cycloalkyl is substituted with $NR^6R^7$ wherein $R^6$ and $R^7$ are each independently H; $C_{1-6}$alkyl, $C_{3-6}$cycloalkyl; C(O)H; or CN. In preferred aspects, $R^6$ and $R^7$ are each independently H or $C_{1-6}$alkyl. In those aspects wherein the $R^2$ cycloalkyl is substituted with $NR^6R^7$, the cycloalkyl ring may optionally be substituted with one or two additional substituents as defined herein for the $R^2$ substituents.

In some aspects, the $R^2$ cycloalkyl is substituted with $C_{1-6}$alkyl, for example, $C_{1-5}$alkyl, $C_{1-4}$alkyl, $C_{1-3}$alkyl, $C_{1-2}$alkyl, or $C_1$alkyl. In some aspects, the $R^2$ cycloalkyl is substituted with one or two $C_{1-6}$alkyl, preferably one $C_{1-6}$alkyl. In those aspects wherein the $R^2$ cycloalkyl is substituted with $C_{1-6}$alkyl, the cycloalkyl ring may optionally be substituted with one or two additional substituents as defined herein for the $R^2$ substituents.

In some aspects, the $R^2$ cycloalkyl is substituted with $C_{1-6}$alk-OH, for example, $C_{1-5}$alk-OH, $C_{1-4}$alk-OH, $C_{1-3}$alk-OH, $C_{1-2}$alk-OH, or $C_1$alk-OH, wherein the —OH moiety can be attached to any carbon of the $C_{1-6}$alk group, preferably the ω carbon. In some aspects, the $R^2$ cycloalkyl is substituted with one or two $C_{1-6}$alk-OH, preferably one $C_{1-6}$alk-OH. In those aspects wherein the $R^2$ cycloalkyl is substituted with $C_{1-6}$alk-OH, the cycloalkyl ring may optionally be substituted with one or two additional substituents as defined herein for the $R^2$ substituents.

In some aspects, the $R^2$ cycloalkyl is substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. In some aspects, the $R^2$ cycloalkyl is substituted with one or two $OC_{1-6}$alkyl, preferably one $OC_{1-6}$alkyl. In those aspects wherein the $R^2$ cycloalkyl is substituted with $OC_{1-6}$alkyl, the cycloalkyl ring may optionally be substituted with one or two additional substituents as defined herein for the $R^2$ substituents.

In some aspects, the $R^2$ cycloalkyl is substituted with a $C_{3-6}$cycloalkyl moiety, for example, a cyclopropyl, cyclobutyl, cyclopentyl, or cyclohexyl moiety. In some aspects, the $R^2$ cycloalkyl is substituted with one or two $C_{3-6}$cycloalkyl, preferably one $C_{3-6}$cycloalkyl. In those aspects wherein the $R^2$ cycloalkyl is substituted with $C_{3-6}$cycloalkyl, the cycloalkyl ring may optionally be substituted with one or two additional substituents as defined herein for the $R^2$ substituents.

In some aspects, the $R^2$ cycloalkyl is substituted with $C_{1-6}$alkaryl, for example, benzyl (i.e., $CH_2$-phenyl). In some aspects, the $R^2$ cycloalkyl is substituted with one or two $C_{1-6}$alkaryl, preferably one $C_{1-6}$alkaryl. In those aspects wherein the $R^2$ cycloalkyl is substituted with $C_{1-6}$alkaryl, the cycloalkyl ring may optionally be substituted with one or two additional substituents as defined herein for the $R^2$ substituents.

In some aspects, the $R^2$ cycloalkyl is substituted with $SO_2C_{1-6}$alkyl, for example, $SO_2C_{1-5}$alkyl, $SO_2C_{1-4}$alkyl, $SO_2C_{1-3}$alkyl, $SO_2C_{1-2}$alkyl, or $SO_2C_1$alkyl. In some aspects, the $R^2$ cycloalkyl is substituted with one or two $SO_2C_{1-6}$alkyl, preferably one $SO_2C_{1-6}$alkyl. In those aspects wherein the $R^2$ cycloalkyl is substituted with $SO_2C_{1-6}$alkyl, the cycloalkyl ring may optionally be substituted with one or two additional substituents as defined herein for the $R^2$ substituents.

In some aspects, the $R^2$ cycloalkyl is substituted with $SO_2C_{2-6}$alkenyl, for example, $-SO_2C_{2-5}$alkenyl, $SO_2C_{2-4}$alkenyl, $SO_2C_{2-3}$alkenyl, or $SO_2C_2$alkenyl. In some aspects, the $R^2$ cycloalkyl is substituted with one or two $SO_2C_{2-6}$alkenyl, preferably one $SO_2C_{2-6}$alkenyl. In those aspects wherein the $R^2$ cycloalkyl is substituted with $SO_2C_{2-6}$alkenyl, the cycloalkyl ring may optionally be substituted with one or two additional substituents as defined herein for the $R^2$ substituents.

In some aspects, the $R^2$ cycloalkyl is substituted with $NR^8$—C(O)H wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)H, preferably one $NR^8$—C(O)H. In those aspects wherein the $R^2$ cycloalkyl is substituted with $NR^8$—C(O)H, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alkyl, for example, $NR^8$—C(O)—$C_{1-5}$alkyl, $NR^8$—C(O)—$C_{1-4}$alkyl, $NR^8$—C(O)—$C_{1-3}$alkyl, $NR^8$—C(O)—$C_{1-2}$alkyl, or $NR^8$—C(O)—$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alkyl, preferably one $NR^8$—C(O)—$C_{1-6}$alkyl. In those aspects wherein the $R^2$ cycloalkyl is substituted with $NR^8$—C(O)—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{3-6}$cycloalkyl, for example, $NR^8$—C(O)-cyclopropyl, $NR^8$—C(O)-cyclobutyl, $NR^8$—C(O)-cyclopentyl, or $NR^8$—C(O)-cyclohexyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{3-6}$cycloalkyl, preferably one $NR^8$—C(O)—$C_{3-6}$cycloalkyl. In those aspects wherein the $R^2$ cycloalkyl is substituted with $NR^8$—C(O)—$C_{3-6}$cycloalkyl, the cycloalkyl ring may optionally be substituted with one or two additional substituents as defined herein for the $R^2$ substituents.

In some aspects, the $R^2$ cycloalkyl is substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. In some aspects, the $R^2$ cycloalkyl is substituted with one or two $C_{1-6}$haloalkyl, preferably one $C_{1-6}$haloalkyl. In those aspects wherein the $R^2$ cycloalkyl is substituted with $C_{1-6}$haloalkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$haloalkyl, for example, $NR^8$—C(O)—$C_{1-5}$haloalkyl, $NR^8$—C(O)—$C_{1-4}$haloalkyl, $NR^8$—C(O)—$C_{1-3}$haloalkyl, $NR^8$—C(O)—$C_{1-2}$haloalkyl, or $NR^8$—C(O)—$C_1$haloalkyl, including $NR^8$—C(O)—$CF_3$, $NR^8$—C(O)—$CH_2CH_2F$, and the like, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$haloalkyl, preferably one $NR^8$—C(O)—$C_{1-6}$haloalkyl. In those aspects wherein the $R^2$ cycloalkyl is substituted with $NR^8$—C(O)—$C_{1-6}$haloalkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{2-6}$alkynyl, for example, $NR^8$—C(O)—$C_{2-5}$alkynyl, $NR^8$—C(O)—$C_{2-4}$alkynyl, $NR^8$—C(O)—$C_{2-3}$alkynyl, or $NR^8$—C(O)—$C_2$alkynyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{2-6}$alkynyl, preferably one $NR^8$—C(O)—$C_{2-6}$alkynyl. In those aspects wherein the $R^2$ cycloalkyl is substituted with $NR^8$—C(O)—$C_{2-6}$alkynyl, the cycloalkyl ring may optionally be substituted with one or two additional substituents as defined herein for the $R^2$ substituents.

In some aspects, the $R^2$ cycloalkyl is substituted with $NR^8$—C(O)—$C_{6-10}$aryl, for example, $NR^8$—C(O)-phenyl or $NR^8$—C(O)-napthalenyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{6-10}$aryl, preferably one $NR^8$—C(O)—$C_{6-10}$aryl. In those aspects wherein the $R^2$ cycloalkyl is substituted with $NR^8$—C(O)—$C_{6-10}$ aryl, the cycloalkyl ring may optionally be substituted with one or two additional substituents as defined herein for the $R^2$ substituents.

In some aspects, the $R^2$ cycloalkyl is substituted with $NR^8$—C(O)-heteroaryl, for example, $NR^8$—C(O)-pyrrolyl, $NR^8$—C(O)-thienyl, $NR^8$—C(O)-oxazolyl, $NR^8$—C(O)-pyrazolyl, $NR^8$—C(O)-pyridyl, $NR^8$—C(O)-pyrimidinyl, and the like, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)-heteroaryl, preferably one $NR^8$—C(O)-heteroaryl. In those aspects wherein the $R^2$ cycloalkyl is substituted with $NR^8$—C(O)-heteroaryl, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-CN, for example, $NR^8$—C(O)

—$C_{1-5}$alk-CN, $NR^8$—C(O)—$C_{1-4}$alk-CN, $NR^8$—C(O)—$C_{1-5}$alk-CN, $NR^8$—C(O)—$C_{1-2}$alk-CN, or $NR^8$—C(O)—$C_1$alk-CN, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-CN, preferably one $NR^8$—C(O)—$C_{1-6}$alk-CN. In those aspects wherein the $R^2$ cycloalkyl is substituted with $NR^8$—C(O)—$C_{1-6}$alk-CN, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-OH, for example, $NR^8$—C(O)—$C_{1-5}$alk-OH, $NR^8$—C(O)—$C_{1-4}$alk-OH, $NR^8$—C(O)—$C_{1-5}$alk-OH, $NR^8$—C(O)—$C_{1-2}$alk-OH, or $NR^8$—C(O)—$C_1$alk-OH, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-OH, preferably one $NR^8$—C(O)—$C_{1-6}$alk-OH. In those aspects wherein the $R^2$ cycloalkyl is substituted with $NR^8$—C(O)—$C_{1-6}$ alk-OH, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-$SO_2$—$C_{1-6}$alkyl, for example, $NR^8$—C(O)—$C_{1-5}$alk-$SO_2$—$C_{1-5}$alkyl, $NR^8$—C(O)—$C_{1-4}$alk-$SO_2$—$C_{1-4}$alkyl, $NR^8$—C(O)—$C_{1-3}$alk-$SO_2$—$C_{1-3}$alkyl, $NR^8$—C(O)—$C_{1-2}$alk-$SO_2$—$C_{1-2}$alkyl, or $NR^8$—C(O)—$C_1$alk-$SO_2$—$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-$SO_2$—$C_{1-6}$alkyl, preferably one $NR^8$—C(O)—$C_{1-6}$alk-$SO_2$—$C_{1-6}$alkyl. In those aspects wherein the $R^2$ cycloalkyl is substituted with $NR^8$—C(O)—$C_{1-6}$alk-$SO_2$—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—O—$C_{1-6}$alkyl, for example, $NR^8$—C(O)—O—$C_{1-5}$alkyl, $NR^8$—C(O)—O—$C_{1-4}$alkyl, $NR^8$—C(O)—O—$C_{1-3}$alkyl, $NR^8$—C(O)—O—$C_{1-2}$alkyl, or $NR^8$—C(O)—O—$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—O—$C_{1-6}$alkyl, preferably one $NR^8$—C(O)—O—$C_{1-6}$alkyl. In those aspects wherein the $R^2$ cycloalkyl is substituted with $NR^8$—C(O)—O—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$ alk-$NR^6R^7$, for example, $NR^8$—C(O)—$C_{1-5}$alk-$NR^6R^7$, $NR^8$—C(O)—$C_{1-4}$alk-$NR^6R^7$, $NR^8$—C(O)—$C_{1-5}$alk-$NR^6R^7$, $NR^8$—C(O)—$C_{1-2}$alk-$NR^6R^7$, or $NR^8$—C(O)—$C_1$alk-$NR^6R^7$, wherein $R^6$ and $R^7$ are each independently H; $C_{1-6}$ alkyl, for example, $C_{1-5}$alkyl, $C_{1-4}$alkyl, $C_{1-3}$alkyl, $C_{1-2}$alkyl, or $C_1$alkyl; $C_{3-6}$cycloalkyl, for example, cyclopropyl, cyclobutyl, cyclopentyl, or cyclohexyl; C(O)H, or CN. In preferred aspects, $R^6$ and $R^7$ are each independently H, $C_{1-6}$alkyl; or $C_{3-6}$cycloalkyl, with H and $C_{1-6}$alkyl being preferred, and H and $C_{1-2}$alkyl being more preferred. In these embodiments, $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-$NR^6R^7$, preferably one $NR^8$—C(O)—$C_{1-6}$alk-$NR^6R^7$. In those aspects wherein the $R^2$ cycloalkyl is substituted with $NR^8$—C(O)—$C_{1-6}$alk-$NR^6R^7$, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-O—$C_{1-6}$alkyl, for example, $NR^8$—C(O)—$C_{1-5}$alk-O—$C_{1-5}$alkyl, $NR^8$—C(O)—$C_{1-4}$alk-O—$C_{1-4}$ alkyl, $NR^8$—C(O)—$C_{1-5}$alk-O—$C_{1-3}$alkyl, $NR^8$—C(O)—$C_{1-2}$alk-O—$C_{1-2}$alkyl, or $NR^8$—C(O)—$C_1$alk-O—$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In certain aspects wherein the $R^2$ cycloalkyl is substituted with $NR^8$—C(O)—$C_{1-6}$alk-O—$C_{1-6}$ alkyl, the $C_{1-6}$alk- is optionally substituted with OH; $OC_{1-6}$alkyl, for example, $OC_{1-5}$alkyl, $OC_{1-4}$alkyl, $OC_{1-3}$alkyl, $OC_{1-2}$alkyl, or $OC_1$alkyl; or $NR^6R^7$, wherein $R^6$ and $R^7$ are each independently H; $C_{1-6}$alkyl, for example, $C_{1-5}$alkyl, $C_{1-4}$alkyl, $C_{1-3}$alkyl, $C_{1-2}$alkyl, or $C_1$alkyl; $C_{3-6}$cycloalkyl; C(O)H; or CN. In preferred aspects, $R^6$ and $R^7$ are each independently H, $C_{1-6}$ alkyl; or $C_{3-6}$cycloalkyl, with H and $C_{1-6}$alkyl being preferred, and H and $C_{1-2}$alkyl being more preferred. In some aspects, the $C_{1-6}$alk- of the $NR^8$—C(O)—$C_{1-6}$alk-O—$C_{1-6}$alkyl moiety is substituted with OH. In other aspects, the $C_{1-6}$alk- is substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. In some aspects, the $R^2$ cycloalkyl is substituted with one or two $NR^8$—C(O)—$C_{1-6}$alk-O—$C_{1-6}$alkyl, preferably one $NR^8$—C(O)—$C_{1-6}$ alk-O—$C_{1-6}$alkyl. In those aspects wherein the $R^2$ cycloalkyl is substituted with $NR^8$—C(O)—$C_{1-6}$alk-O—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{0-6}$alk-heterocycloalkyl, for example, $NR^8$—C(O)—$C_{0-5}$alk-heterocycloalkyl, $NR^8$—C(O)—$C_{0-4}$alk-heterocycloalkyl, $NR^8$—C(O)—$C_{0-5}$alk-heterocycloalkyl, $NR^8$—C(O)—$C_{0-2}$alk-heterocycloalkyl, $NR^8$—C(O)—$C_{0-4}$alk-heterocycloalkyl, $NR^8$—C(O)—$C_1$alk-heterocycloalkyl, or $NR^8$—C(O)—$C_0$alk-heterocycloalkyl, wherein $R^8$ is H or $C_{1-6}$, for example, $C_{1-5}$alkyl, $C_{1-4}$alkyl, $C_{1-3}$alkyl, $C_{1-2}$alkyl, or $C_1$alkyl. In preferred aspects, $R^8$ is H. Preferred substituent heterocycloalkyl groups include tetrahydrofuranyl, piperidinyl, pyrrolidinyl, and the like. In certain aspects wherein the $R^2$ cycloalkyl is substituted with $NR^8$—C(O)—$C_{1-6}$alk-heterocycloalkyl the $C_{1-6}$alk- is optionally substituted with oxo. In certain aspects wherein the $R^2$ cycloalkyl is substituted with $NR^8$—C(O)—$C_{0-6}$alk-heterocycloalkyl, the substituent heterocycloalkyl moiety can be unsubstituted or substituted with $C_{1-6}$alkyl, for example, $C_{1-5}$ alkyl, $C_{1-4}$alkyl, $C_{1-3}$alkyl, $C_{1-2}$alkyl, or $C_1$alkyl. In those aspects wherein the $R^2$ cycloalkyl is substituted with C(O)—$C_{0-6}$alk-heterocycloalkyl, the $R^2$ cycloalkyl ring may optionally be substituted with one or two additional substituents as defined herein for the $R^2$ substituents.

In some aspects, the $R^2$ cycloalkyl is substituted with $NR^8$—C(O)—C($R^3$)=$CR^4(R^5)$, wherein $R^3$, $R^4$, and $R^5$ are as described herein and $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In these aspects, $R^3$ is H; CN; halogen; $C_{1-6}$haloalkyl; or $C_{1-6}$alkyl. In some embodiments, $R^3$ is H. In other aspects, $R^3$ is CN. In still other aspects, $R^3$ is halogen, for example F or Cl. In yet other aspects, $R^3$ is $C_{1-6}$ haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. In further aspects, $R^3$ is $C_{1-6}$alkyl, for example, $C_{1-5}$alkyl, $C_{1-4}$alkyl, $C_{1-3}$alkyl, $C_{1-2}$alkyl, or $C_1$alkyl. In those aspects wherein the $R^2$ cycloalkyl is substituted with $NR^8$—$C(O)$—$C(R^3)$=$CR^4(R^5)$, the cycloalkyl ring may optionally be substituted with one or two additional substituents as defined herein for the $R^2$ substituents.

In preferred aspects, the $R^2$ cycloalkyl is substituted with $NR^8$—$C(O)$—$C(R^3)$=$CR^4(R^5)$; $NR^8$—$C(O)$—$C_{1-6}$alk-$NR^6R^7$; $NR^8$—$C(O)$—$C_{1-6}$alkyl; or $NR^6R^7$. In more preferred aspects, the $R^2$ cycloalkyl is substituted with $NR^8$—$C(O)$—$C(R^3)$=$CR^4(R^5)$. In other preferred aspects, the $R^2$ cycloalkyl is substituted with $NR^8$—$C(O)$—$C_{1-6}$alk-$NR^6R^7$; $NR^8$—$C(O)$—$C_{1-6}$ alkyl; or $NR^6R^7$; wherein $R^6$ and $R^7$ are each independently H or $C_{1-6}$alkyl.

In some preferred aspects, $R^2$ is $CH_2$-cyclohexyl, wherein the cyclohexyl is optionally substituted with OH; 3-hydroxyadamantan-1-yl; or $C_{3-6}$cycloalkyl optionally substituted with 1, 2, or 3 substituents each independently selected from the group consisting of: OH, halogen, $C_{1-6}$ alkyl, $C_{1-6}$haloalkyl, $OC_{1-6}$alkyl, CN, $NR^6R^7$, $NR^8$—$C(O)H$, $NR^8$—$C(O)$—$C_{1-6}$alkyl, $NR^8$—$C(O)$—$C_{1-6}$haloalkyl, $NR^8$—$C(O)$—$O$—$C_{1-6}$alkyl, $NR^8$—$C(O)$—$C_{1-6}$alk-OH, $NR^8$—$C(O)$—$C_{1-6}$alk-$NR^6R^7$, and $NR^8$—$C(O)$—$C(R^3)$=$CR^4(R^5)$; wherein $R^3$ is selected from the group consisting of: H, CN, halogen, $C_{1-6}$ haloalkyl, and $C_{1-6}$alkyl; $R^4$ and $R^5$ are each independently selected from the group consisting of: H; $C_{0-6}$alk-$NR^6R^7$; $C_{1-6}$alk-O—$C_{1-6}$alkyl; $C_{3-6}$cycloalkyl; heterocycloalkyl optionally substituted with $C_{1-6}$alkyl; and -linker-PEG-Biotin; $R^6$ and $R^7$ are each independently selected from the group consisting of: H, $C_{1-6}$alkyl, C(O)H, and CN; and $R^8$ is H. In some aspects, the $R^2$ is substituted with 1 or 2 substituents. In some aspects, the $R^2$ is substituted with at least one substituent, preferably 1 or 2 substituents, independently selected from the group consisting of OH, halogen, $C_{1-6}$alkyl, $C_{1-6}$haloalkyl, $OC_{1-6}$alkyl, and CN.

In some preferred aspects, $R^2$ is $CH_2$-cyclohexyl. In other preferred aspects, $R^2$ is $CH_2$-cyclohexyl wherein the cyclohexyl is substituted with OH.

In some preferred aspects, $R^2$ is 3-hydroxyadamantan-1-yl.

In other preferred aspects, $R^2$ is $C_{3-6}$cycloalkyl. In some other preferred aspects, $R^2$ is $C_{3-6}$cycloalkyl substituted with 1, 2, or 3 substituents. Those substituents can be independently selected from the group consisting of OH, halogen, $C_{1-6}$alkyl, $C_{1-6}$haloalkyl, $OC_{1-6}$alkyl, CN, $NR^6R^7$, $NR^8$—$C(O)H$, $NR^8$—$C(O)$—$C_{1-6}$alkyl, $NR^8$—$C(O)$—$C_{1-6}$haloalkyl, $NR^8$—$C(O)$—$O$—$C_{1-6}$alkyl, $NR^8$—$C(O)$—$C_{1-6}$alk-OH, $NR^8$—$C(O)$—$C_{1-6}$alk-$NR^6R^7$, and $NR^8$—$C(O)$—$C(R^3)$=$CR^4(R^5)$.

In those embodiments employing $R^4$ and $R^5$, that is, those aspects wherein the $R^2$ cycloalkyl is substituted with $NR^8$—$C(O)$—$C(R^3)$=$CR^4(R^5)$, $R^4$ and $R^5$ are each independently H; halogen; $C_{0-6}$alk-$NR^6R^7$; $C_{1-6}$alkyl; $OC_{1-6}$alkyl; $C_{0-6}$alk-$C_{3-6}$cycloalkyl optionally substituted with $C_{1-6}$alkyl; $C_{0-6}$alk-heterocycloalkyl optionally substituted with C(O)$C_{1-6}$alkyl or $C_{1-6}$alkyl; $C_{1-6}$ alk-OH; $C_{1-6}$alk-O—$C_{1-6}$alkyl; $C_{1-6}$alk-NH—$C_{0-6}$alk-O—$C_{1-6}$alkyl; $C_{1-6}$alk-NHSO_2—$C_{1-6}$alkyl; —$C_{1-6}$alk-SO_2—$C_{1-6}$alkyl; —NHC(O)—$C_{1-6}$alkyl; or linker-PEG-Biotin.

Within the scope of this disclosure, the double bond present in —$NR^8$—$C(O)$—$C(R^3)$=$CR^4(R^5)$ may be of the Z or E configuration.

In some aspects, neither $R^4$ nor $R^5$ is H.

In most preferred aspects, each of $R^4$ and $R^5$ is H.

In some aspects, one of $R^4$ and $R^5$ is H. In certain of these aspects, the other of $R^4$ and $R^5$ is halogen, for example F or Cl.

In some aspects, one of $R^4$ and $R^5$ is H. In certain of these aspects, the other of $R^4$ and $R^5$ is $C_{1-6}$alkyl, for example, $C_{1-5}$alkyl, $C_{1-3}$alkyl, $C_{1-2}$alkyl, or $C_1$alkyl.

In some aspects, one of $R^4$ and $R^5$ is H. In certain of these aspects, the other of $R^4$ and $R^5$ is $OC_{1-6}$alkyl, for example, $OC_{1-5}$alkyl, $OC_{1-4}$alkyl, $OC_{1-3}$alkyl, $OC_{1-2}$alkyl, or $OC_1$alkyl.

In some aspects, one of $R^4$ and $R^5$ is H. In certain of these aspects, the other of $R^4$ and $R^5$ is $C_{0-6}$alk-$C_{3-6}$cycloalkyl, for example, $C_{0-5}$alk-$C_{3-5}$cycloalkyl, $C_{0-4}$alk-$C_{3-4}$cycloalkyl, $C_{0-5}$alk-$C_3$cycloalkyl, $C_{0-2}$alk-$C_{3-6}$cycloalkyl, $C_{0-4}$alk-$C_{3-6}$cycloalkyl, $C_0$alk-$C_{3-6}$cycloalkyl or $C_1$alk-$C_{3-6}$cycloalkyl. In these aspects, the cycloalkyl moiety can be unsubstituted or can be substituted with $C_{1-6}$alkyl, for example, $C_{1-5}$alkyl, $C_{1-4}$alkyl, $C_{1-3}$alkyl, $C_{1-2}$ alkyl, or $C_1$alkyl. The substitution can be a spiro-substitution or a non-spiro-substitution.

In some aspects, one of $R^4$ and $R^5$ is H. In certain of these aspects, the other of $R^4$ and $R^5$ is $C_{0-6}$alk-heterocycloalkyl, for example, $C_{1-6}$alk-heterocycloalkyl, $C_{0-4}$alk-heterocycloalkyl, $C_{0-5}$alk-heterocycloalkyl, $C_{0-2}$alk-heterocycloalkyl, $C_{0-4}$alk-heterocycloalkyl, $C_1$alk-heterocycloalkyl, or $C_0$alk-heterocycloalkyl. In these aspects, the substituent heterocycloalkyl is preferably an oxygen-containing heterocycloalkyl, for example, tetrahydropyranyl, tetrahydrofuranyl, or oxetanyl. In other aspects, the heterocycloalkyl is a nitrogen-containing heterocycloalkyl, for example, pyrrolidinyl, aziridinyl, or piperidinyl. In certain of these aspects, the substituent heterocycloalkyl can be substituted with C(O)$C_{1-6}$alkyl, for example, C(O)$C_{1-5}$alkyl, C(O)$C_{1-4}$alkyl, C(O)$C_{1-3}$alkyl, C(O)$C_{1-2}$alkyl, or C(O)$C_1$alkyl. In other aspects, the substituent heterocycloalkyl can be substituted with $C_{1-6}$alkyl, for example, $C_{1-5}$ alkyl, $C_{1-4}$alkyl, $C_{1-3}$alkyl, $C_{1-2}$alkyl, or $C_1$alkyl.

In some aspects, one of $R^4$ and $R^5$ is H. In certain of these aspects, the other of $R^4$ and $R^5$ is $C_{1-6}$alk-OH, for example, $C_{1-5}$alk-OH, $C_{1-4}$alk-OH, $C_{1-3}$alk-OH, $C_{1-2}$alk-OH, or $C_1$alk-OH. The OH moiety can be attached to any carbon of the $C_{1-6}$alk group, preferably the ω carbon.

In some aspects, one of $R^4$ and $R^5$ is H. In certain of these aspects, the other of $R^4$ and $R^5$ is $C_{0-6}$alk-$NR^6R^7$, for example, $C_{0-5}$alk-$NR^6R^7$, $C_{0-4}$alk-$NR^6R^7$, $C_{0-5}$alk-$NR^6R^7$, $C_{0-2}$alk-$NR^6R^7$, $C_{0-1}$alk-$NR^6R^7$, $C_1$alk-$NR^6R^7$, or $C_0$alk-$NR^6R^7$, wherein $R^6$ and $R^7$ are each independently H; $C_{1-6}$alkyl, for example, $C_{1-5}$alkyl, $C_{1-4}$alkyl, $C_{1-3}$alkyl, $C_{1-2}$alkyl, or $C_1$alkyl; $C_{3-6}$cycloalkyl, for example, cyclopropyl, cyclobutyl, cyclopentyl, or cyclohexyl; C(O)H; or CN. In preferred aspects, $R^6$ and $R^7$ are each independently H; $C_{1-6}$alkyl; or $C_{3-6}$cycloalkyl, more preferably, $R^6$ and $R^7$ are each independently H or $C_{1-6}$alkyl.

In some aspects, one of $R^4$ and $R^5$ is H. In certain of these aspects, the other of $R^4$ and $R^5$ is $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$-alk-O—$C_{1-2}$alkyl, or $C_1$alk-O—$C_1$alkyl.

In some aspects, one of $R^4$ and $R^5$ is H. In certain of these aspects, the other of $R^4$ and $R^5$ is $C_{1-6}$alk-NH—$C_{0-6}$alk-O—$C_{1-6}$alkyl, for example, $C_{1-5}$alk-NH—$C_{0-6}$alk-O—$C_{1-5}$alkyl, $C_{1-4}$alk-NH—$C_{0-6}$alk-O—$C_{1-4}$alkyl, $C_{1-5}$alk-NH—$C_{0-6}$alk-O—$C_{1-3}$alkyl, $C_{1-2}$alk-NH—$C_{0-6}$alk-O—$C_{1-2}$alkyl, $C_1$alk-NH—$C_{0-6}$alk-O—$C_1$alkyl, $C_{1-5}$alk-NH—$C_{0-6}$alk-O—$C_{1-5}$ alkyl, $C_{1-5}$-alk-NH—$C_{1-5}$alk-O—$C_{1-4}$alkyl, $C_{1-5}$alk-NH—$C_{1-4}$alk-O—$C_{1-3}$alkyl, $C_{1-2}$-alk-NH—$C_{1-5}$alk-O—$C_{1-2}$ alkyl, $C_1$alk-NH—$C_{1-2}$ alk-O—$C_1$alky, or $C_{1-6}$alk-NH—$C_0$alk-O—$C_{1-6}$alkyl.

In some aspects, one of $R^4$ and $R^5$ is H. In certain of these aspects, the other of $R^4$ and $R^5$ is $C_{1-6}$alk-$NHSO_2$—$C_{1-6}$alkyl, for example, $C_{1-5}$alk-$NHSO_2$—$C_{1-5}$alkyl $C_{1-4}$alk-$NHSO_2$—$C_{1-4}$alkyl, $C_{1-5}$alk-$NHSO_2$—$C_{1-3}$alkyl, $C_{1-2}$-alk-$NHSO_2$—$C_{1-2}$alkyl, or $C_1$alk-$NHSO_2$—$C_1$alkyl.

In some aspects, one of $R^4$ and $R^5$ is H. In certain of these aspects, the other of $R^4$ and $R^5$ is $C_{1-6}$alk-$SO_2$—$C_{1-6}$ alkyl, for example, $C_{1-5}$alk-$SO_2$—$C_{1-5}$alkyl, $C_{1-4}$alk-$SO_2$—$C_{1-4}$ alkyl, $C_{1-3}$alk-$SO_2$—$C_{1-3}$alkyl, $C_{1-2}$-alk-$SO_2$—$C_{1-2}$alkyl, or $C_1$alk-$SO_2$—$C_1$alkyl.

In some aspects, one of $R^4$ and $R^5$ is H. In certain of these aspects, the other of $R^4$ and $R^5$ is NHC(O)—$C_{1-6}$alkyl, for example, NHC(O)—$C_{1-5}$alkyl, NHC(O)—$C_{1-4}$alkyl, NHC(O)—$C_{1-3}$alkyl, NHC(O)—$C_{1-2}$alkyl, or NHC(O)—$C_1$alkyl.

In some aspects, one of $R^4$ and $R^5$ is H. In certain of these aspects, the other of $R^4$ and $R^5$ is linker-PEG-Biotin, preferably joining of $R^1$ and $R^2$ is substituted with 1, 2, or 3 substituents. In preferred aspects, the ring formed by the joining of $R^1$ and $R^2$ is substituted with 1 or 2 substituents, more preferably 1 substituent. In those aspects wherein the ring formed by the joining of $R^1$ and $R^2$ is substituted, the substituents may be independently selected from the group consisting of $NR^8$—C(O)—C($R^3$)=$CR^4(R^5)$; $NR^6R^7$; OH; CN; oxo; O—$C_{1-6}$alkyl; halogen; $C_{1-6}$ alkyl; $C_{1-6}$haloalkyl; $C_{1-6}$alk-OH; $C_{3-6}$cycloalkyl; $C_{1-6}$alkaryl; $SO_2C_{1-6}$alkyl; $SO_2C_{2-6}$alkenyl; —$NR^8$—C(O)—$C_{1-6}$alk-$NR^6R^7$; $NR^8$—C(O)—$C_{1-6}$alkyl; $NR^8$—C(O)—O—$C_{1-6}$alkyl; $NR^8$—C(O)—$C_{3-6}$cycloalkyl; $NR^8$—C(O)H; $NR^8$—C(O)—$C_{3-6}$cycloalkyl; $NR^8$—C(O)—$C_{1-6}$haloalkyl; $NR^8$—C(O)-alkynyl; $NR^8$—C(O)—$C_{6-10}$aryl; $NR^8$—C(O)-heteroaryl; $NR^8$—C(O)—$C_{1-6}$alk-CN; $NR^8$—C(O)—$C_{1-6}$alk-OH; $NR^8$—C(O)—$C_{1-6}$alk-$SO_2$—$C_{1-6}$alkyl; $NR^8$—C(O)—$C_{1-6}$alk-$NR^6R^7$; $NR^8$—C(O)—$C_{1-6}$alk-O—$C_{1-6}$alkyl wherein the $C_{1-6}$alk- is optionally substituted with OH, O$C_{1-6}$alkyl, or

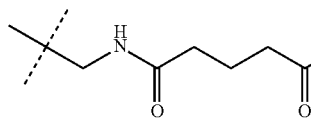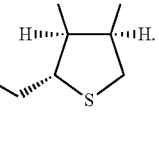

In preferred aspects, one of $R^4$ and $R^5$ is H and the other of $R^4$ and $R^5$ is $C_{1-6}$alkyl (e.g., methyl, t-butyl); cycloalkyl (e.g., cyclopropyl); $C_{1-6}$alk-$NR^6R^7$ (e.g., $CH_2$—$NH_2$, $CH_2$—$NHCH_3$, $CH_2$—$N(CH_3)_2$, $C(CH_3)_2$—$NH_2$, $C(CH_3)_2$—$NHCH_3$, $C(CH_3)_2$—$N(CH_3)_2$); $C_{1-6}$alk-O—$C_{1-6}$alkyl (e.g., $C(CH_3)_2$—$OCH_3$, $C(CH_3)_2$—$OCH_2CH_3$); $C_{0-6}$alk-heterocycloalkyl substituted with $C_{1-6}$alkyl (e.g., $C(CH_3)$-oxetanyl).

In some embodiments, or $R^1$ and $R^2$, together with the nitrogen atom to which they are attached, form an optionally substituted ring that is a pyrrolidinyl ring or a piperidinyl ring, for example, compounds of Formula (I)' or Formula (I)":

(I')

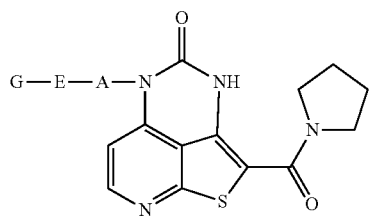

(I")

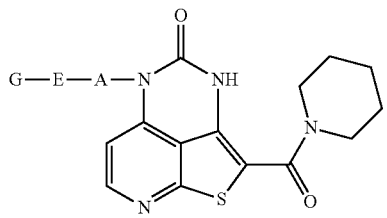

In these aspects, ring formed by the joining of $R^1$ and $R^2$ can be unsubstituted. In some aspects, the ring formed by the $NR^6R^7$; $NR^8$—C(O)—$C_{0-6}$alk-heterocycloalkyl wherein the $C_{0-6}$alk- is optionally substituted with oxo and the heterocycloalkyl is optionally substituted with $C_{1-6}$alkyl; and wherein $R^3$, $R^4$, $R^5$, $R^6$, $R^7$, and $R^8$ are as defined herein.

A preferred subgenus of Formula (I) is a compound of Formula (IA):

(I-A)

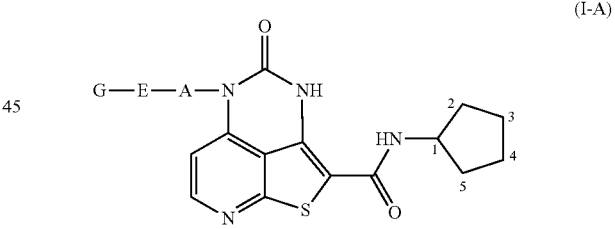

wherein the cyclopentyl ring is substituted at the 2 position with any of the $R^2$ substituents defined herein.

Other preferred subgenera of Formula (I) are:

(I-B-1)

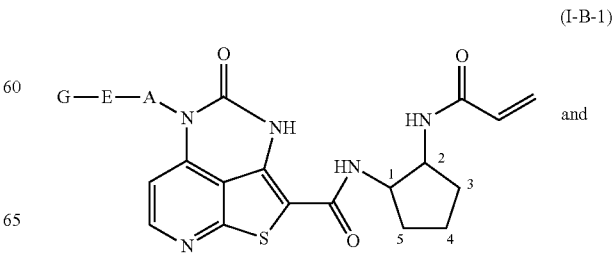

and

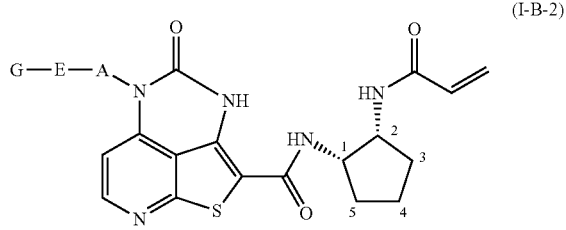

(I-B-2)

Within the scope of the disclosure, A can be a bond. Also within the scope of the disclosure, A can be pyridyl; phenyl; napthalenyl; pyrimidinyl; pyrazinyl; pyridazinyl; benzo[d][1,3]dioxolyl optionally substituted with halogen; benzothiophenyl; or pyrazolyl. Also within the disclosure, A can be pyridyl; phenyl; pyrimidinyl; pyrazinyl; pyridine-2(1H)-one, or pyridazinyl. Also according to the disclosure, any of the A moieties (excluding a bond) can be unsubstituted or substituted with 1, 2, or 3 substituents, preferably 1 or 2 substituents, more preferably 1 substituent, independently selected from the group consisting of $C_{1-6}$alkyl, for example, $C_{1-5}$alkyl, $C_{1-3}$alkyl, $C_{1-2}$alkyl, or $C_1$alkyl; halogen, for example F or Cl; $SF_5$; $OC_{1-6}$alkyl, for example, $OC_{1-5}$alkyl, $OC_{1-4}$alkyl, $OC_{1-3}$alkyl, $OC_{1-2}$alkyl, or $OC_1$alkyl; C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl; and $C_{1-6}$haloalkyl, for example, $C_{1-5}$haloalkyl, $C_{1-3}$haloalkyl, $C_{1-2}$haloalkyl, or $C_1$haloalkyl, including $CF_3$, $CH_2CH_2F$, and the like. Preferably, the A moieties can be substituted with 1, 2, or 3 substituents, preferably 1 or 2 substituents, independently selected from the group consisting of halogen, $C_{1-6}$alkyl, $C_{1-6}$haloalkyl, and $OC_{1-6}$ alkyl.

In some aspects, A is pyridyl. The pyridyl can be attached to any of the compounds of Formula (I) (or its subgenera) through any ring carbon atom, but preferably it attached through the 2- or 3-position carbon. Preferably, the pyridyl is substituted with one or two substituents, preferably one substituent. The pyridyl substituent can be attached to any ring carbon atom of the pyridyl ring. In those embodiments wherein the pyridyl is attached to the compound of Formula (I) through the 3-position carbon, the substituent is preferably attached to the pyridyl at the 2- or 4-position. The pyridyl can be substituted at any available ring carbon atom with $C_{1-6}$ alkyl, for example, $C_{1-5}$alkyl, $C_{1-3}$alkyl, $C_{1-2}$alkyl, or $C_1$alkyl. The pyridyl can be substituted at any available ring carbon atom with halogen, for example F or Cl. The pyridyl can be substituted at any available ring carbon atom with $SF_5$. The pyridyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyridyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyridyl can be substituted at any available ring carbon atom with $C_{1-6}$ haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyridyl include $C_{1-6}$alkyl, with $C_1$alkyl being most preferred, and with one $C_1$alkyl substituent being more preferred. Other preferred substituents include halogen, in particular F and Cl.

In some aspects, A is phenyl. Preferably, the phenyl is substituted with one or two substituents, preferably one substituent. The phenyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The phenyl can be substituted at any available ring carbon atom with halogen, for example F or Cl. The phenyl can be substituted at any available ring carbon atom with —$SF_5$. The phenyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The phenyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The phenyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. The phenyl's substituent can be attached to any ring carbon atom of the phenyl ring, preferably ortho to the phenyl moiety's point of attachment to the compound of Formula (I). Preferred substituents wherein A is phenyl include $C_{1-6}$alkyl, with $C_1$alkyl being most preferred. Other preferred substituents include halogen, in particular F and Cl.

In some aspects, A is napthalenyl. Preferably, the napthalenyl is substituted with one or two substituents, preferably one substituent. The napthalenyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The napthalenyl can be substituted at any available ring carbon atom with halogen, for example F or Cl. The napthalenyl can be substituted at any available ring carbon atom with $SF_5$. The napthalenyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The napthalenyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The napthalenyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. The napthalenyl can be attached through any of its carbon atoms to the compound of Formula (I). The napthalenyl substituent can be attached to any ring carbon atom of the napthalenyl ring, preferably ortho to the napthalenyl moiety's point of attachment to the compound of Formula (I). Preferred substituents wherein A is napthalenyl include $C_{1-6}$alkyl, with $C_1$alkyl being most preferred. Other preferred substituents include halogen, in particular F and Cl.

In some aspects, A is pyrimidinyl. The pyrimidinyl can be attached to any of the compounds of Formula (I) (or its subgenera) through any ring carbon atom through any ring carbon atom. Preferably, the pyrimidinyl is substituted with one or two substituents, preferably one substituent. The pyrimidinyl can be substituted at any available ring carbon atom with $C_{1-6}$ alkyl, for example, $C_{1-5}$alkyl, $C_{1-4}$alkyl, $C_{1-3}$alkyl, $C_{1-2}$alkyl, or $C_1$alkyl. The pyrimidinyl can be substituted at any available ring carbon atom with halogen, for example F or Cl. The pyrimidinyl can be substituted at any available ring carbon atom with $SF_5$. The pyrimidinyl can be substituted at any available ring carbon atom with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The pyrimidinyl can be substituted at any available ring carbon atom with C(O)—$C_{1-6}$alkyl, for example, C(O)—$C_{1-5}$alkyl, C(O)—$C_{1-4}$ alkyl, C(O)—$C_{1-3}$alkyl, C(O)—$C_{1-2}$alkyl, or C(O)—$C_1$alkyl. The pyrimidinyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyrimidinyl include $C_{1-6}$alkyl, with $C_1$alkyl being most preferred. Other preferred substituents include halogen, in particular F and Cl.

In some aspects, A is pyrazinyl. The pyrazinyl can be attached to any of the compounds of Formula (I) (or its subgenera) through any ring carbon atom. Preferably, the pyrazinyl is substituted with one or two substituents, preferably one substituent. The pyrazinyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The pyrazinyl can be substituted at any available ring carbon atom with halogen, for example F or Cl. The pyrazinyl can be substituted at any available ring carbon atom with $SF_5$. The pyrazinyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyrazinyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyrazinyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyrazinyl include $C_{1-6}$alkyl, with $C_1$alkyl being most preferred. Other preferred substituents include halogen, in particular F and Cl.

In some aspects, A is pyridazinyl. The pyridazinyl can be attached to any of the compounds of Formula (I) (or its subgenera) through any ring carbon atom. Preferably, the pyridazinyl is substituted with one or two substituents, preferably one substituent. The pyridazinyl can be substituted at any available ring carbon atom with $C_{1-6}$ alkyl, for example, —$C_{1-5}$alkyl, $C_{1-3}$alkyl, $C_{1-2}$alkyl, or $C_1$alkyl. The pyridazinyl can be substituted at any available ring carbon atom with halogen, for example F or Cl. The pyridazinyl can be substituted at any available ring carbon atom with $SF_5$. The pyridazinyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyridazinyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyridazinyl can be substituted at any available ring carbon atom with $C_{1-6}$haloalkyl, for example, $C_{1-5}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyridazinyl include $C_{1-6}$alkyl, with $C_1$alkyl being most preferred. Other preferred substituents include halogen, in particular F and Cl.

In some aspects, A is benzo[d][1,3]dioxolyl. The benzo[d][1,3]dioxolyl can be attached to any of the compounds of Formula (I) (or its subgenera) through any ring carbon atom. The benzo[d][1,3]dioxolyl can be unsubstituted or can be substituted with one or two halogen, preferably F. Preferably, the benzo[d][1,3]dioxolyl is substituted with one or two other substituents. The benzo[d][1,3]dioxolyl can be substituted at any available ring carbon atom with $C_{1-6}$alkyl, for example, $C_{1-5}$alkyl, $C_{1-3}$alkyl, $C_{1-2}$alkyl, or $C_1$alkyl. The benzo[d][1,3]dioxolyl can be substituted at any available ring carbon atom with halogen, for example F or Cl. The benzo[d][1,3]dioxolyl can be substituted at any available ring carbon atom with —$SF_5$. The benzo[d][1,3]dioxolyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The benzo[d][1,3]dioxolyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The benzo[d][1,3]dioxolyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In some aspects, A is benzothiophenyl. The benzothiophenyl can be attached to any of the compounds of Formula (I) (or its subgenera) through any ring carbon atom. Preferably, the benzothiophenyl is substituted with one or two substituents, preferably one substituent. The benzothiophenyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The benzothiophenyl can be substituted at any available ring carbon atom with halogen, for example F or Cl. The benzothiophenyl can be substituted at any available ring carbon atom with $SF_5$. The benzothiophenyl can be substituted at any available ring carbon atom with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The benzothiophenyl can be substituted at any available ring carbon atom with C(O)—$C_{1-6}$alkyl, for example, C(O)—$C_{1-5}$alkyl, C(O)—$C_{1-4}$ alkyl, C(O)—$C_{1-3}$alkyl, C(O)—$C_{1-2}$alkyl, or C(O)—$C_1$alkyl. The benzothiophenyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In some aspects, A is pyrazolyl. The pyrazolyl can be attached to any of the compounds of Formula (I) (or its subgenera) through any ring carbon atom. Preferably, the pyrazolyl is substituted with one or two substituents, preferably one substituent. The pyrazolyl can be substituted at any available ring carbon atom with $C_{1-6}$alkyl, for example, $C_{1-5}$alkyl, $C_{1-4}$alkyl, $C_{1-3}$ alkyl, $C_{1-2}$alkyl, or $C_1$alkyl. The pyrazolyl can be substituted at any available ring carbon atom with halogen, for example F or Cl. The pyrazolyl can be substituted at any available ring carbon atom with $SF_5$. The pyrazolyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyrazolyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyrazolyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In preferred aspects, A is an unsubstituted or substituted phenyl, pyridyl, pyrimidyl, or pyrazinyl moiety, with pyridyl being particularly preferred. In those aspects wherein the phenyl, pyridyl, pyrimidyl, or pyrazinyl moiety is substituted, the preferred substituents include $C_{1-6}$alkyl (e.g., methyl) and halogen (e.g., F or Cl).

Additional preferred subgenera of Formula (I) are:

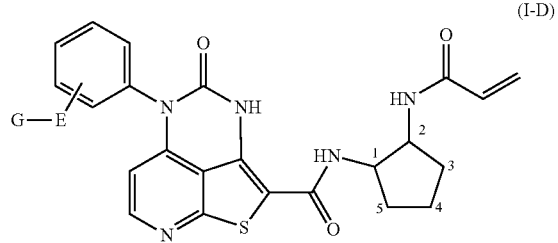

(I-D)

wherein the phenyl moiety can be unsubstituted or substituted with 1 or 2 substituents at any available carbon atom.

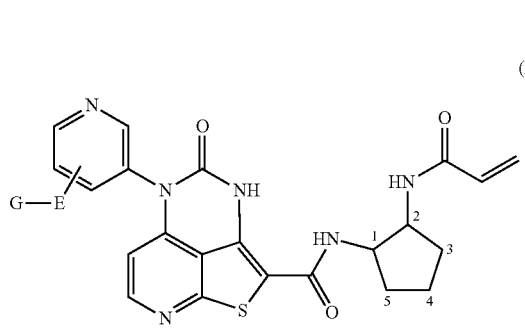
(I-E)

wherein the pyridyl moiety can be unsubstituted or substituted with 1 or 2 substituents at any available carbon atom.

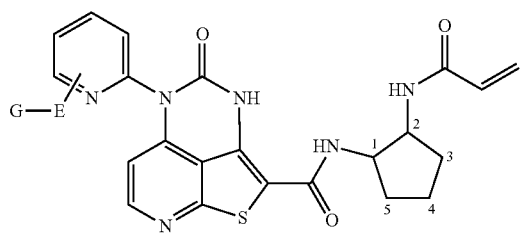
(I-F)

wherein the pyridyl moiety can be unsubstituted or substituted with 1 or 2 substituents at any available carbon atom.

According to the disclosure, E is O, a bond, C(O)—NH, CH$_2$, or CH$_2$—O. The E moiety can be attached through any available carbon atom on the A moiety. The E moiety can also be attached through any available carbon atom on the G moiety.

In some aspects, E is O, a bond, or CH$_2$. In preferred aspects, E is O. In other preferred aspects, E is a bond.

In some aspects of the disclosure, E is C(O)—NH, wherein the A-E-G moiety is A-C(O)—NH-G.

In other aspects of the disclosure, E is CH$_2$.

In yet other aspects of the disclosure, E is CH$_2$—O, wherein the A-E-G moiety is A-CH$_2$—O-G.

Additional preferred subgenera of Formula (I) are:

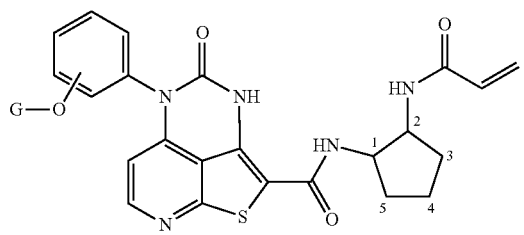
(I-G-1)

wherein the phenyl moiety can be unsubstituted or substituted with 1 or 2 substituents at any available carbon atom.

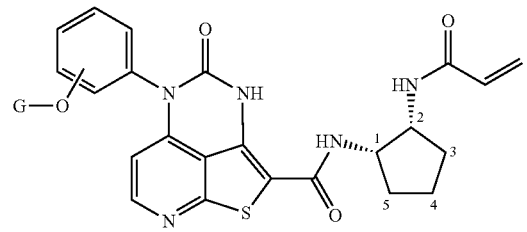
(I-G-2)

wherein the phenyl moiety can be unsubstituted or substituted with 1 or 2 substituents at any available carbon atom.

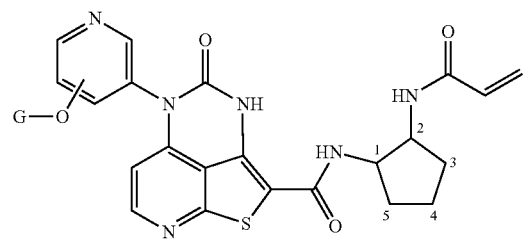
(I-H-1)

wherein the pyridyl moiety can be unsubstituted or substituted with 1 or 2 substituents at any available carbon atom.

(I-H-2)

wherein the pyridyl moiety can be unsubstituted or substituted with 1 or 2 substituents at any available carbon atom.

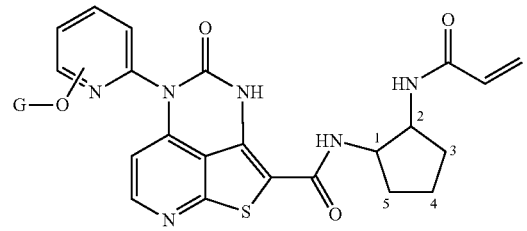
(I-J-1)

wherein the pyridyl moiety can be unsubstituted or substituted with 1 or 2 substituents at any available carbon atom.

(I-J-2)

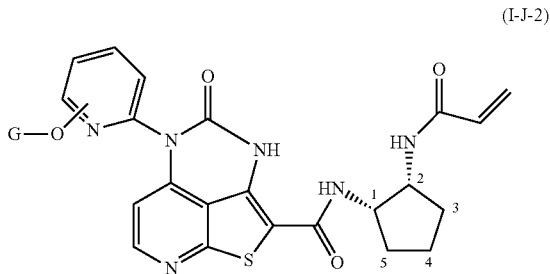

wherein the pyridyl moiety can be unsubstituted or substituted with 1 or 2 substituents at any available carbon atom.

Other preferred subgenera of Formula (I) are:

(I-K-1)

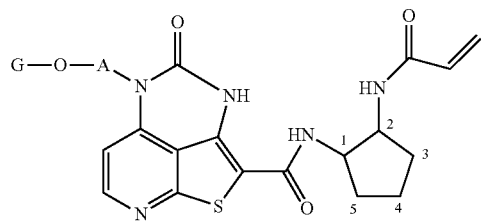

(I-K-2)

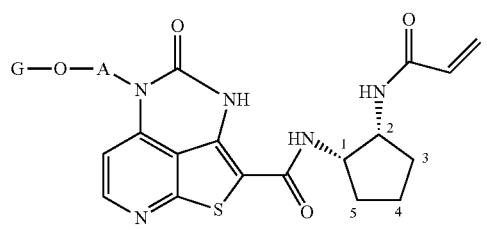

(I-L-1)

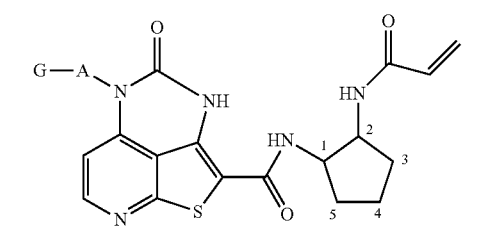

(I-L-2)

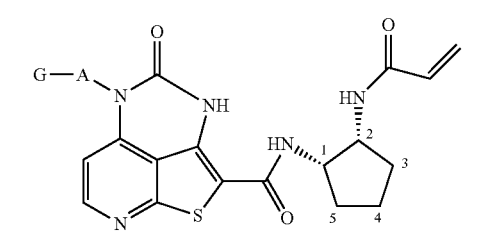

According to the disclosure, G is H; halogen; $C_{1-6}$ alkyl; $C_{1-6}$haloalkyl; NH($C_{1-6}$alkyl); $C_{3-6}$-cycloalkyl; phenyl; pyrimidinyl; pyridyl; pyridazinyl; pyridin-2(1H)-one; heterocycloalkyl that contains an oxygen heteroatom; and phenyl-$CH_2$—O-phenyl, wherein the —O-phenyl is substituted with CN; wherein the phenyl; pyridyl; pyridazinyl; and pyridin-2(1H)-one is optionally substituted with 1, 2, or 3 substituents each independently selected from the group consisting of: halogen, $C_{1-6}$alkyl, $C_{1-6}$haloalkyl, $OC_{1-6}$haloalkyl, and $OC_{1-6}$alkyl, Also according to the disclosure, G is H; $C_{3-6}$cycloalkyl; phenyl; thiophenyl; $C_{1-6}$alkyl; pyrimidinyl; pyridyl; pyridazinyl; benzofuranyl; $C_{1-6}$haloalkyl; heterocycloalkyl that contains an oxygen heteroatom; phenyl-$CH_2$—O-phenyl; $C_{1-6}$alk-O—$C_{1-6}$alkyl; $NR^6R^7$; $SO_2C_{1-6}$alkyl; or OH; wherein the phenyl; pyridyl; pyridazinyl; pyrimidinyl; benzofuranyl; or thiophenyl is optionally substituted with 1, 2, or 3 substituents independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl.

In some aspects, G is H.

In other aspects, G is $C_{3-6}$cycloalkyl, for example, cyclopropyl, cyclobutyl, cyclopentyl, or cyclohexyl.

In some aspects, G is $C_{1-6}$alkyl, for example, $C_{1-5}$alkyl, $C_1$-alkyl, $C_{1-3}$alkyl, $C_{1-2}$alkyl, or $C_1$alkyl.

In some aspects, G is $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In other aspects, G is a heterocycloalkyl that contains an oxygen heteroatom, for example, tetrahydropyranyl, tetrahydrofuranyl, or oxetanyl.

In preferred aspects, G is phenyl-$CH_2$—O-phenyl. In these aspects, the phenyl-$CH_2$—O-phenyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The one or both of the phenyl rings of the phenyl-$CH_2$—O-phenyl moiety can be substituted with halogen, for example F or Cl. The one or both of the phenyl rings of the -phenyl-$CH_2$—O-phenyl moiety can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The one or both of the phenyl rings of the phenyl-$CH_2$—O-phenyl moiety can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The one or both of the phenyl rings of the phenyl-$CH_2$—O-phenyl moiety can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The one or both of the phenyl rings of the phenyl-$CH_2$—O-phenyl moiety can be substituted with $C_{3-6}$cycloalkyl, for example, cyclopropyl, cyclobutyl, cyclopentyl, or cyclohexyl. The one or both of the phenyl rings of the phenyl-$CH_2$—O-phenyl moiety can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The one or both of the phenyl rings of the phenyl-$CH_2$—O-phenyl moiety can be substituted with CN. The one or both of the phenyl rings of the phenyl-$CH_2$—O-phenyl moiety can be substituted with OH. The one or both of the phenyl rings of the phenyl-$CH_2$—O-phenyl moiety can be substituted with $C_{1-6}$alk-O—$C_{1-6}$alkyl, for example, $C_{1-5}$alk-O—$C_{1-5}$alkyl, $C_{1-4}$-alk-O—$C_{1-4}$alkyl, $C_{1-5}$alk-O—$C_{1-3}$alkyl, $C_{1-2}$-alk-O—$C_{1-2}$alkyl, or $C_1$alk-O—$C_1$alkyl. The one or both of the phenyl rings of the phenyl-$CH_2$—O-phenyl moiety can be substituted with C(O)—$NR^6R^7$, wherein $R^6$ and $R^7$ are preferably each independently H; $C_{1-6}$ alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The one or both of the phenyl rings of the phenyl-$CH_2$—O-phenyl moiety can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-5}$alk-O—$C_{1-3}$alkyl, $C_{1-2}$-alk-O—$C_{1-2}$alkyl, or $C_1$alk-O—$C_1$alkyl.

In other aspects, G is $NR^6R^7$, wherein $R^6$ and $R^7$ are each independently H; $C_{1-6}$alkyl; $C_{3-6}$cycloalkyl; C(O)H, or CN. In these aspects, $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$ alkyl, $C_{1-2}$alkyl, or $C_1$alkyl.

In some aspects, G is $SO_2C_{1-6}$alkyl, for example, $SO_2C_{1-5}$alkyl, $SO_2C_{1-4}$alkyl, —$SO_2C_{1-3}$alkyl, $SO_2C_{1-2}$alkyl, or $SO_2C_1$alkyl.

In some aspects, G is OH.

In preferred aspects, G is phenyl. In these aspects, the phenyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The phenyl can be substituted with halogen, for example F or Cl. The phenyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The phenyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The phenyl can be substituted with $OC_{1-6}$haloalkyl, for example, $OC_{1-5}$haloalkyl, $OC_{1-4}$haloalkyl, $OC_{1-3}$ haloalkyl, $OC_{1-2}$haloalkyl, or $OC_1$haloalkyl. The phenyl can be substituted with $C_{3-6}$cycloalkyl, for example, cyclopropyl, cyclobutyl, cyclopentyl, or cyclohexyl. The phenyl can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The phenyl can be substituted with CN. The phenyl can be substituted with OH. The phenyl can be substituted with $C_{1-6}$alk-O—$C_{1-6}$alkyl, for example, $C_{1-5}$alk-O—$C_{1-5}$alkyl, $C_{1-4}$-alk-O—$C_{1-4}$alkyl, $C_{1-5}$alk-O—$C_{1-3}$alkyl, $C_{1-2}$-alk-O—$C_{1-2}$alkyl, or $C_1$alk-O—$C_1$alkyl. The phenyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-3}$ alkyl, $C_{1-2}$alkyl, or $C_1$alkyl. The phenyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is pyridyl. In these aspects, the pyridyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The pyridyl can be substituted with halogen, for example F or Cl. The pyridyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The pyridyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The pyridyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The pyridyl can be substituted with $C_{3-6}$cycloalkyl, for example, cyclopropyl, cyclobutyl, cyclopentyl, or cyclohexyl. The pyridyl can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyridyl can be substituted with CN. The pyridyl can be substituted with —OH. The pyridyl can be substituted with $C_{1-6}$alk-O—$C_{1-6}$alkyl, for example, $C_{1-5}$alk-O—$C_{1-5}$alkyl, $C_{1-4}$-alk-O—$C_{1-4}$alkyl, $C_{1-5}$alk-O—$C_{1-3}$alkyl, $C_{1-2}$alk-O—$C_{1-2}$alkyl, or $C_1$alk-O—$C_1$alkyl. The pyridyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The pyridyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is pyridazinyl. In these aspects, the pyridazinyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The pyridazinyl can be substituted with halogen, for example F or Cl. The pyridazinyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The pyridazinyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The pyridazinyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The pyridazinyl can be substituted with $C_{3-6}$cycloalkyl, for example, cyclopropyl, cyclobutyl, cyclopentyl, or cyclohexyl. The pyridazinyl can be substituted with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The pyridazinyl can be substituted with CN. The pyridazinyl can be substituted with OH. The pyridazinyl can be substituted with $C_{1-6}$alk-O—$C_{1-6}$alkyl, for example, $C_{1-5}$alk-O—$C_{1-5}$alkyl, $C_{1-3}$alk-O—$C_{1-3}$alkyl, $C_{1-2}$alk-O—$C_{1-2}$alkyl, or $C_1$alk-O—$C_1$alkyl. The pyridazinyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-3}$alkyl, $C_{1-2}$alkyl, or $C_1$alkyl. The pyridazinyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is pyrimidinyl. In these aspects, the pyrimidinyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The pyrimidinyl can be substituted with halogen, for example F or Cl. The pyrimidinyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The pyrimidinyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The pyrimidinyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The pyrimidinyl can be substituted with $C_{3-6}$cycloalkyl, for example, cyclopropyl, cyclobutyl, cyclopentyl, or cyclohexyl. The pyrimidinyl can be substituted with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The pyrimidinyl can be substituted with CN. The pyrimidinyl can be substituted with OH. The pyrimidinyl can be substituted with $C_{1-6}$alk-O—$C_{1-6}$alkyl, for example, $C_{1-5}$alk-O—$C_{1-5}$alkyl, $C_{1-3}$alk-O—$C_{1-3}$alkyl, $C_{1-2}$alk-O—$C_{1-2}$alkyl, or $C_1$alk-O—$C_1$alkyl. The pyrimidinyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-3}$alkyl, $C_{1-2}$alkyl, or $C_1$alkyl. The pyrimidinyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is benzofuranyl. In these aspects, the benzofuranyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The benzofuranyl can be substituted with halogen, for example F or Cl. The benzofuranyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The benzofuranyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The benzofuranyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The benzofuranyl can be substituted with $C_{3-6}$cycloalkyl, for example, cyclopropyl, cyclobutyl, cyclopentyl, or cyclohexyl. The benzofuranyl can be substituted with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The benzofuranyl can be substituted with CN. The benzofuranyl can be substituted with OH. The benzofuranyl can be substituted with $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The benzofuranyl can be substituted with C(O)—$NR^6R^7$, wherein $R^6$ and $R^7$ are preferably each independently H; $C_{1-6}$ alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-3}$alkyl, $C_{1-2}$alkyl, or $C_1$alkyl. The benzofuranyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is thiophenyl. In these aspects, the thiophenyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The thiophenyl can be substituted with halogen, for example F or Cl. The thiophenyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The thiophenyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The thiophenyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The thiophenyl can be substituted with $C_{3-6}$cycloalkyl, for example, cyclopropyl, cyclobutyl, cyclopentyl, or cyclohexyl. The thiophenyl can be substituted with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The thiophenyl can be substituted with CN. The thiophenyl can be substituted with OH. The thiophenyl can be substituted with $C_{1-6}$alk-O—$C_{1-6}$ alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$-alk-O—$C_{1-2}$alkyl, or $C_1$alk-O—$C_1$alkyl. The thiophenyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The thiophenyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In preferred aspects, G is unsubstituted or substituted pyridyl, pyridizinyl, or pyrazinyl. In those aspects wherein G is substituted pyridyl, pyridizinyl, or pyrazinyl, preferred substituents include $C_{1-6}$alkyl (e.g., methyl). In other preferred aspects, G is $C_{1-6}$alkyl (e.g., isopropyl).

In preferred aspects, G is unsubstituted or substituted pyridyl, pyridizinyl, or pyrazinyl and E is $CH_2$ or O. In those aspects wherein G is substituted pyridyl, pyridizinyl, or pyrazinyl and E is $CH_2$ or O, preferred substituents include $C_{1-6}$alkyl (e.g., methyl). In other preferred aspects, G is $C_{1-6}$alkyl (e.g., isopropyl) and E is $CH_2$ or O.

In some preferred aspects, A-E-G is:

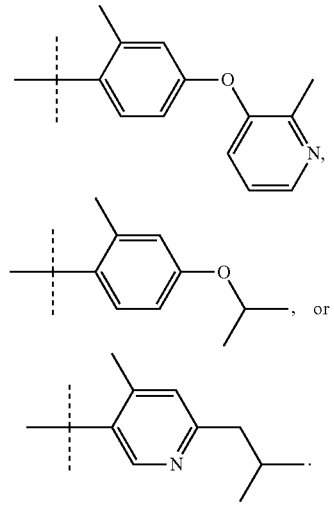

Preferred compounds of the Formula I include those wherein $R^1$ is H; $R^2$ is cyclopentyl substituted with 1 or 2 substituents wherein one of the substituents is $NR^8$—C(O)—$C(R^3)$=$CR^4(R^5)$, wherein $R^3$, $R^4$, and $R^5$ are each H; A is phenyl or pyridyl, wherein the phenyl or pyridyl is substituted with CH$_3$, E is O or a bond; and G is phenyl or C$_{1-6}$alkyl. In more preferred aspects, R$^2$ is substituted with 1 substituent that is NR$^8$—C(O)—C(R$^3$)=CR$^4$(R$^5$). In preferred aspects, A-E-G is
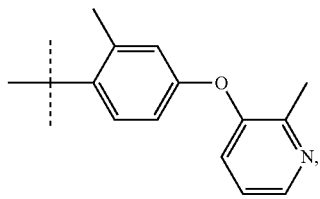
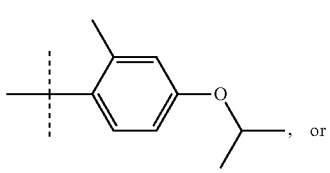, or
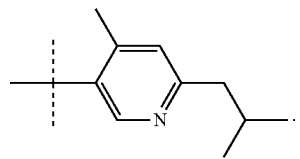.
Preferred subgenera of Formula (I) include:
(I-M-1)
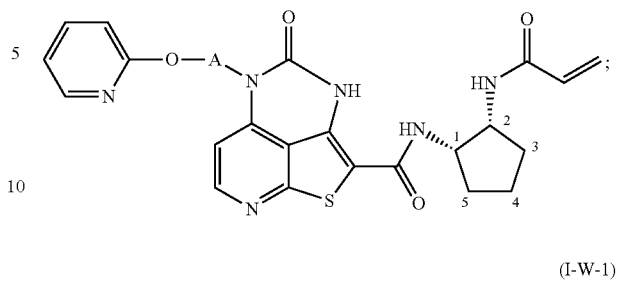
(I-M-2)
(I-V-1)
(I-V-2)
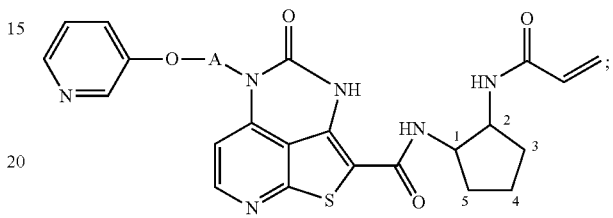
(I-W-1)
(I-W-2)
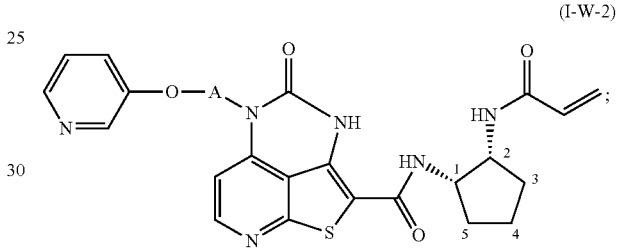
(I-Q-1)

(I-Q-2)
(I-P-1)
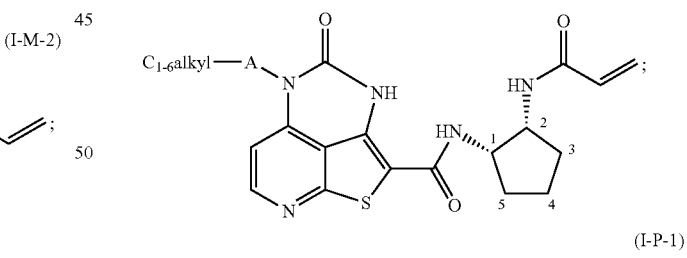
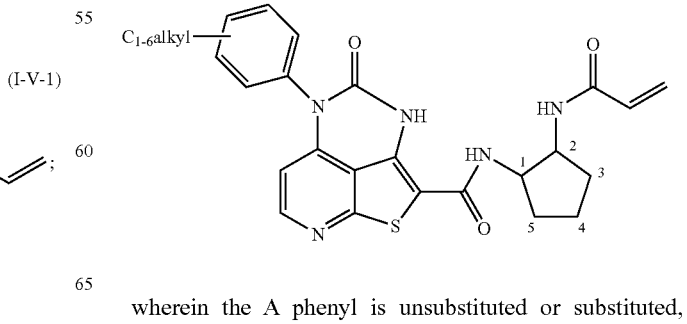
wherein the A phenyl is unsubstituted or substituted, preferably with C$_{1-6}$alkyl;

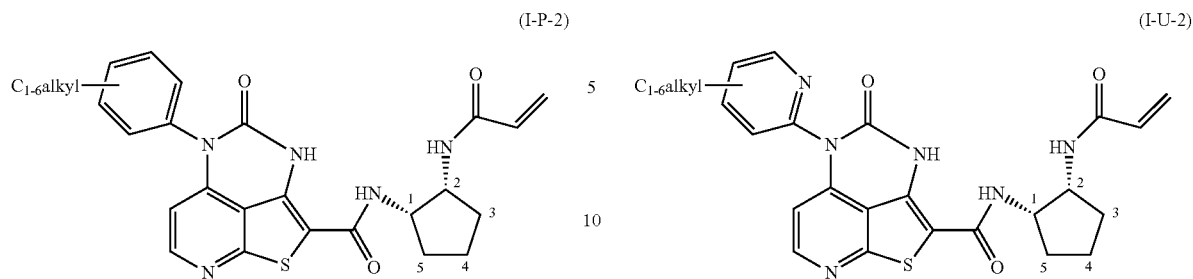

wherein the A phenyl is unsubstituted or substituted, preferably with $C_{1-6}$alkyl;

wherein the A pyridyl is unsubstituted or substituted, preferably with $C_{1-6}$alkyl;

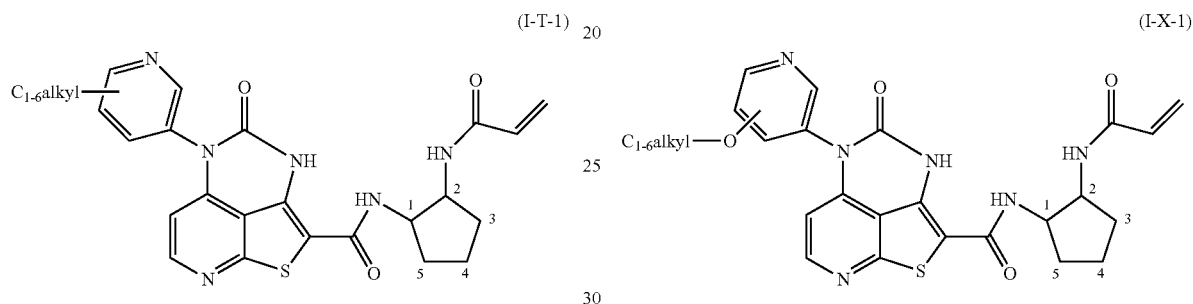

wherein the A pyridyl is unsubstituted or substituted, preferably with $C_{1-6}$alkyl;

wherein the A pyridyl is unsubstituted or substituted, preferably with $C_{1-6}$alkyl;

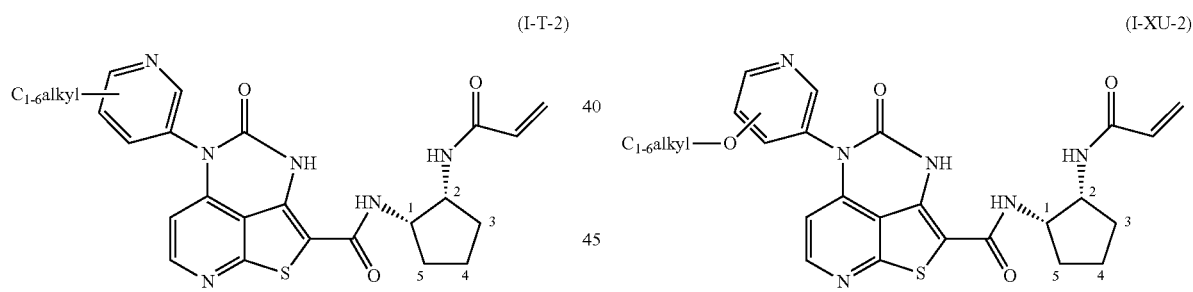

wherein the A pyridyl is unsubstituted or substituted, preferably with $C_{1-6}$alkyl;

wherein the A pyridyl is unsubstituted or substituted, preferably with $C_{1-6}$alkyl;


wherein the A pyridyl is unsubstituted or substituted, preferably with $C_{1-6}$alkyl;

wherein the A phenyl is unsubstituted or substituted, preferably with $C_{1-6}$alkyl; and

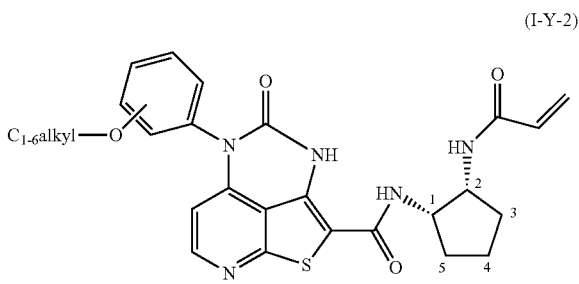
(I-Y-2)

wherein the A phenyl is unsubstituted or substituted, preferably with C$_{1-6}$alkyl.

An additional embodiment of the invention is a compound selected from the group consisting of:

N-((1S,4S)-4-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1R,2R)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-5-(2-methyl-4-phenoxyphenyl)-4-oxo-4,5-dihydro-3H-1-thia-3,5,8-triazaacenaphthylene-2-carboxamide;

N-((1R,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(2-methyl-4-phenoxyphenyl)-4-oxo-4,5-dihydro-3H-1-thia-3,5,8-triazaacenaphthylene-2-carboxamide;

N-((1R,4R)-4-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1R,4R)-4-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1S,4 S)-4-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1R,4R)-4-Methoxy cyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-((E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide;

N-((1S,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1R,2R)-2-(methylamino)cyclopentyl-4-oxo-4,5-dihydro-3H-1-thia-3,5,8-triazaacenaphthylene-2-carboxamide;

N-((1R,2R)-2-Aminocyclopentyl)-5-(2-methyl-4-phenoxyphenyl)-4-oxo-4,5-dihydro-3H-1-thia-3,5,8-triazaacenaphthylene-2-carboxamide;

N-((1S,4S)-4-Cyanamidocyclohexyl)-5-(2-methyl-4-phenoxyphenyl)-4-oxo-4,5-dihydro-3H-1-thia-3,5,8-triazaacenaphthylene-2-carboxamide;

N-((1R,3S)-3-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2R)-2-propionamidocyclopentyl)-4,5-dihydro-3H-1-thia-3,5,8-triazaacenaphthylene-2-carboxamide;

N-((1RS,2RS)-2-Hydroxy cyclohexyl)-5-(2-methyl-4-phenoxyphenyl)-4-oxo-4,5-dihydro-3H-1-thia-3,5,8-triazaacenaphthylene-2-carboxamide;

N-Cyclopentyl-5-(2-methyl-4-phenoxyphenyl)-4-oxo-4,5-dihydro-3H-1-thia-3,5,8-triazaacenaphthylene-2-carboxamide;

N-((1R,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1r,3 s,5R,7S)-3-Hydroxy adamantan-1-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(2-(methylamino)cyclohexyl)-4-oxo-4,5-dihydro-3H-1-thia-3,5,8-triazaacenaphthylene-2-carboxamide;

N-((1S,2 S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2S)-2-propionamidocyclopentyl)-4,5-dihydro-3H-1-thia-3,5,8-triazaacenaphthylene-2-carboxamide;

5-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide;

N-((1RS,2RS)-2-Hydroxy cyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Aminocyclohexyl)-5-(2-methyl-4-phenoxyphenyl)-4-oxo-4,5-dihydro-3H-1-thia-3,5,8-triazaacenaphthylene-2-carboxamide;

N-((1RS,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2R)-2-propionamidocyclohexyl)-4,5-dihydro-3H-1-thia-3,5,8-triazaacenaphthylene-2-carboxamide;

N-((1R,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2 S)-2-propionamidocyclopentyl)-4,5-dihydro-3H-1-thia-3,5,8-triazaacenaphthylene-2-carboxamide;

5-(2-Methyl-4-phenoxyphenyl)-N-((1S,2S)-2-(methylamino)cyclopentyl)-4-oxo-4,5-dihydro-3H-1-thia-3,5,8-triazaacenaphthylene-2-carboxamide;

N-((1R,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,2R)-2-(methylamino)cyclohexyl)-4-oxo-4,5-dihydro-3H-1-thia-3,5,8-triazaacenaphthylene-2-carboxamide;

N-((1RS,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2R)-2-propionamidocyclohexyl)-4,5-dihydro-3H-1-thia-3,5,8-triazaacenaphthylene-2-carboxamide;

N-((1RS,2R)-2-Aminocyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Formamidocyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide;

N-((1S,2S)-2-Acrylamidocyclopentyl)-5-(*R)-(2-methyl-4-phenoxyphenyl)-4-oxo-4,5-dihydro-3H-1-thia-3,5,8-triazaacenaphthylene-2-carboxamide;

N-((1S,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2R)-2-propionamidocyclopentyl)-4,5-dihydro-3H-1-thia-3,5,8-triazaacenaphthylene-2-carboxamide;

5-(2-Methyl-4-phenoxyphenyl)-4-oxo-N-((1S,2S)-2-propionamidocyclohexyl)-4,5-dihydro-3H-1-thia-3,5,8-triazaacenaphthylene-2-carboxamide;

N-((1R,2R)-2-Hydroxycyclopentyl)-5-(*R)-(2-methyl-4-phenoxyphenyl)-4-oxo-4,5-dihydro-3H-1-thia-3,5,8-triazaacenaphthylene-2-carboxamide;

N-((1S,2 S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(4-(methylamino)cyclohexyl)-4-oxo-4,5-dihydro-3H-1-thia-3,5,8-triazaacenaphthylene-2-carboxamide;

N-((1S,4S)-4-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;

N-((1S,4S)-4-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1R,2R)-2-Acetamidocyclopentyl)-5-(*5)-(2-methyl-4-phenoxyphenyl)-4-oxo-4,5-dihydro-3H-1-thia-3,5,8-triazaacenaphthylene-2-carboxamide;

N-((1S,3R)-3-acrylamidocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide;

N-((1S,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1S,3R)-3-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-(2-Amino acetamido)cyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-Aminocyclopentyl)-5-(2-methyl-4-phenoxyphenyl)-4-oxo-4,5-dihydro-3H-1-thia-3,5,8-triazaacenaphthylene-2-carboxamide;

N-((1S,4S)-4-((E)-4-(Dimethylamino)but-2-enamido)cyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,4S)-4-((E)-4-(methylamino)but-2-enamido)cyclohexyl)-4-oxo-4,5-dihydro-3H-1-thia-3,5,8-triazaacenaphthylene-2-carboxamide;

N-((1S,4S)-4-((E)-4-Aminobut-2-enamido)cyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S)-3-(methylamino)cyclopentyl)-4-oxo-4,5-dihydro-3H-1-thia-3,5,8-triazaacenaphthylene-2-carboxamide;

N-Cyclopentyl-5-(*S)-(2-methyl-4-phenoxyphenyl)-4-oxo-4,5-dihydro-3H-1-thia-3,5,8-triazaacenaphthylene-2-carboxamide;

N-Cyclopentyl-5-(*R)-(2-methyl-4-phenoxyphenyl)-4-oxo-4,5-dihydro-3H-1-thia-3,5,8-triazaacenaphthylene-2-carboxamide;

N-((1S,4S)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide;

N-((1R,4R)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,4R)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide;

N-((1S,3R)-3-Acetamido cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-((*E)-2-Cyano-3-cyclopropylacrylamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-((*E)-2-Cyano-3-cyclopropylacrylamido)cyclohexyl)-5-(*R)-(2-methyl-4-phenoxyphenyl)-4-oxo-4,5-dihydro-3H-1-thia-3,5,8-triazaacenaphthylene-2-carboxamide;

N-((1R,2R)-2-Aminocyclopentyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;

5-(*R)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;

N-((1S,4 S)-4-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-Acetamidocyclohexyl)-5-(*R)-(2-methyl-4-phenoxyphenyl)-4-oxo-4,5-dihydro-3H-1-thia-3,5,8-triazaacenaphthylene-2-carboxamide;

N-(rac-(1,3-cis)-3-Aminocyclopentyl)-4-oxo-5-(4-phenoxyphenyl)-4,5-dihydro-3H-1-thia-3,5,8-triazaacenaphthylene-2-carboxamide;

N-((1R,2S)-2-Aminocyclopentyl)-4-oxo-5-(4-phenoxyphenyl)-4,5-dihydro-3H-1-thia-3,5,8-triazaacenaphthylene-2-carboxamide;

N-((1S,2R)-2-Aminocyclopentyl)-4-oxo-5-(4-phenoxyphenyl)-4,5-dihydro-3H-1-thia-3,5,8-triazaacenaphthylene-2-carboxamide;

N-((1S,4S)-4-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-(Dimethylamino)cyclohexyl)-5-(*R)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-(2-(dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1R,2S)-2-acrylamidocyclopentyl)-4-oxo-5-(4-phenoxyphenyl)-4,5-dihydro-3H-1-thia-3,5,8-triazaacenaphthylene-2-carboxamide;

N-((1R,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

5-([1,1'-Biphenyl]-3-yl)-N-((1R,2 S)-2-acrylamidocyclohexyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(4-phenoxyphenyl)-4,5-dihydro-3H-1-thia-3,5,8-triazaacenaphthylene-2-carboxamide;

N-((1S,3R)-3-Acrylamidocyclopentyl)-5-(4-isporopoxy-2-methylphenyl)-4-oxo-4,5-dihydro-3H-1-thia-3,5,8-triazaacenaphthylene-2-carboxamide;

N-((1R,2R)-2-(2-(Dimethylamino)acetamido)cyclopentyl)-5-(*S)-(2-methyl-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1R,2R)-2-(2-(methylamino)acetamido)cyclopentyl)-4-oxo-4,5-dihydro-3H-1-thia-3,5,8-triazaacenaphthylene-2-carboxamide;

N-((1R,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclopentyl)-4-oxo-5-(4-phenoxyphenyl)-4,5-dihydro-3H-1-thia-3,5,8-triazaacenaphthylene-2-carboxamide;

N-((1R,2S)-2-Acrylamidocyclohexyl)-4-oxo-5-(4-phenoxyphenyl)-4,5-dihydro-3H-1-thia-3,5,8-triazaacenaphthylene-2-carboxamide;

N-((1S,4S)-4-Acrylamidocyclohexyl)-4-oxo-5-(4-phenoxyphenyl)-4,5-dihydro-3H-1-thia-3,5,8-triazaacenaphthylene-2-carboxamide;

N-((1R,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclopentyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-N-((1R,2S)-2-(2-(methylamino)acetamido)cyclopentyl)-4-oxo-4,5-dihydro-3H-1-thia-3,5,8-triazaacenaphthylene-2-carboxamide;

N-((1S,2 S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1RS,2R)-2-Acrylamidocyclohexyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-N-((1R,2S)-2-(2-(methylamino)acetamido)cyclohexyl)-4-oxo-4,5-dihydro-3H-1-thia-3,5,8-triazaacenaphthylene-2-carboxamide;

N-((1R,2S)-2-Aminocyclohexyl)-4-oxo-5-(4-phenoxyphenyl)-4,5-dihydro-3H-1-thia-3,5,8-triazaacenaphthylene-2-carboxamide;

N-((1RS,2R)-2-Acrylamidocyclopentyl)-4-oxo-5-(4-phenoxyphenyl)-4,5-dihydro-3H-1-thia-3,5,8-triazaacenaphthylene-2-carboxamide;

N-((1R,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-(2-Aminoacetamido)cyclohexyl)-5-(*5)-(2-methyl-4-phenoxyphenyl)-4-oxo-4,5-dihydro-3H-1-thia-3,5,8-triazaacenaphthylene-2-carboxamide;

N-((1S,2S)-2-(2-Amino acetamido)cyclopentyl)-5-(*5)-(2-methyl-4-phenoxyphenyl)-4-oxo-4,5-dihydro-3H-1-thia-3,5,8-triazaacenaphthylene-2-carboxamide;

N-((1R,2S)-2-(2-Amino acetamido)cyclopentyl)-5-(*5)-(2-methyl-4-phenoxyphenyl)-4-oxo-4,5-dihydro-3H-1-thia-3,5,8-triazaacenaphthylene-2-carboxamide;

N-((1R,2S)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

5-(*5)-(2-Methyl-4-phenoxyphenyl)-N-((1R,2S)-2-(2-(methylamino)acetamido)cyclopentyl)-4-oxo-4,5-dihydro-3H-1-thia-3,5,8-triazaacenaphthylene-2-carboxamide;

N-((1S,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2 S)-2-Aminocyclopentyl)-5-*S)-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclohexyl)-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-5-(3-chloro-4-phenoxyphenyl)-4-oxo-4,5-dihydro-3H-1-thia-3,5,8-triazaacenaphthylene-2-carboxamide;

N-((1R,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Hydroxycyclohexyl)-4-oxo-5-(4-phenoxyphenyl)-4,5-dihydro-3H-1-thia-3,5,8-triazaacenaphthylene-2-carboxamide;

N-((1R,2S)-2-Hydroxycyclopentyl)-4-oxo-5-(4-phenoxyphenyl)-4,5-dihydro-3H-1-thia-3,5,8-triazaacenaphthylene-2-carboxamide;

5-([1,1'-Biphenyl]-3-yl)-N-((1R,2S)-2-aminocyclohexyl)-4-oxo-4,5-dihydro-3H-1-thia-3,5,8-triazaacenaphthylene-2-carboxamide;

N-((1R,3S)-3-Hydroxycyclohexyl)-4-oxo-5-(4-phenoxyphenyl)-4,5-dihydro-3H-1-thia-3,5,8-triazaacenaphthylene-2-carboxamide;

N-((1S,3S)-3-Hydroxycyclohexyl)-4-oxo-5-(4-phenoxyphenyl)-4,5-dihydro-3H-1-thia-3,5,8-triazaacenaphthylene-2-carboxamide;

5-([1,1'-Biphenyl]-3-yl)-N-((1R,2R)-2-hydroxycyclopentyl)-4-oxo-4,5-dihydro-3H-1-thia-3,5,8-triazaacenaphthylene-2-carboxamide;

N-((1S,4S)-4-Aminocyclohexyl)-4-oxo-5-(4-phenoxyphenyl)-4,5-dihydro-3H-1-thia-3,5,8-triazaacenaphthylene-2-carboxamide;

N-(trans-(1R,4R)-4-Aminocyclohexyl)-4-oxo-5-(4-phenoxyphenyl)-4,5-dihydro-3H-1-thia-3,5,8-triazaacenaphthylene-2-carboxamide;

trans-N-((1RS,3RS)-3-Aminocyclopentyl)-4-oxo-5-(4-phenoxyphenyl)-4,5-dihydro-3H-1-thia-3,5,8-triazaacenaphthylene-2-carboxamide;

N-((1S,2S)-2-Aminocyclopentyl)-4-oxo-5-(4-phenoxyphenyl)-4,5-dihydro-3H-1-thia-3,5,8-triazaacenaphthylene-2-carboxamide;

N-((1R,2R)-2-Aminocyclohexyl)-4-oxo-5-(4-phenoxyphenyl)-4,5-dihydro-3H-1-thia-3,5,8-triazaacenaphthylene-2-carboxamide;

tert-Butyl ((1R,3S)-3-(4-oxo-5-(4-phenoxyphenyl)-4,5-dihydro-3H-1-thia-3,5,8-triazaacenaphthylene-2-carboxamido)cyclopentyl)carbamate;

tert-Butyl trans-((1R,4R)-4-(4-oxo-5-(4-phenoxyphenyl)-4,5-dihydro-3H-1-thia-3,5,8-triazaacenaphthylene-2-carboxamido)cyclohexyl)carbamate;

N-((1-Hydroxycyclohexyl)methyl)-4-oxo-5-(4-phenoxyphenyl)-4,5-dihydro-3H-1-thia-3,5,8-triazaacenaphthylene-2-carboxamide;

N-((1S,3R)-3-((E)-4-(Dimethylamino)but-2-enamido)cyclopentyl)-5-(4-isopropoxy-2-methylphenyl)-4-oxo-4,5-dihydro-3H-1-thia-3,5,8-triazaacenaphthylene-2-carboxamide;

N-((1RS,2R)-2-(2-Amino acetamido)cyclopentyl)-5-(*5)-(2-methyl-4-phenoxyphenyl)-4-oxo-4,5-dihydro-3H-1-thia-3,5,8-triazaacenaphthylene-2-carboxamide;

N-((1S,2R)-2-(2-(Dimethylamino)acetamido)cyclopentyl)-5-(*5)-(2-methyl-4-phenoxyphenyl)-4-oxo-4,5-dihydro-3H-1-thia-3,5,8-triazaacenaphthylene-2-carboxamide;

5-(*5)-(2-Methyl-4-phenoxyphenyl)-N-((1RS,2R)-2-(2-(methylamino)acetamido)cyclopentyl)-4-oxo-4,5-dihydro-3H-1-thia-3,5,8-triazaacenaphthylene-2-carboxamide;

N-((1S,3R)-3-Hydroxycyclohexyl)-4-oxo-5-(4-phenoxyphenyl)-4,5-dihydro-3H-1-thia-3,5,8-triazaacenaphthylene-2-carboxamide;

N-((1S,3R)-3-(2-(Dimethylamino)acetamido)cyclopentyl)-5-(4-isopropoxy-2-methylphenyl)-4-oxo-4,5-dihydro-3H-1-thia-3,5,8-triazaacenaphthylene-2-carboxamide;

4-Oxo-5-(2-phenylpyridin-4-yl)-N-((1S,2R)-2-propionamidocyclopentyl)-4,5-dihydro-3H-1-thia-3,5,8-triazaacenaphthylene-2-carboxamide;

N-((1R,2S)-2-Aminocyclohexyl)-5-(4-isopropoxy-2-methylphenyl)-4-oxo-4,5-dihydro-3H-1-thia-3,5,8-triazaacenaphthylene-2-carboxamide;

5-(4-Isopropoxy-2-methylphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1S,2R)-2-Acetamido cyclopentyl)-5-(*S)-(2-methyl-4-phenoxyphenyl)-4-oxo-4,5-dihydro-3H-1-thia-3,5,8-triazaacenaphthylene-2-carboxamide;

tert-Butyl ((1S,4S)-4-(4-oxo-5-(4-phenoxyphenyl)-4,5-dihydro-3H-1-thia-3,5,8-triazaacenaphthylene-2-carboxamido)cyclohexyl)carbamate;

N-((1S,3R)-3-Aminocyclopentyl)-4-oxo-5-(4-phenoxyphenyl)-4,5-dihydro-3H-1-thia-3,5,8-triazaacenaphthylene-2-carboxamide;

N-((1R,2S)-2-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(6-phenylpyrimidin-4-yl)-4,5-dihydro-3H-1-thia-3,5,8-triazaacenaphthylene-2-carboxamide;

N-((1R,2S)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2S)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclopentyl)-4-oxo-5-(5-phenoxypyridin-2-yl)-4,5-dihydro-3H-1-thia-3,5,8-triazaacenaphthylene-2-carboxamide;

N-((1S,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Aminocyclohexyl)-5-(2-methyl-4-phenoxyphenyl)-4-oxo-4,5-dihydro-3H-1-thia-3,5,8-triazaacenaphthylene-2-carboxamide;

N-((1R,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(6-cyclobutoxy-4-methylpyridin-3-yl)-4-oxo-4,5-dihydro-3H-1-thia-3,5,8-triazaacenaphthylene-2-carboxamide;

N-((1R,3R)-3-Acrylamidocyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(5-phenoxypyridin-2-yl)-4,5-dihydro-3H-1-thia-3,5,8-triazaacenaphthylene-2-carboxamide;

N-((1S,3R)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide;

N-((1R,3S)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclopentyl)-4-oxo-5-(4-phenylpyridin-2-yl)-4,5-dihydro-3H-1-thia-3,5,8-triazaacenaphthylene-2-carboxamide;

N-((1S,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1S,3R)-3-Acrylamidocyclopentyl)-5-(3-chloro-4-phenoxyphenyl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-phenylpyridin-3-yl)-4,5-dihydro-3H-1-thia-3,5,8-triazaacenaphthylene-2-carboxamide;

5-([1,1'-Biphenyl]-3-yl)-N-((1R,2S)-2-acrylamidocyclopentyl)-4-oxo-4,5-dihydro-3H-1-thia-3,5,8-triazaacenaphthylene-2-carboxamide;

N-((1R,2S)-2-Acrylamidocyclopentyl)-4-oxo-5-(3-(pyridin-2-yl)phenyl)-4,5-dihydro-3H-1-thia-3,5,8-triazaacenaphthylene-2-carboxamide;

N-((1R,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(2-phenylpyridin-4-yl)-4,5-dihydro-3H-1-thia-3,5,8-triazaacenaphthylene-2-carboxamide;

N-((1S,3R)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclopentyl)-5-(2-methyl-4-(pyridin-3-yloxy)phenyl)-4-oxo-4,5-dihydro-3H-1-thia-3,5,8-triazaacenaphthylene-2-carboxamide;

N-((1R,2R)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-phenoxypyrazin-2-yl)-4,5-dihydro-3H-1-thia-3,5,8-triazaacenaphthylene-2-carboxamide;

N-((1R,2S)-2-Acrylamidocyclopentyl)-4-oxo-5-(3-(pyridin-3-yl)phenyl)-4,5-dihydro-3H-1-thia-3,5,8-triazaacenaphthylene-2-carboxamide;

N-((1R,2S)-2-Acrylamidocyclopentyl)-4-oxo-5-(6-phenylpyridazin-4-yl)-4,5-dihydro-3H-1-thia-3,5,8-triazaacenaphthylene-2-carboxamide;

N-((1R,2S)-2-Acrylamidocyclohexyl)-5-(*S)-(6-cyclobutoxy-2-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-isopropoxyphenyl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(2-isopropylpyridin-4-yl)-4-oxo-4,5-dihydro-3H-1-thia-3,5,8-triazaacenaphthylene-2-carboxamide;

N-((1R,3S)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclohexyl)-5-(*S)-(6-isopropoxy-2-methylpyridin-3-yl)-4-oxo-4,5-dihydro-3H-1-thia-3,5,8-triazaacenaphthylene-2-carboxamide;

N-((1R,2S)-2-(3-Chloropropanamido)cyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide;

N-((1R,3R)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2R)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(5-phenoxypyridin-2-yl)-4,5-dihydro-3H-1-thia-3,5,8-triazaacenaphthylene-2-carboxamide;

N-((1R,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1RS,3RS)-3-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,2R)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-Acrylamidocyclohexyl)-5-(*S)-(6-cyclobutoxy-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(6-isopropoxy-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(6-(cyclopentyloxy)-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclohexyl)-5-(6-isobutoxy-4-methylpyridin-3-yl)-4-oxo-4,5-dihydro-3H-1-thia-3,5,8-triazaacenaphthylene-2-carboxamide;

N-((1S,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1R,3R)-3-(2-(methylamino)acetamido)cyclopentyl)-4-oxo-4,5-dihydro-3H-1-thia-3,5,8-triazaacenaphthylene-2-carboxamide;

N-((1S,3R)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2R)-2-Aminocyclopentyl)-5-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide;

N-((1R,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide;

N-((1R,3R)-3-Aminocyclopentyl)-5-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(*R)-(6-isopropoxy-2-methylpyridin-3-yl)-4-oxo-4,5-dihydro-3H-1-thia-3,5,8-triazaacenaphthylene-2-carboxamide;

N-((1R,2R)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(*R)-(6-cyclobutoxy-2-methylpyridin-3-yl)-4-oxo-4,5-dihydro-3H-1-thia-3,5,8-triazaacenaphthylene-2-carboxamide;

N-((1S,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3S)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,3S)-3-(2-(methylamino)acetamido)cyclopentyl)-4-oxo-4,5-dihydro-3H-1-thia-3,5,8-triazaacenaphthylene-2-carboxamide;

N-((1S,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

5-(3-Chloro-4-phenoxyphenyl)-N-((1S,3R)-3-((E)-4-(dimethylamino)but-2-enamido)cyclopentyl)-4-oxo-4,5-dihydro-3H-1-thia-3,5,8-triazaacenaphthylene-2-carboxamide;

5-([1,1'-Biphenyl]-3-yl)-N-((1R,2S)-2-aminocyclopentyl)-4-oxo-4,5-dihydro-3H-1-thia-3,5,8-triazaacenaphthylene-2-carboxamide;

5-(*S)-(2-Methyl-4-phenoxyphenyl)-N-((1R,3S)-3-(2-(methylamino)acetamido)cyclohexyl)-4-oxo-4,5-dihydro-3H-1-thia-3,5,8-triazaacenaphthylene-2-carboxamide;

N-((1R,3S)-3-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;
N-((1R,2R)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2R)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;
N-((1R,2S)-2-Aminocyclohexyl)-4-oxo-5-(6-phenoxypyridin-3-yl)-4,5-dihydro-3H-1-thia-3,5,8-triazaacenaphthylene-2-carboxamide;
N-((1S,2R)-2-Acetamidocyclopentyl)-4-oxo-5-(2-phenylpyridin-4-yl)-4,5-dihydro-3H-1-thia-3,5,8-triazaacenaphthylene-2-carboxamide;
N-((1S,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide;
N-((1R,2S)-2-Aminocyclohexyl)-4-oxo-5-(2-phenylpyridin-4-yl)-4,5-dihydro-3H-1-thia-3,5,8-triazaacenaphthylene-2-carboxamide;
N-((1R,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;
N-((1R,2S)-2-Aminocyclopentyl)-5-(*R)-(4-isopropoxy-2-methylphenyl)-4-oxo-4,5-dihydro-3H-1-thia-3,5,8-triazaacenaphthylene-2-carboxamide;
N-((1R,2 S)-2-Aminocyclopentyl)-4-oxo-5-(2-phenylpyridin-4-yl)-4,5-dihydro-3H-1-thia-3,5,8-triazaacenaphthylene-2-carboxamide;
N-((1R,2R)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;
N-((1R,2S)-2-Aminocyclopentyl)-4-oxo-5-(6-phenoxypyridin-3-yl)-4,5-dihydro-3H-1-thia-3,5,8-triazaacenaphthylene-2-carboxamide;
N-((1R,2 S)-2-Acrylamidocyclohexyl)-5-(*R)-(6-cyclobutoxy-4-methylpyridin-3-yl)-4-oxo-4,5-dihydro-3H-1-thia-3,5,8-triazaacenaphthylene-2-carboxamide;
N-((1R,2 S)-2-Aminocyclopentyl)-4-oxo-5-(4-phenylpyridin-2-yl)-4,5-dihydro-3H-1-thia-3,5,8-triazaacenaphthylene-2-carboxamide;
N-((1R,2R)-2-Hydroxycyclopentyl)-4-oxo-5-(2-phenylpyridin-4-yl)-4,5-dihydro-3H-1-thia-3,5,8-triazaacenaphthylene-2-carboxamide;
N-((1R,2R)-2-Aminocyclopentyl)-4-oxo-5-(6-phenoxypyridin-3-yl)-4,5-dihydro-3H-1-thia-3,5,8-triazaacenaphthylene-2-carboxamide;
N-((1R,2S)-2-Aminocyclopentyl)-5-(2-isopropylpyridin-4-yl)-4-oxo-4,5-dihydro-3H-1-thia-3,5,8-triazaacenaphthylene-2-carboxamide;
N-((1R,2S)-2-Aminocyclopentyl)-5-(4-isopropoxyphenyl)-4-oxo-4,5-dihydro-3H-1-thia-3,5,8-triazaacenaphthylene-2-carboxamide;
N-((1S,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;
N-((1R,2R)-2-Acrylamidocyclohexyl)-5-(*S)-(4-isopropoxy-2-methylphenyl)-4-oxo-4,5-dihydro-3H-1-thia-3,5,8-triazaacenaphthylene-2-carboxamide;
N-((1S, S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;
N-((1R,3S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;
N-((1R,3S)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;
N-((1R,2R)-2-Aminocyclohexyl)-4-oxo-5-(6-phenoxypyridin-3-yl)-4,5-dihydro-3H-1-thia-3,5,8-triazaacenaphthylene-2-carboxamide;
N-((1R,2S)-2-Aminocyclopentyl)-4-oxo-5-(6-phenylpyridazin-4-yl)-4,5-dihydro-3H-1-thia-3,5,8-triazaacenaphthylene-2-carboxamide;
N-((1S,3S)-3-Acrylamidocyclohexyl)-4-oxo-5-(2-phenylpyridin-4-yl)-4,5-dihydro-3H-1-thia-3,5,8-triazaacenaphthylene-2-carboxamide;
N-((1R,2S)-2-Acetamidocyclopentyl)-4-oxo-5-(2-phenylpyridin-4-yl)-4,5-dihydro-3H-1-thia-3,5,8-triazaacenaphthylene-2-carboxamide;
N-((1R,2S)-2-Aminocyclopentyl)-4-oxo-5-(6-phenylpyrimidin-4-yl)-4,5-dihydro-3H-1-thia-3,5,8-triazaacenaphthylene-2-carboxamide;
N-((1S,3S)-3-Acrylamidocyclopentyl)-4-oxo-5-(2-phenylpyridin-4-yl)-4,5-dihydro-3H-1-thia-3,5,8-triazaacenaphthylene-2-carboxamide;
N-((1R,3S)-3-Acrylamidocyclohexyl)-4-oxo-5-(2-phenylpyridin-4-yl)-4,5-dihydro-3H-1-thia-3,5,8-triazaacenaphthylene-2-carboxamide;
N-((1R,2S)-2-Aminocyclopentyl)-4-oxo-5-(5-phenylpyridin-3-yl)-4,5-dihydro-3H-1-thia-3,5,8-triazaacenaphthylene-2-carboxamide;
N-((1R,2 S)-2-Aminocyclopentyl)-4-oxo-5-(3-(pyridin-2-yl)phenyl)-4,5-dihydro-3H-1-thia-3,5,8-triazaacenaphthylene-2-carboxamide;
N-((1S,2R)-2-(2-(Methylamino)acetamido)cyclopentyl)-4-oxo-5-(2-phenylpyridin-4-yl)-4,5-dihydro-3H-1-thia-3,5,8-triazaacenaphthylene-2-carboxamide;
N-((1R,2S)-2-Aminocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;
N-((1R,2S)-2-Aminocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide;
racemic cisN-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide;
racemic transN-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide;
N-((1R,2S)-2-Acrylamidocyclohexyl)-4-oxo-5-(5-phenoxypyridin-2-yl)-4,5-dihydro-3H-1-thia-3,5,8-triazaacenaphthylene-2-carboxamide;
N-((1RS,2RS)-2-Acrylamidocyclopentyl)-5-(2-methyl-6-phenoxy pyridin-3-yl)-4-oxo-4,5-dihydro-3H-1-thia-3,5,8-triazaacenaphthylene-2-carboxamide;
N-((1RS,3RS)-3-Aminocyclopentyl)-5-(4-methyl-6-phenoxypyridin-3-yl)-4-oxo-4,5-dihydro-3H-1-thia-3,5,8-triazaacenaphthylene-2-carboxamide;
N-((1RS,3RS)-3-Acrylamidocyclopentyl)-4-oxo-5-(6-phenoxypyridin-3-yl)-4,5-dihydro-3H-1-thia-3,5,8-triazaacenaphthylene-2-carboxamide;
N-((1R,2S)-2-Acrylamidocyclohexyl)-4-oxo-5-(5-phenoxypyrazin-2-yl)-4,5-dihydro-3H-1-thia-3,5,8-triazaacenaphthylene-2-carboxamide;
N-((1R,2S)-2-acrylamidocyclopentyl)-4-oxo-5-(5-phenoxypyrimidin-2-yl)-4,5-dihydro-3H-1-thia-3,5,8-triazaacenaphthylene-2-carboxamide;
N-((1R,2S)-2-Acrylamidocyclohexyl)-4-oxo-5-(5-phenoxypyrimidin-2-yl)-4,5-dihydro-3H-1-thia-3,5,8-triazaacenaphthylene-2-carboxamide;

N-((1R,2S)-2-Acrylamidocyclopentyl)-5-(S)-(6-isobutyl-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(*S)-(4-(pyridin-3-yloxy)phenyl)-4,5-dihydro-3H-1-thia-3,5,8-triazaacenaphthylene-2-carboxamide;

N-((1R,2R)-2-Acrylamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(2-phenoxypyrimidin-5-yl)-4,5-dihydro-3H-1-thia-3,5,8-triazaacenaphthylene-2-carboxamide;

N-((1R,2S)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide;

N-((1*S,3*S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Acrylamidocyclopentyl)-4-oxo-5-(5-phenoxypyrimidin-2-yl)-4,5-dihydro-3H-1-thia-3,5,8-triazaacenaphthylene-2-carboxamide;

N-((1*S,3*S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(2-phenoxypyrimidin-5-yl)-4,5-dihydro-3H-1-thia-3,5,8-triazaacenaphthylene-2-carboxamide;

N-((1R,2R)-2-Acrylamidocyclopentyl)-4-oxo-5-(5-phenoxypyrazin-2-yl)-4,5-dihydro-3H-1-thia-3,5,8-triazaacenaphthylene-2-carboxamide;

N-((1R,2S)-2-Acrylamidocyclohexyl)-5-(*S)-(6-isobutoxy-4-methylpyridin-3-yl)-4-oxo-4,5-dihydro-3H-1-thia-3,5,8-triazaacenaphthylene-2-carboxamide;

N-((1S,3R)-3-Acrylamidocyclopentyl)-4-oxo-5-(5-phenoxypyridin-2-yl)-4,5-dihydro-3H-1-thia-3,5,8-triazaacenaphthylene-2-carboxamide;

N-((1R,2R)-2-Acrylamidocyclopentyl)-4-oxo-5-(2-phenoxypyrimidin-5-yl)-4,5-dihydro-3H-1-thia-3,5,8-triazaacenaphthylene-2-carboxamide;

N-((1*S,3*S)-3-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,2R)-2-Acrylamidocyclopentyl)-5-(*S)-(4-isopropoxy-2-methylphenyl)-4-oxo-4,5-dihydro-3H-1-thia-3,5,8-triazaacenaphthylene-2-carboxamide;

5-([2,3'-Bipyridin]-4-yl)-N-((1R,2S)-2-acrylamidocyclopentyl)-4-oxo-4,5-dihydro-3H-1-thia-3,5,8-triazaacenaphthylene-2-carboxamide;

N-((1*R,2*S)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3R)-3-Acrylamidocyclopentyl)-4-oxo-5-(2-phenoxypyrimidin-5-yl)-4,5-dihydro-3H-1-thia-3,5,8-triazaacenaphthylene-2-carboxamide;

N-((1R,2S)-2-Acrylamidocyclopentyl)-4-oxo-5-(5-phenylpyridazin-3-yl)-4,5-dihydro-3H-1-thia-3,5,8-triazaacenaphthylene-2-carboxamide;

N-((1*S,3*S)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2R)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3S)-3-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,2R)-2-Acrylamidocyclopentyl)-4-oxo-5-(3-(pyridin-3-yl)phenyl)-4,5-dihydro-3H-1-thia-3,5,8-triazaacenaphthylene-2-carboxamide;

5-([2,2'-Bipyridin]-4-yl)-N-((1R,2S)-2-acrylamidocyclopentyl)-4-oxo-4,5-dihydro-3H-1-thia-3,5,8-triazaacenaphthylene-2-carboxamide;

5-([2,3'-Bipyridin]-4-yl)-N-((1R,2R)-2-acrylamidocyclopentyl)-4-oxo-4,5-dihydro-3H-1-thia-3,5,8-triazaacenaphthylene-2-carboxamide;

N-((1R,2R)-2-Acrylamidocyclopentyl)-4-oxo-5-(3-(pyridin-2-yl)phenyl)-4,5-dihydro-3H-1-thia-3,5,8-triazaacenaphthylene-2-carboxamide;

N-((1*R,3*S)-3-Acrylamidocyclopentyl)-4-oxo-5-(5-phenoxypyridin-2-yl)-4,5-dihydro-3H-1-thia-3,5,8-triazaacenaphthylene-2-carboxamide;

N-((1*R,3*R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-5-(6-(isopropylamino)-4-methylpyridin-3-yl)-4-oxo-4,5-dihydro-3H-1-thia-3,5,8-triazaacenaphthylene-2-carboxamide;

N-((1*R,3*R)-3-Acrylamidocyclohexyl)-4-oxo-5-(6-phenoxypyridin-3-yl)-4,5-dihydro-3H-1-thia-3,5,8-triazaacenaphthylene-2-carboxamide;

N-((1*R,3*R)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1*R,3*R)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Aminocyclohexyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2R)-2-Aminocyclopentyl)-5-(2-isopropylpyridin-4-yl)-4-oxo-4,5-dihydro-3H-1-thia-3,5,8-triazaacenaphthylene-2-carboxamide;

N-((1R,2R)-2-Acrylamidocyclopentyl)-5-(2-isopropylpyridin-4-yl)-4-oxo-4,5-dihydro-3H-1-thia-3,5,8-triazaacenaphthylene-2-carboxamide;

N-((1R,2R)-2-Acrylamidocyclohexyl)-4-oxo-5-(2-phenoxypyrimidin-5-yl)-4,5-dihydro-3H-1-thia-3,5,8-triazaacenaphthylene-2-carboxamide;

N-((1R,2R)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2S)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*R)-(6-(cyclopentyloxy)-4-methylpyridin-3-yl)-4-oxo-4,5-dihydro-3H-1-thia-3,5,8-triazaacenaphthylene-2-carboxamide;

5-([2,2'-Bipyridin]-4-yl)-N-((1R,2R)-2-acrylamidocyclopentyl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1R,2S)-2-propionamidocyclopentyl)-4,5-dihydro-3H-1-thia-3,5,8-triazaacenaphthylene-2-carboxamide;

N-((1*R,3*R)-3-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,2S)-2-Acetamidocyclopentyl)-5-(*S)-(2-methyl-6-phenoxy pyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1R,2S)-2-propionamidocyclopentyl)-4,5-dihydro-3H-1-thia-3,5,8-triazaacenaphthylene-2-carboxamide;

N-((1R,2S)-2-Acrylamidocyclopentyl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2S)-2-Acrylamidocyclohexyl)-5-(*R)-(6-isopropoxy-4-methylpyridin-3-yl)-4-oxo-4,5-dihydro-3H-1-thia-3,5,8-triazaacenaphthylene-2-carboxamide;

N-((1R,2S)-2-Aminocyclopentyl)-4-oxo-5-(5-phenylpyridazin-3-yl)-4,5-dihydro-3H-1-thia-3,5,8-triazaacenaphthylene-2-carboxamide;

N-((1R,2R)-2-Aminocyclohexyl)-5-(*S)-(2-methyl-6-phenoxy pyridin-3-yl)-4-oxo-4,5-dihydro-3H-1-thia-3,5,8-triazaacenaphthylene-2-carboxamide;

N-((1S,3R)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclohexyl)-5-(*R)-(6-isobutoxy-4-methylpyridin-3-yl)-4-oxo-4,5-dihydro-3H-1-thia-3,5,8-triazaacenaphthylene-2-carboxamide;

5-(*S)-(2-Methyl-6-phenoxy pyridin-3-yl)-4-oxo-N-((1R,2R)-2-propionamidocyclopentyl)-4,5-dihydro-3H-1-thia-3,5,8-triazaacenaphthylene-2-carboxamide;

N-((1R,2S)-2-Aminocyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,3S)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,3S)-3-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2R)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,3S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,3S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1R,3S)-3-propionamidocyclopentyl)-4,5-dihydro-3H-1-thia-3,5,8-triazaacenaphthylene-2-carboxamide;

N-((1R,2R)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,3S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1R,2R)-2-propionamidocyclohexyl)-4,5-dihydro-3H-1-thia-3,5,8-triazaacenaphthylene-2-carboxamide;

N-((1R,3S)-3-Acrylamidocyclopentyl)-5-(6-isobutoxy-4-methylpyridin-3-yl)-4-oxo-4,5-dihydro-3H-1-thia-3,5,8-triazaacenaphthylene-2-carboxamide;

N-((1R,3S)-3-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(4-((6-methylpyridin-2-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(4-((6-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-((2-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(6-isobutoxy-4-methylpyridin-3-yl)-4-oxo-4,5-dihydro-3H-1-thia-3,5,8-triazaacenaphthylene-2-carboxamide;

N-((1R,2S)-2-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2S)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-cyclobutylpyridin-4-yl)-4-oxo-4,5-dihydro-3H-1-thia-3,5,8-triazaacenaphthylene-2-carboxamide;

N-((1R,2S)-2-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Acrylamidocyclopentyl)-5-(2-cyclobutylpyridin-4-yl)-4-oxo-4,5-dihydro-3H-1-thia-3,5,8-triazaacenaphthylene-2-carboxamide;

5-(*S)-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide;

5-(*S)-(4-Methyl-6-phenoxypyridin-3-yl)-4-oxo-N-((1R,2S)-2-propionamidocyclohexyl)-4,5-dihydro-3H-1-thia-3,5,8-triazaacenaphthylene-2-carboxamide;

N-((1R,2R)-2-Acrylamidocyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1R,3S)-3-propionamidocyclohexyl)-4,5-dihydro-3H-1-thia-3,5,8-triazaacenaphthylene-2-carboxamide;

N-((1R,2S)-2-Acrylamidocyclopentyl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-4-oxo-5-(4-(pyridazin-3-yloxy)phenyl)-4,5-dihydro-3H-1-thia-3,5,8-triazaacenaphthylene-2-carboxamide;

5-(*S)-(4-Methyl-6-phenoxypyridin-3-yl)-4-oxo-N-((1R,3R)-3-propionamidocyclopentyl)-4,5-dihydro-3H-1-thia-3,5,8-triazaacenaphthylene-2-carboxamide;

N-((1S,4 S)-4-Acetamidocyclohexyl)-5-(*S)-(4-methyl-6-phenoxy pyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1S,3R)-3-propionamidocyclopentyl)-4,5-dihydro-3H-1-thia-3,5,8-triazaacenaphthylene-2-carboxamide;

N-((1S,3R)-3-Acetamidocyclopentyl)-5-(*S)-(4-methyl-6-phenoxy pyridin-3-yl)-4-oxo-4,5-dihydro-3H-1-thia-3,5,8-triazaacenaphthylene-2-carboxamide;

N-((1R,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Hydroxycyclopentyl)-4-oxo-5-(4-phenoxyphenyl)-4,5-dihydro-3H-1-thia-3,5,8-triazaacenaphthylene-2-carboxamide;

N-((1R,3S)-3-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1S,3S)-3-Acetamidocyclopentyl)-5-(*S)-(4-methyl-6-phenoxy pyridin-3-yl)-4-oxo-4,5-dihydro-3H-1-thia-3,5,8-triazaacenaphthylene-2-carboxamide;

N-((1R,2S)-2-Acetamidocyclopentyl)-4-oxo-5-(4-phenoxyphenyl)-4,5-dihydro-3H-1-thia-3,5,8-triazaacenaphthylene-2-carboxamide;

N-((1R,2S)-2-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide;

4-Oxo-5-(4-phenoxyphenyl)-N-((1R,2S)-2-propionamidocyclopentyl)-4,5-dihydro-3H-1-thia-3,5,8-triazaacenaphthylene-2-carboxamide;

5-(*S)-(4-Methyl-6-phenoxypyridin-3-yl)-4-oxo-N-((1S,3S)-3-propionamidocyclopentyl)-4,5-dihydro-3H-1-thia-3,5,8-triazaacenaphthylene-2-carboxamide;

N-((1S,3S)-3-Acetamidocyclohexyl)-5-(*S)-(4-methyl-6-phenoxy pyridin-3-yl)-4-oxo-4,5-dihydro-3H-1-thia-3,5,8-triazaacenaphthylene-2-carboxamide;

N-((1R,2S)-2-Acrylamidocyclohexyl)-5-(2-methyl-4-(pyridin-2-yloxy)phenyl)-4-oxo-4,5-dihydro-3H-1-thia-3,5,8-triazaacenaphthylene-2-carboxamide;

5-(*S)-(4-Methyl-6-phenoxy pyridin-3-yl)-4-oxo-N-((1S,3S)-3-propionamidocyclohexyl)-4,5-dihydro-3H-1-thia-3,5,8-triazaacenaphthylene-2-carboxamide;

N-((1R,3S)-3-Acetamidocyclopentyl)-5-(*S)-(4-methyl-6-phenoxy pyridin-3-yl)-4-oxo-4,5-dihydro-3H-1-thia-3,5,8-triazaacenaphthylene-2-carboxamide;

N-((1R,2R)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,3S)-3-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(2-methyl-4-(pyridazin-3-yloxy)phenyl)-4-oxo-4,5-dihydro-3H-1-thia-3,5,8-triazaacenaphthylene-2-carboxamide;

N-((1S,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(4-(pyridazin-3-yloxy)phenyl)-4,5-dihydro-3H-1-thia-3,5,8-triazaacenaphthylene-2-carboxamide;

5-(*S)-(2-Methyl-6-phenoxypyridin-3-yl)-4-oxo-N-((1S,3S)-3-propionamidocyclopentyl)-4,5-dihydro-3H-1-thia-3,5,8-triazaacenaphthylene-2-carboxamide;

N-((1S,3S)-3-Acetamidocyclopentyl)-5-(*S)-(2-methyl-6-phenoxy pyridin-3-yl)-4-oxo-4,5-dihydro-3H-1-thia-3,5,8-triazaacenaphthylene-2-carboxamide;

N-((1S,3R)-3-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide;

N-((1S,3R)-3-Acetamido cyclohexyl)-5-(*S)-(2-methyl-6-phenoxy pyridin-3-yl)-4-oxo-4,5-dihydro-3H-1-thia-3,5,8-triazaacenaphthylene-2-carboxamide;

N-((1S,3R)-3-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3S)-3-Aminocyclopentyl)-5-(*S)-(2-methyl-6-phenoxy pyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide;

(S)-5-(2-Methyl-4-phenoxyphenyl)-2-(3-(methylamino)pyrrolidine-1-carbonyl)-3H-1-thia-3,5,8-triazaacenaphthylen-4(5H)-one;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)propionamide;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acetamide;

(S)-2-(3-Aminopyrrolidine-1-carbonyl)-5-(2-methyl-4-phenoxyphenyl)-3H-1-thia-3,5,8-triazaacenaphthylen-4(5H)-one;

(S)-2-(3-(Dimethylamino)pyrrolidine-1-carbonyl)-5-(2-methyl-4-phenoxyphenyl)-3H-1-thia-3,5,8-triazaacenaphthylen-4(5H)-one;

N-((1R,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1R,3R)-3-propionamidocyclohexyl)-4,5-dihydro-3H-1-thia-3,5,8-triazaacenaphthylene-2-carboxamide;

N-((1R,2S)-2-Acrylamido cyclopentyl)-5-(*S)-(2-methyl-4-(pyridazin-3-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyridazin-3-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,3S)-3-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,2S)-2-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,3S)-3-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1S,3R)-3-Acrylamidocyclopentyl)-5-(*S)-(4-methyl-6-phenoxy pyridin-3-yl)-4-oxo-4,5-dihydro-3H-1-thia-3,5,8-triazaacenaphthylene-2-carboxamide;

N-((1S,3R)-3-Aminocyclopentyl)-5-(*S)-(4-methyl-6-phenoxy pyridin-3-yl)-4-oxo-4,5-dihydro-3H-1-thia-3,5,8-triazaacenaphthylene-2-carboxamide;

N-((1r,4r)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide;

(R)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide;

(S,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide;

(R,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide;

N-((1R,2S)-2-Acrylamidocyclopentyl)-4-oxo-5-(4-(pyridin-2-yloxy)phenyl)-4,5-dihydro-3H-1-thia-3,5,8-triazaacenaphthylene-2-carboxamide;

N-((1R,2S)-2-Acrylamidocyclopentyl)-5-(3-isopropylphenyl)-4-oxo-4,5-dihydro-3H-1-thia-3,5,8-triazaacenaphthylene-2-carboxamide;

N-((1R,2R)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Aminocyclohexyl-5-(*S)-(2-methyl-4-phenoxyphenyl)-4-oxo-4,5-dihydro-3H-1-thia-3,5,8-triazaacenaphthylene-2-carboxamide;

N-((1R,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-4-oxo-5-(4-(pyridin-2-yloxy)phenyl)-4,5-dihydro-3H-1-thia-3,5,8-triazaacenaphthylene-2-carboxamide;

5-(*S)-(2-Methyl-4-phenoxyphenyl)-N-((1S,2R)-2-(2-(methylamino)acetamido)cyclohexyl)-4-oxo-4,5-dihydro-3H-1-thia-3,5,8-triazaacenaphthylene-2-carboxamide;

N-((1S,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1RS,2R)-2-Acetamidocyclohexyl)-(*S)-(2-methyl-4-phenoxyphenyl)-4-oxo-4,5-dihydro-3H-1-thia-3,5,8-triazaacenaphthylene-2-carboxamide;

N-((1R,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1R,2R)-2-(2-(methylamino)acetamido)cyclohexyl)-4-oxo-4,5-dihydro-3H-1-thia-3,5,8-triazaacenaphthylene-2-carboxamide;

N-((1RS,2R)-2-(2-(Dimethylamino)acetamido)cyclohexyl-5-(*S)-(2-methyl-4-phenoxyphenyl)-4-oxo-4,5-dihydro-3H-1-thia-3,5,8-triazaacenaphthylene-2-carboxamide;

N-((1RS,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1RS,2R)-2-Acrylamidocyclohexyl)-(2-methyl-4-phenoxyphenyl)-4-oxo-4,5-dihydro-3H-1-thia-3,5,8-triazaacenaphthylene-2-carboxamide;

N-((1S,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(4-isopropoxy-2-methylphenyl)-4-oxo-4,5-dihydro-3H-1-thia-3,5,8-triazaacenaphthylene-2-carboxamide;

N-((1S,3R)-3-Acetamidocyclopentyl)-5-(4-isopropoxy-2-methylphenyl)-4-oxo-4,5-dihydro-3H-1-thia-3,5,8-triazaacenaphthylene-2-carboxamide;

N-((1R,2S)-2-Aminocyclopentyl)-5-(3-isopropylphenyl)-4-oxo-4,5-dihydro-3H-1-thia-3,5,8-triazaacenaphthylene-2-carboxamide;

N-((1R,2R)-2-Hydroxycyclopentyl)-5-(4-isopropoxy-2-methylphenyl)-4-oxo-4,5-dihydro-3H-1-thia-3,5,8-triazaacenaphthylene-2-carboxamide;

N-((1S,2R)-2-Aminocyclohexyl)-4-oxo-5-(4-phenoxyphenyl)-4,5-dihydro-3H-1-thia-3,5,8-triazaacenaphthylene-2-carboxamide;

N-((1S,2S)-2-Acrylamidocyclopentyl)-5-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclopentyl)-5-(2-methyl-4-phenoxyphenyl)-4-oxo-4,5-dihydro-3H-1-thia-3,5,8-triazaacenaphthylene-2-carboxamide;

5-(4-(3-((2-Cyanophenoxy)methyl)phenoxy)-2-methylphenyl)-N-cyclohexyl-4-oxo-4,5-dihydro-3H-1-thia-3,5,8-triazaacenaphthylene-2-carboxamide;

N-(5-(4-(3-((2-Cyanophenoxy)methyl)phenoxy)-2-methylphenyl)-4-oxo-4,5-dihydro-3H-1-thia-3,5,8-triazaacenaphthylen-2-yl)cyclopropanecarboxamide;

N-Cyclohexyl-5-(2-methyl-4-phenoxyphenyl)-4-oxo-4,5-dihydro-3H-1-thia-3,5,8-triazaacenaphthylene-2-carboxamide;

N-Cyclohexyl-4-oxo-5-(4-phenoxyphenyl)-4,5-dihydro-3H-1-thia-3,5,8-triazaacenaphthylene-2-carboxamide;

N1-((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide;

N-((1R,2S)-2-Acrylamidocyclopentyl)-5-(4-methyl-6-(pyrimidin-2-yloxy)pyridin-3-yl)-4-oxo-4,5-dihydro-3H-1-thia-3,5,8-triazaacenaphthylene-2-carboxamide;

N-((1R,2S)-2-((E)-2-Cyano-3-cyclopropylacrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(4-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyrimidin-2-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*R)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclohexyl)-5-(2-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-((2-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(5-(pyridazin-3-yloxy)pyridin-2-yl)-4,5-dihydro-3H-1-thia-3,5,8-triazaacenaphthylene-2-carboxamide;

N-((1R,2S)-2-Acrylamidocyclopentyl)-4-oxo-5-(5-(pyridazin-3-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(6'-methyl-2-oxo-2H[1,2'-bipyridin]-5'-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyridin-2-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(5-((6-methyl-pyridin-2-yl)oxy)pyridin-2-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-(pyridin-2-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(5-((6-methyl-pyridin-3-yl)oxy)pyridin-2-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyrimidin-5-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-((6-methylpyridin-2-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-(pyrimidin-2-yloxy)pyridin-2-yl)-4,5-dihydro-3H-1-thia-3,5,8-triazaacenaphthylene-2-carboxamide;

N-((1R,2S)-2-Acrylamidocyclopentyl)-4-oxo-5-(5-(pyrimidin-5-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(4-methyl-6-(pyrimidin-5-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-((6-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-(pyridin-2-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-((2-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-(pyridin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-(pyridin-3-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(2-methyl-6-(pyrimidin-5-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(5-((2-methyl-pyridin-3-yl)oxy)pyridin-2-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyridin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-((6-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((6-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-((6-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-((E)-2-Cyano-3-(3-methyloxetan-3-yl)acrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2S)-2-((E)-2-Cyano-4-ethoxy-4-methylpent-2-enamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N1-((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide; and N-((1R,2S)-2-acrylamidocyclopentyl)-4-oxo-5-(4-(pyrimidin-5-yloxy)phenyl)-4,5-dihydro-3H-1-thia-3,5,8-triazaacenaphthylene-2-carboxamide; and isotopic variants, and pharmaceutically acceptable salts thereof.

An additional embodiment of the invention is a compound selected from the group consisting of:

N-((1R,2S)-2-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,2R)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-phenoxypyrazin-2-yl)-4,5-dihydro-3H-1-thia-3,5,8-triazaacenaphthylene-2-carboxamide;

N-((1R,2S)-2-Acrylamidocyclohexyl)-4-oxo-5-(5-phenoxypyrimidin-2-yl)-4,5-dihydro-3H-1-thia-3,5,8-triazaacenaphthylene-2-carboxamide;

N-((1R,2S)-2-Acrylamidocyclopentyl)-5-(S)-(6-isobutyl-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide; and N-((1R,2S)-2-Acrylamidocyclopentyl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide; and isotopic variants, and pharmaceutically acceptable salts thereof.

An additional embodiment of the invention is a compound of Formula (I) having the Formula (IIa):

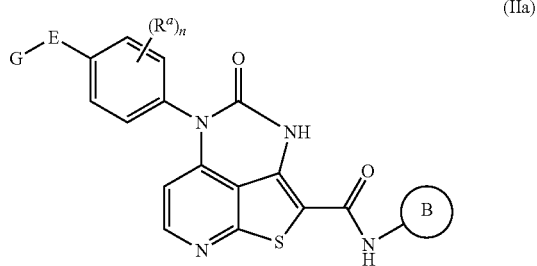

(IIa)

wherein $R^a$ is selected from the group consisting of: H, Cl and $CH_3$;

n is 0 or 1;

E is O;

G is selected from the group consisting of: $C_{1-6}$alkyl, phenyl, pyridyl, pyridyl substituted with $CH_3$, pyrimidinyl, pyridazinyl, tetrahydrofuranyl, tetrahydropyranyl, and

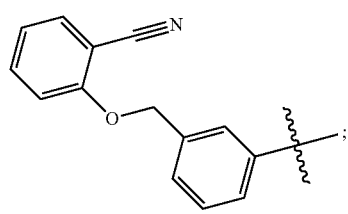 [SMILES: *c1cccc(COc2ccccc2C#N)c1]

Ring B is selected from the group consisting of:

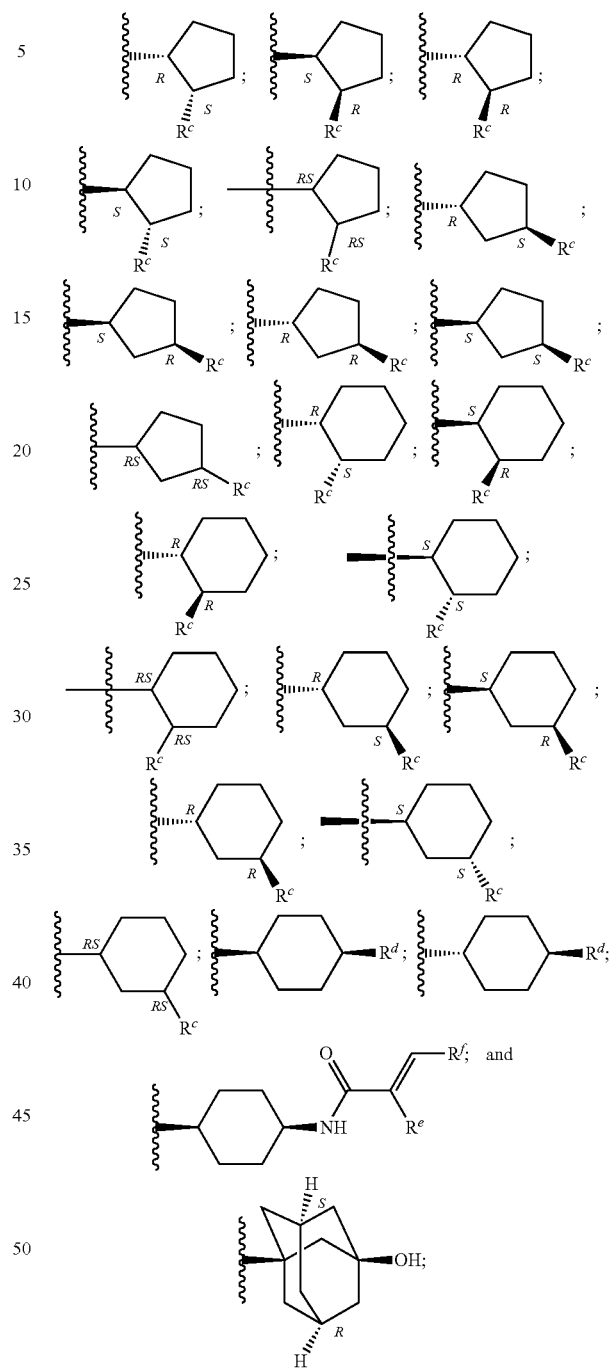

$R^c$ is selected from the group consisting of: OH, $OCH_3$, $NH_2$, $NH(CH_3)$, $N(CH_3)_2$, $NH(CO_2\text{-tert-butyl})$, $NH(C=O)C_{1-3}$alkyl, $NH(C=O)CH=CH_2$, $NH(C=O)CH_2NH_2$, $NH(C=O)CH_2NH(CH_3)$, $NH(C=O)CH_2N(CH_3)_2$, and $NH(C=O)CH=CHCH_2N(CH_3)_2$;

$R^d$ is selected from the group consisting of: OH, $OCH_3$, CN, $NH_2$, $NH(CH_3)$, $N(CH_3)_2$, $NH(CO_2\text{-tert-butyl})$, $NH(C=O)C_{1-3}$alkyl, and $NH(C=O)CH=CH_2$;

$R^e$ is H or CN; and $R^f$ is selected from the group consisting of: $CH_2NH_2$, $CH_2NH(CH_3)$, $CH_2N(CH_3)_2$, and cyclopropyl.

An additional embodiment of the invention is a compound of Formula (I) having the Formula (IIa) wherein: $R^a$ is H or $CH_3$; n is 1; E is O; G is selected from the group consisting of: $C_{1-3}$alkyl, phenyl, pyridyl, and pyridyl substituted with $CH_3$; Ring B is selected from the group consisting of:

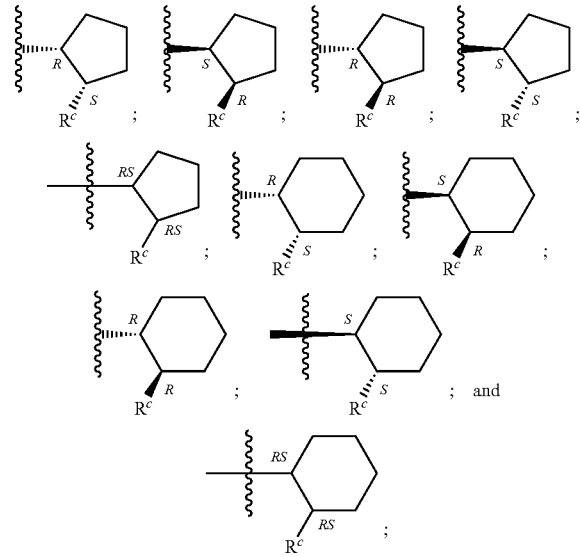

and $R^c$ is $NH(C=O)CH=CH_2$.

An additional embodiment of the invention is a compound of Formula (I) having the Formula (IIb):

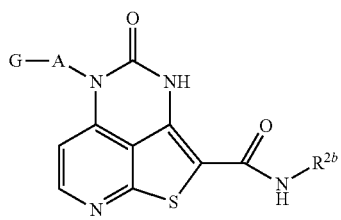

wherein
G-A is selected from the group consisting of:

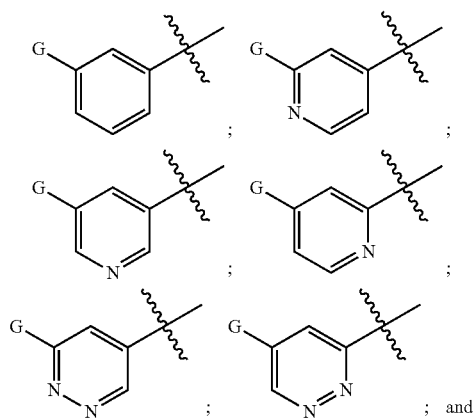

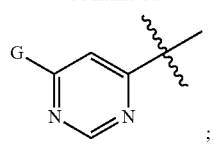

G is selected from the group consisting of: $C_{1-6}$alkyl, $C_{3-6}$cycloalkyl, phenyl, and pyridyl.

$R^{2b}$ is selected from the group consisting of:

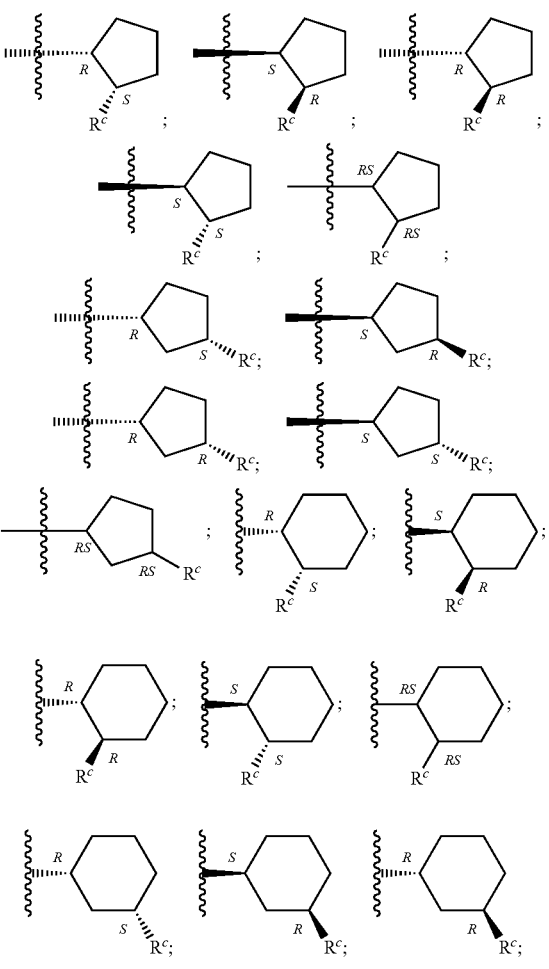

and $R^c$ is selected from the group consisting of: OH, $OCH_3$, $NH_2$, $NH(CH_3)$, $N(CH_3)_2$, $NH(CO_2\text{-tert-butyl})$, $NH(C=O)C_{1-3}$alkyl, $NH(C=O)CH=CH_2$, $NH(C=O)CH_2NH_2$, $NH(C=O)CH_2NH(CH_3)$, $NH(C=O)CH_2N(CH_3)_2$, and $NH(C=O)CH=CHCH_2N(CH_3)_2$.

An additional embodiment of the invention is a compound of Formula (I) having the Formula (IIb) wherein: G-A is

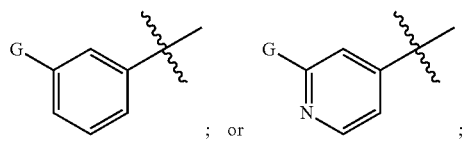; or

G is phenyl or pyridyl; $R^{2b}$ is selected from the group consisting of:

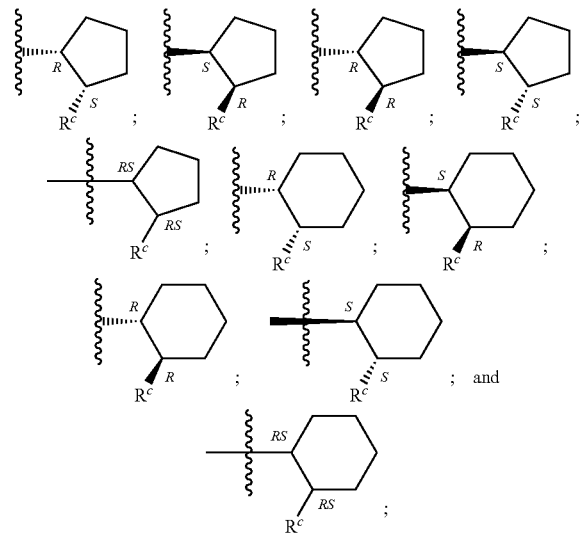

and $R^c$ is NH(C=O)CH=CH$_2$.

An additional embodiment of the invention is a compound of Formula (I) having the Formula (IIc):

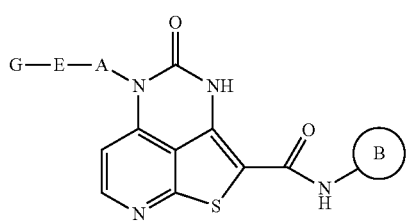

(IIc)

wherein
G-E-A is selected from the group consisting of:

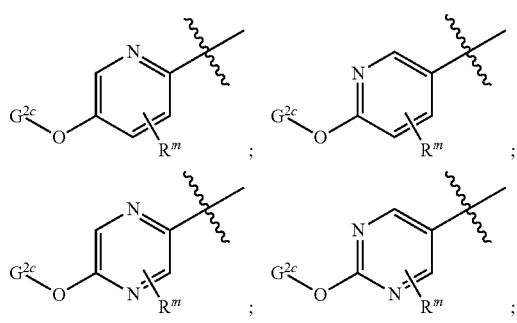

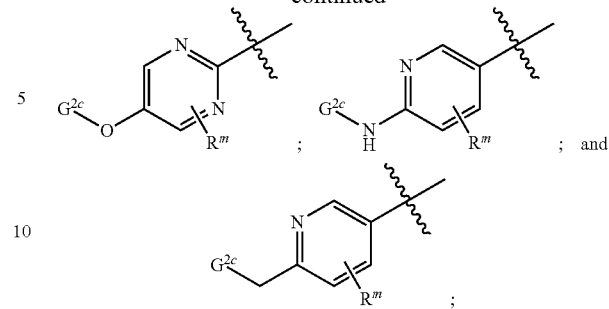

where $G^{2c}$ is selected from the group consisting of: $C_{1-6}$alkyl, phenyl, pyrimidinyl, pyridyl, pyridyl substituted with CH$_3$, and $C_{3-6}$cycloalkyl; and $R^m$ is H or CH$_3$;

Ring B is selected from the group consisting of:

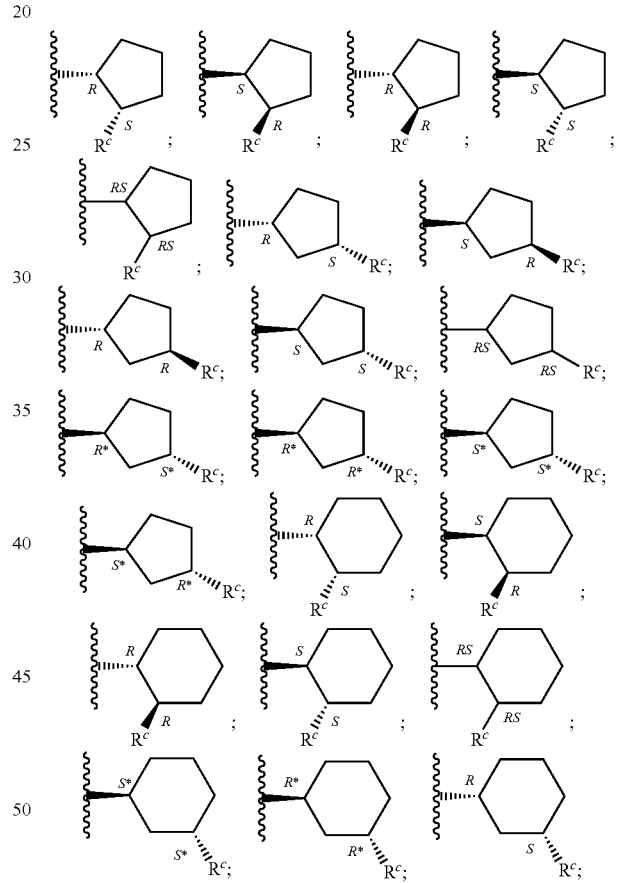

and
$R^c$ is selected from the group consisting of: OH, OCH$_3$, NH$_2$, NH(CH$_3$), N(CH$_3$)$_2$, NH(CO$_2$-tert-butyl), NH(C=O)C$_{1-3}$alkyl, NH(C=O)CH=CH$_2$, NH(C=O)CH$_2$NH$_2$, NH(C=O)CH$_2$NH(CH$_3$), NH(C=O)CH$_2$N(CH$_3$)$_2$, and NH(C=O)CH=CHCH$_2$N(CH$_3$)$_2$.

An additional embodiment of the invention is a compound of Formula (I) having the Formula (IIc) wherein:

An additional embodiment of the invention is a compound of Formula (I) having the Formula (IIc): wherein G-E-A is

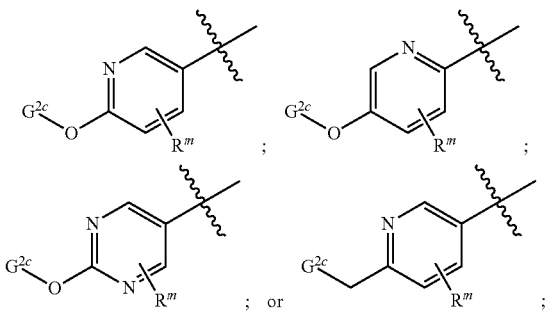

G$^{2c}$ is C$_{1-6}$alkyl, phenyl, or pyridyl; R$^m$ is H or CH$_3$; Ring B is

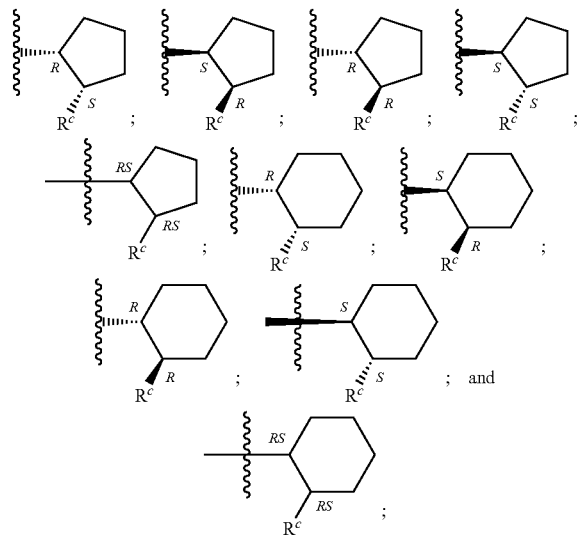

and R$^c$ is NH(C=O)CH=CH$_2$.

The disclosure also relates to methods of using the compounds described herein to treat subjects diagnosed with or suffering from a disease, disorder, or condition mediated by Bruton's tyrosine kinase. These methods are accomplished by administering to the subject a compound of the disclosure in an amount sufficient to inhibit Bruton's tyrosine kinase.

In a further aspect, provided herein are methods for inhibiting Bruton's tyrosine kinase in a subject in need of treatment by administering to the subject a composition containing a therapeutically effective amount of at least one compound of Formula (I). Some aspects of the disclosure are directed to methods of treating a subject suffering from an autoimmune disease by administering to the subject a composition containing a therapeutically effective amount of at least one compound of Formula (I). In some aspects, the autoimmune disease is, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barr syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia. When used for the treatment of an autoimmune disease, the compounds of Formula (I) can be administered as single agents. Alternatively, when used for the treatment of an autoimmune disease, the compounds of Formula (I) can be administered in combination with other agents known to be useful for the treatment of autoimmune diseases.

Other embodiments of the disclosure are directed to methods of treating a subject suffering from a heteroimmune condition by administering to the subject a composition containing a therapeutically effective amount of at least one compound of Formula (I). In some aspects, the heteroimmune condition or disease is, e.g., graft versus host disease, transplantation, transfusion, anaphylaxis, allergy, type I hypersensitivity, allergic conjunctivitis, allergic rhinitis, or atopic dermatitis. When used for the treatment of a heteroimmune condition, the compounds of Formula (I) can be administered as single agents. Alternatively, when used for the treatment of a heteroimmune condition, the compounds of Formula (I) can be administered in combination with other agents known to be useful for the treatment of heteroimmune diseases.

Other embodiments of the disclosure are directed to methods of treating a subject suffering from an inflammatory disease by administering to the subject a composition containing a therapeutically effective amount of at least one compound of Formula (I). In certain embodiments, the inflammatory disease is, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. When used for the treatment of an inflammatory disease, the compounds of Formula (I) can be administered as single agents. Alternatively, when used for the treatment of an inflammatory disease, the compounds of Formula (I) can be administered in combination with other agents known to be useful for the treatment of inflammatory diseases.

Other embodiments of the disclosure are directed to methods of treating a subject suffering from cancer by administering to the subject a composition containing a therapeutically effective amount of at least one compound of Formula (I). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. Cancers that are particularly suited to being treated with compounds of the disclosure include mantle cell lymphoma and chronic lymphocytic leukemia and macroglobulinemia, as well as multiple myeloma. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002. When used for the treatment of cancer, the compounds of Formula (I) can be administered as single agents. Alternatively, when used for the treatment of cancer, the compounds of Formula (I) can be administered in combination with other agents known to be useful for the treatment of cancer.

Other embodiments of the disclosure are directed to methods of treating a subject suffering from a thromboembolic disorder by administering to the subject a composition containing a therapeutically effective amount of at least one compound of Formula (I). In further embodiments, thromboembolic disorder is, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis. When used for the treatment of a thromboembolic disorder, the compounds of Formula (I) can be administered as single agents. Alternatively, when used for the treatment of a thromboembolic disorder, the compounds of Formula (I) can be administered in combination with other agents known to be useful for the treatment of thromboembolic disorders.

Other embodiments of the disclosure are directed to methods of treating a subject suffering from a respiratory disease by administering to the subject a composition containing a therapeutically effective amount of at least one compound of Formula (I). In some aspects, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma. When used for the treatment of a respiratory disease, the compounds of Formula (I) can be administered as single agents. Alternatively, when used for the treatment of a respiratory disease, the compounds of Formula (I) can be administered in combination with other agents known to be useful for the treatment of respiratory diseases.

In another aspect are methods for preventing rheumatoid arthritis and osteoarthritis comprising administering to the subject, at least once, an effective amount of at least one compound of Formula (I). When used for the treatment of rheumatoid arthritis or osteoarthritis, the compounds of Formula (I) can be administered as single agents. Alternatively, when used for the treatment of rheumatoid arthritis or osteoarthritis, the compounds of Formula (I) can be administered in combination with other agents known to be useful for the treatment of rheumatoid arthritis or osteoarthritis.

In another aspect are methods for treating inflammatory responses of the skin comprising administering to the subject, at least once, an effective amount of at least one compound of Formula (I). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a compound of Formula (I). When used for the treatment of these conditions, the compounds of Formula (I) can be administered as single agents. Alternatively, when used for the treatment of these conditions, the compounds of Formula (I) can be administered in combination with other agents known to be useful for the treatment of these conditions.

In preferred aspects, compounds of the disclosure can be used to treat rheumatoid arthritis.

Compounds of the disclosure can also be used to treat systemic lupus erythematosus.

Compounds of the disclosure can also be used to treat pemphigus disorders and pemphigoid disorders.

In some aspects, the compounds of Formula (I) can be administered in combination with a CYP 3A4 inhibitor, according to methods known in the art.

In treatment methods according to the disclosure, an effective amount of a pharmaceutical agent according to the disclosure is administered to a subject suffering from or diagnosed as having such a disease, disorder, or condition. An "effective amount" means an amount or dose sufficient to generally bring about the desired therapeutic benefit in patients in need of such treatment for the designated disease, disorder, or condition. Effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

In addition, the compounds of the disclosure may be used in combination with additional active ingredients in the treatment of the above conditions. The additional active ingredients may be coadministered separately with a compound of the disclosure or included with such an agent in a pharmaceutical composition according to the disclosure. The combination may serve to increase efficacy (e.g., by including in the combination a compound potentiating the potency or effectiveness of an active agent according to the disclosure), decrease one or more side effects, or decrease the required dose of the active agent according to the disclosure.

The compounds of the disclosure are used, alone or in combination with one or more additional active ingredients, to formulate pharmaceutical compositions of the disclosure.

A pharmaceutical composition of the disclosure comprises: (a) an effective amount of at least one compound in accordance with the disclosure; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the disclosure can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the disclosure may be mixed with a solid, semi-solid, or liquid diluent. Soft gelatin capsules may be prepared by mixing the compound of the disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this disclosure may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the disclosure may utilize a patch formulation to affect transdermal delivery.

Compounds of the disclosure may alternatively be administered in methods of this disclosure by inhalation, via the nasal or oral routes, e.g., in a spray formulation also containing a suitable carrier.

Exemplary compounds useful in methods of the disclosure will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Compounds of the disclosure can be prepared using the knowledge of one skilled in the art in combination with the present disclosure. For example, compounds of the disclosure can be prepared according to the following schemes and examples.

Abbreviations

Table 3. Abbreviations and acronyms used herein include the following.

TABLE 3

| Term | Acronym/Abbreviation |
| --- | --- |
| Acetonitrile | ACN, MeCN |
| tert-Butylcarbamoyl | BOC |
| Di-tert-butyl dicarbonate | (Boc)$_2$O |

TABLE 3-continued

| Term | Acronym/Abbreviation |
|---|---|
| Benzotriazol-1-yloxytris(dimethylamino)-phosphonium hexafluorophosphate | BOP |
| 1,1'-Carbonyldiimidazole | CDI |
| Diatomaceous Earth | CELITE ® 545, |
| (1-Cyano-2-ethoxy-2-oxoethylidenaminooxy)dimethylamino-morpholino-carbenium hexafluorophosphate | COMU ® |
| 1,8-Diazabicyclo[5.4.0]undec-7-ene | DBU |
| Methylene chloride, dichloromethane | DCM |
| Diisopropyl azodiformate | DIAD |
| N,N-Diisopropylethylamine | DIPEA, DIEA, Hunig's base |
| N,N-Dimethylformamide | DMF |
| 4-Dimethylaminopyridine | DMAP |
| Dimethyl sulfoxide | DMSO |
| Deutero-dimethyl sulfoxide | DMSO-$d_6$ |
| Diphenylphosphino ferrocene | dppf |
| Bis[(2-diphenylphosphino)phenyl] ether | DPEphos |
| Di-tert-butylphosphino ferrocene | dtbpf |
| 1-Ethyl-3-(3-dimethylaminopropyl)carbodiimide | EDCI, EDC, EDAC |
| Electrospray Ionisation | ESI |
| Ethyl Acetate | EtOAc, or EA, or AcOEt |
| Ethanol | EtOH |
| Flash Column Chromatography | FCC |
| 2-(1H-9-Azobenzotriazole-1-yl)-1,1,3,3-tetramethylaminium hexafluorophosphate | HATU |
| Acetic Acid | HOAc, AcOH |
| 1-Hydroxy-7-azabenzotriazole | HOAT, HOAt |
| 1-Hydroxy-benzotriazole | HOBt |
| High-pressure liquid chromatography | HPLC |
| Isopropyl Alcohol | IPA |
| Deteromethanol | MeOD-$d_4$ |
| Methanol | MeOH |
| Methanesulfonyl chloride | MsCl |
| Methyl tert-butyl ether | MTBE |
| Sodium methoxide | NaOMe |
| Tetrakis(triphenylphosphine)palladium(0) | Pd(PPh$_3$)$_4$ |
| Palladium(II) acetate | Pd(OAc)$_2$ |
| [1,1'-Bis(diphenylphosphino)ferrocene]dichloropalladium(II) | Pd(dppf)Cl$_2$ |
| Palladium(II)bis(triphenylphosphine) dichloride, bis(triphenylphosphine)palladium(II) dichloride | PdCl$_2$(PPh$_3$)$_2$ |
| Triphenylphosphine | PPh$_3$ |
| Precipitate | ppt |
| p-Toluenesulfonic acid | p-TsOH, PTSA |
| (benzotriazol-1-yl-oxytripyrrolidinophosphonium hexafluorophosphate) | PyBOP |
| Bromotripyrrolidinophosphonium hexafluorophosphate | PyBrOP ® |
| Room temperature | rt |
| Supercritical Fluid Chromatography | SFC |
| Thionyl chloride | SOCl$_2$ |
| Tetrabutylammonium fluoride | TBAF |
| tert-Butyl(chloro)dimethylsilane | TBSCl |
| Triethyl amine | TEA |
| Trifluoroacetic acid | TFA |
| Trifluoroacetic anhydride | TFAA |
| Tetrahydrofuran | THF |
| Thin Layer Chromatography | TLC |

Preparative Examples

Exemplary compounds useful in methods of the invention will now be described by reference to the illustrative synthetic schemes for their general preparation below and the specific examples to follow.

SCHEME 1

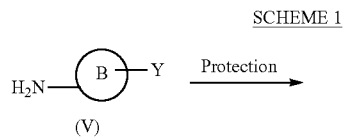

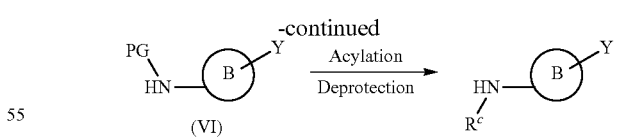

According to SCHEME 1, a compound of formula (VI), where ring B is a $C_{5-6}$cycloalkyl, Y is OH or NH$_2$, and PG is a suitable nitrogen protecting group such as BOC, is commercially available or is synthetically accessible employing conditions known to one skilled in the art, from a compound of formula (V). Acylation of a compound of formula (VI), where Y is NH$_2$, with a suitable acylating agent such as the anhydrides and halides of carboxylic acids such as acetic anhydride, propionic anhydride, prop-2-enoyl chloride, $C_{1-6}$ alkyl(C=O)Cl, and the like, in the presence of a suitable base such as TEA, DIPEA, and the like, with or without the presence of a reagent such as DMAP, in a suitable solvent such as THF, DCM, and the like, at temperatures ranging from 0° C. to 25° C., for a period of 2 to 6 h, to provide a compound of where Y is $NH_2$, and $R^c$ is (C=O)CH=$CH_2$, and (C=O)$C_{1-6}$alkyl. In cases where the amine compound has a tert-butylcarbamate (BOC) protecting group (PG), removal of the tert-butylcarbamate (BOC) protecting group (PG), is accomplished by using an acid such as HCl, TFA, p-toluenesulfonic acid, in a solvent such as MeOH, dioxane, or DCM. In a preferred embodiment, deprotection is achieved with HCl/MeOH or TFA/DCM.

A compound of formula (VI), where ring B is a $C_{5-6}$cycloalkyl, and Y is $NH_2$ is prepared from a compound of formula (VI), where ring B is a $C_{5-6}$cycloalkyl, and Y is OH under Mitsonobu conditions. In two steps, reaction of a compound of formula (VI), where Y is OH, with triphenylphosphane, DIAD, and, phthalimide, followed by hydrazinolysis with hydrazine hydrate in a solvent such as EtOH, provides a compound of formula (VI), where ring B is a $C_{5-6}$cycloalkyl, PG is BOC, and Y is $NH_2$.

A compound of formula (VI), where ring B is a $C_{5-6}$cycloalkyl, PG is BOC, and Y is $CO_2H$, is reacted with diphenyl phosphorazidate (DPPA), phenylmethanol, and a base such as TEA, in a solvent such as toluene, at a temperature of about 100° C., for a period of 18-24 h, to provide a compound (VI) where PG is BOC, and Y is NH—(C=O)$OCH_2$phenyl. Deprotection of the CBz, under conditions known to one skilled in the art, for example, hydrogenation using ($H_2$, 30 psi) using Pd(OH)$_2$, affords a compound of formula (VI), where PG is BOC, and Y is $NH_2$.

a commercially available or synthetically accessible aryl or heteroaryl boronic acid or ester such as phenyl boronic acid a metal catalyst such as copper (II) acetate, a base such as trimethylamine, in a solvent such as DCM, and the like, for a period of about 16 h, provides a compound of formula (XII) where $R^a$ is F and E is O.

A compound of formula (IX), where $R^a$ is $C_{1-6}$alkyl, is reacted with a commercially available or synthetically accessible compound of formula LG-G' (XI), where LG is a leaving group such as Cl, Br, I, or methanesulfonate, and $G^1$ is $C_{1-6}$alkyl, $C_{3-6}$cycloalkyl or $C_{3-6}$heterocycloalkyl, a suitable base such as NaH, $Na_2CO_3$, $NaHCO_3$, $K_2CO_3$, $Cs_2CO_3$, and the like, in a suitable solvent such as DMF, DMA, THF, dioxane, and the like, to provide a compound of formula (XII), where E is O, and $G^1$ is $C_{1-6}$alkyl, $C_{3-6}$cycloalkyl or $C_{3-6}$heterocycloalkyl.

A compound of formula (XII), where ring A is pyridyl, E is N-PG, and $G^1$ is $C_{1-6}$alkyl, is prepared from a compound of formula (VII), where HAL is Cl, and $R^a$ is $C_{1-6}$alkyl. For example, 2-chloro-4-methyl-5-nitropyridine is reacted with an amine such as propan-2-amine, followed by reaction with DMAP, di-tert-butyl dicarbonate, in a solvent such as THF, to provide a compound of formula (XII), where ring A is pyridyl, E is N, substituted with a protecting group (BOC), and $G^1$ is $C_{1-6}$alkyl.

Reduction of the nitro moiety of a compound of formula (XII), where E is O or N-PG, $G^1$ is phenyl, $C_{1-6}$alkyl, $C_{3-6}$cycloalkyl, pyridyl, employing conditions known to one skilled in the art, for example, reduction with iron (Fe), in a solvent such as EtOH/water, in the presence of $NH_4Cl$ or concentrated HCl, at a temperatures ranging from 0° C. to 25° C., for a period of 2 to 6 h, provides the corresponding

SCHEME 2

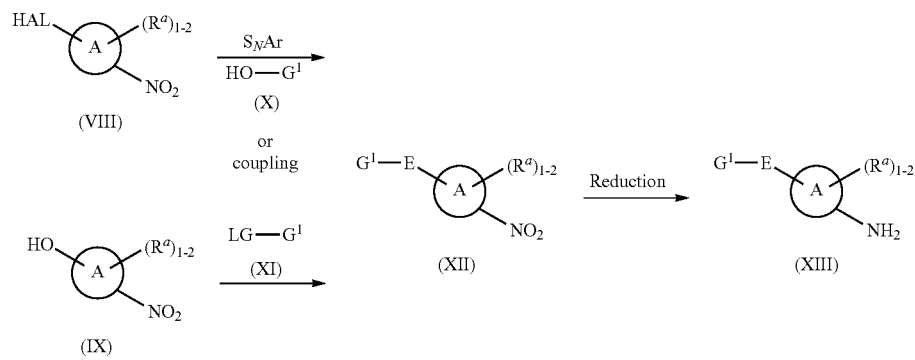

According to SCHEME 2, a synthetically accessible or commercially available compound of formula (VIII), where A is phenyl, or a six membered heteroaryl ring containing one or two nitrogen members, HAL is Br or F, and $R^a$ is independently H, halo, and $CH_3$, is reacted in an aromatic nucleophilic substitution reaction with a commercially available or synthetically accessible alcohol of formula $G^1$-OH (X), where $G^1$ is phenyl, $C_{3-6}$cycloalkyl, or $C_{1-6}$ alkyl, a suitable base such as NaH, $Na_2CO_3$, $NaHCO_3$, $K_2CO_3$, $Cs_2CO_3$, and the like, in a suitable solvent such as DMF, DMA, THF, dioxane, and the like, to provide a compound of formula (XII), where E is O.

In an alternate method, a compound of formula (XII), where E is O, is prepared from a compound of formula (VIII), where HAL is F, and W is OH, in a coupling reaction. For example, reaction of a compound of formula (VIII) with aniline of formula (XIII). Reduction of a nitro compound of formula (VII), is also achieved using hydrogenation conditions, for example, reaction with a palladium catalyst such as Pd/C, Pd(OH)$_2$, Pt/C and the like, in a suitable solvent such as THF, MeOH, EtOAc, or a mixture thereof, in the presence of $H_2$ (for example at atmospheric pressure or at 30 to 50 PSI), at temperatures ranging from rt to 50° C., to provide an amine compound of formula (XIII). Reduction of a nitro compound of formula (XII), is also achieved employing Zn, ammonium chloride, in a suitable solvent or solvent mixture such as acetone/water, at a temperature ranging from 0° C. to rt, for a period of about 2-6 h, to provide an amine compound of formula (XIII).

SCHEME 3

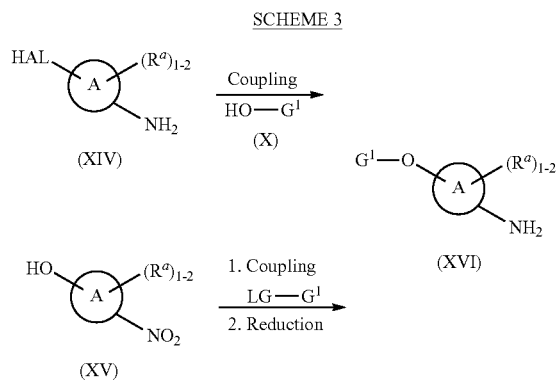

According to SCHEME 3, a compound of formula (XIV), where ring A is a suitably substituted phenyl or heteroaryl containing 1-2 nitrogen members, and HAL is I, Cl, or Br, and $R^a$ is $C_{1-6}$alkyl, is reacted in a Copper-Catalyzed Cross-Coupling reaction with a compound of formula $G^1$-OH, where $G^1$ is phenyl, or heteroaryl containing 1-2 nitrogen members. For example, a compound of formula (XV) such as 2-chloro-4-methylpyrimidin-5-amine, is reacted with a compound of formula (X), such as phenol, a copper catalyst such as Cu, CuI, and the like, N,N-dimethylglycine, a base such as $K_2CO_3$, $Cs_2CO_3$, and the like, in a suitable solvent such as dioxane, DMSO, and the like, at a temperature of about 90° C., for a period of 1 to 3 days, provides 4-methyl-2-phenoxypyrimidin-5-amine. In an alternate method, coupling reactions are performed in the absence of a catalyst, employing microwave or conventional heating, with a base such as $K_2CO_3$, in a solvent such as DMSO.

A compound of formula (XVI) is also prepared from a compound of formula (IX) in two steps. In a first step, coupling with a compound of formula (IX), where ring A is phenyl, or a heteroaryl ring containing 1-2 nitrogen members, $R^a$ is $C_{1-6}$alkyl, is reacted with a compound of formula LG-G', where LG is Cl, and $G^1$ is $C_{1-6}$alkyl, or 6 membered heteroaryl ring containing 1 to 2 nitrogen members as previously described. In a second step, reduction of the nitro moiety employing conditions known to one of skill in the art provides a compound of formula (XVI).

SCHEME 4

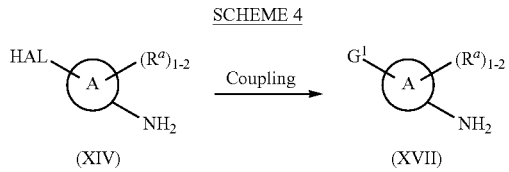

According to SCHEME 4, an aryl halide compound of formula (XIV), where ring A is phenyl, or a heteroaryl ring containing 1-2 nitrogen members, HAL is Cl, Br, and W is H or $C_{1-6}$ alkyl, undergo a transition metal catalyzed cross-coupling reaction such as Suzuki, Negishi, and Grignard reactions. For example, reaction of a compound of formula (XIV) with a commercially available or synthetically accessible alkyl or aryl boronic acid or ester, in the presence of a suitable palladium catalyst such as $Pd(PPh_3)_4$, $Pd(OAc)_2$, $Pd(dppf)Cl_2$, and the like, a base such as $Cs_2CO_3$, $K_2CO_3$, $Na_2CO_3$, and the like, in a suitable solvent such as ACN, THF, MeOH, EtOH, toluene, dioxane, water, or a mixture thereof, employing conventional or microwave heating, at temperatures ranging from 80° C. to 120° C., for a period of 12, to 24 h, to provide a compound of formula (XVII), where $G^1$ is $C_{1-6}$alkyl, or phenyl.

In a similar fashion, an aryl an aryl halide compound of formula (XIV), where ring A is phenyl, or a heteroaryl ring containing 1-2 nitrogen members, HAL is Cl, Br, and $R^a$ is H or $C_{1-6}$ alkyl, is reacted with a Grignard reagent such as such as isopropylmagnisium chloride, or an organozinc reagent such as isobutylzinc(II) bromide, cyclobutylzinc(II) bromide, and the like, in the presence of a palladium catalyst such as $Pd(dppf)Cl_2$ DCM, $Pd(dppf)_2Cl_2$, and the like, in a suitable solvent such THF, at temperatures ranging from −78° C. to the reflux temperature of the solvent, to provide a compound of formula (XVII), where $G^1$ is $C_{1-6}$alkyl.

SCHEME 5

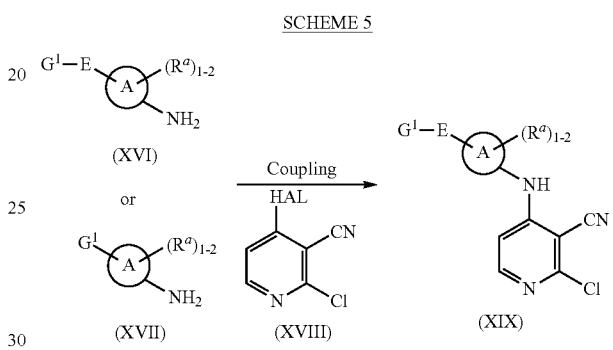

According to SCHEME 5, aryl halides of formula (XVIII), where HAL is I, $C_1$ or Br, undergo a palladium catalyzed acylation with a compound of formula (XVI) or (XVII), where $G^1$ is phenyl, and $C_{3-6}$cycloalkyl, $R^a$ is H or $C_{1-6}$ alkyl, in the presence of a palladium catalyst such as $Pd(OAc)_2$, $Pd_2(dba)_3$, and the like, a ligand such as Xantphos, S-Phos, BINAP, DPEPhos, a suitable base such as NaOtBu, $Cs_2CO_3$, $K_3PO_4$, and the like, in a suitable solvent such as ACN, THF, toluene, dioxane, and the like, employing conventional or microwave heating, at temperatures ranging from 60 to 120° C., to provide a compound of formula (XIX), where E is a bond, or O.

SCHEME 6

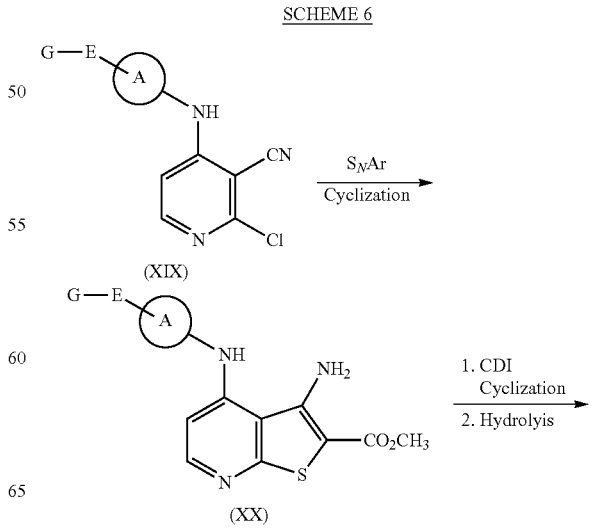

-continued

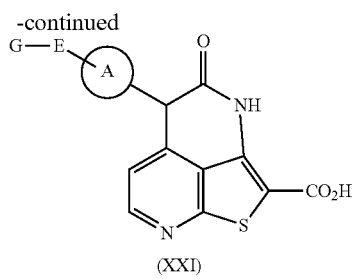

(XXI)

According to SCHEME 6, a nitrile compound of formula (XIX) is reacted in a nucleophilic aromatic substitution reaction with ethyl thioacetate, under basic conditions, followed by ring closure, to afford a thienopyridine-carboxylate compound of formula (XX). A compound of formula (XXI) is prepared in two steps from a compound of formula (XX). In a first step, reaction of a compound of formula (XX) with CDI; in suitable solvent such as 1, dioxane, and the like; at reflux temperature; for a period of 12-24 h. In a second step, hydrolysis of the ester moiety, with a suitable base such as NaOH, LiOH, and the like, in a solvent such as MeOH, and the like, at temperatures ranging from rt to 50° C., for a period of 12 to 24 h, affords an acid compound of formula (XXI).

a preferred embodiment, a compound of formula (V), (VI), or (VII), either as a free base or as an acid salt, is reacted with an acid compound of formula (XXI), in the presence of a dehydrating agent such as HOBt/EDAC, HATU, HOAT, T3P®, and the like; a suitably selected base such as DIPEA, TEA, and the like; in an organic solvent or mixture thereof such as toluene, acetonitrile, ethyl acetate, DMF, THF, methylene chloride, and the like; to afford a compound of Formula (I). In a particularly preferred embodiment, the dehydrating agent is HATU and the base is TEA or DIPEA. In cases where the amine compound of formula (V), (VI), or (VII) has a tert-butylcarbamate (BOC) protecting group (PG), removal of the tert-butylcarbamate (BOC) protecting group (PG), is accomplished by using an acid such as HCl, TFA, p-toluenesulfonic acid, in a solvent such as MeOH, dioxane, or DCM. In a preferred embodiment, deprotection is achieved with HCl/MeOH or TFA/DCM.

A compound of Formula (I), where $R^2$ is $C_{5-6}$cycloalkyl substituted with $NH_2$, is reacted under reductive amination conditions with an suitable aldehyde such as formaldehyde, paraformaldehyde, a reducing agent such as $NaBH_4$, $NaBH(OAc)_3$, and the like, in a suitable solvent such as DCM, MeOH, THF, and the like, to afford a compound of Formula (I), where $R^2$ is $C_{5-6}$cycloalkyl substituted with $N(CH_3)_2$. In an alternate method, a compound of Formula (I), where $R^2$

SCHEME 7

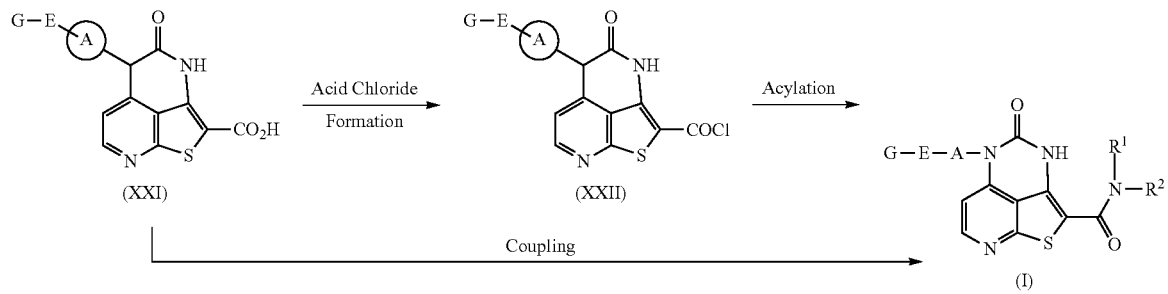

According to SCHEME 7, an acid compound of formula (XXI), as described above, is first converted to an acid chloride compound of formula (XXII). For example, a compound of formula (XXI) is treated with a chlorinating agent such as thionyl chloride and the like; in a solvent such as toluene, and the like, to form a compound of formula (XXII).

Coupling reactions are achieved by conventional amide bond forming techniques which are well known to one of skill in the art as depicted in SCHEME 5. For example, an acyl halide (e.g., chloride) compound of formula (XXI), is reacted with (1s,3r,5R,7S)-3-aminoadamantan-1-ol, or an amine of formula (V), (VI), or (VII) in the presence of an excess of a tertiary amine, such as TEA, pyridine, and the like, optionally in the presence of a suitable catalyst such as DMAP, in a suitable solvent such as DCM or THF, at a temperature ranging from room temperature to the reflux temperature of the solvent, to provide a compound of Formula (I). A variety of other amino acid coupling methodologies are used to couple the compounds of formula (XXI). Reaction of a commercially available or synthetically accessible amine of formula (V), (VI), or (VII); with a suitably substituted acid of formula (XXI) under amide bond forming conditions provides a compound of Formula (I). In is $C_{5-6}$cycloalkyl substituted with $NH_2$, is reacted in a two-step synthesis, with paraformaldehyde, to form the imine in a first step, followed by hydrogenation with $H_2$ and Pd/C to afford a compound of Formula (I), where $R^2$ is $C_{5-6}$cycloalkyl substituted with $NH(CH_3)$.

A compound of Formula (I), where $R^2$ is $C_{5-6}$cycloalkyl substituted with $NH_2$, is reacted with acylating agent such as the anhydrides and halides of carboxylic acids such as acetic anhydride, prop-2-enoyl prop-2-enoate, propionic anhydride, $C_{1-6}$alkyl(C=O)Cl, and the like, under conditions previously described, to provide a compound of Formula (I), where $R^2$ is $C_{5-6}$cycloalkyl substituted with $NH(C=O)C_{1-3}$alkyl, and $NH(C=O)CH=CH_2$.

A compound of Formula (I), where $R^2$ is $C_{5-6}$cycloalkyl substituted with $NH_2$ is reacted with a suitable acid of such as 2-(dimethylamino)acetic acid, Boc-sarcosine, 2-(tert-butoxy carbonylamino)acetic acid, (E)-4-(dimethylamino)but-2-enoic acid, acrylic acid, and the like, under amide bond forming conditions previously described conditions to provide a compound of Formula (I), where $R^2$ is $C_{5-6}$cycloalkyl substituted with $NH(C=O)CH_2NH_2$; $NH(C=O)CH_2NH(CH_3)$; and $NH(C=O)CH_2N(CH_3)_2$. A deprotection step, employing conditions previously described is employed where applicable.

A compound of Formula (I), where $R^2$ is $C_{5-6}$cycloalkyl substituted with $NH_2$ is reacted with an N-cyanating reagent such as BrCN, a base such as TEA, in a solvent such as DCM, to provide a compound of Formula (I), where $R^2$ is $C_{5-6}$cycloalkyl substituted with NH—CN.

A compound of Formula (I), where $R^2$ is $C_{5-6}$cycloalkyl substituted with $NH(CH_3)$ is formed in two steps from a compound of Formula (I), where $R^2$ is $C_{5-6}$cycloalkyl substituted with OH. In a first step, oxidation with an oxidizing agent such as Dess-Martin periodinane and the like, in a suitable solvent such as DCM, for a period of about 16 h. In a second step, reaction of the keto compound under reductive amination conditions previously described, provides a compound of Formula (I), where $R^2$ is $C_{5-6}$cycloalkyl substituted with $NH(CH_3)$.

A compound of Formula (I), where $R^2$ is $C_{5-6}$cycloalkyl substituted with $NH(CH_3)$ may be formed in two steps from a compound of Formula (I), where $R^2$ is $C_{5-6}$cycloalkyl substituted with OH. In a first step, conversion of the OH to the 4-methylbenzenesulfonate, by reaction with a suitable base such as DIEA, 4-methylbenzenesulfonyl chloride, in a suitable solvent such as DCM may provide the 4-methylbenzenesulfonate. Subsequent reaction with a suitable amine such as methyl amine, and the like, may provide a compound of Formula (I), where $R^2$ is $C_{5-6}$cycloalkyl substituted with $NH(CH_3)$.

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

Normal-phase silica gel chromatography (FCC) was performed on silica gel ($SiO_2$) using prepacked cartridges.

Preparative reverse-phase high performance liquid chromatography (RP HPLC) was performed on either:

An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

Quality control testing includes identity, chemical, and radiochemical purity by HPLC using an XBridge C18 (5 μm, 4.6×250 mm) column eluted with a mixture of methanol/ammonium acetate 5 mM, 65/35, v/v at a flow rate of 1 mL/min equipped with serial UV (280 nm) and gamma detection.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as *R or *S are enantiopure compounds where the absolute configuration was not determined.

Chiral Separation Method 1.

The atropisomers were chromatographed to isolate the two separate atropisomers, with the respective single atropisomers arbitrarily labeled as *S or *R to indicate that the compound is a single atropisomer of unknown absolute configuration. In cases for which absolute configuration of a single atropisomeric compound was determined, the atropisomers are named as either S or R throughout (with S corresponding to the alternate designations aS, $S_a$, or P; and with R corresponding to the alternate designations aR, $R_a$, or M). The purification was performed on a chiral SFC column (Stationary phase: Whelk O1 (S,S), 5 μm, 250×21.1 mm column. The mobile phase was: 40% $CO_2$, 60% MeOH (0.2% formic acid)).

Chiral Separation Method 2.

The atropisomers were chromatographed to isolate the two separate atropisomers, with the respective single atropisomers arbitrarily labeled as *S or *R to indicate that the compound is a single atropisomer of unknown absolute configuration. In cases for which absolute configuration of a single atropisomeric compound was determined, the atropisomers are named as either S or R throughout (with S corresponding to the alternate designations aS, $S_a$, or P; and with R corresponding to the alternate designations aR, $R_a$, or M). The purification was performed on a chiral SFC column (Stationary phase: Chiralpak AD-H, 5 μm, 250×21.1 mm column. The mobile phase was: 60% $CO_2$, 40% EtOH (0.3% iPrNH$_2$)).

Intermediate 1. 5-(2-Methyl-4-phenoxyphenyl)-4-oxo-4,5-dihydro-3H-1-thia-3,5,8-triazaacenaphthylene-2-carboxylic acid

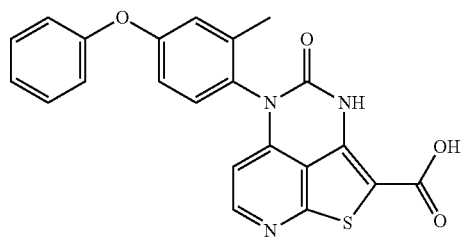 [SMILES: Cc1cc(Oc2ccccc2)ccc1N1C(=O)Nc2c(C(=O)O)sc3nccc1c23]

Step A: 2-Methyl-1-nitro-4-phenoxybenzene

To a round bottom flask were added phenol (42.5 g, 452 mmol), $K_2CO_3$ (125 g, 905 mmol), and DMF (500 mL). To the reaction mixture was added 5-fluoro-2-nitrotoluene (70.2 g, 452 mmol) and the reaction was stirred at 80° C. for 16 h under $N_2$. The reaction was diluted with saturated $NH_4Cl$ and extracted with MTBE (3×400 mL). The organic layers were combined, dried ($Na_2SO_4$), filtered, and concentrated to dryness to yield the title compound (100 g, 92% yield) as a brown oil.

Step B: 2-Methyl-4-phenoxyaniline

To a solution of 2-methyl-1-nitro-4-phenoxybenzene (100 g, 436 mmol) in EtOH/$H_2O$ (3:1 ratio, 2000 mL) were sequentially added $NH_4Cl$ (117 g, 2180 mmol) and Fe (97 g, 1700 mmol). The reaction mixture was heated to reflux for 2 h, then the reaction was cooled to 25° C. and concentrated to dryness. To the residue was added water and EtOAc and the organic layer was separated, washed with saturated $NaHCO_3$ and saturated brine, dried ($MgSO_4$), filtered, and concentrated to dryness to yield the title compound (82 g, 90% yield).

Step C: 2-Chloro-4-(2-methyl-4-phenoxyanilino)pyridine-3-carbonitrile

To a round bottom flask under a $N_2$ atmosphere were added 2-methyl-4-phenoxyaniline (30 g, 150 mmol), 2-chloro-4-iodopyridine-3-carbonitrile (51.6 g, 195 mmol), and dioxane (200 mL), followed by bis(2-diphenylphosphinophenyl)ether (DPEphos) (16 g, 30 mmol), Pd(OAc)$_2$ (3.36 g, 15 mmol), and $K_3PO_4$ (89 g, 420 mmol). The reaction mixture was stirred at 100° C. overnight. The reaction mixture was filtered and purified flash column chromatography to yield the title compound (32 g, 63% yield) as a yellow solid.

Step D: Methyl 3-amino-4-(2-methyl-4-phenoxyanilino)thieno[2,3-b]pyridine-2-carboxylate To a round bottom flask were added 2-chloro-4-(2-methyl-4-phenoxyanilino)pyridine-3-carbonitrile (36 g, 107 mmol) in MeOH (150 mL). To this solution was added NaOMe (14.5 g, 268 mmol) in MeOH (30 mL), followed by methyl 2-sulfanylacetate (23 g, 217 mmol). The reaction mixture was refluxed overnight. The reaction mixture was cooled and the yellow precipitate was filtered off, washed with MeOH, and dried to yield the title compound (30 g, 75% yield) as a yellow solid.

Step E: Methyl 5-(2-methyl-4-phenoxyphenyl)-4-oxo-4,5-dihydro-3H-1-thia-3,5,8-triazaacenaphthylene-2-carboxylate To a round bottom flask were added methyl 3-amino-4-(2-methyl-4-phenoxyanilino)thieno[2,3-b]pyridine-2-carboxylate (30.6 g, 75.5 mmol), carbonyldiimidazole (CDI, 49 g, 300 mmol), and 1,4-dioxane (500 ml). The reaction was stirred at reflux overnight. Then the reaction mixture was concentrated to dryness and to the residue was added to MeOH (200 mL) and the precipitate that formed was filtered off and dried to yield the title compound (28.1 g) as a yellow solid.

Step F: 5-(2-Methyl-4-phenoxyphenyl)-4-oxo-4,5-dihydro-3H-1-thia-3,5,8-triazaacenaphthylene-2-carboxylic acid To a round bottom flask were added methyl 5-(2-methyl-4-phenoxyphenyl)-4-oxo-4,5-dihydro-3H-1-thia-3,5,8-triazaacenaphthylene-2-carboxylate (9.2 g, 21 mmol), lithium hydroxide (4.47 g, 106 mmol), THF (200 mL), MeOH (200 mL), and water (50 mL). The reaction mixture was stirred at 50° C. for 15 h. The mixture was concentrated to dryness and diluted with $H_2O$. The pH was adjusted to 2 with 1 M HCl and the precipitate was filtered and dried to yield the title compound (8.1 g, 91% yield) as yellow solid. MS (ESI): mass calcd. for $C_{22}H_{15}N_3O_4S$, 417.08; m/z found, 418.0 $[M+H]^+$.

Intermediate 2: 4-Oxo-5-(4-phenoxyphenyl)-4,5-dihydro-3H-1-thia-3,5,8-triazaacenaphthylene-2-carboxylic acid

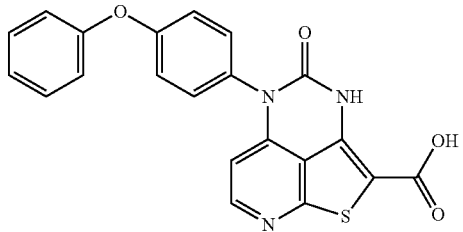

Step A. 1-Nitro-4-phenoxybenzene

The title compound was prepared in a manner analogous to Intermediate 1, Step A, using 4-fluoronitrobenzene and phenol, and substituting sodium carbonate for potassium carbonate.

Step B. 4-Phenoxyaniline

The title compound was prepared in a manner analogous to Intermediate 16, Step B using 1-nitro-4-phenoxybenzene. In an alternate method, the title compound was prepared using Pt/C, in THF, at 50 atm of $H_2$.

Step C. 4-Oxo-5-(4-phenoxyphenyl)-4,5-dihydro-3H-1-thia-3,5,8-triazaacenaphthylene-2-carboxylic acid The title compound was prepared in a manner analogous to Intermediate 1, Steps C-F, using 4-phenoxyaniline and 2-chloro-4-iodopyridine-3-carbonitrile in Step C. MS (ESI): mass calcd. for $C_{21}H_{13}N_3O_4S$, 403.41; m/z found, 404.0 $[M+H]^+$. $^1$H NMR (400 MHz, DMSO-$d_6$): δ 10.07 (br. s., 1H), 8.38 (d, J=5.2 Hz, 1H), 7.51-7.42 (m, 4H), 7.26-7.11 (m, 5H), 6.11 (d, J=5.2 Hz, 1H).

Intermediate 3. 5-(2-Fluoro-6-methyl-4-phenoxyphenyl)-4-oxo-4,5-dihydro-3H-1-thia-3,5,8-triazaacenaphthylene-2-carboxylic acid

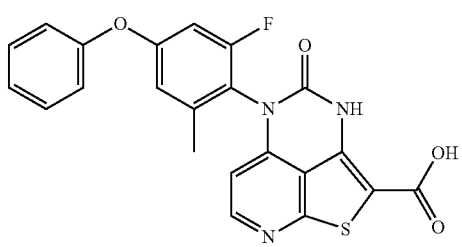 [SMILES: Cc1cc(Oc2ccccc2)cc(F)c1N1C(=O)Nc2c(C(=O)O)sc3nccc1c23]

Step A: 4-Bromo-2-fluoro-6-methylaniline

To a round bottom flask were added 2-fluoro-6-methylaniline (7 g, 56 mmol) and anhydrous DMF (100 mL). The reaction mixture was cooled in an ice bath, placed under a nitrogen atmosphere, and treated with N-bromosuccinimide (10 g, 56 mmol). The reaction was allowed to warm to rt and was stirred at rt for 10 min. The reaction mixture was poured into a water solution of diluted brine and extracted with EtOAc. The combined organic extracts were washed with diluted brine (3×), dried ($MgSO_4$), filtered through a pad of silica, and concentrated to dryness. The residue was purified by flash column chromatography yield the title compound (6.84 g, 60% yield) as a yellow foam.

Step B: 5-(2-Fluoro-6-methyl-4-phenoxyphenyl)-4-oxo-4,5-dihydro-3H-1-thia-3,5,8-triazaacenaphthylene-2-carboxylic acid The title compound was prepared in a manner analogous to Intermediate 1, Steps A and C-F, using 4-bromo-2-fluoro-6-methylaniline in Step A. MS (ESI): mass calcd. for $C_{22}H_{14}FN_3O_4S$, 435.07; m/z found, 436.1 $[M+H]^+$.

Intermediate 4: 2-Chloro-4-[4-(cyclohexoxy)-2-methylanilino]pyridine-3-carbonitrile

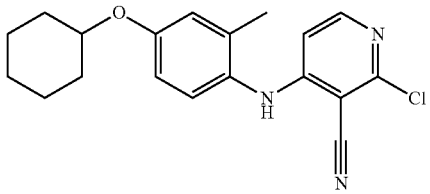 [SMILES: Cc1cc(OC2CCCCC2)ccc1Nc1ccnc(Cl)c1C#N]

Step A: 2-Chloro-4-(4-methoxy-2-methylanilino)pyridine-3-carbonitrile

A mixture of 2-chloro-4-iodopyridine-3-carbonitrile (1.7 g, 6.4 mmol), 4-methoxy-2-methylaniline (880 mg, 6.4 mmol), DPEPhos [bis(2-diphenylphosphinophenyl)ether] 690 mg, 1.3 mmol), palladium(II) acetate (145 mg, 0.646 mmol), and $K_3PO_4$ (3.7 mg, 0.017 mmol) in dioxane (20 mL) was degassed under vacuum and heated at 120° C. overnight. The mixture was cooled to rt, concentrated to dryness, and purified by flash column chromatography to yield the title compound (1.1 g, 63% yield) as a brown solid.

Step B: 2-Chloro-4-(4-hydroxy-2-methylanilino)pyridine-3-carbonitrile

To a solution of 2-chloro-4-(4-methoxy-2-methylanilino)pyridine-3-carbonitrile (1.1 g, 4.0 mmol) in anhydrous DCM (15 mL) was carefully added a solution of boron tribromide in DCM (1 M, 12 mL 3.0 equiv, 12 mmol) at 0° C., and was stirred at rt for 4 h. The reaction was quenched with water (20 mL), extracted with ethyl ether, and concentrated to dryness. The residue was purified by flash column chromatography to yield the title compound (900 mg, 86% yield) as yellow solid.

Step C: 2-Chloro-4-[4-(cyclohexoxy)-2-methylanilino]pyridine-3-carbonitrile

To a mixture of 2-chloro-4-(4-hydroxy-2-methylanilino)pyridine-3-carbonitrile (1.0 g, 3.9 mmol), cyclohexanol (1.16 g, 11.6 mmol), and $PPh_3$ (1.5 g, 5.7 mmol) in THF (20 mL) at 0° C. was added DIAD (1.17 g, 5.79 mmol). The mixture was stirred at rt overnight. The mixture was concentrated to dryness and the residue was purified by flash column chromatography to yield the title compound (400 mg, 30% yield) as yellow solid. MS (ESI): mass calcd. for $C_{19}H_{20}ClN_3O$, 341.13; m/z found, 342 [M+H]$^+$.

Intermediate 5: 5-(4-(Cyclohexyloxy)-2-methylphenyl)-4-oxo-4,5-dihydro-3H-1-thia-3,5,8-triazaacenaphthylene-2-carboxylic acid

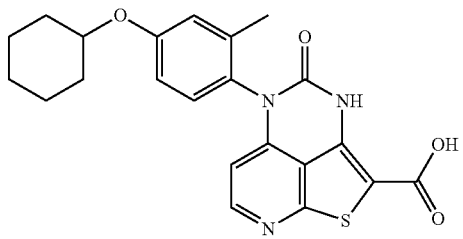 [SMILES: Cc1cc(OC2CCCCC2)ccc1N1C(=O)Nc2c(C(=O)O)sc3nccc1c23]

The title compound was prepared in a manner analogous to Intermediate 1, Steps D-F, using, 2-chloro-4-[4-(cyclohexoxy)-2-methylanilino]pyridine-3-carbonitrile (Intermediate 4, product from Step D) in Step D. MS (ESI): mass calcd. for $C_{22}H_{21}N_3O_4S$, 423.13; m/z found, 424.1 [M+H]$^+$.

Intermediate 6. 5-(2-Fluoro-4-phenoxyphenyl)-4-oxo-4,5-dihydro-3H-1-thia-3,5,8-triazaacenaphthylene-2-carboxylic acid

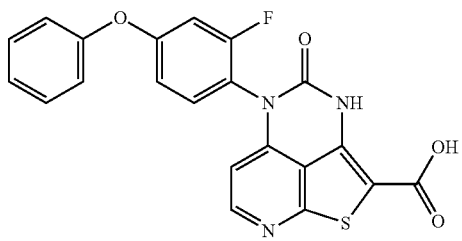 [SMILES: O=C(O)c1sc2nccc3c2c1NC(=O)N3c1ccc(Oc2ccccc2)cc1F]

Step A. 2-Fluoro-1-nitro-4-phenoxybenzene

A solution of phenylboronic acid (1 g, 8.2 mmol), 3-fluoro-4-nitrophenol (2.6 g, 16.5 mmol), copper (II) acetate (1.9 g, 10.5 mmol), trimethylamine (2.5 g, 24.7 mmol), molecular sieves, in DCM (50 mL) was stirred at rt for 16 h. The reaction mixture was filtered and concentrated under reduced pressure. Purification (FCC, SiO$_2$, Petroleum ether: Ethyl acetate=100: 1-50:11) afforded the title compound (400 mg, 21%).

Step B. 5-(2-Fluoro-4-phenoxyphenyl)-4-oxo-4,5-dihydro-3H-1-thia-3,5,8-triazaacenaphthylene-2-carboxylic acid The title compound was prepared in a manner analogous to Intermediate 25, Steps B-C using 2-Fluoro-1-nitro-4-phenoxybenzene in Step B. MS (ESI): mass calcd. for $C_{21}H_{12}FN_3O_4S$, 421.05; m/z found, 422.1 [M+H]$^+$.

Intermediate 7: 5-(4-Isopropoxyphenyl)-4-oxo-4,5-dihydro-3H-1-thia-3,5,8-triazaacenaphthylene-2-carboxylic acid

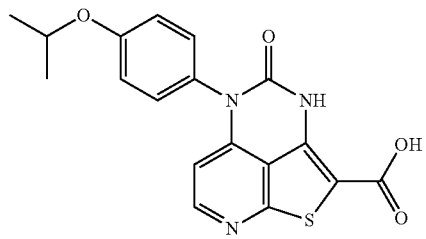 [SMILES: CC(C)Oc1ccc(N2C(=O)Nc3c(C(=O)O)sc4nccc2c34)cc1]

Step A. 1-Isopropoxy-4-nitrobenzene

The title compound was prepared in a manner analogous to Intermediate 1, Step A using 3-methyl-4-nitrophenol and 2-iodopropane.

Step B. 5-(4-Isopropoxyphenyl)-4-oxo-4,5-dihydro-3H-1-thia-3,5,8-triazaacenaphthylene-2-carboxylic acid The title compound was prepared in a manner analogous to Intermediate 25, Steps B-C using 1-isopropoxy-4-nitrobenzene in Step B. MS (ESI): mass calcd. for $C_{18}H_{15}N_3O_4S$, 369.08; m/z found, 370.3 [M+H]$^+$.

Intermediate 8: 5-(2-Methyl-4-phenoxyphenyl)-4-oxo-4,5-dihydro-3H-1-thia-3,5,8-triazaacenaphthylene-2-carbonyl chloride

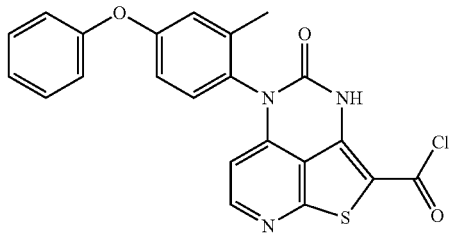 [SMILES: Cc1cc(Oc2ccccc2)ccc1N1C(=O)Nc2c(C(=O)Cl)sc3nccc1c23]

To a solution of 5-(2-methyl-4-phenoxyphenyl)-4-oxo-4,5-dihydro-3H-1-thia-3,5,8-triazaacenaphthylene-2-carboxylic acid (Intermediate 1, 500 mg, 1.20 mmol) in anhydrous DCM (20 mL) was added 2-drops of DMF and cooled to 0° C. Then oxalyl dichloride (760 mg, 6.0 mmol) was added slowly and it was stirred at 40° C. overnight. The reaction mixture was concentrated to dryness to give the title compound (260 mg), which was used in the next step without purification.

Intermediate 9: 4-Oxo-5-(4-phenoxyphenyl)-4,5-dihydro-3H-1-thia-3,5,8-triazaacenaphthylene-2-carbonyl chloride

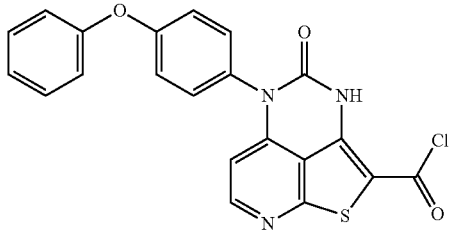 [SMILES: O=C(Cl)c1sc2nccc3c2c1NC(=O)N3c1ccc(Oc2ccccc2)cc1]

To a 200 mL round bottom flask with a stir bar were added 4-oxo-5-(4-phenoxyphenyl)-4,5-dihydro-3H-1-thia-3,5,8-triazaacenaphthylene-2-carboxylic acid (Intermediate 2, 3.9 g, 9.7 mmol) and thionyl chloride (50 mL, 680 mmol) and was warmed in a 90° C. sand bath to reflux for 90 min. The reaction mixture was concentrated to dryness. DCM (75 mL) was added and the reaction mixture was concentrated to dryness (repeated twice) to give the title compound as a stock solution in THF (0.1 M, 100 mL), which was used without further purification.

Intermediate 10. 4-Oxo-5-(6-phenoxypyridin-3-yl)-4,5-dihydro-3H-1-thia-3,5,8-triazaacenaphthylene-2-carbonyl Chloride

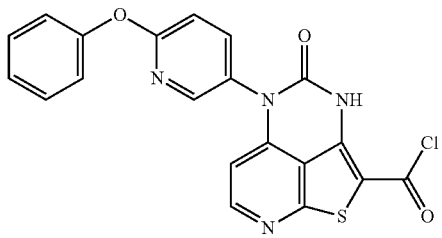 [SMILES: O=C(Cl)c1sc2nccc3c2c1NC(=O)N3c1ccc(Oc2ccccc2)nc1]

The title compound was prepared in a manner analogous to Intermediate 9, using 4-oxo-5-(6-phenoxypyridin-3-yl)-4,5-dihydro-3H-1-thia-3,5,8-triazaacenaphthylene-2-carboxylic acid (Intermediate 28).

Intermediate 11: 5-(4-Ethyl-2-methylphenyl)-4-oxo-4,5-dihydro-3H-1-thia-3,5,8-triazaacenaphthylene-2-carboxylic acid

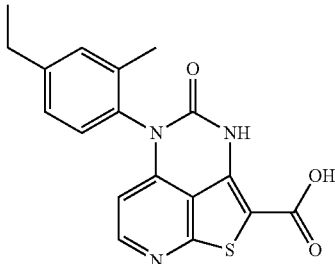 [SMILES: CCc1ccc(N2C(=O)Nc3c(C(=O)O)sc4nccc2c34)c(C)c1]

Step A: 4-Ethyl-2-methylaniline

To a solution of 4-bromo-2-methylaniline (1.86 g, 10.0 mmol), $Cs_2CO_3$ (9.77 g, 30.0 mmol), and Pd(dppf)Cl2 (146 mg, 0.200 mmol) in a Schlenk tube under a $N_2$ atmosphere was added dry THF (30 mL). To the stirred suspension was added triethylborane (30 mL, 1 M solution in THF, 30 mmol) in one portion, and the mixture was refluxed for 5 h. The reaction was cooled to 0° C. and quenched by the addition of 10% aqueous NaOH and 30% aqueous $H_2O_2$. After stirring for 30 min at rt, the mixture was extracted with EtOAc, the combined organic layer washed successively with aqueous $FeSO_4$ and brine, dried over anhydrous $Na_2SO_4$, filtered, and concentrated to dryness. The residue was purified by flash column chromatography to give the title compound as a white solid (1.1 g, 83% yield). MS (ESI): mass calcd. for $C_9H_{13}N$, 135.21; m/z found, 136.2 $[M+H]^+$.

Step B: 5-(4-Ethyl-2-methylphenyl)-4-oxo-4,5-dihydro-3H-1-thia-3,5,8-triazaacenaphthylene-2-carboxylic acid The title compound was prepared in a manner analogous to Intermediate 1, Steps C-F, using 4-ethyl-2-methylaniline and 2-chloro-4-iodopyridine-3-carbonitrile in Step C. MS (ESI): mass calcd. for $C_{18}H_{15}N_3O_3S$, 353.08; m/z found, 353.9 $[M+H]^+$.

Intermediate 12: 5-(2-Methyl-4-((tetrahydro-2H-pyran-4-yl)oxy)phenyl)-4-oxo-4,5-dihydro-3H-1-thia-3,5,8-triazaacenaphthylene-2-carboxylic acid

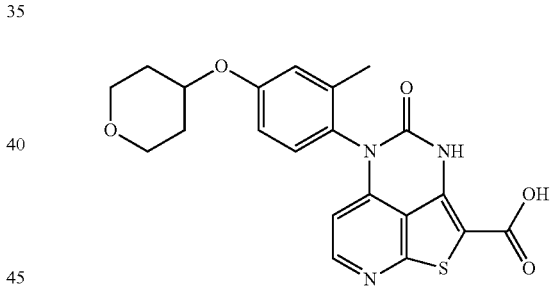

Step A: Tetrahydropyran-4-yl methanesulfonate

A solution of tetrahydropyran-4-ol (2.0 g, 20 mmol) and diisopropylethylamine (3.00 g, 23.5 mmol) in DCM (20 mL) was cooled to 0° C. and methanesulfonyl chloride (2.50 g, 21.5 mmol) was added dropwise and stirred at rt for 2 h. The mixture was concentrated to dryness to give the title compound (3.72 mg, 100% yield), which was used in the next step directly.

Step B: 5-(2-Methyl-4-((tetrahydro-2H-pyran-4-yl)oxy)phenyl)-4-oxo-4,5-dihydro-3H-1-thia-3,5,8-triazaacenaphthylene-2-carboxylic acid The title compound was prepared in a manner analogous to Intermediate 1, Steps A-F using tetrahydropyran-4-yl methanesulfonate and 3-methyl-4-nitrophenol in Step A. MS (ESI): mass calcd. for $C_{21}H_{19}N_3O_5S$, 425.10; m/z found, 426.1 $[M+H]^+$.

Intermediate 13: 5-(4-Methyl-2-phenoxypyrimidin-5-yl)-4-oxo-4,5-dihydro-3H-1-thia-3,5,8-triazaacenaphthylene-2-carboxylic acid

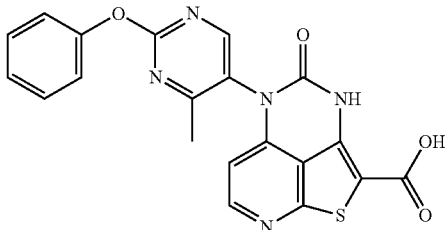

Step A: 4-Methyl-2-phenoxypyrimidin-5-amine

A mixture of 2-chloro-4-methylpyrimidin-5-amine (4.96 g, 34.55 mmol), phenol (4.35 g, 46.22 mmol), CuI (1.35 g, 7.09 mmol), N,N-dimethylglycine (747 mg, 7.24 mmol) in dioxane (40 mL), and $Cs_2CO_3$ (17.13 g, 52.58 mmol) was degassed and heated at 90° C. under $N_2$ for 3 days. The reaction was cooled to room temperature and diluted with water (100 mL) and extracted with EtOAc (2×200 mL). The combined organic layers were dried over anhydrous $Na_2S_2O_4$, filtered, and concentrated to dryness. The residue was purified by flash column chromatography to give the title compound (40.07 g, 57.64% yield) as a white solid. MS (ESI): mass calcd. for $C_{11}H_{11}N_3O$, 201.2; m/z found, 202.1 $[M+H]^+$.

Step B. 5-(4-Methyl-2-phenoxypyrimidin-5-yl)-4-oxo-4,5-dihydro-3H-1-thia-3,5,8-triazaacenaphthylene-2-carboxylic acid The title compound was prepared in a manner analogous to Intermediate 1, Steps C-F, using 4-Methyl-2-phenoxypyrimidin-5-amine and 2-chloro-4-iodopyridine-3-carbonitrile in Step C. MS (ESI): mass calcd. for $C_{20}H_{13}N_5O_4S$, 419.07; m/z found, 419.9 $[M+H]^+$.

Intermediate 14: 4-Oxo-5-(5-phenoxypyrimidin-2-yl)-4,5-dihydro-3H-1-thia-3,5,8-triazaacenaphthylene-2-carboxylic acid

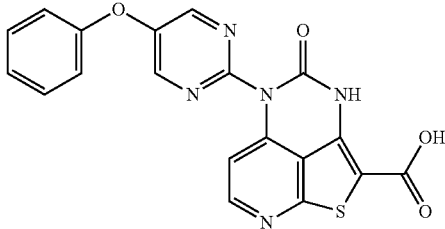 [SMILES: O=C(O)c1sc2nccc3c2c1NC(=O)N3c1ncc(Oc2ccccc2)cn1]

The title compound was prepared in a manner analogous to Intermediate 13, using 5-bromopyrimidin-2-amine and phenol in Step A. MS (ESI): mass calcd. for $C_{19}H_{11}N_5O_4S$, 405.05; m/z found, 406.0 $[M+H]^+$.

Intermediate 15: 5-(2-Methyl-4-(pyrimidin-2-yloxy)phenyl)-4-oxo-4,5-dihydro-3H-1-thia-3,5,8-triazaacenaphthylene-2-carboxylic acid

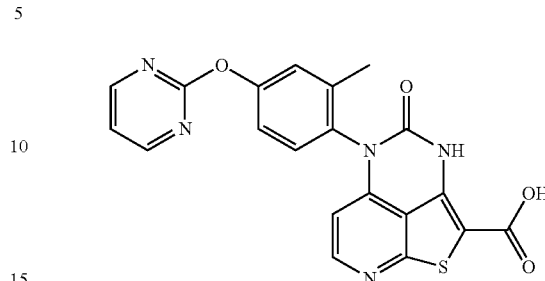

Step A. 2-(3-Methyl-4-nitrophenoxy)pyrimidine

A solution of 3-methyl-4-nitrophenol (3 g, 19.5 mmol), 2-chloropyrimidine (2.2 g, 19.5 mmol), Cu (125 mg, 1.9 mmol), $K_2CO_3$ (5.4 g, 39.1 mmol) in DMSO (20 mL), was stirred at 90 C for 24 h. Water was added and the resulting precipitate was filtered to give the title compound as a yellow solid which was used crude without further purification.

Step B. 2-Methyl-4-(pyrimidin-2-yloxy)aniline 2-(3-Methyl-4-nitrophenoxy)pyrimidine (From Step A) was dissolved in MeOH (150 mL). Pd/C was added (2 g) and the reaction mixture was stirred under $H_2$ for 16 h. The resulting mixture was filtered and concentrated under reduced pressure to afford the title compound as a pale yellow solid (2.8 g, 71% over 2 steps).

Step C. 5-(2-Methyl-4-(pyrimidin-2-yloxy)phenyl)-4-oxo-4,5-dihydro-3H-1-thia-3,5,8-triazaacenaphthylene-2-carboxylic acid The title compound was prepared in a manner analogous to Intermediate 1, Steps C-F using 2-methyl-4-(pyrimidin-2-yloxy)aniline in Step C. MS (ESI): mass calcd. for $C_{20}H_{13}N_5O_4S$, 419.07; m/z found, 420.1 $[M+H]^+$.

Intermediate 16: 5-(2-Isopropylpyridin-4-yl)-4-oxo-4,5-dihydro-3H-1-thia-3,5,8-triazaacenaphthylene-2-carboxylic acid

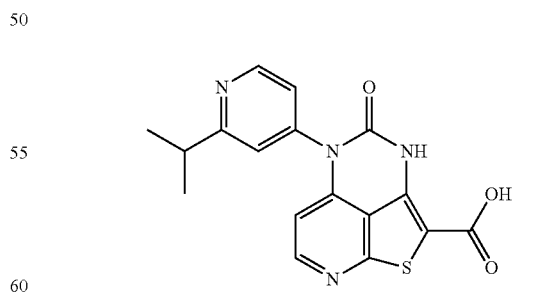

Step A: 4-Nitro-2-(prop-1-en-2-yl)pyridine

A solution of 2-chloro-4-nitropyridine (2.50 g, 15.8 mmol), 4,4,5,5-tetramethyl-2-(prop-1-en-2-yl)-1,3,2-dioxaborolane (3.557 mL, 18.92 mmol), Pd(dppf)C12 (0.643 g, 0.788 mmol), and K$_2$CO$_3$ (3.27 g, 23.7 mmol) in dioxane (40 mL) and H$_2$O (10 mL) was stirred at 80° C. overnight. The reaction was concentrated to dryness and the residue was purified by flash column chromatography to give the title compound (2.2 g, 85% yield). MS (ESI): mass calcd. for C$_8$H$_8$N$_2$O$_2$, 164.16; m/z found, 165.1 [M+H]$^+$.

Step B. 2-Isopropylpyridin-4-amine

To a solution of 4-nitro-2-(prop-1-en-2-yl)pyridine (2.2 g, 13.4 mmol) in MeOH (50 mL), was added 10% Pd/C (200 mg). The reaction mixture was stirred under 1 atm of H$_2$ for 18 h. The reaction mixture was filtered thru a pad of Celite®, and concentrated under reduced pressure to afford the title compound (1.8 g, 99.8%).

Step C: 5-(2-Isopropylpyridin-4-yl)-4-oxo-4,5-dihydro-3H-1-thia-3,5,8-triazaacenaphthylene-2-carboxylic acid The title compound was prepared in a manner analogous to Intermediate 1, Steps C-F, using 2-isopropylpyridin-4-amine Step C. MS (ESI): mass calcd. for C$_{17}$H$_{14}$N$_4$O$_3$S, 354.08; m/z found, 355.0 [M+H]$^+$.

Intermediate 17: 5-(4-Isopropyl-2-methylphenyl)-4-oxo-4,5-dihydro-3H-1-thia-3,5,8-triazaacenaphthylene-2-carboxylic acid

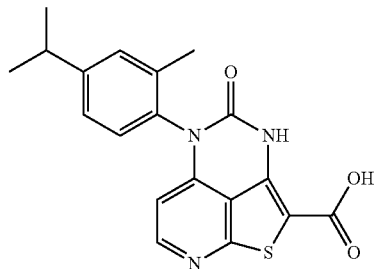 [SMILES: Cc1cc(C(C)C)ccc1N1C(=O)Nc2c(C(=O)O)sc3nccc1c23]

Step A: 4-Isopropyl-2-methyl-aniline

To a solution of 4-iodo-2-methylaniline (4.0 g, 17 mmol) and Pd(dppf)$_2$Cl$_2$ (140 mg, 0.17 mmol) in THF (50 mL) was added isopropylmagnisium chloride (25.5 mL, 51.0 mmol) at −78° C. and was reacted at reflux for 4 h. The reaction was quenched with a saturated solution of NH$_4$Cl, extracted with EtOAc, dried over anhydrous Na$_2$SO$_4$, filtered, and concentrated to dryness. The residue was purified by flash column chromatography to give the title compound as a brown solid (320 mg).

Step B: 5-(4-Isopropyl-2-methylphenyl)-4-oxo-4,5-dihydro-3H-1-thia-3,5,8-triazaacenaphthylene-2-carboxylic acid The title compound was prepared in a manner analogous to Intermediate 1, Steps C-F, using 4-isopropyl-2-methyl-aniline and 2-chloro-4-iodopyridine-3-carbonitrile in Step C.

Intermediate 18: 5-(6-Isobutyl-4-methylpyridin-3-yl)-4-oxo-4,5-dihydro-3H-1-thia-3,5,8-triazaacenaphthylene-2-carboxylic acid

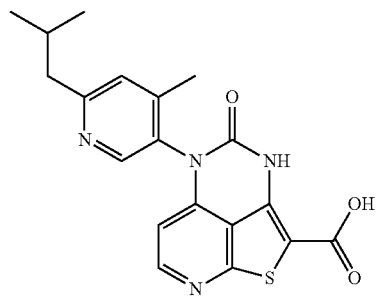 [SMILES: Cc1cc(CC(C)C)ncc1N1C(=O)Nc2c(C(=O)O)sc3nccc1c23]

Step A: 6-Isobutyl-4-methylpyridin-3-amine

To a 200 mL round bottom flask were added 6-bromo-4-methylpyridin-3-amine (5.42 g, 29.0 mmol) and 1,1'-bis(diphenylphosphino)ferrocene-palladium(II)dichloride dichloromethane complex (520 mg, 0.631 mmol). The vessel was evacuated then back filled with nitrogen. THF (20 mL) was added, followed by isobutylzinc(II) bromide (0.5 M in THF, 80 mL, 40 mmol) via syringe, then the reaction mixture was heated to 60° C. for 2 h. The reaction mixture was treated with saturated aqueous sodium bicarbonate (300 mL) and extracted with EtOAc (2×300 mL). The combined organic layers were dried (MgSO$_4$), concentrated under vacuum, and the residue was purified by FCC (SiO$_2$, 40-80% EtOAc/hexanes) to give the title compound (3.646 g, 77% yield) as a brown solid.

Step B: Methyl 3-amino-4-((6-isobutyl-4-methylpyridin-3-yl)amino)thieno[2,3-b]pyridine-2-carboxylate To a round bottom flask under a N$_2$ atmosphere were added 6-isobutyl-4-methylpyridin-3-amine (53.5 g, 326 mmol), 2-chloro-4-iodopyridine-3-carbonitrile (94.8 g, 358 mmol) and dioxane (1000 mL), followed by bis(2-diphenylphosphinophenyl)ether (DPEphos) (10.5 g, 19.5 mmol), Pd(OAc)$_2$ (2.92 g, 13.0 mmol), and Cs$_2$CO$_3$ (265 g, 814 mmol). The reaction mixture was stirred at 105° C. for 3 h. Methyl 2-mercaptoacetate (51.9 g, 489 mmol) was added, and the reaction was stirred at 105° C. overnight. The reaction mixture was filtered and concentrated. The residue was suspended in MeOH (400 mL) and stirred for 2 h at room temperature. The resulting precipitate was isolated by filtration and dried under vacuum to give the title compound (75.3 g, 62% yield) as a yellow solid.

Step C: Methyl 5-(6-isobutyl-4-methylpyridin-3-yl)-4-oxo-4,5-dihydro-3H-1-thia-3,5,8-triazaacenaphthylene-2-carboxylate To a round bottom flask were added methyl 3-amino-4-((6-isobutyl-4-methylpyridin-3-yl)amino)thieno[2,3-b]pyridine-2-carboxylate (30.0 g, 81 mmol), carbonyldiimidazole (CDI, 39.4 g, 243 mmol), triethylamine (24.6 g, 243 mmol) and 1,4-dioxane (300 mL). The reaction was stirred at 100° C. for 6 h, then cooled to 50° C. The resulting precipitate was collected by filtration, rinsed with MeOH and dried under vacuum to yield the title compound (27 g, 84%) as an off-white solid.

Step D: 5-(6-Isobutyl-4-methylpyridin-3-yl)-4-oxo-4,5-dihydro-3H-1-thia-3,5,8-triazaacenaphthylene-2-carboxylic acid To a round bottom flask were added methyl 5-(6-isobutyl-4-methylpyridin-3-yl)-4-oxo-4,5-dihydro-3H-1-thia-3,5,8-triazaacenaphthylene-2-carboxylate (68.0 g, 172 mmol), lithium hydroxide (36.0 g, 858 mmol), and a mixture of 5:2:2 THF:MeOH:$H_2O$ (4 L). The reaction mixture was stirred at 80° C. for 4.5 h. The mixture was concentrated to dryness and diluted with $H_2O$. The solution was acidified by the addition of 1 M HCl and the resulting precipitate was filtered and dried under vacuum to yield the title compound (63 g, 96% yield) as yellow solid. MS (ESI): mass calcd. for $C_{22}H_{15}N_3O_4S$, 417.08; m/z found, 418.0 [M+H]$^+$.

Intermediate 19: 5-([1,1'-Biphenyl]-3-yl)-4-oxo-4,5-dihydro-3H-1-thia-3,5,8-triazaacenaphthylene-2-carboxylic acid

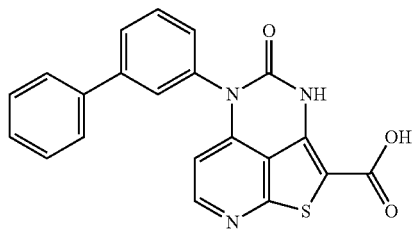 [SMILES: O=C(O)c1sc2nccc3c2c1NC(=O)N3c1cccc(-c2ccccc2)c1]

Step A: 3-Phenylaniline

To a solution of phenylboronic acid (12.19 g, 100 mmol) in MeOH (150 mL) were added $Na_2CO_3$ (21.2 g, 200 mmol) and 3-bromoaniline (17.2 g, 100 mmol) sequentially. To the suspension was added Pd(OAc)$_2$ (562 mg, 2.50 mmol) and the reaction was heated to reflux until a black suspension appeared. The suspension was cooled to room temperature, diluted with MeOH, and the black precipitate was removed by filtration. The filtrate was concentrated to dryness and the residue was taken up in water and DCM. The organic phase was collected, dried over anhydrous $Na_2CO_3$, and concentrated to dryness to give the title compound as a brown oil (18.37 g, 100.0% yield).

Step B: 5-([1,1'-Biphenyl]-3-yl)-4-oxo-4,5-dihydro-3H-1-thia-3,5,8-triazaacenaphthylene-2-carboxylic acid The title compound was prepared in a manner analogous to Intermediate 1, Steps C-F, using 3-phenylaniline and 2-chloro-4-iodopyridine-3-carbonitrile in Step C. MS (ESI): mass calcd. for $C_{21}H_{13}N_3O_3S$, 387.07; m/z found, 388.1 [M+H]$^+$.

Intermediate 20: 4-Oxo-5-(2-phenylpyridin-4-yl)-4,5-dihydro-3H-1-thia-3,5,8-triazaacenaphthylene-2-carboxylic acid

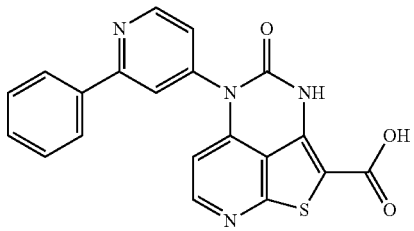 [SMILES: O=C(O)c1sc2nccc3c2c1NC(=O)N3c1ccnc(-c2ccccc2)c1]

Step A. 2-Phenylpyridin-4-amine

A mixture of 4-chloropyridin-2-amine (64 g, 498 mmol), phenyl boronic acid (61 g, 500 mmol), $Na_2CO_3$ (159 g, 1.5 mol), Pd(PPh$_3$)$_4$ (6.4 g) in $H_2O$/EtOH/toluene (500 mL) was heated to 90° C. in sealed vessel for 14 h. The crude mixture was cooled, filtered, and concentrated under reduced pressure. Purification (FCC, SiO$_2$, PE:EtOAc (100:1) afforded the title compound (64 g, 75%).

Step B. 4-Oxo-5-(2-phenylpyridin-4-yl)-4,5-dihydro-3H-1-thia-3,5,8-triazaacenaphthylene-2-carboxylic acid The title compound was prepared in a manner analogous to Intermediate 1, Steps C-F, using 2-phenylpyridin-4-amine and 2-chloro-4-iodopyridine-3-carbonitrile in Step C. MS (ESI): mass calcd. for $C_{20}H_{12}N_4O_3S$, 388.06; m/z found, 388.8 [M+H]$^+$.

Intermediate 21: 4-Oxo-5-(4-phenylpyridin-2-yl)-4,5-dihydro-3H-1-thia-3,5,8-triazaacenaphthylene-2-carboxylic acid

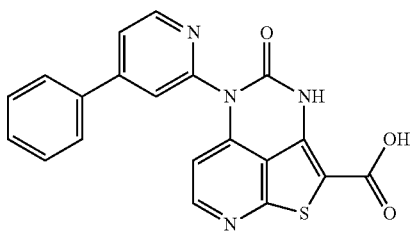 [SMILES: O=C(O)c1sc2nccc3c2c1NC(=O)N3c1cc(-c2ccccc2)ccn1]

The title compound was prepared in a manner analogous to Intermediate 20, substituting 4-bromopyridin-2-amine for 4-chloropyridin-2-amine, and substituting Pd(dppf)Cl2CH$_2$Cl$_2$ for Pd(PPh$_3$)$_4$ in Step A. MS (ESI): mass calcd. for $C_{20}H_{12}N_4O_3S$, 388.06; m/z found, 389.0 [M+H]$^+$.

Intermediate 22. 4-Oxo-5-(5-phenylpyridin-3-yl)-4,5-dihydro-3H-1-thia-3,5,8-triazaacenaphthylene-2-carboxylic acid

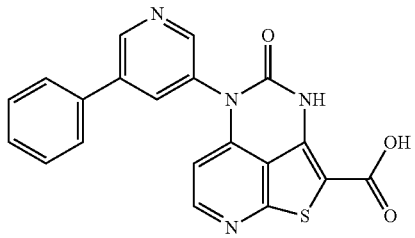 [SMILES: O=C(O)c1sc2nccc3c2c1NC(=O)N3c1cncc(-c2ccccc2)c1]

The title compound was prepared in a manner analogous to Intermediate 20, substituting 5-bromopyridin-3-amine for 4-chloropyridin-2-amine in Step A. MS (ESI): mass calcd. for $C_{20}H_{12}N_4O_3S$, 388.06; m/z found, 388.8 $[M+H]^+$.

Intermediate 23: 4-Oxo-5-(6-phenylpyrimidin-4-yl)-4,5-dihydro-3H-1-thia-3,5,8-triazaacenaphthylene-2-carboxylic acid

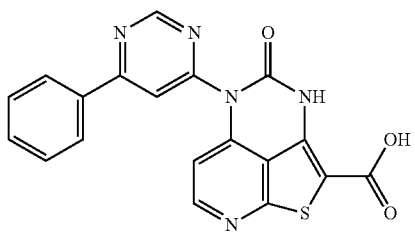

The title compound was prepared in a manner analogous to Intermediate 20, substituting 6-chloropyrimidin-4-amine for 4-chloropyridin-2-amine, and substituting Pd(dppf)Cl$_2$—CH$_2$Cl$_2$ for Pd(PPh$_3$)$_4$ in Step A. MS (ESI): mass calcd. for $C_{19}H_{11}N_5O_3S$, 389.06; m/z found, 390.2 $[M+H]^+$.

Intermediate 24: 5-(6-Cyclobutoxy-4-methylpyridin-3-yl)-4-oxo-4,5-dihydro-3H-1-thia-3,5,8-triazaacenaphthylene-2-carboxylic acid

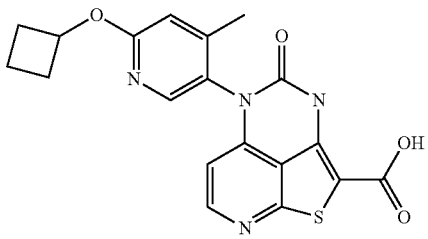 [SMILES: Cc1cc(OC2CCC2)ncc1N1C(=O)Nc2c(C(=O)O)sc3nccc1c23]

Step A. 2-Cyclobutoxy-4-methyl-5-nitropyridine

To a solution of cyclobutanol (2 g, 28.8 mmol), Cs$_2$CO$_3$ (12.5 g, 38.4 mmol) in ACN (19.2 mL) was added dropwise 2-fluoro-4-methyl-5-nitropyridine (3 g, 19.2 mmol). The reaction mixture was stirred at rt for 20 h. H$_2$O (300 mL) and DCM (200 mL) were added to the reaction mixture. The reaction mixture was extracted with DCM. The combined organics were separated, dried (Na$_2$SO$_4$), filtered, and concentrated under reduced pressure. The crude title compound, as a red oil, was used without further purification.

Step B. 6-Cyclobutoxy-4-methylpyridin-3-amine

Crude 2-cyclobutoxy-4-methyl-5-nitropyridine, from step A, was dissolved in 5:1 Acetone/water (96 mL), and ammonium chloride (5 g), and cooled in an ice bath. To the reaction mixture was added Zn (12.5 g, 192 mmol) in chunks. The cooled mix was stirred for 5 minutes at 0° C. then at room temperature for 2.5 h. To the reaction mixture was added Mg$_2$SO$_4$ (40 g) and EtOAc (300 mL), and the reaction mix was stirred for an additional 2-3 h. The reaction mixture was filtered thru Celite®, and the resulting organics were concentrated under reduced pressure to afford the title compound (3 g, 89% over 2 steps).

Step C. Methyl 5-(6-cyclobutoxy-4-methylpyridin-3-yl)-4-oxo-4,5-dihydro-3H-1-thia-3,5,8-triazaacenaphthylene-2-carboxylate The title compound was prepared in a manner analogous to Intermediate 1, Step C, using 6-cyclobutoxy-4-methylpyridin-3-amine, and substituting Cs$_2$CO$_3$ for K$_3$PO$_4$.

Step D. 5-(6-Cyclobutoxy-4-methylpyridin-3-yl)-4-oxo-4,5-dihydro-3H-1-thia-3,5,8-triazaacenaphthylene-2-carboxylic acid The title compound was prepared in a manner analogous to Intermediate 1, Steps D-F. MS (ESI): mass calcd. for $C_{19}H_{16}N_4O_4S$, 396.09; m/z found, 397.1 $[M+H]^+$.

Intermediate 25. 5-(6-(cyclopentyloxy)-4-methylpyridin-3-yl)-4-oxo-4,5-dihydro-3H-1-thia-3,5,8-triazaacenaphthylene-2-carboxylic acid

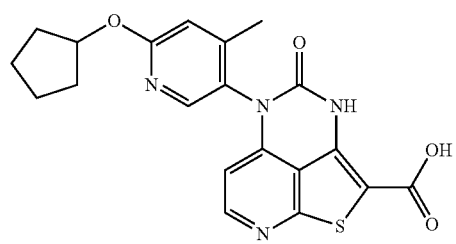 [SMILES: Cc1cc(OC2CCCC2)ncc1N1C(=O)Nc2c(C(=O)O)sc3nccc1c23]

Step A. 2-Cyclopentyloxy-4-methyl-5-nitropyridine

The title compound was prepared in a manner analogous to Intermediate 24, Step A, using 2-fluoro-4-methyl-5-nitropyridine and cyclopentanol.

Step B. 6-Cyclopentyloxy-4-methylpyridin-3-amine

The title compound was prepared in a manner analogous to Intermediate 16, Step B, using 2-cyclopentyloxy-4-methyl-5-nitropyridine.

Step C. 5-(6-(Cyclopentyloxy)-4-methylpyridin-3-yl)-4-oxo-4,5-dihydro-3H-1-thia-3,5,8-triazaacenaphthylene-2-carboxylic acid The title compound was prepared in a manner analogous to Intermediate 1, Steps C-F, using 6-cyclopentyloxy-4-methylpyridin-3-amine in Step C. MS (ESI): mass calcd. for $C_{20}H_{18}N_4O_4S$, 410.10; m/z found, 411.0 [M+H]$^+$.

Intermediate 26: 4-Oxo-5-(5-phenoxypyridin-2-yl)-4,5-dihydro-3H-1-thia-3,5,8-triazaacenaphthylene-2-carboxylic acid

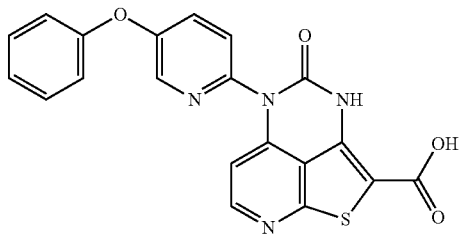 [SMILES: O=C(O)c1sc2nccc3c2c1NC(=O)N3c1ccc(Oc2ccccc2)cn1]

The title compound was prepared in a manner analogous to Intermediate 25, using 5-bromo-2-nitropyridine and phenol in Step A. MS (ESI): mass calcd. for $C_{20}H_{12}N_4O_4S$, 404.06; m/z found, 404.7 [M+H]$^+$.

Intermediate 27: 5-(4-Methyl-6-phenoxypyridin-3-yl)-4-oxo-4,5-dihydro-3H-1-thia-3,5,8-triazaacenaphthylene-2-carboxylic acid

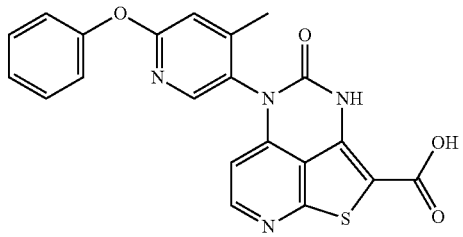 [SMILES: Cc1cc(Oc2ccccc2)ncc1N1C(=O)Nc2c(C(=O)O)sc3nccc1c23]

The title compound was prepared in a manner analogous to Intermediate 25, using 2-fluoro-4-methyl-5-nitropyridine or 2-chloro-4-methyl-5-nitropyridine and phenol, and DMF or ACN in Step A. MS (ESI): mass calcd. for $C_{21}H_{14}N_4O_4S$, 418.07; m/z found, 419 [M+H]$^+$.

Intermediate 28: 4-Oxo-5-(6-phenoxypyridin-3-yl)-4,5-dihydro-3H-1-thia-3,5,8-triazaacenaphthylene-2-carboxylic acid

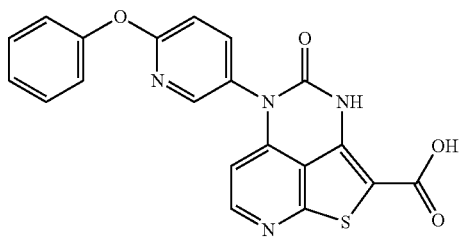 [SMILES: O=C(O)c1sc2nccc3c2c1NC(=O)N3c1ccc(Oc2ccccc2)nc1]

The title compound was prepared in a manner analogous to Intermediate 25, using 2-chloro-5-nitropyridine and phenol in Step A. MS (ESI): mass calcd. for $C_{20}H_{12}N_4O_4S$, 404.06; m/z found, 405.0 [M+H]$^+$.

Intermediate 29: 5-(2-Methyl-6-phenoxypyridin-3-yl)-4-oxo-4,5-dihydro-3H-1-thia-3,5,8-triazaacenaphthylene-2-carboxylic acid

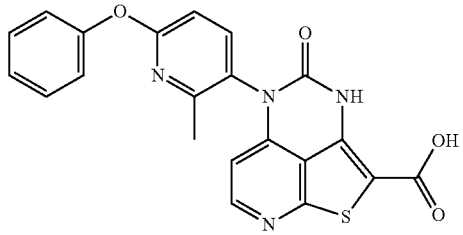 [SMILES: Cc1nc(Oc2ccccc2)ccc1N1C(=O)Nc2c(C(=O)O)sc3nccc1c23]

The title compound was prepared in a manner analogous to Intermediate 25, using 6-chloro-2-methyl-3-nitropyridine and phenol in Step A. MS (ESI): mass calcd. for $C_{21}H_{14}N_4O_4S$, 418.07; m/z found, 419.0 [M+H]$^+$.

Intermediate 30. 5-(6-Isopropoxy-4-methylpyridin-3-yl)-4-oxo-4,5-dihydro-3H-1-thia-3,5,8-triazaacenaphthylene-2-carboxylic acid

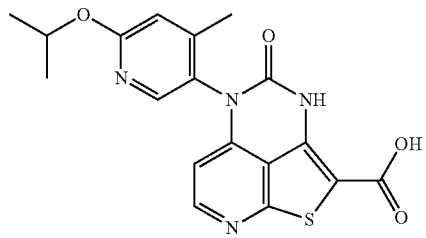 [SMILES: Cc1cc(OC(C)C)ncc1N1C(=O)Nc2c(C(=O)O)sc3nccc1c23]

The title compound was prepared in a manner analogous to Intermediate 25, using 2-fluoro-4-methyl-5-nitropyridine and propan-2-ol in Step A. MS (ESI): mass calcd. for $C_{19}H_{16}N_4O_4S$, 384.09; m/z found, 385.0 [M+H]$^+$.

Intermediate 31: 5-(4-Isopropoxy-2-methylphenyl)-4-oxo-4,5-dihydro-3H-1-thia-3,5,8-triazaacenaphthylene-2-carboxylic acid

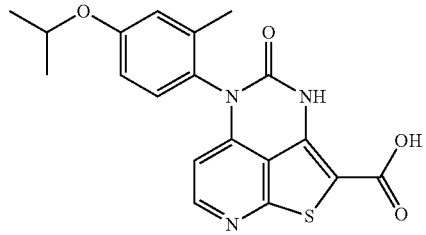 [SMILES: Cc1cc(OC(C)C)ccc1N1C(=O)Nc2c(C(=O)O)sc3nccc1c23]

The title compound was prepared in a manner analogous to Intermediate 25, using 3-methyl-4-nitrophenol and 2-iodopropane in Step A. MS (ESI): mass calcd. for $C_{19}H_{17}N_3O_4S$, 383.09; m/z found, 384.1 [M+H]$^+$.

Intermediate 32. 5-(4-((6-Methylpyridin-3-yl)oxy)phenyl)-4-oxo-4,5-dihydro-3H-1-thia-3,5,8-triazaacenaphthylene-2-carboxylic acid

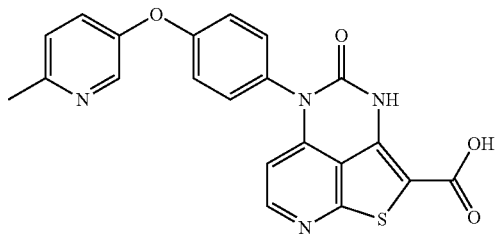 [SMILES: Cc1ccc(Oc2ccc(N3C(=O)Nc4c(C(=O)O)sc5nccc3c45)cc2)cn1]

The title compound was prepared in a manner analogous to Intermediate 25, using 1-fluoro-4-nitrobenzene and 6-methylpyridin-3-ol Step A. MS (ESI): mass calcd. for $C_{21}H_{14}N_4O_4S$, 418.07; m/z found, 419.0 [M+H]$^+$.

Intermediate 33. 5-(6-Isobutoxy-4-methylpyridin-3-yl)-4-oxo-4,5-dihydro-3H-1-thia-3,5,8-triazaacenaphthylene-2-carboxylic acid

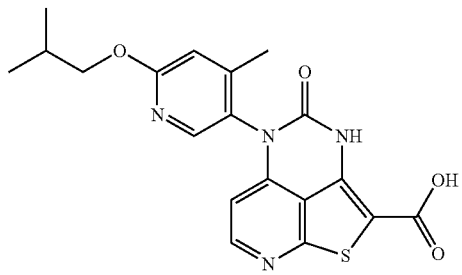 [SMILES: Cc1cc(OCC(C)C)ncc1N1C(=O)Nc2c(C(=O)O)sc3nccc1c23]

The title compound was prepared in a manner analogous to Intermediate 25, using 2-fluoro-4-methyl-5-nitropyridine and 2-methyl-1-propanol Step A. MS (ESI): mass calcd. for $C_{19}H_{18}N_4O_4S$, 398.10; m/z found, 399.0 [M+H]$^+$.

Intermediate 34: (E)-4-(tert-Butoxycarbonylamino)but-2-enoic acid

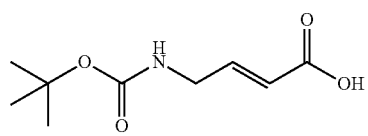

Step A: (E)-4-Aminobut-2-enoic acid

To a solution of (E)-4-bromobut-2-enoic acid (1.0 g, 6.1 mmol) in THF (20 mL) in an ice-bath was added aqueous NH$_4$OH (10 mL) and was stirred at room temperature for 6 hours. The mixture was concentrated to dryness to give the title compound (0.613 g, 100% yield), which was used in the next step without further purification.

Step B: (E)-4-(tert-Butoxycarbonylamino)but-2-enoic acid

A solution of (E)-4-aminobut-2-enoic acid (0.613 g, 6.06 mmol), (Boc)$_2$O (1.587 g, 7.272 mmol), K$_2$CO$_3$ (1.675 g, 12.12 mmol), THF (30 mL), and water (15 mL) was stirred at room temperature overnight. The mixture was dispersed between EtOAc and water. The organic layer was collected, concentrated to dryness to give the title compound (0.305 g, 25.0% yield), which was used in the nest step without further purification. MS (ESI): mass calcd. for $C_9H_{15}NO_4$, 201.10; m/z found, 102 [M-Boc+H]$^+$.

Intermediate 35: tert-Butyl((1S,4S)-4-aminocyclohexyl)carbamate

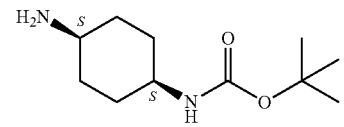

Step A: tert-Butyl ((1R,4R)-4-hydroxycyclohexyl)carbamate

To a solution of di-tert-butyl dicarbonate (4.087 mL, 21.01 mmol) and diisopropylethylamine (2.87 mL, 17.4 mmol) in THF (60 mL) was added (1R,4R)-4-aminocyclohexanol (2.00 g, 17.4 mmol) and was stirred at rt for 4 h. The reaction was concentrated to dryness and the residue was dried under reduced pressure to yield the title compound as a white solid (3.49 g, 87.0% yield), which was used without further purification.

Step B: tert-Butyl ((1S,4S)-4-(1,3-dioxoisoindolin-2-yl)cyclohexyl)carbamate To a stirred solution of tert-butyl((1R,4R)-4-hydroxycyclohexyl)carbamate (3.49 g, 16.2 mmol), phthalimide (2.50 g, 17.0 mmol), and triphenylphosphine (6.38 g, 24.3 mmol) in THF (50 mL) under nitrogen at 0° C. was added diisopropyl azodicarboxylate (4.82 g, 24.3 mmol) and was stirred at rt overnight. The reaction was concentrated to dryness and the residue was purified by flash column chromatography to yield the title compound (2.24 g, 40.1% yield) as a white solid. MS (ESI): mass calcd. for $C_{19}H_{24}N_2O_4$, 344.40; m/z found, 345.0 [M+H]$^+$.

Step C: tert-Butyl ((1S,4S)-4-aminocyclohexyl)carbamate

A solution of tert-butyl ((1S,4S)-4-(1,3-dioxoisoindolin-2-yl)cyclohexyl)carbamate (2.238 g, 6.498 mmol) and hydrazine hydrate (1.104 mL, 19.49 mmol) in EtOH (20 mL) was stirred at 80° C. for 2 hours. The mixture was diluted with 1M NaOH and extracted with DCM. The organic layer was separated, dried (MgSO$_4$), filtered, and concentrated to dryness. The residue was diluted with toluene and distilled at reduced pressure twice to yield the title compound (1.342 g, 96.00% yield), which was used without further purification. MS (ESI): mass calcd. for $C_{11}H_{22}N_2O_2$, 214.30; m/z found, 215.0 [M+H]$^+$.

Intermediate 36. N-((1S,2R)-2-Aminocyclopentyl)acrylamide

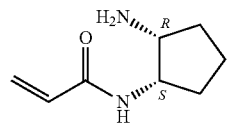

Method A:

Step A: tert-Butyl ((1R,2S)-2-acrylamidocyclopentyl)carbamate

To a solution of tert-butyl ((1R,2S)-2-aminocyclopentyl)carbamate (15 g, 75 mmol) in DCM (300 mL) was added triethylamine (13.53 mL, 97.36 mmol), followed by prop-2-enoyl chloride (6.97 mL, 86.1 mmol) at 0° C. with stirring. The cooling bath was removed, and the mixture was stirred for 60 minutes at room temperature. The reaction was quenched with aqueous 1% HCl and extracted with DCM. The organic phases were combined and washed consecutively with aqueous NaHCO$_3$ and brine and dried over anhydrous sodium sulfate. The solution was filtered, concentrated to dryness, and the residue was purified by recrystallization from DCM to give the title compound (14.5 g, 75.1% yield) as a white solid. MS (ESI): mass calcd. for C$_{13}$H$_{22}$N$_2$O$_3$, 254.32; m/z found, 155.1 (minus Boc group) [M+H]$^+$. $^1$H NMR (400 MHz, DMSO-d$_6$): δ 7.68-7.50 (m, 1H), 6.47-6.31 (m, 1H), 6.28-6.16 (m, 1H), 6.12-5.96 (m, 1H), 5.60-5.46 (m, 1H), 4.13-3.98 (m, 1H), 3.88-3.68 (m, 1H), 1.87-1.58 (m, 3H), 1.55-1.37 (m, 3H), 1.32 (s, 9H).

Step B: N-((1S,2R)-2-Aminocyclopentyl)acrylamide

To a solution of tert-butyl ((1R,2S)-2-acrylamidocyclopentyl)carbamate (800 mg, 3.146 mmol) in DCM (20 mL) was added methanesulfonic acid (1.208 g, 12.58 mmol) and was stirred at room temperature for 30 minutes. The reaction was concentrated to dryness to give the title compound (485 mg, 100% yield) as a yellow oil, which was used without further purification.

Method B:

Step A: tert-Butyl ((1R,2S)-2-acrylamidocyclohexyl)carbamate

To a solution of tert-butyl ((1R,2S)-2-aminocyclohexyl)carbamate (1.0 g, 5.0 mmol) and triethylamine (0.606 g, 5.99 mmol) in DCM (10 mL) was added acrylic anhydride (824 mg, 6.53 mmol) dropwise in an ice bath and was stirred at room temperature for 1 h. The reaction was diluted with DCM, washed with HCl (1.0 M), saturated aqueous NaHCO$_3$, and aqueous NaCl successively. The organic phase was collected, dried over anhydrous Na$_2$SO$_4$, and concentrated to dryness to give the title compound (1.1 g, 87% yield) as a white solid, which was used without further purification in next reaction. MS (ESI): mass calcd. for C$_{13}$H$_{22}$N$_2$O$_3$, 254.32; m/z found, 255.0 [M+H]$^+$.

Step B: N-((1S,2R)-2-Aminocyclopentyl)acrylamide

A solution of tert-butyl ((1R,2S)-2-acrylamidocyclohexyl)carbamate (800 mg, 1.90 mmol) in 4 M HCl in MeOH (2 mL) was stirred at room temperature for 60 minutes. The reaction was concentrated to dryness to give the title compound which was used without further purification.

Intermediate 37: tert-Butyl N-[(1R,3S)-3-aminocyclopentyl]carbamate

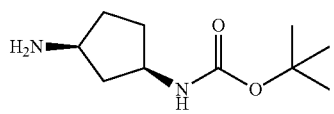

Step A: tert-Butyl N-[(1R,3S)-3-(benzyloxycarbonylamino)cyclopentyl]carbamate To a solution of (1S,3R)-3-(tert-butoxycarbonylamino)cyclopentanecarboxylic acid (10.0 g, 43.6 mmol), phenylmethanol (9.04 mL), and triethylamine (9 mL) in toluene (100 mL) was added diphenyl phosphorazidate (9.7 mL). The reaction was warmed to 100° C. and reacted overnight. The mixture was washed with saturated NaHCO$_3$ and extracted with ethyl acetate. The organic phase was evaporated to dryness and was purified by flash column chromatography to yield the title compound (9.6 g, 66% yield).

Step B: tert-Butyl N-[(1R,3S)-3-aminocyclopentyl]carbamate

A mixture of tert-butyl N-[(1R,3S)-3-(benzyloxycarbonylamino)cyclopentyl]carbamate (9.6 g, 29 mmol) in ethanol (100 mL) was hydrogenated at room temperature (H$_2$, 30 psi) using Pd(OH)$_2$ (20% on carbon, 2 g). The reaction was stirred overnight and the catalyst was filtered off and the filtrate was evaporated to dryness to yield the crude title compound (5.4 g, 94% yield).

Intermediate 38: tert-Butyl((1R,2S)-2-acrylamidocyclohexyl)carbamate

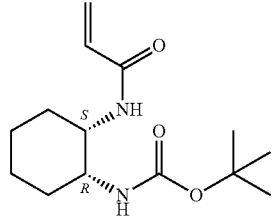

To a solution of tert-butyl ((1R,2S)-2-aminocyclohexyl)carbamate (411.5 mg, 1.92 mmol) and triethylamine (291, 2.88 mmol) in DCM (5 mL) was added acrylic anhydride (208.5 mg, 2.304 mmol) dropwise in an ice bath and was stirred at room temperature for 30 minutes. The reaction was diluted with DCM, washed with HCl (1 M), saturated aqueous NaHCO$_3$, and brine successively. The organic phase was collected and concentrated to dryness. The residue was dissolved in DCM (2 mL) and methanesulfonic acid (369 mg, 3.84 mmol) was added and was stirred at room temperature for 5 h. The reaction was concentrated to dryness to give the title compound (611 mg, 189% yield), which was used without further purification in next reaction.

Intermediate 39: N-((1S,4S)-4-aminocyclohexyl)acrylamide

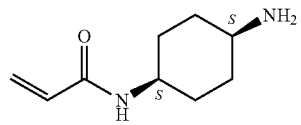

The title compound was prepared in a manner analogous to Intermediate 36, using tert-butyl ((1s,4s)-4-aminocyclohexyl)carbamate in Step A.

Intermediate 40: N-[(1S,2R)-2-aminocyclohexyl]prop-2-enamide

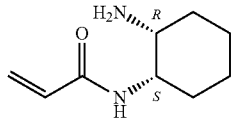

Step A: tert-Butyl ((1R,2S)-2-acrylamidocyclohexyl)carbamate

To a solution of tert-butyl ((1R,2S)-2-aminocyclohexyl)carbamate (1.4 g, 6.5 mmol) and triethylamine (1.32 g, 13.1 mmol) in DCM (15 mL) was added acrylic anhydride (824 mg, 6.53 mmol) dropwise in an ice bath and was stirred at room temperature for 1 h. The reaction was washed with HCl (0.5 M), aqueous NaHCO$_3$, and aqueous NaCl. The organic phase was collected, dried over anhydrous Na$_2$SO$_4$, and concentrated to dryness to give the title compound (1.3 g, 74% yield) as a yellow solid, which was used without further purification in next reaction.

Step B: N-((1S,2R)-2-Aminocyclohexyl)acrylamide

To a solution of tert-butyl ((1R,2S)-2-acrylamidocyclohexyl)carbamate (Intermediate 38) in MeOH (2 mL) was added HCl (1 mL) and was stirred at room temperature for 30 min. The reaction was concentrated to dryness to give the title compound (72 mg), which was used in next step without further purification. MS (ESI): mass calcd. for C$_9$H$_{16}$N$_2$O, 168.24; m/z found, 169.1 [M+H]$^+$.

Intermediate 41: N-((1R,2R)-2-aminocyclohexyl)acrylamide

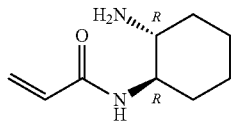

The title compound was prepared in a manner analogous to Intermediate 36, using tert-butyl ((1R,2R)-2-aminocyclohexyl)carbamate in Step A.

Intermediate 42: 2-((3-(4-Amino-3-methylphenoxy)benzyl)oxy)benzonitrile

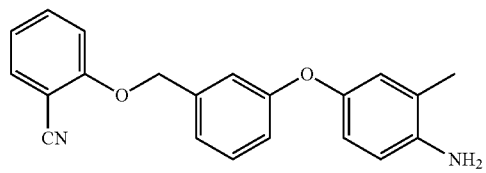 [SMILES: Cc1cc(Oc2cccc(COc3ccccc3C#N)c2)ccc1N]

Step A: 3-((tert-butyldimethylsilyl)oxy)benzaldehyde

To a mixture of 3-hydroxybenzaldehyde (24.4 g, 200 mmol) in DCM (500 mL) was added Et$_3$N (30.3 g, 300 mmol) and TBSCl (33.1 g, 220 mmol) and stirred room temperature for 3 hours. The reaction was dispersed between DCM and saturated NH$_4$Cl aq solution. The organic layer was collected, condensed and was purified by flash column chromatography (PE/EA) to give the title compound (47.3 g, 100% yield).

Step B: (3-((tert-butyldimethylsilyl)oxy)phenyl)methanol

To a mixture of 3-((tert-butyldimethylsilyl)oxy)benzaldehyde (47.3 g, 200 mmol) in MeOH (30 mL) cooled to 0° C. was added portion wise NaBH$_4$ (3.78 g, 100 mmol). After the addition was completed the reaction was stirred at room temperature for 2 hours. Volatiles were removed under vacuo. Water and EtOAc were added to the residue, the organic layer was separated, washed with brine, dried over Na$_2$SO$_4$, filtered and concentrated under vacuo to provide target product as yellow oil, which was used forward next step without further purification.

Step C: 2-((3-((tert-butyldimethylsilyl)oxy)benzyl)oxy)benzonitrile

To a mixture of (3-((tert-butyldimethylsilyl)oxy)phenyl)methanol (13.94 g, 60 mmol) in THF (200 mL) were sequentially added 2-hydroxybenzonitrile (8.58 g, 72 mmol), Ph$_3$P (18.88 g, 72 mmol) and DIAD (14.56 g, 72 mmol) dropwise at room temperature and the reaction was stirred for one hour. Saturated aqueous NH$_4$Cl and EtOAc were added, the organic layer was separated, washed with brine, dried over Na$_2$SO$_4$, filtered, condensed under vacuo and was purified by flash column chromatography (PE/EA) to give the title compound (17.0 g, 83% yield).

Step D: 2-((3-hydroxybenzyl)oxy)benzonitrile

To a mixture of 2-((3-((tert-butyldimethylsilyl)oxy)benzyl)oxy)benzonitrile (17.0 g, 50 mmol) in THF (250 mL) was added a 1M solution TBAF (60 mL, 60 mmol) and the reaction was stirred at room temperature for 30 minutes. A saturated aqueous NH$_4$Cl solution and EtOAc were added, the organic layer was separated, washed with brine, dried over Na$_2$SO$_4$, filtered, condensed and was purified by flash column chromatography (MeOH/DCM) to give the title compound (11.3 g, 100% yield).

Step E: 2-((3-(3-methyl-4-nitrophenoxy)benzyl)oxy)benzonitrile

To a mixture of 2-((3-hydroxybenzyl)oxy)benzonitrile (11.3 g, 50 mmol), 4-fluoro-2-methyl-1-nitrobenzene (7.8 g, 50 mmol), K$_2$CO$_3$ (13.8 g, 100 mmol) in 200 mL of DMSO was stirred under N$_2$ at 150° C. for 4 hours. The mixture was condensed and was purified by flash column chromatography (PE/EA) to give the title compound (15.1 g, 84% yield).

Step F: 2-((3-(4-amino-3-methylphenoxy)benzyl)oxy)benzonitrile

To a mixture of 2-((3-(3-methyl-4-nitrophenoxy)benzyl)oxy)benzonitrile (15.1 g, 42 mmol) in EtOH (420 mL) and water (140 mL) were sequentially added NH$_4$Cl (11.2 g, 210 mmol), iron (9.38 g, 168 mmol) and the reaction mixture was stirred at reflux for 4 hours and then cooled to room temperature, The mixture was diluted with DCM (500 mL) and water (200 mL), the organic layer was collected, condensed and was purified by flash column chromatography (MeOH/water) to give the title compound (13.9 g, 100% yield). MS (ESI): mass calcd. for $C_{21}H_{18}N_2O_2$, 330.14; m/z found, 331.1 $[M+H]^+$.

Intermediate 43: Methyl 5-(4-(3-((2-cyanophenoxy)methyl)phenoxy)-2-methylphenyl)-4-oxo-4,5-dihydro-3H-1-thia-3,5,8-triazaacenaphthylene-2-carboxylate

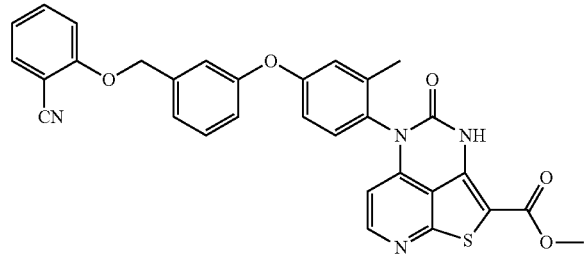 [SMILES: COC(=O)c1sc2nccc3c2c1NC(=O)N3c1ccc(Oc2cccc(COc3ccccc3C#N)c2)cc1C]

The title compound was prepared in a manner analogous to Intermediate 1 Steps C-E, using 2-((3-(4-amino-3-methylphenoxy)benzyl)oxy)benzonitrile (Intermediate 42) in place of 2-methyl-4-phenoxyaniline in Step C.

Intermediate 44: (E)-2-Cyano-3-cyclopropylacrylic acid

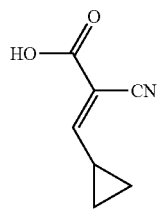

To a 50 mL round bottom flask fitted with a stir bar under $N_2$ were added cyanoacetic acid (1.70 g, 20 mmol), cyclopropanecarbaldehyde (1.40 g, 20 mmol), ammonium acetate (60 mg, 0.8 mmol), and toluene (20 mL) and was warmed in a sand bath set at 110° C. The reaction mixture was cooled to room temperature, the solid was filtered and dried to give the title compound as a light yellow solid (2.02 g, 73% yield).

Intermediate 45: N-[(1S,3R)-3-Aminocyclopentyl]prop-2-enamide

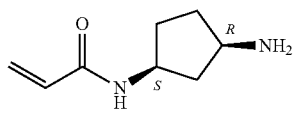

To a cooled (−20° C.) solution of tert-butyl ((1R,3S)-3-aminocyclopentyl)carbamate (235.7 mg, 1.17 mmol) and TEA (0.245 mL, 1.76 mmol) in DCM (10 mL) was added dropwise acryloyl chloride (0.12 mL, 1.41 mmol). The reaction mixture was allowed to warm to rt, and in the same vessel was added 2 mL of TFA. The reaction mixture was concentrated under reduced pressure and 2M $NH_3$/MeOH (5 mL) was added. The crude reaction mixture was dissolved in DCM (5 mL) and passed thru a silica gel plug. The tile compound was used without further purification.

Intermediate 46: N-[(1R,2R)-2-Aminocyclopentyl]prop-2-enamide

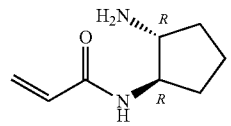

The title compound was prepared in a manner analogous to Intermediate 36, using tert-butyl ((1R,2R)-2-aminocyclopentyl)carbamate. $^1$H NMR (400 MHz, $CDCl_3$) δ 7.05 (s, 1H), 6.27 (dd, J=17.1, 1.6 Hz, 1H), 6.11 (dd, J=17.0, 10.2 Hz, 1H), 5.61 (dd, J=10.3, 1.6 Hz, 1H), 5.25-4.96 (m, 1H), 4.36-4.20 (m, 1H), 3.95-3.72 (m, 1H), 2.50-2.32 (m, 1H), 2.13 (s, 1H), 1.98-1.62 (m, 5H).

Example 1: N-((1S,4S)-4-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide

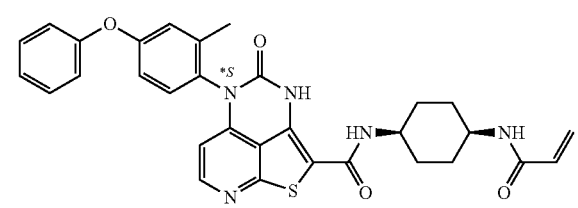

Step A: N-((1S,4S)-4-aminocyclohexyl)-5-(*S)-(2-methyl-4-phenoxyphenyl)-4-oxo-4,5-dihydro-3H-1-thia-3,5,8-triazaacenaphthylene-2-carboxamide To a round bottom flask were added 5-(*S)-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer, 42 mg, 0.10 mmol), tert-butyl ((1S,4S)-4-aminocyclohexyl)carbamate (Intermediate 35, 32 mg, 0.15 mmol), triethylamine (20 mg, 0.20 mmol), HATU (57 mg, 0.15 mmol), and DMF (1 mL). The reaction mixture was stirred at rt for 2 h. The intermediate was purified by flash column chromatography. The intermediate was dissolved in MeOH (15 mL) and saturated aqueous HCl (5 mL) was added. The resulting mixture was concentrated to dryness. The residue was dispersed between DCM and 10% aqueous $NH_3$. The organic layer was collected and concentrated to dryness to yield the title compound (51.4 mg, 100% yield), which was used in the next step without further purification.

Step B: N-((1S,4S)-4-acrylamidocyclohexyl)-5-(*S)-(2-methyl-4-phenoxyphenyl)-4-oxo-4,5-dihydro-3H-1-thia-3,5,8-triazaacenaphthylene-2-carboxamide To a solution of N-((1S,4S)-4-aminocyclohexyl)-5-(*S)-(2-methyl-4-phenoxyphenyl)-4-oxo-4,5-dihydro-3H-1-thia- 3,5,8-triazaacenaphthylene-2-carboxamide (51.4 mg, 0.100 mmol), and triethylamine (20 mg, 0.20 mmol), in DCM (15 mL) was added prop-2-enoyl chloride (9.0 mg, 0.10 mmol) dropwise at 0° C. The reaction mixture was stirred at rt for 5 min. The reaction was dispersed between DCM and water, the organic layer was collected, and concentrated to dryness. The residue was purified by flash column chromatography to yield the title compound (25 mg, 42% yield). MS (ESI): mass calcd. for $C_{31}H_{29}N_5O_4S$, 567.66; m/z found, 568.3 $[M+H]^+$. $^1H$ NMR (400 MHz, DMSO-$d_6$): δ 10.15 (br, 1H), 8.35-8.21 (m, 1H), 8.18-7.85 (m, 2H), 7.45-7.39 (m, 2H), 7.36-7.27 (m, 1H), 7.20-7.15 (m, 1H), 7.13-7.07 (m, 2H), 7.07-7.03 (m, 1H), 6.98-6.92 (m, 1H), 6.37-6.25 (m, 1H), 6.10-6.03 (m, 1H), 5.98-5.84 (m, 1H), 5.58-5.51 (m, 1H), 3.85-3.76 (m, 2H), 2.03 (s, 3H), 1.76-1.55 (m, 8H).

Example 2: N-((1R,3S)-3-Acrylamidocyclohexyl)-5-(2-methyl-4-phenoxyphenyl)-4-oxo-4,5-dihydro-3H-1-thia-3,5,8-triazaacenaphthylene-2-carboxamide

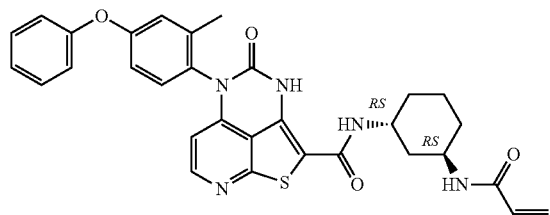

The title compound was prepared in a manner analogous to Example 1 using tert-butyl ((1S,3R)-3-aminocyclohexyl)carbamate and 5-(2-methyl-4-phenoxyphenyl)-4-oxo-4,5-dihydro-3H-1-thia-3,5,8-triazaacenaphthylene-2-carboxylic acid (Intermediate 1). MS (ESI): mass calcd. for $C_{31}H_{29}N_5O_4S$, 567.7; m/z found, 568.2 $[M+H]^+$. $^1H$ NMR (400 MHz, $CD_3OD$): δ 8.32 (d, J=5.4 Hz, 1H), 7.45-7.36 (m, 2H), 7.34-7.26 (m, 1H), 7.22-7.15 (m, 1H), 7.12-7.03 (m, 3H), 7.01-6.93 (m, 1H), 6.25-6.17 (m, 2H), 6.07 (d, J=5.3 Hz, 1H), 5.67-5.60 (m, 1H), 4.04-3.95 (m, 1H), 3.91-3.80 (m, 1H), 2.22-2.08 (m, 5H), 2.01-1.83 (m, 4H), 1.51-1.43 (m, 1H), 1.24-1.16 (m, 1H).

Example 3: N-((1S,4S)-4-Acrylamidocyclohexyl)-5-(2-methyl-4-phenoxyphenyl)-4-oxo-4,5-dihydro-3H-1-thia-3,5,8-triazaacenaphthylene-2-carboxamide

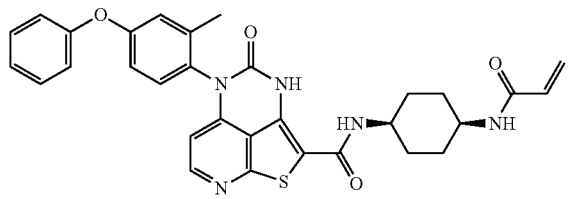 [SMILES: C=CC(=O)N[C@H]1CC[C@@H](NC(=O)c2sc3nccc4c3c2NC(=O)N4c2ccc(Oc3ccccc3)cc2C)CC1]

Step A: 5-(2-Methyl-4-phenoxyphenyl)-4-oxo-4,5-dihydro-3H-1-thia-3,5,8-triazaacenaphthylene-2-carbonyl chloride To a solution of 5-(2-methyl-4-phenoxyphenyl)-4-oxo-4,5-dihydro-3H-1-thia-3,5,8-triazaacenaphthylene-2-carboxylic acid (Intermediate 1, 500 mg, 1.20 mmol) in anhydrous DCM (20 mL) was added 2-drops of DMF and cooled to 0° C. Then oxalyl dichloride (760 mg, 6.0 mmol) was added slowly and it was stirred at 40° C. overnight. The reaction mixture was concentrated to dryness to give the title compound (260 mg), which was used in the next step without purification.

Step B: N-((1S,4S)-4-Acrylamidocyclohexyl)-5-(2-methyl-4-phenoxyphenyl)-4-oxo-4,5-dihydro-3H-1-thia-3,5,8-triazaacenaphthylene-2-carboxamide To a solution of 5-(2-Methyl-4-phenoxyphenyl)-4-oxo-4,5-dihydro-3H-1-thia-3,5,8-triazaacenaphthylene-2-carbonyl chloride (372.2 mg, 0.854 mmol), trimethylamine (259 mg, 2.5 mmol), in DCM (50 mL), was added N-((1S,4S)-4-aminocyclohexyl)acrylamide (252 mg, 1.5 mmol). The reaction mixture was stirred at room temp for 5 minutes, then concentrated under reduced pressure. Purification (FCC, $SiO_2$, (MeOH/water), then by preparative TLC (DCM/MeOH=15/1) afforded the title compound (74 mg, 15%). MS (ESI): mass calcd. for $C_{31}H_{29}N_5O_4S$, 567.7; m/z found, 568.3 $[M+H]^+$. $^1H$ NMR (400 MHz, DMSO-$d_6$): δ 8.34-7.88 (m, 2H), 7.47-7.38 (m, 2H), 7.30-7.14 (m, 2H), 7.12-7.08 (m, 2H), 7.07-7.02 (m, 1H), 6.97-6.90 (m, 1H), 6.38-6.27 (m, 1H), 6.10-6.01 (m, 1H), 5.89-5.65 (m, 1H), 5.56-5.49 (m, 1H), 3.92-3.75 (m, 2H), 2.02 (s, 3H), 177-1.73 (s, 8H).

Example 4: N-((1R,2R)-2-Hydroxycyclopentyl)-5-(S)-(2-methyl-4-phenoxyphenyl)-4-oxo-4,5-dihydro-3H-1-thia-3,5,8-triazaacenaphthylene-2-carboxamide

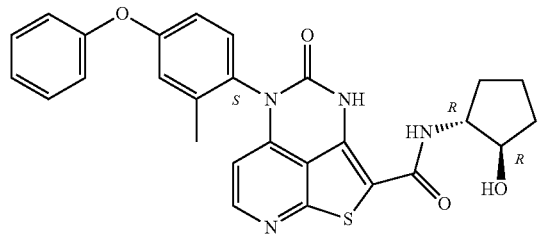

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and (1R,2R)-2-aminocyclopentanol. Absolute stereochemical configuration of the title compound was confirmed via X-ray analysis after cocrystallization with BTK protein. MS (ESI): mass calcd. for $C_{27}H_{24}N_4O_4S$, 500.6; m/z found, 501.2 $[M+H]^+$. $^1H$ NMR (400 MHz, $CDCl_3$): δ 9.53 (s, 1H), 8.40-8.29 (m, 1H), 7.42-7.35 (m, 2H), 7.20-7.14 (m, 2H), 7.11-7.06 (m, 2H), 7.01-6.97 (m, 1H), 6.96-6.92 (m, 1H), 6.02-5.98 (m, 1H), 5.86-5.79 (m, 1H), 4.40 (s, 1H), 4.13-3.98 (m, 2H), 2.30-2.17 (m, 1H), 2.15-2.03 (m, 4H), 1.91-1.81 (m, 1H), 1.77-1.66 (m, 2H), 1.62-1.48 (m, 1H).

Example 5: N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide

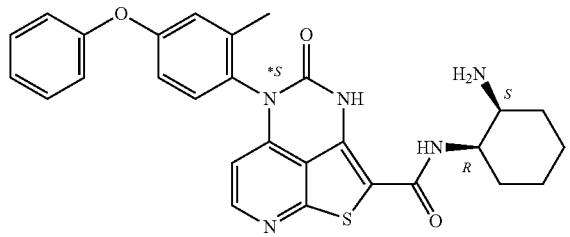

Step A: tert-Butyl ((1S,2R)-2-(5-(*S)-(2-methyl-4-phenoxyphenyl)-4-oxo-4,5-dihydro-3H-1-thia-3,5,8-triazaacenaphthylene-2-carboxamido)cyclohexyl) carbamate The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2R)-2-aminocyclohexyl]carbamate, HCl/MeOH deprotection done in next step.

Step B: N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide A mixture of tert-butyl ((1S,2R)-2-(5-(*S)-(2-methyl-4-phenoxyphenyl)-4-oxo-4,5-dihydro-3H-1-thia-3,5,8-triazaacenaphthylene-2-carboxamido)cyclohexyl)carbamate (644 mg, 1.05 mmol), concentrated HCl (3 mL), and MeOH (20 mL) was stirred at rt for 2 h. The mixture was condensed under reduced pressure. The residue was dispersed between DCM and 10% NH$_3$ aq. The organic layer was collected, dried, and concentrated under reduced pressure. Purification (reverse phase eluting with gradient MeOH/water (ratio: 0-100%) afforded the title compound (455 mg, 84%) as a yellow solid. MS (ESI): mass calcd. for $C_{28}H_{27}N_5O_3S$, 513.6; m/z found, 514.2 [M+H]$^+$. $^1$H NMR (400 MHz, CDCl$_3$): δ 8.39-8.30 (m, 1H), 7.44-7.36 (m, 2H), 7.21-7.15 (m, 2H), 7.14-7.07 (m, 2H), 7.03-6.99 (m, 1H), 6.98-6.94 (m, 1H), 6.52-6.41 (m, 1H), 6.04-5.96 (m, 1H), 4.05-3.97 (m, 1H), 3.14-3.07 (m, 1H), 2.13 (s, 3H), 1.84-1.77 (m, 1H), 1.71-1.63 (m, 3H), 1.55-1.43 (m, 4H).

Example 6: N-((1R,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide

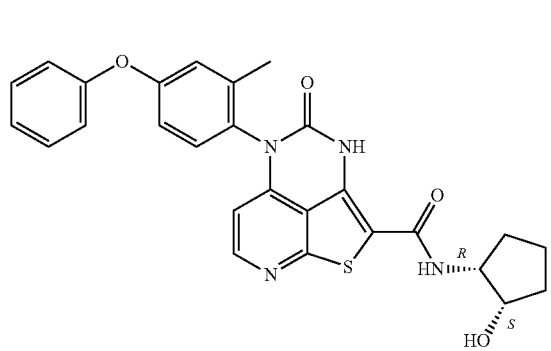

The title compound was prepared in a manner analogous to Example 3, Step B, using 5-(2-methyl-4-phenoxyphenyl)-4-oxo-4,5-dihydro-3H-1-thia-3,5,8-triazaacenaphthylene-2-carbonyl chloride (Intermediate 8) and (1S,2R)-2-aminocyclopentanol. MS (ESI): mass calcd. for $C_{27}H_{24}N_4O_4S$, 500.6; m/z found, 501.1 [M+H]$^+$. $^1$H NMR (400 MHz, CD$_3$OD): δ 8.34-8.27 (m, 1H), 7.44-7.34 (m, 2H), 7.33-7.25 (m, 1H), 7.20-7.13 (m, 1H), 7.11-7.02 (m, 3H), 7.00-6.92 (m, 1H), 6.10-6.03 (m, 1H), 4.27-4.17 (m, 1H), 4.17-4.09 (m, 1H), 2.12 (s, 3H), 2.05-1.87 (m, 3H), 1.79-1.53 (m, 3H).

Example 7: N-((1R,2S)-2-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide

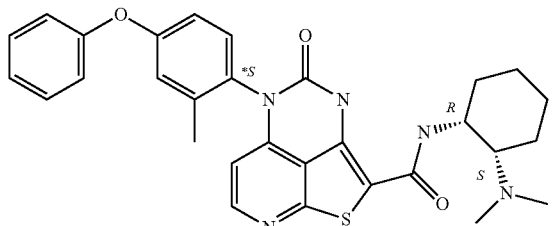

Step A: N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 5, Steps A-B, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2R)-2-aminocyclohexyl]carbamate, in Step A.

Step B: N-((1R,2S)-2-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide To a solution of N-((1R,2S)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (60 mg, 0.12 mmol) in MeOH (5 mL) was added formaldehyde (1 mL) slowly. The reaction was stirred for 10 min, then NaBH$_4$(OAc)$_3$ (64 mg, 0.30 mmol) was added slowly and the mixture was stirred for 2 h. The reaction was quenched by addition of NaOH (2 mL) and was purified by flash column chromatography to yield the title compound (12 mg) as a yellow solid. MS (ESI): mass calcd. for $C_{30}H_{31}N_5O_3S$, 541.7; m/z found, 542.2 [M+H]$^+$.

Example 8: N-((1R,2S)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide

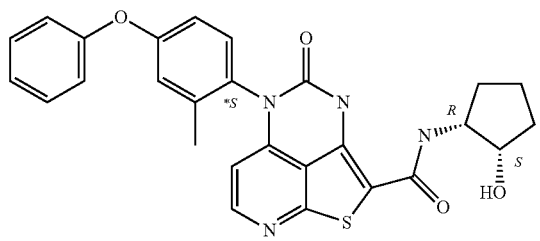

Step A: 5-(*S)-(2-Methyl-4-phenoxyphenyl)-4-oxo-4,5-dihydro-3H-1-thia-3,5,8-triazaacenaphthylene-2-carbonyl chloride To a mixture of 5-(*S)-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer, 50 mg, 0.12 mmol) in DCM (10 mL) was added oxalyl dichloride (2 mL) and was reacted at 60° C. overnight. The reaction mixture was concentrated to dryness to yield the title compound (60 mg) as a brown solid.

Step B: N-((1R,2S)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide To a mixture of (1S,2R)-2-aminocyclopentanol (40 mg, 0.29 mmol) and triethylamine (30 mg, 0.30 mmol) in DCM (4 mL) was added 5-(*S)-(2-methyl-4-phenoxyphenyl)-4-oxo-4,5-dihydro-3H-1-thia-3,5,8-triazaacenaphthylene-2-carbonyl chloride (50 mg, 0.12 mmol) and was reacted at rt for 20 min. The reaction was quenched by the addition of H$_2$O (10 mL), extracted with DCM, dried over anhydrous Na$_2$SO$_4$, filtered, and concentrated to dryness. The residue was purified by flash column chromatography to yield the title compound (18 mg) as a yellow solid. MS (ESI): mass calcd. for $C_{27}H_{24}N_4O_4S$, 500.6; m/z found, 501.2 [M+H]$^+$.

Example 9: N-((1R,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide

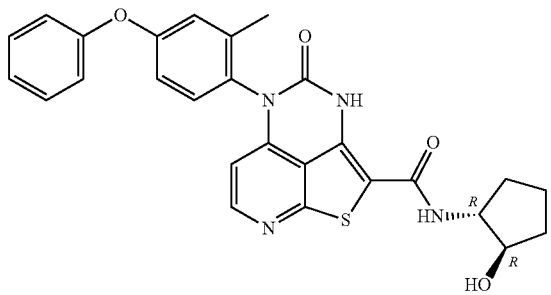

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1R,2R)-2-aminocyclopentanol. MS (ESI): mass calcd. for $C_{27}H_{24}N_4O_4S$, 500.6; m/z found, 501.2 [M+H]$^+$. $^1$H NMR (400 MHz, CD$_3$OD): δ 8.34-8.27 (m, 1H), 7.44-7.34 (m, 2H), 7.33-7.25 (m, 1H), 7.20-7.13 (m, 1H), 7.11-7.02 (m, 3H), 7.00-6.92 (m, 1H), 6.10-6.03 (m, 1H), 4.18-4.07 (m, 2H), 2.16-2.06 (m, 4H), 2.03-1.94 (m, 1H), 1.82-1.70 (m, 2H), 1.64-1.54 (m, 2H).

Example 10: N#1R,2S)-2-Aminocyclohexyl)-5-(2-methyl-4-phenoxyphenyl)-4-oxo-4,5-dihydro-3H-1-thia-3,5,8-triazaacenaphthylene-2-carboxamide

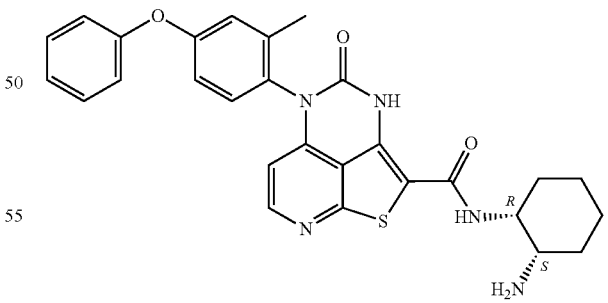

The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2R)-2-aminocyclohexyl]carbamate. MS (ESI): mass calcd. for $C_{28}H_{27}N_5O_3S$, 513.6; m/z found, 514.2 [M+H]$^+$.

Example 11: N-((1R,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide

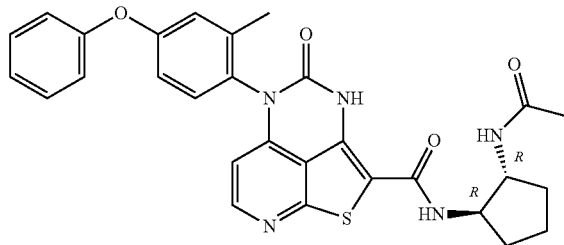

Step A: N-((1R,2R)-2-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,2R)-2-aminocyclopentyl]carbamate, in Step A.

Step B: N-((1R,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step B, using N-((1R,2R)-2-aminocyclopentyl)-5-(2-methyl-4-phenoxyphenyl)-4-oxo-4,5-dihydro-3H-1-thia-3,5,8-triazaacenaphthylene-2-carboxamide and acetyl chloride. MS (ESI): mass calcd. for $C_{29}H_{27}N_5O_4S$, 541.6; m/z found, 542.4 [M+H]$^+$. $^1$H NMR (400 MHz, DMSO-d$_6$): δ 10.20 (s, 1H), 8.32-8.23 (m, 1H), 8.18 (br, 1H), 8.03-7.91 (m, 1H), 7.45-7.37 (m, 2H), 7.36-7.28 (m, 1H), 7.20-7.14 (m, 1H), 7.14-7.02 (m, 3H), 6.98-6.89 (m, 1H), 5.99-5.82 (m, 1H), 4.22-3.97 (m, 2H), 2.03 (s, 3H), 1.98-1.89 (m, 2H), 1.75 (s, 3H), 1.68-1.58 (m, 2H), 1.55-1.46 (m, 1H), 1.42-1.33 (m, 1H).

Example 12: N-((1R,2S)-2-Aminocyclopentyl)-5-(2-methyl-4-phenoxyphenyl)-4-oxo-4,5-dihydro-3H-1-thia-3,5,8-triazaacenaphthylene-2-carboxamide

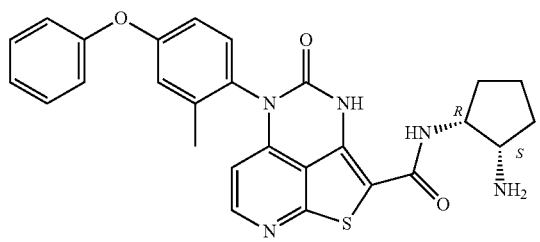

The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2R)-2-aminocyclopentyl]carbamate in Step A. The resulting HCl salt was converted to the free base using 2 M NaOH to yield the title compound (44 mg). MS (ESI): mass calcd. for $C_{27}H_{25}N_5O_3S$, 499.6; m/z found, 500.2 [M+H]$^+$. $^1$H NMR (400 MHz, CD$_3$OD): δ 8.07 (d, J=3.8, 1H), 7.42-7.33 (m, 2H), 7.21-7.16 (m, 1H), 7.15-7.10 (m, 1H), 7.10-7.05 (m, 2H), 7.05-7.00 (m, 1H), 6.98-6.92 (m, 1H), 5.84-5.77 (m, 1H), 4.4-4.31 (m, 1H), 3.46-3.35 (m, 1H), 2.16-2.01 (m, 5H), 1.94-1.80 (m, 2H), 1.69-1.54 (m, 2H).

Example 13: N-((1R,4R)-4-Acrylamidocyclohexyl)-5-(2-methyl-4-phenoxyphenyl)-4-oxo-4,5-dihydro-3H-1-thia-3,5,8-triazaacenaphthylene-2-carboxamide

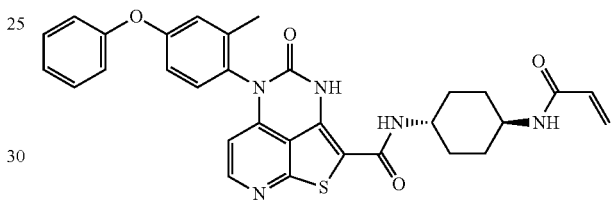

Step A: tert-Butyl ((1R,4R)-4-(5-(2-methyl-4-phenoxyphenyl)-4-oxo-4,5-dihydro-3H-1-thia-3,5,8-triazaacenaphthylene-2-carboxamido)cyclohexyl) carbamate The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-(4-aminocyclohexyl)carbamate.

Step B: N-((1R,4R)-4-Acrylamidocyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step B, using tert-butyl 41R,4R)-4-(5-(2-methyl-4-phenoxyphenyl)-4-oxo-4,5-dihydro-3H-1-thia-3,5,8-triazaacenaphthylene-2-carboxamido)cyclohexyl)carbamate and prop-2-enoyl chloride. MS (ESI): mass calcd. for $C_{31}H_{29}N_5O_4S$, 567.7; m/z found, 568.4 [M+H]$^+$. $^1$H NMR (400 MHz, DMSO-d$_6$): δ 10.15 (br, 1H), 8.34-8.23 (m, 1H), 8.15-7.97 (m, 2H), 7.47-7.39 (m, 2H), 7.37-7.28 (m, 1H), 7.20-7.15 (m, 1H), 7.14-7.08 (m, 2H), 7.08-7.03 (m, 1H), 6.99-6.92 (m, 1H), 6.21-6.13 (m, 1H), 6.08-6.02 (m, 1H), 5.96-5.87 (m, 1H), 5.57-5.51 (m, 1H), 3.80-3.69 (m, 2H), 2.03 (s, 3H), 1.89-1.80 (m, 4H), 1.50-1.39 (m, 2H), 1.33-1.24 (m, 2H).

Example 14: N#1R,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide

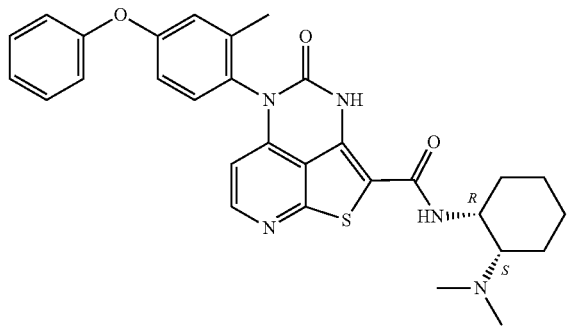

The title compound was prepared in a manner analogous to Example 7, Step B, using N-((1R,2S)-2-aminocyclohexyl)-5-(2-methyl-4-phenoxyphenyl)-4-oxo-4,5-dihydro-3H-1-thia-3,5,8-triazaacenaphthylene-2-carboxamide (Example 10). MS (ESI): mass calcd. for $C_{30}H_{31}N_5O_3S$, 541.7; m/z found, 542.2 [M+H]$^+$. $^1$H NMR (400 MHz, CD$_3$OD): δ 12.38-12.24 (m, 1H), 9.70-9.58 (m, 1H), 8.40-8.32 (m, 1H), 7.41-7.36 (m, 2H), 7.20-7.12 (m, 2H), 7.11-7.07 (m, 2H), 7.00-6.98 (m, 1H), 6.97-6.93 (m, 1H), 6.08-5.99 (m, 1H), 4.94-4.84 (m, 1H), 3.13-3.01 (m, 1H), 2.99-2.74 (m, 6H), 2.74-2.65 (m, 1H), 2.36-2.28 (m, 1H), 2.25-2.15 (m, 2H), 2.12-2.08 (m, 3H), 2.06-2.01 (m, 1H), 1.66-1.45 (m, 3H).

Example 15: N-((1R,4R)-4-Hydroxycyclohexyl)-5-(2-methyl-4-phenoxyphenyl)-4-oxo-4,5-dihydro-3H-1-thia-3,5,8-triazaacenaphthylene-2-carboxamide

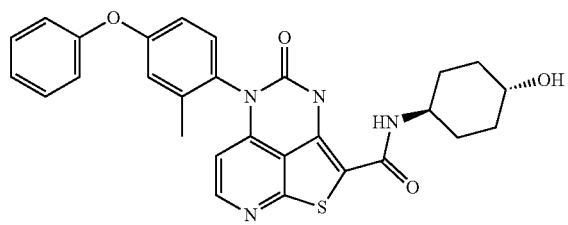 [SMILES: Cc1cc(Oc2ccccc2)ccc1N1C(=O)Nc2c(C(=O)N[C@H]3CC[C@H](O)CC3)sc3nccc1c23]

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1R,4R)-4-aminocyclohexanol. MS (ESI): mass calcd. for $C_{28}H_{26}N_4O_4S$, 514.6; m/z found, 515.80 [M+H]$^+$.

Example 16: N-((1S,4S)-4-Hydroxycyclohexyl)-5-(2-methyl-4-phenoxyphenyl)-4-oxo-4,5-dihydro-3H-1-thia-3,5,8-triazaacenaphthylene-2-carboxamide

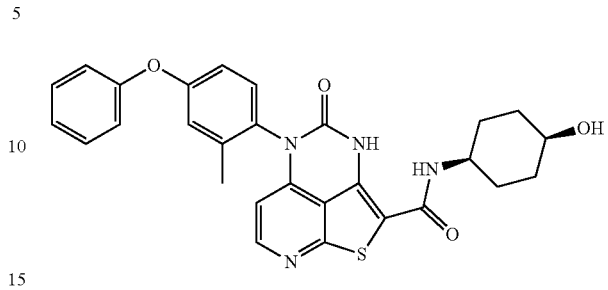

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1S,4S)-4-aminocyclohexanol. MS (ESI): mass calcd. for $C_{28}H_{26}N_4O_4S$, 514.6; m/z found, 515.70 [M+H]$^+$. $^1$H NMR (400 MHz, DMSO-d$_6$): δ 10.34-10.21 (m, 1H), 8.38-8.24 (m, 1H), 8.16-7.89 (m, 1H), 7.49-7.42 (m, 2H), 7.40-7.34 (m, 1H), 7.24-7.17 (m, 1H), 7.16-7.11 (m, 2H), 7.10-7.07 (m, 1H), 7.01-6.95 (m, 1H), 6.03-5.84 (m, 1H), 4.43-4.36 (m, 1H), 3.84-3.74 (m, 2H), 2.07 (s, 3H), 1.85-1.67 (m, 4H), 1.56-1.44 (m, 4H).

Example 17: N-((1R,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide

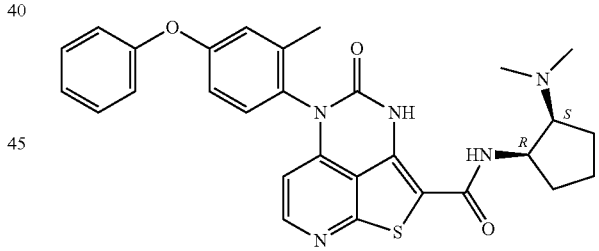

The title compound was prepared in a manner analogous to Example 7 using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2R)-2-aminocyclopentyl]carbamate in Step A. MS (ESI): mass calcd. for $C_{29}H_{29}N_5O_3S$, 527.6; m/z found, 528.2 [M+H]$^+$. $^1$H NMR (400 MHz, CD$_3$OD): δ 8.21-8.13 (m, 1H), 7.42-7.34 (m, 2H), 7.28-7.18 (m, 1H), 7.17-7.11 (m, 1H), 7.09-7.06 (m, 2H), 7.05-7.01 (m, 1H), 6.99-6.91 (m, 1H), 5.95-5.83 (m, 1H), 4.58-4.44 (m, 1H), 2.63-2.52 (m, 1H), 2.41-2.32 (m, 6H), 2.14-2.10 (m, 3H), 2.07-1.97 (m, 3H), 1.87-1.79 (m, 2H), 1.75-1.65 (m, 1H).

Example 18: N-((1R,4R)-4-Methoxycyclohexyl)-5-(2-methyl-4-phenoxyphenyl)-4-oxo-4,5-dihydro-3H-1-thia-3,5,8-triazaacenaphthylene-2-carboxamide

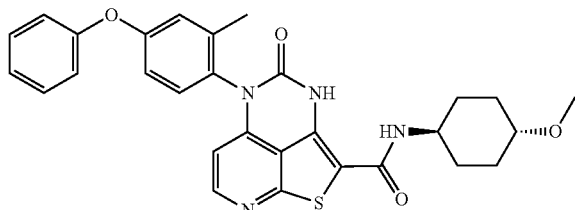

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1R,4R)-4-methoxycyclohexanamine. MS (ESI): mass calcd. for $C_{29}H_{28}N_4O_4S$, 528.6; m/z found, 529.2 $[M+H]^+$. $^1$H NMR (400 MHz, DMSO-$d_6$ and CD$_3$OD): δ 8.24 (d, J=5.2 Hz, 1H), 7.40-7.29 (m, 2H), 7.27-7.20 (m, 1H), 7.14-7.06 (m, 1H), 7.06-7.00 (m, 2H), 7.00-6.96 (m, 1H), 6.94-6.84 (m, 1H), 5.95 (d, J=5.3 Hz, 1H), 3.83-3.68 (m, 1H), 3.22 (s, 3H), 3.12-3.05 (m, 1H), 2.11-1.95 (m, 5H), 1.91-1.80 (m, 2H), 1.44-1.30 (m, 2H), 1.21-1.15 (m, 2H).

Example 19: N-((1S,4S)-4-((E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide

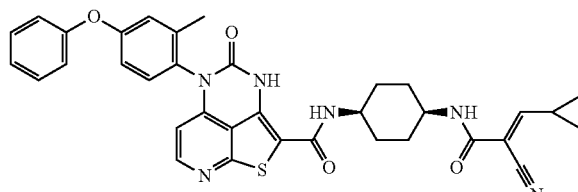

Step A: N-((1S,4S)-4-Aminocyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1 Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl ((1S,4S)-4-aminocyclohexyl)carbamate.

Step B: N-((1S,4S)-4-((E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide To a solution of (E)-2-cyano-3-cyclopropylprop-2-enoic acid (27 mg, 0.20 mmol), HATU (114 mg, 0.300 mmol), and triethylamine (40 mg, 0.40 mmol) in DMF (2 mL) was added N-((1S,4S)-4-aminocyclohexyl)-5-(2-methyl-4-phenoxyphenyl)-4-oxo-4,5-dihydro-3H-1-thia-3,5,8-triazaacenaphthylene-2-carboxamide (also Example 25, 103 mg, 0.200 mmol) and was stirred at rt for 4 hours. The mixture was purified by flash column chromatography, then by preparative TLC to yield the title compound (43 mg, 33% yield). MS (ESI): mass calcd. for $C_{35}H_{32}N_6O_4S$, 632.7; m/z found, 633.2 $[M+H]^+$. $^1$H NMR (400 MHz, DMSO-$d_6$): δ 10.17 (br, 1H), 8.40-8.24 (m, 1H), 7.94-7.78 (m, 1H), 7.76-7.61 (m, 1H), 7.46-7.40 (m, 2H), 7.39-7.28 (m, 1H), 7.21-7.15 (m, 1H), 7.13-7.03 (m, 3H), 6.99-6.88 (m, 2H), 6.04-5.86 (m, 1H), 3.92-3.81 (m, 1H), 3.79-3.72 (m, 1H), 2.04 (s, 3H), 1.85-1.50 (m, 9H), 1.20-1.08 (m, 2H), 0.99-0.81 (m, 2H).

Example 20: N-((1S,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide

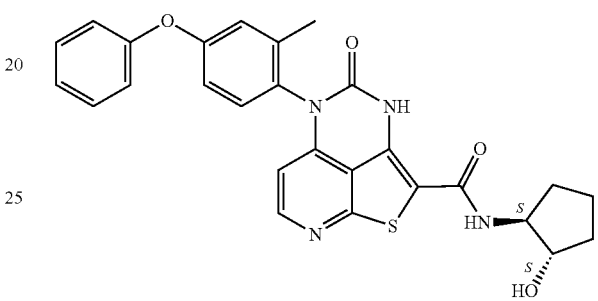

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1S,2S)-2-aminocyclopentanol. MS (ESI): mass calcd. for $C_{27}H_{24}N_4O_4S$, 500.6; m/z found, 501.1 $[M+H]^+$. $^1$H NMR (400 MHz, CD$_3$OD): δ 8.34-8.27 (m, 1H), 7.44-7.34 (m, 2H), 7.33-7.25 (m, 1H), 7.20-7.13 (m, 1H), 7.11-7.02 (m, 3H), 7.00-6.92 (m, 1H), 6.10-6.03 (m, 1H), 4.17-4.07 (m, 2H), 2.19-2.09 (m, 4H), 2.03-1.95 (m, 1H), 1.80-1.72 (m, 2H), 1.64-1.55 (m, 2H).

Example 21: 5-(2-Methyl-4-phenoxyphenyl)-N-((1R,2R)-2-(methylamino)cyclopentyl)-4-oxo-4,5-dihydro-3H-1-thia-3,5,8-triazaacenaphthylene-2-carboxamide

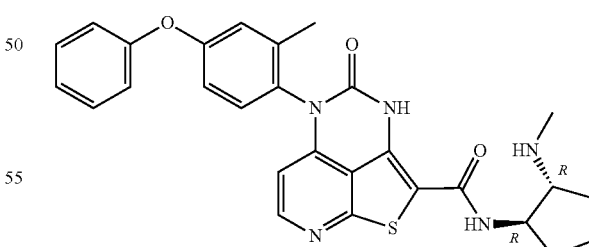

Step A: N-((1R,2R)-2-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,2R)-2-aminocyclopentyl]carbamate, in Step A.

Step B: 5-(2-Methyl-4-phenoxyphenyl)-N-((1R,2R)-2-(methylamino)cyclopentyl)-4-oxo-4,5-dihydro-3H-1-thia-3,5,8-triazaacenaphthylene-2-carboxamide A solution of N-((1R,2R)-2-aminocyclopentyl)-5-(2-methyl-4-phenoxyphenyl)-4-oxo-4,5-dihydro-3H-1-thia-3,5,8-triazaacenaphthylene-2-carboxamide (248 mg, 0.463 mmol), paraformaldehyde (2 g), 4 A molecular Sieve (4 g) in DCM (75 mL) was stirred at rt under $N_2$ for 16 h. The mixture was filtered and concentrated to dryness to yield the title compound (19 mg, 8% yield). MS (ESI): mass calcd. for $C_{28}H_{27}N_5O_3S$, 513.6; m/z found, 514.7 $[M+H]^+$.

Example 22: N-((1R,2R)-2-Aminocyclopentyl)-5-(2-methyl-4-phenoxyphenyl)-4-oxo-4,5-dihydro-3H-1-thia-3,5,8-triazaacenaphthylene-2-carboxamide

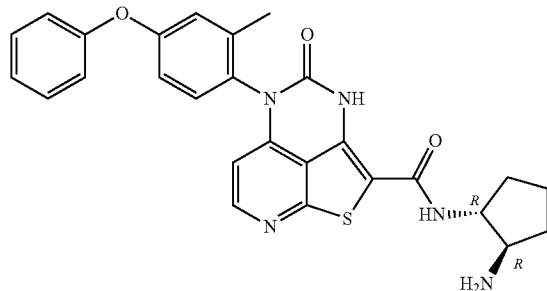

The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,2R)-2-aminocyclopentyl]carbamate, in Step A. MS (ESI): mass calcd. for $C_{27}H_{25}N_5O_3S$, 499.6; m/z found, 500.1 $[M+H]^+$. $^1$H NMR (400 MHz, DMSO-d$_6$ and CD$_3$OD): δ 8.05-7.98 (m, 1H), 7.38-7.28 (m, 2H), 7.12-7.05 (m, 2H), 7.05-6.98 (m, 2H), 6.98-6.94 (m, 1H), 6.89-6.84 (m, 1H), 5.70-5.65 (m, 1H), 4.04-3.86 (m, 2H), 3.29-3.22 (m, 1H), 2.10-2.00 (m, 2H), 1.99-1.96 (m, 3H), 1.74-1.62 (m, 3H), 1.56-1.47 (m, 1H).

Example 23: N-((1S,4S)-4-Cyanamidocyclohexyl)-5-(2-methyl-4-phenoxyphenyl)-4-oxo-4,5-dihydro-3H-1-thia-3,5,8-triazaacenaphthylene-2-carboxamide

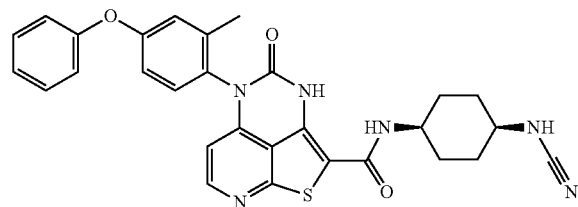 [SMILES: Cc1cc(Oc2ccccc2)ccc1N1C(=O)Nc2c(C(=O)N[C@H]3CC[C@@H](NC#N)CC3)sc3nccc1c23]

To a solution of N-((1S,4S)-4-aminocyclohexyl)-5-(2-methyl-4-phenoxyphenyl)-4-oxo-4,5-dihydro-3H-1-thia-3,5,8-triazaacenaphthylene-2-carboxamide (Example 25, 103 mg, 0.200 mmol) and triethylamine (40 mg, 0.4 mmol) in DCM (5 mL) was added BrCN (21 mg, 0.20 mmol) and was stirred at rt for 2 h. The mixture was purified by flash column chromatography to yield the title compound (30 mg, 28% yield). MS (ESI): mass calcd. for $C_{29}H_{26}N_6O_3S$, 538.6; m/z found, 539.3 $[M+H]^+$. $^1$H NMR (400 MHz, DMSO-d$_6$): δ 10.22 (br, 1H), 8.37-8.21 (m, 1H), 8.15-7.89 (m, 1H), 7.46-7.40 (m, 2H), 7.40-7.29 (m, 1H), 7.20-7.16 (m, 1H), 7.13-7.09 (m, 2H), 7.08-7.04 (m, 1H), 6.99-6.93 (m, 1H), 6.80-6.70 (m, 1H), 6.04-5.83 (m, 1H), 3.87-3.76 (m, 1H), 3.37-3.35 (m, 1H), 2.04 (s, 3H), 1.75-1.57 (m, 8H).

Example 24: N-((1R,3S)-3-(Dimethylamino)cyclohexyl)-5-(2-methyl-4-phenoxyphenyl)-4-oxo-4,5-dihydro-3H-1-thia-3,5,8-triazaacenaphthylene-2-carboxamide

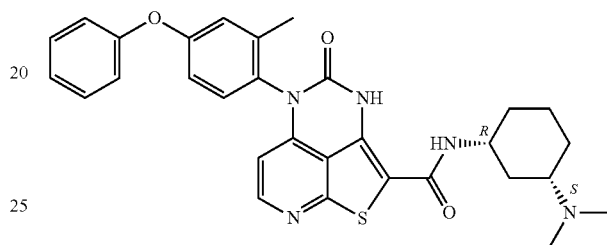

Step A: N-((1R,3S)-3-Aminocyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1S,3R)-cyclohexane-1,3-diamine.

Step B: N-((1R,3S)-3-(Dimethylamino)cyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 7, Step B. MS (ESI): mass calcd. for $C_{30}H_{31}N_5O_3S$, 541.7; m/z found, 542.2 $[M+H]^+$. $^1$H NMR (400 MHz, CD$_3$OD): δ 8.17 (d, J=5.6 Hz, 1H), 7.42-7.35 (m, 2H), 7.25-7.20 (m, 1H), 7.17-7.12 (m, 1H), 7.11-7.06 (m, 2H), 7.05-7.02 (m, 1H), 7.00-6.93 (m, 1H), 5.91 (d, J=5.6 Hz, 1H), 3.98-3.89 (m, 1H), 2.59-2.49 (m, 1H), 2.37 (s, 6H), 2.24-2.18 (m, 1H), 2.11 (s, 3H), 2.02-1.97 (m, 1H), 1.95-1.86 (m, 2H), 1.49-1.39 (m, 2H), 1.35-1.30 (m, 2H).

Example 25: N-((1S,4S)-4-Aminocyclohexyl)-5-(2-methyl-4-phenoxyphenyl)-4-oxo-4,5-dihydro-3H-1-thia-3,5,8-triazaacenaphthylene-2-carboxamide

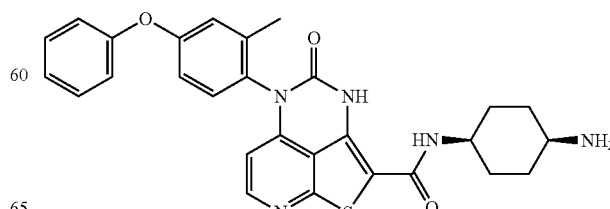

The title compound is Example 19, product from Step A. MS (ESI): mass calcd. for $C_{28}H_{27}N_5O_3S$, 513.6; m/z found, 514.3 [M+H]+.

Example 26: 5-(2-Methyl-4-phenoxyphenyl)-4-oxo-N-((1R,2R)-2-propionamidocyclopentyl)-4,5-dihydro-3H-1-thia-3,5,8-triazaacenaphthylene-2-carboxamide

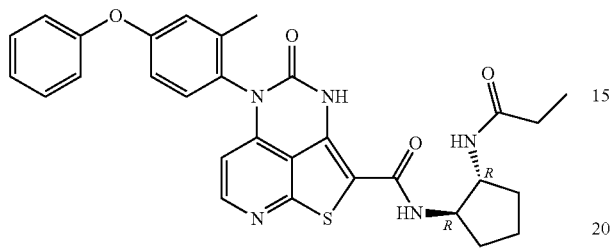

The title compound was prepared in a manner analogous to Example 11, Step B, using N-((1R,2R)-2-aminocyclopentyl)-5-(2-methyl-4-phenoxyphenyl)-4-oxo-4,5-dihydro-3H-1-thia-3,5,8-triazaacenaphthylene-2-carboxamide (Example 11, product from Step A) and propanoyl chloride. MS (ESI): mass calcd. for $C_{30}H_{29}N_5O_4S$, 555.6; m/z found, 556.6 [M+H]+. 1H NMR (400 MHz, DMSO-$d_6$): δ 10.20 (s, 1H), 8.39-8.03 (m, 2H), 7.92-7.83 (m, 1H), 7.46-7.37 (m, 2H), 7.37-7.27 (m, 1H), 7.19-7.13 (m, 1H), 7.12-7.03 (m, 3H), 6.98-6.91 (m, 1H), 5.98-5.80 (m, 1H), 4.16-4.02 (m, 2H), 2.05-1.98 (m, 5H), 1.97-1.89 (m, 2H), 1.68-1.59 (m, 2H), 1.56-1.47 (m, 1H), 1.42-1.34 (m, 1H), 0.92 (t, J=7.6 Hz, 3H).

Example 27: N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide

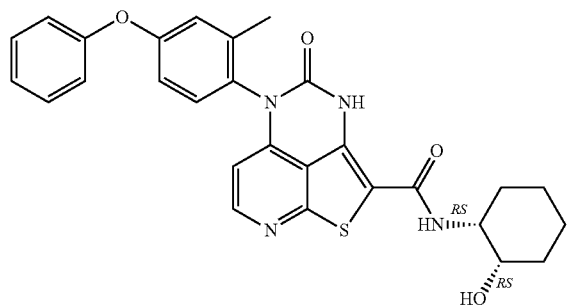 [SMILES: Cc1cc(Oc2ccccc2)ccc1N1C(=O)Nc2c(C(=O)N[C@@H]3CCCC[C@@H]3O)sc3nccc1c23]

The title compound was prepared in a manner analogous to Example 3, using 5-(2-methyl-4-phenoxyphenyl)-4-oxo-4,5-dihydro-3H-1-thia-3,5,8-triazaacenaphthylene-2-carbonyl chloride (Intermediate 8) and (1RS,2RS)-2-aminocyclohexanol in Step B. MS (ESI): mass calcd. for $C_{28}H_{26}N_4O_4S$, 514.6; m/z found, 515.1 [M+H]+. 1H NMR (400 MHz, CD3OD): δ 8.36-8.31 (m, 1H), 7.44-7.34 (m, 2H), 7.33-7.25 (m, 1H), 7.20-7.13 (m, 1H), 7.11-7.02 (m, 3H), 7.00-6.92 (m, 1H), 6.10-6.03 (m, 1H), 4.06-3.90 (m, 2H), 2.13 (s, 3H), 1.87-1.76 (m, 3H), 1.67-1.59 (m, 3H), 1.50-1.38 (m, 2H).

Example 28: N-Cyclopentyl-5-(2-methyl-4-phenoxyphenyl)-4-oxo-4,5-dihydro-3H-1-thia-3,5,8-triazaacenaphthylene-2-carboxamide

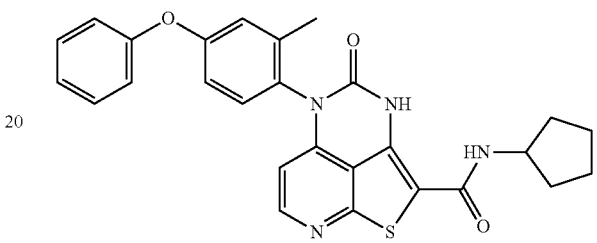

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and cyclopentanamine, no HCl/MeOH deprotection. MS (ESI): mass calcd. for $C_{27}H_{24}N_4O_3S$, 484.6; m/z found, 485.2 [M+H]+. 1H NMR (400 MHz, CD3OD): δ 8.32 (d, J=5.6 Hz, 1H), 7.45-7.36 (m, 2H), 7.34-7.27 (m, 1H), 7.22-7.14 (m, 1H), 7.12-7.03 (m, 3H), 7.02-6.92 (m, 1H), 6.06 (d, J=5.5 Hz, 1H), 4.35-4.26 (m, 1H), 2.12 (s, 3H), 2.06-1.98 (m, 2H), 1.83-1.75 (m, 2H), 1.67-1.56 (m, 4H).

Example 29: N-((1R,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide

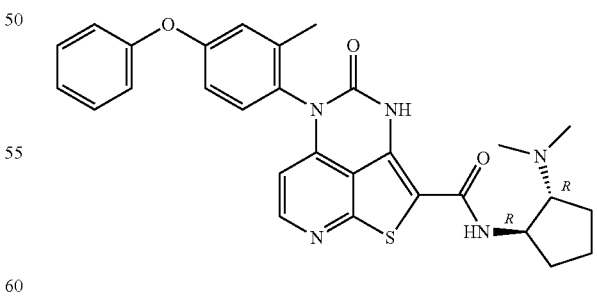

The title compound was prepared in a manner analogous to Example 7, Step B, using N-((1R,2R)-2-aminocyclopentyl)-5-(2-methyl-4-phenoxyphenyl)-4-oxo-4,5-dihydro-3H-1-thia-3,5,8-triazaacenaphthylene-2-carboxamide (Example 22). MS (ESI): mass calcd. for $C_{29}H_{29}N_5O_3S$, 527.6; m/z found, 528.0 [M+H]+.

Example 30: N-((1r,3s,5R,7S)-3-Hydroxyadamantan-1-yl)-5-(2-methyl-4-phenoxyphenyl)-4-oxo-4,5-dihydro-3H-1-thia-3,5,8-triazaacenaphthylene-2-carboxamide

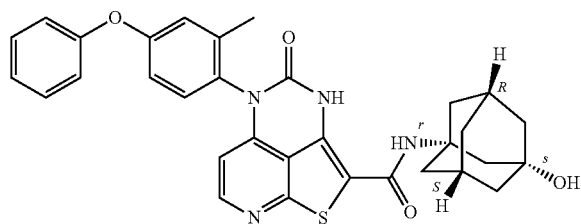

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1s,3r,5R,7S)-3-aminoadamantan-1-ol. MS (ESI): mass calcd. for $C_{32}H_{30}N_4O_4S$, 566.7; m/z found, 567.0 [M+H]$^+$.

Example 31: 5-(2-Methyl-4-phenoxyphenyl)-N-(2-(methylamino)cyclohexyl)-4-oxo-4,5-dihydro-3H-1-thia-3,5,8-triazaacenaphthylene-2-carboxamide

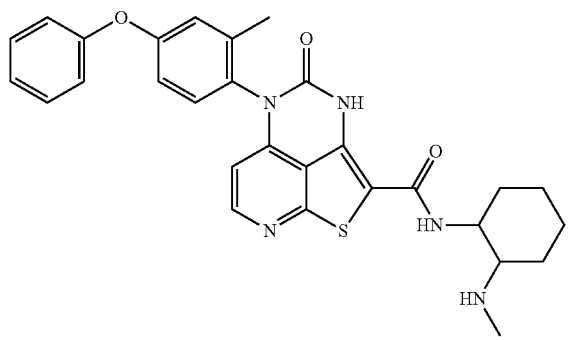 [SMILES: CNC1CCCCC1NC(=O)c1sc2nccc3c2c1NC(=O)N3c1ccc(Oc2ccccc2)cc1C]

Step A: 5-(2-Methyl-4-phenoxyphenyl)-4-oxo-N-(2-oxocyclohexyl)-4,5-dihydro-3H-1-thia-3,5,8-triazaacenaphthylene-2-carboxamide To a solution of N-(2-hydroxycyclohexyl)-5-(2-methyl-4-phenoxyphenyl)-4-oxo-4,5-dihydro-3H-1-thia-3,5,8-triazaacenaphthylene-2-carboxamide (Example 36, 800 mg, 1.55 mmol) in DCM (10 mL) was added Dess-Martin periodinane (988 mg, 2.33 mmol) and was reacted at rt for 4 h, concentrated to dryness, and purified by flash column chromatography to give the title compound as a yellow solid (500 mg).

Step B: 5-(2-Methyl-4-phenoxyphenyl)-N-(2-(methylamino)cyclohexyl)-4-oxo-4,5-dihydro-3H-1-thia-3,5,8-triazaacenaphthylene-2-carboxamide To a solution of 5-(2-methyl-4-phenoxyphenyl)-4-oxo-N-(2-oxocyclohexyl)-4,5-dihydro-3H-1-thia-3,5,8-triazaacenaphthylene-2-carboxamide (500 mg, 0.98 mmol) in DCM (5 mL) were added methylamine (5 mL) and NaBH(OAc)$_3$ (500 mg, 0.98 mmol) and was reacted at rt for 4 h. The reaction was quenched by the addition of H$_2$O (20 mL), extracted with DCM, dried over anhydrous Na$_2$SO$_4$, filtered, and concentrated to dryness. The residue was purified by flash column chromatography to give the title compound as a yellow solid (200 mg). MS (ESI): mass calcd. for $C_{29}H_{29}N_5O_3S$, 527.6; m/z found, 528.2 [M+H]$^+$. $^1$H NMR (400 MHz, CD$_3$OD): δ 8.38 (s, 1H), 8.35-8.29 (m, 1H), 7.44-7.34 (m, 2H), 7.30-7.25 (m, 1H), 7.20-7.13 (m, 1H), 7.11-7.02 (m, 3H), 7.00-6.92 (m, 1H), 6.12-6.05 (m, 1H), 4.72-4.02 (m, 1H), 3.38-3.01 (m, 1H), 2.77-2.64 (m, 3H), 2.29-2.15 (m, 1H), 2.15-2.05 (m, 3H), 2.04-1.73 (m, 4H), 1.65-1.38 (m, 3H).

Example 32: N-((1S,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide

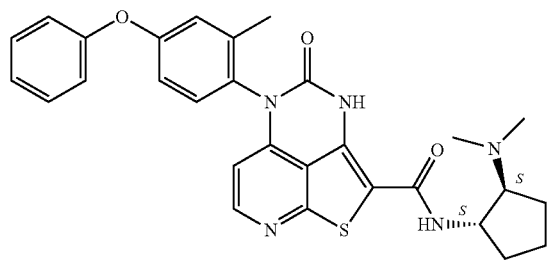

The title compound was prepared in a manner analogous to Example 7, Step B, using N-((1S,2S)-2-amino cyclopentyl)-5-(2-methyl-4-phenoxyphenyl)-4-oxo-4,5-dihydro-3H-1-thia-3,5,8-triazaacenaphthylene-2-carboxamide (Example 41). MS (ESI): mass calcd. for $C_{29}H_{29}N_5O_3S$, 527.6; m/z found, 528.1 [M+H]$^+$.

Example 33: N-((1R,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide

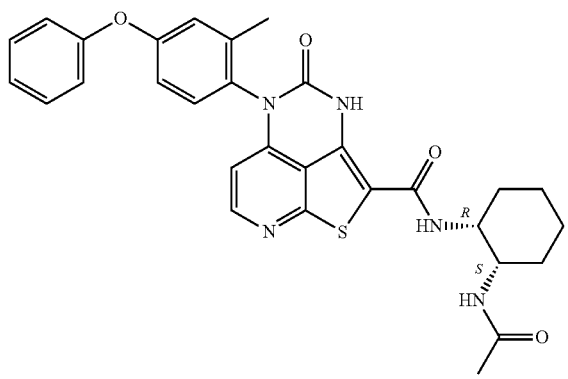

The title compound was prepared in a manner analogous to Example 11, Steps A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2R)-2-aminocyclohexyl]carbamate, in Step A. MS (ESI): mass calcd. for $C_{30}H_{29}N_5O_4S$, 555.6; m/z found, 556.2 [M+H]$^+$. $^1$H NMR (400 MHz, CDCl$_3$): δ 9.55-9.38

(m, 1H), 8.37-8.27 (m, 1H), 7.41-7.33 (m, 2H), 7.19-7.13 (m, 2H), 7.11-7.05 (m, 2H), 7.01-6.89 (m, 3H), 6.18-6.04 (m, 1H), 6.01-5.93 (m, 1H), 4.20-4.07 (m, 2H), 2.12-2.09 (m, 3H), 2.07 (s, 3H), 2.02-1.98 (m, 1H), 1.88-1.75 (m, 3H), 1.65-1.56 (m, 4H).

Example 34: 5-(2-Methyl-4-phenoxyphenyl)-4-oxo-N-((1R,2S)-2-propionamidocyclopentyl)-4,5-dihydro-3H-1-thia-3,5,8-triazaacenaphthylene-2-carboxamide

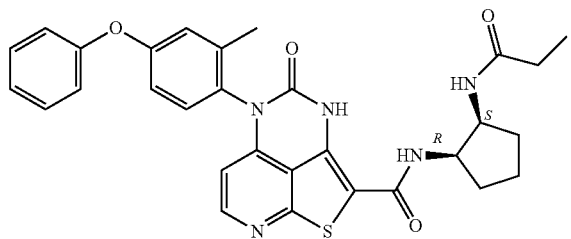

The title compound was prepared in a manner analogous to Example 11, Steps A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2R)-2-aminocyclopentyl]carbamate, in Step A, and propanoyl chloride in Step B. MS (ESI): mass calcd. for $C_{30}H_{29}N_5O_4S$, 555.6; m/z found, 556.2 [M+H]$^+$. $^1$H NMR (400 MHz, CD$_3$OD): δ 8.29 (d, J=5.0, 1H), 7.45-7.35 (m, 2H), 7.32-7.25 (m, 1H), 7.20-7.14 (m, 1H), 7.12-7.03 (m, 3H), 7.01-6.92 (m, 1H), 6.04 (d, J=5.3, 1H), 4.44-4.30 (m, 2H), 2.25-2.17 (m, 2H), 2.11 (s, 3H), 2.08-1.97 (m, 2H), 1.93-1.84 (m, 1H), 1.78-1.60 (m, 3H), 1.08 (t, J=7.6, 3H).

Example 35: 5-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide

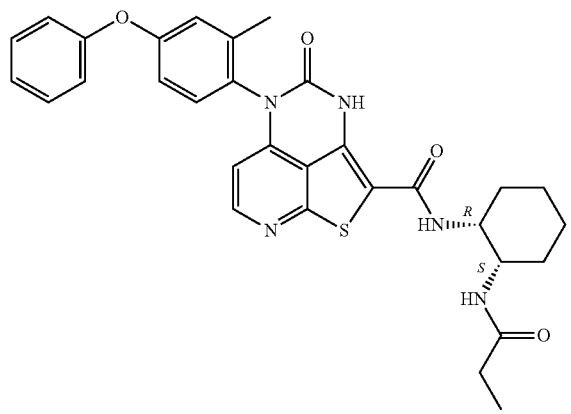

To a solution of N-((1R,2S)-2-aminocyclohexyl)-5-(2-methyl-4-phenoxyphenyl)-4-oxo-4,5-dihydro-3H-1-thia-3,5,8-triazaacenaphthylene-2-carboxamide (Example 10, 150 mg, 0.29 mmol) in DCM was added triethylamine, then propanoyl propanoate (38 mg, 0.29 mmol) in DCM was added dropwise and was stirred at rt for 2 h. The reaction was concentrated to dryness and purified by flash column chromatography, then preparative TLC to give the title compound as a yellow solid (55 mg). MS (ESI): mass calcd. for $C_{31}H_{31}N_5O_4S$, 569.7; m/z found, 570.3 [M+H]$^+$. $^1$H NMR (400 MHz, CDCl$_3$): δ 9.72-9.60 (m, 1H), 8.45-8.30 (m, 1H), 7.41-7.37 (m, 3H), 7.23-7.14 (m, 2H), 7.10-7.06 (m, 2H), 7.00-6.93 (m, 2H), 6.52-6.31 (m, 1H), 6.26-6.06 (m, 1H), 4.31-4.22 (m, 1H), 4.16-4.08 (m, 1H), 2.43-2.25 (m, 2H), 2.16-2.05 (m, 3H), 1.97-1.89 (m, 1H), 1.78-1.68 (m, 3H), 1.62-1.41 (m, 4H), 1.21-1.13 (m, 3H).

Example 36: N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide

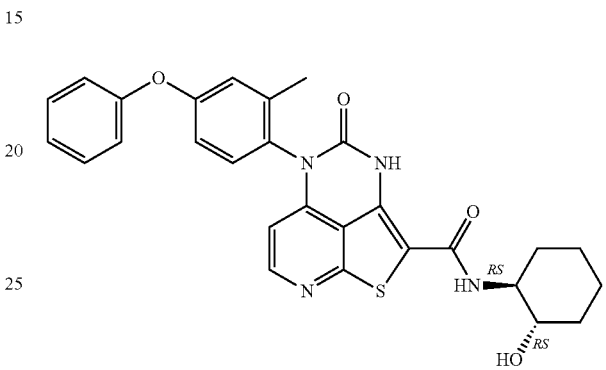

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1RS,2RS)-2-aminocyclohexanol. MS (ESI): mass calcd. for $C_{28}H_{26}N_4O_4S$, 514.6; m/z found, 515.2 [M+H]$^+$. $^1$H NMR (400 MHz, CD$_3$OD): δ 8.35-8.26 (m, 1H), 7.46-7.35 (m, 2H), 7.31-7.28 (m, 1H), 7.19-7.12 (m, 1H), 7.08-7.04 (m, 3H), 7.00-6.93 (m, 1H), 6.09-6.02 (m, 1H), 3.85-3.74 (m, 1H), 3.56-3.43 (m, 1H), 2.11 (s, 3H), 2.05-1.93 (m, 2H), 1.82-1.66 (m, 2H), 1.39-1.27 (m, 4H).

Example 37: N-((1R,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide

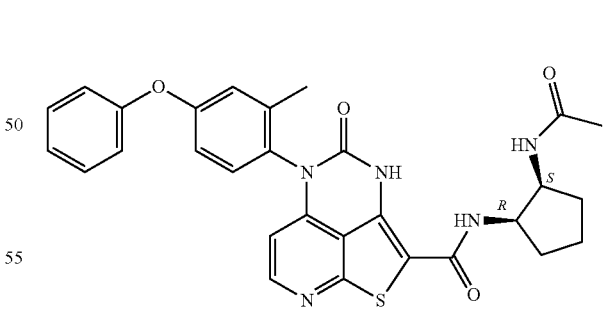

The title compound was prepared in a manner analogous to Example 11, Steps A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2R)-2-aminocyclopentyl]carbamate in Step A, and acetyl chloride in Step B. MS (ESI): mass calcd. for $C_{29}H_{27}N_5O_4S$, 541.6; m/z found, 542.2 [M+H]$^+$. $^1$H NMR (400 MHz, CD$_3$OD): δ 8.31 (d, J=5.6, 1H), 7.43-7.36 (m, 2H), 7.32-7.24 (m, 1H), 7.19-7.13 (m, 1H), 7.11-7.03 (m, 3H), 7.00-6.93 (m, 1H), 6.08-6.03 (m, 1H), 4.44-4.28 (m, 2H), 2.14-2.09 (m, 3H), 2.09-1.97 (m, 2H), 1.95-1.92 (m, 3H), 1.92-1.81 (m, 1H), 1.77-1.59 (m, 3H).

Example 38: N-((1R,2R)-2-Aminocyclohexyl)-5-(2-methyl-4-phenoxyphenyl)-4-oxo-4,5-dihydro-3H-1-thia-3,5,8-triazaacenaphthylene-2-carboxamide

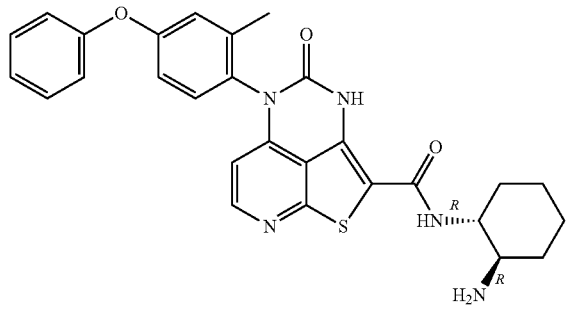

Step A: tert-Butyl ((1R,2R)-2-(5-(2-methyl-4-phenoxyphenyl)-4-oxo-4,5-dihydro-3H-1-thia-3,5,8-triazaacenaphthylene-2-carboxamido)cyclohexyl)carbamate A solution of 5-(2-methyl-4-phenoxyphenyl)-4-oxo-4,5-dihydro-3H-1-thia-3,5,8-triazaacenaphthylene-2-carbonyl chloride (Intermediate 8, 980 mg, 2.25 mmol), tert-butyl N-[(1R,2R)-2-aminocyclohexyl]carbamate (1.0 g, 4.7 mmol), and triethylamine (227 mg, 2.25 mmol) in DCM (10 mL) was reacted at rt for 2 h, then quenched with $H_2O$ (10 mL), extracted with DCM, dried over anhydrous $Na_2SO_4$, filtered, and concentrated to dryness to give the title compound as a yellow solid (1.3 g, 94% yield).

Step B: N-((1R,2R)-2-Aminocyclohexyl)-5-(2-methyl-4-phenoxyphenyl)-4-oxo-4,5-dihydro-3H-1-thia-3,5,8-triazaacenaphthylene-2-carboxamide To a solution of tert-butyl ((1R,2R)-2-(5-(2-methyl-4-phenoxyphenyl)-4-oxo-4,5-dihydro-3H-1-thia-3,5,8-triazaacenaphthylene-2-carboxamido)cyclohexyl)carbamate (1.3 g, 2.1 mmol) in MeOH (10 mL) was added concentrated HCl (2 mL) and was stirred at rt for 20 min. The reaction was quenched by the addition of $H_2O$ (10 mL), extracted with DCM, dried over anhydrous $Na_2SO_4$, filtered, and concentrated to dryness. The residue was purified by flash column chromatography to give the title compound as a yellow solid (800 mg, 74% yield). MS (ESI): mass calcd. for $C_{28}H_{27}N_5O_3S$, 513.6; m/z found, 514.1 [M+H]$^+$. $^1$H NMR (400 MHz, $CD_3OD$): δ 8.16-8.12 (m, 1H), 7.42-7.33 (m, 2H), 7.27-7.12 (m, 2H), 7.09-7.01 (m, 3H), 7.00-6.92 (m, 1H), 5.91-5.85 (m, 1H), 3.91-3.81 (m, 1H), 3.11-2.96 (m, 1H), 2.13-2.01 (m, 5H), 1.85-1.77 (m, 2H), 1.55-1.35 (m, 4H).

Example 39: N-((1S,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide

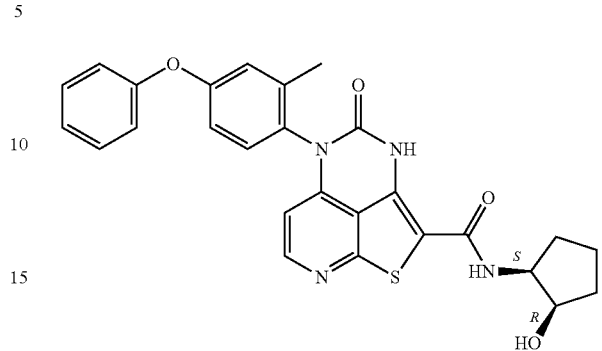

The title compound was prepared in a manner analogous to Example 3, Steps A-B, using 5-(2-methyl-4-phenoxyphenyl)-4-oxo-4,5-dihydro-3H-1-thia-3,5,8-triazaacenaphthylene-2-carbonyl chloride and (1R,2S)-2-aminocyclopentanol in Step B. MS (ESI): mass calcd. for $C_{27}H_{24}N_4O_4S$, 500.6; m/z found, 501.2 [M+H]$^+$. $^1$H NMR (400 MHz, $CD_3OD$): δ 8.34-8.27 (m, 1H), 7.44-7.34 (m, 2H), 7.33-7.25 (m, 1H), 7.20-7.13 (m, 1H), 7.11-7.02 (m, 3H), 7.00-6.92 (m, 1H), 6.10-6.03 (m, 1H), 4.26-4.11 (m, 2H), 2.12 (s, 3H), 2.05-1.87 (m, 3H), 1.79-1.60 (m, 3H).

Example 40: N-((1S,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide

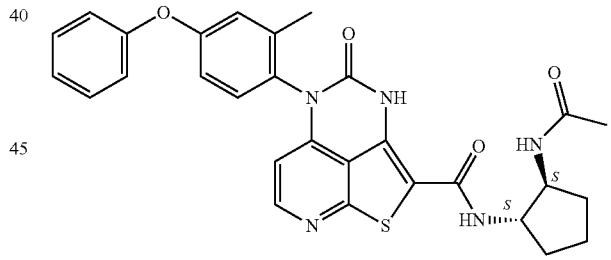

The title compound was prepared in a manner analogous to Example 11, Steps A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2S)-2-aminocyclopentyl]carbamate in Step A, and acetyl chloride in Step B. MS (ESI): mass calcd. for $C_{29}H_{27}N_5O_4S$, 541.6; m/z found, 542.4 [M+H]$^+$. $^1$H NMR (400 MHz, DMSO-$d_6$): δ 10.21 (s, 1H), 8.29 (d, J=5.3 Hz, 1H), 8.20-8.05 (m, 1H), 8.03-7.90 (m, 1H), 7.47-7.38 (m, 2H), 7.38-7.32 (m, 1H), 7.21-7.15 (m, 1H), 7.12-7.07 (m, 2H), 7.07-7.02 (m, 1H), 6.98-6.90 (m, 1H), 5.93 (d, J=5.1 Hz, 1H), 4.21-3.98 (m, 2H), 2.03 (s, 3H), 1.99-1.89 (m, 2H), 1.75 (s, 3H), 1.71-1.60 (m, 2H), 1.59-1.45 (m, 1H), 1.4-1.34 (m, 1H).

Example 41: N-((1S,2S)-2-Aminocyclopentyl)-5-(2-methyl-4-phenoxyphenyl)-4-oxo-4,5-dihydro-3H-1-thia-3,5,8-triazaacenaphthylene-2-carboxamide

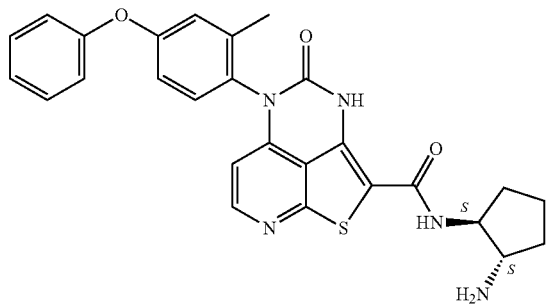

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2S)-2-aminocyclopentyl]carbamate. MS (ESI): mass calcd. for $C_{27}H_{25}N_5O_3S$, 499.6; m/z found, 500.1 $[M+H]^+$.

Example 42: 5-(2-Methyl-4-phenoxyphenyl)-4-oxo-N-((1S,2R)-2-propionamidocyclohexyl)-4,5-dihydro-3H-1-thia-3,5,8-triazaacenaphthylene-2-carboxamide

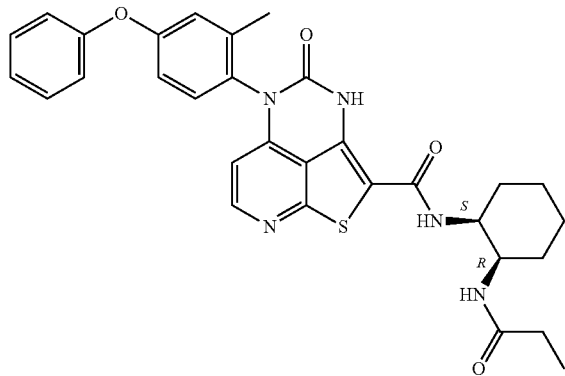

Step A: N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,2S)-2-aminocyclohexyl]carbamate, in Step A.

Step B: 5-(2-Methyl-4-phenoxyphenyl)-4-oxo-N-((1S,2R)-2-propionamidocyclohexyl)-4,5-dihydro-3H-1-thia-3,5,8-triazaacenaphthylene-2-carboxamide To a solution of N-((1S,2R)-2-amino cyclohexyl)-5-(2-methyl-4-phenoxyphenyl)-4-oxo-4,5-dihydro-3H-1-thia-3,5,8-triazaacenaphthylene-2-carboxamide (120 mg, 0.22 mmol) in DCM (30 mL) were added propionic anhydride (34 mg, 0.26 mmol) and DMAP (2.7 mg, 0.022 mmol). The reaction was stirred at rt for 30 min, concentrated to dryness, and purified by flash column chromatography to give the title compound as a yellow solid (81 mg, 64% yield). MS (ESI): mass calcd. for $C_{31}H_{31}N_5O_4S$, 569.7; m/z found, 570.3 $[M+H]^+$. $^1H$ NMR (400 MHz, DMSO-$d_6$): δ 9.98 (d, J=11.8 Hz, 1H), 8.32 (d, J=5.4 Hz, 1H), 7.80-7.64 (m, 1H), 7.57-7.47 (m, 1H), 7.47-7.40 (m, 2H), 7.39-7.32 (m, 1H), 7.24-7.14 (m, 1H), 7.14-7.03 (m, 3H), 7.02-6.88 (m, 1H), 5.97 (d, J=5.4 Hz, 1H), 4.20-4.05 (m, 1H), 4.04-3.92 (m, 1H), 2.26-2.12 (m, 2H), 2.05 (s, 3H), 1.72-1.60 (m, 4H), 1.58-1.47 (m, 2H), 1.42-1.28 (m, 2H), 1.03-0.92 (m, 3H).

Example 43: N-((1R,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide

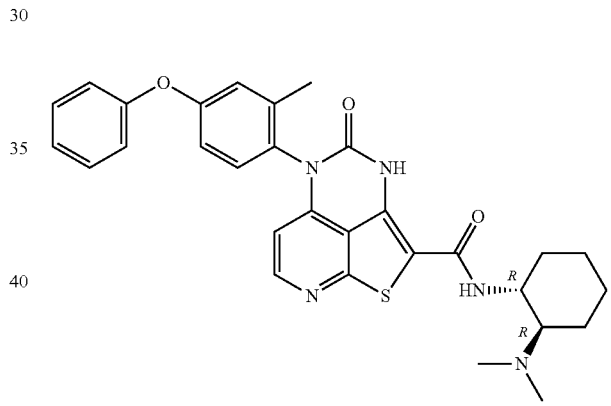

To a solution of N-((1R,2R)-2-aminocyclohexyl)-5-(2-methyl-4-phenoxyphenyl)-4-oxo-4,5-dihydro-3H-1-thia-3,5,8-triazaacenaphthylene-2-carboxamide (Example 38, 100 mg, 0.2 mmol) in DCM (4 mL) were added formaldehyde (1 mL) and NaBH(OAc)$_3$ (200 mg, 0.94 mmol) and was reacted at rt overnight. The reaction was quenched by the addition of H$_2$O (10 mL), extracted with DCM, dried over anhydrous Na$_2$SO$_4$, filtered, and concentrated to dryness. The residue was purified by flash column chromatography to give the title compound as a yellow solid (41 mg, 39% yield). MS (ESI): mass calcd. for $C_{30}H_{31}N_5O_3S$, 541.7; m/z found, 542.2 $[M+H]^+$. $^1H$ NMR (400 MHz, CD$_3$OD): δ 8.31-8.27 (m, 1H), 7.43-7.35 (m, 2H), 7.32-7.23 (m, 1H), 7.20-7.13 (m, 1H), 7.11-7.03 (m, 3H), 7.00-6.94 (m, 1H), 6.09-6.02 (m, 1H), 4.33-4.17 (m, 1H), 3.44-3.31 (m, 1H), 2.82 (s, 3H), 2.81 (s, 3H), 2.21-2.11 (m, 1H), 2.10-2.06 (m, 3H), 2.05-2.00 (m, 1H), 1.98-1.91 (m, 1H), 1.87-1.79 (m, 1H), 1.71-1.51 (m, 2H), 1.49-1.36 (m, 2H).

Example 44: N-((1S,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide

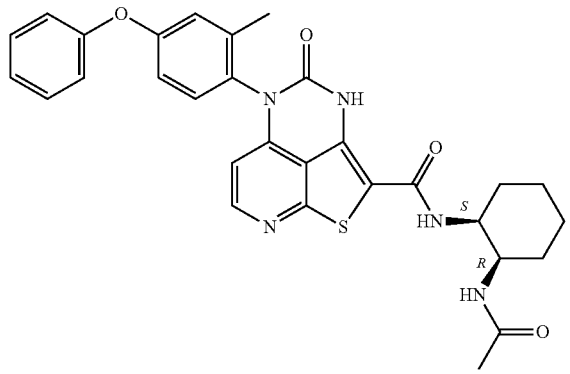

The title compound was prepared in a manner analogous to Example 11, Steps A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl, in Step A, and using acetyl chloride in Step B. MS (ESI): mass calcd. for $C_{30}H_{29}N_5O_4S$, 555.6; m/z found, 556.2 [M+H]$^+$. $^1$H NMR (400 MHz, DMSO-d$_6$): δ 9.98 (s, 1H), 8.32 (d, J=5.4 Hz, 1H), 7.76 (d, J=7.2 Hz, 1H), 7.68-7.56 (m, 1H), 7.49-7.32 (m, 3H), 7.23-7.14 (m, 1H), 7.14-7.05 (m, 3H), 7.02-6.88 (m, 1H), 5.97 (d, J=5.5 Hz, 1H), 4.17-4.04 (m, 1H), 4.04-3.90 (m, 1H), 2.05 (s, 3H), 1.89 (s, 3H), 1.74-1.59 (m, 4H), 1.58-1.46 (m, 2H), 1.42-1.30 (m, 2H).

Example 45: 5-(2-Methyl-4-phenoxyphenyl)-4-oxo-N-((1S,2S)-2-propionamidocyclopentyl)-4,5-dihydro-3H-1-thia-3,5,8-triazaacenaphthylene-2-carboxamide

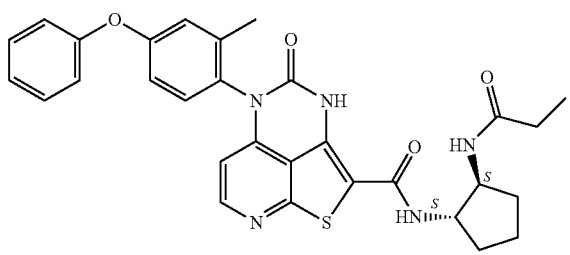

Step A: N-((1S,2S)-2-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2S)-2-aminocyclopentyl]carbamate, in Step A.

Step B: 5-(2-Methyl-4-phenoxyphenyl)-4-oxo-N-((1S,2S)-2-propionamidocyclopentyl)-4,5-dihydro-3H-1-thia-3,5,8-triazaacenaphthylene-2-carboxamide The title compound was prepared in a manner analogous to Example 42, Step B. To a solution of N-((1S,2S)-2-aminocyclopentyl)-5-(2-methyl-4-phenoxyphenyl)-4-oxo-4,5-dihydro-3H-1-thia-3,5,8-triazaacenaphthylene-2-carboxamide (100 mg, 0.2 mmol) in DCM (25 mL) was added propionic anhydride (31 mg, 0.24 mmol), followed by DMAP. The reaction was stirred at rt for 30 min, concentrated to dryness, and purified by flash column chromatography to give the title compound as a yellow solid (68 mg, 61% yield). MS (ESI): mass calcd. for $C_{30}H_{29}N_5O_4S$, 555.6; m/z found, 556.5 [M+H]$^+$. $^1$H NMR (400 MHz, DMSO-d$_6$): δ 10.19 (s, 1H), 8.28 (d, J=5.3 Hz, 1H), 8.20-8.04 (m, 1H), 7.95-7.80 (m, 1H), 7.52-7.25 (m, 3H), 7.25-7.01 (m, 4H), 6.99-6.85 (m, 1H), 5.93 (d, J=5.1 Hz, 1H), 4.30-3.95 (m, 2H), 2.14-1.79 (m, 7H), 1.70-1.58 (m, 2H), 1.57-1.33 (m, 2H), 0.92 (t, J=6.8 Hz, 3H).

Example 46: 5-(2-Methyl-4-phenoxyphenyl)-N-((1S,2S)-2-(methylamino)cyclopentyl)-4-oxo-4,5-dihydro-3H-1-thia-3,5,8-triazaacenaphthylene-2-carboxamide

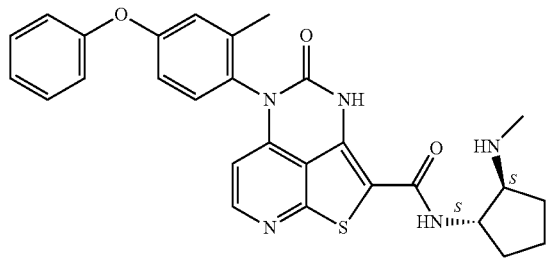

Step A: N-((1S,2S)-2-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 5, Step A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2S)-2-aminocyclopentyl]carbamate, in Step A.

Step B: 5-(2-Methyl-4-phenoxyphenyl)-N-((1S,2S)-2-(methylamino)cyclopentyl)-4-oxo-4,5-dihydro-3H-1-thia-3,5,8-triazaacenaphthylene-2-carboxamide To an oven dried round bottom flask under an N$_2$ atmosphere fitted with a reflux condenser were added N-((1S,2S)-2-aminocyclopentyl)-5-(2-methyl-4-phenoxyphenyl)-4-oxo-4,5-dihydro-3H-1-thia-3,5,8-triazaacenaphthylene-2-carboxamide (300 mg, 0.60 mmol), paraformaldehyde (200 mg, 2.2 mmol), and activated 4 A molecular sieves in anhydrous DCM (50 mL) and the reaction was refluxed for 16 hours. The reaction mixture was filtered, washed with DCM, the organic phases combined, and concentrated to dryness. The residue was purified by flash column chromatography to give the title compound as a slight yellow solid (20 mg, 6.3% yield). MS (ESI): mass calcd. for $C_{28}H_{27}N_5O_3S$, 513.6; m/z found, 514.3 [M+H]$^+$. $^1$H NMR (400 MHz, CD$_3$OD): δ 8.44 (s, 1H), 8.33 (d, J=5.4 Hz, 1H), 7.46-7.35 (m, 2H), 7.34-7.26 (m, 1H), 7.22-7.13 (m, 1H), 7.12-7.03 (m, 3H), 7.02-6.92 (m, 1H), 6.13-6.01 (m, 1H), 4.42-4.30 (m, 1H), 3.56-3.38 (m, 1H), 2.87-2.74 (m, 3H), 2.31-2.15 (m, 2H), 2.13-2.07 (m, 3H), 1.97-1.70 (m, 4H).

Example 47: N-((1R,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide

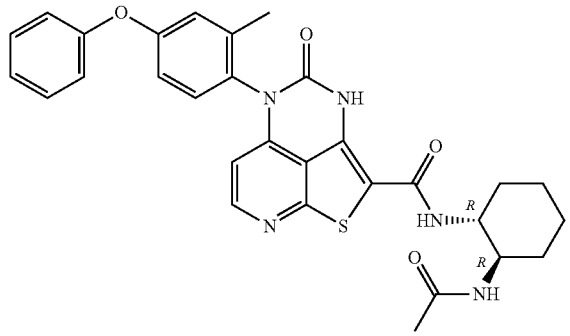

The title compound was prepared in a manner analogous to Example 3, Steps A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,2R)-2-aminocyclohexyl]carbamate in Step A, and using acetyl chloride in Step B. MS (ESI): mass calcd. for $C_{30}H_{29}N_5O_4S$, 555.6; m/z found, 556.1 [M+H]$^+$. $^1$H NMR (400 MHz, CD$_3$OD): δ 8.30 (d, J=5.5 Hz, 1H), 7.46-7.34 (m, 2H), 7.30-7.23 (m, 1H), 7.19-7.10 (m, 1H), 7.10-7.01 (m, 3H), 6.99-6.91 (m, 1H), 6.05 (d, J=5.5 Hz, 1H), 3.85-3.71 (m, 2H), 2.14-2.08 (m, 3H), 2.07-1.98 (m, 1H), 1.98-1.91 (m, 1H), 1.86 (s, 3H), 1.83-1.72 (m, 2H), 1.48-1.28 (m, 4H).

Example 48: N-((1S,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide

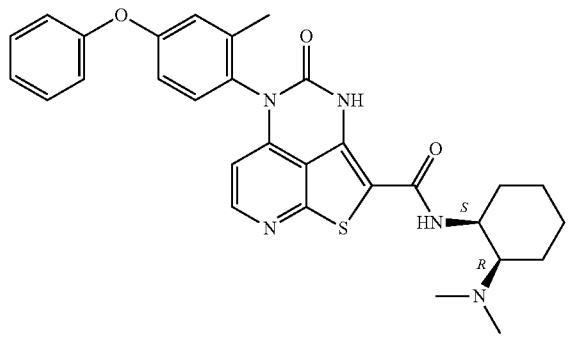

Step A: N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 3, Step B, using 5-(2-methyl-4-phenoxyphenyl)-4-oxo-4,5-dihydro-3H-1-thia-3,5,8-triazaacenaphthylene-2-carbonyl chloride (Intermediate 20) and tert-butyl N-[(1R,2S)-2-aminocyclohexyl]carbamate; followed by deprotection with HCl/MeOH.

Step B: N-((1S,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide To a solution of N-((1S,2R)-2-aminocyclohexyl)-5-(2-methyl-4-phenoxyphenyl)-4-oxo-4,5-dihydro-3H-1-thia-3,5,8-triazaacenaphthylene-2-carboxamide (150 mg, 0.27 mmol) and formaldehyde (0.5 mL) in MeOH (5 mL) was added NaBH(OAc)$_3$ (174 mg, 0.819 mmol) and was stirred at rt for 16 h, concentrated to dryness, and purified by flash column chromatography to give the title compound as a yellow solid (40 mg, 26% yield). MS (ESI): mass calcd. for $C_{30}H_{31}N_5O_3S$, 541.7; m/z found, 542.0 [M+H]$^+$. $^1$H NMR (400 MHz, DMSO-d$_6$ and CD$_3$OD): δ 8.26-8.20 (m, 1H), 8.18 (s, 1H), 7.49-7.35 (m, 2H), 7.31-7.20 (m, 1H), 7.19-7.13 (m, 1H), 7.11-7.01 (m, 3H), 6.97-6.90 (m, 1H), 5.92-5.83 (m, 1H), 4.71-4.57 (m, 1H), 2.85-2.68 (m, 1H), 2.61 (s, 3H), 2.57 (s, 3H), 2.07-2.03 (m, 3H), 1.90-1.77 (m, 2H), 1.75-1.63 (m, 1H), 1.64-1.38 (m, 4H), 1.35-1.25 (m, 1H).

Example 49: N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide

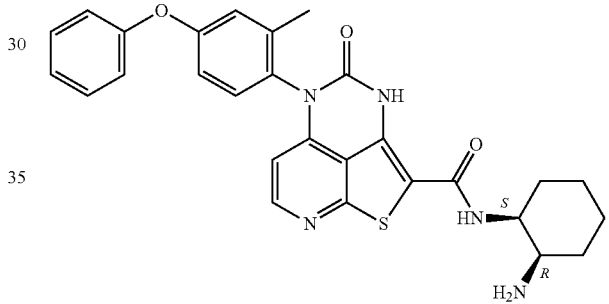

The title compound was is Example 48, product from Step A. MS (ESI): mass calcd. for $C_{28}H_{27}N_5O_3S$, 513.6; m/z found, 514.1 [M+H]$^+$.

Example 50: 5-(2-Methyl-4-phenoxyphenyl)-N-((1S,2R)-2-(methylamino)cyclohexyl)-4-oxo-4,5-dihydro-3H-1-thia-3,5,8-triazaacenaphthylene-2-carboxamide

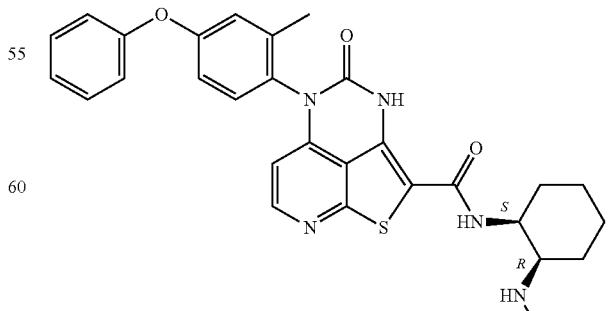

Step A: N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide The title compound is Example 48, product from Step A.

Step B: 5-(2-Methyl-4-phenoxyphenyl)-N-((1S,2R)-2-(methyleneamino)cyclohexyl)-4-oxo-4,5-dihydro-3H-1-thia-3,5,8-triazaacenaphthylene-2-carboxamide To an oven dried round bottom flask under an argon atmosphere fitted with a reflux condenser were added N-((1S,2R)-2-aminocyclohexyl)-5-(2-methyl-4-phenoxyphenyl)-4-oxo-4,5-dihydro-3H-1-thia-3,5,8-triazaacenaphthylene-2-carboxamide (100 mg, 0.20 mmol), paraformaldehyde (53 mg, 0.59 mmol), activated 4 A molecular sieves (100 mg), and anhydrous DCM (30 mL) and was refluxed for 16 hours. The reaction mixture was filtered and the residue washed with DCM. The organic phases were combined and concentrated to dryness to give the title compound as a yellow solid (100 mg, 100% yield).

Step C: (1R,2S)—N-Methyl-2-(5-(2-methyl-4-phenoxyphenyl)-4-oxo-4,5-dihydro-3H-1-thia-3,5,8-triazaacenaphthylene-2-carboxamido)-N-methylenecyclohexanaminium To a solution of 5-(2-methyl-4-phenoxyphenyl)-N-((1S,2R)-2-(methyleneamino)cyclohexyl)-4-oxo-4,5-dihydro-3H-1-thia-3,5,8-triazaacenaphthylene-2-carboxamide (410 mg, 0.78 mmol) and Pd/C (10% on carbon, 200 mg) in MeOH/EtOAc (1/3, 30 mL) was reflux under $H_2$ for 72 h, then cooled to rt, filtered, and concentrated to dryness to give the title compound as a yellow solid (280 mg, 66% yield).

Step D: 5-(2-Methyl-4-phenoxyphenyl)-N-((1S,2R)-2-(methylamino)cyclohexyl)-4-oxo-4,5-dihydro-3H-1-thia-3,5,8-triazaacenaphthylene-2-carboxamide To a solution of (1R,2S)—N-methyl-2-(5-(2-methyl-4-phenoxyphenyl)-4-oxo-4,5-dihydro-3H-1-thia-3,5,8-triazaacenaphthylene-2-carboxamido)-N-methylenecyclohexanaminium (280 mg, 0.52 mmol) in 6.0 M HCl/MeOH (15 mL) was heated at reflux overnight, then concentrated to dryness and purified by flash column chromatography to give the title compound as a yellow solid (162 mg, 59.3% yield). MS (ESI): mass calcd. for $C_{29}H_{29}N_5O_3S$, 527.6; m/z found, 528.1 [M+H]$^+$.

Example 51: N-((1S,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide

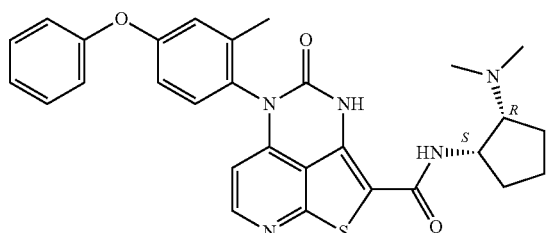

Step A: N-((1S,2R)-2-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1 Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,2S)-2-aminocyclopentyl]carbamate. MS (ESI): mass calcd. for $C_{27}H_{25}N_5O_3S$, 499.58; m/z found, 500.1 [M+H]$^+$. $^1$H NMR (400 MHz, CD$_3$OD): δ 8.08 (d, J=5.6 Hz, 1H), 7.40-7.34 (m, 2H), 7.21-7.15 (m, 1H), 7.15-7.10 (m, 1H), 7.10-7.05 (m, 2H), 7.04-7.01 (m, 1H), 6.97-6.93 (m, 1H), 5.81 (d, J=5.6 Hz, 1H), 4.45-4.36 (m, 1H), 3.50-3.38 (m, 1H), 2.13-2.01 (m, 5H), 1.92-1.80 (m, 2H), 1.68-1.58 (m, 2H).

Step B: N-((1S,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide To a solution of N-((1S,2R)-2-aminocyclopentyl)-5-(2-methyl-4-phenoxyphenyl)-4-oxo-4,5-dihydro-3H-1-thia-3,5,8-triazaacenaphthylene-2-carboxamide (150 mg, 0.30 mmol) in MeOH (5 mL) was added formaldehyde (98 mg, 3.3 mmol) and was stirred at rt for 10 min, then NaBH(OAc)$_3$ (318 mg, 1.50 mmol) was added and was stirred at rt overnight. The pH was adjusted to pH>7 with 2 M aqueous NaOH. The reaction mixture was concentrated to dryness and the residue was purified by flash column chromatography and preparative TLC to give the title compound as a yellow solid (56 mg, 35% yield). MS (ESI): mass calcd. for $C_{29}H_{29}N_5O_3S$, 527.6; m/z found, 528.2 [M+H]$^+$. $^1$H NMR (400 MHz, CD$_3$OD): δ 8.25 (d, J=5.4 Hz, 1H), 7.44-7.32 (m, 2H), 7.29-7.19 (m, 1H), 7.19-7.11 (m, 1H), 7.11-7.01 (m, 3H), 6.99-6.92 (m, 1H), 6.04-5.95 (m, 1H), 4.54-4.43 (m, 1H), 2.76-2.60 (m, 1H), 2.53-2.33 (m, 6H), 2.15-1.99 (m, 5H), 1.96-1.82 (m, 2H), 1.80-1.66 (m, 2H).

Example 52: 5-(2-Methyl-4-phenoxyphenyl)-4-oxo-N-((1R,2R)-2-propionamidocyclohexyl)-4,5-dihydro-3H-1-thia-3,5,8-triazaacenaphthylene-2-carboxamide

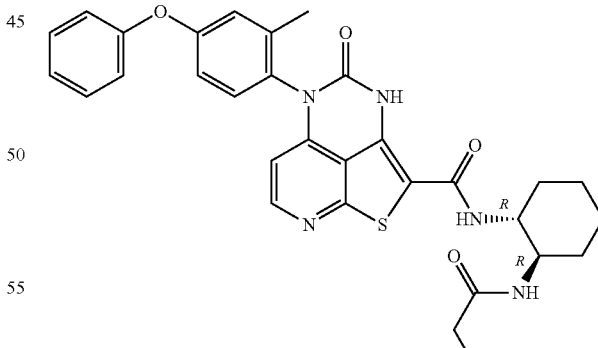

Step A: tert-Butyl ((1R,2R)-2-(5-(2-methyl-4-phenoxyphenyl)-4-oxo-4,5-dihydro-3H-1-thia-3,5,8-triazaacenaphthylene-2-carboxamido)cyclohexyl)carbamate A solution of 5-(2-methyl-4-phenoxyphenyl)-4-oxo-4,5-dihydro-3H-1-thia-3,5,8-triazaacenaphthylene-2-carbonyl chloride (Intermediate 8, 980 mg, 2.25 mmol), tert-butyl N-[(1R,2R)-2-aminocyclohexyl]carbamate (1.0 g, 4.7 mmol), and triethylamine (227 mg, 2.25 mmol) in DCM (10 mL) was reacted at rt for 2 h. The reaction was quenched with $H_2O$ (10 mL), extracted with DCM, dried over anhydrous $Na_2SO_4$, filtered, and concentrated to dryness to give the title compound as a yellow solid (1.3 g, 94% yield). MS (ESI): mass calcd. for $C_{33}H_{35}N_5O_5S$, 613.73; m/z found, 614.1 [M+H]+.

Step B: N-((1R,2R)-2-Aminocyclohexyl)-5-(2-methyl-4-phenoxyphenyl)-4-oxo-4,5-dihydro-3H-1-thia-3,5,8-triazaacenaphthylene-2-carboxamide To a solution of tert-butyl ((1R,2R)-2-(5-(2-methyl-4-phenoxyphenyl)-4-oxo-4,5-dihydro-3H-1-thia-3,5,8-triazaacenaphthylene-2-carboxamido)cyclohexyl)carbamate (1.3 g, 2.1 mmol) in MeOH (10 mL), was added concentrated HCl (2 mL) and was reacted at rt for 20 min. The reaction was quenched with $H_2O$ (10 mL), extracted with DCM, dried over anhydrous $Na_2SO_4$, filtered, and concentrated to dryness. The residue was purified by flash column chromatography to give the title compound (800 mg, 73.5% yield) as a yellow solid. MS (ESI): mass calcd. for $C_{28}H_{27}N_5O_3S$, 513.61; m/z found, 514.1 [M+H]+. 1H NMR (400 MHz, $CD_3OD$): δ 8.16-8.12 (m, 1H), 7.42-7.33 (m, 2H), 7.27-7.12 (m, 2H), 7.09-7.01 (m, 3H), 7.00-6.92 (m, 1H), 5.91-5.85 (m, 1H), 3.91-3.81 (m, 1H), 3.11-2.96 (m, 1H), 2.13-2.01 (m, 5H), 1.85-1.77 (m, 2H), 1.55-1.35 (m, 4H).

Step C: 5-(2-Methyl-4-phenoxyphenyl)-4-oxo-N-((1R,2R)-2-propionamidocyclohexyl)-4,5-dihydro-3H-1-thia-3,5,8-triazaacenaphthylene-2-carboxamide To a solution of N-((1R,2R)-2-aminocyclohexyl)-5-(2-methyl-4-phenoxyphenyl)-4-oxo-4,5-dihydro-3H-1-thia-3,5,8-triazaacenaphthylene-2-carboxamide (150 mg, 0.29 mmol) and triethylamine (50 mg, 0.50 mmol) in DCM (5 mL) was added propanoyl propanoate (38 mg, 0.29 mmol) and was reacted at rt for 20 min. The reaction was quenched with $H_2O$ (10 mL), extracted with DCM, dried over anhydrous $Na_2SO_4$, filtered, and concentrated to dryness. The residue was purified by flash column chromatography to give the title compound as a yellow solid (108 mg, 65.0% yield). MS (ESI): mass calcd. for $C_{31}H_{31}N_5O_4S$, 569.7; m/z found, 570.1 [M+H]+. 1H NMR (400 MHz, $CD_3OD$): δ 8.30 (d, J=5.5 Hz, 1H), 7.45-7.34 (m, 2H), 7.31-7.24 (m, 1H), 7.20-7.11 (m, 1H), 7.11-7.01 (m, 3H), 7.00-6.90 (m, 1H), 6.05 (d, J=5.5 Hz, 1H), 3.87-3.74 (m, 2H), 2.18-2.07 (m, 5H), 2.06-1.99 (m, 1H), 1.97-1.89 (m, 1H), 1.82-1.73 (m, 2H), 1.50-1.29 (m, 4H), 1.06-0.96 (m, 3H).

Example 53: N-((1S,2R)-2-Aminocyclopentyl)-5-(2-methyl-4-phenoxyphenyl)-4-oxo-4,5-dihydro-3H-1-thia-3,5,8-triazaacenaphthylene-2-carboxamide

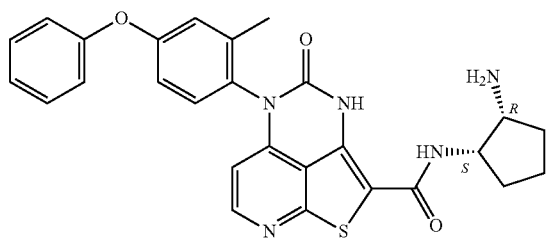

The title compound is the product from Step A, Example 51. MS (ESI): mass calcd. for $C_{27}H_{25}N_5O_3S$, 499.6; m/z found, 500.1 [M+H]+. 1H NMR (400 MHz, $CD_3OD$): δ 8.08 (d, J=5.6 Hz, 1H), 7.40-7.34 (m, 2H), 7.21-7.15 (m, 1H), 7.15-7.10 (m, 1H), 7.10-7.05 (m, 2H), 7.04-7.01 (m, 1H), 6.97-6.93 (m, 1H), 5.81 (d, J=5.6 Hz, 1H), 4.45-4.36 (m, 1H), 3.50-3.38 (m, 1H), 2.13-2.01 (m, 5H), 1.92-1.80 (m, 2H), 1.68-1.58 (m, 2H).

Example 54: N-((1S,2S)-2-Formamidocyclohexyl)-5-(2-methyl-4-phenoxyphenyl)-4-oxo-4,5-dihydro-3H-1-thia-3,5,8-triazaacenaphthylene-2-carboxamide

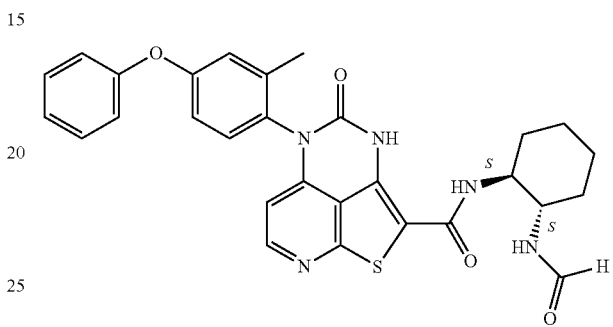

Step A: N-((1S,2S)-2-Aminocyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2S)-2-aminocyclohexyl]carbamate, in Step A. MS (ESI): mass calcd. for $C_{28}H_{27}N_5O_3S$, 513.61; m/z found, 514.1 [M+H]+. 1H NMR (400 MHz, $CD_3OD$): δ 8.37-8.28 (m, 1H), 7.46-7.35 (m, 2H), 7.32-7.23 (m, 1H), 7.21-7.12 (m, 1H), 7.13-7.02 (m, 3H), 7.01-6.93 (m, 1H), 6.11-6.02 (m, 1H), 4.07-3.97 (m, 1H), 3.16-3.03 (m, 1H), 2.17-2.12 (m, 1H), 2.11-2.04 (m, 3H), 2.02-1.95 (m, 1H), 1.91-1.80 (m, 2H), 1.64-1.47 (m, 2H), 1.46-1.35 (m, 2H).

Step B: N-((1S,2S)-2-Formamidocyclohexyl)-5-(2-methyl-4-phenoxyphenyl)-4-oxo-4,5-dihydro-3H-1-thia-3,5,8-triazaacenaphthylene-2-carboxamide To a solution of N-((1S,2S)-2-aminocyclohexyl)-5-(2-methyl-4-phenoxyphenyl)-4-oxo-4,5-dihydro-3H-1-thia-3,5,8-triazaacenaphthylene-2-carboxamide (Example 58, 130 mg, 0.25 mmol) and DMAP (10 mg, 0.082 mmol) in DCM (5 mL) was added propanoyl propanoate (33 mg, 0.25 mmol) and was stirred at rt for 1 h, concentrated to dryness, and purified by flash column chromatography to give the title compound as a yellow solid (63 mg, 46% yield) and 5-(2-methyl-4-phenoxyphenyl)-4-oxo-N-((1S,2S)-2-propionamidocyclohexyl)-4,5-dihydro-3H-1-thia-3,5,8-triazaacenaphthylene-2-carboxamide (Example 60). MS (ESI): mass calcd. for $C_{29}H_{27}N_5O_4S$, 541.6; m/z found, 542.2 [M+H]+. 1H NMR (400 MHz, DMSO-$d_6$): δ 10.20 (s, 1H), 8.42-8.26 (m, 1H), 8.14-7.87 (m, 3H), 7.52-7.33 (m, 3H), 7.25-7.16 (m, 1H), 7.17-7.05 (m, 3H), 7.04-6.92 (m, 1H), 6.05-5.89 (m, 1H), 3.94-3.66 (m, 2H), 2.07 (s, 3H), 1.92-1.79 (m, 2H), 1.76-1.63 (m, 2H), 1.56-1.40 (m, 1H), 1.31-1.21 (m, 3H).

Example 55: N-((1S,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide

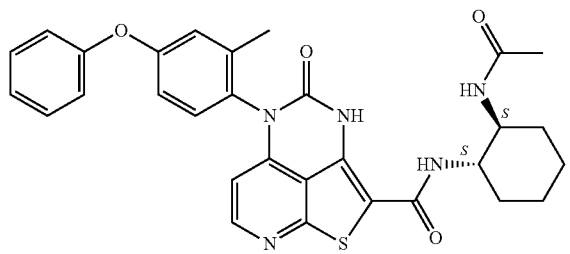

The title compound was prepared in a manner analogous to Example 11, Steps A-B, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,2S)-2-aminocyclohexyl]carbamate, in Step A, and acetyl chloride in Step B. MS (ESI): mass calcd. for $C_{30}H_{29}N_5O_4S$, 555.6; m/z found, 556.1 [M+H]$^+$. $^1$H NMR (400 MHz, DMSO-d$_6$): δ 10.17 (s, 1H), 8.40-8.20 (m, 1H), 8.05-7.78 (m, 2H), 7.48-7.31 (m, 3H), 7.27-7.05 (m, 4H), 7.04-6.91 (m, 1H), 6.04-5.85 (m, 1H), 3.75-3.65 (m, 2H), 2.06 (s, 3H), 1.90-1.79 (m, 2H), 1.76 (s, 3H), 1.72-1.63 (m, 2H), 1.48-1.40 (m, 1H), 1.31-1.23 (m, 3H).

Example 56: N-((1S,2S)-2-Acrylamidocyclopentyl)-5-(*R)-(2-methyl-4-phenoxyphenyl)-4-oxo-4,5-dihydro-3H-1-thia-3,5,8-triazaacenaphthylene-2-carboxamide

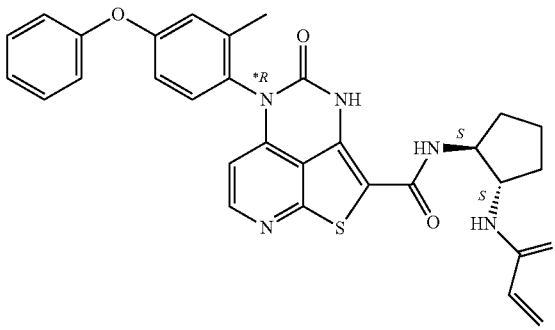

Step A: N-((1S,2S)-2-Aminocyclopentyl)-5-(*R)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *R atropisomer) and tert-butyl N-[(1S,2S)-2-aminocyclopentyl]carbamate.

Step B: N-((1S,2S)-2-Acrylamidocyclopentyl)-5-(*R)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step B. MS (ESI): mass calcd. for $C_{30}H_{27}N_5O_4S$, 553.6; m/z found, 554.2 [M+H]$^+$. $^1$H NMR (400 MHz, CD$_3$OD): δ 8.38-8.23 (m, 1H), 7.46-7.35 (m, 2H), 7.33-7.25 (m, 1H), 7.23-7.12 (m, 1H), 7.12-7.02 (m, 3H), 6.99-6.94 (m, 1H), 6.28-6.17 (m, 2H), 6.09-6.00 (m, 1H), 5.67-5.54 (m, 1H), 4.31-4.18 (m, 2H), 2.23-2.07 (m, 5H), 1.88-1.76 (m, 2H), 1.72-1.55 (m, 2H).

Example 57: N-((1S,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide

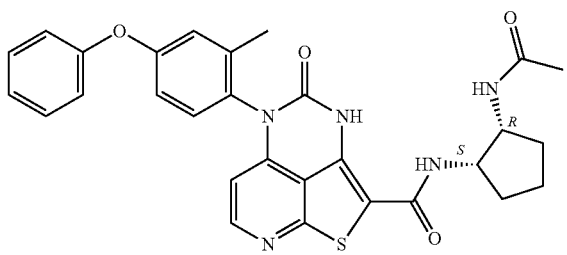

The title compound was prepared in a manner analogous to Example 11, Step B, using N-((1S,2R)-2-aminocyclopentyl)-5-(2-methyl-4-phenoxyphenyl)-4-oxo-4,5-dihydro-3H-1-thia-3,5,8-triazaacenaphthylene-2-carboxamide, Example 51, product from Step A, and acetyl chloride. MS (ESI): mass calcd. for $C_{29}H_{27}N_5O_4S$, 541.6; m/z found, 542.1 [M+H]$^+$. $^1$H NMR (400 MHz, CD$_3$OD): δ 8.29 (d, J=5.4 Hz, 1H), 7.45-7.34 (m, 2H), 7.33-7.24 (m, 1H), 7.21-7.12 (m, 1H), 7.12-7.02 (m, 3H), 7.02-6.92 (m, 1H), 6.04 (d, J=5.3 Hz, 1H), 4.45-4.30 (m, 2H), 2.11 (s, 3H), 2.08-1.99 (m, 2H), 1.94 (s, 3H), 1.90-1.84 (m, 1H), 1.78-1.56 (m, 3H).

Example 58: N-((1S,2S)-2-Aminocyclohexyl)-5-(2-methyl-4-phenoxyphenyl)-4-oxo-4,5-dihydro-3H-1-thia-3,5,8-triazaacenaphthylene-2-carboxamide

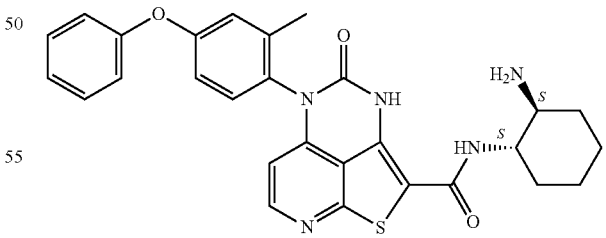

The title compound is the product from Step A, Example 54. MS (ESI): mass calcd. for $C_{28}H_{27}N_5O_3S$, 513.6; m/z found, 514.1 [M+H]$^+$. $^1$H NMR (400 MHz, CD$_3$OD): δ 8.37-8.28 (m, 1H), 7.46-7.35 (m, 2H), 7.32-7.23 (m, 1H), 7.21-7.12 (m, 1H), 7.13-7.02 (m, 3H), 7.01-6.93 (m, 1H), 6.11-6.02 (m, 1H), 4.07-3.97 (m, 1H), 3.16-3.03 (m, 1H), 2.17-2.12 (m, 1H), 2.11-2.04 (m, 3H), 2.02-1.95 (m, 1H), 1.91-1.80 (m, 2H), 1.64-1.47 (m, 2H), 1.46-1.35 (m, 2H).

Example 59: 5-(2-Methyl-4-phenoxyphenyl)-4-oxo-N-((1S,2R)-2-propionamidocyclopentyl)-4,5-dihydro-3H-1-thia-3,5,8-triazaacenaphthylene-2-carboxamide

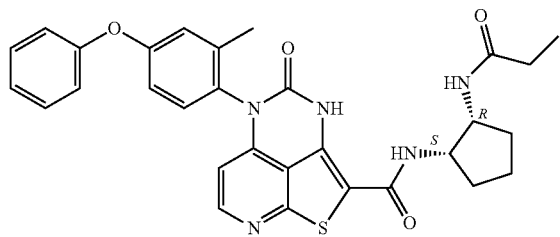

The title compound was prepared in a manner analogous to Example 11, Step B, using N-((1S,2R)-2-aminocyclopentyl)-5-(2-methyl-4-phenoxyphenyl)-4-oxo-4,5-dihydro-3H-1-thia-3,5,8-triazaacenaphthylene-2-carboxamide, Example 51, product from Step A, and propanoyl chloride. MS (ESI): mass calcd. for $C_{30}H_{29}N_5O_4S$, 555.6; m/z found, 556.2 $[M+H]^+$. $^1H$ NMR (400 MHz, cd3od) d 8.30 (d, J=5.3 Hz, 1H), 7.43-7.35 (m, 2H), 7.33-7.24 (m, 1H), 7.20-7.12 (m, 1H), 7.12-7.02 (m, 3H), 7.01-6.93 (m, 1H), 6.05 (d, J=5.4 Hz, 1H), 4.43-4.30 (m, 2H), 2.24-2.17 (m, 2H), 2.11 (s, 3H), 2.07-1.98 (m, 2H), 1.92-1.82 (m, 1H), 1.76-1.58 (m, 3H), 1.08 (t, J=7.6 Hz, 3H).

Example 60: 5-(2-Methyl-4-phenoxyphenyl)-4-oxo-N-((1S,2S)-2-propionamidocyclohexyl)-4,5-dihydro-3H-1-thia-3,5,8-triazaacenaphthylene-2-carboxamide

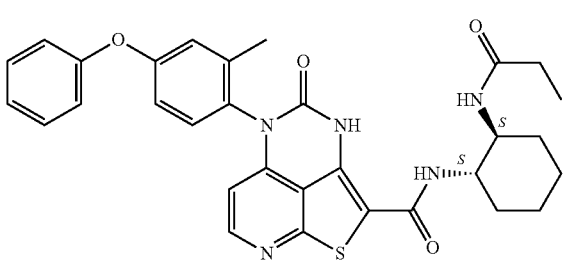

To a solution of N-((1S,2S)-2-aminocyclohexyl)-5-(2-methyl-4-phenoxyphenyl)-4-oxo-4,5-dihydro-3H-1-thia-3,5,8-triazaacenaphthylene-2-carboxamide (Example 58, 130 mg, 0.25 mmol) and DMAP (10 mg, 0.082 mmol) in DCM (5 mL) was added propanoyl propanoate (33 mg, 0.25 mmol) and was stirred at rt for 1 h, concentrated to dryness, and purified by flash column chromatography to give the title compound as a yellow solid (36 mg 25% yield) and N-((1S,2S)-2-Formamidocyclohexyl)-5-(2-methyl-4-phenoxyphenyl)-4-oxo-4,5-dihydro-3H-1-thia-3,5,8-triazaacenaphthylene-2-carboxamide (Example 54). MS (ESI): mass calcd. for $C_{31}H_{31}N_5O_4S$, 569.7; m/z found, 570.2 $[M+H]^+$.

Example 61: N-((1R,2R)-2-Hydroxycyclopentyl)-5-(*R)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Steps A-B, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *R atropisomer) and (1R,2R)-2-aminocyclopentanol in Step A. MS (ESI): mass calcd. for $C_{27}H_{24}N_4O_4S$, 500.6; m/z found, 501.2 $[M+H]^+$. $^1H$ NMR (400 MHz, $CD_3OD$): δ 8.33-8.25 (m, 1H), 7.43-7.34 (m, 2H), 7.32-7.26 (m, 1H), 7.21-7.14 (m, 1H), 7.11-7.02 (m, 3H), 7.00-6.92 (m, 1H), 6.06-6.00 (m, 1H), 4.19-4.06 (m, 2H), 2.18-2.13 (m, 1H), 2.11 (s, 3H), 2.05-1.93 (m, 1H), 1.81-1.70 (m, 2H), 1.67-1.55 (m, 2H).

Example 62: N-((1S,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide To a solution of N-((1S,2S)-2-aminocyclohexyl)-5-(2-methyl-4-phenoxyphenyl)-4-oxo-4,5-dihydro-3H-1-thia-3,5,8-triazaacenaphthylene-2-carboxamide (Example 58, 63 mg, 0.12 mmol) and formaldehyde (0.3 mL) in MeOH (5 mL) was added $NaBH(OAc)_3$ (78 mg, 0.37 mmol) and was stirred at rt for 1 h, concentrated to dryness, and purified by flash column chromatography to give the title compound as a yellow solid (45 mg, 63% yield). MS (ESI): mass calcd. for $C_{30}H_{31}N_5O_3S$, 541.7; m/z found, 542.1 $[M+H]^+$. $^1H$ NMR (400 MHz, $CD_3OD$): δ 8.48 (s, 1H), 8.40-8.24 (m, 1H), 7.46-7.34 (m, 2H), 7.31-7.23 (m, 1H), 7.21-7.13 (m, 1H), 7.13-7.02 (m, 3H), 7.01-6.95 (m, 1H), 6.13-6.01 (m, 1H), 4.31-4.17 (m, 1H), 3.28-3.17 (m, 1H), 2.89-2.76 (m, 6H), 2.20-2.12 (m, 1H), 2.12-2.06 (m, 3H), 2.06-2.00 (m, 1H), 2.00-1.92 (m, 1H), 1.88-1.79 (m, 1H), 1.66-1.53 (m, 2H), 1.49-1.36 (m, 2H).

Example 63: 5-(2-Methyl-4-phenoxyphenyl)-N-(4-(methylamino)cyclohexyl)-4-oxo-4,5-dihydro-3H-1-thia-3,5,8-triazaacenaphthylene-2-carboxamide

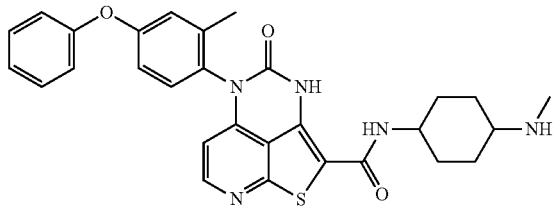 [SMILES: CNC1CCC(NC(=O)c2sc3nccc4c3c2NC(=O)N4c2ccc(Oc3ccccc3)cc2C)CC1]

Step A: 5-(2-Methyl-4-phenoxyphenyl)-4-oxo-N-(4-oxocyclohexyl)-4,5-dihydro-3H-1-thia-3,5,8-triazaacenaphthylene-2-carboxamide A solution of N-((1R,4R)-4-hydroxy cyclohexyl)-5-(2-methyl-4-phenoxyphenyl)-4-oxo-4,5-dihydro-3H-1-thia-3,5,8-triazaacenaphthylene-2-carboxamide (Example 15, 150 mg, 0.30 mmol) and (1,1-diacetoxy-3-oxo-isobenzofuran-1-yl) acetate (250 mg, 0.60 mmol) in DCM (20 mL) was stirred at rt for 16 hours. To the mixture was added water and DCM and was filtered. The organic layer was collected, concentrated to dryness, and purified by flash column chromatography to give the title compound (138 mg, 90.0% yield).

Step B: 5-(2-Methyl-4-phenoxyphenyl)-N-(4-(methylamino)cyclohexyl)-4-oxo-4,5-dihydro-3H-1-thia-3,5,8-triazaacenaphthylene-2-carboxamide To a solution of 5-(2-methyl-4-phenoxyphenyl)-4-oxo-N-(4-oxo cyclohexyl)-4,5-dihydro-3H-1-thia-3,5,8-triazaacenaphthylene-2-carboxamide (154 mg, 0.301 mmol) and methylamine in MeOH (0.5 mL) in DCM (5 mL) was added NaBH(OAc)₃ (200 mg, 0.94 mmol) and stirred at rt for 16 hours. To the mixture was added a 1 M aqueous solution of NH₃ and DCM. The organic layer was collected, concentrated to dryness, and purified by flash column chromatography, then by preparative TLC to give the title compound (36 mg, 22% yield). MS (ESI): mass calcd. for $C_{29}H_{29}N_5O_3S$, 527.6; m/z found, 528.3 [M+H]⁺. ¹H NMR (400 MHz, a mixture of CD₃OD and DMSO-d₆): δ 8.09-8.03 (m, 1H), 7.39-7.31 (m, 2H), 7.16-7.08 (m, 2H), 7.07-7.01 (m, 2H), 7.00-6.96 (m, 1H), 6.91-6.86 (m, 1H), 5.75-5.67 (m, 1H), 3.74-3.66 (m, 1H), 2.78-2.66 (m, 1H), 2.45 (s, 3H), 2.04-1.94 (m, 7H), 1.43-1.24 (m, 4H).

Example 64: N-((1S,4S)-4-Acetamidocyclohexyl)-5-(2-methyl-4-phenoxyphenyl)-4-oxo-4,5-dihydro-3H-1-thia-3,5,8-triazaacenaphthylene-2-carboxamide

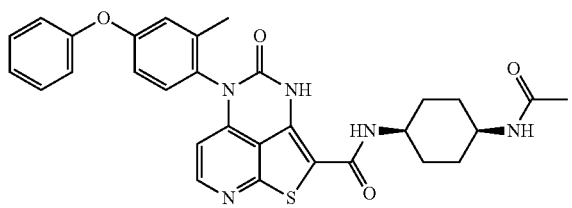 [SMILES: CC(=O)N[C@H]1CC[C@@H](NC(=O)c2sc3nccc4c3c2NC(=O)N4c2ccc(Oc3ccccc3)cc2C)CC1]

To a solution of N-((1S,4S)-4-aminocyclohexyl)-5-(2-methyl-4-phenoxyphenyl)-4-oxo-4,5-dihydro-3H-1-thia-3,5,8-triazaacenaphthylene-2-carboxamide (Example 25, 150 mg, 0.30 mmol) and triethylamine (340 mg, 0.90 mmol) in DCM (10 mL) was added acetic anhydride (30 mg, 0.30 mmol) and stirred at rt for 2 hours. The mixture was purified by flash column chromatography, then by preparative TLC to give the title compound (103 mg, 62.0% yield). MS (ESI): mass calcd. for $C_{30}H_{29}N_5O_4S$, 555.6; m/z found, 553.4 [M+H]⁺. ¹H NMR (400 MHz, DMSO-d₆): δ 10.17 (br, 1H), 8.37-8.24 (m, 1H), 7.96-7.82 (m, 1H), 7.69-7.58 (m, 1H), 7.49-7.39 (m, 2H), 7.39-7.32 (m, 1H), 7.22-7.15 (m, 1H), 7.15-7.03 (m, 3H), 7.01-6.92 (m, 1H), 6.02-5.89 (m, 1H), 3.87-3.72 (m, 1H), 3.72-3.60 (m, 1H), 2.05 (s, 3H), 1.81 (s, 3H), 1.76-1.65 (m, 4H), 1.64-1.48 (m, 4H).

Example 65: 5-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide

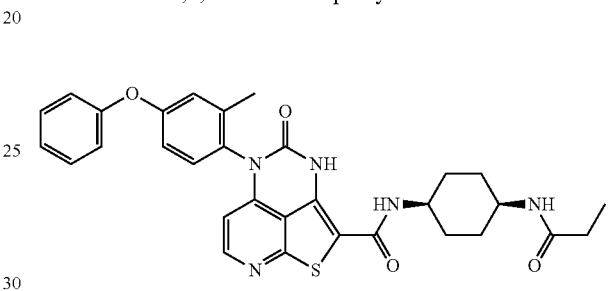

To a solution of N-((1S,4S)-4-aminocyclohexyl)-5-(2-methyl-4-phenoxyphenyl)-4-oxo-4,5-dihydro-3H-1-thia-3,5,8-triazaacenaphthylene-2-carboxamide (Example 25, 154 mg, 0.300 mmol) and triethylamine (342 mg, 0.900 mmol) in DCM (10 mL) was added propanoyl propanoate (28 mg, 0.21 mmol) and was stirred at room temperature for 2 hours. The mixture was purified by flash column chromatography, then by preparative TLC to give the title compound (76 mg, 44% yield). MS (ESI): mass calcd. for $C_{31}H_{31}N_5O_4S$, 569.7; m/z found, 570.3 [M+H]⁺. ¹H NMR (400 MHz, a mixture of CD₃OD and DMSO-d₆): δ 8.33-8.20 (m, 1H), 7.59-7.46 (m, 1H), 7.42-7.33 (m, 2H), 7.32-7.25 (m, 1H), 7.16-7.11 (m, 1H), 7.09-6.98 (m, 3H), 6.95-6.89 (m, 1H), 6.02-5.85 (m, 1H), 3.85-3.79 (m, 1H), 3.74-3.70 (m, 1H), 2.12-2.06 (m, 2H), 2.03 (s, 3H), 1.71-1.50 (m, 8H), 0.99 (t, J=7.5 Hz, 3H).

Example 66: N-((1S,4S)-4-(Dimethylamino)cyclohexyl)-5-(2-methyl-4-phenoxyphenyl)-4-oxo-4,5-dihydro-3H-1-thia-3,5,8-triazaacenaphthylene-2-carboxamide

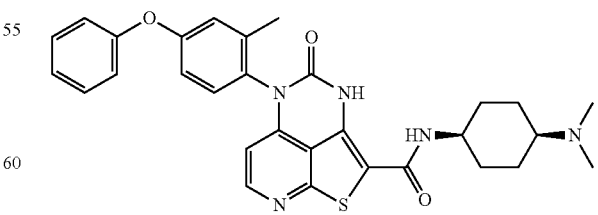

To a solution of N-((1S,4S)-4-aminocyclohexyl)-5-(2-methyl-4-phenoxyphenyl)-4-oxo-4,5-dihydro-3H-1-thia-3,5,8-triazaacenaphthylene-2-carboxamide (Example 25,150 mg, 0.30 mmol), formaldehyde (37% in water) in DCM was added NaBH(OAc)₃ and was stirred at room temperature for 16 hours. To the mixture was added a 1 M aqueous solution of NH₃ and DCM. The organic layer was collected, concentrated to dryness, and purified by flash column chromatography, then by preparative TLC to give the title compound (100 mg, 61% yield). MS (ESI): mass calcd. for $C_{30}H_{31}N_5O_3S$, 541.7; m/z found, 542.3 [M+H]⁺.

Example 67: N-((1R,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide

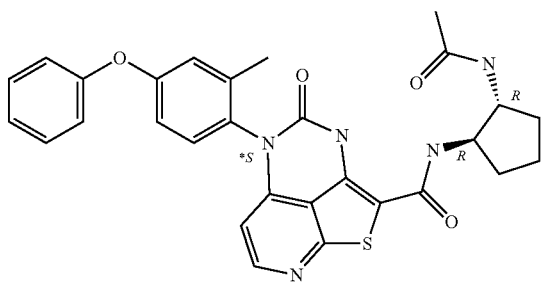

Step A. N-((1R,2R)-2-aminocyclopentyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2R)-2-aminocyclopentyl]carbamate.

Step B: N-((1R,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide To a solution of N-((1R,2R)-2-aminocyclopentyl)-5-(*S)-(2-methyl-4-phenoxyphenyl)-4-oxo-4,5-dihydro-3H-1-thia-3,5,8-triazaacenaphthylene-2-carboxamide (28.5 mg, 0.0570 mmol) and triethylamine (65 mg, 0.17 mmol) in DCM (10 mL) was added acetic anhydride (5.8 mg, 0.57 mmol) and stirred at room temperature for 15 minutes. The mixture was purified by flash column chromatography, then by preparative TLC to give the title compound (25 mg, 81% yield). MS (ESI): mass calcd. for $C_{29}H_{27}N_5O_4S$, 541.6; m/z found, 542.3 [M+H]⁺. ¹H NMR (400 MHz, DMSO-d₆): δ 10.21 (br, 1H), 8.35-7.99 (m, 2H), 7.98-7.93 (m, 1H), 7.45-7.40 (m, 2H), 7.38-7.27 (m, 1H), 7.20-7.16 (m, 1H), 7.12-7.08 (m, 2H), 7.07-7.05 (m, 1H), 6.97-6.93 (m, 1H), 5.98-5.80 (m, 1H), 4.17-4.01 (m, 2H), 2.04 (s, 3H), 2.00-1.91 (m, 2H), 1.77 (s, 3H), 1.69-1.61 (m, 2H), 1.57-1.49 (m, 1H), 1.44-1.36 (m, 1H).

Example 68: N-((1S,3R)-3-acrylamidocyclopentyl)-5-(2-methyl-4-phenoxyphenyl)-4-oxo-4,5-dihydro-3H-1-thia-3,5,8-triazaacenaphthylene-2-carboxamide

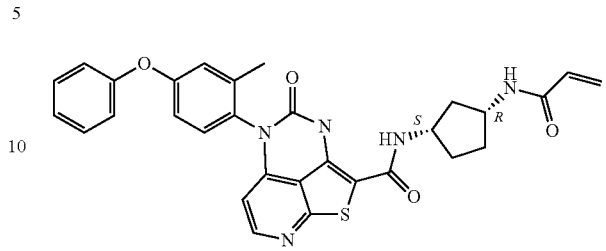

Step A: N-((1S,3R)-3-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,3S)-3-aminocyclopentyl]carbamate, in Step A.

Step B: N-((1S,3R)-3-acrylamidocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step B. MS (ESI): mass calcd. for $C_{30}H_{27}N_5O_4S$, 553.6; m/z found, 554.4 [M+H]⁺. ¹H NMR (400 MHz, DMSO-d₆): δ 10.21-10.10 (m, 1H), 8.34-8.28 (m, 1H), 8.27-8.11 (m, 2H), 7.46-7.40 (m, 2H), 7.39-7.32 (m, 1H), 7.21-7.16 (m, 1H), 7.13-7.08 (m, 2H), 7.08-7.05 (m, 1H), 6.99-6.93 (m, 1H), 6.26-6.16 (m, 1H), 6.12-6.04 (m, 1H), 6.00-5.89 (m, 1H), 5.59-5.52 (m, 1H), 4.26-4.15 (m, 1H), 4.08-3.99 (m, 1H), 2.31-2.23 (m, 1H), 2.05 (s, 3H), 1.95-1.85 (m, 2H), 1.77-1.66 (m, 1H), 1.64-1.47 (m, 2H).

Example 69: 5-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide

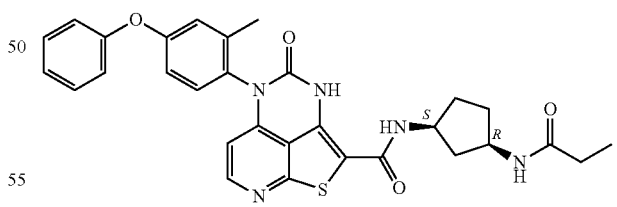

To a solution of N-((1S,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 68, product from Step A, 150 mg, 0.30 mmol) and triethylamine (91 mg, 0.90 mmol) in DCM (10 mL) was added propanoyl propanoate (39 mg, 0.30 mmol) and was stirred at room temperature for 2 hours. The mixture was purified by flash column chromatography, then by preparative TLC to give the title compound (140 mg, 83% yield). MS (ESI): mass calcd. for $C_{30}H_{29}N_5O_4S$, 555.6; m/z found, 556.3 [M+H]⁺.

¹H NMR (400 MHz, DMSO-d₆): δ 10.14 (br, 1H), 8.34-8.16 (m, 2H), 7.84-7.77 (m, 1H), 7.45-7.40 (m, 2H), 7.37-7.31 (m, 1H), 7.21-7.16 (m, 1H), 7.13-7.08 (m, 2H), 7.08-7.05 (m, 1H), 6.98-6.93 (m, 1H), 5.98-5.86 (m, 1H), 4.24-4.12 (m, 1H), 4.01-3.90 (m, 1H), 2.26-2.17 (m, 1H), 2.09-2.01 (m, 5H), 1.94-1.78 (m, 2H), 1.74-1.63 (m, 1H), 1.61-1.42 (m, 2H), 0.97 (t, J=7.6 Hz, 3H).

Example 70: N-((1S,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide

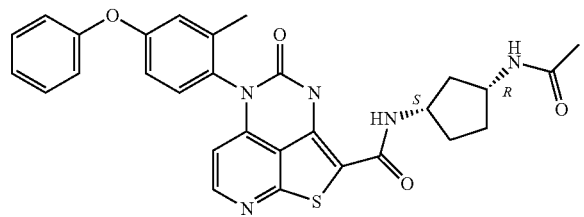

To a solution of N-((1S,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 68, product from Step A, 150 mg, 0.30 mmol) and triethylamine (91 mg, 0.90 mmol) in DCM (10 mL) was added acetic anhydride (30 mg, 0.29 mmol) and was stirred at room temperature for 2 hours. The mixture was purified by flash column chromatography, then by preparative TLC to give the title compound (130 mg, 32% yield). MS (ESI): mass calcd. for $C_{29}H_{27}N_5O_4S$, 541.6; m/z found, 542.3 [M+H]⁺. ¹H NMR (400 MHz, DMSO-d₆): δ 10.14 (s, 1H), 8.34-8.28 (m, 1H), 8.22-8.12 (m, 1H), 7.93-7.86 (m, 1H), 7.46-7.40 (m, 2H), 7.38-7.33 (m, 1H), 7.21-7.16 (m, 1H), 7.14-7.09 (m, 2H), 7.09-7.05 (m, 1H), 6.99-6.94 (m, 1H), 5.99-5.92 (m, 1H), 4.25-4.13 (m, 1H), 4.00-3.88 (m, 1H), 2.25-2.17 (m, 1H), 2.05 (s, 3H), 1.92-1.81 (m, 2H), 1.79 (s, 3H), 1.72-1.64 (m, 1H), 1.59-1.43 (m, 2H).

Example 71: N-((1S,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide

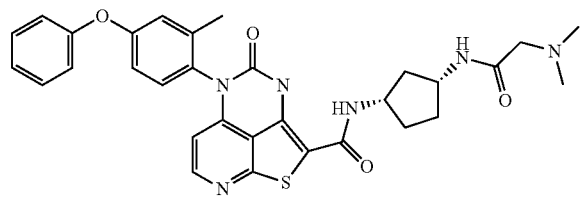 [SMILES: Cc1cc(Oc2ccccc2)ccc1N1C(=O)Nc2c(C(=O)N[C@H]3CC[C@@H](NC(=O)CN(C)C)C3)sc3nccc1c23]

To a solution of N-((1S,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 68, product from Step A, 150 mg, 0.30 mmol), HATU (137 mg, 0.360 mmol), and triethylamine (91 mg, 0.90 mmol) in DMF (3 mL) was added 2-(dimethylamino)acetic acid (37 mg, 0.36 mmol) and was stirred at rt for 4 hours. The mixture was purified by flash column chromatography, then by preparative TLC to give the title compound (70 mg, 39% yield). MS (ESI): mass calcd. for $C_{31}H_{32}N_6O_4S$, 584.7; m/z found, 585.3 [M+H]⁺. ¹H NMR (400 MHz, CD₃OD and DMSO-d₆): δ 8.28-8.21 (m, 1H), 7.40-7.32 (m, 2H), 7.28-7.23 (m, 1H), 7.15-7.09 (m, 1H), 7.07-7.02 (m, 2H), 7.02-6.99 (m, 1H), 6.93-6.88 (m, 1H), 5.97-5.89 (m, 1H), 4.24-4.20 (m, 1H), 4.06-4.02 (m, 1H), 2.89-2.84 (m, 2H), 2.30-2.24 (m, 1H), 2.20 (s, 6H), 2.02 (s, 3H), 1.89-1.79 (m, 2H), 1.76-1.68 (m, 1H), 1.66-1.58 (m, 1H), 1.57-1.50 (m, 1H).

Example 72: 5-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide

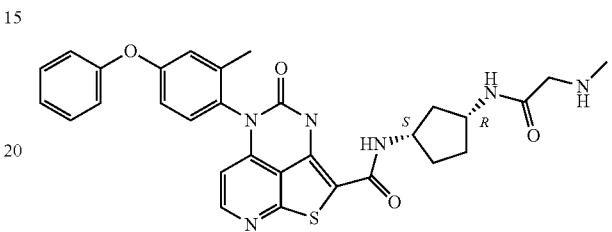

Step A: tert-butylmethyl(2-(((1S,3R)-3-(5-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate To a solution of N-Boc-N-methylglycine (0.14 g, 0.74 mmol), HATU (0.274 g, 0.720 mmol), and triethylamine (0.182 g, 1.80 mmol) in DMF (3 mL) was added N-((1S,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 68, product from Step A, 0.30 g, 0.60 mmol) and stirred at rt for 1 hour. The mixture was purified by flash column chromatography to give the title compound (362 mg, 90.0% yield).

Step B: 5-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide A solution of tert-butyl methyl(2-(41S,3R)-3-(5-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate (362 mg, 0.540 mmol), concentrated HCl (1.0 mL), and MeOH (5 mL) was stirred for 5 min at rt and then concentrated to dryness. The residue was dispersed between a 1 M aqueous NH₄OH solution and DCM. The organic layer was collected and concentrated to dryness to give the title compound (267 mg, 82% yield). MS (ESI): mass calcd. for $C_{30}H_{30}N_6O_4S$, 570.7; m/z found, 571.3 [M+H]⁺. ¹H NMR (400 MHz, CD₃OD/DMSO-d₆): δ 8.21-8.14 (m, 1H), 7.38-7.32 (m, 2H), 7.24-7.19 (m, 1H), 7.14-7.09 (m, 1H), 7.06-7.01 (m, 2H), 7.01-6.98 (m, 1H), 6.92-6.88 (m, 1H), 5.87-5.81 (m, 1H), 4.24-4.20 (m, 1H), 4.07-4.03 (m, 1H), 3.38-3.27 (m, 2H), 2.35 (s, 3H), 2.29-2.21 (m, 1H), 2.02 (s, 3H), 1.96-1.83 (m, 2H), 1.77-1.68 (m, 1H), 1.68-1.59 (m, 1H), 1.59-1.51 (m, 1H).

Example 73: N-((1S,3R)-3-(Dimethylamino)cyclopentyl)-5-(2-methyl-4-phenoxyphenyl)-4-oxo-4,5-dihydro-3H-1-thia-3,5,8-triazaacenaphthylene-2-carboxamide

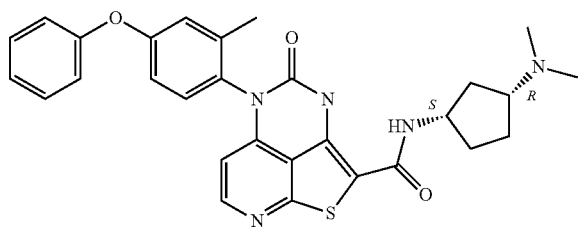

To a solution of N-((1S,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 68, product from Step A, 150 mg, 0.30 mmol) and formaldehyde (37% in water, 1.0 mL) in DCM (10 mL) was added NaBH(OAc)$_3$ (318 mg, 1.50 mmol) and was stirred at room temperature for 6 hours. To the mixture was added 1 M aqueous NH$_3$ and DCM. The organic layer was collected, concentrated to dryness, and purified by flash column chromatography, then by preparative TLC to give the title compound (109 mg, 67.0% yield). MS (ESI): mass calcd. for C$_{29}$H$_{29}$N$_5$O$_3$S, 527.6; m/z found, 528.2 [M+H]$^+$. $^1$H NMR (400 MHz, DMSO-d$_6$/CD$_3$OD): δ 8.23-8.17 (m, 1H), 7.40-7.31 (m, 2H), 7.26-7.21 (m, 1H), 7.15-7.08 (m, 1H), 7.07-6.98 (m, 2H), 7.00 (d, J=2.5 Hz, 1H), 6.93-6.88 (m, 1H), 5.91-5.85 (m, 1H), 4.25-4.22 (m, 1H), 2.69-2.60 (m, 1H), 2.26 (s, 6H), 2.21-2.13 (m, 1H), 2.02 (s, 3H), 1.93-1.77 (m, 2H), 1.70-1.59 (m, 2H), 1.56-1.48 (m, 1H).

Example 74: N-((1S,3R)-3-Hydroxycyclopentyl)-5-(2-methyl-4-phenoxyphenyl)-4-oxo-4,5-dihydro-3H-1-thia-3,5,8-triazaacenaphthylene-2-carboxamide

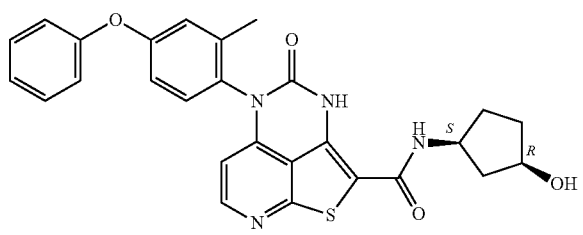

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (1R,3S)-3-aminocyclopentanol. MS (ESI): mass calcd. for C$_{27}$H$_{24}$N$_4$O$_4$S, 500.6; m/z found, 501.3 [M+H]$^+$. $^1$H NMR (400 MHz, DMSO-d$_6$): δ 10.15 (s, 1H), 8.35-8.25 (m, 1H), 8.11-7.97 (m, 1H), 7.46-7.39 (m, 2H), 7.38-7.32 (m, 1H), 7.21-7.15 (m, 1H), 7.15-7.04 (m, 3H), 6.99-6.92 (m, 1H), 5.98-5.91 (m, 1H), 4.75-4.67 (m, 1H), 4.24-4.14 (m, 1H), 4.13-4.05 (m, 1H), 2.16-2.08 (m, 1H), 2.04 (s, 3H), 1.89-1.81 (m, 1H), 1.78-1.66 (m, 2H), 1.64-1.49 (m, 2H).

Example 75: N-((1S,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide

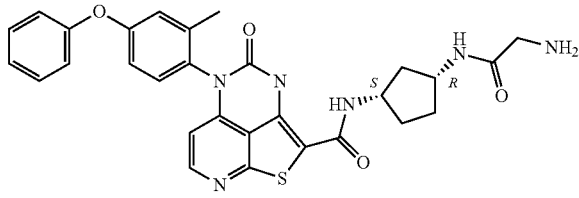

Step A: tert-Butyl (2-(41R,3S)-3-(5-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate A solution of N-((1S,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 68, product from Step A, 0.15 g, 0.30 mmol), N-Boc-glycine (0.037 g, 0.21 mmol), HATU (0.137 g, 0.360 mmol), and triethylamine (0.091 g, 0.91 mmol) in DMF (3 mL) was stirred at rt for 1 hour. The mixture was purified by flash column chromatography to give the title compound (177 mg, 90.0% yield).

Step B: N-((1S,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide A solution of tert-butyl (2-(41R,3S)-3-(5-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate (177 mg, 0.270 mmol) in concentrated HCl (1 mL) and MeOH (5 mL) was concentrated to dryness. The residue was dispersed between 1 M aqueous NH$_4$OH solution and DCM. The organic layer was collected and purified by flash column chromatography, then by preparative TLC to give the title compound (130 mg, 85% yield). MS (ESI): mass calcd. for C$_{29}$H$_{28}$H$_6$O$_4$S, 556.6; m/z found, 557.2 [M+H]$^+$. $^1$H NMR (400 MHz, CD$_3$OD and DMSO-d$_6$): δ 8.24-8.16 (m, 1H), 7.40-7.31 (m, 2H), 7.24-7.20 (m, 1H), 7.14-7.08 (m, 1H), 7.07-7.01 (m, 2H), 7.01-6.97 (m, 1H), 6.92-6.87 (m, 1H), 5.92-5.83 (m, 1H), 4.27-4.22 (m, 1H), 4.07-4.02 (m, 1H), 3.47-3.34 (m, 2H), 2.33-2.20 (m, 1H), 2.02 (s, 3H), 1.95-1.85 (m, 2H), 1.78-1.68 (m, 1H), 1.68-1.59 (m, 1H), 1.59-1.50 (m, 1H).

Example 76: N-((1S,3R)-3-Aminocyclopentyl)-5-(2-methyl-4-phenoxyphenyl)-4-oxo-4,5-dihydro-3H-1-thia-3,5,8-triazaacenaphthylene-2-carboxamide

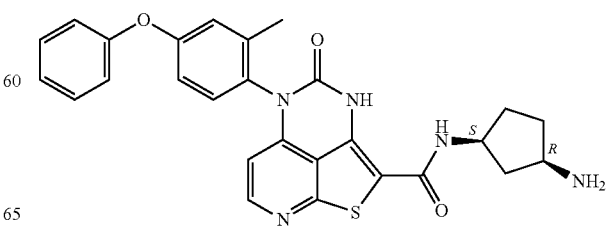

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,3S)-3-aminocyclopentyl]carbamate. MS (ESI): mass calcd. for $C_{27}H_{25}N_5O_3S$, 499.6; m/z found, 500.3 [M+H]$^+$. $^1$H NMR (400 MHz, CD$_3$OD and DMSO-d$_6$): δ 8.06-8.03 (m, 1H), 7.37-7.32 (m, 2H), 7.15-7.07 (m, 2H), 7.05-7.01 (m, 2H), 6.99-6.96 (m, 1H), 6.90-6.86 (m, 1H), 5.73-5.69 (m, 1H), 4.23-4.20 (m, 1H), 3.52-3.42 (m, 1H), 2.43-2.34 (m, 1H), 2.00 (s, 3H), 1.97-1.88 (m, 2H), 1.87-1.79 (m, 1H), 1.76-1.68 (m, 1H), 1.62-1.53 (m, 1H).

Example 77: N-((1S,4S)-4-((E)-4-(Dimethylamino)but-2-enamido)cyclohexyl)-5-(2-methyl-4-phenoxyphenyl)-4-oxo-4,5-dihydro-3H-1-thia-3,5,8-triazaacenaphthylene-2-carboxamide

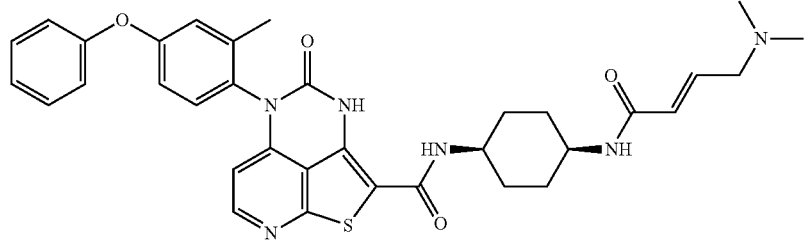 [SMILES: Cc1cc(Oc2ccccc2)ccc1N1C(=O)Nc2c(C(=O)N[C@H]3CC[C@@H](NC(=O)/C=C/CN(C)C)CC3)sc3nccc1c23]

Step A: tert-Butyl ((E)-4-(((1S,4S)-4-(5-(2-methyl-4-phenoxyphenyl)-4-oxo-4,5-dihydro-3H-1-thia-3,5,8-triazaacenaphthylene-2-carboxamido)cyclohexyl)amino)-4-oxobut-2-en-1-yl)carbamate To a solution of (E)-4-(tert-butoxycarbonylamino)but-2-enoic acid (Intermediate 34, 150 mg, 0.75 mmol), HATU (190 mg, 0.50 mmol), and triethylamine (101 mg, 1.00 mmol) in DMF (2 mL) was added N-((1S,4S)-4-aminocyclohexyl)-5-(2-methyl-4-phenoxyphenyl)-4-oxo-4,5-dihydro-3H-1-thia-3,5,8-triazaacenaphthylene-2-carboxamide (Example 25, 154 mg, 0.300 mmol) and was stirred at rt for 4 hours. The mixture was purified by flash column chromatography to give the title compound (30 mg, 14% yield).

Step B: N-((1S,4S)-4-((E)-4-Aminobut-2-enamido)cyclohexyl)-5-(2-methyl-4-phenoxyphenyl)-4-oxo-4,5-dihydro-3H-1-thia-3,5,8-triazaacenaphthylene-2-carboxamide To a solution of tert-butyl ((E)-4-(((1S,4S)-4-(5-(2-methyl-4-phenoxyphenyl)-4-oxo-4,5-dihydro-3H-1-thia-3,5,8-triazaacenaphthylene-2-carboxamido)cyclohexyl)amino)-4-oxobut-2-en-1-yl)carbamate (56 mg, 0.080 mmol) in MeOH (2 mL) was added concentrated aqueous HCl (0.2 mL). The mixture was concentrated to dryness and was purified by preparative TLC to give the title compound (48 mg, 99% yield).

Step C: N-((1S,4S)-4-((E)-4-(Dimethylamino)but-2-enamido)cyclohexyl)-5-(2-methyl-4-phenoxyphenyl)-4-oxo-4,5-dihydro-3H-1-thia-3,5,8-triazaacenaphthylene-2-carboxamide To a solution of N-((1S,4S)-4-((E)-4-aminobut-2-enamido)cyclohexyl)-5-(2-methyl-4-phenoxyphenyl)-4-oxo-4,5-dihydro-3H-1-thia-3,5,8-triazaacenaphthylene-2-carboxamide (32 mg, 0.054 mmol) and formaldehyde (37% in water, 1.0 mL) in DCM (10 mL) was added NaBH(OAc)$_3$ (200 mg, 0.94 mmol) and was stirred at room temperature for 16 hours. To the mixture was added a 1 M aqueous NH$_4$OH solution and DCM. The organic layer was collected, concentrated to dryness, and purified by flash column chromatography, then by preparative TLC to give the title compound (15 mg, 43% yield). MS (ESI): mass calcd. for $C_{34}H_{36}N_6O_4S$, 624.8; m/z found, 625.3 [M+H]$^+$.

Example 78: 5-(2-Methyl-4-phenoxyphenyl)-N-((1S,4S)-4-((E)-4-(methylamino)but-2-enamido)cyclohexyl)-4-oxo-4,5-dihydro-3H-1-thia-3,5,8-triazaacenaphthylene-2-carboxamide

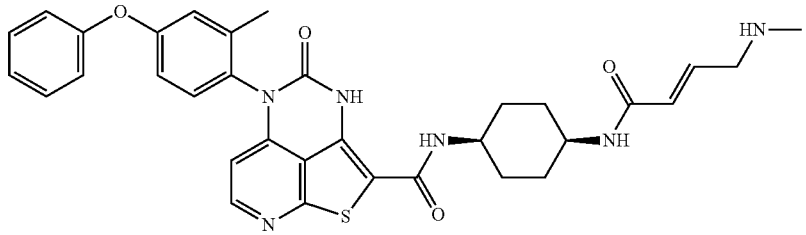 [SMILES: CNC/C=C/C(=O)N[C@H]1CC[C@@H](NC(=O)c2sc3nccc4c3c2NC(=O)N4c2ccc(Oc3ccccc3)cc2C)CC1]

Step A: tert-Butyl methyl((E)-4-(((1S,4S)-4-(5-(2-methyl-4-phenoxyphenyl)-4-oxo-4,5-dihydro-3H-1-thia-3,5,8-triazaacenaphthylene-2-carboxamido)cyclohexyl)amino)-4-oxobut-2-en-1-yl)carbamate A solution of N-((1S,4S)-4-aminocyclohexyl)-5-(2-methyl-4-phenoxyphenyl)-4-oxo-4,5-dihydro-3H-1-thia-3,5,8-triazaacenaphthylene-2-carboxamide (Example 25, 100 mg, 0.20 mmol), (E)-4-(tert-butoxycarbonylamino)but-2-enoic acid (Intermediate 34, 43 mg, 0.20 mmol), HATU (114 mg, 0.300 mmol), and triethylamine (40 mg, 0.40 mmol) in DMF (2 mL) was stirred at rt for 4 hours. The reaction mixture was purified by flash column chromatography to give the title compound (71 mg, 50% yield).

Step B: 5-(2-Methyl-4-phenoxyphenyl)-N-((1S,4S)-4-((E)-4-(methylamino)but-2-enamido)cyclohexyl)-4-oxo-4,5-dihydro-3H-1-thia-3,5,8-triazaacenaphthylene-2-carboxamide To a solution of tert-butyl methyl((E)-4-(((1S,4S)-4-(5-(2-methyl-4-phenoxyphenyl)-4-oxo-4,5-dihydro-3H-1-thia-3,5,8-triazaacenaphthylene-2-carboxamido)cyclohexyl)amino)-4-oxobut-2-en-1-yl)carbamate (71 mg, 0.10 mmol) in MeOH (3 mL) was added concentrated aqueous HCl (0.5 mL). The mixture was concentrated to dryness and the residue was dispersed between DCM and 10% aqueous NH₄OH. The organic layer was collected, concentrated to dryness, and purified by flash column chromatography, then by preparative TLC to give the title compound (22 mg, 35% yield). MS (ESI): mass calcd. for C₃₃H₃₄N₆O₄S, 610.7; m/z found, 611.3 [M+H]⁺.

Example 79: N-((1S,4S)-4-((E)-4-Aminobut-2-enamido)cyclohexyl)-5-(2-methyl-4-phenoxyphenyl)-4-oxo-4,5-dihydro-3H-1-thia-3,5,8-triazaacenaphthylene-2-carboxamide

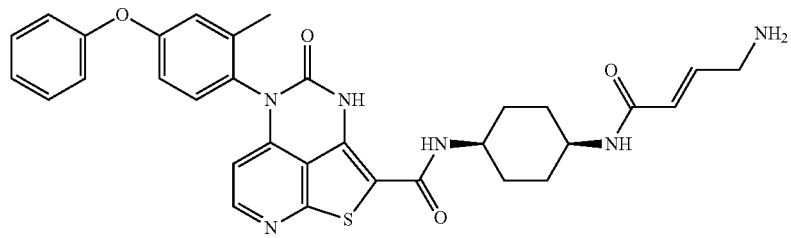 [SMILES: Cc1cc(Oc2ccccc2)ccc1N1C(=O)Nc2c(C(=O)N[C@H]3CC[C@@H](NC(=O)/C=C/CN)CC3)sc3nccc1c23]

The title compound is the product from Step B, Example 77. MS (ESI): mass calcd. for C₃₂H₃₂N₆O₄S, 596.7; m/z found, 597.3 [M+H]⁺.

Example 80: 5-(2-Methyl-4-phenoxyphenyl)-N-((1S)-3-(methylamino)cyclopentyl)-4-oxo-4,5-dihydro-3H-1-thia-3,5,8-triazaacenaphthylene-2-carboxamide

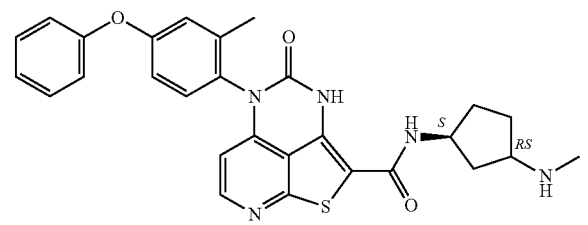

Step A: (S)-5-(2-Methyl-4-phenoxyphenyl)-4-oxo-N-(3-oxocyclopentyl)-4,5-dihydro-3H-1-thia-3,5,8-triazaacenaphthylene-2-carboxamide A solution of N-((1S,3R)-3-hydroxycyclopentyl)-5-(2-methyl-4-phenoxyphenyl)-4-oxo-4,5-dihydro-3H-1-thia-3,5,8-triazaacenaphthylene-2-carboxamide (Example 74, 250 mg, 0.50 mmol) and Dess-Martin periodinane (424 mg, 1.00 mmol) in DCM (20 mL) was stirred at room temperature for 16 hours. Water and DCM were added to the mixture and then it was filtered. The organic layer was collected, concentrated to dryness, and purified by flash column chromatography to give the title compound (249 mg, 100% yield).

Step B: 5-(2-Methyl-4-phenoxyphenyl)-N-((1S)-3-(methylamino)cyclopentyl)-4-oxo-4,5-dihydro-3H-1-thia-3,5,8-triazaacenaphthylene-2-carboxamide To a solution of (S)-5-(2-methyl-4-phenoxyphenyl)-4-oxo-N-(3-oxocyclopentyl)-4,5-dihydro-3H-1-thia-3,5,8-triazaacenaphthylene-2-carboxamide (249 mg, 0.499 mmol) and a methanolic solution of methylamine (1.0 mL) in DCM (8 mL) was added NaBH(OAc)₃ (318 mg, 1.50 mmol) and was stirred at room temperature for 6 hours. The mixture was dispersed between DCM and water. The organic layer was collected, concentrated to dryness and purified by flash column chromatography and then by preparative TLC to give the title compound (20 mg, 8% yield). MS (ESI): mass calcd. for C₂₈H₂₇N₅O₃S, 513.6; m/z found, 514.3 [M+H]⁺. ¹H NMR (400 MHz, CD₃OD and DMSO-d₆): δ 8.09-8.03 (m, 1H), 7.38-7.30 (m, 2H), 7.16-7.12 (m, 1H), 7.12-7.07 (m, 1H), 7.05-7.01 (m, 2H), 6.99-6.96 (m, 1H), 6.90-6.86 (m, 1H), 5.76-5.69 (m, 1H), 4.42-4.34 (m, 1H), 3.46-3.40 (m, 1H), 2.43 (s, 3H), 2.14-2.04 (m, 2H), 2.00 (s, 3H), 1.95-1.90 (m, 2H), 1.64-1.57 (m, 1H), 1.54-1.46 (m, 1H).

Example 81: N-Cyclopentyl-5-(*S)-(2-methyl-4-phenoxyphenyl)-4-oxo-4,5-dihydro-3H-1-thia-3,5,8-triazaacenaphthylene-2-carboxamide

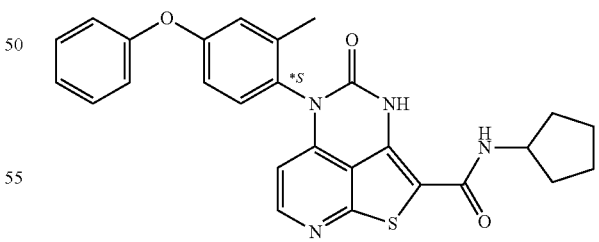

A chiral purification was performed on N-cyclopentyl-5-(2-methyl-4-phenoxyphenyl)-4-oxo-4,5-dihydro-3H-1-thia-3,5,8-triazaacenaphthylene-2-carboxamide (Example 28; 794 mg) via chiral SFC (Stationary phase: CHIRALCEL OJ-H, 5 μm, 250×20 mm, Mobile phase: 60% CO₂, 40% MeOH) to give the title compound (as the *S atropisomer; 67 mg). MS (ESI): mass calcd. for C₂₇H₂₄N₄O₃S, 484.6; m/z found, 484.1 [M+H]⁺. ¹H NMR (600 MHz, CDCl₃): δ

9.53 (s, 1H), 8.33 (d, J=5.5 Hz, 1H), 7.47-7.33 (m, 2H), 7.23-6.88 (m, 6H), 6.01 (d, J=5.4 Hz, 1H), 5.71 (d, J=7.2 Hz, 1H), 4.36 (q, J=7.1 Hz, 1H), 2.18-2.02 (m, 5H), 1.81-1.59 (m, 4H), 1.51 (ddq, J=13.5, 8.6, 6.7 Hz, 2H).

Example 82: N-Cyclopentyl-5-(*R)-(2-methyl-4-phenoxyphenyl)-4-oxo-4,5-dihydro-3H-1-thia-3,5,8-triazaacenaphthylene-2-carboxamide

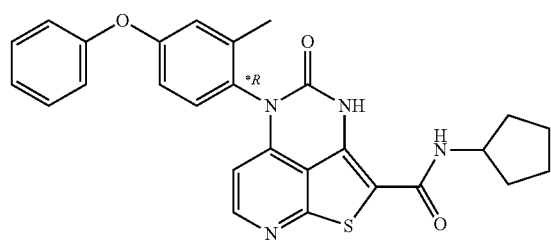 [SMILES: Cc1cc(Oc2ccccc2)ccc1N1C(=O)Nc2c(C(=O)NC3CCCC3)sc3nccc1c23]

A chiral purification was performed on N-cyclopentyl-5-(2-methyl-4-phenoxyphenyl)-4-oxo-4,5-dihydro-3H-1-thia-3,5,8-triazaacenaphthylene-2-carboxamide (Example 28; 794 mg) via chiral SFC (Stationary phase: CHIRALCEL OJ-H, 5 μm, 250×20 mm, Mobile phase: 60% $CO_2$, 30% MeOH) to give the title compound (as the *R atropisomer; 67 mg). MS (ESI): mass calcd. for $C_{27}H_{24}N_4O_3S$, 484.6; m/z found, 484.1 $[M+H]^+$. $^1$H NMR (600 MHz, $CDCl_3$): δ 9.53 (s, 1H), 8.32 (d, J=5.5 Hz, 1H), 7.45-7.33 (m, 2H), 7.25-6.91 (m, 6H), 6.00 (d, J=5.4 Hz, 1H), 5.79 (d, J=7.0 Hz, 1H), 4.36 (h, J=7.1 Hz, 1H), 2.17-2.02 (m, 5H), 1.79-1.62 (m, 4H), 1.62-1.40 (m, 2H).

Example 83: N-((1S,4S)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide

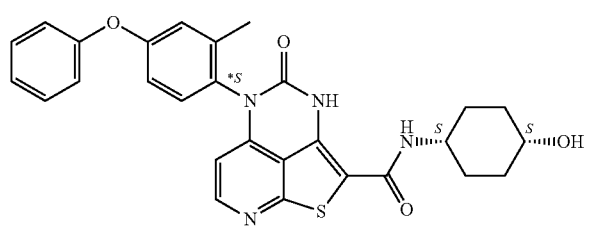

A chiral purification was performed on N-cyclopentyl-5-(2-methyl-4-phenoxyphenyl)-4-oxo-4,5-dihydro-3H-1-thia-3,5,8-triazaacenaphthylene-2-carboxamide (Example 16, 843 mg) via chiral SFC (Stationary phase: CHIRALCEL OJ-H, 5 μm, 250×20 mm, Mobile phase: 55% $CO_2$, 45% MeOH) to give the title compound (as the *S atropisomer; 37 mg). MS (ESI): mass calcd. for $C_{28}H_{26}N_4O_4S$, 514.6; m/z found, 514.2 $[M+H]^+$. $^1$H NMR (600 MHz, $CDCl_3$): δ 9.44 (s, 1H), 8.34 (d, J=5.4 Hz, 1H), 7.46-7.34 (m, 2H), 7.27-6.91 (m, 7H), 6.01 (d, J=5.4 Hz, 1H), 5.67 (d, J=7.9 Hz, 1H), 4.14-3.93 (m, 2H), 2.13 (s, 3H), 1.84-1.66 (m, 8H).

Example 84: N-((1S,4S)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide

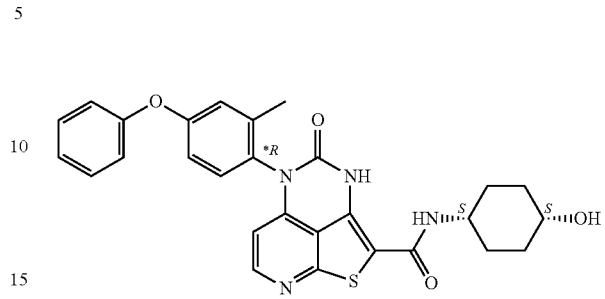

A chiral purification was performed on N-cyclopentyl-5-(2-methyl-4-phenoxyphenyl)-4-oxo-4,5-dihydro-3H-1-thia-3,5,8-triazaacenaphthylene-2-carboxamide (Example 16, 843 mg) via chiral SFC (Stationary phase: CHIRALCEL OJ-H, 5 μm, 250×20 mm, Mobile phase: 55% $CO_2$, 45% MeOH) to give the title compound (as the *R atropisomer; 35 mg). MS (ESI): mass calcd. for $C_{28}H_{26}N_4O_4S$, 514.6; m/z found, 514.2 $[M+H]^+$.

Example 85: N-((1R,4R)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide

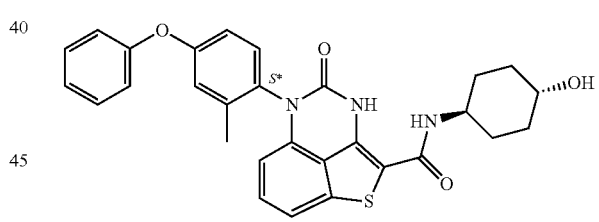

A chiral purification was performed on N-((1R,4R)-4-hydroxycyclohexyl)-5-(2-methyl-4-phenoxyphenyl)-4-oxo-4,5-dihydro-3H-1-thia-3,5,8-triazaacenaphthylene-2-carboxamide (Example 15; 843 mg) via chiral SFC (Stationary phase: CHIRALCEL OD-H, 5 μm, 250×20 mm, Mobile phase: 70% $CO_2$, 30% EtOH) to give the title compound (as the *S atropisomer; 18 mg). MS (ESI): mass calcd. for $C_{28}H_{26}N_4O_4S$, 514.6; m/z found, 514.2 $[M+H]^+$. $^1$H NMR (500 MHz, $CDCl_3$): δ 9.47 (s, 1H), 8.35 (d, J=5.5 Hz, 1H), 7.46-7.34 (m, 2H), 7.21-7.07 (m, 4H), 7.07-6.91 (m, 2H), 6.02 (d, J=5.5 Hz, 1H), 5.38 (d, J=7.9 Hz, 1H), 4.05-3.85 (m, 1H), 3.76-3.59 (m, 1H), 2.20-2.00 (m, 7H), 1.53-1.42 (m, 2H), 1.42-1.28 (m, 2H), 1.28-1.20 (m, 1H).

Example 86: N-((1R,4R)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide

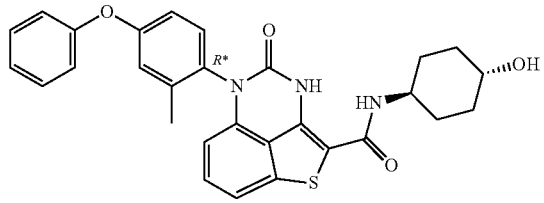

A chiral purification was performed on N-((1R,4R)-4-hydroxycyclohexyl)-5-(2-methyl-4-phenoxyphenyl)-4-oxo-4,5-dihydro-3H-1-thia-3,5,8-triazaacenaphthylene-2-carboxamide (Example 15; 843 mg) via chiral SFC (Stationary phase: CHIRALCEL OD-H, 5 µm, 250×20 mm, Mobile phase: 70% $CO_2$, 30% EtOH) to give the title compound (as the *R atropisomer; 18 mg). MS (ESI): mass calcd. for $C_{28}H_{26}N_4O_4S$, 514.6; m/z found, 514.2 $[M+H]^+$. $^1H$ NMR (500 MHz, $CDCl_3$): δ 9.47 (s, 1H), 8.35 (d, J=5.5 Hz, 1H), 7.50-7.35 (m, 2H), 7.23-7.07 (m, 4H), 7.06-6.90 (m, 2H), 6.02 (d, J=5.5 Hz, 1H), 5.37 (d, J=7.9 Hz, 1H), 4.02-3.85 (m, 1H), 3.75-3.67 (m, 1H), 2.14-2.02 (m, 7H), 1.54-1.42 (m, 2H), 1.42-1.29 (m, 2H), 1.27-1.21 (m, 1H).

Example 87: 5-(*S)-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide

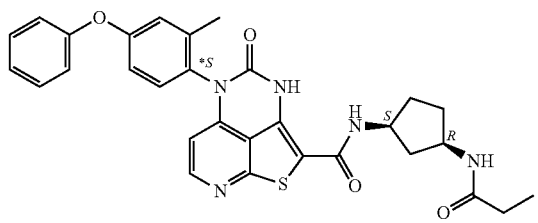

Step A: N-((1S,3R)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 5, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3S)-3-aminocyclopentyl]carbamate, in Step A.

Step B: 5-(*S)-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide To a solution of N-((1S,3R)-3-aminocyclopentyl)-5-(*S)-(2-methyl-4-phenoxyphenyl)-4-oxo-4,5-dihydro-3H-1-thia-3,5,8-triazaacenaphthylene-2-carboxamide (90 mg, 0.18 mmol) and triethylamine (57 mg, 0.56 mmol) in DCM (5 mL) was added propanoyl propanoate (24 mg, 0.18 mmol) and was stirred at room temperature for 2 hours. The mixture was purified by flash column chromatography, then by preparative TLC to give the title compound (53 mg, 51% yield). MS (ESI): mass calcd. for $C_{30}H_{29}N_5O_4S$, 555.6; m/z found, 556.4 $[M+H]^+$. $^1H$ NMR (400 MHz, DMSO-$d_6$): δ 10.15 (s, 1H), 8.33-8.26 (m, 1H), 8.25-8.12 (m, 1H), 7.86-7.78 (m, 1H), 7.46-7.39 (m, 2H), 7.38-7.29 (m, 1H), 7.20-7.15 (m, 1H), 7.12-7.08 (m, 2H), 7.08-7.04 (m, 1H), 6.98-6.93 (m, 1H), 5.98-5.89 (m, 1H), 4.23-4.12 (m, 1H), 4.00-3.88 (m, 1H), 2.26-2.17 (m, 1H), 2.08-2.01 (m, 5H), 1.91-1.78 (m, 2H), 1.73-1.62 (m, 1H), 1.58-1.41 (m, 2H), 0.97 (t, J=7.6 Hz, 3H).

Example 88: N-((1S,3R)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide

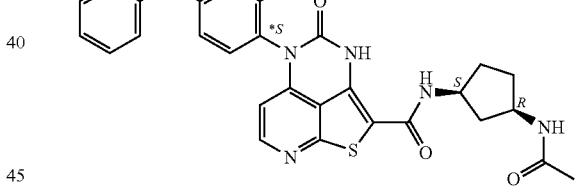

To a solution of N-((1S,3R)-3-aminocyclopentyl)-5-(*S)-(2-methyl-4-phenoxyphenyl)-4-oxo-4,5-dihydro-3H-1-thia-3,5,8-triazaacenaphthylene-2-carboxamide (Example 87, product from Step A, 90 mg, 0.18 mmol) and triethylamine (57 mg, 0.56 mmol) in DCM (5 mL) was added acetic anhydride (24 mg, 0.24 mmol) and was stirred at room temperature for 2 hours. The mixture was purified by flash column chromatography, then by preparative TLC to give the title compound (53 mg, 53% yield). MS (ESI): mass calcd. for $C_{29}H_{27}N_5O_4S$, 541.6; m/z found, 542.4 $[M+H]^+$. $^1H$ NMR (400 MHz, DMSO-$d_6$): δ 10.16 (s, 1H), 8.37-8.12 (m, 2H), 7.95-7.87 (m, 1H), 7.45-7.39 (m, 2H), 7.36-7.29 (m, 1H), 7.20-7.15 (m, 1H), 7.12-7.08 (m, 2H), 7.08-7.05 (m, 1H), 6.98-6.93 (m, 1H), 5.97-5.87 (m, 1H), 4.24-4.12 (m, 1H), 3.99-3.90 (m, 1H), 2.25-2.17 (m, 1H), 2.03 (s, 3H), 1.91-1.80 (m, 2H), 1.78 (s, 3H), 1.72-1.62 (m, 1H), 1.60-1.50 (m, 1H), 1.49-1.40 (m, 1H).

Example 89: N-((1S,4S)-4-((*E)-2-Cyano-3-cyclopropylacrylamido)cyclohexyl)-5-(*S)-(2-methyl-4-phenoxyphenyl)-4-oxo-4,5-dihydro-3H-1-thia-3,5,8-triazaacenaphthylene-2-carboxamide

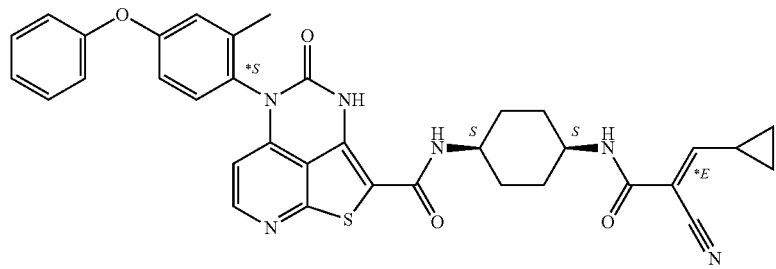

Step A: N-((1S,4S)-4-((*E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 7 using 5-(2-methyl-4-phenoxyphenyl)-4-oxo-4,5-dihydro-3H-1-thia-3,5,8-triazaacenaphthylene-2-carboxylic acid (Intermediate 1) and tert-butyl ((1S,4S)-4-aminocyclohexyl)carbamate in Step A.

Step B: N-((1S,4S)-4-((*E)-2-Cyano-3-cyclopropylacrylamido)cyclohexyl)-5-(*S)-(2-methyl-4-phenoxyphenyl)-4-oxo-4,5-dihydro-3H-1-thia-3,5,8-triazaacenaphthylene-2-carboxamide A chiral purification was performed on N-((1S,4S)-4-((*E)-2-cyano-3-cyclopropylacrylamido)cyclohexyl)-5-(*S)-(2-methyl-4-phenoxyphenyl)-4-oxo-4,5-dihydro-3H-1-thia-3,5,8-triazaacenaphthylene-2-carboxamide (29.5 mg) via chiral SFC (Stationary phase: CHIRALCEL OJ-H, 5 μm, 250×20 mm, Mobile phase: 60% $CO_2$, 40% MeOH) to give the title compound (as the *S atropisomer; 10 mg). MS (ESI): mass calcd. for $C_{35}H_{32}N_6O_4S$, 632.7; m/z found, 632.2 $[M+H]^+$. $^1H$ NMR (400 MHz, $CD_3OD$): δ 8.33 (d, J=5.5 Hz, 1H), 7.49-6.84 (m, 9H), 6.08 (d, J=5.5 Hz, 1H), 4.14-3.88 (m, 2H), 2.17-1.68 (m, 12H), 1.38-1.18 (m, 3H), 1.03-0.79 (m, 2H).

Example 90: N-((1S,4S)-4-((*E)-2-Cyano-3-cyclopropylacrylamido)cyclohexyl)-5-(*R)-(2-methyl-4-phenoxyphenyl)-4-oxo-4,5-dihydro-3H-1-thia-3,5,8-triazaacenaphthylene-2-carboxamide

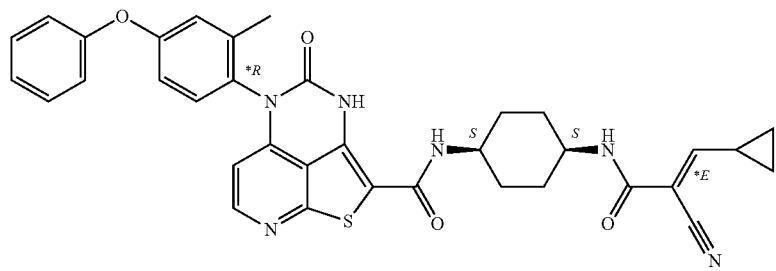

Step A: N-((1S,4S)-4-((*E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide The title compound was prepared using steps A-B in Example 19 (43 mg).

Step B: N-((1S,4S)-4-((*E)-2-Cyano-3-cyclopropylacrylamido)cyclohexyl)-5-(*R)-(2-methyl-4-phenoxyphenyl)-4-oxo-4,5-dihydro-3H-1-thia-3,5,8-triazaacenaphthylene-2-carboxamide A chiral purification was performed on N-((1S,4S)-4-((*E)-2-cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide (Example 19; 29.5 mg) via chiral SFC (Stationary phase: CHIRALCEL OJ-H, 5 μm, 250×20 mm, Mobile phase: 60% $CO_2$, 40% MeOH) to give the title compound (as the *R atropisomer; 11 mg). MS (ESI): mass calcd. for $C_{35}H_{32}N_6O_4S$, 632.7; m/z found, 632.2 $[M+H]^+$. $^1H$ NMR (400 MHz, $CD_3OD$): δ 8.33 (d, J=5.6 Hz, 1H), 7.49-6.87 (m, 9H), 6.07 (d, J=5.5 Hz, 1H), 4.11-3.89 (m, 2H), 2.17-1.68 (m, 12H), 1.37-1.23 (m, 3H), 1.05-0.77 (m, 3H).

Example 91: N-((1R,2R)-2-Aminocyclopentyl)-4-oxo-5-(4-phenoxyphenyl)-4,5-dihydro-3H-1-thia-3,5,8-triazaacenaphthylene-2-carboxamide

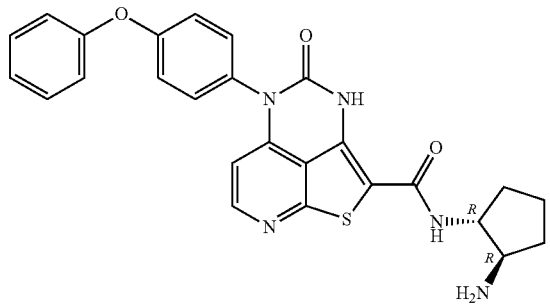

To a dry scintillation vial under Ar with a stir bar containing (1R,2R)-trans-N-Boc-1,2-cyclopentanediamine (306.6 mg, 1.531 mmol), diisopropylethylamine (0.525 mL, 3.00 mmol), and THF (4 mL) was slowly added at room temperature 4-oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol) dropwise via syringe and was stirred at rt. A precipitate formed in the reaction solution, which was filtered and rinsed with ether. The residue was dissolved in DCM and an excess of HCL in dioxane (4 M, 5 mL) was added and was stirred for 90 min at 50° C. The reaction mixture was concentrated to dryness and the residue was dissolved in DMSO and purified by HPLC to give the title compound (189.1 mg, 38.94% yield). MS (ESI): mass calcd. for $C_{26}H_{23}N_5O_3S$, 485.6; m/z found, 486.1 [M+H]$^+$.

Example 92: 5-(*S)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide

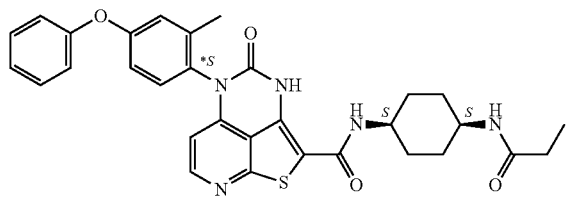

A chiral purification was performed on 5-(2-methyl-4-phenoxyphenyl)-4-oxo-N-((1S,4S)-4-propionamidocyclohexyl)-4,5-dihydro-3H-1-thia-3,5,8-triazaacenaphthylene-2-carboxamide (Example 65; 76 mg) via chiral SFC (Stationary phase: CHIRALCEL OD-H, 5 μm, 250×20 mm, Mobile phase: 50% $CO_2$, 50% EtOH) to give the title compound (as the *S atropisomer; 33 mg, 17% yield). MS (ESI): mass calcd. for $C_{31}H_{31}N_5O_4S$, 569.7; m/z found, 569.2 [M+H]$^+$.

Example 93: 5-(*R)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide

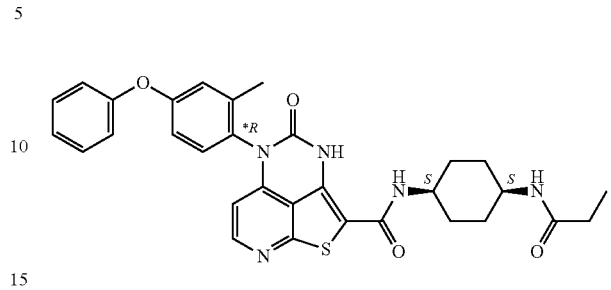

A chiral purification was performed on 5-(2-methyl-4-phenoxyphenyl)-4-oxo-N-((1S,4S)-4-propionamidocyclohexyl)-4,5-dihydro-3H-1-thia-3,5,8-triazaacenaphthylene-2-carboxamide (Example 65; 76 mg) via chiral SFC (Stationary phase: CHIRALCEL OD-H, 5 μm, 250×20 mm, Mobile phase: 50% $CO_2$, 50% EtOH) to give the title compound (as the *R atropisomer; 30 mg, 16% yield). MS (ESI): mass calcd. for $C_{31}H_{31}N_5O_4S$, 569.7; m/z found, 569.2 [M+H]$^+$.

Example 94: N-((1S,4S)-4-Acetamidocyclohexyl)-5-(*S)-(2-methyl-4-phenoxyphenyl)-4-oxo-4,5-dihydro-3H-1-thia-3,5,8-triazaacenaphthylene-2-carboxamide


A chiral purification was performed on N-((1S,4S)-4-acetamidocyclohexyl)-5-(2-methyl-4-phenoxyphenyl)-4-oxo-4,5-dihydro-3H-1-thia-3,5,8-triazaacenaphthylene-2-carboxamide (Example 64; 103 mg) via chiral SFC (Stationary phase: CHIRALCEL OD-H, 5 μm, 250×20 mm, Mobile phase: 50% $CO_2$, 50% EtOH) to give the title compound (as the *S atropisomer; 36 mg, 19% yield). MS (ESI): mass calcd. for $C_{30}H_{29}N_5O_4S$, 555.7; m/z found, 555.2 [M+H]$^+$.

Example 95: N-((1S,4S)-4-Acetamidocyclohexyl)-5-(*R)-(2-methyl-4-phenoxyphenyl)-4-oxo-4,5-dihydro-3H-1-thia-3,5,8-triazaacenaphthylene-2-carboxamide

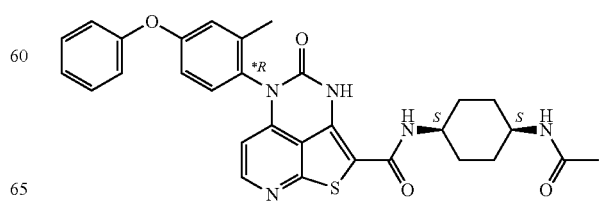

A chiral purification was performed on N-((1S,4S)-4-acetamidocyclohexyl)-5-(2-methyl-4-phenoxyphenyl)-4-oxo-4,5-dihydro-3H-1-thia-3,5,8-triazaacenaphthylene-2-carboxamide (Example 64; 103 mg) via chiral SFC (Stationary phase: CHIRALCEL OD-H, 5 μm, 250×20 mm, Mobile phase: 50% CO$_2$, 50% EtOH) to give the title compound (as the *R atropisomer; 36 mg, 19% yield). MS (ESI): mass calcd. for C$_{30}$H$_{29}$N$_5$O$_4$S, 555.7; m/z found, 555.2 [M+H]$^+$. $^1$H NMR (600 MHz, CDCl$_3$): δ 9.48 (s, 1H), 8.36 (d, J=5.5 Hz, 1H), 7.49-7.34 (m, 2H), 7.22-7.14 (m, 2H), 7.13-7.05 (m, 2H), 7.05-6.91 (m, 2H), 6.03 (d, J=5.4 Hz, 1H), 5.62 (dd, J=49.6, 7.4 Hz, 2H), 4.20-3.87 (m, 2H), 2.13 (s, 3H), 2.01 (s, 3H), 1.93-1.81 (m, 4H), 1.81-1.76 (m, 2H), 1.74-1.68 (m, 2H).

Example 96: N-(rac-(1,3-cis)-3-Aminocyclopentyl)-4-oxo-5-(4-phenoxyphenyl)-4,5-dihydro-3H-1-thia-3,5,8-triazaacenaphthylene-2-carboxamide

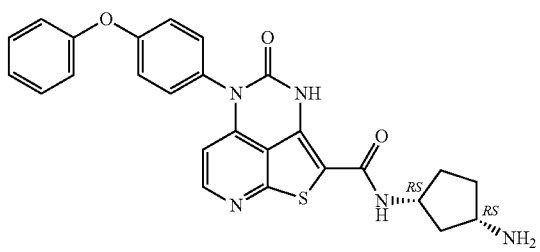 [SMILES: N[C@H]1CC[C@@H](NC(=O)c2sc3nccc4c3c2NC(=O)N4c2ccc(Oc3ccccc3)cc2)C1]

Step A: Racemic-tert-butyl (3-(4-oxo-5-(4-phenoxyphenyl)-4,5-dihydro-3H-1-thia-3,5,8-triazaacenaphthylene-2-carboxamido)cyclopentyl)carbamate To a dry scintillation vial under Ar with a stir bar containing tert-butyl rac-[(1S,3R)-3-aminocyclopentyl]carbamate (295 mg, 1.48 mmol), THF (4 mL), and DIPEA (0.525 mL, 3 mmol) was added slowly (dropwise) at rt 4-oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol). When LCMS showed that the reaction had gone to completion, the reaction was concentrated to dryness and dissolved in DCM.

Step B: N-(rac-(1,3-cis)-3-Aminocyclopentyl)-4-oxo-5-(4-phenoxyphenyl)-4,5-dihydro-3H-1-thia-3,5,8-triazaacenaphthylene-2-carboxamide A solution of racemic-tert-butyl (3-(4-oxo-5-(4-phenoxyphenyl)-4,5-dihydro-3H-1-thia-3,5,8-triazaacenaphthylene-2-carboxamido)cyclopentyl)carbamate in HCl in dioxane (4 M, 5 mL) was stirred at 50° C. for 2 hrs. The reaction mixture was concentrated to dryness, dissolved in DMF and purified by HPLC to give the title compound (231.6 mg, 47.70% yield). MS (ESI): mass calcd. for C$_{26}$H$_{23}$N$_5$O$_3$S, 485.6; m/z found, 486.1 [M+H]$^+$. $^1$H NMR (500 MHz, CD$_3$OD): δ 8.14 (d, J=5.7 Hz, 1H), 7.47-7.26 (m, 4H), 7.22-7.02 (m, 5H), 6.01 (d, J=5.7 Hz, 1H), 4.45-4.30 (m, 1H), 3.61-3.51 (m, 1H), 2.60-2.46 (m, 1H), 2.21-1.60 (m, 5H).

Example 97: N-((1R,2S)-2-Aminocyclopentyl)-4-oxo-5-(4-phenoxyphenyl)-4,5-dihydro-3H-1-thia-3,5,8-triazaacenaphthylene-2-carboxamide

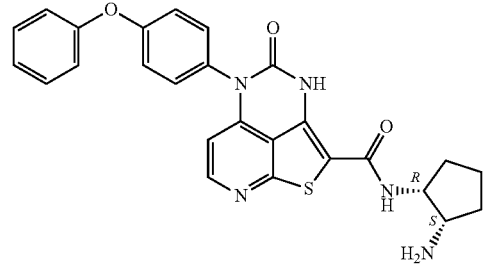

Step A: tert-butyl ((1S,2R)-2-(4-oxo-5-(4-phenoxyphenyl)-4,5-dihydro-3H-1-thia-3,5,8-triazaacenaphthylene-2-carboxamido)cyclopentyl)carbamate To a dry scintillation vial under Ar with a stir bar containing tert-butyl ((1S,2R)-2-aminocyclopentyl)carbamate (301.2 mg, 1.504 mmol), THF (4 mL), and diisopropylethylamine (0.525 mL, 3.00 mmol) was added slowly (dropwise) at rt 4-oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol). The reaction progress was monitored by LCMS. A precipitate formed that was filtered and rinsed with ether.

Step B: N-((1R,2S)-2-Aminocyclopentyl)-4-oxo-5-(4-phenoxyphenyl)-4,5-dihydro-3H-1-thia-3,5,8-triazaacenaphthylene-2-carboxamide The precipitate from Step A was dissolved in DCM and an excess of HCl in dioxane (4 M, 5 mL) was added and was stirred at 50° C. for 90 min. The reaction mixture was concentrated to dryness and the residue was dissolved in DMF and purified by HPLC to give the title compound (142.3 mg, 29.31% yield). MS (ESI): mass calcd. for C$_{26}$H$_{23}$N$_5$O$_3$S, 485.6; m/z found, 486.1 [M+H]$^+$. $^1$H NMR (500 MHz, CD$_3$OD): δ 8.24 (s, 1H), 7.48-7.27 (m, 4H), 7.24-7.03 (m, 6H), 6.11 (s, 1H), 4.59-4.38 (m, 1H), 3.78-3.58 (m, 1H), 2.22-2.06 (m, 2H), 1.98-1.65 (m, 4H).

Example 98: N-((1S,2R)-2-Aminocyclopentyl)-4-oxo-5-(4-phenoxyphenyl)-4,5-dihydro-3H-1-thia-3,5,8-triazaacenaphthylene-2-carboxamide

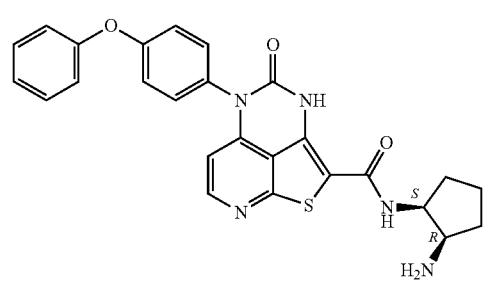

Step A: tert-Butyl ((1R,2S)-2-(4-oxo-5-(4-phenoxyphenyl)-4,5-dihydro-3H-1-thia-3,5,8-triazaacenaphthylene-2-carboxamido)cyclopentyl)carbamate To a dry scintillation vial under Ar with a stir bar containing (1R,2S)-2-amino-1-(N-Boc-amino)cyclopentane (296.5 mg, 1.480 mmol), THF (4 mL), and diisopropylethylamine (0.525 mL, 3.00 mmol) was added slowly (dropwise) at rt 4-oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol). The reaction progress was monitored by LCMS. A precipitate formed that was filtered and rinsed with ether.

Step B: N-((1S,2R)-2-Aminocyclopentyl)-4-oxo-5-(4-phenoxyphenyl)-4,5-dihydro-3H-1-thia-3,5,8-triazaacenaphthylene-2-carboxamide The precipitate, from Step A, was dissolved in DCM and an excess of HCl in dioxane (4 M, 5 mL) was added and was stirred at 50° C. for 90 min. The reaction mixture was concentrated to dryness and the residue was dissolved in DMF and purified by HPLC to give the title compound (126.6 mg, 26.07% yield). MS (ESI): mass calcd. for $C_{26}H_{23}N_5O_3S$, 485.6; m/z found, 486.1 [M+H]$^+$. $^1$H NMR (500 MHz, CD$_3$OD): δ 8.15 (d, J=5.6 Hz, 1H), 7.48-7.24 (m, 4H), 7.21-7.04 (m, 5H), 6.02 (d, J=5.7 Hz, 1H), 4.56-4.43 (m, 1H), 3.62 (s, 1H), 2.28-2.05 (m, 2H), 2.04-1.58 (m, 4H).

Example 99: N-((1S,4S)-4-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide

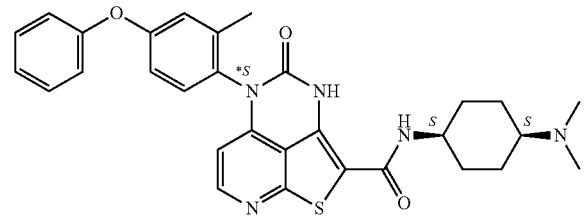

A chiral purification was performed on N-((1S,4S)-4-(dimethylamino)cyclohexyl)-5-(2-methyl-4-phenoxyphenyl)-4-oxo-4,5-dihydro-3H-1-thia-3,5,8-triazaacenaphthylene-2-carboxamide (Example 66; 100 mg) via chiral SFC (Stationary phase: CHIRALCEL OJ-H, 5 μm, 250×20 mm, Mobile phase: 70% CO$_2$, 30% EtOH) to give the title compound (as the *S atropisomer; 30 mg, 17% yield). MS (ESI): mass calcd. for $C_{30}H_{31}N_5O_3S$, 541.7; m/z found, 541.2 [M+H]$^+$. $^1$H NMR (600 MHz, CDCl$_3$): δ 8.35 (d, J=5.5 Hz, 1H), 7.46-7.35 (m, 2H), 7.27 (s, OH), 7.23-7.06 (m, 4H), 7.03-6.89 (m, 2H), 6.01 (d, J=5.5 Hz, 1H), 5.82 (d, J=7.9 Hz, 1H), 4.18 (dq, J=6.7, 3.8 Hz, 1H), 2.33 (s, 6H), 2.13 (s, 4H), 1.92-1.55 (m, 8H).

Example 100: N-((1S,4S)-4-(Dimethylamino)cyclohexyl)-5-(*R)-(2-methyl-4-phenoxyphenyl)-4-oxo-4,5-dihydro-3H-1-thia-3,5,8-triazaacenaphthylene-2-carboxamide

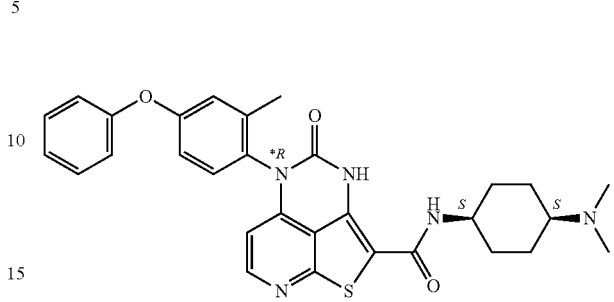

A chiral purification was performed on N-((1S,4S)-4-(dimethylamino)cyclohexyl)-5-(2-methyl-4-phenoxyphenyl)-4-oxo-4,5-dihydro-3H-1-thia-3,5,8-triazaacenaphthylene-2-carboxamide (Example 66; 100 mg) via chiral SFC (Stationary phase: CHIRALCEL OJ-H, 5 μm, 250×20 mm, Mobile phase: 70% CO$_2$, 30% EtOH) to give the title compound (as the *R atropisomer; 32 mg, 18% yield). MS (ESI): mass calcd. for $C_{30}H_{31}N_5O_3S$, 541.7; m/z found, 541.2 [M+H]$^+$. $^1$H NMR (600 MHz, CDCl$_3$): δ 8.35 (d, J=5.4 Hz, 1H), 7.49-7.35 (m, 2H), 7.27 (s, 1H), 7.25-7.06 (m, 4H), 7.06-6.92 (m, 2H), 6.01 (d, J=5.4 Hz, 1H), 5.70 (d, J=7.9 Hz, 1H), 4.22-4.08 (m, 1H), 2.31 (s, 6H), 2.13 (s, 4H), 1.92-1.63 (m, 8H).

Example 101: N-((1S,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

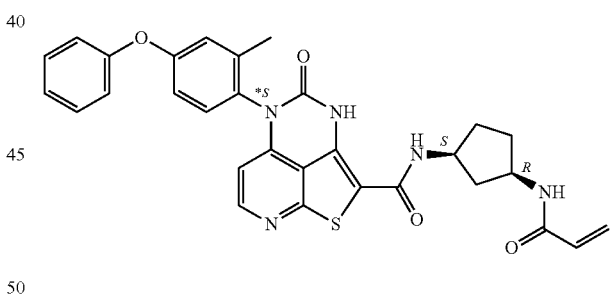

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3S)-3-aminocyclopentyl]carbamate (Intermediate 37) in Step A. MS (ESI): mass calcd. for $C_{30}H_{27}N_5O_4S$, 553.6; m/z found, 554.4 [M+H]$^+$. $^1$H NMR (400 MHz, DMSO-d$_6$): δ 10.16 (s, 1H), 8.33-8.27 (m, 1H), 8.26-8.10 (m, 2H), 7.45-7.40 (m, 2H), 7.38-7.32 (m, 1H), 7.21-7.15 (m, 1H), 7.13-7.08 (m, 2H), 7.08-7.05 (m, 1H), 6.98-6.94 (m, 1H), 6.25-6.16 (m, 1H), 6.10-6.04 (m, 1H), 5.97-5.90 (m, 1H), 5.58-5.52 (m, 1H), 4.26-4.15 (m, 1H), 4.09-3.98 (m, 1H), 2.31-2.22 (m, 1H), 2.04 (s, 3H), 1.94-1.83 (m, 2H), 1.75-1.65 (m, 1H), 1.64-1.56 (m, 1H), 1.56-1.47 (m, 1H).

Example 102: N-((1S,3R)-3-(2-(dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide

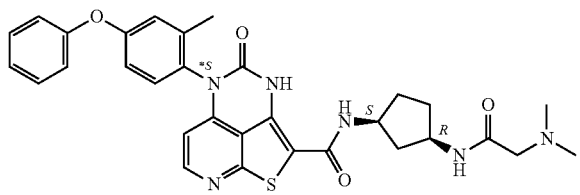

To a mixture of 2-(dimethylamino)acetic acid (32 mg, 0.31 mmol), HATU (119 mg, 0.313 mmol), and triethylamine (95 mg, 0.94 mmol) in DMF (3 mL) was added N-((1S,3R)-3-aminocyclopentyl)-5-(*S)-(2-methyl-4-phenoxyphenyl)-4-oxo-4,5-dihydro-3H-1-thia-3,5,8-triazaacenaphthylene-2-carboxamide (Example 87, product from Step A, 156 mg, 0.312 mmol) and was stirred at rt for 1 hour. The mixture was purified by flash column chromatography and then by preparative TLC to yield the title compound (59 mg, 96% yield). MS (ESI): mass calcd. for $C_{31}H_{32}N_6O_4S$, 584.7; m/z found, 585.4 $[M+H]^+$.

Example 103: 5-(*S)-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide

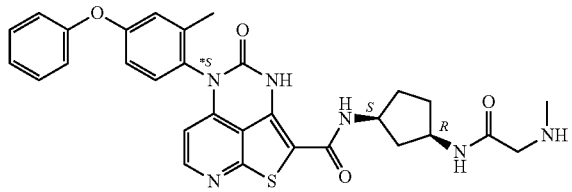

Step A: tert-Butyl methyl(2-((((1R,3S)-3-(5-(*S)-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate To a mixture of Boc-sarcosine (31 mg, 0.16 mmol), HATU (61 mg, 0.16 mmol), and triethylamine (49 mg, 0.48 mmol) in DMF (3 mL) was added N-((1S,3R)-3-aminocyclopentyl)-5-(*S)-(2-methyl-4-phenoxyphenyl)-4-oxo-4,5-dihydro-3H-1-thia-3,5,8-triazaacenaphthylene-2-carboxamide (Example 87, product from Step A, 80 mg, 0.16 mmol) and was stirred at rt for 1 hour. The mixture was purified by flash column chromatography to yield the title compound (107 mg, 100% yield).

Step B: 5-(*S)-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide A solution of tert-butylmethyl(2-((((1R,3S)-3-(5-(*S)-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate (107 mg, 0.16 mmol) in concentrated HCl (1 mL) and MeOH (5 mL) was concentrated to dryness. The residue was dispersed between an aqueous 1 M $NH_3$ solution and DCM. The organic layer was collected and purified by flash column chromatography to yield the title compound (57 mg, 63% yield). MS (ESI): mass calcd. for $C_{30}H_{30}N_6O_4S$, 570.7; m/z found, 571.4 $[M+H]^+$.

Example 104: N-((1R,2S)-2-acrylamidocyclopentyl)-4-oxo-5-(4-phenoxyphenyl)-4,5-dihydro-3H-1-thia-3,5,8-triazaacenaphthylene-2-carboxamide

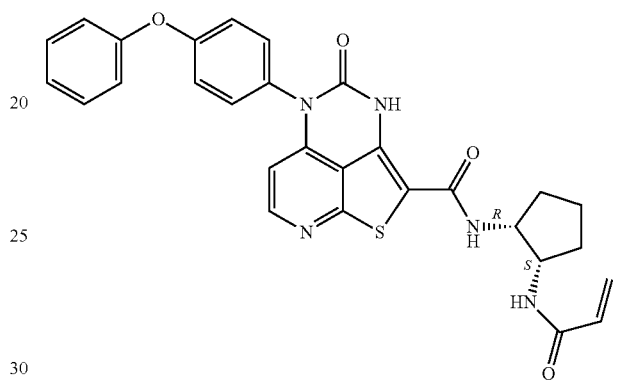

Step A: tert-Butyl ((1S,2R)-2-(4-oxo-5-(4-phenoxyphenyl)-4,5-dihydro-3H-1-thia-3,5,8-triazaacenaphthylene-2-carboxamido)cyclopentyl)carbamate To a dry scintillation vial under Ar containing a stir bar were added tert-butyl N-((1S,2R)-2-aminocyclopentyl)carbamate (301.2 mg, 1.504 mmol), THF (4 mL), and diisopropylethylamine (0.525 mL, 3.00 mmol). 4-Oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol) was added dropwise to the above reaction solution. A solid precipitate that formed was filtered and rinsed with ether. The crude product was used in the next step without further purification.

Step B: N-((1R,2S)-2-Aminocyclopentyl)-4-oxo-5-(4-phenoxyphenyl)-4,5-dihydro-3H-1-thia-3,5,8-triazaacenaphthylene-2-carboxamide tert-Butyl ((1S,2R)-2-(5-(2-methyl-4-phenoxyphenyl)-4-oxo-4,5-dihydro-3H-1-thia-3,5,8-triazaacenaphthylene-2-carboxamido)cyclopentyl)carbamate was dissolved in DCM and an excess of HCl in dioxane (4 M, 5 mL) was added and was reacted for 90 min at 50° C. The reaction mixture was concentrated to dryness and the residue was dissolved in DMF and was purified by basic reverse phase HPLC to yield the title compound (142 mg, 29.3% yield).

Step C: N-((1R,2S)-2-Acrylamidocyclopentyl)-4-oxo-5-(4-phenoxyphenyl)-4,5-dihydro-3H-1-thia-3,5,8-triazaacenaphthylene-2-carboxamide To a small oven dried microwave vial under argon were added N-((1R,2S)-2-aminocyclopentyl)-5-(4-phenoxyphenyl)-4-oxo-4,5-dihydro-3H-1-thia-3,5,8-triazaacenaphthylene-2-carboxamide (45.8 mg, 0.094 mmol), DCM (1.0 mL), and triethylamine (0.067 mL, 0.47 mmol). The vial was cooled to −20° C. in an ice/acetone bath and a 0.17 mL solution of prop-2-enoyl chloride in DCM (0.5 mL in 10 mL DCM) was added dropwise over 10-15 min and then allowed to warm to rt slowly over 5 min. The reaction mixture was purified by flash column chromatography, and then by reverse phase basic HPLC to yield the title compound (7.6 mg, 15% yield). MS (ESI): mass calcd. for $C_{29}H_{25}N_5O_4S$, 539.6; m/z found, 540.2 [M+H]$^+$. $^1$H NMR (500 MHz, CD$_3$OD): δ 8.26 (s, 1H), 7.49-7.27 (m, 4H), 7.27-7.04 (m, 5H), 6.38-6.04 (m, 3H), 5.61 (dd, J=10.2, 1.9 Hz, 1H), 4.51-4.38 (m, 2H), 2.16-1.99 (m, 2H), 1.99-1.55 (m, 4H).

Example 105: N-((1R,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

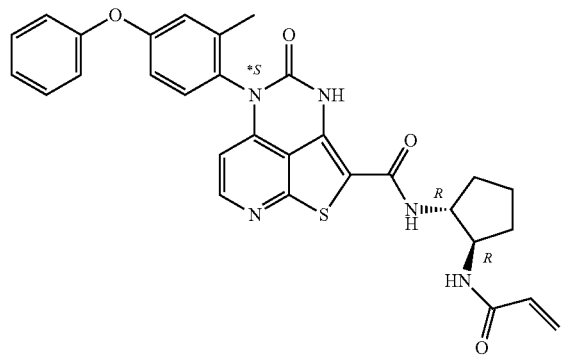

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3R)-3-aminocyclopentyl]carbamate in place of tert-butyl ((1S,4S)-4-aminocyclohexyl)carbamate in Step A. MS (ESI): mass calcd. for $C_{30}H_{27}N_5O_4S$, 553.6; m/z found, 554.4 [M+H]$^+$. $^1$H NMR (400 MHz, CD$_3$OD): δ 8.30 (d, J=5.5 Hz, 1H), 7.45-7.35 (m, 2H), 7.30-7.24 (mz, 1H), 7.21-7.12 (m, 1H), 7.11-7.02 (m, 3H), 7.00-6.93 (m, 1H), 6.29-6.15 (m, 2H), 6.05 (d, J=5.5 Hz, 1H), 5.65-5.58 (m, 1H), 4.33-4.16 (m, 2H), 2.23-2.09 (m, 5H), 1.87-1.75 (m, 2H), 1.72-1.51 (m, 2H).

Example 106: 5-([1,1'-Biphenyl]-3-yl)-N-((1R,2S)-2-acrylamidocyclohexyl)-4-oxo-4,5-dihydro-3H-1-thia-3,5,8-triazaacenaphthylene-2-carboxamide

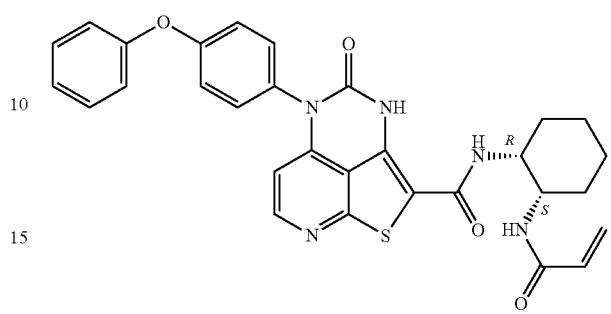

The title compound was prepared in a manner analogous to Example 1, using 5-([1,1'-biphenyl]-3-yl)-4-oxo-4,5-dihydro-3H-1-thia-3,5,8-triazaacenaphthylene-2-carboxylic acid (Intermediate 19) and tert-butyl N-[(1S,2R)-2-aminocyclohexyl]carbamate in Step A. MS (ESI): mass calcd. for $C_{30}H_{27}N_5O_3S$, 537.6; m/z found, 538.2 [M+H]$^+$. $^1$H NMR (400 MHz, DMSO-d$_6$): δ 9.94 (s, 1H), 8.33-8.22 (m, 1H), 7.87-7.73 (m, 4H), 7.70-7.64 (m, 3H), 7.48-7.40 (m, 3H), 7.39-7.34 (m, 1H), 6.45-6.34 (m, 1H), 6.16-6.08 (m, 1H), 6.08-6.01 (m, 1H), 5.62-5.52 (m, 1H), 4.27-4.11 (m, 1H), 4.07-3.96 (m, 1H), 1.76-1.60 (m, 4H), 1.59-1.50 (m, 2H), 1.44-1.31 (m, 2H).

Example 107: N-((1R,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

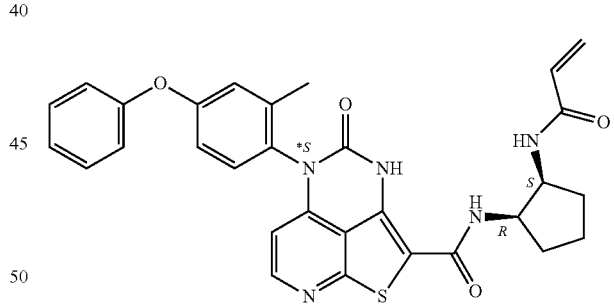

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2R)-2-aminocyclopentyl]carbamate in Step A. MS (ESI): mass calcd. for $C_{30}H_{27}N_5O_4S$, 553.6; m/z found, 554.5 [M+H]$^+$. $^1$H NMR (400 MHz, CD$_3$OD): δ 8.30 (d, J=5.6 Hz, 1H), 7.44-7.33 (m, 2H), 7.30-7.24 (m, 1H), 7.20-7.13 (m, 1H), 7.12-7.02 (m, 3H), 7.00-6.92 (m, 1H), 6.31-6.14 (m, 2H), 6.04 (d, J=5.6 Hz, 1H), 5.65-5.56 (m, 1H), 4.48-4.33 (m, 2H), 2.17-2.03 (m, 5H), 1.95-1.85 (m, 1H), 1.80-1.60 (m, 3H).

Example 108: N-((1R,2S)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide

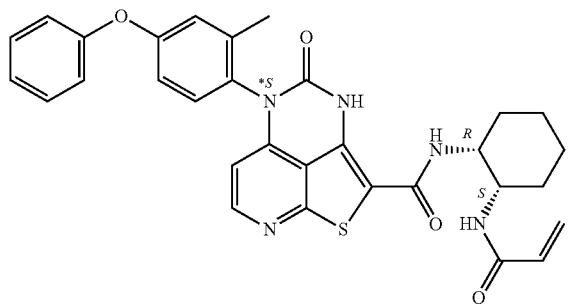

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxy c acid (Intermediate 1, including CHIRAL SEPARATION METHOD 1 to obtain the *S atropisomer) and tert-butyl N-[(1S,2R)-2-aminocyclohexyl]carbamate in Step A. MS (ESI): mass calcd. for $C_{31}H_{29}N_5O_4S$, 567.7; m/z found, 568.2 [M+H]$^+$. $^1$H NMR (400 MHz, DMSO-d$_6$): δ 9.97 (s, 1H), 8.36-8.24 (m, 1H), 7.96-7.71 (m, 2H), 7.45-7.39 (m, 2H), 7.38-7.32 (m, 1H), 7.20-7.15 (m, 1H), 7.13-7.04 (m, 3H), 6.99-6.93 (m, 1H), 6.45-6.33 (m, 1H), 6.18-6.08 (m, 1H), 6.00-5.88 (m, 1H), 5.62-5.53 (m, 1H), 4.28-4.12 (m, 1H), 4.06-3.98 (m, 1H), 2.04 (s, 3H), 1.76-1.61 (m, 4H), 1.59-1.51 (m, 2H), 1.43-1.32 (m, 2H).

Example 109: N-((1RS,3RS)-3-Acrylamidocyclopentyl)-4-oxo-5-(4-phenoxyphenyl)-4,5-dihydro-3H-1-thia-3,5,8-triazaacenaphthylene-2-carboxamide

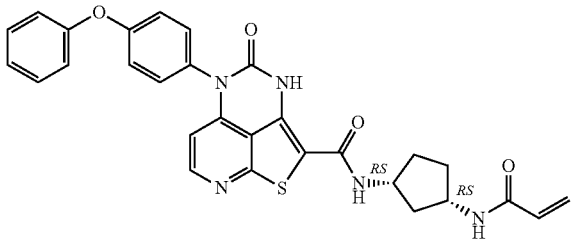

The title compound was prepared in a manner analogous to Example 104, using 4-oxo-5-(4-phenoxyphenyl)-4,5-dihydro-3H-1-thia-3,5,8-triazaacenaphthylene-2-carbonyl chloride (Intermediate 9) and tert-butyl rac-[(1S,3R)-3-aminocyclopentyl]carbamate in Step A. MS (ESI): mass calcd. for $C_{29}H_{25}N_5O_4S$, 539.6; m/z found, 540.2 [M+H]$^+$. $^1$H NMR (500 MHz, CDCl$_3$): δ 9.54 (s, 1H), 8.34 (d, J=5.5 Hz, 1H), 7.50-7.34 (m, 3H), 7.31-7.27 (m, 2H), 7.23-7.10 (m, 5H), 6.41 (dd, J=16.8, 1.3 Hz, 1H), 6.16-6.04 (m, 2H), 5.69 (dd, J=10.3, 1.4 Hz, 1H), 4.41-4.35 (m, 1H), 4.27-4.04 (m, 1H), 3.79-3.49 (m, 1H), 2.46-1.75 (m, 6H).

Example 110: N-((1S,3R)-3-Acrylamidocyclopentyl)-5-(4-isopropoxy-2-methylphenyl)-4-oxo-4,5-dihydro-3H-1-thia-3,5,8-triazaacenaphthylene-2-carboxamide

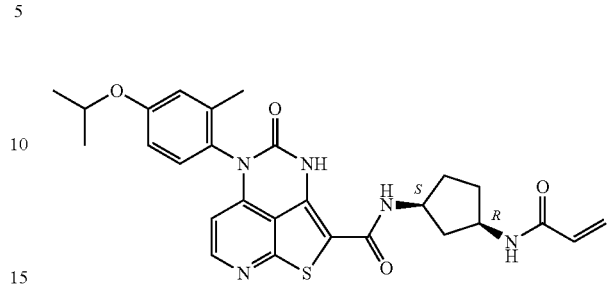

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31) and tert-butyl N-[(1R,3S)-3-aminocyclopentyl]carbamate in Step A. MS (ESI): mass calcd. for $C_{27}H_{29}N_5O_4S$, 519.6; m/z found, 520.5 [M+H]$^+$. $^1$H NMR (400 MHz, CD$_3$OD): δ 8.29 (d, J=5.4 Hz, 1H), 7.29-7.11 (m, 1H), 7.06-6.82 (m, 2H), 6.37-6.15 (m, 2H), 6.02 (d, J=5.5 Hz, 1H), 5.76-5.52 (m, 1H), 4.72-4.58 (m, 1H), 4.44-4.11 (m, 2H), 2.58-2.40 (m, 1H), 2.19-1.95 (m, 5H), 1.88-1.71 (m, 2H), 1.68-1.54 (m, 1H), 1.40-1.30 (m, 6H).

Example 111: N-((1R,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide

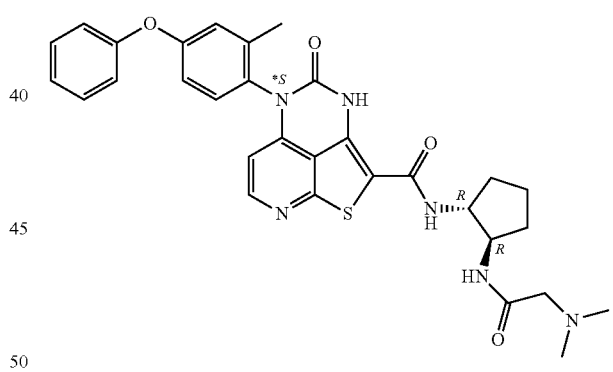

To a stirred solution of N-((1R,2R)-2-aminocyclopentyl)-5-(*S)-(2-methyl-4-phenoxyphenyl)-4-oxo-4,5-dihydro-3H-1-thia-3,5,8-triazaacenaphthylene-2-carboxamide (Example 67, product from Step A, 100 mg, 0.2 mmol) in DMF (3 mL) were added 2-(dimethylamino)acetic acid (22 mg, 0.16 mmol), HATU (75 mg, 0.20 mmol), and triethylamine (40 mg, 0.40 mmol). The reaction mixture was stirred at room temperature overnight. The reaction mixture was concentrated to dryness and the residue was partitioned between ethyl acetate and water. The organic layer was separated, shaken with brine and dried over anhydrous Na$_2$SO$_4$. The residue was purified by flash column chromatography to give the title compound as yellow solid (59 mg, 50% yield). MS (ESI): mass calcd. for $C_{31}H_{32}N_6O_4S$, 584.7; m/z found, 585.2 [M+H]$^+$. $^1$H NMR (400 MHz, CD$_3$OD): δ 8.29 (d, J=5.5 Hz, 1H), 7.45-7.35 (m, 2H), 7.32-7.24 (m, 1H), 7.20-7.12 (m, 1H), 7.12-7.03 (m, 3H), 7.00-6.92 (m, 1H), 6.04 (d, J=5.5 Hz, 1H), 4.39-4.11 (m, 2H), 3.04-2.88 (m, 2H), 2.29-2.25 (m, 6H), 2.18-2.06 (m, 5H), 1.87-1.74 (m, 2H), 1.75-1.50 (m, 2H).

Example 112: 5-(*S)-(2-Methyl-4-phenoxyphenyl)-N-((1R,2R)-2-(2-(methylamino)acetamido)cyclopentyl)-4-oxo-4,5-dihydro-3H-1-thia-3,5,8-triazaacenaphthylene-2-carboxamide

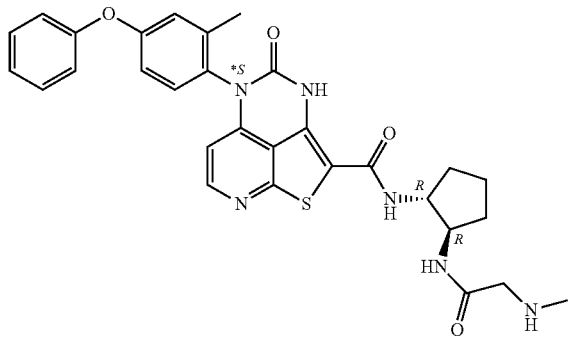

Step A: tert-Butyl methyl(2-(((1R,2R)-2-(5-(*S)-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate To a stirred solution of N-((1R,2R)-2-aminocyclopentyl)-5-(*S)-(2-methyl-4-phenoxyphenyl)-4-oxo-4,5-dihydro-3H-1-thia-3,5,8-triazaacenaphthylene-2-carboxamide (Example 67, Product from Step A, 80 mg, 0.16 mmol) in DMF (3 mL) were added 2-[tert-butoxy carbonyl(methyl)amino-acetic acid (36 mg, 0.16 mmol), HATU (73 mg, 0.19 mmol), and diisopropylethylamine (45 mg, 0.35 mmol). The resulting mixture was stirred at room temperature overnight. The reaction mixture was concentrated to dryness and the residue was partitioned between ethyl acetate and water. The organic layer was separated, shaken with brine and dried over anhydrous $Na_2SO_4$. The residue was purified by flash column chromatography to give the title compound as yellow solid (70 mg, 65% yield).

Step B: 5-(*S)-(2-Methyl-4-phenoxyphenyl)-N-((1R,2R)-2-(2-(methylamino)acetamido)cyclopentyl)-4-oxo-4,5-dihydro-3H-1-thia-3,5,8-triazaacenaphthylene-2-carboxamide A solution of tert-butyl methyl(2-(41R,2R)-2-(5-(*S)-(2-methyl-4-phenoxyphenyl)-4-oxo-4,5-dihydro-3H-1-thia-3,5,8-triazaacenaphthylene-2-carboxamido)cyclopentyl)amino)-2-oxoethyl)carbamate (70 mg, 0.10 mmol) in concentrated HCl (2 mL) and MeOH (15 mL) was stirred at room temperature for about 2 hours. The reaction mixture was concentrated to dryness and the residue was purified by flash column chromatography to give the title compound as yellow solid (56 mg, 87% yield). MS (ESI): mass calcd. for $C_{30}H_{30}N_6O_4S$, 570.7; m/z found, 571.2 $[M+H]^+$. $^1H$ NMR (400 MHz, $CD_3OD$): δ 8.46 (s, 1H), 8.32 (d, J=5.5 Hz, 1H), 7.45-7.35 (m, 2H), 7.32-7.24 (m, 1H), 7.19-7.13 (m, 1H), 7.12-7.03 (m, 3H), 7.01-6.92 (m, 1H), 6.07 (d, J=5.5 Hz, 1H), 4.32-4.16 (m, 2H), 3.66 (s, 2H), 2.61 (s, 3H), 2.21-2.04 (m, 5H), 1.91-1.76 (m, 2H), 1.75-1.52 (m, 2H).

Example 113: N-((1R,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide

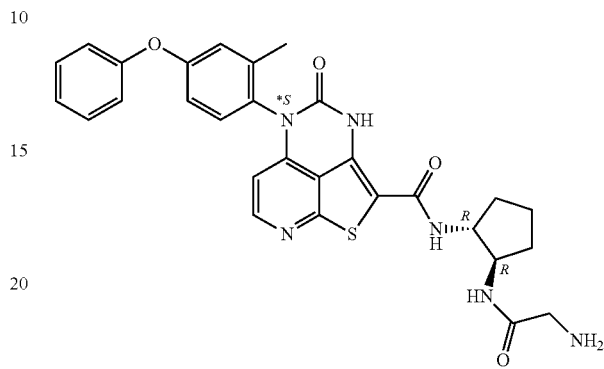

The title compound was prepared in a manner analogous to Example 112, using 2-(tert-butoxycarbonylamino)acetic acid in Step A. MS (ESI): mass calcd. for $C_{29}H_{28}N_6O_4S$, 556.6; m/z found, 557.5 $[M+H]^+$. $^1H$ NMR (400 MHz, $CD_3OD$): δ 8.49 (s, 1H), 8.31 (d, J=5.5 Hz, 1H), 7.48-7.35 (m, 2H), 7.32-7.25 (m, 1H), 7.22-7.13 (m, 1H), 7.12-7.02 (m, 3H), 7.00-6.92 (m, 1H), 6.06 (d, J=5.5 Hz, 1H), 4.29-4.15 (m, 2H), 3.57 (s, 2H), 2.25-2.05 (m, 5H), 1.90-1.76 (m, 2H), 1.72-1.52 (m, 2H).

Example 114: N-((1S,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

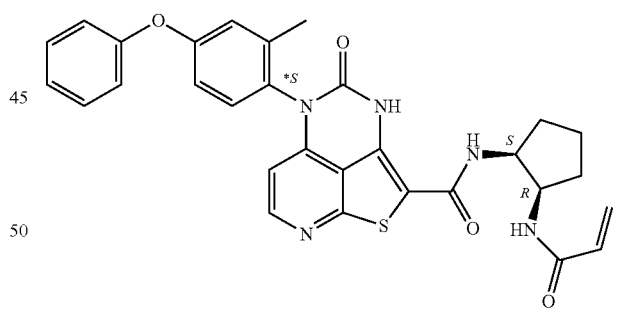

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2S)-2-aminocyclopentyl]carbamate in Step A. MS (ESI): mass calcd. for $C_{30}H_{27}N_5O_4S$, 553.6; m/z found, 554.2 $[M+H]^+$. $^1H$ NMR (400 MHz, $CD_3OD$): δ 8.28 (d, J=5.0 Hz, 1H), 7.46-7.31 (m, 2H), 7.30-7.20 (m, 1H), 7.19-7.10 (m, 1H), 7.09-6.98 (m, 3H), 6.97-6.89 (m, 1H), 6.35-6.12 (m, 2H), 6.03 (d, J=5.5 Hz, 1H), 5.68-5.52 (m, 1H), 4.48-4.32 (m, 2H), 2.24-1.99 (m, 5H), 1.96-1.81 (m, 1H), 1.81-1.54 (m, 3H).

Example 115: N-((1R,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide


The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2R)-2-aminocyclopentyl]carbamate. MS (ESI): mass calcd. for $C_{27}H_{25}N_5O_3S$, 499.6; m/z found, 500.3 $[M+H]^+$. $^1H$ NMR (400 MHz, $CD_3OD$): δ 8.49 (s, 1H), 8.30 (d, J=5.5 Hz, 1H), 7.44-7.35 (m, 2H), 7.34-7.24 (m, 1H), 7.19-7.13 (m, 1H), 7.12-7.02 (m, 3H), 7.02-6.93 (m, 1H), 6.04 (d, J=5.6 Hz, 1H), 4.52-4.43 (m, 1H), 3.78-3.69 (m, 1H), 2.21-2.11 (m, 2H), 2.09 (s, 3H), 2.01-1.86 (m, 2H), 1.80-1.67 (m, 2H).

Example 116: N-((1S,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

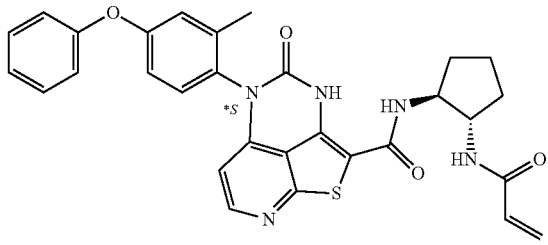 [SMILES: C=CC(=O)N[C@H]1CCC[C@@H]1NC(=O)c1sc2nccc3c2c1NC(=O)N3c1ccc(Oc2ccccc2)cc1C]

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2S)-2-aminocyclopentyl]carbamate. MS (ESI): mass calcd. for $C_{30}H_{27}N_5O_4S$, 553.6; m/z found, 554.1 $[M+H]^+$. $^1H$ NMR (400 MHz, $CD_3OD$): δ 8.30 (d, J=5.5 Hz, 1H), 7.44-7.34 (m, 2H), 7.31-7.23 (m, 1H), 7.18-7.13 (m, 1H), 7.11-7.01 (m, 3H), 6.99-6.92 (m, 1H), 6.27-6.16 (m, 2H), 6.04 (d, J=5.5 Hz, 1H), 5.66-5.57 (m, 1H), 4.33-4.15 (m, 2H), 2.23-2.05 (m, 5H), 1.86-1.72 (m, 2H), 1.70-1.52 (m, 2H).

Example 117: N-((1S,3R)-3-Acrylamidocyclopentyl)-4-oxo-5-(4-phenoxyphenyl)-4,5-dihydro-3H-1-thia-3,5,8-triazaacenaphthylene-2-carboxamide

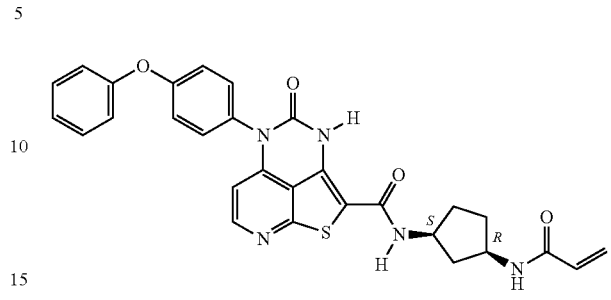

Step A. tert-Butyl ((1R,3S)-3-(4-oxo-5-(4-phenoxyphenyl)-4,5-dihydro-3H-1-thia-3,5,8-triazaacenaphthylene-2-carboxamido)cyclopentyl)carbamate To a dry scintillation vial under Ar containing a stir bar were added tert-butyl ((1R,3S)-3-aminocyclopentyl)carbamate (309.3 mg, 1.544 mmol), diisopropylethylamine (0.50 mL, 2.9 mmol), and THF (4 mL). Next, 4-oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol) was slowly added via a syringe at room temperature for 1 hour. The reaction was purified by gilson reverse phase acidic HPLC.

Step B. N-((1S,3R)-3-Aminocyclopentyl)-4-oxo-5-(4-phenoxyphenyl)-4,5-dihydro-3H-1-thia-3,5,8-triazaacenaphthylene-2-carboxamide tert-Butyl ((1R,3S)-3-(4-oxo-5-(4-phenoxyphenyl)-4,5-dihydro-3H-1-thia-3,5,8-triazaacenaphthylene-2-carboxamido)cyclopentyl)carbamate was dissolved in DCM (5 mL) and 2 M HCl in ether (5 mL) and was stirred over night (20 hours) at rt. The reaction was filtered and the precipitate was rinsed with DCM. The residue was dissolved in methanol and acetonitrile was added. The reaction was concentrated to dryness and lyophilized to give the title compound (252.1 mg, 51.9% over two steps). MS (ESI): mass calcd. for $C_{26}H_{23}N_5O_3S$, 485.57; m/z found, 486.1 $[M+H]^+$. $^1H$ NMR (400 MHz, $CD_3OD$): δ 8.35 (d, J=5.6 Hz, 1H), 7.48-7.36 (m, 4H), 7.24-7.08 (m, 6H), 6.21 (d, J=5.6 Hz, 1H), 4.38-4.30 (m, 1H), 3.73-3.62 (m, 1H), 2.61-2.49 (m, 1H), 2.21-1.76 (m, 5H).

Step C: N-((1S,3R)-3-Acrylamidocyclopentyl)-4-oxo-5-(4-phenoxyphenyl)-4,5-dihydro-3H-1-thia-3,5,8-triazaacenaphthylene-2-carboxamide To a dry scintillation vial under Ar containing a stir bar were added N-((1S,3R)-3-aminocyclopentyl)-4-oxo-5-(4-phenoxyphenyl)-4,5-dihydro-3H-1-thia-3,5,8-triazaacenaphthylene-2-carboxamide (112.7 mg, 0.232 mmol), DCM (3.38 mL), and triethylamine (0.225 mL, 1.62 mmol). The white suspension was cooled to ~−20° C. in an ice/acetone bath. To the solution was slowly added prop-2-enoyl chloride (0.0187 mL, 0.22 mmol) as a solution in DCM (0.5 mL in 10 mL, adding 0.37 mL of this solution). The reaction was allowed to warm to rt with stirring and was stirred for 10 minutes. The reaction was concentrated to dryness and the residue was dissolved in methanol and was purified by reverse phase basic HPLC on a dionex column to give the title compound (16.3 mg, 13.0% yield). MS (ESI): mass calcd. for $C_{29}H_{25}N_5O_4S$, 539.6; m/z found, 540.1 $[M+H]^+$. $^1$H NMR (400 MHz, CDCl$_3$): δ 9.54 (s, 1H), 8.35 (d, J=5.5 Hz, 1H), 7.46-7.36 (m, 3H), 7.29 (s, 1H), 7.25-7.04 (m, 6H), 6.48-6.25 (m, 2H), 6.21-6.03 (m, 2H), 5.70 (d, J=10.3 Hz, 1H), 4.48-4.00 (m, 2H), 2.57-2.40 (m, 1H), 2.05 (d, J=4.3 Hz, 1H), 1.99-1.81 (m, 4H).

Example 118: N-((1R,2S)-2-Acrylamidocyclohexyl)-4-oxo-5-(4-phenoxyphenyl)-4,5-dihydro-3H-1-thia-3,5,8-triazaacenaphthylene-2-carboxamide

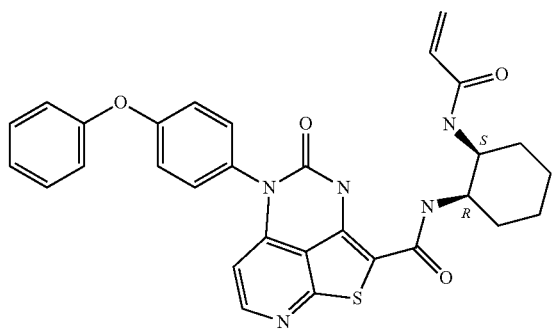

The title compound was prepared in a manner analogous to Example 104, using 4-oxo-5-(4-phenoxyphenyl)-4,5-dihydro-3H-1-thia-3,5,8-triazaacenaphthylene-2-carbonyl chloride (Intermediate 9) and tert-butyl ((1S,2R)-2-aminocyclohexyl)carbamate in Step A. MS (ESI): mass calcd. for $C_{30}H_{27}N_5O_4S$, 553.6; m/z found, 554.1 $[M+H]^+$. $^1$H NMR (500 MHz, CD$_3$OD): δ 8.30 (d, J=7.7 Hz, 1H), 7.41 (dddd, J=10.7, 8.7, 6.4, 2.1 Hz, 4H), 7.22-7.05 (m, 5H), 6.49-6.35 (m, 1H), 6.27 (dd, J=17.0, 1.9 Hz, 1H), 6.23-6.09 (m, 1H), 5.67 (dd, J=10.3, 1.8 Hz, 1H), 4.41 (s, 1H), 4.18 (s, 1H), 1.89-1.44 (m, 9H).

Example 119: N-((1S,4S)-4-Acrylamidocyclohexyl)-4-oxo-5-(4-phenoxyphenyl)-4,5-dihydro-3H-1-thia-3,5,8-triazaacenaphthylene-2-carboxamide

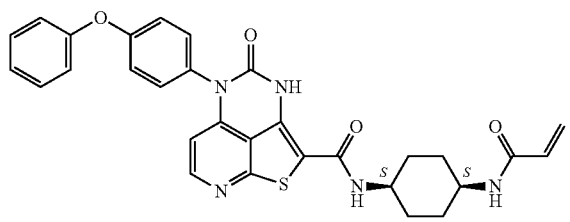

The title compound was prepared in a manner analogous to Example 104, using 4-oxo-5-(4-phenoxyphenyl)-4,5-dihydro-3H-1-thia-3,5,8-triazaacenaphthylene-2-carbonyl chloride (Intermediate 9) and 1-N-boc-cis-1,4-cyclohexyldiamine in Step A. MS (ESI): mass calcd. for $C_{30}H_{27}N_5O_4S$, 553.6; m/z found, 554.1 $[M+H]^+$. $^1$H NMR (500 MHz, CD$_3$OD): δ 8.36-8.24 (m, 1H), 7.43-7.36 (m, 4H), 7.20-7.13 (m, 3H), 7.13-7.09 (m, 2H), 6.38-6.28 (m, 1H), 6.27-6.14 (m, 2H), 5.75-5.57 (m, 1H), 4.05-3.88 (m, 1H), 1.92-1.64 (m, 8H).

Example 120: N-((1R,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide

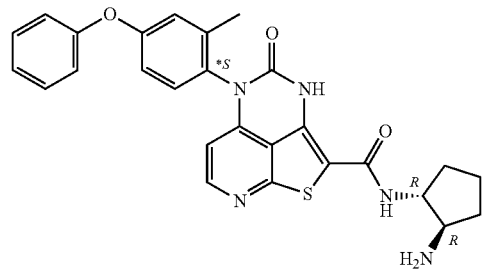

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2R)-2-aminocyclopentyl]carbamate in Step A. MS (ESI): mass calcd. for $C_{27}H_{25}N_5O_3S$, 499.6; m/z found, 500.4 $[M+H]^+$. $^1$H NMR (400 MHz, CD$_3$OD): δ 8.50 (s, 1H), 8.33 (d, J=5.6 Hz, 1H), 7.45-7.35 (m, 2H), 7.32-7.25 (m, 1H), 7.21-7.13 (m, 1H), 7.11-7.04 (m, 3H), 7.01-6.94 (m, 1H), 6.07 (d, J=5.6 Hz, 1H), 4.31-4.18 (m, 1H), 3.52-3.40 (m, 1H), 2.31-2.15 (m, 2H), 2.10 (s, 3H), 1.94-1.82 (m, 3H), 1.79-1.67 (m, 1H).

Example 121: N-((1R,3S)-3-Acrylamidocyclopentyl)-4-oxo-5-(4-phenoxyphenyl)-4,5-dihydro-3H-1-thia-3,5,8-triazaacenaphthylene-2-carboxamide

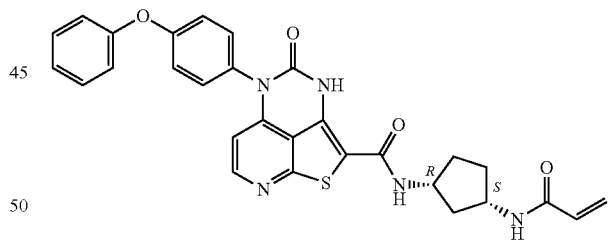

The title compound was prepared in a manner analogous to Example 104, Step A using 4-oxo-5-(4-phenoxyphenyl)-4,5-dihydro-3H-1-thia-3,5,8-triazaacenaphthylene-2-carbonyl chloride (Intermediate 9) and N-[(1S,3R)-3-aminocyclopentyl]prop-2-enamide (Intermediate 45). MS (ESI): mass calcd. for $C_{29}H_{25}N_5O_4S$, 539.6; m/z found, 540.0 $[M+H]^+$. $^1$H NMR (500 MHz, CDCl$_3$): δ 9.54 (s, 1H), 8.35 (d, J=5.5 Hz, 1H), 7.47-7.34 (m, 2H), 7.29-7.28 (m, 1H), 7.27 (s, 2H), 7.25-7.02 (m, 6H), 6.41 (dd, J=16.9, 1.3 Hz, 1H), 6.19-5.91 (m, 2H), 5.70 (dd, J=10.3, 1.3 Hz, 1H), 4.47-4.31 (m, 1H), 4.18-4.00 (m, 1H), 2.74-1.77 (m, 6H).

Example 122: 5-(*S)-(2-Methyl-4-phenoxyphenyl)-N-((1R,2S)-2-(2-(methylamino)acetamido)cyclopentyl)-4-oxo-4,5-dihydro-3H-1-thia-3,5,8-triazaacenaphthylene-2-carboxamide

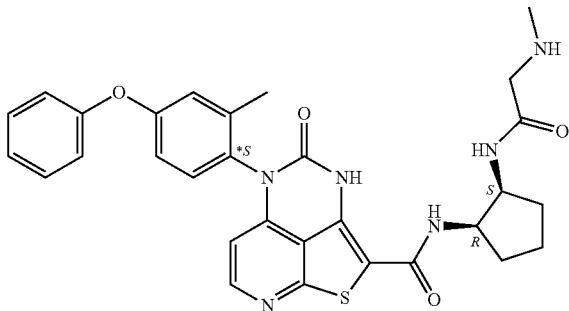

Step A. N-((1R,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2R)-2-aminocyclopentyl]carbamate.

Step B: 5-(*S)-(2-Methyl-4-phenoxyphenyl)-N-((1R,2S)-2-(2-(methylamino)acetamido)cyclopentyl)-4-oxo-4,5-dihydro-3H-1-thia-3,5,8-triazaacenaphthylene-2-carboxamide A solution of N-((1R,2S)-2-aminocyclopentyl)-5-(*S)-(2-methyl-4-phenoxyphenyl)-4-oxo-4,5-dihydro-3H-1-thia-3,5,8-triazaacenaphthylene-2-carboxamide (70 mg, 0.14 mmol), 2[tert-butoxycarbonyl)methyl)amino]acetic acid (26 mg, 0.14 mmol), triethylamine (28 mg, 0.28 mmol), and HATU (53 mg, 0.14 mmol) in DMF (3 mL) was stirred at rt for 3 h. Water was added and the precipitate was filtered to give a pale yellow solid. The solid was dissolved in MeOH (2 mL) and HCl (2 mL) and was heated at 50° C. for 30 min. The reaction mixture was concentrated to dryness and the residue was purified by flash column chromatography to give the title compound (62 mg, 98% yield). MS (ESI): mass calcd. for $C_{30}H_{30}N_6O_4S$, 570.7; m/z found, 571.4 [M+H]$^+$. $^1$H NMR (400 MHz, CD$_3$OD): δ 8.45 (s, 1H), 8.28 (d, J=5.5 Hz, 1H), 7.46-7.34 (m, 2H), 7.30-7.24 (m, 1H), 7.20-7.12 (m, 1H), 7.12-7.03 (m, 3H), 7.01-6.93 (m, 1H), 6.02 (d, J=5.5 Hz, 1H), 4.49-4.35 (m, 2H), 3.68 (s, 2H), 2.62 (s, 3H), 2.14-1.99 (m, 5H), 1.96-1.86 (m, 1H), 1.80-1.61 (m, 3H).

Example 123: N-((1S,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide

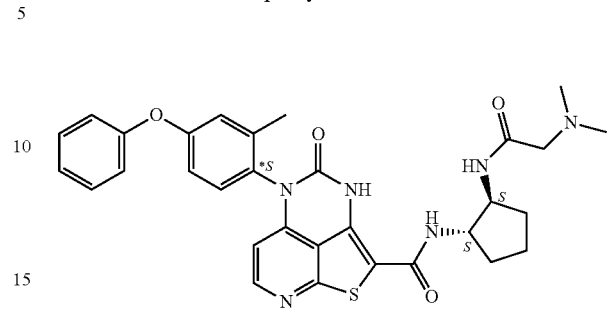

The title compound was prepared in a manner analogous to Example 122 using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2S)-2-aminocyclopentyl]carbamate in Step A, and 2-(dimethylamino)acetic acid in Step B. MS (ESI): mass calcd. for $C_{31}H_{32}N_6O_4S$, 584.7; m/z found, 585.2 [M+H]$^+$. $^1$H NMR (400 MHz, CD$_3$OD): δ 8.30 (d, J=5.6 Hz, 1H), 7.43-7.33 (m, 2H), 7.30-7.22 (m, 1H), 7.21-7.12 (m, 1H), 7.11-7.02 (m, 3H), 7.01-6.89 (m, 1H), 6.04 (d, J=5.6 Hz, 1H), 4.33-4.22 (m, 1H), 4.22-4.12 (m, 1H), 3.02-2.89 (m, 2H), 2.26 (s, 6H), 2.16-2.07 (m, 5H), 1.86-1.75 (m, 2H), 1.75-1.66 (m, 1H), 1.62-1.51 (m, 1H).

Example 124: N-((1S,2R)-2-Acrylamidocyclohexyl)-4-oxo-5-(4-phenoxyphenyl)-4,5-dihydro-3H-1-thia-3,5,8-triazaacenaphthylene-2-carboxamide

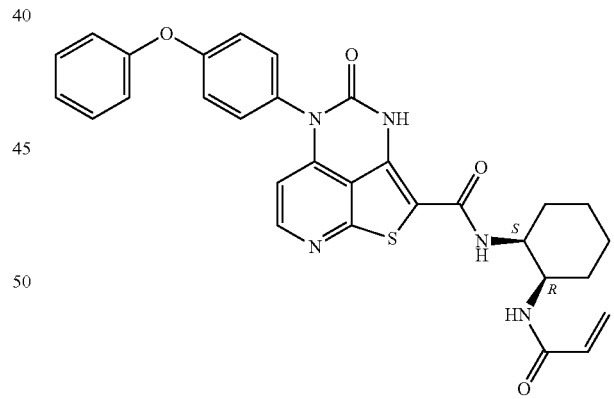

The title compound was prepared in a manner analogous to Example 104, using 4-oxo-5-(4-phenoxyphenyl)-4,5-dihydro-3H-1-thia-3,5,8-triazaacenaphthylene-2-carbonyl chloride (Intermediate 9) and tert-butyl N-[(1R,2S)-2-aminocyclohexyl]carbamate in Step A. MS (ESI): mass calcd. for $C_{30}H_{27}N_5O_4S$, 553.6; m/z found, 554.1 [M+H]$^+$. $^1$H NMR (500 MHz, CD$_3$OD): δ 8.31 (d, J=5.6 Hz, 1H), 7.46-7.34 (m, 4H), 7.22-7.06 (m, 5H), 6.49-6.36 (m, 1H), 6.31-6.25 (m, 1H), 6.18 (d, J=5.6 Hz, 1H), 5.67 (dd, J=10.2, 1.8 Hz, 1H), 4.45-4.37 (m, 1H), 4.21-4.08 (m, 1H), 1.89-1.41 (m, 9H).

Example 125: 5-(*S)-(2-Methyl-4-phenoxyphenyl)-N-((1R,2S)-2-(2-(methylamino)acetamido)cyclohexyl)-4-oxo-4,5-dihydro-3H-1-thia-3,5,8-triazaacenaphthylene-2-carboxamide

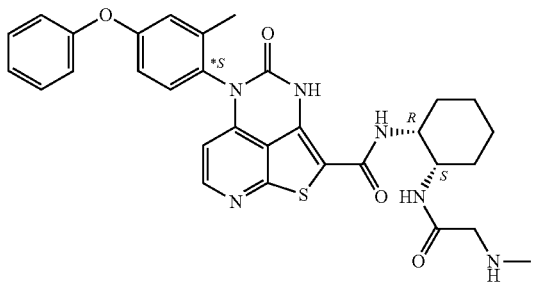

Step A. N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2S)-2-aminocyclohexyl]carbamate.

Step B. 5-(*S)-(2-Methyl-4-phenoxyphenyl)-N-((1R,2S)-2-(2-(methylamino)acetamido)cyclohexyl)-4-oxo-4,5-dihydro-3H-1-thia-3,5,8-triazaacenaphthylene-2-carboxamide The title compound was prepared in a manner analogous to Example 122, Step B, using 2[tert-butoxycarbonyl(methyl)amino]acetic acid. MS (ESI): mass calcd. for $C_{31}H_{32}N_6O_4S$, 584.7; m/z found, 585.2 $[M+H]^+$.

Example 126: N-((1R,2S)-2-Aminocyclohexyl)-4-oxo-5-(4-phenoxyphenyl)-4,5-dihydro-3H-1-thia-3,5,8-triazaacenaphthylene-2-carboxamide

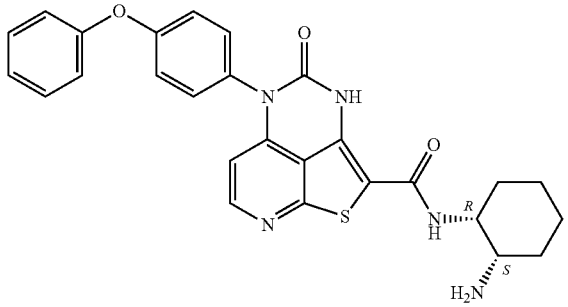

The title compound was prepared in a manner analogous to Example 104, Step A-B, using 4-oxo-5-(4-phenoxyphenyl)-4,5-dihydro-3H-1-thia-3,5,8-triazaacenaphthylene-2-carbonyl chloride (Intermediate 9) and tert-butyl N-[(1S,2R)-2-aminocyclohexyl]carbamate. MS (ESI): mass calcd. for $C_{27}H_{25}N_5O_3S$, 499.6; m/z found, 500.1 $[M+H]^+$. $^1$H NMR (400 MHz, CD$_3$OD): δ 8.54 (s, 1H), 8.15 (d, J=5.6 Hz, 1H), 7.49-7.24 (m, 4H), 7.19-7.08 (m, 3H), 7.08-7.03 (m, 2H), 6.01 (d, J=5.5 Hz, 1H), 4.33-4.24 (m, 1H), 3.66-3.53 (m, 1H), 1.93-1.38 (m, 9H).

Example 127: N-((1S,2R)-2-Acrylamidocyclopentyl)-4-oxo-5-(4-phenoxyphenyl)-4,5-dihydro-3H-1-thia-3,5,8-triazaacenaphthylene-2-carboxamide

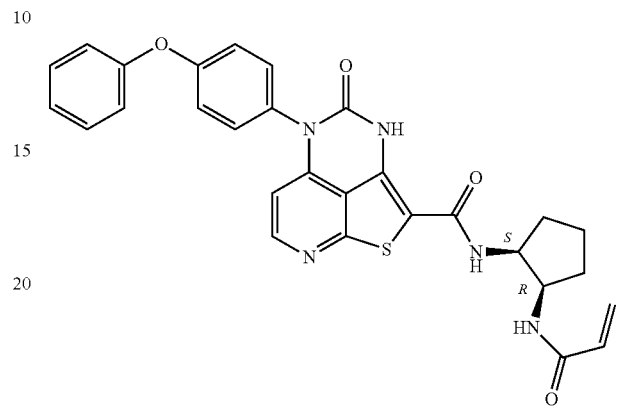

The title compound was prepared in a manner analogous to Example 104, using 4-oxo-5-(4-phenoxyphenyl)-4,5-dihydro-3H-1-thia-3,5,8-triazaacenaphthylene-2-carbonyl chloride (Intermediate 9) and tert-butyl N-[(1R,2S)-2-aminocyclopentyl]carbamate in Step A. MS (ESI): mass calcd. for $C_{29}H_{25}N_5O_4S$, 539.6; m/z found, 540.1 $[M+H]^+$.

Example 128: N-((1R,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide

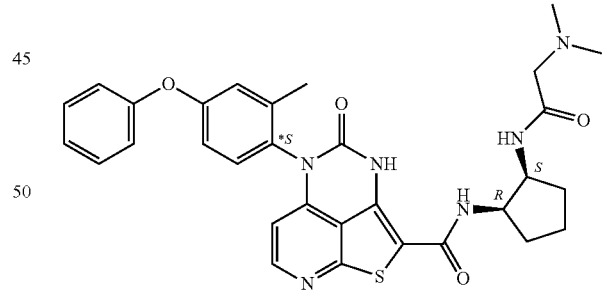

The title compound was prepared in a manner analogous to Example 122, using 2-(dimethylamino)acetic acid in Step B. MS (ESI): mass calcd. for $C_{31}H_{32}N_6O_4S$, 584.7; m/z found, 585.4 $[M+H]^+$. $^1$H NMR (400 MHz, CD$_3$OD): δ 8.30 (d, J=5.5 Hz, 1H), 7.43-7.35 (m, 2H), 7.31-7.21 (m, 1H), 7.19-7.13 (m, 1H), 7.10-7.03 (m, 3H), 7.00-6.92 (m, 1H), 6.04 (d, J=5.5 Hz, 1H), 4.47-4.34 (m, 2H), 3.16 (s, 2H), 2.36 (s, 6H), 2.13-2.02 (m, 5H), 1.95-1.85 (m, 1H), 1.79-1.59 (m, 3H).

Example 129: N-((1R,2S)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide

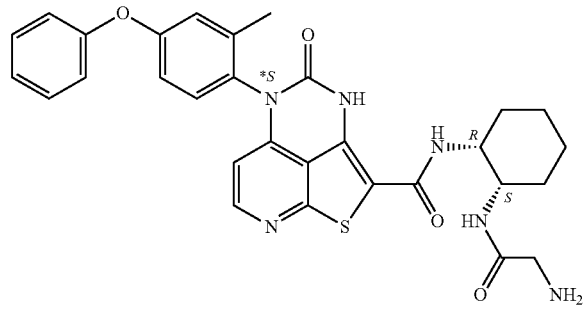

The title compound was prepared in a manner analogous to Example 122, Step B, using N-((1R,2S)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 125, product from Step A), and 2-(tert-butoxycarbonylamino)acetic acid. MS (ESI): mass calcd. for $C_{30}H_{30}N_6O_4S$, 570.7; m/z found, 571.2 [M+H]$^+$.

Example 130: N-((1S,2S)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide

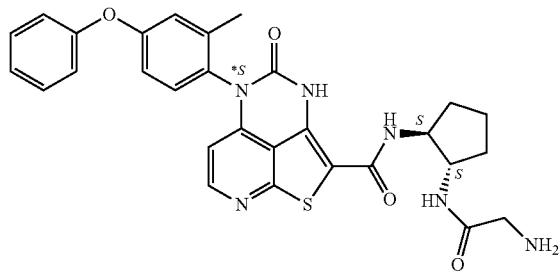

The title compound was prepared in a manner analogous to Example 122 using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2S)-2-aminocyclopentyl]carbamate in Step A, and (2-tert-butoxy-2-oxo-ethyl)carbamic acid in Step B. MS (ESI): mass calcd. for $C_{29}H_{28}N_6O_4S$, 556.6; m/z found, 557.2 [M+H]$^+$. $^1$H NMR (400 MHz, CD$_3$OD): δ 8.03 (d, J=5.6 Hz, 1H), 7.42-7.29 (m, 2H), 7.20-7.06 (m, 4H), 7.04-6.99 (m, 1H), 6.98-6.91 (m, 1H), 5.76 (d, J=5.6 Hz, 1H), 4.35-4.26 (m, 1H), 4.20-4.09 (m, 1H), 3.25-3.19 (m, 2H), 2.27-2.13 (m, 2H), 2.10 (s, 3H), 1.88-1.74 (m, 3H), 1.64-1.50 (m, 1H).

Example 131: N-((1R,2S)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide

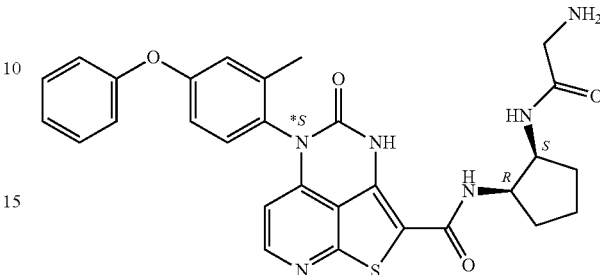

To a solution of N-((1R,2S)-2-aminocyclopentyl)-5-(*S)-(2-methyl-4-phenoxyphenyl)-4-oxo-4,5-dihydro-3H-1-thia-3,5,8-triazaacenaphthylene-2-carboxamide (Example 115, 52.0 mg, 0.104 mmol) and triethylamine (21 mg, 0.21 mmol) in DCM (10 mL) was added (2,5-dioxopyrrolidin-1-yl) 2-(tert-butoxycarbonylamino)acetate (57 mg, 0.21 mmol) in an ice bath, then stirred at rt for 1 h. The reaction mixture was concentrated to dryness and the residue was dissolved in HCl (2 mL) and MeOH (mL) and heated to 50° C. and stirred for 30 min. The reaction mixture was concentrated to dryness and was purified by flash column chromatography to give the title compound (43 mg, 97% yield). MS (ESI): mass calcd. for $C_{29}H_{28}N_6O_4S$, 556.6; m/z found, 557.4 [M+H]$^+$. $^1$H NMR (400 MHz, CD$_3$OD): δ 8.48 (s, 1H), 8.26 (d, J=5.5 Hz, 1H), 7.44-7.35 (m, 2H), 7.29-7.24 (m, 1H), 7.20-7.13 (m, 1H), 7.11-7.03 (m, 3H), 6.99-6.93 (m, 1H), 6.00 (d, J=5.6 Hz, 1H), 4.47-4.35 (m, 2H), 3.60 (s, 2H), 2.16-2.08 (m, 4H), 2.07-2.00 (m, 1H), 1.96-1.85 (m, 1H), 1.78-1.64 (m, 3H).

Example 132: N-((1R,2S)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide

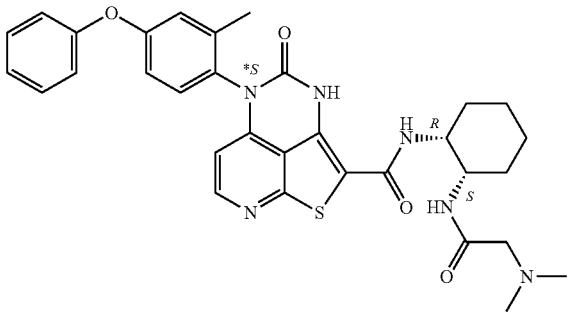

The title compound was prepared in a manner analogous to Example 122, Step B, using N-((1R,2S)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 125, product from Step A) and 2-(dimethylamino)acetic acid. MS (ESI): mass calcd. for $C_{32}H_{34}N_6O_4S$, 598.7; m/z found, 599.3 [M+H]$^+$. $^1$H NMR (400 MHz, DMSO-d$_6$): δ 8.24-8.20 (m, 1H), 8.20-8.09 (m, 1H), 7.77-7.70 (m, 1H), 7.44-7.39 (m, 2H), 7.32-7.36 (m, 1H), 7.19-7.14 (m, 1H), 7.11-7.07 (m, 2H), 7.06-7.03 (m, 1H), 6.95-6.91 (m, 1H), 5.88-5.82 (m, 1H), 4.13-4.03 (m, 2H), 3.22-3.19 (m, 1H), 3.12-3.07 (m, 1H), 2.29 (s, 6H), 2.02 (s, 3H), 1.74-1.59 (m, 4H), 1.55-1.49 (m, 1H), 1.47-1.33 (m, 3H).

Example 133: 5-(*S)-(2-Methyl-4-phenoxyphenyl)-N-((1S,2S)-2-(2-(methylamino)acetamido)cyclopentyl)-4-oxo-4,5-dihydro-3H-1-thia-3,5,8-triazaacenaphthylene-2-carboxamide

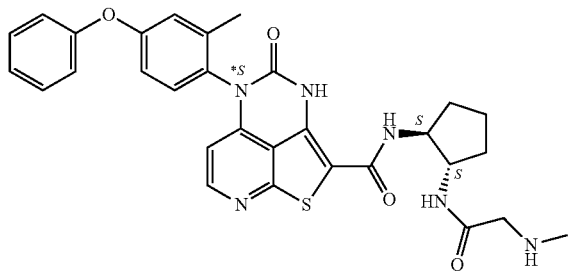

The title compound was prepared in a manner analogous to Example 122 using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2S)-2-aminocyclopentyl]carbamate in Step A, and 2-[tert-butoxycarbonyl(methyl)amino]acetic acid in Step B. MS (ESI): mass calcd. for $C_{30}H_{30}N_6O_4S$, 570.7; m/z found, 571.2 [M+H]$^+$. $^1$H NMR (400 MHz, CD$_3$OD): δ 8.03 (d, J=5.6 Hz, 1H), 7.43-7.30 (m, 2H), 7.17-7.11 (m, 2H), 7.10-7.06 (m, 2H), 7.06-6.99 (m, 1H), 6.97-6.91 (m, 1H), 5.75 (d, J=5.7 Hz, 1H), 4.37-4.23 (m, 1H), 4.22-4.04 (m, 1H), 3.17-3.13 (m, 2H), 2.31 (s, 3H), 2.26-2.12 (m, 2H), 2.09 (s, 3H), 1.91-1.74 (m, 3H), 1.61-1.49 (m, 1H).

Example 134: N-((1S,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide

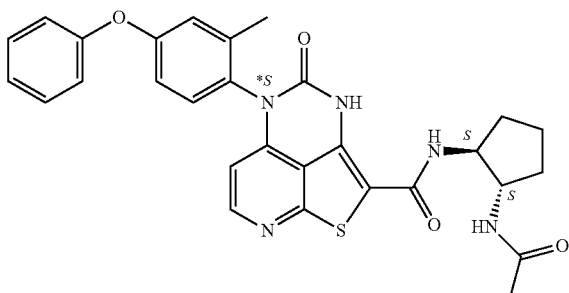

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2S)-2-aminocyclopentyl]carbamate in Step A, and acetyl chloride Step B. MS (ESI): mass calcd. for $C_{29}H_{27}N_5O_4S$, 541.6; m/z found, 542.1 [M+H]$^+$. $^1$H NMR (400 MHz, CD$_3$OD): δ 8.23 (d, J=5.5 Hz, 1H), 7.44-7.31 (m, 2H), 7.30-7.19 (m, 1H), 7.18-7.12 (m, 1H), 7.10-7.00 (m, 3H), 6.97-6.92 (m, 1H), 5.97 (d, J=5.6 Hz, 1H), 4.25-4.08 (m, 2H), 2.18-2.08 (m, 5H), 1.91 (s, 3H), 1.86-1.74 (m, 2H), 1.73-1.63 (m, 1H), 1.61-1.43 (m, 1H).

Example 135: N-((1S,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide

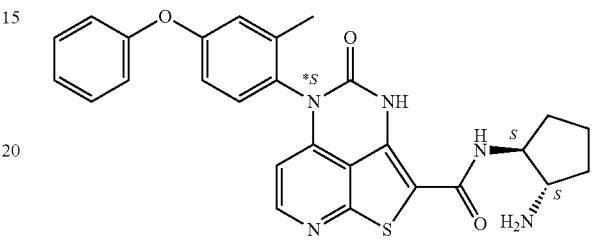

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2S)-2-aminocyclopentyl]carbamate. MS (ESI): mass calcd. for $C_{27}H_{25}N_5O_3S$, 499.6; m/z found, 500.2 [M+H]$^+$. $^1$H NMR (400 MHz, CD$_3$OD): δ 8.03 (d, J=5.7 Hz, 1H), 7.41-7.31 (m, 2H), 7.19-7.04 (m, 4H), 7.04-7.00 (m, 1H), 6.98-6.89 (m, 1H), 5.76 (d, J=5.6 Hz, 1H), 4.03-3.91 (m, 1H), 3.26-3.19 (m, 1H), 2.22-2.13 (m, 1H), 2.10 (s, 3H), 2.07-1.99 (m, 1H), 1.82-1.66 (m, 3H), 1.50-1.39 (m, 1H).

Example 136: N-((1R,2S)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide

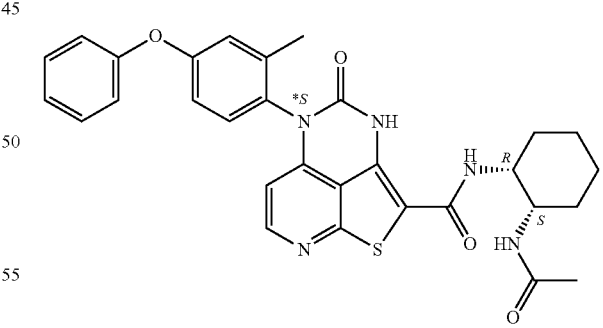

To a solution of N-((1R,2S)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 125, product from Step A, 77 mg, 0.15 mmol) and triethylamine (46 mg, 0.45 mmol) in DCM (5 mL) was added acetic anhydride (15 mg, 0.15 mmol) and was stirred at room temperature for 2 hours. The mixture was purified by flash column chromatography, then by preparative TLC to give the title compound (64 mg, 77% yield). MS (ESI): mass calcd. for $C_{30}H_{29}N_5O_4S$, 555.6; m/z found, 556.2 [M+H]$^+$. $^1$H NMR (400 MHz, DMSO-d$_6$): δ 9.96 (s, 1H), 8.36-8.22 (m, 1H), 7.82-7.64 (m, 1H), 7.63-7.57 (m, 1H), 7.44-7.39 (m, 2H), 7.39-7.28 (m, 1H), 7.19-7.14 (m, 1H), 7.12-7.07 (m, 2H), 7.07-7.04 (m, 1H), 6.97-6.92 (m, 1H), 6.01-5.86 (m, 1H), 4.14-4.01 (m, 1H), 4.01-3.93 (m, 1H), 2.03 (s, 3H), 1.87 (s, 3H), 1.70-1.58 (m, 4H), 1.55-1.44 (m, 2H), 1.40-1.29 (m, 2H).

Example 137: N-((1R,2S)-2-Aminocyclohexyl)-5-(3-chloro-4-phenoxyphenyl)-4-oxo-4,5-dihydro-3H-1-thia-3,5,8-triazaacenaphthylene-2-carboxamide

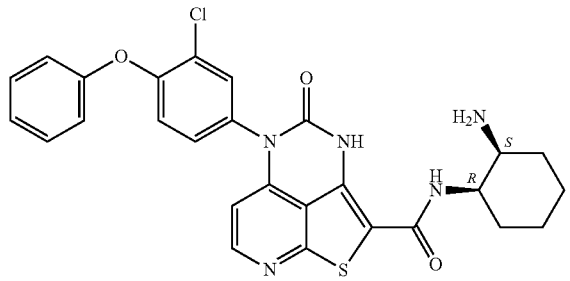

Step A. 5-(3-Chloro-4-phenoxyphenyl)-4-oxo-4,5-dihydro-3H-1-thia-3,5,8-triazaacenaphthylene-2-carboxylic acid The title compound was prepared in a manner analogous to Intermediate 1, using 2-chloro-1-fluoro-4-nitrobenzene in Step A.

Step B. N-((1R,2S)-2-Aminocyclohexyl)-5-(3-chloro-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(3-chloro-4-phenoxyphenyl)-4-oxo-4,5-dihydro-3H-1-thia-3,5,8-triazaacenaphthylene-2-carboxylic acid and tert-butyl N-[(1S,2R)-2-aminocyclohexyl]carbamate. MS (ESI): mass calcd. for $C_{27}H_{24}ClN_5O_3S$, 534.0; m/z found, 534.1 [M+H]$^+$. $^1$H NMR (400 MHz, CD$_3$OD): δ 8.16-8.10 (m, 1H), 7.57-7.49 (m, 1H), 7.42-7.34 (m, 2H), 7.30-7.23 (m, 1H), 7.18-7.11 (m, 2H), 7.08-7.02 (m, 2H), 6.05-6.00 (m, 1H), 4.45-4.38 (m, 1H), 3.42-3.33 (m, 1H), 1.91-1.77 (m, 4H), 1.76-1.66 (m, 2H), 1.62-1.54 (m, 1H), 1.52-1.43 (m, 1H).

Example 138: N-((1R,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide

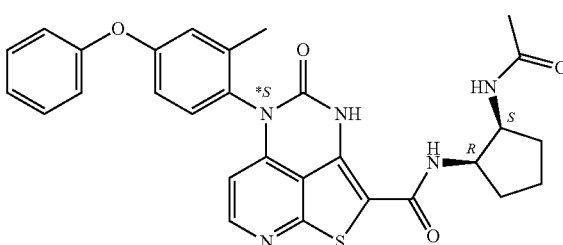

The title compound was prepared in a manner analogous to Example 136 using N-((1R,2S)-2-aminocyclopentyl)-5-(*S)-(2-methyl-4-phenoxyphenyl)-4-oxo-4,5-dihydro-3H-1-thia-3,5,8-triazaacenaphthylene-2-carboxamide (Example 115). MS (ESI): mass calcd. for $C_{29}H_{27}N_5O_4S$, 541.6; m/z found, 542.5 [M+H]$^+$. $^1$H NMR (400 MHz, CD$_3$OD): δ 8.30 (d, J=5.5 Hz, 1H), 7.45-7.33 (m, 2H), 7.31-7.24 (m, 1H), 7.20-7.12 m, 1H), 7.12-7.02 (m, 3H), 6.99-6.93 (m, 1H), 6.04 (d, J=5.4 Hz, 1H), 4.40-4.29 (m, 2H), 2.11 (s, 3H), 2.08-1.99 (m, 2H), 1.93 (s, 3H), 1.89-1.82 (m, 1H), 1.75-1.62 (m, 3H).

Example 139: N-((1R,3R)-3-Hydroxycyclohexyl)-4-oxo-5-(4-phenoxyphenyl)-4,5-dihydro-3H-1-thia-3,5,8-triazaacenaphthylene-2-carboxamide

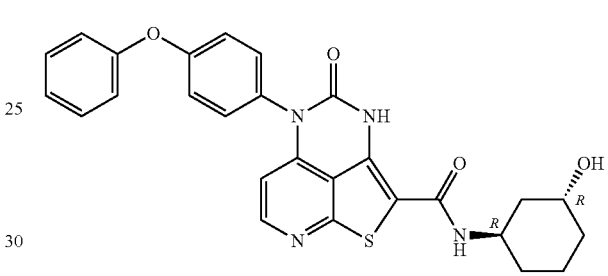

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and (1R,3R)-3-aminocyclohexanol. MS (ESI): mass calcd. for $C_{27}H_{24}N_4O_4S$, 500.6; m/z found, 501.1 [M+H]$^+$. $^1$H NMR (500 MHz, CDCl$_3$): δ 9.55 (s, 1H), 8.36 (s, 1H), 7.47-7.35 (m, 2H), 7.29-7.26 (m, 1H), 7.23-7.04 (m, 5H), 6.21 (s, 1H), 5.43 (d, J=7.8 Hz, 1H), 4.49-4.29 (m, 1H), 4.29-4.13 (m, 2H), 3.82-3.56 (m, OH), 2.66-2.28 (m, 1H), 2.12-1.80 (m, 3H), 1.77-1.52 (m, 4H), 1.47-1.17 (m, 1H).

Example 140: N-((1R,2S)-2-Hydroxycyclopentyl)-4-oxo-5-(4-phenoxyphenyl)-4,5-dihydro-3H-1-thia-3,5,8-triazaacenaphthylene-2-carboxamide

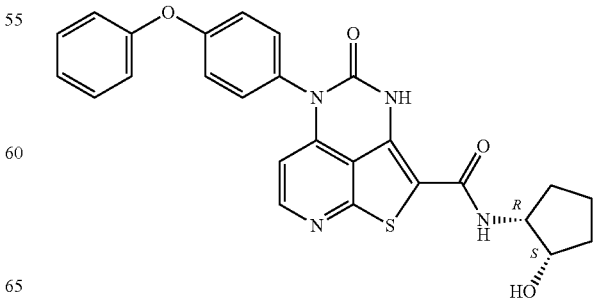

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and (1S,2R)-2-aminocyclopentanol. MS (ESI): mass calcd. for $C_{26}H_{22}N_4O_4S$, 486.6; m/z found, 487 [M+H]$^+$. $^1$H NMR (500 MHz, CD$_3$OD): δ 8.30 (d, J=5.6 Hz, 1H), 7.47-7.32 (m, 4H), 7.26-7.03 (m, 5H), 6.17 (d, J=5.6 Hz, 1H), 4.31-4.05 (m, 2H), 2.11-1.53 (m, 7H).

Example 141: 5-([1,1'-Biphenyl]-3-yl)-N-((1R,2S)-2-aminocyclohexyl)-4-oxo-4,5-dihydro-3H-1-thia-3,5,8-triazaacenaphthylene-2-carboxamide

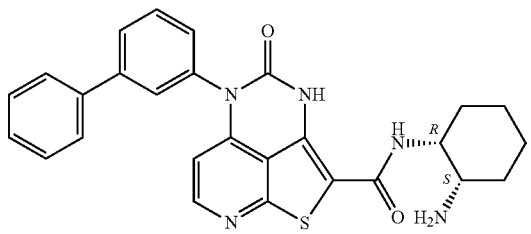

The title compound was prepared in a manner analogous to Example 1, Step A, using 5-([1,1'-biphenyl]-3-yl)-4-oxo-4,5-dihydro-3H-1-thia-3,5,8-triazaacenaphthylene-2-carboxy c acid (Intermediate 19) and tert-butyl N-[(1S,2R)-2-aminocyclohexyl]carbamate. MS (ESI): mass calcd. for $C_{27}H_{25}N_5O_2S$, 483.6; m/z found, 484.2 [M+H]$^+$.

Example 142: N-((1R,3S)-3-Hydroxycyclohexyl)-4-oxo-5-(4-phenoxyphenyl)-4,5-dihydro-3H-1-thia-3,5,8-triazaacenaphthylene-2-carboxamide

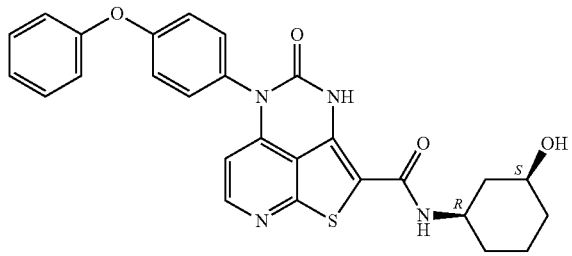

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and (1R,3R)-3-aminocyclohexanol. MS (ESI): mass calcd. for $C_{27}H_{24}N_4O_4S$, 500.6; m/z found, 501.0 [M+H]$^+$. $^1$H NMR (500 MHz, CDCl$_3$): δ 9.52 (s, 1H), 8.38 (s, 1H), 7.48-7.38 (m, 2H), 7.32-7.27 (m, 1H), 7.23-7.07 (m, 5H), 6.21 (s, 1H), 4.19 (s, 1H), 4.05 (s, 1H), 3.42 (s, 3H), 2.14-2.01 (m, 1H), 1.98-1.40 (m, 7H).

Example 143: N-((1S,3S)-3-Hydroxycyclohexyl)-4-oxo-5-(4-phenoxyphenyl)-4,5-dihydro-3H-1-thia-3,5,8-triazaacenaphthylene-2-carboxamide

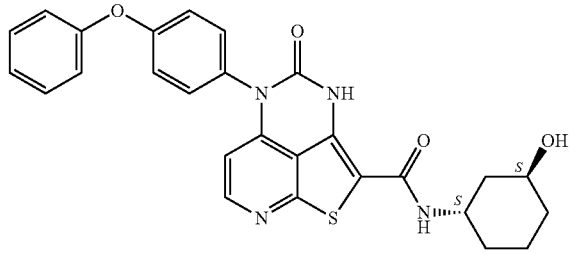

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and (1S,3S)-3-aminocyclohexanol. MS (ESI): mass calcd. for $C_{27}H_{24}N_4O_4S$, 500.6; m/z found, 501.1 [M+H]$^+$. $^1$H NMR (500 MHz, CDCl$_3$): δ 9.64 (s, 1H), 8.35 (d, J=5.9 Hz, 1H), 7.47-7.37 (m, 2H), 7.30-7.26 (m, 1H), 7.25 (d, J=3.5 Hz, 1H), 7.24-7.08 (m, 5H), 6.25 (d, J=5.9 Hz, 1H), 5.65 (d, J=7.8 Hz, 1H), 4.44-4.29 (m, 1H), 4.21 (s, 1H), 2.16-1.29 (m, 9H).

Example 144: 5-([1,1')-Biphenyl]-3-yl)-N-((1R,2R)-2-hydroxycyclopentyl)-4-oxo-4,5-dihydro-3H-1-thia-3,5,8-triazaacenaphthylene-2-carboxamide

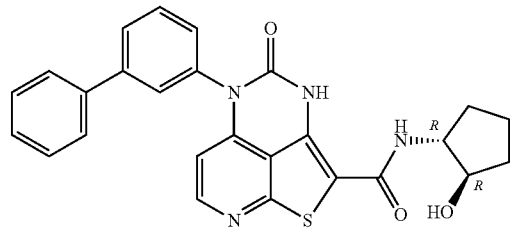

The title compound was prepared in a manner analogous to Example 1, Step A, using 5-([1,1'-biphenyl]-3-yl)-4-oxo-4,5-dihydro-3H-1-thia-3,5,8-triazaacenaphthylene-2-carboxylic acid (Intermediate 19) and (1R,2R)-2-aminocyclopentanol, no deprotection with HCl necessary as (1R,2R)-2-aminocyclopentanol was used. MS (ESI): mass calcd. for $C_{26}H_{22}N_4O_3S$, 470.5; m/z found, 471.1 [M+H]$^+$. $^1$H NMR (400 MHz, DMSO-d$_6$): δ 10.10 (s, 1H), 8.31-8.26 (m, 1H), 8.05-7.97 (m, 1H), 7.84-7.80 (m, 1H), 7.79-7.76 (m, 1H), 7.70-7.67 (m, 2H), 7.67-7.63 (m, 1H), 7.48-7.43 (m, 3H), 7.39-7.34 (m, 1H), 6.07-6.03 (m, 1H), 4.80-4.73 (m, 1H), 4.02-3.94 (m, 2H), 2.01-1.93 (m, 1H), 1.89-1.79 (m, 1H), 1.67-1.59 (m, 2H), 1.53-1.41 (m, 2H).

Example 145: N-((1S,4S)-4-Aminocyclohexyl)-4-oxo-5-(4-phenoxyphenyl)-4,5-dihydro-3H-1-thia-3,5,8-triazaacenaphthylene-2-carboxamide

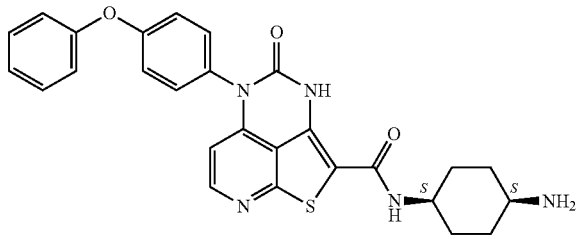

The title compound was prepared in a manner analogous to Example 104, Step A-B, using 4-oxo-5-(4-phenoxyphenyl)-4,5-dihydro-3H-1-thia-3,5,8-triazaacenaphthylene-2-carbonyl chloride (Intermediate 9) and tert-butyl N-(4-aminocyclohexyl)carbamate. MS (ESI): mass calcd. for $C_{27}H_{25}N_5O_3S$, 499.6; m/z found, [M+H]$^+$.

Example 146: N-(trans-(1R,4R)-4-Aminocyclohexyl)-4-oxo-5-(4-phenoxyphenyl)-4,5-dihydro-3H-1-thia-3,5,8-triazaacenaphthylene-2-carboxamide

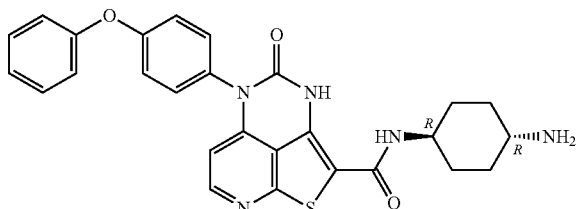

The title compound was prepared in a manner analogous to Example 104, Step A-B, using 4-oxo-5-(4-phenoxyphenyl)-4,5-dihydro-3H-1-thia-3,5,8-triazaacenaphthylene-2-carbonyl chloride (Intermediate 9) and trans-N-Boc-1,4-cyclohexanediamine. MS (ESI): mass calcd. for $C_{27}H_{25}N_5O_3S$, 499.6; m/z found, [M+H]$^+$. $^1$H NMR (500 MHz, CD$_3$OD): δ 8.31 (d, J=5.6 Hz, 1H), 7.49-7.35 (m, 4H), 7.23-7.05 (m, 5H), 6.18 (d, J=5.6 Hz, 1H), 3.90 (ddt, J=11.7, 7.7, 4.0 Hz, 1H), 3.17-3.02 (m, 1H), 2.10 (dq, J=13.9, 4.3 Hz, 4H), 1.68-1.39 (m, 4H).

Example 147: trans-N-((1RS,3RS)-3-Aminocyclopentyl)-4-oxo-5-(4-phenoxyphenyl)-4,5-dihydro-3H-1-thia-3,5,8-triazaacenaphthylene-2-carboxamide

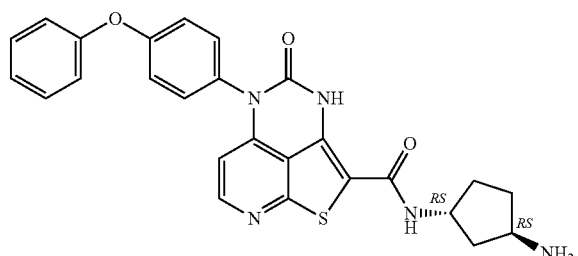

The title compound was prepared in a manner analogous to Example 104, Step A-B, using 4-oxo-5-(4-phenoxyphenyl)-4,5-dihydro-3H-1-thia-3,5,8-triazaacenaphthylene-2-carbonyl chloride (Intermediate 9) and trans-tert-butyl N-[(1R,3R)-3-aminocyclopentyl]carbamate. MS (ESI): mass calcd. for $C_{26}H_{23}N_5O_3S$, 485.6; m/z found, 486.1 [M+H]$^+$. $^1$H NMR (400 MHz, CD$_3$OD): δ 8.21 (d, J=5.6 Hz, 1H), 7.47-7.30 (m, 4H), 7.25-7.03 (m, 5H), 6.09 (d, J=5.6 Hz, 1H), 4.60-4.43 (m, 1H), 3.90-3.59 (m, 1H), 2.35-2.05 (m, 4H), 1.84-1.56 (m, 2H).

Example 148: N-((1S,2S)-2-Aminocyclopentyl)-4-oxo-5-(4-phenoxyphenyl)-4,5-dihydro-3H-1-thia-3,5,8-triazaacenaphthylene-2-carboxamide

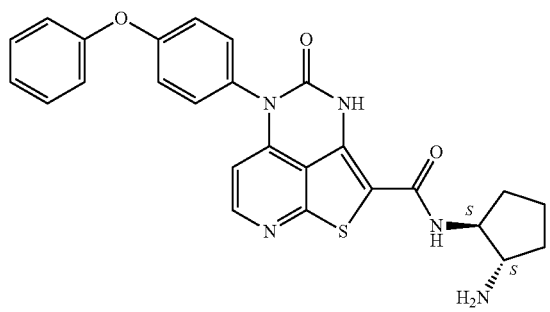

The title compound was prepared in a manner analogous to Example 104, Step A-B, using 4-oxo-5-(4-phenoxyphenyl)-4,5-dihydro-3H-1-thia-3,5,8-triazaacenaphthylene-2-carbonyl chloride (Intermediate 9) and tert-butyl N-[(1S,2S)-2-aminocyclopentyl]carbamate. MS (ESI): mass calcd. for $C_{26}H_{23}N_5O_3S$, 485.6; m/z found, 486.1 [M+H]$^+$. $^1$H NMR (400 MHz, CD$_3$OD): δ 8.43 (s, 1H), 8.30 (d, J=5.6 Hz, 1H), 7.86-7.79 (m, 1H), 7.73-7.62 (m, 4H), 7.47-7.38 (m, 3H), 7.37-7.31 (m, 1H), 6.19 (d, J=5.6 Hz, 1H), 4.67-4.50 (m, 1H), 3.70-3.58 (m, 1H), 3.55-3.45 (m, 2H), 3.27-3.15 (m, 1H), 2.92 (s, 3H), 2.60-2.45 (m, 1H), 2.30-2.15 (m, 1H).

Example 149: N-((1R,2R)-2-Aminocyclohexyl)-4-oxo-5-(4-phenoxyphenyl)-4,5-dihydro-3H-1-thia-3,5,8-triazaacenaphthylene-2-carboxamide

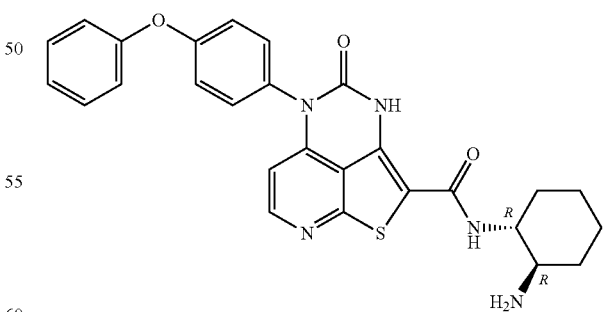

The title compound was prepared in a manner analogous to Example 104, Step A-B, using 4-oxo-5-(4-phenoxyphenyl)-4,5-dihydro-3H-1-thia-3,5,8-triazaacenaphthylene-2-carbonyl chloride (Intermediate 9) and tert-butyl N-[(1R,2R)-2-aminocyclohexyl]carbamate. MS (ESI): mass calcd. for $C_{27}H_{25}N_5O_3S$, 499.6; m/z found, 500.1 [M+H]$^+$. $^1$H NMR (500 MHz, CD$_3$OD): δ 8.17 (d, J=5.6 Hz, 1H), 7.50-7.23 (m, 4H), 7.23-6.97 (m, 5H), 6.04 (d, J=5.7 Hz, 1H), 4.01-3.79 (m, 1H), 3.08-2.94 (m, 1H), 2.22-1.75 (m, 4H), 1.62-1.23 (m, 4H).

Example 150: tert-Butyl ((1R,3S)-3-(4-oxo-5-(4-phenoxyphenyl)-4,5-dihydro-3H-1-thia-3,5,8-triazaacenaphthylene-2-carboxamido)cyclopentyl)carbamate

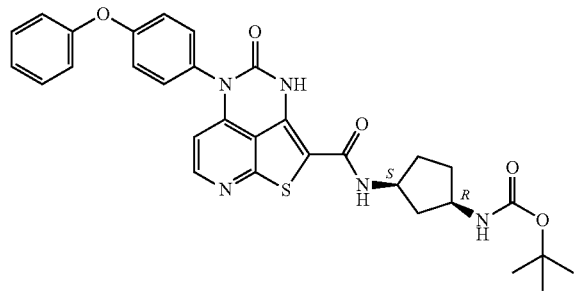

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and tert-butyl N-[(1R,2R)-2-aminocyclohexyl]carbamate. MS (ESI): mass calcd. for C$_{31}$H$_{31}$N$_5$O$_5$S, 585.7; m/z found, 486.1 (minus Boc) [M+H]$^+$. $^1$H NMR (400 MHz, CDCl$_3$): δ 8.34 (d, J=5.6 Hz, 1H), 7.44-7.36 (m, 2H), 7.31-7.27 (m, 2H), 7.23-7.06 (m, 5H), 6.13 (d, J=5.3 Hz, 1H), 5.03-4.96 (m, 1H), 4.48-4.34 (m, 1H), 3.85-3.72 (m, 1H), 2.53-2.35 (m, 1H), 2.04-1.64 (m, 6H), 1.50 (s, 9H), 1.45-1.43 (m, 1H).

Example 151: tert-Butyl trans-((1R,4R)-4-(4-oxo-5-(4-phenoxyphenyl)-4,5-dihydro-3H-1-thia-3,5,8-triazaacenaphthylene-2-carboxamido)cyclohexyl)carbamate

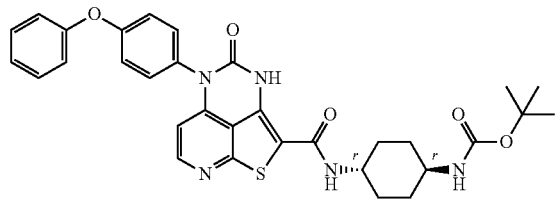

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and trans-N-Boc-1,4-cyclohexanediamine. MS (ESI): mass calcd. for C32H$_{33}$N$_5$O$_5$S, 599.7; m/z found, 600.2 [M+H]$^+$. $^1$H NMR (400 MHz, CDCl$_3$): δ 9.48 (s, 1H), 8.35 (d, J=5.5 Hz, 1H), 7.44-7.36 (m, 2H), 7.23-7.08 (m, 5H), 6.17 (d, J=5.6 Hz, 1H), 5.35 (d, J=7.9 Hz, 1H), 4.51-4.31 (m, 1H), 3.90 (s, 1H), 3.47 (s, 1H), 2.19-1.99 (m, 5H), 1.52-1.15 (m, 14H).

Example 152: N-((1-Hydroxycyclohexyl)methyl)-4-oxo-5-(4-phenoxyphenyl)-4,5-dihydro-3H-1-thia-3,5,8-triazaacenaphthylene-2-carboxamide

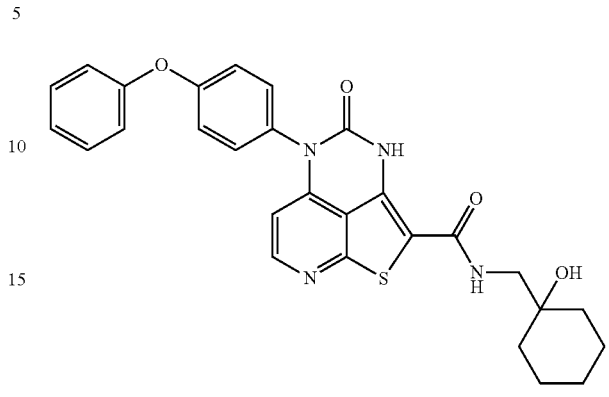

The title compound was prepared in a manner analogous to Example 1, Step A, using oxo-5-(4-phenoxyphenyl)-4,5-dihydro-3H-1-thia-3,5,8-triazaacenaphthylene-2-carboxylic acid (Intermediate 2) and 1-aminomethyl-1-cyclohexanol hydrochloride, no deprotection step with HCl used in Step A. MS (ESI): mass calcd. for C$_{28}$H$_{26}$N$_4$O$_4$S, 514.6; m/z found, 515.0 [M+H]$^+$. $^1$H NMR (400 MHz, CDCl$_3$): δ 9.55 (s, 1H), 8.33 (s, 1H), 8.02 (s, 1H), 7.45-7.34 (m, 2H), 7.36-7.25 (m, 2H), 7.23-7.06 (m, 5H), 6.39 (t, J=5.9 Hz, 1H), 6.14 (s, 1H), 3.46 (d, J=5.7 Hz, 2H), 2.96 (s, 2H), 1.63-1.45 (m, 7H), 1.35 (q, J=10.0, 8.3 Hz, 1H).

Example 153: N-((1S,3R)-3-((E)-4-(Dimethylamino)but-2-enamido)cyclopentyl)-5-(4-isopropoxy-2-methylphenyl)-4-oxo-4,5-dihydro-3H-1-thia-3,5,8-triazaacenaphthylene-2-carboxamide

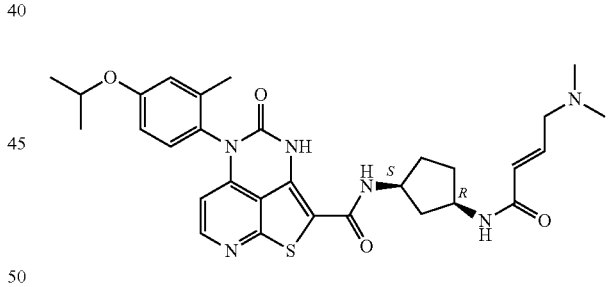

The title compound was prepared in a manner analogous to Example 122 using 5-(4-isopropoxy-2-methylphenyl)-4-oxo-4,5-dihydro-3H-1-thia-3,5,8-triazaacenaphthylene-2-carboxylic acid (Intermediate 31) and tert-butyl N-[(1R,2S)-2-aminocyclopentyl]carbamate in Step A, and (E)-4-(dimethylamino)but-2-enoic acid in Step B. MS (ESI): mass calcd. for C$_{30}$H$_{36}$N$_6$O$_4$S, 576.7; m/z found, 577.6 [M+H]$^+$. $^1$H NMR (400 MHz, CD$_3$OD): δ 8.48 (s, 1H), 8.28 (d, J=5.5 Hz, 1H), 7.28-7.13 (m, 1H), 7.01-6.86 (m, 2H), 6.84-6.68 (m, 1H), 6.34-6.16 (m, 1H), 6.01 (d, J=5.5 Hz, 1H), 4.74-4.58 (m, 1H), 4.43-4.29 (m, 1H), 4.25-4.13 (m, 1H), 3.67-3.51 (m, 2H), 2.60 (s, 6H), 2.55-2.40 (m, 1H), 2.10 (s, 3H), 2.07-1.95 (m, 2H), 1.92-1.71 (m, 2H), 1.68-1.57 (m, 1H), 1.42-1.27 (m, 6H).

Example 154: N-((1S,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide

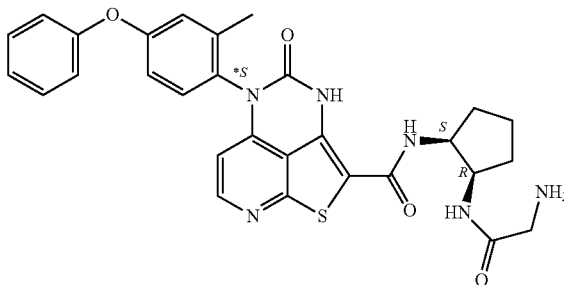

The title compound was prepared in a manner analogous to Example 122 using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2S)-2-aminocyclopentyl]carbamate in Step A, and using 2-(tert-butoxy carbonylamino)acetic acid in Step B. MS (ESI): mass calcd. for $C_{29}H_{28}H_6O_4S$, 556.6; m/z found, 557.4 [M+H]$^+$. $^1$H NMR (400 MHz, CD$_3$OD): δ 8.41 (s, 1H), 8.29 (d, J=5.5 Hz, 1H), 7.45-7.33 (m, 2H), 7.28-7.23 (m, 1H), 7.22-7.13 (m, 1H), 7.11-7.02 (m, 3H), 7.00-6.91 (m, 1H), 6.04 (d, J=5.6 Hz, 1H), 4.51-4.31 (m, 2H), 3.77-3.55 (m, 2H), 2.19-1.99 (m, 5H), 1.98-1.83 (m, 1H), 1.80-1.60 (m, 3H).

Example 155: N-((1S,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide

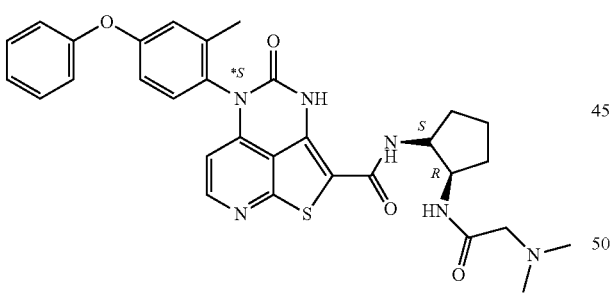

The title compound was prepared in a manner analogous to Example 122 using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2S)-2-aminocyclopentyl]carbamate in Step A, and using 2-(dimethylamino)acetic acid in Step B. MS (ESI): mass calcd. for $C_{31}H_{32}N_6O_4S$, 584.7; m/z found, 585.5 [M+H]$^+$. $^1$H NMR (400 MHz, CD$_3$OD): δ 8.36 (s, 1H), 8.33-8.24 (m, 1H), 7.46-7.31 (m, 2H), 7.28-7.20 (m, 1H), 7.19-7.11 (m, 1H), 7.11-6.99 (m, 3H), 6.99-6.89 (m, 1H), 6.13-5.95 (m, 1H), 4.50-4.27 (m, 2H), 3.61-3.38 (m, 2H), 2.70-2.38 (m, 6H), 2.20-1.95 (m, 5H), 1.94-1.53 (m, 4H).

Example 156: 5-(*S)-(2-Methyl-4-phenoxyphenyl)-N-((1S,2R)-2-(2-(methylamino)acetamido)cyclopentyl)-4-oxo-4,5-dihydro-3H-1-thia-3,5,8-triazaacenaphthylene-2-carboxamide

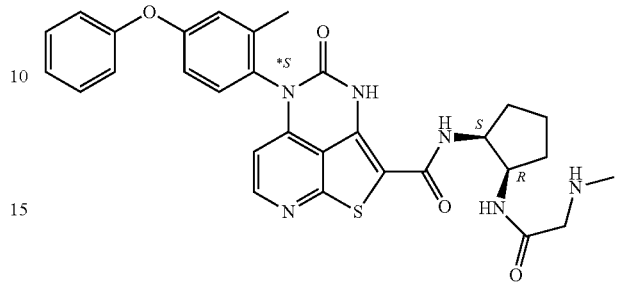

The title compound was prepared in a manner analogous to Example 122 using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2S)-2-aminocyclopentyl]carbamate in Step A, and using 2-[tert-butoxy carbonyl(methyl)amino]acetic acid in Step B. MS (ESI): mass calcd. for $C_{30}H_{30}N_6O_4S$, 570.7; m/z found, 571.4 [M+H]$^+$. $^1$H NMR (400 MHz, CD$_3$OD): δ 8.42 (s, 1H), 8.29 (d, J=5.4 Hz, 1H), 7.46-7.33 (m, 2H), 7.28-7.21 (m, 1H), 7.20-7.13 (m, 1H), 7.12-7.01 (m, 3H), 6.99-6.91 (m, 1H), 6.04 (d, J=5.6 Hz, 1H), 4.51-4.33 (m, 2H), 3.77-3.55 (m, 2H), 2.63 (s, 3H), 2.17-1.98 (m, 5H), 1.97-1.84 (m, 1H), 1.80-1.60 (m, 3H).

Example 157: N-((1S,3R)-3-Hydroxycyclohexyl)-4-oxo-5-(4-phenoxyphenyl)-4,5-dihydro-3H-1-thia-3,5,8-triazaacenaphthylene-2-carboxamide

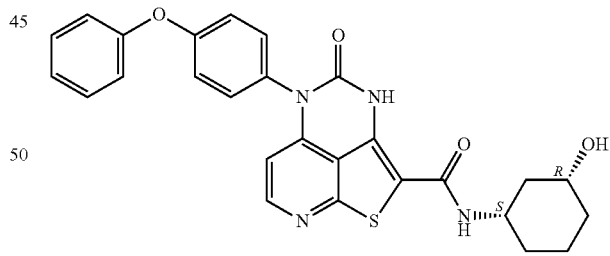

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and (1R,3S)-3-amino-cyclohexanol hydrochloride. MS (ESI): mass calcd. for $C_{27}H_{24}N_4O_4S$, 500.6; m/z found, 501.1 [M+H]$^+$. $^1$H NMR (500 MHz, CDCl$_3$): δ 9.47 (s, 1H), 8.31 (d, J=5.6 Hz, 1H), 7.45-7.27 (m, 4H), 7.22-6.99 (m, 5H), 6.75 (s, 1H), 6.13 (d, J=5.4 Hz, 1H), 4.27-3.94 (m, 2H), 2.18-1.20 (m, 9H).

Example 158: N-((1S,3R)-3-(2-(Dimethylamino)acetamido)cyclopentyl)-5-(4-isopropoxy-2-methylphenyl)-4-oxo-4,5-dihydro-3H-1-thia-3,5,8-triazaacenaphthylene-2-carboxamide

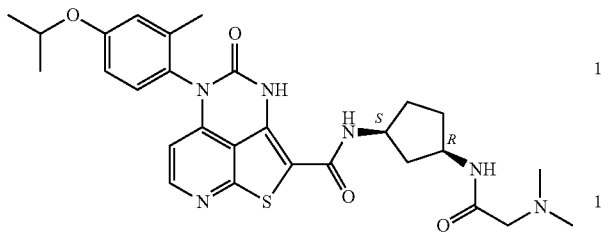

The title compound was prepared in a manner analogous to Example 122 using 5-(4-isopropoxy-2-methylphenyl)-4-oxo-4,5-dihydro-3H-1-thia-3,5,8-triazaacenaphthylene-2-carboxylic acid (Intermediate 31) and tert-butyl N-[(1R,2S)-2-aminocyclopentyl]carbamate in Step A, and 2-(dimethylamino)acetic acid in Step B. MS (ESI): mass calcd. for $C_{28}H_{34}N_6O_4S$, 550.7; m/z found, 552.1 $[M+H]^+$. $^1$H NMR (400 MHz, CD$_3$OD): δ 8.45 (s, 1H), 8.29 (d, J=4.9 Hz, 1H), 7.29-7.16 (m, 1H), 7.01-6.95 (m, 1H), 6.91 (dd, J=8.6, 2.4 Hz, 1H), 6.02 (d, J=5.0 Hz, 1H), 4.73-4.60 (m, 1H), 4.38-4.10 (m, 2H), 3.47 (s, 2H), 2.63 (s, 6H), 2.51-2.37 (m, 1H), 2.11 (s, 3H), 2.07-1.93 (m, 2H), 1.91-1.71 (m, 2H), 1.70-1.58 (m, 1H), 1.41-1.29 (m, 6H).

Example 159: 4-Oxo-5-(2-phenylpyridin-4-yl)-N-((1S,2R)-2-propionamidocyclopentyl)-4,5-dihydro-3H-1-thia-3,5,8-triazaacenaphthylene-2-carboxamide

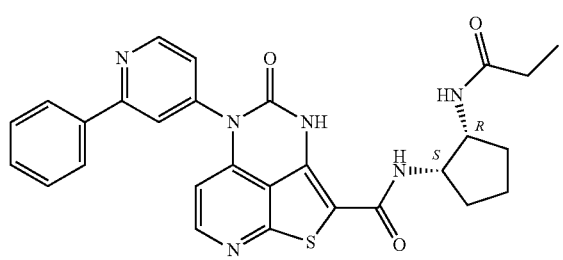

Step A: N-((1S,2R)-2-Aminocyclopentyl)-4-oxo-5-(2-phenylpyridin-4-yl)-4,5-dihydro-3H-1-thia-3,5,8-triazaacenaphthylene-2-carboxamide The title compound was prepared in a manner analogous to Example 1, Step A, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1R,2S)-2-aminocyclopentyl]carbamate. MS (ESI): mass calcd. for $C_{25}H_{22}N_6O_2S$, 470.55; m/z found, 471.1 $[M+H]^+$.

Step B: 4-Oxo-5-(2-phenylpyridin-4-yl)-N-((1S,2R)-2-propionamidocyclopentyl)-4,5-dihydro-3H-1-thia-3,5,8-triazaacenaphthylene-2-carboxamide To a solution of N-((1S,2R)-2-aminocyclopentyl)-4-oxo-5-(2-phenylpyridin-4-yl)-4,5-dihydro-3H-1-thia-3,5,8-triazaacenaphthylene-2-carboxamide (50 mg, 0.11 mmol) and a catalytic amount of DMAP in DCM (25 mL) was added propionic anhydride (21 mg, 0.16 mmol) and was stirred at rt for 20 min. The reaction was concentrated to dryness and the residue was purified by flash column chromatography to give the title compound as a light yellow solid (28 mg, 48% yield). MS (ESI): mass calcd. for $C_{28}H_{26}N_6O_3S$, 526.6; m/z found, 527.6 $[M+H]^+$. $^1$H NMR (400 MHz, CD$_3$OD): δ 8.85 (d, J=5.2 Hz, 1H), 8.31 (d, J=5.6 Hz, 1H), 8.10-7.95 (m, 3H), 7.57-7.36 (m, 4H), 6.29 (d, J=5.6 Hz, 1H), 4.45-4.25 (m, 2H), 2.27-2.15 (m, 2H), 2.13-1.94 (m, 2H), 1.93-1.81 (m, 1H), 1.79-1.54 (m, 3H), 1.08 (t, J=7.6 Hz, 3H).

Example 160: N-((1R,2S)-2-Aminocyclohexyl)-5-(4-isopropoxy-2-methylphenyl)-4-oxo-4,5-dihydro-3H-1-thia-3,5,8-triazaacenaphthylene-2-carboxamide

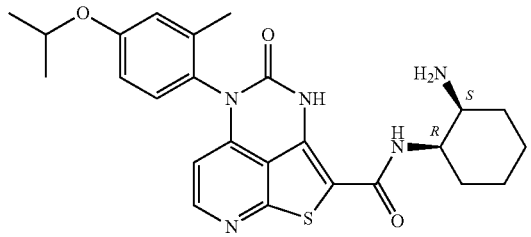

The title compound was prepared in a manner analogous to Example 1, Step A, using 5-(4-isopropoxy-2-methylphenyl)-4-oxo-4,5-dihydro-3H-1-thia-3,5,8-triazaacenaphthylene-2-carboxylic acid (Intermediate 31) and tert-butyl N-[(1S,2R)-2-aminocyclohexyl]carbamate. MS (ESI): mass calcd. for $C_{25}H_{29}N_5O_3S$, 479.6; m/z found, 480.5 $[M+H]^+$. $^1$H NMR (400 MHz, CD$_3$OD): δ 8.46 (s, 1H), 8.29 (d, J=5.5 Hz, 1H), 7.29-7.13 (m, 1H), 7.01-6.86 (m, 2H), 6.06-5.96 (m, 1H), 4.73-4.58 (m, 1H), 4.47-4.31 (m, 1H), 3.68-3.53 (m, 1H), 2.19-1.98 (m, 3H), 1.95-1.65 (m, 6H), 1.61-1.47 (m, 2H), 1.42-1.29 (m, 6H).

Example 161: 5-(4-Isopropoxy-2-methylphenyl)-N-((1S,3R)-3-(2-(methylamino)acetamido)cyclopentyl)-4-oxo-4,5-dihydro-3H-1-thia-3,5,8-triazaacenaphthylene-2-carboxamide

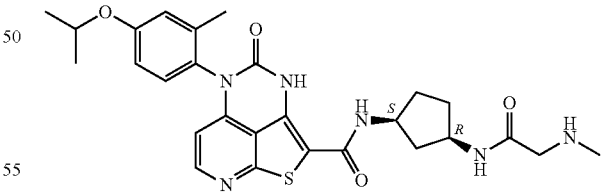

The title compound was prepared in a manner analogous to Example 122 using 5-(4-isopropoxy-2-methylphenyl)-4-oxo-4,5-dihydro-3H-1-thia-3,5,8-triazaacenaphthylene-2-carboxylic acid (Intermediate 31) and tert-butyl N-[(1R,3S)-3-aminocyclopentyl]carbamate in Step A and 2-[tert-butoxycarbonyl(methyl)amino]acetic acid in Step B. MS (ESI): mass calcd. for $C_{27}H_{32}N_6O_4S$, 536.6; 537.6 $[M+H]^+$. $^1$H NMR (400 MHz, CD$_3$OD): δ 8.46 (s, 1H), 8.30 (d, J=5.4 Hz, 1H), 7.30-7.12 (m, 1H), 7.04-6.83 (m, 2H), 6.02 (d, J=5.4 Hz, 1H), 4.70-4.62 (m, 1H), 4.47-

4.26 (m, 1H), 4.22-4.08 (m, 1H), 3.70 (s, 2H), 2.67 (s, 3H), 2.55-2.40 (m, 1H), 2.17-1.97 (m, 5H), 1.90-1.58 (m, 3H), 1.39-1.27 (m, 6H).

Example 162: N-((1S,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide

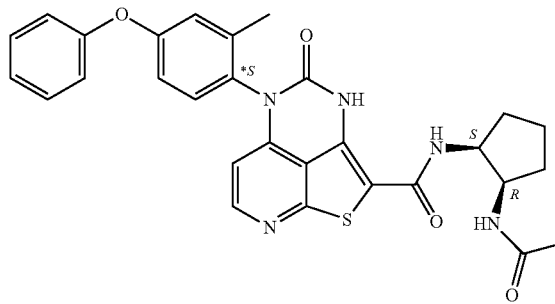

Step A. N-((1S,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,2S)-2-aminocyclopentyl]carbamate.

Step B. N-((1S,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 159, step B, using acetic anhydride. MS (ESI): mass calcd. for $C_{29}H_{27}N_5O_4S$, 541.6; m/z found, 542.2 [M+H]$^+$. $^1$H NMR (400 MHz, CD$_3$OD): δ 8.37-8.25 (m, 1H), 7.45-7.34 (m, 2H), 7.30-7.23 (m, 1H), 7.22-7.13 (m, 1H), 7.12-7.02 (m, 3H), 7.00-6.95 (m, 1H), 6.12-6.02 (m, 1H), 4.42-4.27 (m, 2H), 2.14-2.09 (m, 3H), 2.08-1.96 (m, 2H), 1.95-1.91 (m, 3H), 190-1.81 (m, 1H), 1.79-1.58 (m, 3H).

Example 163: tert-Butyl ((1S,4S)-4-(4-oxo-5-(4-phenoxyphenyl)-4,5-dihydro-3H-1-thia-3,5,8-triazaacenaphthylene-2-carboxamido)cyclohexyl)carbamate

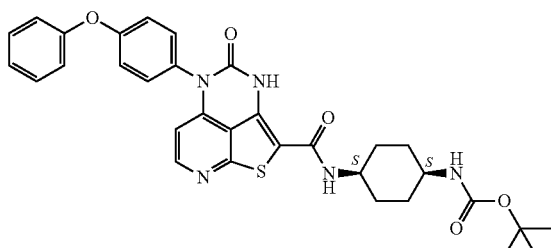

The title compound was prepared in a manner analogous to Example 104, Step A, using 4-oxo-5-(4-phenoxyphenyl)-4,5-dihydro-3H-1-thia-3,5,8-triazaacenaphthylene-2-carbonyl chloride (Intermediate 9) and 1-N-Boc-cis-1,4-cyclohexyldiamine. MS (ESI): mass calcd. for $C_{32}H_{33}N_5O_5S$, 599.7; m/z found, 600.1 [M+H]$^+$. $^1$H NMR (400 MHz, CDCl$_3$): δ 9.46 (s, 1H), 8.36 (d, J=5.5 Hz, 1H), 7.46-7.35 (m, 2H), 7.29-7.27 (m, 1H), 7.22-7.02 (m, 5H), 6.16 (d, J=5.5 Hz, 1H), 5.46 (d, J=7.6 Hz, 1H), 4.69-4.52 (m, 1H), 4.19-3.95 (m, 1H), 3.82-3.62 (m, 1H), 1.95-1.60 (m, 9H), 1.46 (s, 9H).

Example 164: N-((1S,3R)-3-Aminocyclopentyl)-4-oxo-5-(4-phenoxyphenyl)-4,5-dihydro-3H-1-thia-3,5,8-triazaacenaphthylene-2-carboxamide

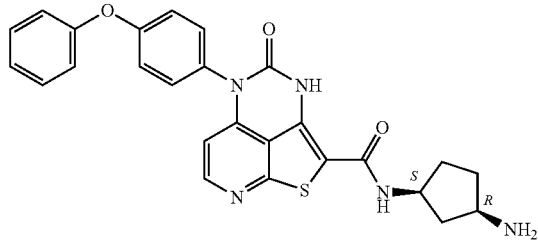

The title compound was prepared in a manner analogous to Example 104, Steps A-B, using 4-oxo-5-(4-phenoxyphenyl)-4,5-dihydro-3H-1-thia-3,5,8-triazaacenaphthylene-2-carbonyl chloride (Intermediate 9) and tert-butyl ((1R,3S)-3-aminocyclopentyl)carbamate. MS (ESI): mass calcd. for $C_{26}H_{23}N_5O_3S$, 485.6; m/z found, 486.1 [M+H]$^+$. $^1$H NMR (500 MHz, CD$_3$OD): δ 8.35 (d, J=5.6 Hz, 1H), 7.48-7.36 (m, 4H), 7.24-7.08 (m, 6H), 6.21 (d, J=5.6 Hz, 1H), 4.38-4.30 (m, 1H), 3.73-3.62 (m, 1H), 2.61-2.49 (m, 1H), 2.21-1.76 (m, 5H).

Example 165: N-((1R,2S)-2-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide

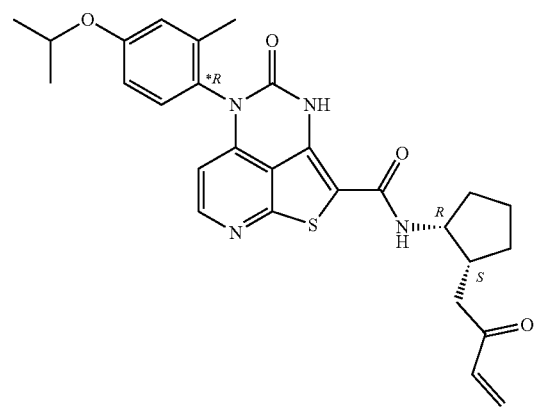

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPA- RATION METHOD 1 to obtain the *R atropisomer) and tert-butyl N-[(1S,2R)-2-aminocyclopentyl]carbamate. MS (ESI): mass calcd. for $C_{27}H_{29}N_5O_4S$, 519.6; m/z found, 520.2 [M+H]$^+$. $^1$H NMR (400 MHz, CD$_3$OD): δ 8.28-8.22 (m, 1H), 7.24-7.18 (m, 1H), 6.97-6.87 (m, 2H), 6.32-6.14 (m, 2H), 6.01-5.95 (m, 1H), 5.63-5.57 (m, 1H), 4.71-4.61 (m, 1H), 4.46-4.34 (m, 2H), 2.16-1.99 (m, 5H), 1.97-1.84 (m, 1H), 1.82-1.59 (m, 3H), 1.37-1.29 (m, 6H).

Example 166: N-((1R,2S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide

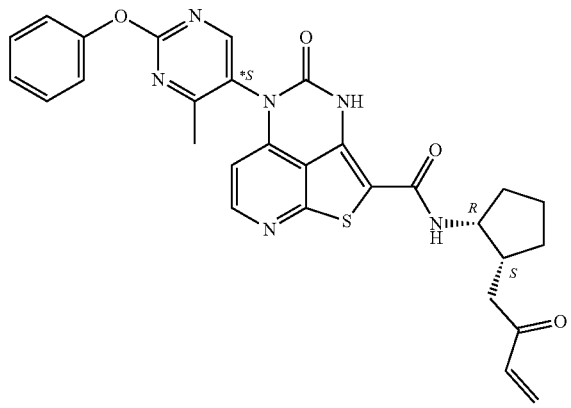

Step A: tert-Butyl ((1R,2S)-2-(5-(*S)-(4-methyl-2-phenoxypyrimidin-5-yl)-4-oxo-4,5-dihydro-3H-1-thia-3,5,8-triazaacenaphthylene-2-carboxamido)cyclopentyl)carbamate To a solution of 5-(4-methyl-2-phenoxypyrimidin-5-yl)-4-oxo-4,5-dihydro-3H-1-thia-3,5,8-triazaacenaphthylene-2-carboxylic acid (Intermediate 13, including CHIRAL SEPARATION METHOD 1 to obtain the *S atropisomer; 400 mg, 0.95 mmol), tert-butyl ((1S,2R)-2-aminocyclopentyl)carbamate (382 mg, 1.9 mmol) DIPEA (1.6 mL, 9.5 mmol) in DMF (3.8 mL) was added dropwise 1-propanephosphonic anhydride (T3P®) (3.17 mL, 4.76 mmol). The reaction mixture was stirred at room temperature for 1 h. To the reaction mixture was added water and EtOAc. The organics were separated, washed with water, and brine. The aq was back extracted with EtOAc, and the combined organics were dried (Na$_2$SO$_4$), filtered, and concentrated under reduced pressure. Purification (FCC, SiO$_2$, 20-100% EtOAc/hexane) afforded the title compound (395 mg, 68%).

Step B. N-((1R,2S)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide A solution of tert-butyl 41R,2S)-2-(5-(4-methyl-2-phenoxypyrimidin-5-yl)-4-oxo-4,5-dihydro-3H-1-thia-3,5,8-triazaacenaphthylene-2-carboxamido)cyclopentyl)carbamate (395 mg, 0.65 mmol) in HCl (4 M in dioxane, 0.82 mL) was stirred at room temperature for 1 h. Ether was added and the reaction mixture was stirred for 15 min. The resulting solids were filtered and dried under reduced pressure to afford the title compound (272 mg, 77%). MS (ESI): mass calcd. for $C_{25}H_{23}N_7O_3S$, 501.56; m/z found, 502.0 [M+H]$^+$. $^1$H NMR (500 MHz, CD$_3$OD): δ 8.57 (s, 1H), 8.51 (d, J=5.9 Hz, 1H), 7.50-7.42 (m, 2H), 7.32-7.27 (m, 1H), 7.27-7.24 (m, 2H), 6.50 (d, J=6.0 Hz, 1H), 4.50 (q, J=6.6 Hz, 1H), 3.78 (q, J=6.9 Hz, 1H), 2.34 (s, 3H), 2.23-2.13 (m, 2H), 2.05-1.91 (m, 2H), 1.84-1.72 (m, 2H).

Step C: N-((1R,2S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide To a 40 mL vial containing N-((1R,2S)-2-aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide (Example 254, 100 mg, 0.186 mmol), DMF (1.86 mL), acrylic acid (0.103 mL, 1.49 mmol), and diisopropylethylamine (0.16 mL, 0.93 mmol), stirred under N$_2$, was added dropwise 2,4,6-tripropyl-1,3,5,2,4,6-trioxatriphosphorinane-2,4,6-trioxide (1.11 mL, 1.86 mmol, 5 eq). After 1 h, another 5 eq 2,4,6-tripropyl-1,3,5,2,4,6-trioxatriphosphorinane-2,4,6-trioxide (1.11 mL, 1.86 mmol) was added. After 15 min, the reaction was extracted with EtOAc, and washed with water and brine. The aqueous solution was extracted with more EtOAc, the combined organic phases were dried over anhydrous Na$_2$SO$_4$, filtered, and concentrated to dryness. The residue was purified by flash column chromatography to give the title compound (23.9 mg, 23.1% yield). MS (ESI): mass calcd. for $C_{28}H_{25}N_7O_4S$, 555.6; m/z found, 556.0 [M+H]$^+$. $^1$H NMR (500 MHz, CD$_3$OD): δ 8.52 (s, 1H), 8.40-8.31 (m, 1H), 7.48-7.43 (m, 2H), 7.30-7.26 (m, 1H), 7.26-7.23 (m, 2H), 6.29 (dd, J=17.1, 10.0 Hz, 2H), 6.23-6.17 (m, 1H), 5.62 (d, J=11.9 Hz, 1H), 4.48-4.37 (m, 2H), 2.33 (s, 3H), 2.14-2.04 (m, 2H), 1.97-1.86 (m, 1H), 1.83-1.63 (m, 3H).

Example 167: N-((1R,2S)-2-Acrylamidocyclopentyl)-4-oxo-5-(6-phenylpyrimidin-4-yl)-4,5-dihydro-3H-1-thia-3,5,8-triazaacenaphthylene-2-carboxamide

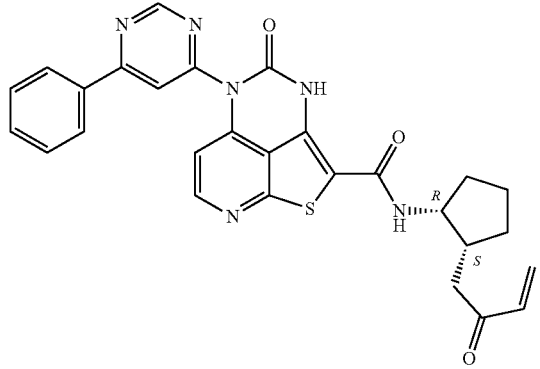

The title compound was prepared in a manner analogous to Example 1, Step A, using 4-oxo-5-(6-phenylpyrimidin-4-yl)-4,5-dihydro-3H-1-thia-3,5,8-triazaacenaphthylene-2-carb oxy c acid (Intermediate 23) and N-[(1S,2R)-2-aminocyclopentyl]prop-2-enamide (Intermediate 36), no deprotection step with HCl was used. MS (ESI): mass calcd. for $C_{27}H_{23}N_7O_3S$, 525.6; m/z found, 526.5 [M+H]$^+$. $^1$H NMR (400 MHz, DMSO-d$_6$): δ 10.26 (s, 1H), 9.38 (s, 1H), 8.42-8.32 (m, 2H), 8.25-8.16 (m, 2H), 7.93-7.74 (m, 2H), 7.62-7.54 (m, 3H), 6.57-6.49 (m, 1H), 6.27-6.16 (m, 1H), 6.10-6.02 (m, 1H), 5.60-5.49 (m, 1H), 4.37-4.19 (m, 2H), 1.96-1.85 (m, 2H), 1.80-1.70 (m, 2H), 1.67-1.57 (m, 2H).

Example 168: N-((1R,2S)-2-Acrylamidocyclohexyl)-4-oxo-5-(2-phenylpyridin-4-yl)-4,5-dihydro-3H-1-thia-3,5,8-triazaacenaphthylene-2-carboxamide

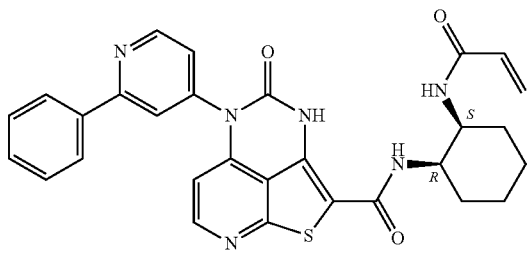

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,2R)-2-aminocyclohexyl]carbamate. MS (ESI): mass calcd. for $C_{29}H_{26}N_6O_3S$, 538.6; m/z found, 539.2 [M+H]$^+$. $^1$H NMR (400 MHz, CD$_3$OD): δ 8.90-8.82 (m, 1H), 8.36-8.27 (m, 1H), 8.06-8.01 (m, 3H), 7.52-7.43 (m, 4H), 6.47-6.36 (m, 1H), 6.33-6.22 (m, 2H), 5.69-5.63 (m, 1H), 4.47-4.36 (m, 1H), 4.22-4.10 (m, 1H), 1.83-1.62 (m, 6H), 1.58-1.46 (m, 2H).

Example 169: N-((1R,2S)-2-Acrylamidocyclopentyl)-4-oxo-5-(2-phenylpyridin-4-yl)-4,5-dihydro-3H-1-thia-3,5,8-triazaacenaphthylene-2-carboxamide

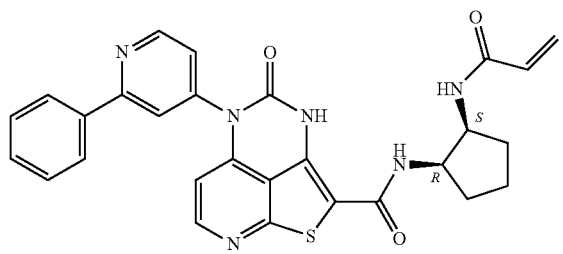

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,2R)-2-aminocyclopentyl]carbamate. MS (ESI): mass calcd. for $C_{28}H_{24}N_6O_3S$, 524.6; m/z found, 525.2 [M+H]$^+$. $^1$H NMR (400 MHz, CD$_3$OD): δ 8.84 (d, J=5.2 Hz, 1H), 8.29 (d, J=5.6 Hz, 1H), 8.09-7.95 (m, 3H), 7.54-7.40 (m, 4H), 6.41-6.10 (m, 3H), 5.60 (dd, J=9.8, 2.2 Hz, 1H), 4.49-4.29 (m, 2H), 2.17-1.98 (m, 2H), 1.97-1.83 (m, 1H), 1.82-1.57 (m, 3H).

Example 170: N-((1R,2S)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide

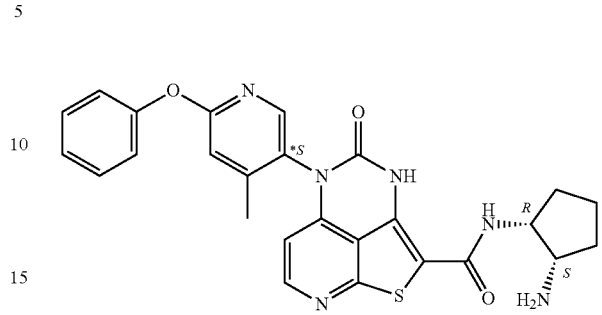

The title compound was prepared in a manner analogous to Example 166, Step A-B, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,2R)-2-aminocyclopentyl)carbamate. MS (ESI): mass calcd. for $C_{26}H_{24}N_6O_3S$, 500.6; m/z found, 501.1 [M+H]$^+$. $^1$H NMR (500 MHz, CDCl$_3$): δ 8.29 (d, J=5.4 Hz, 1H), 8.07 (s, 1H), 7.46-7.38 (m, 2H), 7.27-7.15 (m, 3H), 6.95 (s, 2H), 5.99 (d, J=5.4 Hz, 1H), 5.28 (s, 1H), 4.17 (q, J=6.9 Hz, 1H), 4.04-3.99 (m, 4H), 3.49-3.42 (m, 1H), 2.22 (s, 3H), 1.86-1.75 (m, 1H), 1.71-1.47 (m, 3H).

Example 171: N-((1R,2S)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

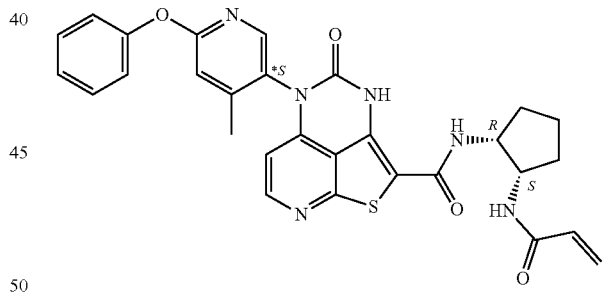

The title compound was prepared in a manner analogous to Example 166, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,2R)-2-aminocyclopentyl)carbamate in Step A. MS (ESI): mass calcd. for $C_{29}H_{26}N_6O_4S$, 554.6; m/z found, 555.2 [M+H]$^+$. $^1$H NMR (500 MHz, CDCl$_3$): δ 9.58 (s, 1H), 8.33 (d, J=5.5 Hz, 1H), 8.05 (s, 1H), 7.48-7.40 (m, 2H), 7.29-7.16 (m, 3H), 6.97-6.93 (m, 1H), 6.84 (d, J=6.3 Hz, 1H), 6.57 (d, J=6.8 Hz, 1H), 6.35 (dd, J=16.9, 1.5 Hz, 1H), 6.21-6.10 (m, 1H), 6.02 (d, J=5.5 Hz, 1H), 5.66 (dd, J=10.3, 1.4 Hz, 1H), 4.44-4.29 (m, 2H), 4.12 (q, J=7.2 Hz, 1H), 2.30-2.08 (m, 3H), 1.93-1.82 (m, 2H), 1.80-1.64 (m, 3H).

Example 172: N-((1R,2S)-2-Acrylamidocyclohexyl)-4-oxo-5-(6-phenoxypyridin-3-yl)-4,5-dihydro-3H-1-thia-3,5,8-triazaacenaphthylene-2-carboxamide

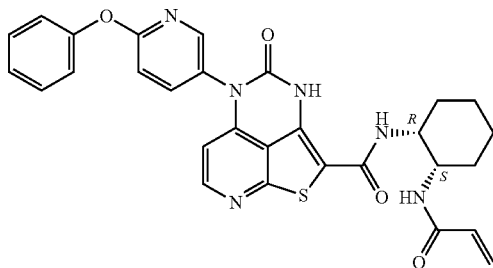

The title compound was prepared in a manner analogous to Example 166, using 4-oxo-5-(6-phenoxypyridin-3-yl)-4,5-dihydro-3H-1-thia-3,5,8-triazaacenaphthylene-2-carboxylic acid (Intermediate 28) and tert-butyl ((1S,2R)-2-aminocyclohexyl)carbamate in Step A. MS (ESI): mass calcd. for $C_{29}H_{26}N_6O_4S$, 554.6; m/z found, 555.2 [M+H]$^+$. $^1$H NMR (400 MHz, CDCl$_3$): δ 8.29 (d, J=5.4 Hz, 1H), 8.24-8.17 (m, 1H), 7.77 (ddd, J=20.3, 8.3, 2.9 Hz, 1H), 7.49-7.39 (m, 2H), 7.31-6.98 (m, 4H), 6.37 (dd, J=17.0, 1.8 Hz, 1H), 6.30-6.17 (m, 1H), 6.11 (d, J=5.5 Hz, 1H), 5.66 (dd, J=10.0, 1.8 Hz, 1H), 4.30 (d, J=7.9 Hz, 1H), 4.13 (dq, J=14.3, 7.1, 6.5 Hz, 2H), 2.04 (s, 3H), 1.90-1.80 (m, 1H), 1.71 (d, J=15.2 Hz, 1H), 1.60 (dd, J=19.0, 9.7 Hz, 3H), 1.25 (t, J=7.1 Hz, 1H), 1.08 (d, J=6.7 Hz, 1H).

Example 173: N-((1R,2S)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

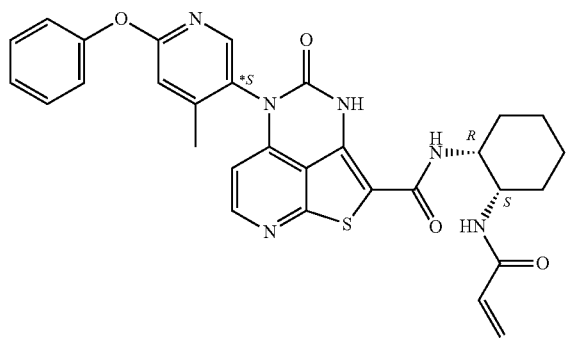

The title compound was prepared in a manner analogous to Example 166, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and N-((1S,2R)-2-aminocyclohexyl)acrylamide. MS (ESI): mass calcd. for $C_{30}H_{28}N_6O_4S$, 568.7; m/z found, 569.1 [M+H]$^+$. $^1$H NMR (500 MHz, CDCl$_3$): δ 9.53 (s, 1H), 8.35 (d, J=5.4 Hz, 1H), 8.04 (s, 1H), 7.48-7.39 (m, 2H), 7.28-7.16 (m, 3H), 7.05 (s, 1H), 6.97-6.93 (m, 2H), 6.41 (dd, J=16.9, 1.4 Hz, 1H), 6.20 (dd, J=16.9, 10.3 Hz, 1H), 6.02 (d, J=5.5 Hz, 1H), 5.73 (dd, J=10.2, 1.4 Hz, 1H), 4.30 (tt, J=6.5, 3.0 Hz, 1H), 4.16 (h, J=4.3, 3.8 Hz, 1H), 2.89 (d, J=0.6 Hz, 1H), 2.21 (d, J=0.8 Hz, 3H), 2.08-1.99 (m, 1H), 1.92 (ddd, J=13.9, 10.2, 3.8 Hz, 1H), 1.77-1.54 (m, 6H).

Example 174: N-((1R,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide

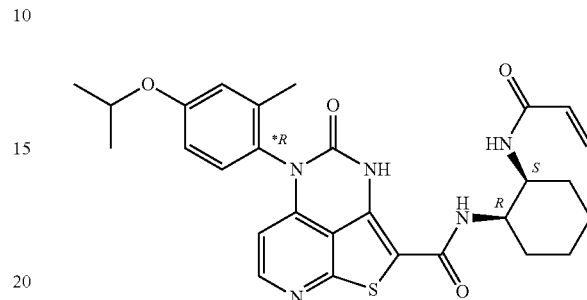

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1S,2R)-2-aminocyclohexyl]carbamate. MS (ESI): mass calcd. for $C_{25}H_{31}N_5O_4S$, 533.6; m/z found, 534.2 [M+H]$^+$. $^1$H NMR (400 MHz, CD$_3$OD): δ 8.33-8.22 (m, 1H), 7.21-7.16 (m, 1H), 6.98-6.95 (m, 1H), 6.93-6.89 (m, 1H), 6.46-6.36 (m, 1H), 6.28-6.22 (m, 1H), 6.02-5.96 (m, 1H), 5.68-5.63 (m, 1H), 4.69-4.62 (m, 1H), 4.46-4.38 (m, 1H), 4.18-4.12 (m, 1H), 2.10 (s, 3H), 1.82-1.72 (m, 4H), 1.71-1.60 (m, 2H), 1.58-1.48 (m, 2H), 1.34 (d, J=6.0 Hz, 6H).

Example 175: N-((1R,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

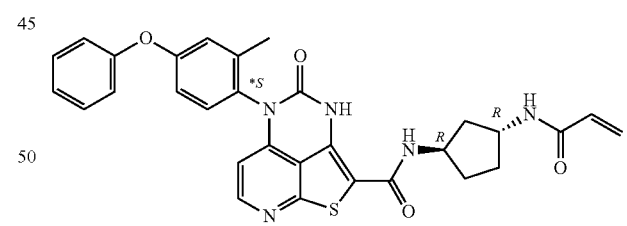

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including step F2 to obtain the *S atropisomer), and tert-butyl N-[(1R,3R)-3-aminocyclopentyl]carbamate. MS (ESI): mass calcd. for $C_{30}H_{27}N_5O_4S$, 553.6; m/z found, 554.4 [M+H]$^+$. $^1$H NMR (400 MHz, CD$_3$OD): δ 8.31 (d, J=5.6 Hz, 1H), 7.43-7.35 (m, 2H), 7.33-7.24 (m, 1H), 7.18-7.12 (m, 1H), 7.12-7.01 (m, 3H), 6.99-6.90 (m, 1H), 6.26-6.18 (m, 2H), 6.06 (d, J=5.6 Hz, 1H), 5.68-5.55 (m, 1H), 4.57-4.45 (m, 1H), 4.44-4.30 (m, 1H), 2.28-2.14 (m, 2H), 2.11 (s, 3H), 2.04-1.86 (m, 2H), 1.73-1.45 (m, 2H).

Example 176: N-((1S,3R)-3-Acrylamidocyclo-hexyl)-5-(*S)-(2-methyl-4-phenoxyphenyl)-4-oxo-4,5-dihydro-3H-1-thia-3,5,8-triazaacenaphthylene-2-carboxamide

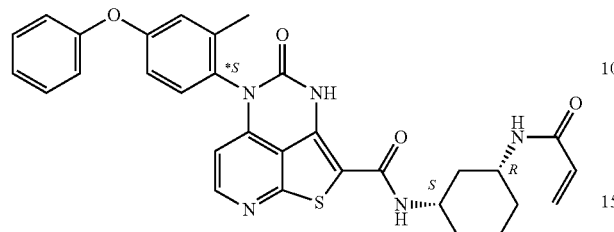

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including step F2 to obtain the *S atropisomer), and tert-butyl N-[(1R,3S)-3-aminocyclohexyl]carbamate. MS (ESI): mass calcd. for $C_{31}H_{29}N_5O_4S$, 567.7; m/z found, 568.2 [M+H]$^+$. $^1$H NMR (400 MHz, CD$_3$OD:DMSO-d$_6$=2:1): δ 8.43-8.35 (m, 1H), 7.54-7.45 (m, 2H), 7.42-7.36 (m, 1H), 7.30-7.22 (m, 1H), 7.21-7.11 (m, 3H), 7.08-7.01 (m, 1H), 6.31-6.21 (m, 2H), 6.13-6.07 (m, 1H), 5.73-5.62 (m, 1H), 4.08-3.97 (m, 1H), 3.89-3.79 (m, 1H), 2.20-2.16 (m, 4H), 1.98-1.89 (m, 3H), 1.52-1.36 (m, 4H).

Example 177: N-((1R,2R)-2-Acrylamidocyclopentyl)-4-oxo-5-(6-phenoxypyridin-3-yl)-4,5-dihydro-3H-1-thia-3,5,8-triazaacenaphthylene-2-carboxamide

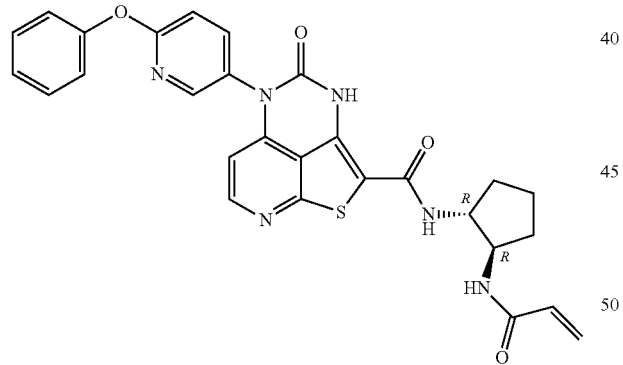

The title compound was prepared in a manner analogous to Example 1, using oxo-5-(6-phenoxypyridin-3-yl)-4,5-dihydro-3H-1-thia-3,5,8-triazaacenaphthylene-2-carboxylic acid (Intermediate 28) and tert-butyl N-[(1R,2R)-2-aminocyclopentyl]carbamate and BOC deprotection using TFA in Step A. MS (ESI): mass calcd. for $C_{28}H_{24}N_6O_4S$, 540.6; m/z found, 541.0 [M+H]$^+$. $^1$H NMR (500 MHz, CDCl$_3$): δ 9.58 (s, 1H), 8.33 (d, J=5.6 Hz, 1H), 8.18 (s, 1H), 7.73 (t, J=11.1 Hz, 1H), 7.44 (t, J=7.7 Hz, 2H), 7.29-7.17 (m, 3H), 7.10 (d, J=8.7 Hz, 1H), 7.05 (d, J=6.2 Hz, 1H), 6.29 (d, J=16.9 Hz, 2H), 6.18-6.03 (m, 2H), 5.62 (d, J=10.4 Hz, 1H), 4.15 (dq, J=40.1, 7.9 Hz, 2H), 2.28 (ddd, J=27.6, 12.4, 5.9 Hz, 2H), 1.81 (dd, J=14.7, 7.6 Hz, 2H), 1.67-1.45 (m, 2H).

Example 178: N-((1R,2S)-2-Acrylamidocyclopentyl)-4-oxo-5-(6-phenoxypyridin-3-yl)-4,5-dihydro-3H-1-thia-3,5,8-triazaacenaphthylene-2-carboxamide

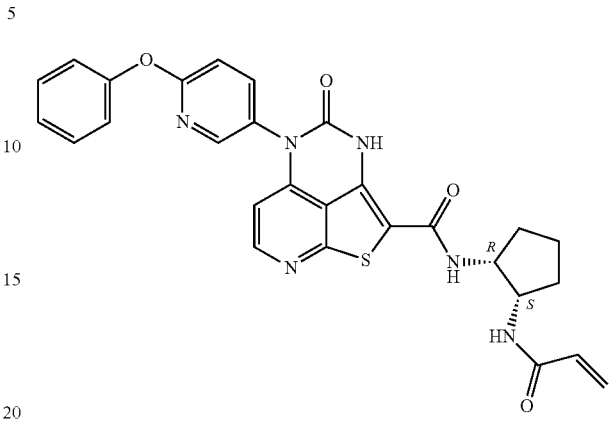

The title compound was prepared in a manner analogous to Example 1, using oxo-5-(6-phenoxypyridin-3-yl)-4,5-dihydro-3H-1-thia-3,5,8-triazaacenaphthylene-2-carboxylic acid (Intermediate 28) and tert-butyl ((1S,2R)-2-aminocyclopentyl)carbamate and BOC deprotection using TFA in Step A. MS (ESI): mass calcd. for $C_{28}H_{24}N_6O_4S$, 540.6; m/z found, 541.0 [M+H]$^+$. $^1$H NMR (500 MHz, CDCl$_3$): δ 8.27 (d, J=5.5 Hz, 1H), 8.17 (s, 1H), 7.76-7.67 (m, 1H), 7.47-7.39 (m, 2H), 7.28-7.15 (m, 3H), 7.08 (d, J=8.7 Hz, 1H), 7.00 (s, 1H), 6.84 (d, J=18.9 Hz, 1H), 6.29 (d, J=16.9 Hz, 1H), 6.20-6.06 (m, 2H), 6.00 (s, 1H), 5.59 (d, J=9.8 Hz, 1H), 4.36 (q, J=7.1, 6.3 Hz, 2H), 2.19 (dt, J=11.9, 6.6 Hz, 1H), 2.13-2.02 (m, 1H), 1.89-1.61 (m, 4H).

Example 179: N-((1R,2S)-2-Acrylamidocyclopentyl)-4-oxo-5-(5-phenoxypyridin-2-yl)-4,5-dihydro-3H-1-thia-3,5,8-triazaacenaphthylene-2-carboxamide

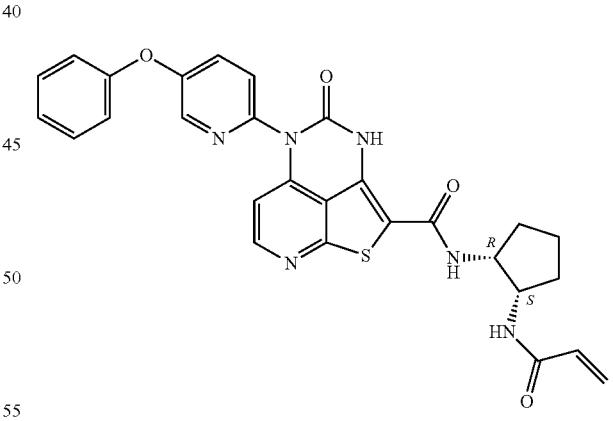

The title compound was prepared in a manner analogous to Example 1, using 4-oxo-5-(5-phenoxypyridin-2-yl)-4,5-dihydro-3H-1-thia-3,5,8-triazaacenaphthylene-2-carboxylic acid (Intermediate 26) and tert-butyl ((1S,2R)-2-aminocyclopentyl)carbamate. MS (ESI): mass calcd. for $C_{28}H_{24}N_6O_4S$, 540.6; m/z found, 541.0 [M+H]$^+$. $^1$H NMR (400 MHz, CDCl$_3$): δ 9.27 (s, 1H), 8.38 (dd, J=16.8, 4.2 Hz, 2H), 7.56-7.31 (m, 4H), 7.24 (d, J=7.6 Hz, 1H), 7.14 (d, J=7.9 Hz, 2H), 6.66 (d, J=5.6 Hz, 1H), 6.37 (d, J=16.8 Hz, 1H), 6.27-6.06 (m, 3H), 5.69 (d, J=10.3 Hz, 1H), 4.44-4.24 (m, 2H), 2.43-2.03 (m, 2H), 1.96-1.67 (m, 4H).

Example 180: N-((1S,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide

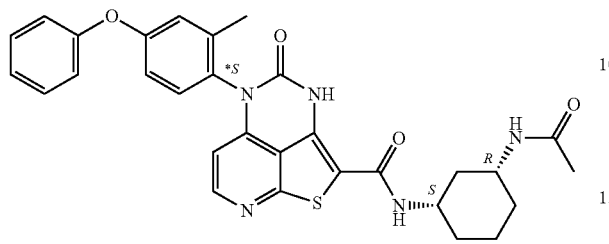

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3S)-3-aminocyclohexyl]carbamate in Step A, and acetic anhydride in Step B. MS (ESI): mass calcd. for $C_{30}H_{29}N_5O_4S$, 555.6; m/z found, 556.2 [M+H]$^+$. $^1$H NMR (400 MHz, CD$_3$OD): δ 8.34-8.29 (m, 1H), 7.43-7.35 (m, 2H), 7.31-7.25 (m, 1H), 7.20-7.13 (m, 1H), 7.11-7.03 (m, 3H), 7.01-6.93 (m, 1H), 6.09-6.03 (m, 1H), 4.02-3.89 (m, 1H), 3.81-3.71 (m, 1H), 2.17-2.08 (m, 4H), 1.97-1.83 (m, 6H), 1.47-1.15 (m, 4H).

Example 181: N-((1R,3R)-3-Aminocyclohexyl)-5-(2-methyl-4-phenoxyphenyl)-4-oxo-4,5-dihydro-3H-1-thia-3,5,8-triazaacenaphthylene-2-carboxamide

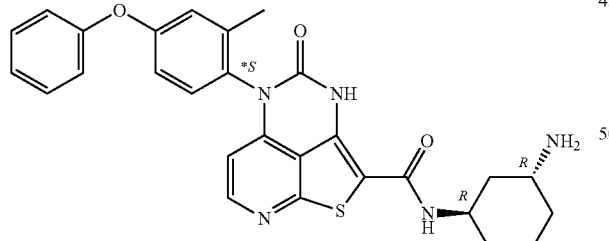

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3R)-3-aminocyclohexyl]carbamate. MS (ESI): mass calcd. for $C_{28}H_{27}N_5O_3S$, 513.6; m/z found, 514.2 [M+H]$^+$.

Example 182: N-((1R,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide

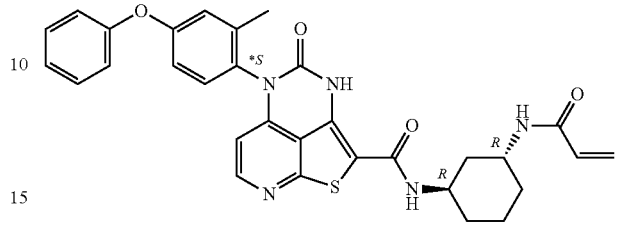

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3R)-3-aminocyclohexyl]carbamate. MS (ESI): mass calcd. for $C_{31}H_{29}N_5O_4S$, 567.7; m/z found, 568.5 [M+H]$^+$. $^1$H NMR (400 MHz, CD$_3$OD): δ 8.33 (d, J=5.6 Hz, 1H), 7.43-7.37 (m, 2H), 7.31-7.27 (m, 1H), 7.20-7.15 (m, 1H), 7.11-7.03 (m, 3H), 7.01-6.95 (m, 1H), 6.41-6.31 (m, 1H), 6.27-6.19 (m, 1H), 6.08 (d, J=5.7 Hz, 1H), 5.68-5.62 (m, 1H), 4.25-4.15 (m, 2H), 2.12 (s, 3H), 1.95-1.78 (m, 3H), 1.74-1.54 (m, 5H).

Example 183: N-((1R,2S)-2-Acrylamidocyclohexyl)-5-(6-cyclobutoxy-4-methylpyridin-3-yl)-4-oxo-4,5-dihydro-3H-1-thia-3,5,8-triazaacenaphthylene-2-carboxamide

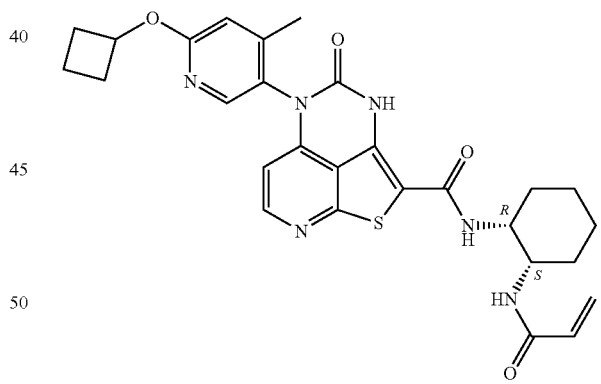

The title compound was prepared in a manner analogous to Example 1, Step A, using 5-(6-cyclobutoxy-4-methylpyridin-3-yl)-4-oxo-4,5-dihydro-3H-1-thia-3,5,8-triazaacenaphthylene-2-carboxylic acid (Intermediate 24) and N-[(1S,2R)-2-aminocyclohexyl]prop-2-enamide (Intermediate 40), no MeOH/HCl deprotection. MS (ESI): mass calcd. for $C_{28}H_{30}N_6O_4S$, 546.6; m/z found, 547.2 [M+H]$^+$. $^1$H NMR (500 MHz, CD$_3$OD): δ 8.32 (d, J=5.5 Hz, 1H), 8.05 (d, J=3.8 Hz, 1H), 6.84 (s, 1H), 6.42 (dd, J=17.0, 10.3 Hz, 1H), 6.32-6.22 (m, 1H), 6.10 (d, J=5.4 Hz, 1H), 5.71-5.64 (m, 1H), 5.25-5.14 (m, 1H), 4.44 (s, 1H), 4.17 (s, 1H), 2.52-2.43 (m, 2H), 2.22-2.10 (m, 5H), 1.89-1.63 (m, 8H), 1.60-1.46 (m, 2H).

Example 184: N-((1R,3R)-3-Acrylamidocyclopentyl)-5-(2-methyl-4-phenoxyphenyl)-4-oxo-4,5-dihydro-3H-1-thia-3,5,8-triazaacenaphthylene-2-carboxamide

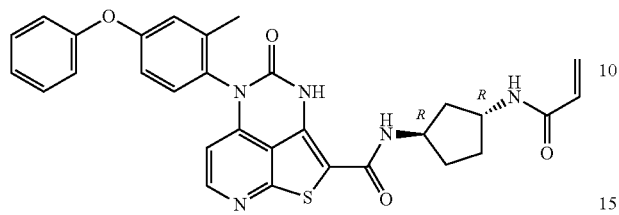

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,3R)-3-aminocyclopentyl]carbamate. MS (ESI): mass calcd. for $C_{30}H_{27}N_5O_4S$, 553.6; m/z found, 554.2 [M+H]$^+$.

Example 185: N-((1R,2R)-2-Acrylamidocyclopentyl)-4-oxo-5-(5-phenoxypyridin-2-yl)-4,5-dihydro-3H-1-thia-3,5,8-triazaacenaphthylene-2-carboxamide

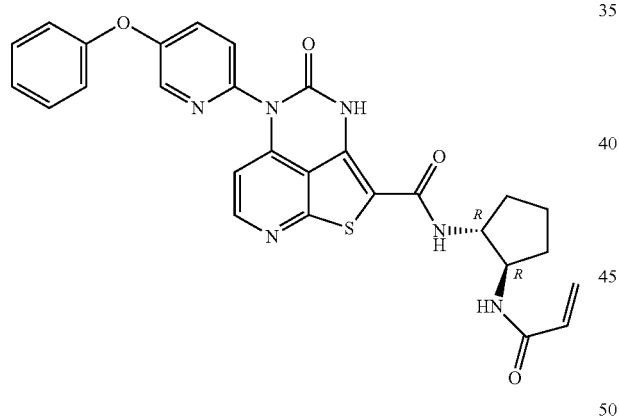

The title compound was prepared in a manner analogous to Example 1, using 4-oxo-5-(5-phenoxypyridin-2-yl)-4,5-dihydro-3H-1-thia-3,5,8-triazaacenaphthylene-2-carboxylic acid (Intermediate 26) and tert-butyl N-[(1R,2R)-2-aminocyclopentyl]carbamate. MS (ESI): mass calcd. for $C_{28}H_{24}N_6O_4S$, 540.6; m/z found, 541.0 [M+H]$^+$. $^1$H NMR (500 MHz, CDCl$_3$): δ 9.45 (s, 1H), 8.45-8.30 (m, 2H), 7.50-7.36 (m, 4H), 7.26-7.21 (m, 1H), 7.17-7.09 (m, 2H), 6.80 (d, J=5.8 Hz, 1H), 6.42 (d, J=6.4 Hz, 1H), 6.36-6.07 (m, 3H), 5.67 (dd, J=10.3, 1.4 Hz, 1H), 4.25-4.03 (m, 2H), 2.40-2.26 (m, 2H), 1.92-1.79 (m, 2H), 1.65-1.58 (m, 1H), 1.58-1.48 (m, 1H).

Example 186: N-((1S,3R)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide

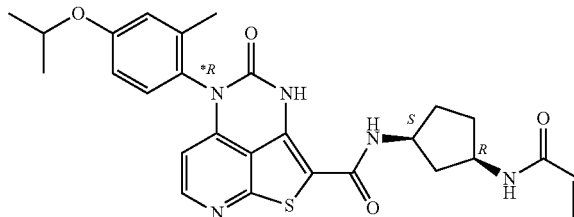

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1R,3S)-3-aminocyclopentyl]carbamate. MS (ESI): mass calcd. for $C_{27}H_{29}N_5O_4S$, 519.6; m/z found, 520.2 [M+H]$^+$. $^1$H NMR (400 MHz, CD$_3$OD): δ 8.35-8.23 (m, 1H), 7.25-7.13 (m, 1H), 6.99-6.95 (m, 1H), 6.94-6.89 (m, 1H), 6.27-6.19 (m, 2H), 6.06-5.98 (m, 1H), 5.68-5.61 (m, 1H), 4.70-4.63 (m, 1H), 4.41-4.30 (m, 1H), 4.25-4.15 (m, 1H), 2.52-2.43 (m, 1H), 2.11 (s, 3H), 2.08-1.98 (m, 2H), 1.83-1.73 (m, 2H), 1.65-1.58 (m, 1H), 1.34 (d, J=6.0 Hz, 6H).

Example 187: N-((1R,2S)-2-Acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide

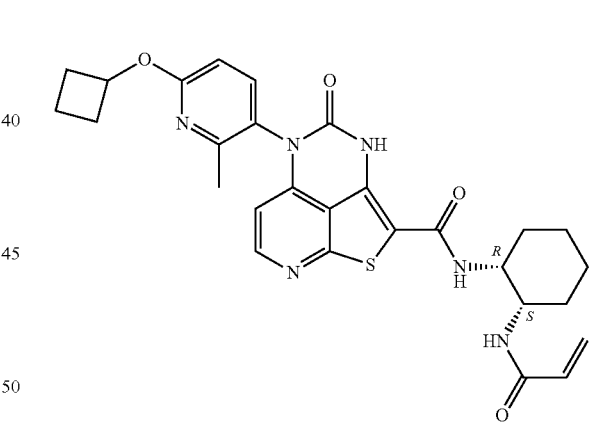

Step A. 5-(6-Cyclobutoxy-2-methylpyridin-3-yl)-4-oxo-4,5-dihydro-3H-1-thia-3,5,8-triazaacenaphthylene-2-carboxylic acid The title compound was prepared in a manner analogous to Intermediate 24, using 6-fluoro-2-methyl-3-nitropyridine in Step A.

Step B. N-((1R,2S)-2-Acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide The title compound was prepared in a manner analogous to Example 1, Step A, using 5-(6-cyclobutoxy-2-methylpyridin-3-yl)-4-oxo-4,5-dihydro-3H-1-thia-3,5,8-triazaacenaphthylene-2-carboxylic acid and N-[(1S,2R)-2-aminocyclohexyl]prop-2-enamide (Intermediate 40), no MeOH/HCl deprotection. MS (ESI): mass calcd. for $C_{28}H_{30}N_6O_4S$, 546.6; m/z found, 547.2 [M+H]$^+$. $^1$H NMR (500 MHz, CD$_3$OD): δ 8.32 (d, J=5.3 Hz, 1H), 7.61 (dd, J=8.6, 2.3 Hz, 1H), 6.76 (d, J=8.6 Hz, 1H), 6.42 (dd, J=17.0, 10.3 Hz, 1H), 6.27 (d, J=17.0 Hz, 1H), 6.08 (d, J=5.4 Hz, 1H), 5.67 (dd, J=10.2, 1.7 Hz, 1H), 5.26-5.16 (m, 1H), 4.44 (s, 1H), 4.22-4.12 (m, 1H), 2.55-2.45 (m, 2H), 2.25 (s, 3H), 2.21-2.11 (m, 2H), 1.90-1.62 (m, 8H), 1.60-1.45 (m, 2H).

Example 188: N-((1RS,3RS)-3-Acrylamidocyclopentyl)-4-oxo-5-(6-phenoxypyridin-3-yl)-4,5-dihydro-3H-1-thia-3,5,8-triazaacenaphthylene-2-carboxamide

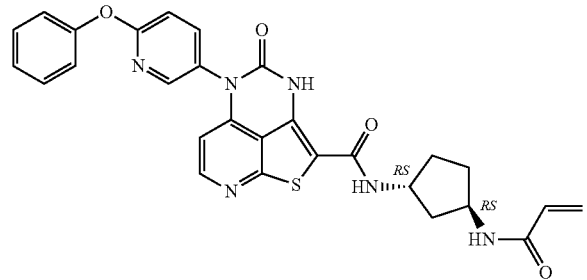 [SMILES: C=CC(=O)N[C@@H]1CC[C@@H](NC(=O)c2sc3nccc4c3c2NC(=O)N4c2ccc(Oc3ccccc3)nc2)C1]

The title compound was prepared in a manner analogous to Example 104, Step B, using N-((1RS,3RS)-3-aminocyclopentyl)-4-oxo-5-(6-phenoxypyridin-3-yl)-4,5-dihydro-3H-1-thia-3,5,8-triazaacenaphthylene-2-carboxamide (Example 289) and acryloyl chloride. MS (ESI): mass calcd. for $C_{28}H_{24}N_6O_4S$, 540.6; m/z found, 541.1 [M+H]$^+$. $^1$H NMR (500 MHz, CDCl$_3$): δ 9.54 (s, 1H), 8.32 (s, 1H), 8.20 (d, J=12.1 Hz, 1H), 7.78-7.68 (m, 1H), 7.57-7.49 (m, 1H), 7.49-7.40 (m, 2H), 7.30-7.17 (m, 3H), 7.11 (d, J=8.7 Hz, 1H), 6.84-6.77 (m, 1H), 6.42-6.34 (m, 1H), 6.16-6.05 (m, 2H), 5.69-5.62 (m, 1H), 4.38 (dh, J=7.6, 4.1 Hz, 1H), 4.11 (tt, J=13.9, 11.3, 5.3 Hz, 1H), 3.52-3.44 (m, 1H), 2.46 (dt, J=14.3, 8.7 Hz, 1H), 2.07-1.80 (m, 4H).

Example 189: N-((1R,2S)-2-Acrylamidocyclopentyl)-4-oxo-5-(4-phenylpyridin-2-yl)-4,5-dihydro-3H-1-thia-3,5,8-triazaacenaphthylene-2-carboxamide

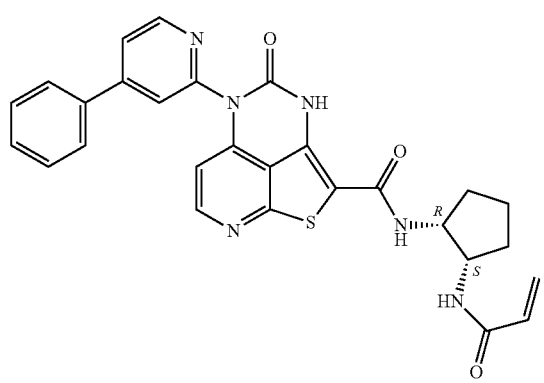

The title compound was prepared in a manner analogous to Example 1, using 4-oxo-5-(4-phenylpyridin-2-yl)-4,5-dihydro-3H-1-thia-3,5,8-triazaacenaphthylene-2-carboxylic acid (Intermediate 21) and tert-butyl N-[(1S,2R)-2-aminocyclopentyl]carbamate. MS (ESI): mass calcd. for $C_{28}H_{24}N_6O_3S$, 524.6; m/z found, 525.1 [M+H]$^+$. $^1$H NMR (400 MHz, CD$_3$OD): δ 8.73-8.67 (m, 1H), 8.34-8.29 (m, 1H), 7.93-7.87 (m, 2H), 7.84-7.80 (m, 2H), 7.54-7.48 (m, 3H), 6.31-6.14 (m, 3H), 5.64-5.59 (m, 1H), 4.58-4.54 (m, 1H), 4.45-4.41 (m, 1H), 2.21-1.98 (m, 2H), 1.97-1.56 (m, 4H).

Example 190: N-((1S,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide

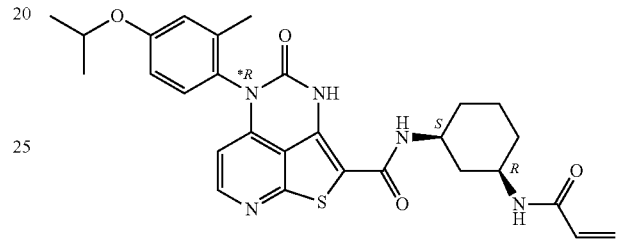

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer), tert-butyl N-[(1R,3S)-3-aminocyclohexyl]carbamate. MS (ESI): mass calcd. for $C_{28}H_{31}N_5O_4S$, 533.6; m/z found, 534.7 [M+H]$^+$. $^1$H NMR (400 MHz, CD$_3$OD): δ 8.28 (d, J=5.5 Hz, 1H), 7.30-7.14 (m, 1H), 7.05-6.80 (m, 2H), 6.34-6.14 (m, 2H), 6.00 (d, J=5.5 Hz, 1H), 5.71-5.54 (m, 1H), 4.71-4.57 (m, 1H), 4.08-3.75 (m, 2H), 2.21-2.14 (m, 1H), 2.10 (s, 3H), 2.00-1.82 (m, 3H), 1.55-1.37 (m, 2H), 1.36-1.31 (m, 6H), 1.30-1.11 (m, 2H).

Example 191: N-((1S,3R)-3-Acrylamidocyclopentyl)-5-(3-chloro-4-phenoxyphenyl)-4-oxo-4,5-dihydro-3H-1-thia-3,5,8-triazaacenaphthylene-2-carboxamide

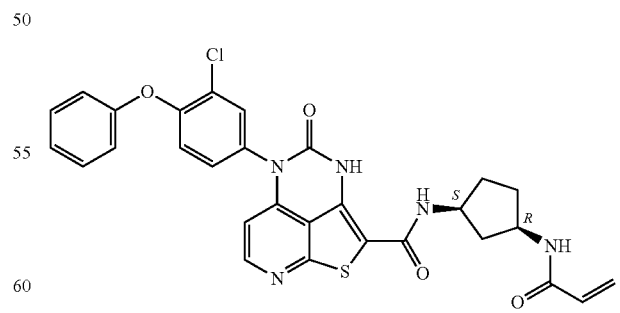

The title compound was prepared in a manner analogous to Example 1, using 5-(3-chloro-4-phenoxyphenyl)-4-oxo-4,5-dihydro-3H-1-thia-3,5,8-triazaacenaphthylene-2-carboxylic acid (Example 137, product from Step A) and tert-butyl N-[(1R,3S)-3-aminocyclopentyl]carbamate. MS (ESI): mass calcd. for $C_{29}H_{24}ClN_5O_4S$, 574.1; m/z found, 574.1 [M+H]⁺. ¹H NMR (400 MHz, CD₃OD): δ 8.33-8.29 (m, 1H), 7.70-7.64 (m, 1H), 7.43-7.33 (m, 3H), 7.20-7.12 (m, 2H), 7.09-7.02 (m, 2H), 6.26-6.18 (m, 3H), 5.67-5.60 (m, 1H), 4.38-4.28 (m, 1H), 4.23-4.14 (m, 1H), 2.51-2.42 (m, 1H), 2.09-1.96 (m, 2H), 1.84-1.70 (m, 2H), 1.64-1.55 (m, 1H).

Example 192: N-((1R,2S)-2-Acrylamidocyclopentyl)-4-oxo-5-(5-phenylpyridin-3-yl)-4,5-dihydro-3H-1-thia-3,5,8-triazaacenaphthylene-2-carboxamide

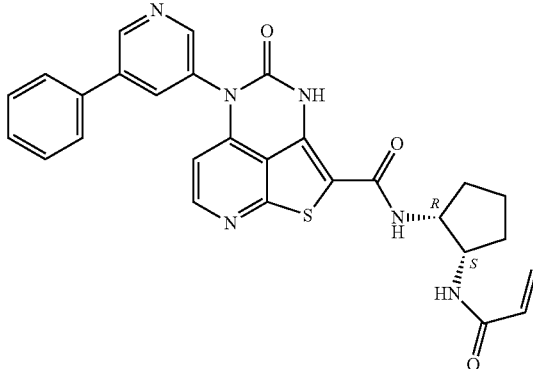

The title compound was prepared in a manner analogous to Example 1, using 4-oxo-5-(5-phenylpyridin-3-yl)-4,5-dihydro-3H-1-thia-3,5,8-triazaacenaphthylene-2-carboxylic acid (Intermediate 22) and tert-butyl N-[(1S,2R)-2-aminocyclopentyl]carbamate. MS (ESI): mass calcd. for $C_{28}H_{24}N_6O_3S$, 524.6; m/z found, 525.1 [M+H]⁺. ¹H NMR (400 MHz, CD₃OD): δ 9.00-8.96 (m, 1H), 8.65-8.61 (m, 1H), 8.35-8.29 (m, 1H), 8.27-8.23 (m, 1H), 7.78-7.71 (m, 2H), 7.56-7.42 (m, 3H), 6.33-6.14 (m, 3H), 5.65-5.58 (m, 1H), 4.49-4.37 (m, 2H), 2.16-2.00 (m, 2H), 1.98-1.87 (m, 1H), 1.78-1.63 (m, 3H).

Example 193: 5-([1,1'-Biphenyl]-3-yl)-N-((1R,2S)-2-acrylamidocyclopentyl)-4-oxo-4,5-dihydro-3H-1-thia-3,5,8-triazaacenaphthylene-2-carboxamide

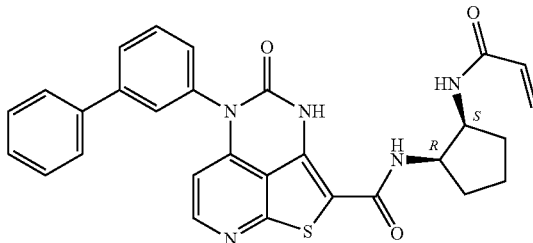

The title compound was prepared in a manner analogous to Example 1, using 5-([1,1'-biphenyl]-3-yl)-4-oxo-4,5-dihydro-3H-1-thia-3,5,8-triazaacenaphthylene-2-carboxylic acid (Intermediate 19) and tert-butyl N-[(1S,2R)-2-aminocyclopentyl]carbamate. MS (ESI): mass calcd. for $C_{29}H_{25}N_5O_3S$, 523.6; m/z found, 524.2 [M+H]⁺. ¹H NMR (400 MHz, CD₃OD): δ 8.28-8.15 (m, 1H), 7.80-7.76 (m, 1H), 7.69-7.63 (m, 4H), 7.46-7.41 (m, 2H), 7.38-7.32 (m, 2H), 6.33-6.06 (m, 3H), 5.64-5.56 (m, 1H), 4.47-7.38 (m, 2H), 2.14-2.02 (m, 2H), 1.94-1.85 (m, 1H), 1.83-1.72 (m, 2H), 1.69-1.61 (m, 1H).

Example 194: N-((1R,2S)-2-Acrylamidocyclopentyl)-4-oxo-5-(3-(pyridin-2-yl)phenyl)-4,5-dihydro-3H-1-thia-3,5,8-triazaacenaphthylene-2-carboxamide

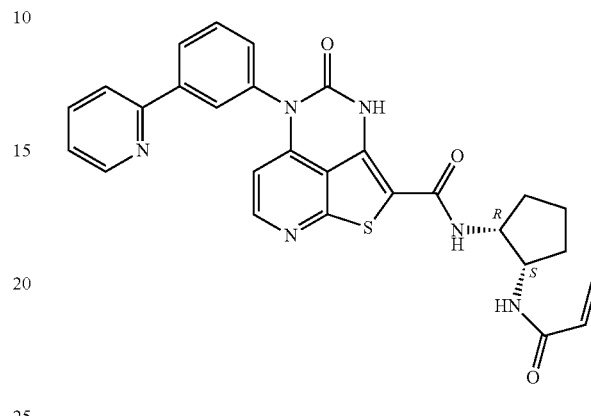

Step A. 4-Oxo-5-(3-(pyridin-2-yl)phenyl)-4,5-dihydro-3H-1-thia-3,5,8-triazaacenaphthylene-2-carboxylic acid The title compound was prepared in a manner analogous to Intermediate 1, Steps C-G, using 3-(2-pyridyl)aniline in place of 2-methyl-4-phenoxyaniline in step C.

Step B. N-((1R,2S)-2-Acrylamidocyclopentyl)-4-oxo-5-(3-(pyridin-2-yl)phenyl)-4,5-dihydro-3H-1-thia-3,5,8-triazaacenaphthylene-2-carboxamide The title compound was prepared in a manner analogous to Example 1, using 4-oxo-5-(3-(pyridin-2-yl)phenyl)-4,5-dihydro-3H-1-thia-3,5,8-triazaacenaphthylene-2-carboxylic acid and tert-butyl N-[(1S,2R)-2-aminocyclopentyl]carbamate in Step A. MS (ESI): mass calcd. for $C_{28}H_{24}N_6O_3S$, 524.6; m/z found, 525.5 [M+H]⁺. ¹H NMR (400 MHz, CD₃OD): δ 8.69-8.52 (m, 1H), 8.23 (d, J=5.5 Hz, 1H), 8.17-8.10 (m, 1H), 8.08-8.02 (m, 1H), 7.97-7.85 (m, 2H), 7.77-7.66 (m, 1H), 7.55-7.44 (m, 1H), 7.41-7.30 (m, 1H), 6.44-6.09 (m, 3H), 5.70-5.48 (m, 1H), 4.50-4.32 (m, 2H), 2.16-1.99 (m, 2H), 1.94-1.85 (m, 1H), 1.81-1.55 (m, 3H).

Example 195: N-((1R,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide

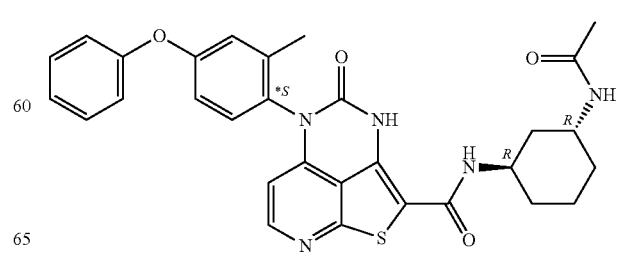

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3R)-3-aminocyclohexyl]carbamate, in Step A, and acetic anhydride in Step B. MS (ESI): mass calcd. for $C_{30}H_{29}N_5O_4S$, 555.6; m/z found, 556.2 [M+H]+.

Example 196: N-((1R,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

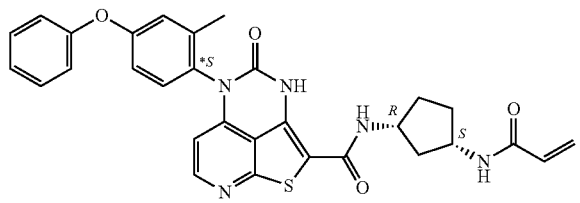

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,2R)-2-aminocyclopentyl]carbamate. MS (ESI): mass calcd. for $C_{30}H_{27}N_5O_4S$, 553.6; m/z found, 554.5 [M+H]+. 1H NMR (400 MHz, CD3OD): δ 8.30 (d, J=5.1 Hz, 1H), 7.51-7.36 (m, 2H), 7.33-7.25 (m, 1H), 7.22-7.14 (m, 1H), 7.13-7.03 (m, 3H), 7.00-6.94 (m, 1H), 6.31-6.19 (m, 2H), 6.04 (d, J=4.9 Hz, 1H), 5.73-5.59 (m, 1H), 4.48-4.33 (m, 1H), 4.29-4.12 (m, 1H), 2.57-2.42 (m, 1H), 2.12 (s, 3H), 2.09-1.96 (m, 2H), 1.88-1.70 (m, 2H), 1.68-1.54 (m, 1H).

Example 197: N-((1R,2R)-2-Acrylamidocyclopentyl)-4-oxo-5-(2-phenylpyridin-4-yl)-4,5-dihydro-3H-1-thia-3,5,8-triazaacenaphthylene-2-carboxamide

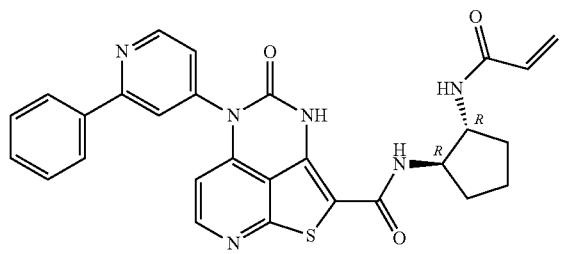

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1R,2R)-2-aminocyclopentyl]carbamate. MS (ESI): mass calcd. for $C_{28}H_{24}N_6O_3S$, 524.6; m/z found, 525.4 [M+H]+. 1H NMR (400 MHz, CD3OD): δ 8.85 (d, J=5.3 Hz, 1H), 8.32 (d, J=5.6 Hz, 1H), 8.08-8.00 (m, 3H), 7.54-7.41 (m, 4H), 6.30 (d, J=5.6 Hz, 1H), 6.24-6.18 (m, 2H), 5.68-5.58 (m, 1H), 4.35-4.17 (m, 2H), 2.26-2.08 (m, 2H), 1.91-1.75 (m, 2H), 1.73-1.47 (m, 2H).

Example 198: N-((1S,3R)-3-Acrylamidocyclopentyl)-4-oxo-5-(2-phenylpyridin-4-yl)-4,5-dihydro-3H-1-thia-3,5,8-triazaacenaphthylene-2-carboxamide

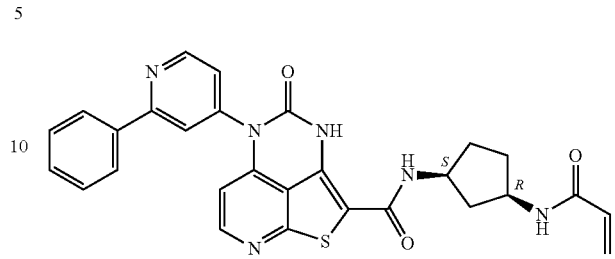

The title compound was prepared in a manner analogous to Example 1, using 4-oxo-5-(2-phenylpyridin-4-yl)-4,5-dihydro-3H-1-thia-3,5,8-triazaacenaphthylene-2-carboxy c acid (Intermediate 20) and tert-butyl N-[(1R,3S)-3-aminocyclopentyl]carbamate. MS (ESI): mass calcd. for $C_{28}H_{24}N_6O_3S$, 524.6; m/z found, 525.2 [M+H]+. 1H NMR (400 MHz, CD3OD): δ 8.88-8.82 (m, 1H), 8.33-8.27 (m, 1H), 8.05-7.99 (m, 3H), 7.50-7.42 (m, 4H), 6.30-6.26 (m, 1H), 6.26-6.21 (m, 2H), 5.66-5.60 (m, 1H), 4.39-4.30 (m, 1H), 4.23-4.14 (m, 1H), 2.51-2.42 (m, 1H), 2.08-2.96 (m, 2H), 1.84-1.71 (m, 2H), 1.65-1.57 (m, 1H).

Example 199: N-((1R,2S)-2-Acrylamidocyclopentyl)-5-(2-methyl-4-(pyridin-3-yloxy)phenyl)-4-oxo-4,5-dihydro-3H-1-thia-3,5,8-triazaacenaphthylene-2-carboxamide

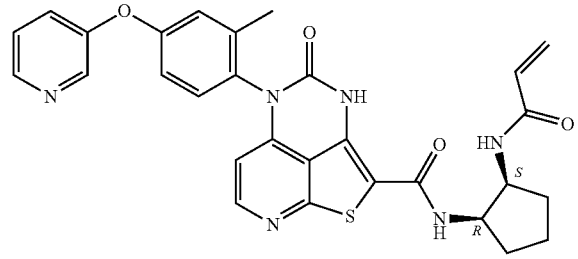

Step A. 3-(3-Methyl-4-nitrophenoxy)pyridine

The title compound was prepared using analogous conditions described in Intermediate 1, Step A, using 4-fluoro-2-methyl-1-nitrobenzene and pyridin-3-ol. MS (ESI): mass calcd. for $C_{12}H_{10}N_2O_3$, 230.07; m/z found, 231.1 [M+H]+.

Step B. 5-(2-Methyl-4-(pyridin-3-yloxy)phenyl)-4-oxo-4,5-dihydro-3H-1-thia-3,5,8-triazaacenaphthylene-2-carboxylic acid The title compound was prepared in a manner analogous to Intermediate 25, Steps B-C, using 3-(3-methyl-4-nitrophenoxy)pyridine. In an alternate method, Intermediate 1, Step B is used. MS (ESI): mass calcd. for $C_{21}H_{14}N_4O_4S$, 418.07, m/z found, 419.0 [M+H]+.

Step C. N-((1R,2S)-2-Acrylamidocyclopentyl)-5-(2-methyl-4-(pyridin-3-yloxy)phenyl)-4-oxo-4,5-dihydro-3H-1-thia-3,5,8-triazaacenaphthylene-2-carboxamide The title compound was prepared in a manner analogous to Example 1, using 5-(2-methyl-4-(pyridin-3-yloxy)phenyl)-4-oxo-4,5-dihydro-3H-1-thia-3,5,8-triazaacenaphthylene-2-carboxylic acid and N-[(1S,2R)-2-aminocyclopentyl]prop-2-enamide (Intermediate 36) in Step A (no HCl/MeOH deprotection). MS (ESI): mass calcd. for $C_{29}H_{26}N_6O_4S$, 554.6; m/z found, 555.3 [M+H]+. $^1$H NMR (400 MHz, CD$_3$OD): δ 8.55 (s, 1H), 8.50-8.41 (m, 1H), 8.33 (d, J=5.5 Hz, 1H), 7.91-7.84 (m, 1H), 7.77-7.66 (m, 1H), 7.47-7.38 (m, 1H), 7.29-7.20 (m, 1H), 7.19-7.12 (m, 1H), 34-6.1623 (m, 2H), 6.15-6.06 (m, 1H), 5.68-5.57 (m, 1H), 4.49-4.35 (m, 2H), 2.20-2.15 (m, 3H), 2.14-2.03 (m, 2H), 1.97-1.87 (m, 1H), 1.82-1.63 (m, 3H).

Example 200: N-((1R,2R)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

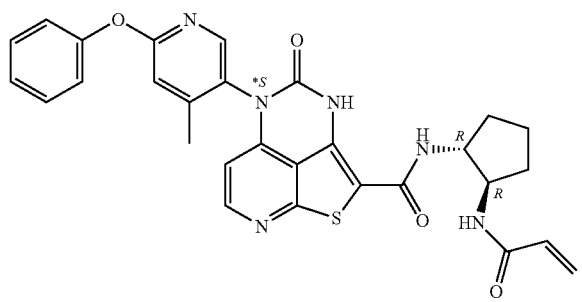

Step A. N-((1R,2R)-2-aminocyclopentyl)-5-(*S)-(4-methyl-6-phenoxypyridin-3-yl)-4-oxo-4,5-dihydro-3H-1-thia-3,5,8-triazaacenaphthylene-2-carboxamide The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl N-[(1R,2R)-2-amino cyclopentyl]carbamate.

Step B. N-((1R,2R)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide The title compound was prepared in a manner analogous to Example 166, Step C. MS (ESI): mass calcd. for $C_{29}H_{26}N_6O_4S$, 554.6; m/z found, 555.2 [M+H]+. $^1$H NMR (400 MHz, CDCl$_3$): δ 8.34 (d, J=5.4 Hz, 1H), 8.05 (s, 1H), 7.48-7.36 (m, 2H), 7.29-7.14 (m, 3H), 7.06 (d, J=5.6 Hz, 1H), 6.95 (s, 1H), 6.87 (d, J=5.9 Hz, 1H), 6.29 (ddd, J=17.0, 3.1, 1.6 Hz, 1H), 6.11-5.97 (m, 2H), 5.61 (dd, J=10.2, 1.6 Hz, 1H), 4.26-4.07 (m, 3H), 2.39-2.18 (m, 5H), 2.04 (s, 1H), 1.81 (ddd, J=15.4, 10.7, 6.7 Hz, 2H), 1.50 (dq, J=12.6, 9.5 Hz, 1H).

Example 201: N-((1R,2S)-2-Acrylamidocyclopentyl)-4-oxo-5-(5-phenoxypyrazin-2-yl)-4,5-dihydro-3H-1-thia-3,5,8-triazaacenaphthylene-2-carboxamide

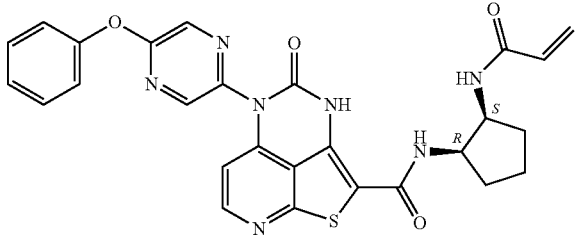

Step A. 4-Oxo-5-(5-phenoxypyrazin-2-yl)-4,5-dihydro-3H-1-thia-3,5,8-triazaacenaphthylene-2-carboxylic acid The title compound was prepared in a manner analogous to Intermediate 13, using 5-bromopyrazin-2-amine and phenol in Step A.

Step B. N-((1R,2S)-2-Acrylamidocyclopentyl)-4-oxo-5-(5-phenoxypyrazin-2-yl)-4,5-dihydro-3H-1-thia-3,5,8-triazaacenaphthylene-2-carboxamide The title compound was prepared in a manner analogous to Example 1, Step A, using 4-oxo-5-(5-phenoxypyrazin-2-yl)-4,5-dihydro-3H-1-thia-3,5,8-triazaacenaphthylene-2-carboxylic acid and N-[(1S,2R)-2-aminocyclopentyl]prop-2-enamide (Intermediate 36) (no deprotection HCl/MeOH). MS (ESI): mass calcd. for $C_{27}H_{23}N_7O_4S$, 541.6; m/z found, 542.1 [M+H]+. $^1$H NMR (400 MHz, DMSO-d$_6$): δ 10.20 (s, 1H), 8.66-8.59 (m, 1H), 8.45-8.39 (m, 1H), 8.34 (d, J=5.5 Hz, 1H), 7.94-7.85 (m, 1H), 7.83-7.74 (m, 1H), 7.56-7.42 (m, 2H), 7.36-7.23 (m, 3H), 6.35 (d, J=5.5 Hz, 1H), 6.29-6.15 (m, 1H), 6.13-5.98 (m, 1H), 5.61-5.48 (m, 1H), 4.34-4.20 (m, 2H), 2.00-1.84 (m, 2H), 1.82-1.69 (m, 2H), 1.67-1.58 (m, 1H), 1.56-1.47 (m, 1H).

Example 202: N-((1R,2S)-2-Acrylamidocyclopentyl)-4-oxo-5-(3-(pyridin-3-yl)phenyl)-4,5-dihydro-3H-1-thia-3,5,8-triazaacenaphthylene-2-carboxamide

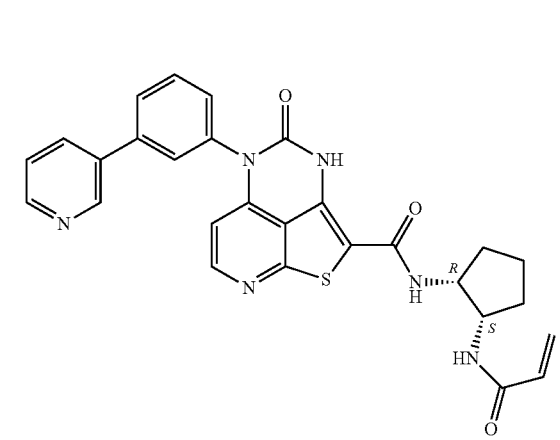

Step A. 4-Oxo-5-(3-(pyridin-3-yl)phenyl)-4,5-dihydro-3H-1-thia-3,5,8-triazaacenaphthylene-2-carboxylic acid The title compound was prepared in a manner analogous to Intermediate 1, Steps C-F, using 3-(3-pyridyl)aniline and 2-chloro-4-iodopyridine-3-carbonitrile, and substituting $Cs_2CO_3$ for $K_3PO_4$ in Step C.

Step B. N-((1R,2S)-2-Acrylamidocyclopentyl)-4-oxo-5-(3-(pyridin-3-yl)phenyl)-4,5-dihydro-3H-1-thia-3,5,8-triazaacenaphthylene-2-carboxamide The title compound was prepared in a manner analogous to Example 1, Step A, using 4-oxo-5-(3-(pyridin-3-yl)phenyl)-4,5-dihydro-3H-1-thia-3,5,8-triazaacenaphthylene-2-carboxylic acid and N-[(1S,2R)-2-aminocyclopentyl]prop-2-enamide (Intermediate 36) (no HCl/MeOH deprotection). MS (ESI): mass calcd. for $C_{28}H_{24}N_6O_3S$, 524.6; m/z found, 525.2 [M+H]$^+$. $^1$H NMR (400 MHz, CD$_3$OD): δ 8.90-8.83 (m, 1H), 8.57-8.52 (m, 1H), 8.33-8.26 (m, 1H), 8.18-8.12 (m, 1H), 7.90-7.83 (m, 1H), 7.81-7.72 (m, 2H), 7.56-7.44 (m, 2H), 6.35-6.14 (m, 3H), 5.66-5.56 (m, 1H), 4.47-4.34 (m, 2H), 2.20-2.00 (m, 2H), 1.96-1.84 (m, 1H), 1.82-1.60 (m, 3H).

Example 203: N-((1R,2S)-2-Acrylamidocyclopentyl)-4-oxo-5-(6-phenylpyridazin-4-yl)-4,5-dihydro-3H-1-thia-3,5,8-triazaacenaphthylene-2-carboxamide

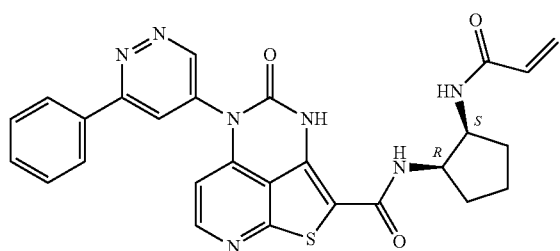

Step A. 6-Phenylpyridazin-4-amine

The title compound was prepared in manner analogous to Intermediate 20, Step A, using 6-chloropyridazin-4-amine and phenyl boronic acid and substituting Pd(dppf) C12 for Pd(PPh$_3$)$_4$.

Step B. 4-Oxo-5-(6-phenylpyridazin-4-yl)-4,5-dihydro-3H-1-thia-3,5,8-triazaacenaphthylene-2-carboxylic acid The title compound was prepared in a manner analogous to Intermediate 1, Steps C-F, using 6-phenylpyridazin-4-amine and 2-chloro-4-iodopyridine-3-carbonitrile in Step C.

Step C. N-((1R,2S)-2-Acrylamidocyclopentyl)-4-oxo-5-(6-phenylpyridazin-4-yl)-4,5-dihydro-3H-1-thia-3,5,8-triazaacenaphthylene-2-carboxamide The title compound was prepared in a manner analogous to Example 1, using 4-oxo-5-(6-phenylpyridazin-4-yl)-4,5-dihydro-3H-1-thia-3,5,8-triazaacenaphthylene-2-carboxylic acid and tert-butyl N-[(1S,2R)-2-aminocyclopentyl]carbamate in Step A. MS (ESI): mass calcd. for $C_{27}H_{23}N_7O_3S$, 525.6; m/z found, 526.5 [M+H]$^+$. $^1$H NMR (400 MHz, DMSO-d$_6$): δ 10.28 (s, 1H), 9.39 (s, 1H), 8.55 (s, 1H), 8.40-8.30 (m, 1H), 8.20-8.16 (m, 2H), 7.92-7.83 (m, 1H), 7.82-7.75 (m, 1H), 7.60-7.55 (m, 3H), 6.48-6.41 (m, 1H), 6.27-6.18 (m, 1H), 6.09-6.02 (m, 1H), 5.60-5.51 (m, 1H), 4.33-4.24 (m, 2H), 1.98-1.86 (m, 2H), 1.82-1.70 (m, 2H), 1.68-1.49 (m, 2H).

Example 204: N-((1R,2S)-2-Acrylamidocyclohexyl)-5-(*S)-(6-cyclobutoxy-2-methylpyridin-3-yl)-4-oxo-4,5-dihydro-3H-1-thia-3,5,8-triazaacenaphthylene-2-carboxamide

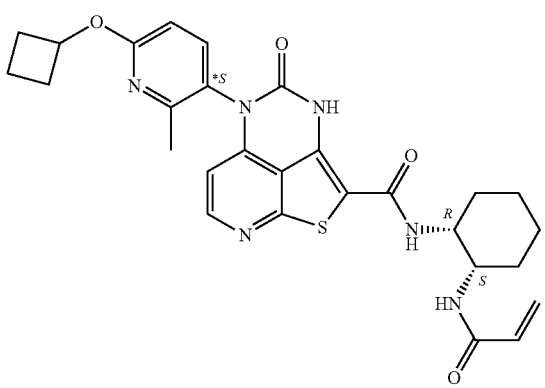

Chiral SFC (Stationary phase: Chiralpak AS-H 5 μm 250*20 mm, Mobile phase: 70% CO$_2$, 30% MeOH) of N-((1R,2S)-2-Acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide (Example 187) afforded the title compound. MS (ESI): mass calcd. for $C_{28}H_{30}N_6O_4S$, 546.7; m/z found, 547.2 [M+H]$^+$. $^1$H NMR (400 MHz, CD$_3$OD): δ 8.30 (d, J=5.1 Hz, 1H), 7.62 (d, J=8.6 Hz, 1H), 6.75 (d, J=8.6 Hz, 1H), 6.42 (dd, J=17.0, 10.2 Hz, 1H), 6.26 (d, J=17.0 Hz, 1H), 6.05 (d, J=5.2 Hz, 1H), 5.66 (d, J=10.2 Hz, 1H), 5.28-5.14 (m, 1H), 4.42 (s, 1H), 4.22-4.11 (m, 1H), 2.54-2.44 (m, 2H), 2.24 (s, 3H), 2.19-2.07 (m, 2H), 1.91-1.60 (m, 8H), 1.59-1.45 (m, 2H).

Example 205: N-((1R,2S)-2-Acrylamidocyclopentyl)-5-(4-isopropoxyphenyl)-4-oxo-4,5-dihydro-3H-1-thia-3,5,8-triazaacenaphthylene-2-carboxamide

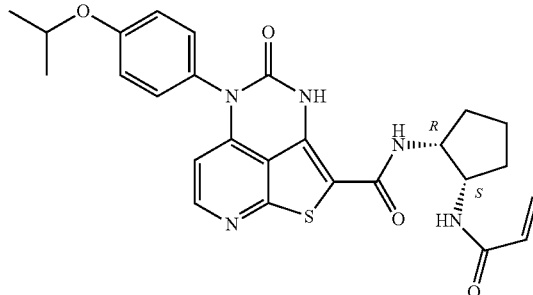

The title compound was prepared in a manner analogous to Example 1, Step A, using 5-(4-isopropoxyphenyl)-4-oxo-4,5-dihydro-3H-1-thia-3,5,8-triazaacenaphthylene-2-carboxylic acid (Intermediate 7) and N—[(S,2R)-2-aminocyclopentyl]prop-2-enamide (Intermediate 36), no deprotection step with HCl. MS (ESI): mass calcd. for $C_{26}H_{27}N_5O_4S$, 505.6; m/z found, 506.2 [M+H]$^+$. $^1$H NMR (400 MHz, CD$_3$OD): δ 8.27 (d, J=5.6 Hz, 1H), 7.36-7.23 (m, 2H), 7.17-7.03 (m, 2H), 6.35-6.15 (m, 2H), 6.12 (d, J=5.6 Hz, 1H), 5.66-5.57 (m, 1H), 4.74-4.62 (m, 1H), 4.50-4.32 (m, 2H), 2.18-2.01 (m, 2H), 1.96-1.85 (m, 1H), 1.8-1.57 (m, 3H), 1.38-1.33 (m, 6H).

Example 206: N-((1R,2S)-2-Acrylamidocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide

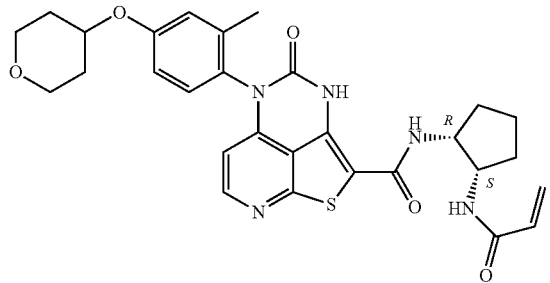

The title compound was prepared in a manner analogous to Example 1, using 5-(2-methyl-4-((tetrahydro-2H-pyran-4-yl)oxy)phenyl)-4-oxo-4,5-dihydro-3H-1-thia-3,5,8-triazaacenaphthylene-2-carboxylic acid (Intermediate 12) and tert-butyl N-[(1S,2R)-2-aminocyclopentyl]carbamate in step A. MS (ESI): mass calcd. for $C_{29}H_{31}N_5O_5S$, 561.7; m/z found, 562.2 [M+H]$^+$. $^1$H NMR (400 MHz, CD$_3$OD): δ 8.29-8.23 (m, 1H), 7.24-7.16 (m, 1H), 7.06-7.00 (m, 1H), 6.99-6.93 (m, 1H), 6.32-6.14 (m, 2H), 6.02-5.96 (m, 1H), 5.63-5.56 (m, 1H), 4.68-4.56 (m, 1H), 4.46-4.33 (m, 2H), 3.99-3.89 (m, 2H), 3.66-3.54 (m, 2H), 2.18-1.98 (m, 7H), 1.96-1.83 (m, 1H), 1.81-1.61 (m, 5H)

Example 207: N-((1R,2S)-2-Acrylamidocyclopentyl)-5-(2-isopropylpyridin-4-yl)-4-oxo-4,5-dihydro-3H-1-thia-3,5,8-triazaacenaphthylene-2-carboxamide

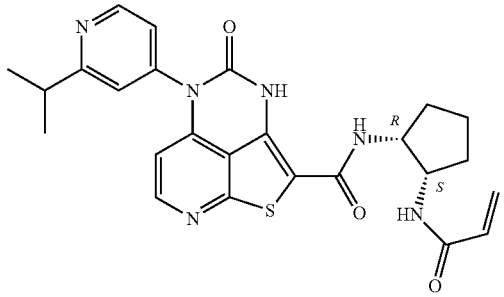

The title compound was prepared in a manner analogous to Example 1, using 5-(2-isopropylpyridin-4-yl)-4-oxo-4,5-dihydro-3H-1-thia-3,5,8-triazaacenaphthylene-2-carboxylic acid (Intermediate 16) and tert-butyl N-[(1S,2R)-2-aminocyclopentyl]carbamate. MS (ESI): mass calcd. for $C_{25}H_{26}N_6O_3S$, 490.6; m/z found, 491.2 [M+H]$^+$. $^1$H NMR (400 MHz, CD$_3$OD): δ 8.65 (d, J=5.3 Hz, 1H), 8.16-8.02 (m, 1H), 7.48-7.38 (m, 1H), 7.35-7.28 (m, 1H), 6.37-7.24 (m, 1H), 6.22-6.10 (m, 1H), 6.00 (d, J=5.5 Hz, 1H), 5.62-5.51 (m, 1H), 4.57-4.47 (m, 1H), 4.44-4.33 (m, 1H), 3.21-3.09 (m, 1H), 2.12-1.97 (m, 2H), 1.92-1.74 (m, 3H), 1.670-1.57 (m, 1H), 1.35 (d, J=6.9 Hz, 6H).

Example 208: N-((1R,3S)-3-Acrylamidocyclopentyl)-4-oxo-5-(2-phenylpyridin-4-yl)-4,5-dihydro-3H-1-thia-3,5,8-triazaacenaphthylene-2-carboxamide

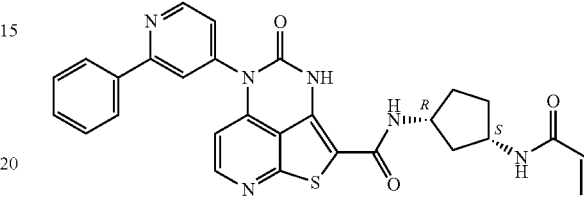

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,3R)-3-aminocyclopentyl]carbamate. MS (ESI): mass calcd. for $C_{28}H_{24}N_6O_3S$, 524.6; m/z found, 525.2 [M+H]$^+$. $^1$H NMR (400 MHz, CD$_3$OD): δ 8.90-8.82 (m, 1H), 8.37-8.28 (m, 1H), 8.07-8.00 (m, 3H), 7.52-7.43 (m, 4H), 6.33-6.28 (m, 1H), 6.27-6.20 (m, 2H), 5.68-5.60 (m, 1H), 4.41-4.29 (m, 1H), 4.24-4.14 (m, 1H), 2.53-2.43 (m, 1H), 2.09-1.96 (m, 2H), 1.87-1.73 (m, 2H), 1.65-1.56 (m, 1H).

Example 209: N-((1R,2S)-2-Acrylamidocyclohexyl)-5-(*S)-(6-isopropoxy-2-methylpyridin-3-yl)-4-oxo-4,5-dihydro-3H-1-thia-3,5,8-triazaacenaphthylene-2-carboxamide

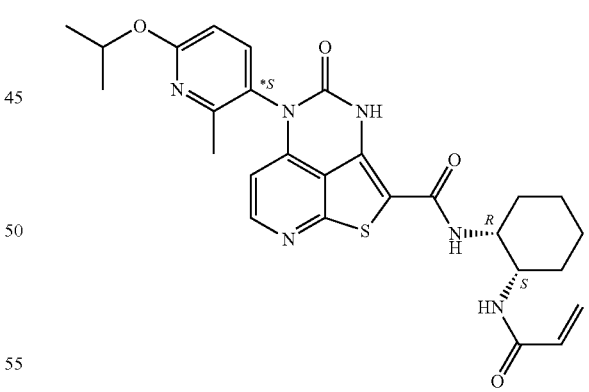

Chiral SFC purification (Stationary phase: Chiralpak AS-H 5 μm 250*20 mm, Mobile phase: 70% CO$_2$, 30% MeOH) of N-((1R,2S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide (Example 211) afforded the title compound. MS (ESI): mass calcd. for $C_{27}H_{30}N_6O_4S$, 534.6; m/z found, 535.2 [M+H]$^+$. $^1$H NMR (500 MHz, CD$_3$OD): δ 8.31 (d, J=4.5 Hz, 1H), 7.58 (d, J=8.6 Hz, 1H), 6.73 (d, J=8.6 Hz, 1H), 6.42 (dd, J=17.0, 10.2 Hz, 1H), 6.30-6.24 (m, 1H), 6.12-6.02 (m, 1H), 5.67 (dd, J=10.3, 1.6 Hz, 1H), 5.40-5.29 (m, 1H), 4.43 (s, 1H), 4.23-4.10 (m, 1H), 2.26 (s, 3H), 1.86-1.61 (m, 6H), 1.59-1.47 (m, 2H), 1.37 (dd, J=6.1, 2.8 Hz, 6H).

Example 210: N-((1R,2S)-2-(3-Chloropropanamido)cyclopentyl)-5-(*S)-(4-methyl-6-phenoxypyridin-3-yl)-4-oxo-4,5-dihydro-3H-1-thia-3,5,8-triazaacenaphthylene-2-carboxamide

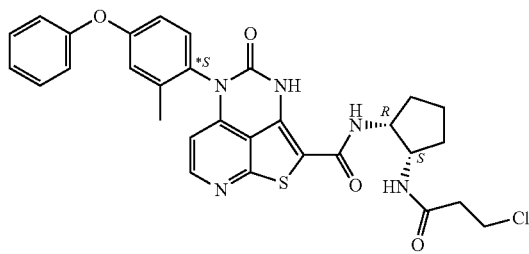

The title compound was prepared in a manner analogous to Example 166, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and N-[(1S,2R)-2-aminocyclopentyl]-3-chloropropanamide. MS (ESI): mass calcd. for $C_{29}H_{27}ClN_6O_4S$, 591.1; m/z found, 591.0 [M+H]$^+$. $^1$H NMR (400 MHz, CDCl$_3$): δ 9.65 (s, 1H), 8.35 (d, J=5.5 Hz, 1H), 8.04 (d, J=6.5 Hz, 3H), 7.44 (dd, J=8.3, 7.1 Hz, 2H), 7.31-7.15 (m, 2H), 6.98-6.87 (m, 3H), 6.04 (d, J=5.4 Hz, 1H), 4.38 (tt, J=14.0, 6.7 Hz, 2H), 3.81 (qt, J=10.6, 6.4 Hz, 2H), 2.68 (t, J=6.4 Hz, 2H), 2.20 (s, 3H), 2.10 (dd, J=13.9, 7.2 Hz, 1H), 1.90-1.65 (m, 4H).

Example 211: N-((1R,2S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide

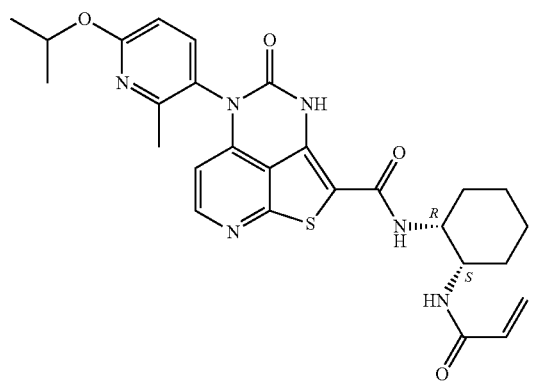

Step A. 5-(6-Isopropoxy-2-methylpyridin-3-yl)-4-oxo-4,5-dihydro-3H-1-thia-3,5,8-triazaacenaphthylene-2-carboxylic acid The title compound was prepared in a manner analogous to Intermediate 24, using 6-fluoro-2-methylpyridin-3-amine, 2-propanol in Step A.

Step B. N-((1R,2S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide The title compound was prepared in a manner analogous to Example 166, Step A, using and using N-[(1S,2R)-2-aminocyclohexyl]prop-2-enamide (Intermediate 40) and 5-(6-isopropoxy-2-methylpyridin-3-yl)-4-oxo-4,5-dihydro-3H-1-thia-3,5,8-triazaacenaphthylene-2-carboxylic acid. MS (ESI): mass calcd. for $C_{27}H_{30}N_6O_4S$, 534.6; m/z found, 535.2 [M+H]$^+$. $^1$H NMR (400 MHz, CD$_3$OD): δ 8.33 (d, J=5.5 Hz, 1H), 7.58 (dd, J=8.6, 2.1 Hz, 1H), 6.73 (d, J=8.6 Hz, 1H), 6.42 (dd, J=17.0, 10.2 Hz, 1H), 6.31-6.23 (m, 1H), 6.09 (d, J=5.4 Hz, 1H), 5.67 (dd, J=10.2, 1.8 Hz, 1H), 5.41-5.29 (m, 1H), 4.44 (s, 1H), 4.17 (d, J=8.1 Hz, 1H), 2.26 (s, 3H), 1.88-1.46 (m, 8H), 1.37 (dd, J=6.2, 2.2 Hz, 6H).

Example 212: N-((1R,3R)-3-Acrylamidocyclopentyl)-4-oxo-5-(2-phenylpyridin-4-yl)-4,5-dihydro-3H-1-thia-3,5,8-triazaacenaphthylene-2-carboxamide

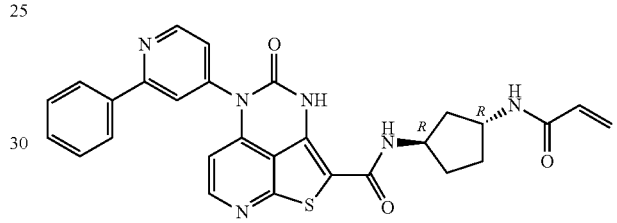

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1R,3R)-3-aminocyclopentyl]carbamate. MS (ESI): mass calcd. for $C_{28}H_{24}N_6O_3S$, 524.6; m/z found, 525.1 [M+H]$^+$. $^1$H NMR (400 MHz, CD$_3$OD): δ 8.87-8.79 (m, 1H), 8.27-8.19 (m, 1H), 8.05-8.00 (m, 2H), 8.00-7.95 (m, 1H), 7.52-7.43 (m, 4H), 6.27-6.16 (m, 3H), 5.68-5.59 (m, 1H), 4.55-4.46 (m, 1H), 4.44-4.36 (m, 1H), 2.26-2.15 (m, 2H), 2.06-1.94 (m, 2H), 1.76-1.65 (m, 1H), 1.61-1.52 (m, 1H).

Example 213: N-((1R,2R)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

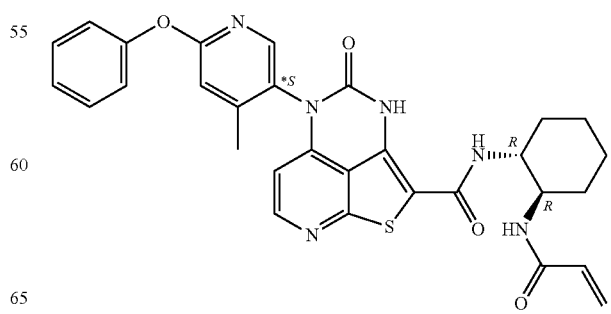

The title compound was prepared in a manner analogous to Example 166, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl N-[(1R,2R)-2-aminocyclohexyl]carbamate. MS (ESI): mass calcd. for $C_{30}H_{28}N_6O_4S$, 568.7; m/z found, 569.0 [M+H]$^+$. $^1$H NMR (500 MHz, CDCl$_3$): δ 9.73 (s, 1H), 8.33 (d, J=5.4 Hz, 1H), 8.04 (s, 1H), 7.47-7.39 (m, 2H), 7.28-7.14 (m, 3H), 6.95 (s, 1H), 6.75 (d, J=7.3 Hz, 1H), 6.56-6.49 (m, 1H), 6.28 (dd, J=17.0, 1.5 Hz, 1H), 6.09-5.98 (m, 2H), 5.59 (dd, J=10.3, 1.5 Hz, 1H), 3.96-3.77 (m, 2H), 2.20 (s, 3H), 2.04 (s, 2H), 1.83-1.76 (m, 2H), 1.45-1.21 (m, 4H).

Example 214: N-((1RS,3RS)-3-Acrylamidocyclopentyl)-4-oxo-5-(5-phenoxypyridin-2-yl)-4,5-dihydro-3H-1-thia-3,5,8-triazaacenaphthylene-2-carboxamide

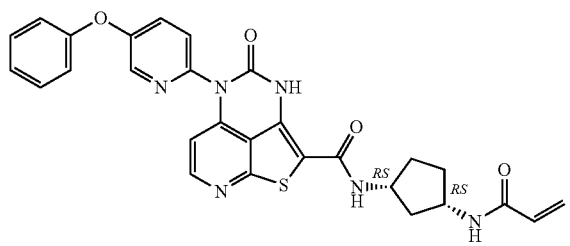

To a cooled solution, 0° C., of 4-oxo-5-(5-phenoxypyridin-2-yl)-4,5-dihydro-3H-1-thia-3,5,8-triazaacenaphthylene-2-carboxylic acid (Intermediate 26, 911.4 mg, 2.25 mmol), N-[(1RS,3RS)-3-aminocyclopentyl]prop-2-enamide (382.3 mg, 2.48 mmol), and diisopropylethylamine (1.9 mL) in DMF (10 mL) was added propylphosphonic anhydride ((T3P®), 50 wt. % in ethyl acetate, 2 mL, 9.29 mmol) dropwise. Upon completion by LCMS, the reaction mixture was partitioned with EtOAc and sat. aq. NaHCO$_3$. The organics were dried (Na$_2$SO$_4$), filtered, and concentrated under reduced pressure. The resulting crude title compound was triturated with DCM to provide the title compound as a white solid. Chiral SFC (Stationary phase: Chiralpak IA 5 μm 250*20 mm, Mobile phase: 55% CO$_2$, 45% iPrOH) afforded the title compound, N-((1S,3R)-3-Acrylamidocyclopentyl)-4-oxo-5-(5-phenoxypyridin-2-yl)-4,5-dihydro-3H-1-thia-3,5,8-triazaacenaphthylene-2-carboxamide (Example 313) and N-((1*R,3*S)-3-Acrylamidocyclopentyl)-4-oxo-5-(5-phenoxypyridin-2-yl)-4,5-dihydro-3H-1-thia-3,5,8-triazaacenaphthylene-2-carboxamide (Example 328). MS (ESI): mass calcd. for $C_{28}H_{24}N_6O_4S$, 540.6; m/z found, 541.0 [M+H]$^+$.

Example 215: N-((1R,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide

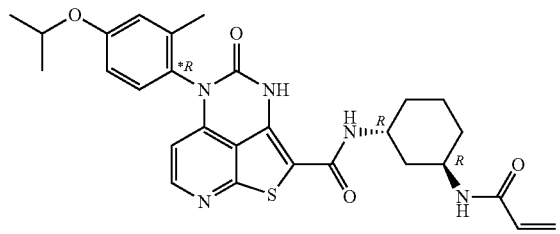

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1R,3R)-3-(prop-2-enoylamino)cyclohexyl]carbamate. MS (ESI): mass calcd. for $C_{28}H_{31}N_5O_4S$, 533.6; m/z found, 534.5 [M+H]$^+$. $^1$H NMR (400 MHz, CD$_3$OD): δ 8.31 (d, J=5.6 Hz, 1H), 7.19 (d, J=8.6 Hz, 1H), 6.99-6.95 (m, 1H), 6.94-6.88 (m, 1H), 6.41-6.31 (m, 1H), 6.27-6.18 (m, 1H), 6.06-6.00 (m, 1H), 5.70-5.62 (m, 1H), 4.71-4.60 (m, 1H), 4.26-4.10 (m, 2H), 2.11 (s, 3H), 1.98-1.75 (m, 3H), 1.75-1.50 (m, 5H), 1.34 (d, J=6.0 Hz, 6H).

Example 216: N-((1RS,3RS)-3-Acrylamidocyclohexyl)-4-oxo-5-(5-phenoxypyridin-2-yl)-4,5-dihydro-3H-1-thia-3,5,8-triazaacenaphthylene-2-carboxamide

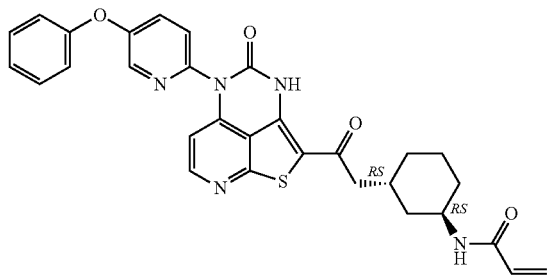

The title compound was prepared in a manner analogous to Example 166, using 4-oxo-5-(5-phenoxypyridin-2-yl)-4,5-dihydro-3H-1-thia-3,5,8-triazaacenaphthylene-2-carboxylic acid (Intermediate 26) and tert-butyl N-[(1R,3R)-3-aminocyclohexyl]carbamate. MS (ESI): mass calcd. for $C_{29}H_{26}N_6O_4S$, 554.6; m/z found, 555.0 [M+H]$^+$. $^1$H NMR (400 MHz, DMSO-d$_6$): δ 10.23 (s, 1H), 8.50-8.28 (m, 2H), 8.03 (dd, J=53.5, 7.6 Hz, 2H), 7.73-7.55 (m, 2H), 7.55-7.42 (m, 2H), 7.38-7.16 (m, 3H), 6.39 (dd, J=17.1, 10.2 Hz, 1H), 6.21 (d, J=5.5 Hz, 1H), 6.09 (dd, J=17.1, 2.4 Hz, 1H), 5.57 (dd, J=10.1, 2.4 Hz, 1H), 4.28-4.04 (m, 2H), 1.91-1.46 (m, 8H).

Example 217: N-((1R,3R)-3-(2-(Dimethylamino) acetamido)cyclopentyl)-5-(2-methyl-4-phenoxyphenyl)-4-oxo-4,5-dihydro-3H-1-thia-3,5,8-triazaacenaphthylene-2-carboxamide

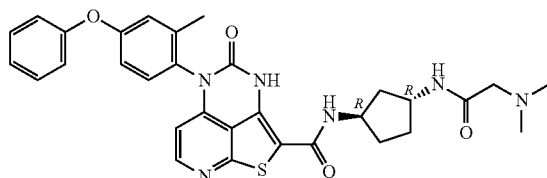

Step A. N-((1R,3R)-3-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,3R)-3-aminocyclopentyl]carbamate.

Step B. N-((1R,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 2-(dimethylamino)acetic acid, no deprotection step with HCl needed. MS (ESI): mass calcd. for $C_{31}H_{32}N_6O_4S$, 584.7; m/z found, 585.2 [M+H]$^+$. $^1$H NMR (400 MHz, CD$_3$OD): δ 8.34-8.27 (m, 1H), 7.44-7.34 (m, 2H), 7.31-7.26 (m, 1H), 7.19-7.13 (m, 1H), 7.12-7.06 (m, 2H), 7.06-7.03 (m, 1H), 6.99-6.94 (m, 1H), 6.09-6.01 (m, 1H), 4.54-4.43 (m, 1H), 4.40-4.30 (m, 1H), 3.03-2.94 (m, 2H), 2.30 (s, 6H), 2.22-2.14 (m, 2H), 2.11 (s, 3H), 2.03-1.89 (m, 2H), 1.71-1.61 (m, 1H), 1.60-1.50 (m, 1H).

Example 218: N-((1R,2R)-2-Acrylamidocyclohexyl)-4-oxo-5-(5-phenoxypyridin-2-yl)-4,5-dihydro-3H-1-thia-3,5,8-triazaacenaphthylene-2-carboxamide

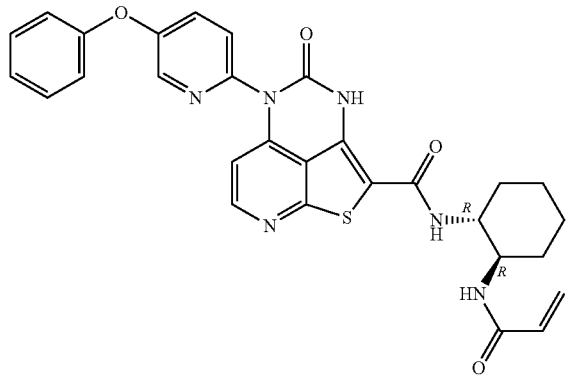

The title compound was prepared in a manner analogous to Example 166, using 4-oxo-5-(5-phenoxypyridin-2-yl)-4,5-dihydro-3H-1-thia-3,5,8-triazaacenaphthylene-2-carboxylic acid (Intermediate 26) and tert-butyl N-[(1R,2R)-2-aminocyclohexyl]carbamate. MS (ESI): mass calcd. for $C_{29}H_{26}N_6O_4S$, 554.6; m/z found, 555.1 [M+H]$^+$. $^1$H NMR (500 MHz, CDCl$_3$): δ 9.51 (s, 1H), 8.45-8.31 (m, 2H), 7.51-7.33 (m, 4H), 7.26-7.19 (m, 1H), 7.18-7.08 (m, 2H), 6.52 (d, J=7.2 Hz, 1H), 6.33-6.13 (m, 3H), 6.10-5.99 (m, 1H), 5.62 (dd, J=10.3, 1.4 Hz, 1H), 3.96-3.73 (m, 2H), 2.31-2.06 (m, 2H), 1.89-1.77 (m, 2H), 1.46-1.24 (m, 4H).

Example 219: N-((1R,2R)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide

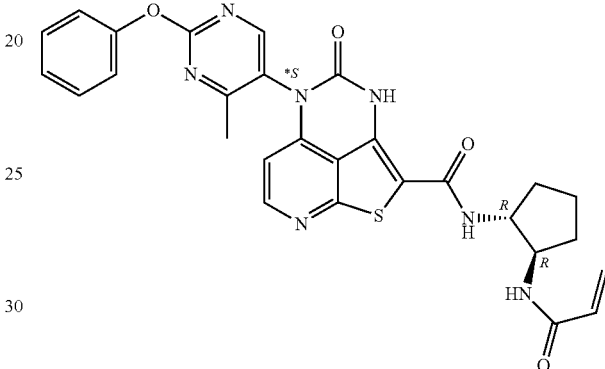

The title compound was prepared in a manner analogous to Example 1, using 5-(4-methyl-2-phenoxypyrimidin-5-yl)-4-oxo-4,5-dihydro-3H-1-thia-3,5,8-triazaacenaphthylene-2-carboxylic acid (Intermediate 13, including CHIRAL SEPARATION METHOD 1 to obtain the *S atropisomer and tert-butyl N-[(1R,2R)-2-aminocyclopentyl]carbamate, and substituting diisopropylethylamine for trimethylamine. MS (ESI): mass calcd. for $C_{28}H_{25}N_7O_4S$, 555.6; m/z found, 556.0 [M+H]$^+$. $^1$H NMR (600 MHz, CD$_3$OD): δ 8.54-8.53 (s, 1H), 8.38-8.36 (d, J=5.6 Hz, 1H), 7.48-7.43 (m, 2H), 7.31-7.22 (m, 3H), 6.31-6.27 (d, J=5.5 Hz, 1H), 6.25-6.20 (m, 2H), 5.66-5.62 (m, 1H), 4.32-4.19 (m, 2H), 2.35-2.31 (s, 3H), 2.22-2.10 (m, 2H), 1.88-1.77 (m, 2H), 1.72-1.56 (m, 2H).

Example 220: N-((1R,2S)-2-Acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide

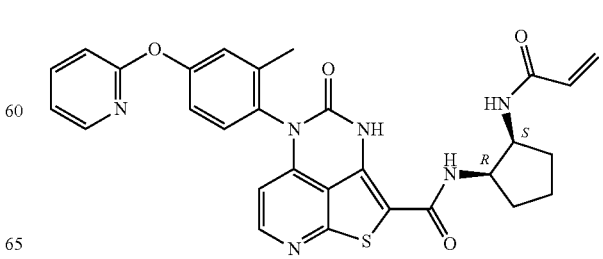

Step A. 5-(2-Methyl-4-(pyridin-2-yloxy)phenyl)-4-oxo-4,5-dihydro-3H-1-thia-3,5,8-triazaacenaphthylene-2-carboxylic acid The title compound was prepared in a manner analogous to Intermediate 1, Steps A, and C-F, using 2-fluoropyridine and 4-amino-3-methylphenol in place of 5-fluoro-2-nitrotoluene and phenol in Step A.

Step B. N-((1R,2S)-2-Acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide The title compound was prepared in a manner analogous to Example 1, Step A, using N-[(1S,2R)-2-aminocyclopentyl]prop-2-enamide (Intermediate 36) and 5-(2-methyl-4-(pyridin-2-yloxy)phenyl)-4-oxo-4,5-dihydro-3H-1-thia-3,5,8-triazaacenaphthylene-2-carboxylic acid (no HCl/MeOH deprotection). MS (ESI): mass calcd. for $C_{29}H_{26}N_6O_4S$, 554.6; m/z found, 555.2 [M+H]$^+$. $^1$H NMR (400 MHz, CD$_3$OD): δ 8.33 (d, J=5.5 Hz, 1H), 8.21-8.13 (m, 1H), 7.92-7.81 (m, 1H), 7.43-7.31 (m, 1H), 7.25-7.20 (m, 1H), 7.19-7.11 (m, 2H), 7.09-7.04 (m, 1H), 6.33-6.16 (m, 3H), 5.67-5.55 (m, 1H), 4.48-4.35 (m, 2H), 2.20-2.14 (m, 3H), 2.13-2.01 (m, 2H), 1.97-1.87 (m, 1H), 1.83-1.61 (m, 3H).

Example 221: N-((1R,2S)-2-Acrylamidocyclohexyl)-5-(*S)-(6-cyclobutoxy-4-methylpyridin-3-yl)-4-oxo-4,5-dihydro-3H-1-thia-3,5,8-triazaacenaphthylene-2-carboxamide

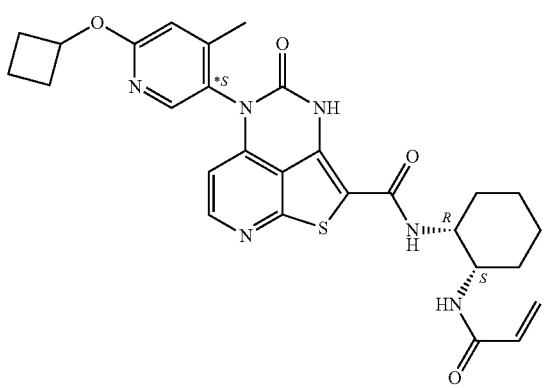

Chiral separation of (chiral SFC (Stationary phase: Chiralpak AS-H 5 μm 250*20 mm, Mobile phase: 70% CO$_2$, 30% MeOH) N-((1R,2S)-2-Acrylamidocyclohexyl)-5-(6-cyclobutoxy-4-methylpyridin-3-yl)-4-oxo-4,5-dihydro-3H-1-thia-3,5,8-triazaacenaphthylene-2-carboxamide (Example 183) provides the title compound. MS (ESI): mass calcd. for $C_{28}H_{30}N_6O_4S$, 546.7; m/z found, 547.1 [M+H]$^+$. $^1$H NMR (500 MHz, CD$_3$OD): δ 8.31 (d, J=5.5 Hz, 1H), 8.06 (s, 1H), 6.84 (s, 1H), 6.42 (dd, J=17.0, 10.3 Hz, 1H), 6.26 (dd, J=17.0, 1.7 Hz, 1H), 6.09 (d, J=5.5 Hz, 1H), 5.67 (dd, J=10.3, 1.7 Hz, 1H), 5.23-5.13 (m, 1H), 4.44 (s, 1H), 4.15 (d, J=10.3 Hz, 1H), 2.53-2.45 (m, 2H), 2.22-2.10 (m, 5H), 1.90-1.61 (m, 8H), 1.59-1.46 (m, 2H).

Example 222: N-((1R,2S)-2-Acrylamidocyclohexyl)-5-(6-isopropoxy-4-methylpyridin-3-yl)-4-oxo-4,5-dihydro-3H-1-thia-3,5,8-triazaacenaphthylene-2-carboxamide

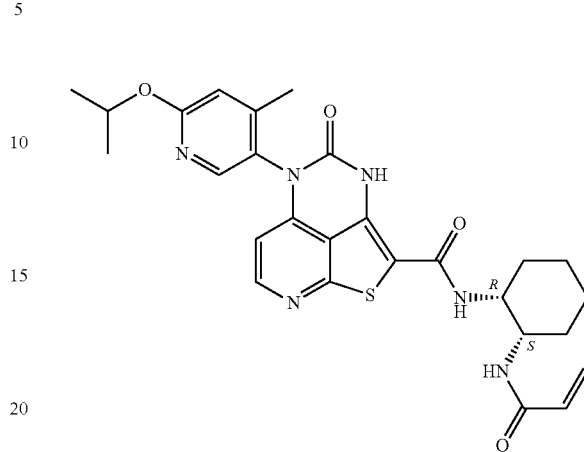

The title compound was prepared in a manner analogous to Example 166, Step A, using 5-(6-isopropoxy-4-methylpyridin-3-yl)-4-oxo-4,5-dihydro-3H-1-thia-3,5,8-triazaacenaphthylene-2-carboxylic acid (Intermediate 30) and N-[(1S,2R)-2-aminocyclohexyl]prop-2-enamide (Intermediate 40). MS (ESI): mass calcd. for $C_{27}H_{30}N_6O_4S$, 534.6; m/z found, 535.2 [M+H]$^+$. $^1$H NMR (500 MHz, CD$_3$OD): δ 8.33 (d, J=5.6 Hz, 1H), 8.05 (d, J=3.3 Hz, 1H), 6.81 (s, 1H), 6.42 (dd, J=17.0, 10.2 Hz, 1H), 6.32-6.23 (m, 1H), 6.12 (d, J=5.5 Hz, 1H), 5.70-5.64 (m, 1H), 5.34-5.26 (m, 1H), 4.44 (s, 1H), 4.22-4.13 (m, 1H), 2.14 (s, 3H), 1.86-1.61 (m, 6H), 1.59-1.46 (m, 2H), 1.36 (dd, J=6.1, 3.8 Hz, 6H).

Example 223: N-((1R,2S)-2-Acrylamidocyclohexyl)-5-(6-(cyclopentyloxy)-4-methylpyridin-3-yl)-4-oxo-4,5-dihydro-3H-1-thia-3,5,8-triazaacenaphthylene-2-carboxamide

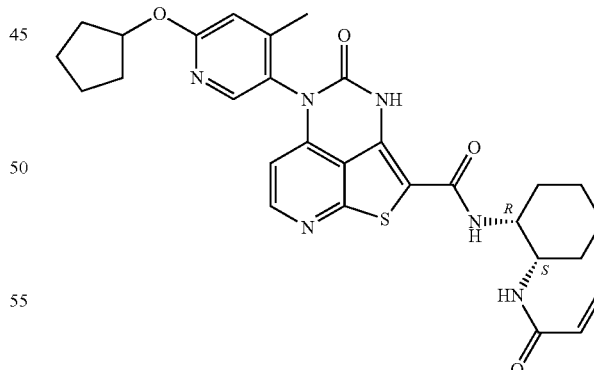

The title compound was prepared in a manner analogous to Example 166, Step A, using 5-(6-(cyclopentyloxy)-4-methylpyridin-3-yl)-4-oxo-4,5-dihydro-3H-1-thia-3,5,8-triazaacenaphthylene-2-carboxylic acid (Intermediate 25) and N-[(1S,2R)-2-aminocyclohexyl]prop-2-enamide (Intermediate 40). MS (ESI): mass calcd. for $C_{29}H_{32}N_6O_4S$, 560.7; m/z found, 561.1 [M+H]$^+$. $^1$H NMR (400 MHz, CD$_3$OD): δ 8.33 (d, J=5.4 Hz, 1H), 8.06 (d, J=2.1 Hz, 1H), 6.83 (s, 1H), 6.47-6.38 (m, 1H), 6.33-6.24 (m, 1H), 6.11 (d, J=5.3 Hz, 1H), 5.70-5.65 (m, 1H), 5.44-5.37 (m, 1H), 4.44 (s, 1H), 4.21-4.13 (m, 1H), 2.14 (s, 3H), 2.05-1.94 (m, 2H), 1.90-1.75 (m, 8H), 1.73-1.63 (m, 4H), 1.61-1.45 (m, 2H).

Example 224: N-((1R,2S)-2-Acrylamidocyclopentyl)-5-(2-methyl-4-(pyrimidin-2-yloxy)phenyl)-4-oxo-4,5-dihydro-3H-1-thia-3,5,8-triazaacenaphthylene-2-carboxamide

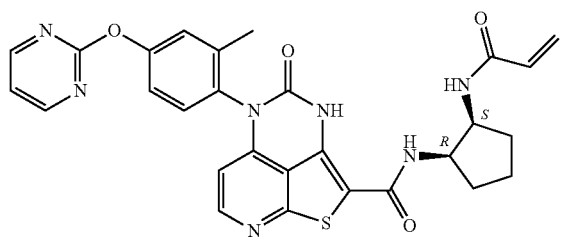

The title compound was prepared in a manner analogous to Example 1, Step A, using N-[(1S,2R)-2-aminocyclopentyl]prop-2-enamide (Intermediate 36) and 5-(2-methyl-4-(pyrimidin-2-yloxy)phenyl)-4-oxo-4,5-dihydro-3H-1-thia-3,5,8-triazaacenaphthylene-2-carb oxy c acid (Intermediate 15), no deprotection with HCl/MeOH. MS (ESI): mass calcd. for $C_{28}H_{25}N_7O_4S$, 555.6; m/z found, 556.1 [M+H]$^+$. $^1$H NMR (400 MHz, CD$_3$OD): δ 8.69-8.58 (m, 2H), 8.39-8.25 (m, 1H), 7.45-7.36 (m, 1H), 7.33-7.19 (m, 3H), 6.37-6.14 (m, 3H), 5.64-5.56 (m, 1H), 4.48-4.40 (m, 2H), 2.21-2.14 (m, 3H), 2.13-2.01 (m, 2H), 1.96-1.87 (m, 1H), 1.85-1.70 (m, 2H), 1.68-1.58 (m, 1H).

Example 225: N-((1R,2S)-2-Acrylamidocyclohexyl)-5-(6-isobutoxy-4-methylpyridin-3-yl)-4-oxo-4,5-dihydro-3H-1-thia-3,5,8-triazaacenaphthylene-2-carboxamide

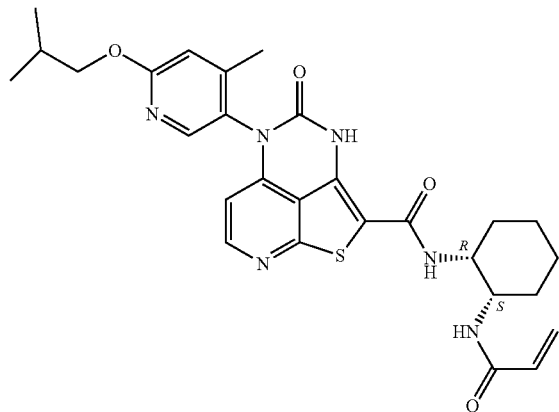

The title compound was prepared in a manner analogous to Example 166, Step A, using 5-(6-isobutoxy-4-methylpyridin-3-yl)-4-oxo-4,5-dihydro-3H-1-thia-3,5,8-triazaacenaphthylene-2-carboxylic acid (Intermediate 33) and N-[(1S,2R)-2-aminocyclohexyl]prop-2-enamide (Intermediate 40). MS (ESI): mass calcd. for $C_{28}H_{32}N_6O_4S$, 548.7; m/z found, 549.1 [M+H]$^+$. $^1$H NMR (400 MHz, CD$_3$OD): δ 8.33 (s, 1H), 8.06 (s, 1H), 6.90 (s, 1H), 6.48-6.37 (m, 1H), 6.32-6.24 (m, 1H), 6.12 (s, 1H), 5.67 (d, J=10.5 Hz, 1H), 4.44 (s, 1H), 4.21-4.13 (m, 1H), 4.13-4.08 (m, 2H), 2.16 (s, 3H), 2.13-2.04 (m, 1H), 1.88-1.62 (m, 6H), 1.61-1.46 (m, 2H), 1.04 (d, J=6.6 Hz, 6H).

Example 226: N-((1S,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide

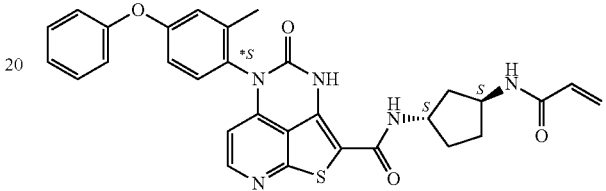

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3S)-3-aminocyclopentyl]carbamate. MS (ESI): mass calcd. for $C_{30}H_{27}N_5O_4S$, 553.6; m/z found, 554.5 [M+H]$^+$.

Example 227: N-((1R,2R)-2-Acrylamidocyclohexyl)-4-oxo-5-(2-phenylpyridin-4-yl)-4,5-dihydro-3H-1-thia-3,5,8-triazaacenaphthylene-2-carboxamide

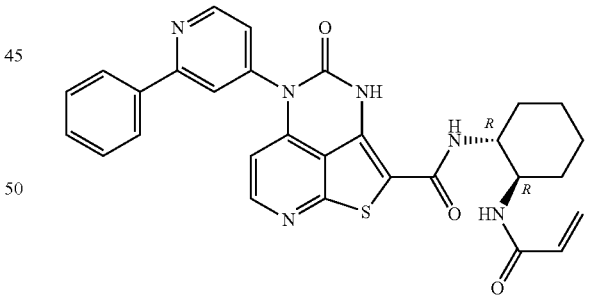

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1R,2R)-2-aminocyclohexyl]carbamate. MS (ESI): mass calcd. for $C_{29}H_{26}N_6O_3S$, 538.6; m/z found, 539.1 [M+H]$^+$. $^1$H NMR (400 MHz, CD$_3$OD): δ 8.90-8.79 (m, 1H), 8.32-8.28 (m, 1H), 8.05-8.00 (m, 3H), 7.51-7.43 (m, 4H), 6.31-6.25 (m, 1H), 6.21-6.15 (m, 2H), 5.61-5.54 (m, 1H), 3.91-3.78 (m, 2H), 2.07-1.93 (m, 2H), 1.84-1.71 (m, 2H), 1.54-1.32 (m, 4H).

Example 228: N-((1R,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide

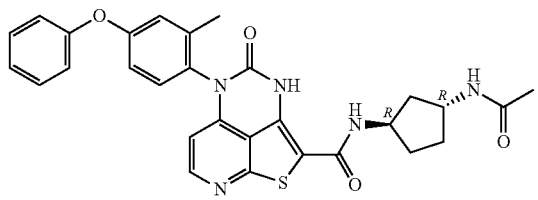

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1R,3R)-3-aminocyclopentyl]carbamate, in Step A, and acetic anhydride in Step B. MS (ESI): mass calcd. for $C_{29}H_{27}N_5O_4S$, 541.6; m/z found, 542.2 $[M+H]^+$. $^1H$ NMR (400 MHz, $CD_3OD$): δ 8.34-8.30 (m, 1H), 7.43-7.36 (m, 2H), 7.31-7.27 (m, 1H), 7.19-7.14 (m, 1H), 7.11-7.06 (m, 2H), 7.06-7.03 (m, 1H), 6.98-6.94 (m, 1H), 6.08-6.05 (m, 1H), 4.52-4.44 (m, 1H), 4.31-4.24 (m, 1H), 2.21-2.13 (m, 2H), 2.12 (s, 3H), 1.99-1.93 (m, 1H), 1.92 (s, 3H), 1.91-1.85 (m, 1H), 1.69-1.58 (m, 1H), 1.56-1.45 (m, 1H).

Example 229: 5-(2-Methyl-4-phenoxyphenyl)-N-((1R,3R)-3-(2-(methylamino)acetamido)cyclopentyl)-4-oxo-4,5-dihydro-3H-1-thia-3,5,8-triazaacenaphthylene-2-carboxamide

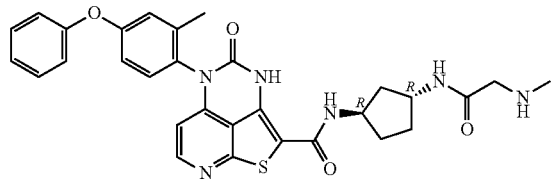

The title compound was prepared in a manner analogous to Example 1, Step A, using N-((1R,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 217, product from Step A) and 2-[tert-butoxycarbonyl (methyl)amino]acetic acid. MS (ESI): mass calcd. for $C_{30}H_{30}N_6O_4S$, 570.7; m/z found, 571.2 $[M+H]^+$. $^1H$ NMR (400 MHz, $CD_3OD$): δ 8.31-8.24 (m, 1H), 7.43-7.35 (m, 2H), 7.31-7.23 (m, 1H), 7.18-7.13 (m, 1H), 7.11-7.06 (m, 2H), 7.06-7.03 (m, 1H), 6.98-6.94 (m, 1H), 6.05-5.99 (m, 1H), 4.52-4.44 (m, 1H), 4.38-4.30 (m, 1H), 3.26-3.23 (m, 2H), 2.40 (s, 3H), 2.23-2.14 (m, 2H), 2.11 (s, 3H), 2.04-1.89 (m, 2H), 1.72-1.61 (m, 1H), 1.60-1.48 (m, 1H).

Example 230: N-((1S,3R)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide

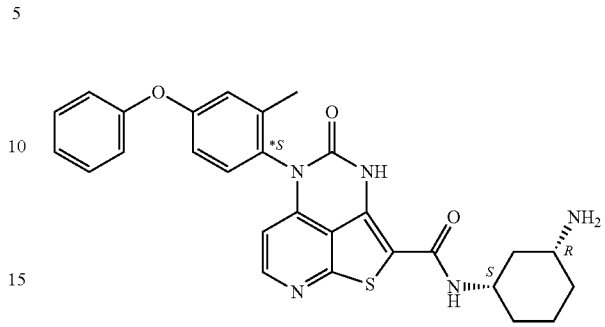

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1R,3S)-3-aminocyclohexyl]carbamate. MS (ESI): mass calcd. for $C_{28}H_{27}N_5O_3S$, 513.6; m/z found, 514.2 $[M+H]^+$. $^1H$ NMR (400 MHz, $CD_3OD$): δ 8.45 (s, 1H), 8.36-8.30 (m, 1H), 7.45-7.37 (m, 2H), 7.31-7.25 (m, 1H), 7.20-7.14 (m, 1H), 7.12-7.03 (m, 3H), 7.00-6.94 (m, 1H), 6.10-6.06 (m, 1H), 4.07-3.91 (m, 1H), 3.26-3.14 (m, 1H), 2.34-2.23 (m, 1H), 2.12 (s, 3H), 2.07-1.88 (m, 3H), 1.57-1.27 (m, 4H).

Example 231: N-((1S,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide

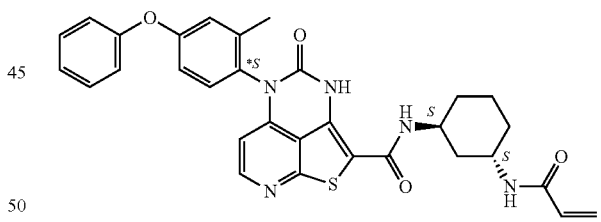

The title compound was prepared in a manner analogous to Example 1, Steps A-B, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3S)-3-aminocyclohexyl]carbamate. MS (ESI): mass calcd. for $C_{31}H_{29}N_5O_4S$, 567.7; m/z found, 568.2 $[M+H]^+$. $^1H$ NMR (400 MHz, $CD_3OD$): δ 8.32 (d, J=5.6 Hz, 1H), 7.45-7.35 (m, 2H), 7.31-7.24 (m, 1H), 7.21-7.14 (m, 1H), 7.11-7.02 (m, 3H), 7.01-6.92 (m, 1H), 6.39-6.18 (m, 2H), 6.06 (d, J=5.6 Hz, 1H), 5.69-5.59 (m, 1H), 4.24-4.13 (m, 2H), 2.12 (s, 3H), 1.95-1.77 (m, 3H), 1.76-1.62 (m, 4H), 1.59-1.51 (m, 1H).

Example 232: N-((1R,3R)-3-Acrylamidocyclohexyl)-4-oxo-5-(2-phenylpyridin-4-yl)-4,5-dihydro-3H-1-thia-3,5,8-triazaacenaphthylene-2-carboxamide

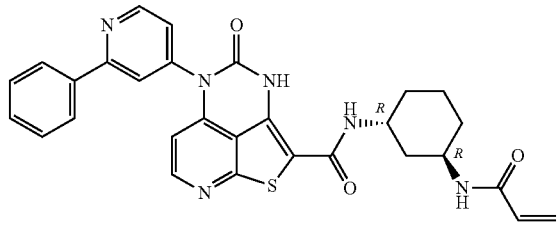

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1R,3R)-3-aminocyclohexyl]carbamate. MS (ESI): mass calcd. for $C_{29}H_{26}N_6O_3S$, 538.6; m/z found, 539.4 [M+H]$^+$. $^1$H NMR (400 MHz, DMSO-d$_6$): δ 10.24 (s, 1H), 8.89 (d, J=5.2 Hz, 1H), 8.32 (d, J=5.5 Hz, 1H), 8.18-7.93 (m, 5H), 7.54-7.44 (m, 4H), 6.42-6.31 (m, 1H), 6.21 (d, J=5.5 Hz, 1H), 6.12-6.02 (m, 1H), 5.59-5.51 (m, 1H), 4.25-4.09 (m, 2H), 1.82-1.41 (m, 8H).

Example 233: N-((1R,2R)-2-Aminocyclopentyl)-5-(4-methyl-6-phenoxypyridin-3-yl)-4-oxo-4,5-dihydro-3H-1-thia-3,5,8-triazaacenaphthylene-2-carboxamide

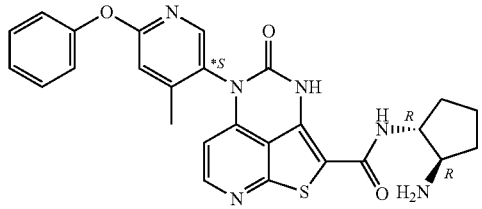

The title compound was prepared in a manner analogous to Example 166, Steps A-B, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and (1R,2R)-trans-N-Boc-1,2-cyclopentanediamine, in Step A. MS (ESI): mass calcd. for $C_{26}H_{24}N_6O_3S$, 500.6; m/z found, 501.1 [M+H]$^+$. $^1$H NMR (400 MHz, CDCl$_3$): δ 8.31 (dt, J=5.4, 1.3 Hz, 1H), 8.06 (s, 1H), 7.49-7.38 (m, 2H), 7.29-7.16 (m, 3H), 6.95 (s, 1H), 6.11 (d, J=10.7 Hz, 1H), 6.01 (dd, J=5.3, 1.4 Hz, 1H), 4.00 (p, J=7.5 Hz, 1H), 3.46 (s, 4H), 3.18 (q, J=7.7 Hz, 1H), 2.21 (s, 3H), 2.05 (dtd, J=12.7, 7.7, 4.9 Hz, 1H), 1.76 (dddd, J=20.6, 13.4, 9.5, 5.2 Hz, 2H), 1.60-1.38 (m, 2H).

Example 234: N-((1R,2S)-2-Acrylamidocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide

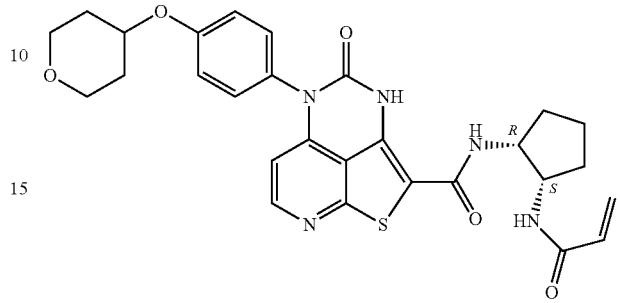

The title compound was prepared in a manner analogous to Example 1, Step A, using 5-(2-methyl-4-((tetrahydro-2H-pyran-4-yl)oxy)phenyl)-4-oxo-4,5-dihydro-3H-1-thia-3,5,8-triazaacenaphthylene-2-carboxylic acid (Intermediate 12) and N-[(1S,2R)-2-aminocyclopentyl]prop-2-enamide (Intermediate 36) (no HCl/MeOH deprotection). MS (ESI): mass calcd. for $C_{28}H_{29}N_5O_5S$, 547.6; m/z found, 548.5 [M+H]$^+$.

Example 235: N-((1R,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide

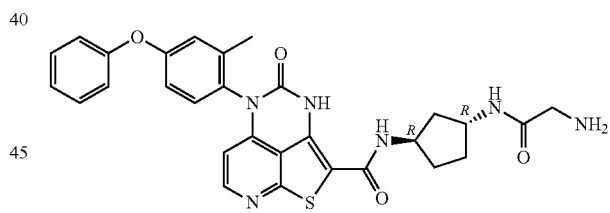

The title compound was prepared in a manner analogous to Example 1, Step A, using N-((1R,3R)-3-aminocyclopentyl)-5-(2-methyl-4-phenoxyphenyl)-4-oxo-4,5-dihydro-3H-1-thia-3,5,8-triazaacenaphthylene-2-carboxamide (Example 217, product from Step A) and 2-(tert-butoxy carbonylamino)acetic acid. MS (ESI): mass calcd. for $C_{29}H_{28}N_6O_4S$, 556.6; m/z found, 557.2 [M+H]$^+$. $^1$H NMR (400 MHz, CD$_3$OD): δ 8.31-8.24 (m, 1H), 7.42-7.36 (m, 2H), 7.29-7.25 (m, 1H), 7.18-7.13 (m, 1H), 7.11-7.06 (m, 2H), 7.06-7.03 (m, 1H), 6.98-6.95 (m, 1H), 6.06-5.99 (m, 1H), 4.53-4.44 (m, 1H), 4.38-4.30 (m, 1H), 3.28-3.21 (m, 2H), 2.23-2.15 (m, 2H), 2.11 (s, 3H), 2.03-1.92 (m, 2H), 1.73-1.61 (m, 1H), 1.60-1.48 (m, 1H).

Example 236: N-((1R,3R)-3-Aminocyclopentyl)-5-(2-methyl-4-phenoxyphenyl)-4-oxo-4,5-dihydro-3H-1-thia-3,5,8-triazaacenaphthylene-2-carboxamide

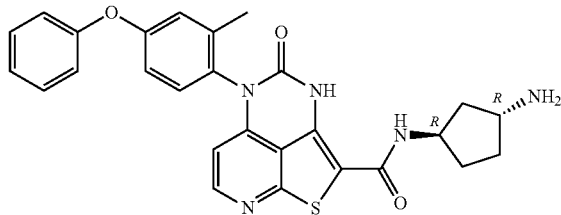

The title compound was prepared in a manner analogous to Example 166, Step A-B, using 4-oxo-5-(5-phenoxypyridin-2-yl)-4,5-dihydro-3H-1-thia-3,5,8-triazaacenaphthylene-2-carboxylic acid (Intermediate 26) and tert-butyl N-[(1R,2R)-2-aminocyclohexyl]carbamate. MS (ESI): mass calcd. for $C_{27}H_{25}N_5O_3S$, 499.6; m/z found, 500.4 [M+H]$^+$. $^1$H NMR (400 MHz, CD$_3$OD): δ 8.15-8.09 (m, 1H), 7.41-7.34 (m, 2H), 7.22-7.18 (m, 1H), 7.16-7.00 (m, 1H), 7.11-7.05 (m, 2H), 7.04-7.02 (m, 1H), 6.98-6.94 (m, 1H), 5.89-5.83 (m, 1H), 4.56-4.47 (m, 1H), 3.80-3.70 (m, 1H), 2.33-2.20 (m, 2H), 2.20-2.12 (m, 1H), 2.10 (s, 3H), 2.02-1.94 (m, 1H), 1.86-1.75 (m, 1H), 1.64-1.53 (m, 1H).

Example 237: N-((1R,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide

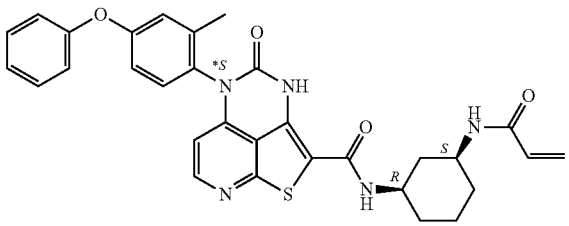

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and using tert-butyl N-[(1S,3R)-3-aminocyclohexyl]carbamate. MS (ESI): mass calcd. for $C_{31}H_{29}N_5O_4S$, 567.7; m/z found, 568.2 [M+H]$^+$. $^1$H NMR (400 MHz, CD$_3$OD): δ 8.34-8.28 (m, 1H), 7.44-7.36 (m, 2H), 7.33-7.26 (m, 1H), 7.20-7.13 (m, 1H), 7.11-7.04 (m, 3H), 6.99-6.93 (m, 1H), 6.23-6.17 (m, 2H), 6.08-6.04 (m, 1H), 5.66-5.58 (m, 1H), 4.04-3.94 (m, 1H), 3.91-3.77 (m, 1H), 2.23-2.15 (m, 1H), 2.12 (s, 3H), 1.99-1.83 (m, 3H), 1.51-1.18 (m, 4H).

Example 238: N-((1R,2S)-2-Acrylamidocyclohexyl)-5-(*R)-(6-isopropoxy-2-methylpyridin-3-yl)-4-oxo-4,5-dihydro-3H-1-thia-3,5,8-triazaacenaphthylene-2-carboxamide

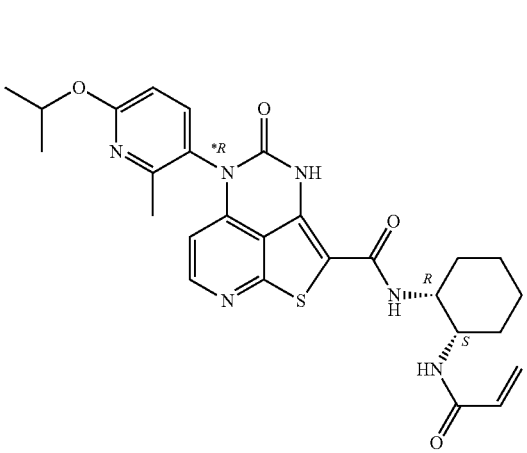

Chiral SFC purification (Stationary phase: Chiralpak AS-H 5 μm 250*20 mm, Mobile phase: 70% CO$_2$, 30% MeOH) of N-((1R,2S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide (Example 211) afforded the title compound. MS (ESI): mass calcd. for $C_{27}H_{30}N_6O_4S$, 534.6; m/z found, 535.2 [M+H]$^+$. $^1$H NMR (500 MHz, CD$_3$OD): δ 8.32 (d, J=5.5 Hz, 1H), 7.58 (d, J=8.6 Hz, 1H), 6.73 (d, J=8.6 Hz, 1H), 6.42 (dd, J=17.0, 10.3 Hz, 1H), 6.27 (dd, J=17.0, 1.5 Hz, 1H), 6.08 (d, J=5.4 Hz, 1H), 5.67 (dd, J=10.3, 1.6 Hz, 1H), 5.39-5.30 (m, 1H), 4.42 (s, 1H), 4.17 (d, J=10.2 Hz, 1H), 2.26 (s, 3H), 1.89-1.60 (m, 6H), 1.59-1.45 (m, 2H), 1.37 (dd, J=6.1, 2.7 Hz, 6H).

Example 239: N-((1R,2R)-2-Acrylamidocyclohexyl)-4-oxo-5-(6-phenoxypyridin-3-yl)-4,5-dihydro-3H-1-thia-3,5,8-triazaacenaphthylene-2-carboxamide

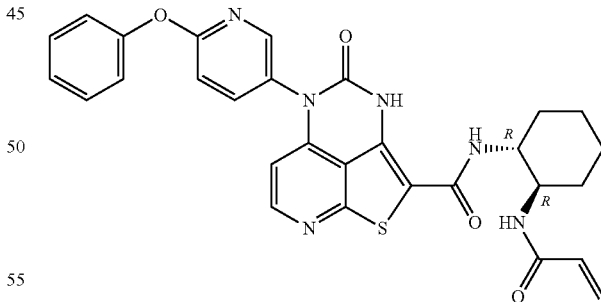

The title compound was prepared in a manner analogous to Example 166, using 4-oxo-5-(6-phenoxypyridin-3-yl)-4,5-dihydro-3H-1-thia-3,5,8-triazaacenaphthylene-2-carboxylic acid (Intermediate 28) and tert-butyl N-[(1R,2R)-2-aminocyclohexyl]carbamate in Step A. MS (ESI): mass calcd. for $C_{29}H_{26}N_6O_4S$, 554.6; m/z found, 555.2 [M+H]$^+$. $^1$H NMR (400 MHz, CDCl$_3$): δ 9.73 (s, 1H), 8.30 (d, J=4.8 Hz, 1H), 8.18 (d, J=2.7 Hz, 1H), 7.75 (td, J=8.6, 8.1, 3.1 Hz, 1H), 7.42 (t, J=7.8 Hz, 2H), 7.20 (dd, J=19.5, 7.6 Hz, 3H), 7.10 (d, J=8.7 Hz, 1H), 7.04-6.92 (m, 2H), 6.24 (d, J=17.1

Hz, 1H), 6.14-5.96 (m, 2H), 5.55 (dd, J=10.0, 1.6 Hz, 1H), 4.11 (q, J=7.1 Hz, 1H), 3.87 (dt, J=22.2, 10.5 Hz, 2H), 2.52 (s, 1H), 2.20 (d, J=12.0 Hz, 1H), 2.04 (s, 3H), 1.30 (dt, J=36.2, 6.5 Hz, 2H).

Example 240: N-((1R,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide

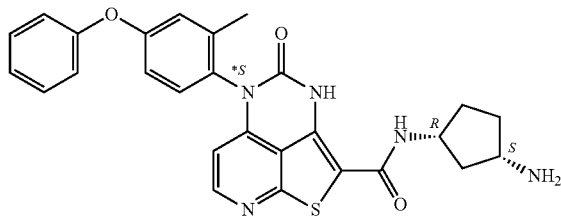

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3R)-3-aminocyclopentyl]carbamate. MS (ESI): mass calcd. for $C_{27}H_{25}N_5O_3S$, 499.6; m/z found, 500.4 [M+H]$^+$. $^1$H NMR (400 MHz, CD$_3$OD): δ 8.52 (s, 1H), 8.32 (d, J=5.6 Hz, 1H), 7.49-7.36 (m, 2H), 7.33-7.25 (m, 1H), 7.23-7.14 (m, 1H), 7.14-7.04 (m, 3H), 7.02-6.93 (m, 1H), 6.07 (d, J=5.5 Hz, 1H), 4.37-4.20 (m, 1H), 3.74-3.60 (m, 1H), 2.64-2.49 (m, 1H), 2.23-1.98 (m, 6H), 1.97-1.70 (m, 2H).

Example 241: N-((1S,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide

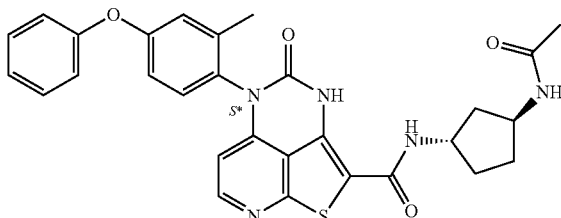

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3S)-3-aminocyclopentyl]carbamate in Step A, and acetic anhydride in Step B. MS (ESI): mass calcd. for $C_{29}H_{27}N_5O_4S$, 541.6; m/z found, 542.5 [M+H]$^+$. $^1$H NMR (400 MHz, CD$_3$OD): δ 8.32 (d, J=5.1 Hz, 1H), 7.45-7.35 (m, 2H), 7.34-7.24 (m, 1H), 7.23-7.14 (m, 1H), 7.13-7.02 (m, 3H), 7.01-6.91 (m, 1H), 6.06 (d, J=5.0 Hz, 1H), 4.55-4.40 (m, 1H), 4.35-4.21 (m, 1H), 2.24-2.06 (m, 5H), 2.02-1.85 (m, 5H), 1.73-1.57 (m, 1H), 1.57-1.44 (m, 1H).

Example 242: N-((1R,2S)-2-Acrylamidocyclohexyl)-5-(*R)-(6-cyclobutoxy-2-methylpyridin-3-yl)-4-oxo-4,5-dihydro-3H-1-thia-3,5,8-triazaacenaphthylene-2-carboxamide

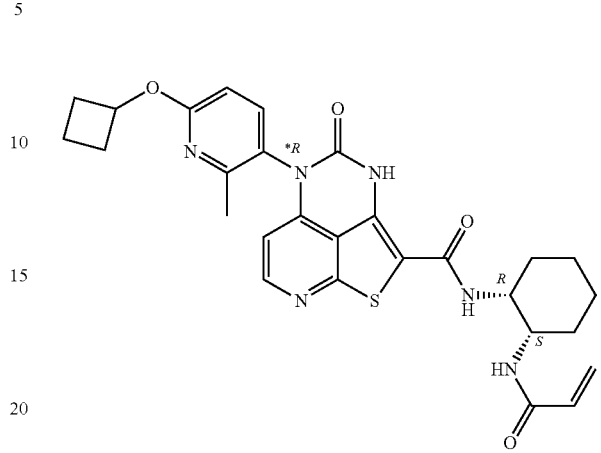

Chiral SFC (Stationary phase: Chiralpak AS-H 5 μm 250*20 mm, Mobile phase: 70% CO$_2$, 30% MeOH) of N-((1R,2S)-2-acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide (Example 187) afforded the title compound. MS (ESI): mass calcd. for $C_{28}H_{30}N_6O_4S$, 546.7; m/z found, 547.2 [M+H]$^+$. $^1$H NMR (500 MHz, CD$_3$OD): δ 8.31 (d, J=5.2 Hz, 1H), 7.60 (d, J=8.6 Hz, 1H), 6.76 (d, J=8.6 Hz, 1H), 6.42 (dd, J=17.0, 10.2 Hz, 1H), 6.27 (dd, J=17.0, 1.5 Hz, 1H), 6.07 (d, J=5.0 Hz, 1H), 5.67 (dd, J=10.3, 1.6 Hz, 1H), 5.26-5.14 (m, 1H), 4.42 (s, 1H), 4.17 (d, J=9.3 Hz, 1H), 2.54-2.45 (m, 2H), 2.25 (s, 3H), 2.21-2.10 (m, 2H), 1.91-1.61 (m, 8H), 1.59-1.45 (m, 2H).

Example 243: N-((1S,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide

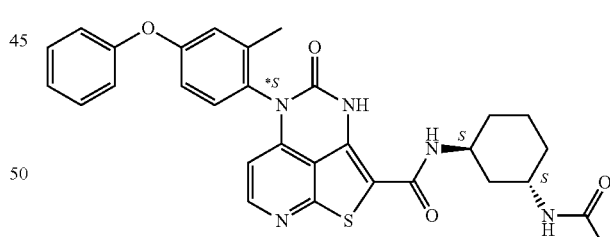

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3S)-3-aminocyclohexyl]carbamate in Step A, and acetyl chloride in Step B. MS (ESI): mass calcd. for $C_{30}H_{29}N_5O_4S$, 555.6; m/z found, 556.2 [M+H]$^+$. $^1$H NMR (400 MHz, CD$_3$OD): δ 8.32 (d, J=5.5 Hz, 1H), 7.44-7.35 (m, 2H), 7.32-7.26 (m, 1H), 7.20-7.14 (m, 1H), 7.11-7.03 (m, 3H), 7.00-6.93 (m, 1H), 6.07 (d, J=5.6 Hz, 1H), 4.20-4.07 (m, 2H), 2.12 (s, 3H), 1.97 (s, 3H), 1.92-1.81 (m, 2H), 1.77-1.66 (m, 3H), 1.64-1.48 (m, 3H).

Example 244: N-((1R,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide

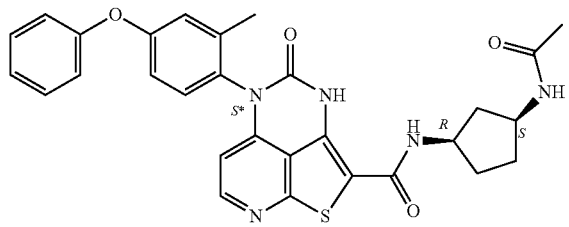

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3R)-3-aminocyclopentyl]carbamate in Step A, and acetic anhydride in Step B. MS (ESI): mass calcd. for $C_{29}H_{27}N_5O_4S$, 541.6; m/z found, 542.5 [M+H]$^+$. $^1$H NMR (400 MHz, CD$_3$OD): δ 8.30 (d, J=5.6 Hz, 1H), 7.48-7.36 (m, 2H), 7.33-7.25 (m, 1H), 7.22-7.14 (m, 1H), 7.13-7.03 (m, 3H), 7.00-6.92 (m, 1H), 6.05 (d, J=5.6 Hz, 1H), 4.41-4.24 (m, 1H), 4.20-4.04 (m, 1H), 2.54-2.35 (m, 1H), 2.12 (s, 3H), 2.08-1.95 (m, 2H), 1.93 (s, 3H), 1.84-1.65 (m, 2H), 1.61-1.49 (m, 1H).

Example 245: N-((1S,3S)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide

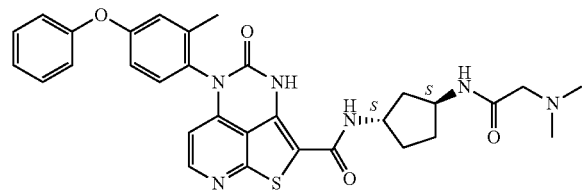

Step A. N-((1S,3S)-3-Aminocyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(1S,3S)-3-amino cyclopentyl]carbamate.

Step B. N-((1S,3S)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using N-((1S,3S)-3-amino cyclopentyl)-5-(2-methyl-4-phenoxyphenyl)-4-oxo-4,5-dihydro-3H-1-thia-3,5,8-triazaacenaphthylene-2-carboxamide and 2-(dimethylamino)acetic acid. MS (ESI): mass calcd. for $C_{31}H_{32}N_6O_4S$, 584.7; m/z found, 585.2 [M+H]$^+$. $^1$H NMR (400 MHz, CD$_3$OD): δ 8.41 (s, 1H), 8.32 (d, J=5.5 Hz, 1H), 7.46-7.35 (m, 2H), 7.34-7.23 (m, 1H), 7.20-7.13 (m, 1H), 7.11-7.02 (m, 3H), 7.00-6.93 (m, 1H), 6.07 (d, J=5.6 Hz, 1H), 4.58-4.43 (m, 1H), 4.43-4.30 (m, 1H), 3.48 (s, 2H), 2.64 (s, 6H), 2.26-2.14 (m, 2H), 2.12 (s, 3H), 2.05-1.89 (m, 2H), 1.75-1.46 (m, 2H).

Example 246: 5-(2-Methyl-4-phenoxyphenyl)-N-((1S,3S)-3-(2-(methylamino)acetamido)cyclopentyl)-4-oxo-4,5-dihydro-3H-1-thia-3,5,8-triazaacenaphthylene-2-carboxamide

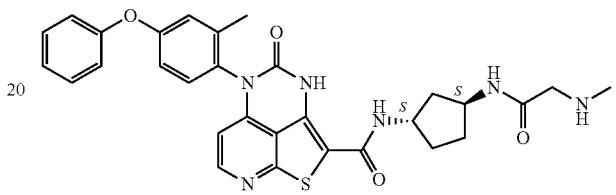

The title compound was prepared in a manner analogous to Example 1, Step A, using N-((1S,3S)-3-aminocyclopentyl)-5-(2-methyl-4-phenoxyphenyl)-4-oxo-4,5-dihydro-3H-1-thia-3,5,8-triazaacenaphthylene-2-carboxamide (Example 245, product from Step A) and 2-[tert-butoxycarbonyl(methyl)amino]acetic acid. MS (ESI): mass calcd. for $C_{30}H_{30}N_6O_4S$, 570.7; m/z found, 571.5 [M+H]$^+$. $^1$H NMR (400 MHz, CD$_3$OD): δ 8.43 (s, 1H), 8.33 (d, J=5.5 Hz, 1H), 7.45-7.35 (m, 2H), 7.34-7.25 (m, 1H), 7.23-7.12 (m, 1H), 7.10-7.01 (m, 3H), 7.00-6.92 (m, 1H), 6.07 (d, J=5.6 Hz, 1H), 4.57-4.43 (m, 1H), 4.40-4.26 (m, 1H), 3.70 (s, 2H), 2.69 (s, 3H), 2.27-2.13 (m, 2H), 2.12 (s, 3H), 2.04-1.90 (m, 2H), 1.71-1.47 (m, 2H).

Example 247: N-((1S,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide

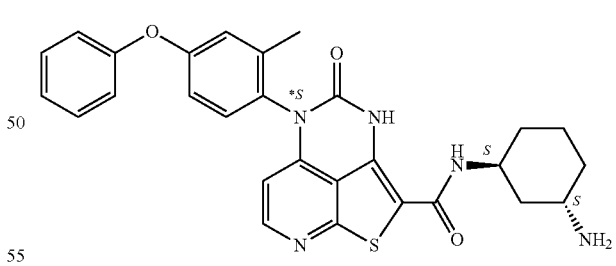

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3S)-3-aminocyclohexyl]carbamate in place of tert-butyl ((1S 4S)-4-aminocyclohexyl)carbamate in step G (400 mg). MS (ESI): mass calcd. for $C_{28}H_{27}N_5O_3S$, 513.6; m/z found, 514.2 [M+H]$^+$. $^1$H NMR (400 MHz, CD$_3$OD): δ 8.03 (d, J=5.7 Hz, 1H), 7.42-7.33 (m, 2H), 7.19-7.11 (m, 2H), 7.10-7.06 (m, 2H), 7.05-7.00 (m, 1H), 6.97-6.90 (m, 1H), 5.75 (d, J=5.2 Hz, 1H), 4.36-4.27 (m, 1H), 3.23-3.13 (m, 1H), 2.11 (s, 3H), 2.02-1.94 (m, 1H), 1.85-1.63 (m, 5H), 1.59-1.52 (m, 1H), 1.32-1.23 (m, 1H).

Example 248: 5-(3-Chloro-4-phenoxyphenyl)-N-((1S,3R)-3-((E)-4-(dimethylamino)but-2-enamido)cyclopentyl)-4-oxo-4,5-dihydro-3H-1-thia-3,5,8-triazaacenaphthylene-2-carboxamide

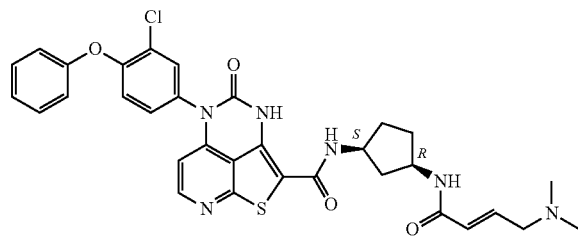

Step A. N-((1S,3R)-3-Aminocyclopentyl)-5-(3-chloro-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(3-chloro-4-phenoxyphenyl)-4-oxo-4,5-dihydro-3H-1-thia-3,5,8-triazaacenaphthylene-2-carboxylic acid (Example 137, product from Step A) and tert-butyl N-[(1R,3S)-3-aminocyclopentyl]carbamate.

Step B. 5-(3-Chloro-4-phenoxyphenyl)-N-((1S,3R)-3-((E)-4-(dimethylamino)but-2-enamido)cyclopentyl)-4-oxo-4,5-dihydro-3H-1-thia-3,5,8-triazaacenaphthylene-2-carboxamide The title compound was prepared in a manner analogous to Example 1, Step A, using N-((1S,3R)-3-amino cyclopentyl)-5-(3-chloro-4-phenoxyphenyl)-4-oxo-4,5-dihydro-3H-1-thia-3,5,8-triazaacenaphthylene-2-carboxamide and (E)-4-(dimethylamino)but-2-enoic acid, no HCl/MeOH deprotection. MS (ESI): mass calcd. for $C_{32}H_{31}ClN_6O_4S$, 631.1; m/z found, 631.2 [M+H]$^+$. $^1$H NMR (400 MHz, CD$_3$OD): δ 8.18-8.12 (m, 1H), 7.58-7.53 (m, 1H), 7.42-7.36 (m, 2H), 7.31-7.25 (m, 1H), 7.18-7.12 (m, 2H), 7.08-7.04 (m, 2H), 6.78-6.68 (m, 1H), 6.16-6.09 (m, 1H), 6.08-6.01 (m, 1H), 4.42-4.33 (m, 1H), 4.28-4.20 (m, 1H), 3.11-3.06 (m, 2H), 2.46-2.37 (m, 1H), 2.21 (s, 6H), 2.11-1.96 (m, 2H), 1.92-1.84 (m, 1H), 1.83-1.74 (m, 1H), 1.73-1.64 (m, 1H).

Example 249: 5-([1,1'-Biphenyl]-3-yl)-N-((1R,2S)-2-aminocyclopentyl)-4-oxo-4,5-dihydro-3H-1-thia-3,5,8-triazaacenaphthylene-2-carboxamide

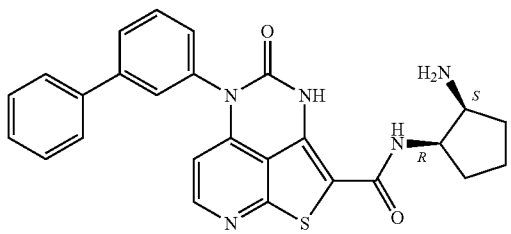

The title compound was prepared in a manner analogous to Example 1, Step A, using 5-([1,1'-biphenyl]-3-yl)-4-oxo-4,5-dihydro-3H-1-thia-3,5,8-triazaacenaphthylene-2-carboxylic acid (Intermediate 19) and tert-butyl N-[(1S,2R)-2-aminocyclopentyl]carbamate. MS (ESI): mass calcd. for $C_{26}H_{23}N_5O_2S$, 469.6; m/z found, 470.4 [M+H]$^+$. $^1$H NMR (400 MHz, CD$_3$OD): δ 8.16-8.11 (mz, 1H), 7.79-7.74 (m, 1H), 7.68-7.63 (m, 3H), 7.62-7.57 (m, 1H), 7.46-7.41 (m, 2H), 7.38-7.29 (m, 2H), 6.05-6.01 (m, 1H), 4.52-4.44 (m, 1H), 3.62-3.56 (m, 1H), 2.18-2.08 (m, 2H), 1.97-1.81 (m, 2H), 1.77-1.61 (m, 2H).

Example 250: 5-(*S)-(2-Methyl-4-phenoxyphenyl)-N-((1R,3S)-3-(2-(methylamino)acetamido)cyclohexyl)-4-oxo-4,5-dihydro-3H-1-thia-3,5,8-triazaacenaphthylene-2-carboxamide

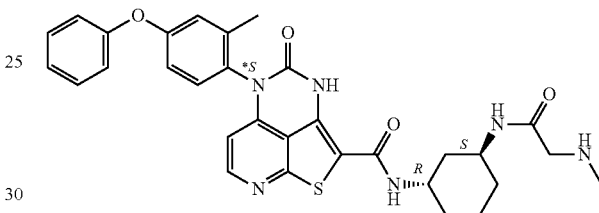

Step A. N-((1R,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3R)-3-aminocyclohexyl]carbamate.

Step B. 5-(*S)-(2-Methyl-4-phenoxyphenyl)-N-((1R,3S)-3-(2-(methylamino)acetamido)cyclohexyl)-4-oxo-4,5-dihydro-3H-1-thia-3,5,8-triazaacenaphthylene-2-carboxamide The title compound was prepared in a manner analogous to Example 1, Step A, using N-((1R,3S)-3-aminocyclohexyl)-5-(*S)-(2-methyl-4-phenoxyphenyl)-4-oxo-4,5-dihydro-3H-1-thia-3,5,8-triazaacenaphthylene-2-carboxamide and 2-[tert-butoxycarbonyl(methyl)amino]acetic acid. MS (ESI): mass calcd. for $C_{31}H_{32}N_6O_4S$, 584.7; m/z found, 585.2 [M+H]$^+$. $^1$H NMR (400 MHz, CD$_3$OD): δ 8.45 (s, 1H), 8.35-8.29 (m, 1H), 7.44-7.35 (m, 2H), 7.31-7.24 (m, 1H), 7.20-7.13 (m, 1H), 7.11-7.04 (m, 3H), 6.99-6.93 (m, 1H), 6.10-6.04 (m, 1H), 4.04-3.91 (m, 1H), 3.88-3.73 (m, 1H), 3.66 (s, 2H), 2.67 (s, 6H), 2.23-2.15 (m, 1H), 2.12 (s, 3H), 1.99-1.83 (m, 3H), 1.53-1.18 (m, 4H).

Example 251: N-((1R,3S)-3-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide

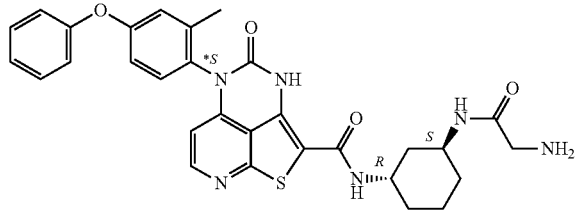

The title compound was prepared in a manner analogous to Example 1, Step A, using N-((1R,3S)-3-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 250, product from Step A) and 2-(tert-butoxycarbonylamino)acetic acid. MS (ESI): mass calcd. for $C_{30}H_{30}N_6O_4S$, 570.7; m/z found, 571.2 $[M+H]^+$. $^1$H NMR (400 MHz, $CD_3OD$): δ 8.38 (s, 1H), 8.34-8.30 (m, 1H), 7.43-7.36 (m, 2H), 7.31-7.25 (m, 1H), 7.20-7.13 (m, 1H), 7.10-7.03 (m, 3H), 6.99-6.93 (m, 1H), 6.10-6.05 (m, 1H), 4.05-3.90 (m, 1H), 3.88-3.75 (m, 1H), 3.60 (s, 2H), 2.22-2.15 (m, 1H), 2.12 (s, 3H), 1.98-1.83 (m, 3H), 1.52-1.13 (m, 4H).

Example 252: N-((1R,3S)-3-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide

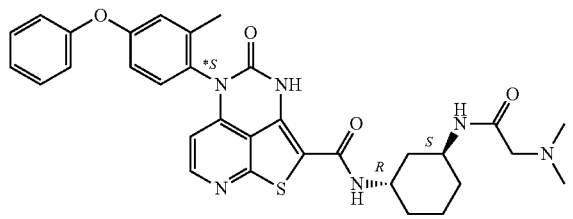

The title compound was prepared in a manner analogous to Example 1, Step A, using N-((1R,3S)-3-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 250, product from Step A) and 2-(dimethylamino)acetic acid. MS (ESI): mass calcd. for $C_{32}H_{34}N_6O_4S$, 598.7; m/z found, 599.2 $[M+H]^+$. $^1$H NMR (400 MHz, $CD_3OD$): δ 8.35 (s, 1H), 8.34-8.29 (m, 1H), 7.44-7.35 (m, 2H), 7.32-7.26 (m, 1H), 7.20-7.13 (m, 1H), 7.10-7.03 (m, 3H), 6.99-6.93 (m, 1H), 6.10-6.04 (m, 1H), 4.03-3.91 (m, 1H), 3.87-3.73 (m, 1H), 3.56 (s, 2H), 2.69 (s, 6H), 2.21-2.15 (m, 1H), 2.12 (s, 3H), 1.98-1.82 (m, 3H), 1.49-1.16 (m, 4H).

Example 253: N-((1R,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide

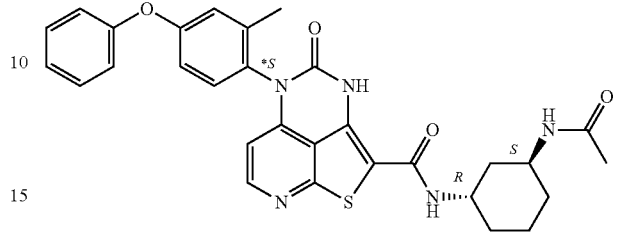

The title compound was prepared in a manner analogous to Example 1, Step B, using N-((1R,3S)-3-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 250, product from Step A) and acetic anhydride. MS (ESI): mass calcd. for $C_{30}H_{29}N_5O_4S$, 555.6; m/z found, 556.2 $[M+H]^+$. $^1$H NMR (400 MHz, $CD_3OD$): δ 8.35-8.29 (m, 1H), 7.44-7.35 (m, 2H), 7.32-7.26 (m, 1H), 7.19-7.12 (m, 1H), 7.11-7.04 (m, 3H), 6.99-6.93 (m, 1H), 6.09-6.04 (m, 1H), 4.02-3.91 (m, 1H), 3.80-3.67 (m, 1H), 2.17-2.07 (m, 4H), 1.95-1.84 (m, 6H), 1.51-1.37 (m, 1H), 1.35-1.26 (m, 2H), 1.21-1.07 (m, 1H).

Example 254: N-((1R,2S)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide

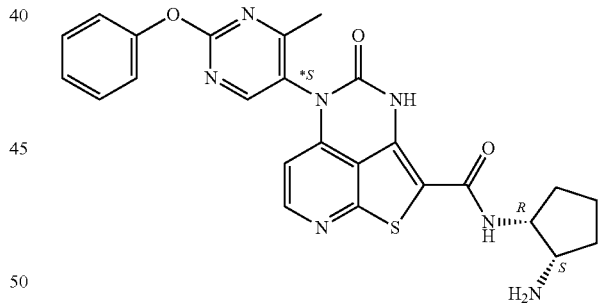

The title compound was prepared in a manner analogous to Example 166, Steps A-B, using 5-(4-methyl-2-phenoxypyrimidin-5-yl)-4-oxo-4,5-dihydro-3H-1-thia-3,5,8-triazaacenaphthylene-2-carboxylic acid (Intermediate 13, including CHIRAL SEPARATION METHOD 1 to obtain the *S atropisomer) and tert-butyl ((1S,2R)-2-aminocyclopentyl)carbamate in Step A. MS (ESI): mass calcd. for $C_{25}H_{23}N_7O_3S$, 501.6; m/z found, 502.0 $[M+H]^+$. $^1$H NMR (500 MHz, $CD_3OD$): δ 8.57 (s, 1H), 8.51 (d, J=5.9 Hz, 1H), 7.50-7.42 (m, 2H), 7.32-7.27 (m, 1H), 7.27-7.24 (m, 2H), 6.50 (d, J=6.0 Hz, 1H), 4.50 (q, J=6.6 Hz, 1H), 3.78 (q, J=6.9 Hz, 1H), 2.34 (s, 3H), 2.23-2.13 (m, 2H), 2.05-1.91 (m, 2H), 1.84-1.72 (m, 2H).

Example 255: N-((1R,2R)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide

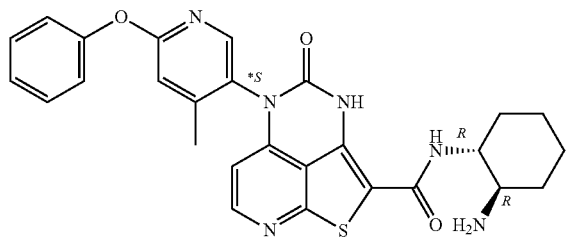

The title compound was prepared in a manner analogous to Example 166, Step A-B, using 5-(4-methyl-6-phenoxy-pyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl N-[(1R,2R)-2-aminocyclohexyl] carbamate. MS (ESI): mass calcd. for $C_{27}H_{26}N_6O_3S$, 514.6; m/z found, 515.1 [M+H]$^+$. $^1$H NMR (500 MHz, CDCl$_3$): δ 8.19 (d, J=5.3 Hz, 1H), 8.13 (s, 1H), 7.47-7.39 (m, 2H), 7.28-7.16 (m, 3H), 7.06 (s, 1H), 6.93 (s, 1H), 5.87 (s, 1H), 4.68 (s, 4H), 3.71 (d, J=10.6 Hz, 1H), 3.46 (s, 2H), 2.74 (s, 1H), 2.21 (s, 3H), 2.07 (dd, J=14.0, 10.0 Hz, 2H), 1.39-1.30 (m, 2H), 1.16 (s, 1H).

Example 256: N-((1R,2R)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide

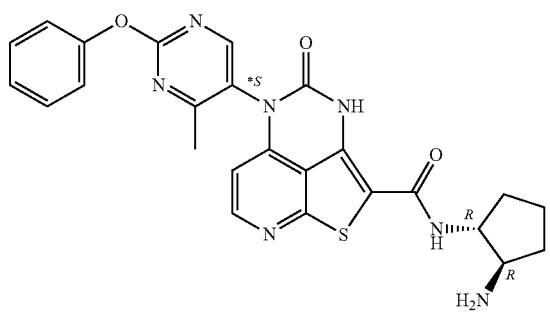

The title compound was prepared in a manner analogous to Example 166, Steps A-B, using 5-(4-methyl-2-phenoxy-pyrimidin-5-yl)-4-oxo-4,5-dihydro-3H-1-thia-3,5,8-triazaacenaphthylene-2-carboxylic acid (Intermediate 13, including CHIRAL SEPARATION METHOD 1 to obtain the *S atropisomer) and tert-butyl N-[(1R,2R)-2-aminocyclopentyl]carbamate in Step A. MS (ESI): mass calcd. for $C_{25}H_{23}N_7O_3S$, 501.6; m/z found, 502.0 [M+H]$^+$. $^1$H NMR (400 MHz, CD$_3$OD): δ 8.55-8.45 (m, 1H), 8.24-8.13 (m, 1H), 7.50-7.37 (m, 2H), 7.32-7.19 (m, 3H), 6.11-6.00 (m, 1H), 4.28-4.15 (m, 1H), 3.58-3.44 (m, 1H), 2.33-2.17 (m, 5H), 1.94-1.81 (m, 2H), 1.79-1.61 (m, 2H).

Example 257: N-((1R,2S)-2-Aminocyclohexyl)-4-oxo-5-(6-phenoxypyridin-3-yl)-4,5-dihydro-3H-1-thia-3,5,8-triazaacenaphthylene-2-carboxamide

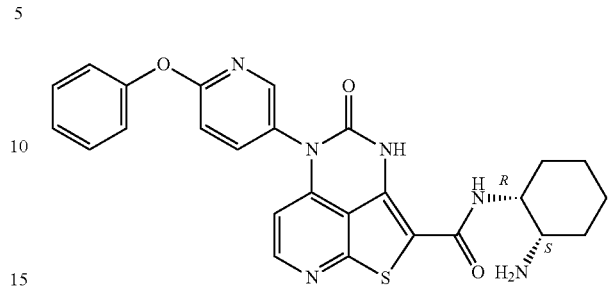

The title compound was prepared in a manner analogous to Example 1, Step A, using 4-oxo-5-(6-phenoxypyridin-3-yl)-4,5-dihydro-3H-1-thia-3,5,8-triazaacenaphthylene-2-carboxylic acid (Intermediate 28) and tert-butyl N-[(1S,2R)-2-aminocyclohexyl]carbamate, and substituting diisopropylethylamine for triethylamine. MS (ESI): mass calcd. for $C_{26}H_{24}N_6O_3S$, 500.6; m/z found, 501.1 [M+H]$^+$. $^1$H NMR (500 MHz, CDCl$_3$): δ 8.26 (q, J=5.9, 5.4 Hz, 3H), 8.15 (s, 1H), 7.81 (d, J=7.3 Hz, 1H), 7.67 (d, J=8.6 Hz, 1H), 7.49-7.41 (m, 4H), 7.30-7.18 (m, 2H), 7.12 (dd, J=15.5, 8.7 Hz, 2H), 6.45 (s, 2H), 6.12-6.04 (m, 2H), 3.21 (s, 1H), 1.73-1.37 (m, 4H), 1.21 (t, J=7.0 Hz, 1H).

Example 258: N-((1S,2R)-2-Acetamidocyclopentyl)-4-oxo-5-(2-phenylpyridin-4-yl)-4,5-dihydro-3H-1-thia-3,5,8-triazaacenaphthylene-2-carboxamide

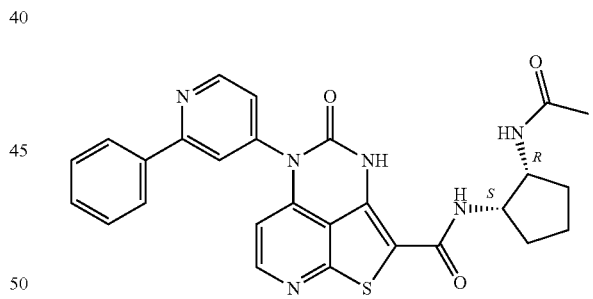

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and using tert-butyl N-[(1R,2S)-2-aminocyclopentyl]carbamate in Step A, and acetic anhydride and DMAP in Step B. MS (ESI): mass calcd. for $C_{27}H_{24}N_6O_3S$, 512.6; m/z found, 513.5 [M+H]$^+$. $^1$H NMR (400 MHz, CD$_3$OD): δ 8.86 (d, J=5.1 Hz, 1H), 8.31 (d, J=5.2 Hz, 1H), 8.14-7.95 (m, 3H), 7.60-7.38 (m, 4H), 6.30 (d, J=5.6 Hz, 1H), 4.43-4.25 (m, 2H), 2.10-1.81 (m, 6H), 1.79-1.51 (m, 3H).

Example 259: N-((1S,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide

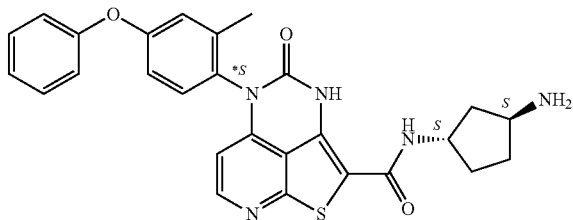

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3S)-3-aminocyclopentyl]carbamate. MS (ESI): mass calcd. for $C_{27}H_{25}N_5O_3S$, 499.6; m/z found, 500.3 [M+H]+. 1H NMR (400 MHz, CD3OD): δ 8.49 (s, 1H), 8.33 (d, J=5.6 Hz, 1H), 7.47-7.36 (m, 2H), 7.33-7.25 (m, 1H), 7.22-7.13 (m, 1H), 7.12-7.03 (m, 3H), 7.02-6.92 (m, 1H), 6.08 (d, J=5.5 Hz, 1H), 4.62-4.47 (m, 1H), 3.88-3.70 (m, 1H), 2.39-2.19 (m, 2H), 2.16-2.03 (m, 5H), 1.83-1.57 (m, 2H).

Example 260: N-((1R,2S)-2-Aminocyclohexyl)-4-oxo-5-(2-phenylpyridin-4-yl)-4,5-dihydro-3H-1-thia-3,5,8-triazaacenaphthylene-2-carboxamide

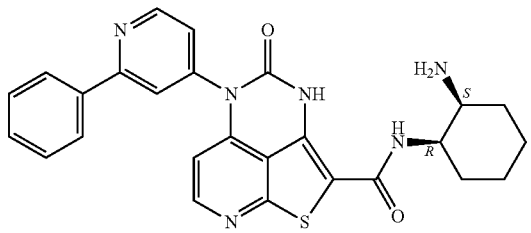

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,2R)-2-aminocyclohexyl]carbamate. MS (ESI): mass calcd. for $C_{26}H_{24}N_6O_2S$, 484.6; m/z found, 485.2 [M+H]+. 1H NMR (400 MHz, CD3OD): δ 8.83-8.78 (m, 1H), 8.14-8.09 (m, 1H), 8.03-7.99 (m, 2H), 7.92-7.89 (m, 1H), 7.51-7.44 (m, 3H), 7.42-7.39 (m, 1H), 6.13-6.10 (m, 1H), 4.47-4.42 (m, 1H), 3.42-3.35 (m, 1H), 1.92-1.69 (m, 6H), 1.62-1.55 (m, 1H), 1.51-1.42 (m, 1H).

Example 261: N-((1R,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide

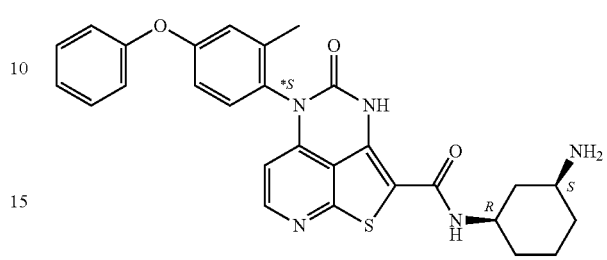

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl N-[(1S,3R)-3-aminocyclohexyl]carbamate. MS (ESI): mass calcd. for $C_{28}H_{27}N_5O_3S$, 513.6; m/z found, 514.2 [M+H]+. 1H NMR (400 MHz, CD3OD): δ 8.47 (s, 1H), 8.36-8.30 (m, 1H), 7.43-7.36 (m, 2H), 7.30-7.24 (m, 1H), 7.20-7.13 (m, 1H), 7.10-7.03 (m, 3H), 6.99-6.93 (m, 1H), 6.11-6.04 (m, 1H), 4.05-3.93 (m, 1H), 3.25-3.16 (m, 1H), 2.33-2.23 (m, 1H), 2.12 (s, 3H), 2.06-1.91 (m, 3H), 1.57-1.31 (m, 4H).

Example 262: N-((1R,2S)-2-Aminocyclopentyl)-5-(*R)-(4-isopropoxy-2-methylphenyl)-4-oxo-4,5-dihydro-3H-1-thia-3,5,8-triazaacenaphthylene-2-carboxamide

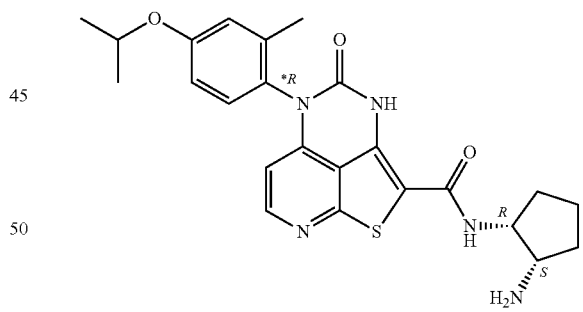

The title compound was prepared in a manner analogous to Example 1, Step A, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1S,2R)-2-aminocyclopentyl]carbamate. MS (ESI): mass calcd. for $C_{24}H_{27}N_5O_3S$, 465.6; m/z found, 466.2 [M+H]+. 1H NMR (400 MHz, CD3OD): δ 8.46 (s, 1H), 8.33-8.29 (m, 1H), 7.24-7.18 (m, 1H), 7.00-6.89 (m, 2H), 6.06-6.01 (m, 1H), 4.71-4.61 (m, 1H), 4.51-4.42 (m, 1H), 3.80-3.70 (m, 1H), 2.22-2.09 (m, 2H), 2.04 (s, 3H), 2.01-1.85 (m, 2H), 1.83-1.65 (m, 2H), 1.38-1.31 (m, 6H).

Example 263: N-((1R,2S)-2-Aminocyclopentyl)-4-oxo-5-(2-phenylpyridin-4-yl)-4,5-dihydro-3H-1-thia-3,5,8-triazaacenaphthylene-2-carboxamide

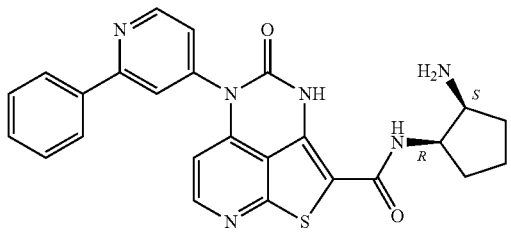

The title compound was prepared in a manner analogous to Example 1, Step A, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,2R)-2-aminocyclopentyl]carbamate. MS (ESI): mass calcd. for $C_{25}H_{22}N_6O_2S$, 470.5; m/z found, 471.3 [M+H]$^+$. $^1$H NMR (400 MHz, CD$_3$OD): δ 8.81 (d, J=5.3 Hz, 1H), 8.12 (d, J=5.6 Hz, 1H), 8.07-7.96 (m, 2H), 7.94-7.89 (m, 1H), 7.55-7.36 (m, 4H), 6.11 (d, J=5.7 Hz, 1H), 4.61-4.46 (m, 1H), 3.70-3.58 (m, 1H), 2.26-2.05 (m, 2H), 2.01-1.61 (m, 4H).

Example 264: N-((1R,2R)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide

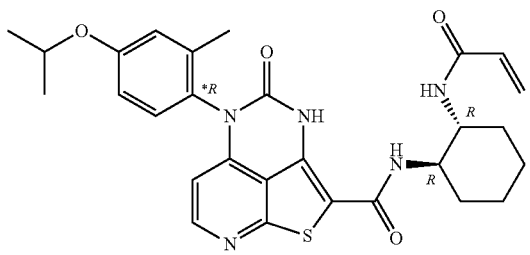

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1R,2R)-2-aminocyclohexyl]carbamate. MS (ESI): mass calcd. for $C_{28}H_{31}N_5O_4S$, 533.6; m/z found, 534.2 [M+H]$^+$. $^1$H NMR (400 MHz, CD$_3$OD): δ 8.32-8.24 (m, 1H), 7.22-7.15 (m, 1H), 7.00-6.94 (m, 1H), 6.94-6.86 (m, 1H), 6.21-6.16 (m, 2H), 6.03-5.98 (m, 1H), 5.62-5.55 (m, 1H), 4.70-4.61 (m, 1H), 3.91-3.81 (m, 2H), 2.10 (s, 3H), 2.07-1.96 (m, 2H), 1.84-1.76 (m, 2H), 1.50-1.36 (m, 4H), 1.36-1.32 (m, 6H).

Example 265: N-((1R,2S)-2-Aminocyclopentyl)-4-oxo-5-(6-phenoxypyridin-3-yl)-4,5-dihydro-3H-1-thia-3,5,8-triazaacenaphthylene-2-carboxamide

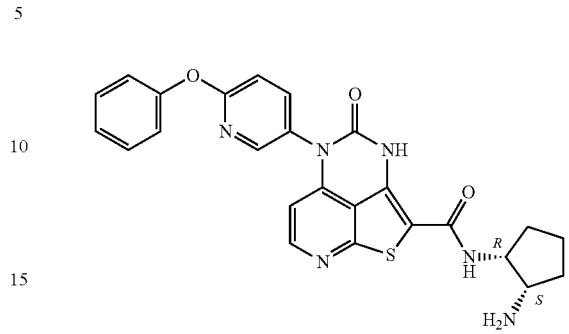

The title compound was prepared in a manner analogous to Example 1, Step A, using oxo-5-(6-phenoxypyridin-3-yl)-4,5-dihydro-3H-1-thia-3,5,8-triazaacenaphthylene-2-carboxylic acid (Intermediate 28) and tert-butyl ((1S,2R)-2-aminocyclopentyl)carbamate. MS (ESI): mass calcd. for $C_{25}H_{22}N_6O_3S$, 486.6; m/z found, 486.9 [M+H]$^+$. $^1$H NMR (500 MHz, Chloroform-d) δ 8.27 (s, 1H), 8.03 (s, 1H), 7.45 (td, J=7.3, 1.6 Hz, 2H), 7.30-7.18 (m, 2H), 7.11 (d, J=8.7 Hz, 2H), 6.82-6.56 (m, 3H), 6.12 (s, 1H), 4.16 (s, 2H), 3.52-3.44 (m, 2H), 1.84-1.61 (m, 4H), 1.56-1.46 (m, 2H).

Example 266: N-((1R,2S)-2-Acrylamidocyclohexyl)-5-(*R)-(6-cyclobutoxy-4-methylpyridin-3-yl)-4-oxo-4,5-dihydro-3H-1-thia-3,5,8-triazaacenaphthylene-2-carboxamide

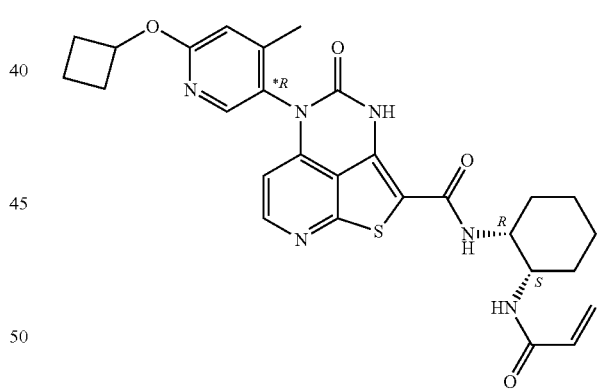

Chiral separation of (chiral SFC (Stationary phase: Chiralpak AS-H 5 μm 250*20 mm, Mobile phase: 70% CO$_2$, 30% MeOH) N-((1R,2S)-2-Acrylamidocyclohexyl)-5-(6-cyclobutoxy-4-methylpyridin-3-yl)-4-oxo-4,5-dihydro-3H-1-thia-3,5,8-triazaacenaphthylene-2-carboxamide (Example 183) provides the title compound. MS (ESI): mass calcd. for $C_{28}H_{30}N_6O_4S$, 546.7; m/z found, 547.2 [M+H]$^+$. $^1$H NMR (400 MHz, CD$_3$OD): δ 8.32 (d, J=5.5 Hz, 1H), 8.04 (s, 1H), 6.84 (s, 1H), 6.48-6.38 (m, 1H), 6.28 (dd, J=17.0, 1.8 Hz, 1H), 6.09 (d, J=5.5 Hz, 1H), 5.67 (dd, J=10.2, 1.9 Hz, 1H), 5.25-5.12 (m, 1H), 4.47-4.37 (m, 1H), 4.17 (d, J=10.3 Hz, 1H), 2.54-2.43 (m, 2H), 2.23-2.09 (m, 5H), 1.91-1.63 (m, 8H), 1.60-1.46 (m, 2H).

Example 267: N-((1R,2S)-2-Aminocyclopentyl)-4-oxo-5-(4-phenylpyridin-2-yl)-4,5-dihydro-3H-1-thia-3,5,8-triazaacenaphthylene-2-carboxamide

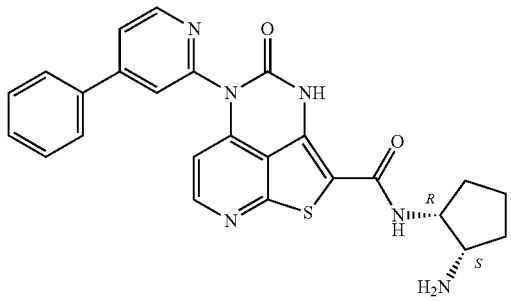

The title compound was prepared in a manner analogous to Example 1, Step A, using 4-oxo-5-(4-phenylpyridin-2-yl)-4,5-dihydro-3H-1-thia-3,5,8-triazaacenaphthylene-2-carboxylic acid (Intermediate 21) and tert-butyl N-[(1S,2R)-2-aminocyclopentyl]carbamate. MS (ESI): mass calcd. for $C_{25}H_{22}N_6O_2S$, 470.5; m/z found, 471.1 [M+H]$^+$. $^1$H NMR (400 MHz, CD$_3$OD): δ 8.73-8.67 (m, 1H), 8.42 (s, 1H), 8.36-8.29 (m, 1H), 7.93-7.87 (m, 2H), 7.85-7.78 (m, 2H), 7.56-7.48 (m, 3H), 6.27-6.23 (m, 1H), 4.52-4.44 (m, 1H), 3.80-3.69 (m, 1H), 2.22-2.08 (m, 2H), 2.04-1.85 (m, 2H), 1.81-1.68 (s, 2H).

Example 268: N-((1R,2R)-2-Hydroxycyclopentyl)-4-oxo-5-(2-phenylpyridin-4-yl)-4,5-dihydro-3H-1-thia-3,5,8-triazaacenaphthylene-2-carboxamide

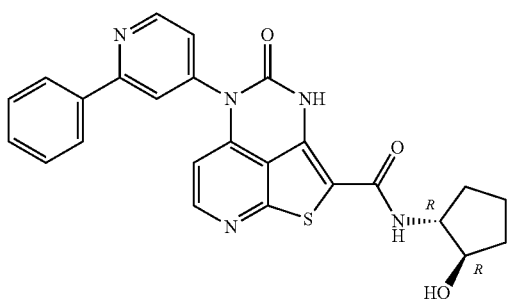

The title compound was prepared in a manner analogous to Example 1, Step A, using oxo-5-(2-phenylpyridin-4-yl)-4,5-dihydro-3H-1-thia-3,5,8-triazaacenaphthylene-2-carboxylic acid (Intermediate 20) and (1R,2R)-2-aminocyclopentanol in place of tert-butyl ((1S,4S)-4-aminocyclohexyl)carbamate in step G (91 mg). MS (ESI): mass calcd. for $C_{25}H_{21}N_5O_3S$, 471.5; m/z found, 472.1 [M+H]$^+$. $^1$H NMR (400 MHz, CD$_3$OD): δ 8.90-8.79 (m, 1H), 8.36-8.24 (m, 1H), 8.07-7.98 (m, 3H), 7.51-7.41 (m, 4H), 6.32-6.22 (m, 1H), 4.16-4.07 (m, 2H), 2.18-2.07 (m, 1H), 2.04-1.94 (m, 1H), 1.82-1.70 (m, 2H), 1.66-1.54 (m, 2H).

Example 269: N-((1R,2R)-2-Aminocyclopentyl)-4-oxo-5-(6-phenoxypyridin-3-yl)-4,5-dihydro-3H-1-thia-3,5,8-triazaacenaphthylene-2-carboxamide

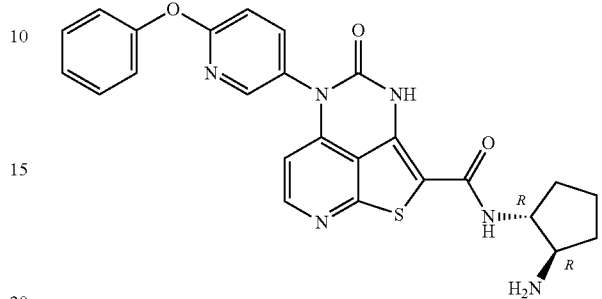

The title compound was prepared in a manner analogous to Example 1, Step A, using oxo-5-(6-phenoxypyridin-3-yl)-4,5-dihydro-3H-1-thia-3,5,8-triazaacenaphthylene-2-carboxylic acid (Intermediate 28) and tert-butyl N-[(1R,2R)-2-aminocyclopentyl]carbamate. MS (ESI): mass calcd. for $C_{25}H_{22}N_6O_3S$, 486.6; m/z found, 487.1 [M+H]$^+$. $^1$H NMR (400 MHz, CDCl$_3$): δ 8.35 (d, J=5.5 Hz, 1H), 8.17 (d, J=2.6 Hz, 1H), 7.70 (dd, J=8.8, 2.7 Hz, 1H), 7.46 (t, J=7.9 Hz, 2H), 7.32-7.17 (m, 3H), 7.11 (d, J=8.7 Hz, 1H), 6.18 (d, J=5.5 Hz, 1H), 3.96 (q, J=8.1 Hz, 1H), 3.46-3.36 (m, 3H), 3.14 (q, J=7.8 Hz, 1H), 2.82-2.75 (m, 5H), 1.78 (dt, J=14.7, 7.6 Hz, 2H).

Example 270: N-((1R,2S)-2-Aminocyclopentyl)-5-(2-isopropylpyridin-4-yl)-4-oxo-4,5-dihydro-3H-1-thia-3,5,8-triazaacenaphthylene-2-carboxamide

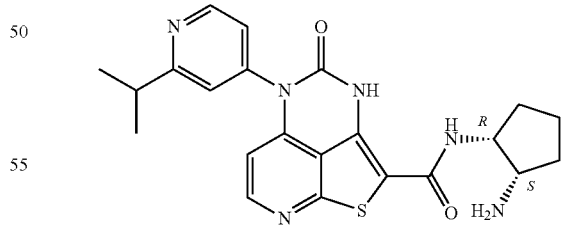

The title compound was prepared in a manner analogous to Example 1, Step A, using 5-(2-isopropylpyridin-4-yl)-4-oxo-4,5-dihydro-3H-1-thia-3,5,8-triazaacenaphthylene-2-carboxylic acid (Intermediate 16) and tert-butyl N-[(1S,2R)-2-aminocyclopentyl]carbamate. MS (ESI): mass calcd. for $C_{22}H_{24}N_6O_2S$, 436.5; m/z found, 437.1 [M+H]$^+$.

Example 271: N-((1R,2S)-2-Aminocyclopentyl)-5-(4-isopropoxyphenyl)-4-oxo-4,5-dihydro-3H-1-thia-3,5,8-triazaacenaphthylene-2-carboxamide

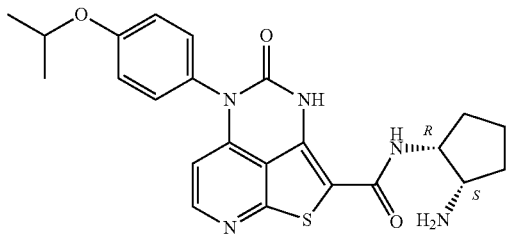

The title compound was prepared in a manner analogous to Example 1, Step A, using 5-(4-isopropoxyphenyl)-4-oxo-4,5-dihydro-3H-1-thia-3,5,8-triazaacenaphthylene-2-carboxylic acid and tert-butyl N-[(1S,2R)-2-aminocyclopentyl]carbamate. MS (ESI): mass calcd. for $C_{23}H_{25}N_5O_3S$, 451.5; m/z found, 452.4 $[M+H]^+$. $^1H$ NMR (400 MHz, $CD_3OD$): δ 8.52 (s, 1H), 8.26 (d, J=5.6 Hz, 1H), 7.35-7.22 (m, 2H), 7.14-7.02 (m, 2H), 6.10 (d, J=5.6 Hz, 1H), 4.72-4.65 (m, 1H), 4.53-4.42 (m, 1H), 3.79-3.64 (m, 1H), 2.23-2.09 (m, 2H), 2.05-1.82 (m, 2H), 1.81-1.66 (m, 2H), 1.41-1.32 (m, 6H).

Example 272: N-((1S,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide

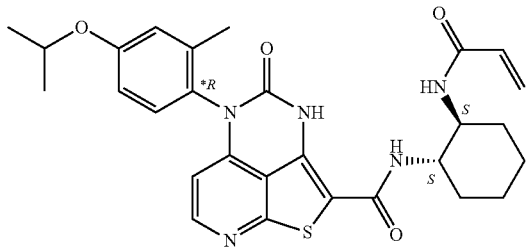

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1S,2S)-2-aminocyclohexyl]carbamate. MS (ESI): mass calcd. for $C_{28}H_{31}N_5O_4S$, 533.6; m/z found, 534.2 $[M+H]^+$. $^1H$ NMR (400 MHz, $CD_3OD$): δ 8.30-8.26 (m, 1H), 7.21-7.15 (m, 1H), 7.00-6.94 (m, 1H), 6.94-6.86 (m, 1H), 6.21-6.16 (m, 2H), 6.03-5.98 (m, 1H), 5.62-5.55 (m, 1H), 4.70-4.61 (m, 1H), 3.91-3.81 (m, 2H), 2.10 (s, 3H), 2.07-1.96 (m, 2H), 1.84-1.76 (m, 2H), 1.54-1.36 (m, 4H), 1.36-1.32 (m, 6H).

Example 273: N-((1R,2R)-2-Acrylamidocyclohexyl)-5-(*S)-(4-isopropoxy-2-methylphenyl)-4-oxo-4,5-dihydro-3H-1-thia-3,5,8-triazaacenaphthylene-2-carboxamide

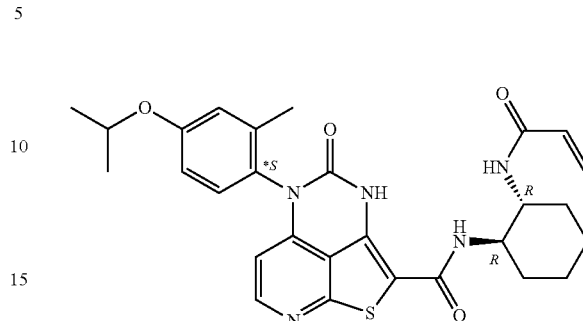

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *S atropisomer) and tert-butyl N-[(1R,2R)-2-aminocyclohexyl]carbamate. MS (ESI): mass calcd. for $C_{28}H_{31}N_5O_4S$, 533.6; m/z found, 534.2 $[M+H]^+$. $^1H$ NMR (400 MHz, $CD_3OD$): δ 8.30-8.24 (m, 1H), 7.20-7.15 (m, 1H), 7.00-6.94 (m, 1H), 6.94-6.86 (m, 1H), 6.21-6.16 (m, 2H), 6.03-5.98 (m, 1H), 5.62-5.55 (m, 1H), 4.72-4.59 (m, 1H), 3.93-3.82 (m, 2H), 2.11 (s, 3H), 2.07-1.94 (m, 2H), 1.84-1.74 (m, 2H), 1.54-1.36 (m, 4H), 1.36-1.32 (m, 6H).

Example 274: N-((1S, S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide

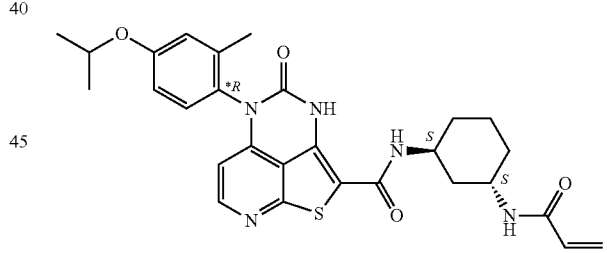

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1S,3S)-3-aminocyclohexyl]carbamate. MS (ESI): mass calcd. for $C_{28}H_{31}N_5O_4S$, 533.6; m/z found, 534.2 $[M+H]^+$. $^1H$ NMR (400 MHz, $CD_3OD$): δ 8.30 (d, J=5.6 Hz, 1H), 7.23-7.16 (m, 1H), 6.99-6.96 (m, 1H), 6.94-6.87 (m, 1H), 6.41-6.29 (m, 1H), 6.27-6.18 (m, 1H), 6.02 (d, J=5.6 Hz, 1H), 5.69-5.59 (m, 1H), 4.71-4.62 (m, 1H), 4.25-4.13 (m, 2H), 2.11 (s, 3H), 1.94-1.77 (m, 3H), 1.74-1.61 (m, 4H), 1.59-1.51 (m, 1H), 1.34 (d, J=6.0 Hz, 6H).

Example 275: N-((1R,3S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide

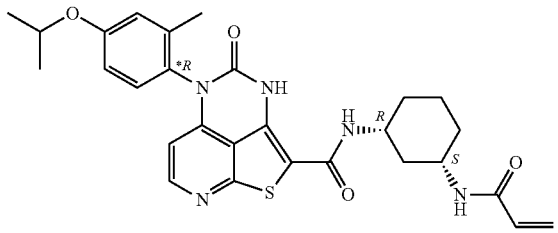

Step A: tert-Butyl N-[(1R,3S)-3-(prop-2-enoylamino)cyclohexyl]carbamate

To a solution of tert-butyl N-[(1R,3S)-3-aminocyclohexyl]carbamate (200 mg, 0.798 mmol) in DCM (50 mL) was added triethylamine (0.403 g, 3.99 mmol), followed by the addition of prop-2-enoyl chloride (0.0794 g, 0.877 mmol) in an ice-bath and the reaction was stirred at rt for 1 h. The reaction was concentrated to dryness and purified by flash column chromatography to give the title compound (155 mg, 72.4% yield) as a light yellow solid.

Step B. N-((1S,3R)-3-aminocyclohexyl)acrylamide

The title compound was prepared in a manner analogous to Example 5, step B.

Step C: N-((1R,3S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and using N-((1S,3R)-3-aminocyclohexyl)acrylamide. MS (ESI): mass calcd. for $C_{28}H_{31}N_5O_4S$, 533.6; m/z found, 534.7 [M+H]$^+$. $^1$H NMR (400 MHz, CD$_3$OD): δ 8.30 (d, J=5.5 Hz, 1H), 7.20 (d, J=8.6 Hz, 1H), 6.99-6.95 (m, 1H), 6.94-6.86 (m, 1H), 6.25-6.17 (m, 2H), 6.02 (d, J=5.6 Hz, 1H), 5.67-5.57 (m, 1H), 4.71-4.60 (m, 1H), 4.05-3.92 (m, 1H), 3.91-3.78 (m, 1H), 2.21-2.13 (m, 1H), 2.11 (s, 3H), 1.99-1.80 (m, 3H), 1.56-1.36 (m, 2H), 1.34 (d, J=6.0 Hz, 6H), 1.31-1.12 (m, 2H).

Example 276: N-((1R,3S)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide

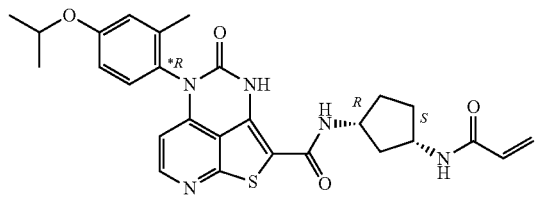

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *R atropisomer) and tert-butyl N-[(1S,3R)-3-aminocyclopentyl]carbamate. MS (ESI): mass calcd. for $C_{27}H_{29}N_5O_4S$, 519.6; m/z found, 520.4 [M+H]$^+$. $^1$H NMR (400 MHz, CD$_3$OD): δ 8.29 (d, J=5.6 Hz, 1H), 7.29-7.13 (m, 1H), 7.02-6.79 (m, 2H), 6.36-6.18 (m, 2H), 6.02 (d, J=5.5 Hz, 1H), 5.71-5.59 (m, 1H), 4.74-4.57 (m, 1H), 4.45-4.30 (m, 1H), 4.25-4.11 (m, 1H), 2.55-2.40 (m, 1H), 2.11 (s, 3H), 2.08-1.96 (m, 2H), 1.88-1.69 (m, 2H), 1.69-1.53 (m, 1H), 1.40-1.30 (m, 6H).

Example 277: N-((1R,2R)-2-Aminocyclohexyl)-4-oxo-5-(6-phenoxypyridin-3-yl)-4,5-dihydro-3H-1-thia-3,5,8-triazaacenaphthylene-2-carboxamide

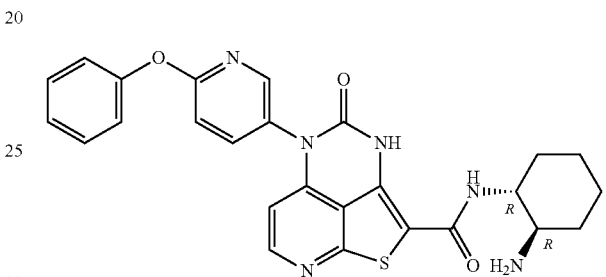

The title compound was prepared in a manner analogous to Example 166, Steps A-B, using 5-(4-methyl-6-phenoxypyridin-3-yl)-4-oxo-4,5-dihydro-3H-1-thia-3,5,8-triazaacenaphthylene-2-carboxylic acid (Intermediate 27) and tert-butyl N-[(1R,2R)-2-aminocyclohexyl]carbamate. MS (ESI): mass calcd. for $C_{26}H_{24}N_6O_3S$, 500.6; m/z found, 501.1 [M+H]$^+$. $^1$H NMR (400 MHz, CDCl$_3$): δ 8.45 (d, J=2.8 Hz, 1H), 8.21 (d, J=2.7 Hz, 1H), 8.03 (dd, J=8.7, 2.7 Hz, 1H), 7.95 (dd, J=5.8, 2.5 Hz, 2H), 7.69 (dd, J=9.0, 2.8 Hz, 1H), 7.45 (q, J=7.2 Hz, 4H), 7.10 (d, J=8.7 Hz, 1H), 6.04 (s, 1H), 6.00-5.92 (m, 1H), 5.80 (dd, J=42.2, 5.5 Hz, 2H), 3.77 (qd, J=11.4, 10.4, 3.7 Hz, 2H), 3.45 (s, 1H), 1.82 (dd, J=23.7, 10.9 Hz, 2H), 1.40-1.15 (m, 4H).

Example 278: N-((1R,2S)-2-Aminocyclopentyl)-4-oxo-5-(6-phenylpyridazin-4-yl)-4,5-dihydro-3H-1-thia-3,5,8-triazaacenaphthylene-2-carboxamide

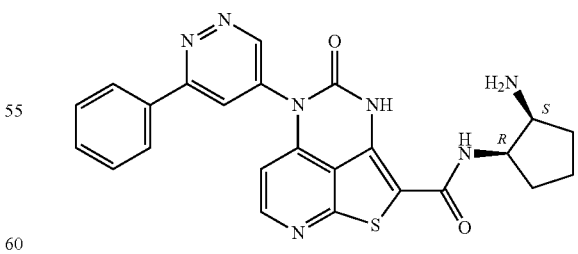

The title compound was prepared in a manner analogous to Example 1, Step A, using 4-oxo-5-(6-phenylpyridazin-4-yl)-4,5-dihydro-3H-1-thia-3,5,8-triazaacenaphthylene-2-carboxylic acid (Example 203, product from Step B) and tert-butyl N-[(1S,2R)-2-aminocyclopentyl]carbamate in Step A. MS (ESI): mass calcd. for $C_{24}H_{21}N_7O_2S$, 471.5; m/z found, 472.2 [M+H]+. 1H NMR (400 MHz, CD3OD and DMSO-d6): δ 9.28 (d, J=2.2 Hz, 1H), 8.45-8.38 (m, 1H), 8.22-8.18 (m, 4H), 7.64-7.53 (m, 3H), 6.33-6.23 (m, 1H), 4.42-4.36 (m, 1H), 3.62-3.56 (m, 1H), 2.12-1.97 (m, 2H), 1.90-1.77 (m, 2H), 1.75-1.56 (m, 2H).

Example 279: N-((1S,3S)-3-Acrylamidocyclohexyl)-4-oxo-5-(2-phenylpyridin-4-yl)-4,5-dihydro-3H-1-thia-3,5,8-triazaacenaphthylene-2-carboxamide

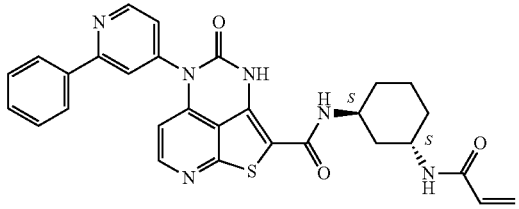

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,3S)-3-aminocyclohexyl]carbamate. MS (ESI): mass calcd. for C29H26N6O3S, 538.6; m/z found, 539.2 [M+H]+. 1H NMR (400 MHz, DMSO-d6): δ 10.28 (s, 1H), 8.89 (d, J=5.2 Hz, 1H), 8.38-8.28 (m, 1H), 8.17 (s, 1H), 8.14-8.07 (m, 3H), 8.02-7.93 (m, 1H), 7.55-7.41 (m, 4H), 6.43-6.31 (m, 1H), 6.22 (d, J=5.5 Hz, 1H), 6.12-6.03 (m, 1H), 5.61-5.51 (m, 1H), 4.21-4.08 (m, 2H), 1.82-1.59 (m, 5H), 1.53-1.36 (m, 3H).

Example 280: N-((1R,2S)-2-Acetamidocyclopentyl)-4-oxo-5-(2-phenylpyridin-4-yl)-4,5-dihydro-3H-1-thia-3,5,8-triazaacenaphthylene-2-carboxamide

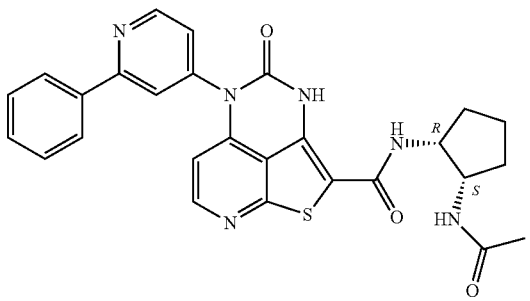

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,2R)-2-aminocyclopentyl]carbamate in Step A, and substituting acetic anhydride for prop-2-enoyl chloride in Step B. MS (ESI): mass calcd. for C27H24N6O3S, 512.6; m/z found, 513.4 [M+H]+. 1H NMR (400 MHz, CD3OD): δ 8.85 (d, J=5.3 Hz, 1H), 8.31 (d, J=5.6 Hz, 1H), 8.07-8.00 m, 3H), 7.55-7.43 (m, 4H), 6.29 (d, J=5.5 Hz, 1H), 4.42-4.28 (m, 2H), 2.11-1.96 (m, 2H), 1.94 (s, 3H), 1.92-1.82 (m, 1H), 1.79-1.57 (m, 3H).

Example 281: N-((1R,2S)-2-Aminocyclopentyl)-4-oxo-5-(6-phenylpyrimidin-4-yl)-4,5-dihydro-3H-1-thia-3,5,8-triazaacenaphthylene-2-carboxamide

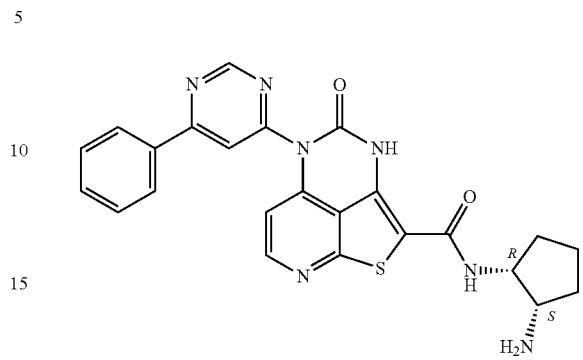

The title compound was prepared in a manner analogous to Example 1, Step A, using 4-oxo-5-(6-phenylpyrimidin-4-yl)-4,5-dihydro-3H-1-thia-3,5,8-triazaacenaphthylene-2-carboxylic acid (Intermediate 23) and tert-butyl N-[(1S,2R)-2-aminocyclopentyl]carbamate. MS (ESI): mass calcd. for C24H21N7O2S, 471.5; m/z found, 472.2 [M+H]+. 1H NMR (400 MHz, CD3OD): δ 9.35-9.26 (m, 1H), 8.40-8.36 (m, 2H), 8.27-8.20 (m, 3H), 7.61-7.52 (m, 3H), 6.62-6.56 (m, 1H), 4.57-4.41 (m, 1H), 3.80-3.68 (m, 1H), 2.28-2.10 (m, 2H), 2.08-1.85 (m, 2H), 1.81-1.65 (m, 2H).

Example 282: N-((1S,3S)-3-Acrylamidocyclopentyl)-4-oxo-5-(2-phenylpyridin-4-yl)-4,5-dihydro-3H-1-thia-3,5,8-triazaacenaphthylene-2-carboxamide

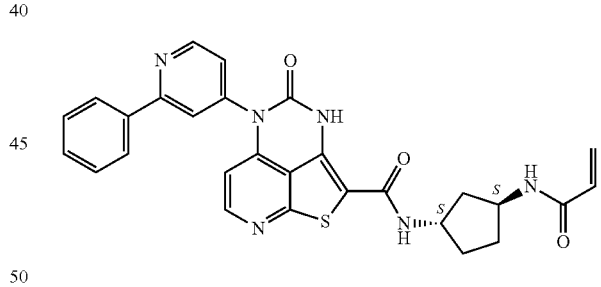

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,3S)-3-aminocyclopentyl]carbamate, in Step A, and acetic anhydride in Step B. MS (ESI): mass calcd. for C28H24N6O3S, 524.6; m/z found, 525.4 [M+H]+. 1H NMR (400 MHz, CD3OD): δ 8.81 (d, J=5.0 Hz, 1H), 8.26 (d, J=5.4 Hz, 1H), 8.12-7.94 (m, 3H), 7.55-7.30 (m, 4H), 6.31-6.12 (m, 3H), 5.72-5.48 (m, 1H), 4.53-4.23 (m, 2H), 2.23-2.07 (m, 2H), 2.07-1.79 (m, 2H), 1.71-1.41 (m, 2H).

Example 283: N-((1R,3S)-3-Acrylamidocyclohexyl)-4-oxo-5-(2-phenylpyridin-4-yl)-4,5-dihydro-3H-1-thia-3,5,8-triazaacenaphthylene-2-carboxamide

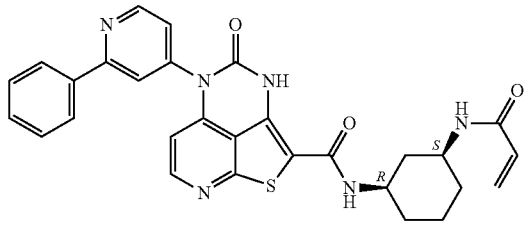

The title compound was prepared in a manner analogous to Example 1, using 4-oxo-5-(2-phenylpyridin-4-yl)-4,5-dihydro-3H-1-thia-3,5,8-triazaacenaphthylene-2-carboxylic acid (Intermediate 20) and tert-butyl N-[(1S,3R)-3-aminocyclohexyl]carbamate in Step A. MS (ESI): mass calcd. for $C_{29}H_{26}N_6O_3S$, 538.6; m/z found, 539.2 [M+H]$^+$. $^1$H NMR (400 MHz, DMSO-$d_6$): δ 10.26 (s, 1H), 8.91-8.85 (m, 1H), 8.35-8.27 (m, 1H), 8.19-8.11 (m, 1H), 8.10-8.03 (m, 4H), 7.52-7.45 (m, 4H), 6.23-6.12 (m, 2H), 6.10-5.98 (m, 1H), 5.58-5.50 (m, 1H), 3.89-3.79 (m, 1H), 3.73-3.59 (m, 1H), 2.03-1.95 (m, 1H), 1.80-1.73 (m, 3H), 1.37-1.27 (m, 3H), 1.13-1.08 (m, 1H).

Example 284: N-((1R,2S)-2-Aminocyclopentyl)-4-oxo-5-(5-phenylpyridin-3-yl)-4,5-dihydro-3H-1-thia-3,5,8-triazaacenaphthylene-2-carboxamide

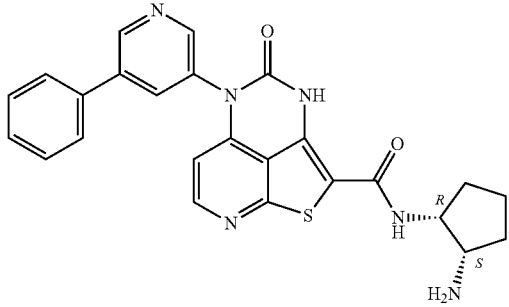

The title compound was prepared in a manner analogous to Example 1, Step A, using 4-oxo-5-(5-phenylpyridin-3-yl)-4,5-dihydro-3H-1-thia-3,5,8-triazaacenaphthylene-2-carboxylic acid (Intermediate 22) and tert-butyl N-[(1S,2R)-2-aminocyclopentyl]carbamate. MS (ESI): mass calcd. for $C_{25}H_{22}N_6O_2S$, 470.5; m/z found, 471.1 [M+H]$^+$. $^1$H NMR (400 MHz, CD$_3$OD): δ 9.00-8.96 (m, 1H), 8.65-8.58 (m, 1H), 8.45-8.39 (m, 1H), 8.36-8.30 (m, 1H), 8.26-8.21 (m, 1H), 7.77-7.69 (m, 2H), 7.55-7.47 (m, 2H), 7.47-7.41 (m, 1H), 6.31-6.23 (m, 1H), 4.54-4.42 (m, 1H), 3.78-3.70 (m, 1H), 2.21-2.11 (m, 2H), 2.04-1.85 (m, 2H), 1.83-1.69 (m, 2H).

Example 285: N-((1R,2S)-2-Aminocyclopentyl)-4-oxo-5-(3-(pyridin-2-yl)phenyl)-4,5-dihydro-3H-1-thia-3,5,8-triazaacenaphthylene-2-carboxamide

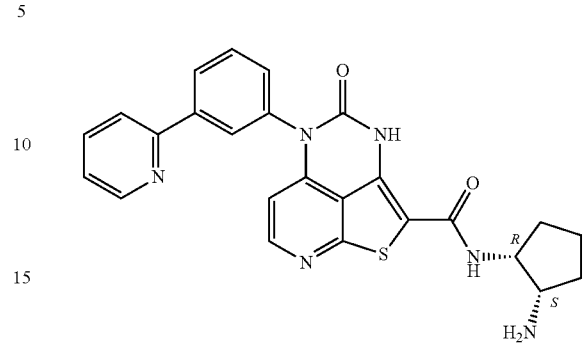

The title compound was prepared in a manner analogous to Example 1, Step A, using 4-oxo-5-(3-(pyridin-2-yl)phenyl)-4,5-dihydro-3H-1-thia-3,5,8-triazaacenaphthylene-2-carboxylic acid (Example 194, product from Step A) and tert-butyl N-[(1S,2R)-2-aminocyclopentyl]carbamate. MS (ESI): mass calcd. for $C_{25}H_{22}N_6O_2S$, 470.5; m/z found, 471.4 [M+H]$^+$. $^1$H NMR (400 MHz, CD$_3$OD): δ 8.65-8.57 (m, 1H), 8.20-8.07 (m, 2H), 8.04-7.98 (m, 1H), 7.96-7.84 (m, 2H), 7.77-7.65 (m, 1H), 7.52-7.41 (m, 1H), 7.41-7.32 (m, 1H), 6.03 (d, J=5.6 Hz, 1H), 4.55-4.44 (m, 1H), 3.71-3.56 (m, 1H), 2.22-2.06 (m, 2H), 1.97-1.82 (m, 2H), 1.80-1.62 (m, 2H).

Example 286: N-((1S,2R)-2-(2-(Methylamino)acetamido)cyclopentyl)-4-oxo-5-(2-phenylpyridin-4-yl)-4,5-dihydro-3H-1-thia-3,5,8-triazaacenaphthylene-2-carboxamide

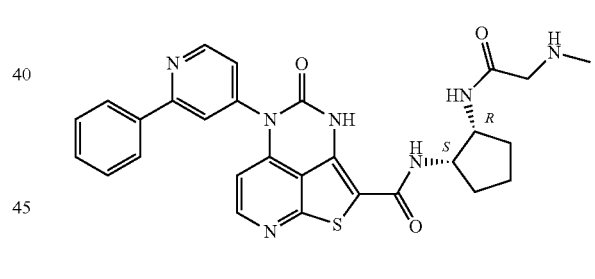

Step A. N-((1S,2R)-2-Aminocyclopentyl)-4-oxo-5-(2-phenylpyridin-4-yl)-4,5-dihydro-3H-1-thia-3,5,8-triazaacenaphthylene-2-carboxamide The title compound was prepared in a manner analogous to Example 1, Step A, using 4-oxo-5-(2-phenylpyridin-4-yl)-4,5-dihydro-3H-1-thia-3,5,8-triazaacenaphthylene-2-carboxylic acid (Intermediate 20) and using tert-butyl N-[(1R,2S)-2-aminocyclopentyl]carbamate.

Step B. N-((1S,2R)-2-(2-(Methylamino)acetamido)cyclopentyl)-4-oxo-5-(2-phenylpyridin-4-yl)-4,5-dihydro-3H-1-thia-3,5,8-triazaacenaphthylene-2-carboxamide The title compound was prepared in a manner analogous to Example 1, Step A, using 2-[tert-butoxycarbonyl(methyl)

amino]acetic acid and HATU, no deprotection HCl/MeOH. MS (ESI): mass calcd. for $C_{28}H_{27}N_7O_3S$, 541.6; m/z found, 542.5 [M+H]$^+$. $^1$H NMR (400 MHz, CD$_3$OD): δ 8.84 (d, J=5.2 Hz, 1H), 8.41 (s, 1H), 8.27 (d, J=5.6 Hz, 1H), 8.08-7.96 (m, 3H), 7.52-7.41 (m, 4H), 6.24 (d, J=5.6 Hz, 1H), 4.50-4.36 (m, 2H), 3.75 (s, 2H), 2.65 (s, 3H), 2.16-1.96 (m, 2H), 1.95-1.82 (m, 1H), 1.80-1.58 (m, 3H).

Example 287: N-((1R,2S)-2-Aminocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide

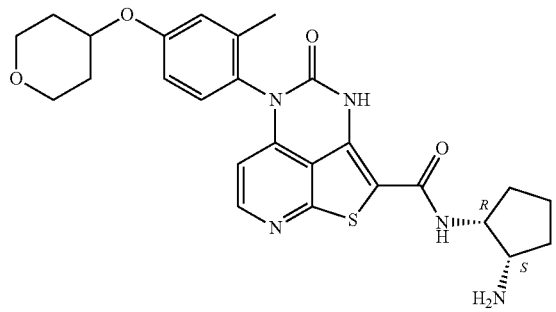

The title compound was prepared in a manner analogous to Example 1, Step A, using 5-(2-methyl-4-((tetrahydro-2H-pyran-4-yl)oxy)phenyl)-4-oxo-4,5-dihydro-3H-1-thia-3,5,8-triazaacenaphthylene-2-carboxylic acid (Intermediate 12) and tert-butyl N-[(1S,2R)-2-aminocyclopentyl]carbamate in place of tert-butyl ((1S,4S)-4-aminocyclohexyl)carbamate. MS (ESI): mass calcd. for $C_{26}H_{29}N_5O_4S$, 507.6; m/z found, 508.2 [M+H]$^+$. $^1$H NMR (400 MHz, CD$_3$OD): δ 8.50 (s, 1H), 8.33-8.27 (m, 1H), 7.25-7.15 (m, 1H), 7.06-6.94 (m, 2H), 6.04-5.99 (m, 1H), 4.70-4.60 (m, 1H), 4.52-4.41 (m, 1H), 4.01-3.90 (m, 2H), 3.79-3.69 (m, 1H), 3.65-3.56 (m, 2H), 2.19-2.02 (m, 7H), 2.01-1.86 (m, 2H), 1.81-1.66 (m, 4H).

Example 288: N-((1R,2S)-2-Aminocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide

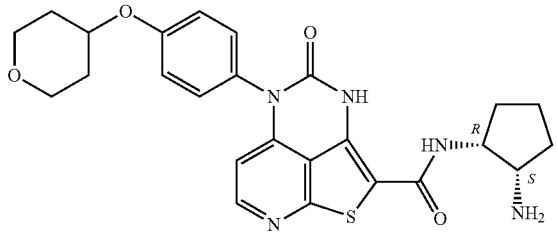

The title compound was prepared in a manner analogous to Example 1, Step A, using 5-(2-methyl-4-((tetrahydro-2H-pyran-4-yl)oxy)phenyl)-4-oxo-4,5-dihydro-3H-1-thia-3,5,8-triazaacenaphthylene-2-carboxylic acid (Intermediate 12) and tert-butyl N-[(1S,2R)-2-aminocyclopentyl]carbamate. MS (ESI): mass calcd. for $C_{25}H_{27}N_5O_4S$, 493.6; m/z found, 494.4 [M+H]$^+$. $^1$H NMR (400 MHz, CD$_3$OD): δ 8.46 (s, 1H), 8.29 (d, J=5.6 Hz, 1H), 7.37-7.21 (m, 2H), 7.19-7.12 (m, 2H), 6.14 (d, J=5.6 Hz, 1H), 4.71-4.60 (m, 1H), 4.52-4.41 (m, 1H), 4.04-3.90 (m, 2H), 3.80-3.68 (m, 1H), 3.67-3.52 (m, 2H), 2.25-2.02 (m, 4H), 2.02-1.84 (m, 2H), 1.81-1.63 (m, 4H).

Example 289: racemic cis N-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide

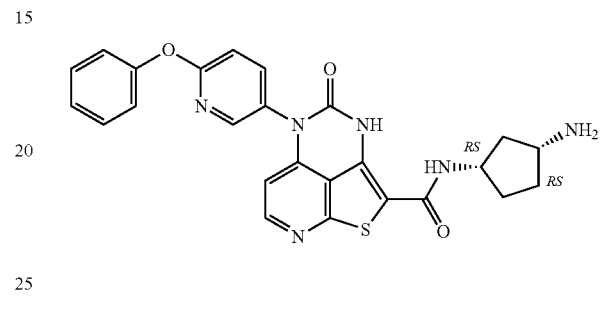

The title compound was prepared in a manner analogous to Example 104, Steps A-B, using 4-oxo-5-(6-phenoxy pyridin-3-yl)-4,5-dihydro-3H-1-thia-3,5,8-triazaacenaphthylene-2-carbonyl chloride (Intermediate 10) and racemic tert-butyl((1S,3R)-3-aminocyclopentyl)carbamate. MS (ESI): mass calcd. for $C_{25}H_{22}N_6O_3S$, 486.6; m/z found, 486.9 [M+H]$^+$. $^1$H NMR (500 MHz, CDCl$_3$): δ 8.31 (d, J=5.5 Hz, 1H), 8.22-8.16 (m, 1H), 7.85-7.79 (m, 1H), 7.71 (t, J=6.4 Hz, 1H), 7.48-7.40 (m, 2H), 7.29-7.17 (m, 3H), 7.10 (dd, J=8.7, 0.7 Hz, 1H), 6.12 (d, J=5.5 Hz, 1H), 4.55 (q, J=7.1 Hz, 1H), 3.94 (s, 3H), 3.75 (tt, J=5.5, 2.2 Hz, 2H), 3.48 (s, 1H), 2.11-1.89 (m, 4H).

Example 290: racemic trans N-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide

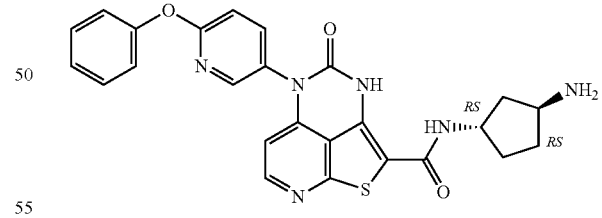

The title compound was prepared in a manner analogous to Example 104, Steps A-B, using 4-oxo-5-(6-phenoxy pyridin-3-yl)-4,5-dihydro-3H-1-thia-3,5,8-triazaacenaphthylene-2-carbonyl chloride (Intermediate 10) and racemic tert-butyl N-[(1R,3R)-3-aminocyclopentyl]carbamate. MS (ESI): mass calcd. for $C_{25}H_{22}N_6O_3S$, 486.6; m/z found, 486.9 [M+H]$^+$. $^1$H NMR (500 MHz, CDCl$_3$): δ 8.33 (d, J=5.5 Hz, 1H), 8.18 (q, J=2.8, 2.3 Hz, 1H), 7.73 (t, J=7.8 Hz, 1H), 7.46 (t, J=7.9 Hz, 2H), 7.29 (d, J=7.4 Hz, 1H), 7.21 (d, J=8.0 Hz, 2H), 7.12 (d, J=8.7 Hz, 1H), 6.17 (d, J=5.6 Hz, 1H), 4.52 (p, J=7.1 Hz, 1H), 3.84-3.68 (m, 5H), 2.28 (dq, J=18.3, 7.2 Hz, 2H), 2.19-2.04 (m, 2H), 1.71 (tt, J=13.1, 4.7 Hz, 2H).

Example 291: N-((1R,2S)-2-Acrylamidocyclohexyl)-4-oxo-5-(5-phenoxypyridin-2-yl)-4,5-dihydro-3H-1-thia-3,5,8-triazaacenaphthylene-2-carboxamide

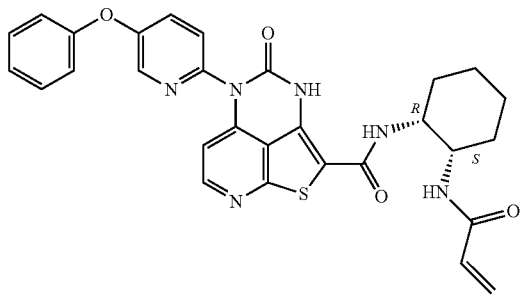

Step A. N-((1R,2S)-2-aminocyclohexyl)-4-oxo-5-(5-phenoxypyridin-2-yl)-4,5-dihydro-3H-1-thia-3,5,8-triazaacenaphthylene-2-carboxamide The title compound was prepared in a manner analogous to Example 166, Steps A-B, using 4-oxo-5-(5-phenoxypyridin-2-yl)-4,5-dihydro-3H-1-thia-3,5,8-triazaacenaphthylene-2-carboxylic acid (Intermediate 26) and using tert-butyl ((1S,2R)-2-aminocyclohexyl)carbamate.

Step B. N-((1R,2S)-2-Acrylamidocyclohexyl)-4-oxo-5-(5-phenoxypyridin-2-yl)-4,5-dihydro-3H-1-thia-3,5,8-triazaacenaphthylene-2-carboxamide The title compound was prepared in a manner analogous to Example 337 using N-((1R,2S)-2-aminocyclohexyl)-4-oxo-5-(5-phenoxypyridin-2-yl)-4,5-dihydro-3H-1-thia-3,5,8-triazaacenaphthylene-2-carboxamide. MS (ESI): mass calcd. for $C_{29}H_{26}N_6O_4S$, 554.6; m/z found, 555.1 $[M+H]^+$. $^1$H NMR (400 MHz, CDCl$_3$): δ 9.48 (s, 1H), 8.47-8.33 (m, 2H), 7.58-7.35 (m, 4H), 7.25-7.21 (m, 1H), 7.20-6.90 (m, 2H), 6.48-6.06 (m, 4H), 5.73 (dd, J=10.3, 1.4 Hz, 1H), 4.38-4.10 (m, 2H), 1.97-1.47 (m, 9H).

Example 292: N-((1RS,2RS)-2-Acrylamidocyclopentyl)-5-(2-methyl-6-phenoxypyridin-3-yl)-4-oxo-4,5-dihydro-3H-1-thia-3,5,8-triazaacenaphthylene-2-carboxamide

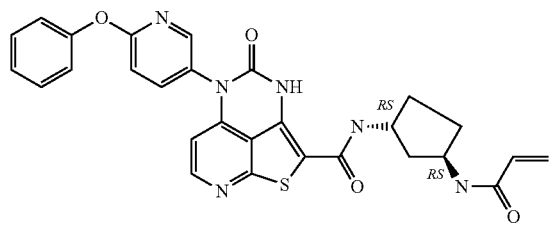

The title compound was prepared in a manner analogous to Example 337, using racemic trans N-((1RS,3RS)-3-aminocyclopentyl)-4-oxo-5-(6-phenoxypyridin-3-yl)-4,5-dihydro-3H-1-thia-3,5,8-triazaacenaphthylene-2-carboxamide (Example 290). MS (ESI): mass calcd. for $C_{29}H_{26}N_6O_4S$, 554.6; m/z found, 555.0 $[M+H]^+$. $^1$H NMR (600 MHz, CD$_3$OD): δ 8.34 (s, 1H), 7.76 (d, J=8.7 Hz, 1H), 7.51-7.35 (m, 2H), 7.29-7.15 (m, 3H), 6.90 (d, J=8.5 Hz, 1H), 6.36-6.07 (m, 3H), 5.73-5.53 (m, 1H), 4.49-4.37 (m, 2H), 2.24 (s, 3H), 2.19-1.64 (m, 8H).

Example 293: N-((1RS,3RS)-3-Aminocyclopentyl)-5-(4-methyl-6-phenoxypyridin-3-yl)-4-oxo-4,5-dihydro-3H-1-thia-3,5,8-triazaacenaphthylene-2-carboxamide

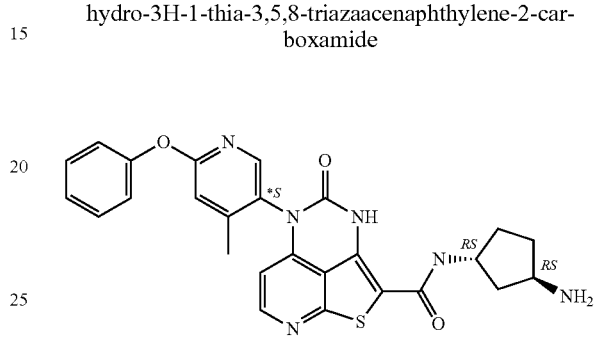

The title compound was prepared in a manner analogous to Example 166, Step A-B, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl N-[(1R,3R)-3-aminocyclopentyl]carbamate in Step A. MS (ESI): mass calcd. for $C_{26}H_{24}N_6O_3S$, 500.6; m/z found, 500.9 $[M+H]^+$. $^1$H NMR (400 MHz, CDCl$_3$): δ 8.24 (dd, J=5.1, 2.8 Hz, 1H), 8.06 (d, J=7.5 Hz, 1H), 7.45-7.35 (m, 2H), 7.26-7.11 (m, 3H), 6.90 (s, 1H), 6.68 (s, 1H), 5.99-5.92 (m, 1H), 4.97 (s, 2H), 4.57-4.48 (m, 1H), 3.64 (s, 1H), 3.43 (s, 4H), 2.24 (s, 1H), 2.16 (d, J=3.6 Hz, 3H), 1.98 (d, J=19.7 Hz, 2H).

Example 294: N-((1RS,3RS)-3-Acrylamidocyclopentyl)-4-oxo-5-(6-phenoxypyridin-3-yl)-4,5-dihydro-3H-1-thia-3,5,8-triazaacenaphthylene-2-carboxamide

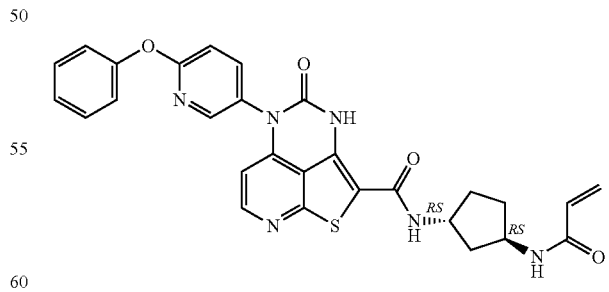

The title compound was prepared in a manner analogous to Example 1, Step B, using N-((1RS,3RS)-3-amino cyclopentyl)-4-oxo-5-(6-phenoxypyridin-3-yl)-4,5-dihydro-3H-1-thia-3,5,8-triazaacenaphthylene-2-carboxamide (Example 290). MS (ESI): mass calcd. for $C_{28}H_{24}N_6O_4S$, 540.6; m/z found, 541.0 $[M+H]^+$. $^1$H NMR (500 MHz, CDCl$_3$): δ 8.26

(d, J=68.3 Hz, 1H), 7.76 (d, J=9.3 Hz, 1H), 7.65-7.02 (m, 4H), 6.18 (p, J=6.3, 4.9 Hz, 1H), 4.65-4.08 (m, 7H), 3.70-3.33 (m, 5H), 2.50 (dt, J=125.7, 7.2 Hz, 1H), 2.24 (ddq, J=24.3, 13.3, 7.4, 6.3 Hz, 1H), 2.11-1.82 (m, 1H), 1.74-1.40 (m, 1H), 1.41-1.15 (m, 1H).

Example 295: N-((1R,2S)-2-Acrylamidocyclohexyl)-4-oxo-5-(5-phenoxypyrazin-2-yl)-4,5-dihydro-3H-1-thia-3,5,8-triazaacenaphthylene-2-carboxamide

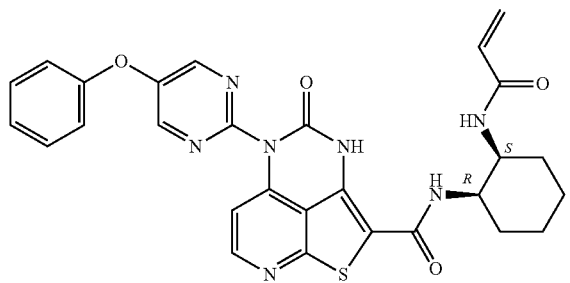

The title compound was prepared in a manner analogous to Example 1, Step A using 4-oxo-5-(5-phenoxypyrazin-2-yl)-4,5-dihydro-3H-1-thia-3,5,8-triazaacenaphthylene-2-carboxylic acid (Example 201, product from Step A) and N-[(1S,2R)-2-aminocyclohexyl]prop-2-enamide (Intermediate 40) (no deprotection HCl/MeOH). MS (ESI): mass calcd. for $C_{28}H_{25}N_7O_4S$, 555.6; m/z found, 556.2 [M+H]$^+$. $^1$H NMR (400 MHz, DMSO-d$_6$): δ 10.15 (s, 1H), 8.61 (s, 1H), 8.47-8.25 (m, 2H), 7.97-7.77 (m, 2H), 7.56-7.40 (m, 2H), 7.36-7.18 (m, 3H), 6.54-6.28 (m, 2H), 6.20-6.04 (m, 1H), 5.66-5.50 (m, 1H), 4.29-4.14 (m, 1H), 4.08-3.94 (m, 1H), 1.77-1.61 (m, 4H), 1.59-1.49 (m, 2H), 1.45-1.28 (m, 2H).

Example 296: N-((1R,2S)-2-acrylamidocyclopentyl)-4-oxo-5-(5-phenoxypyrimidin-2-yl)-4,5-dihydro-3H-1-thia-3,5,8-triazaacenaphthylene-2-carboxamide

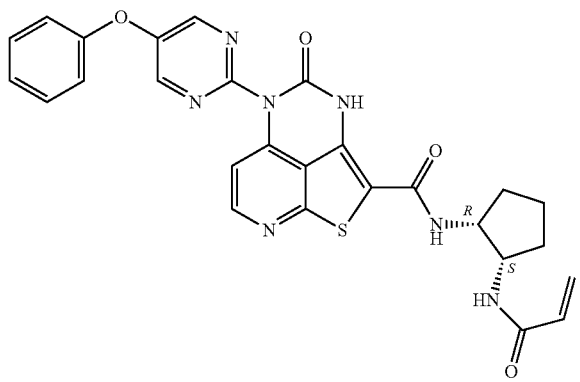

The title compound was prepared in a manner analogous to Example 1, Step A using 4-oxo-5-(5-phenoxypyrimidin-2-yl)-4,5-dihydro-3H-1-thia-3,5,8-triazaacenaphthylene-2-carboxylic acid (Intermediate 14) and N-[(1S,2R)-2-aminocyclopentyl]prop-2-enamide (Intermediate 36) (no HCl/MeOH deprotection). MS (ESI): mass calcd. for $C_{27}H_{23}N_7O_4S$, 541.6; m/z found, 542.4 [M+H]$^+$. $^1$H NMR (400 MHz, CD$_3$OD): δ 8.68 (s, 2H), 8.30-8.26 (m, 1H), 7.55-7.46 (m, 2H), 7.33-7.22 (m, 3H), 6.30-6.15 (m, 3H), 5.63-5.57 (m, 1H), 4.49-4.33 (m, 2H), 2.22-1.99 (m, 2H), 1.97-1.82 (m, 1H), 1.79-1.59 (m, 3H).

Example 297: N-((1R,2S)-2-Acrylamidocyclohexyl)-4-oxo-5-(5-phenoxypyrimidin-2-yl)-4,5-dihydro-3H-1-thia-3,5,8-triazaacenaphthylene-2-carboxamide

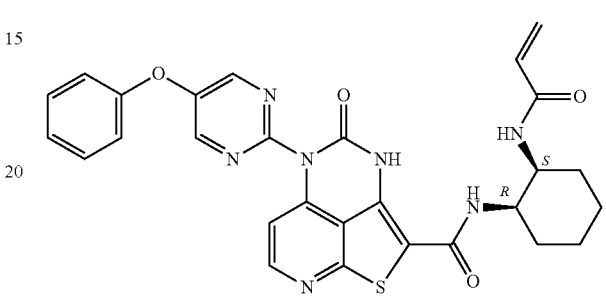

The title compound was prepared in a manner analogous to Example 1, Step A, using 4-oxo-5-(5-phenoxypyrimidin-2-yl)-4,5-dihydro-3H-1-thia-3,5,8-triazaacenaphthylene-2-carboxylic acid (Intermediate 14) and N-[(1S,2R)-2-aminocyclohexyl]prop-2-enamide (Intermediate 40), no HCl/MeOH deprotection. MS (ESI): mass calcd. for $C_{28}H_{25}N_7O_4S$, 555.6; m/z found, 556.4 [M+H]$^+$. $^1$H NMR (400 MHz, CD$_3$OD): δ 8.68 (s, 2H), 8.32-8.26 (m, 1H), 7.55-7.46 (m, 2H), 7.35-7.22 (m, 3H), 6.47-6.35 (m, 1H), 6.31-6.21 (m, 2H), 5.69-5.59 (m, 1H), 4.58-4.37 (m, 1H), 4.21-4.09 (m, 1H), 1.83-1.49 (m, 8H).

Example 298: N-((1R,2S)-2-Acrylamidocyclopentyl)-5-(S)-(6-isobutyl-4-methylpyridin-3-yl)-4-oxo-4,5-dihydro-3H-1-thia-3,5,8-triazaacenaphthylene-2-carboxamide

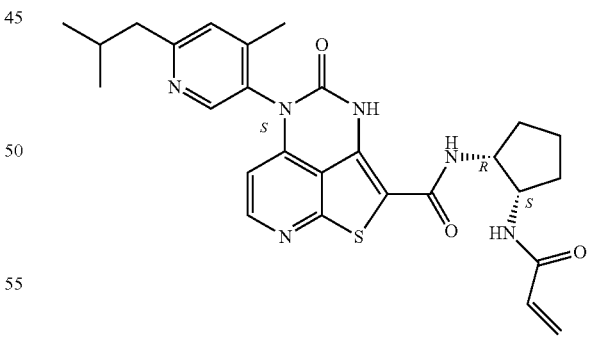

Step A: 5-(*S)-(6-Isobutyl-4-methylpyridin-3-yl)-4-oxo-4,5-dihydro-3H-1-thia-3,5,8-triazaacenaphthylene-2-carboxylic acid The title compound was prepared by treating 5-(6-isobutyl-4-methylpyridin-3-yl)-4-oxo-4,5-dihydro-3H-1-thia-3,5, 8-triazaacenaphthylene-2-carboxylic acid (Intermediate 18) with CHIRAL SEPARATION METHOD 2 to obtain the *S atropisomer as the isopropylamine salt. Salt removal procedure: The isopropylamine salt of 5-(*S)-(6-Isobutyl-4-methylpyridin-3-yl)-4-oxo-4,5-dihydro-3H-1-thia-3,5,8-triazaacenaphthylene-2-carboxylic acid (73 g, 165 mmol) was dissolved in MeOH (438 mL) and H$_2$O (219 mL). LiOH—H$_2$O (34.7 g, 826 mmol) was added and the mixture was stirred at rt for 1 h. The mixture was concentrated to removed half of the original volume, the solution was cooled to 0° C., and the pH was adjusted to 4-5 by adding 1 N HCl slowly. The resulting precipitate was filtered and dried under vacuum to give the title compound (56.1 g, 88%) as a yellow solid.

Step B: N-((1R,2S)-2-Acrylamidocyclopentyl)-5-(S)-(6-isobutyl-4-methylpyridin-3-yl)-4-oxo-4,5-dihydro-3H-1-thia-3,5,8-triazaacenaphthylene-2-carboxamide To a round bottom flask were added 5-(*S)-(6-isobutyl-4-methylpyridin-3-yl)-4-oxo-4,5-dihydro-3H-1-thia-3,5,8-triazaacenaphthylene-2-carboxylic acid (1.0 g, 2.62 mmol), HATU (1.29 g, 3.40 mmol), TEA (0.397 g, 3.93 mmol) and DMF (10 mL). The mixture was stirred for 10 minutes at room temperature, and then added to a stirred solution N-((1S,2R)-2-aminocyclopentyl)acrylamide (Intermediate 36, 0.53 g, 3.44 mmol) and TEA (0.529 mg, 5.24 mmol) in DMF (4 mL) and the mixture was stirred for 30 minutes at room temperature. The reaction mixture was treated with water (50 mL), the precipitate was isolated by filtration and dried under vacuum. The crude product was purified by FCC (SiO$_2$, eluting with a 3:100 mixture of MeOH:DCM) to afford the title compound (0.81 g, 58%) as a white solid. Absolute stereochemical configuration of the title compound was confirmed via single crystal X-ray analysis. MS (ESI): mass calcd. for C$_{27}$H$_{30}$N$_6$O$_3$S, 518.6; m/z found, 519.1 [M+H]$^+$. $^1$H NMR (400 MHz, CDCl$_3$): δ 9.65 (s, 1H), 8.40 (s, 1H), 8.33 (d, J=5.5 Hz, 1H), 7.19 (s, 1H), 7.05-6.95 (m, 2H), 6.32 (dd, J=17.0, 1.7 Hz, 1H), 6.19 (dd, J=17.0, 10.1 Hz, 1H), 5.93 (d, J=5.5 Hz, 1H), 5.64 (dd, J=10.2, 1.6 Hz, 1H), 4.50-4.30 (m, 2H), 2.70 (d, J=7.1 Hz, 2H), 2.27-2.02 (m, 6H), 1.92-1.61 (m, 4H), 0.99 (d, J=6.6 Hz, 6H).

Example 299: N-((1R,2S)-2-Acrylamidocyclohexyl)-5-(*S)-(6-isopropoxy-4-methylpyridin-3-yl)-4-oxo-4,5-dihydro-3H-1-thia-3,5,8-triazaacenaphthylene-2-carboxamide

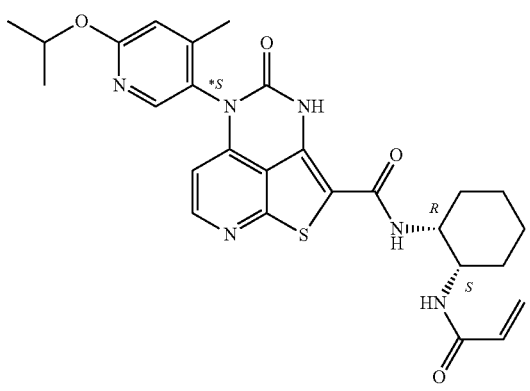

Chiral SFC purification of N-((1R,2S)-2-Acrylamidocyclohexyl)-5-(6-isopropoxy-4-methylpyridin-3-yl)-4-oxo-4, 5-dihydro-3H-1-thia-3,5,8-triazaacenaphthylene-2-carboxamide (Example 222) afforded the title compound (Stationary phase: Chiralpak AS-H 5 μm 250*20 mm, Mobile phase: 70% CO$_2$, 30% MeOH). MS (ESI): mass calcd. for C$_{27}$H$_{30}$N$_6$O$_4$S, 534.6; m/z found, 535.2 [M+H]$^+$. $^1$H NMR (500 MHz, CD$_3$OD): δ 8.33 (d, J=5.5 Hz, 1H), 8.06 (s, 1H), 6.81 (s, 1H), 6.42 (dd, J=17.0, 10.2 Hz, 1H), 6.27 (dd, J=17.0, 1.8 Hz, 1H), 6.11 (d, J=5.5 Hz, 1H), 5.67 (dd, J=10.3, 1.8 Hz, 1H), 5.35-5.25 (m, 1H), 4.44 (s, 1H), 4.16 (d, J=10.6 Hz, 1H), 2.14 (s, 3H), 1.86-1.61 (m, 6H), 1.60-1.46 (m, 2H), 1.36 (dd, J=6.1, 3.8 Hz, 6H).

Example 300: N-((1R,2S)-2-Acrylamidocyclopentyl)-4-oxo-5-(*S)-(4-(pyridin-3-yloxy)phenyl)-4,5-dihydro-3H-1-thia-3,5,8-triazaacenaphthylene-2-carboxamide

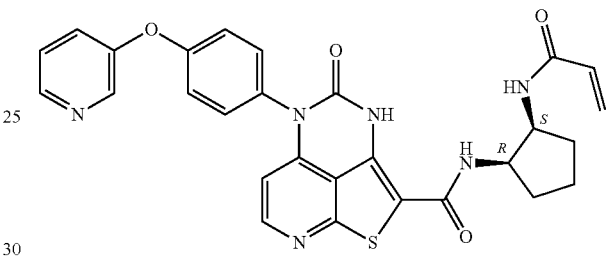

Step A. 3-(4-Nitrophenoxy)pyridine

The title compound was prepared using analogous conditions described in Intermediate 1, Step A, using 1-fluoro-4-nitrobenzene and pyridin-3-ol.

Step B. 4-Oxo-5-(4-(pyridin-3-yloxy)phenyl)-4,5-dihydro-3H-1-thia-3,5,8-triazaacenaphthylene-2-carboxylic acid The title compound was prepared in a manner analogous to Intermediate 25, Steps B-C, using 3-(4-nitrophenoxy)pyridine.

Step C. N-((1R,2S)-2-Acrylamidocyclopentyl)-5-(2-methyl-4-(pyridin-3-yloxy)phenyl)-4-oxo-4,5-dihydro-3H-1-thia-3,5,8-triazaacenaphthylene-2-carboxamide The title compound was prepared in a manner analogous to Example 1, Step A, using 4-oxo-5-(4-(pyridin-3-yloxy)phenyl)-4,5-dihydro-3H-1-thia-3,5,8-triazaacenaphthylene-2-carboxylic acid and N-[(1S,2R)-2-aminocyclopentyl]prop-2-enamide (Intermediate 36) (no HCl/MeOH deprotection). MS (ESI): mass calcd. for C$_{28}$H$_{24}$N$_6$O$_4$S, 540.6; m/z found, 541.1 [M+H]$^+$. $^1$H NMR (400 MHz, CD$_3$OD): δ 8.44-8.40 (m, 1H), 8.38-8.34 (m, 1H), 8.33-8.28 (m, 1H), 7.62-7.57 (m, 1H), 7.50-7.44 (m, 3H), 7.29-7.25 (m, 2H), 6.32-6.24 (m, 1H), 6.23-6.16 (m, 2H), 5.64-5.59 (m, 1H), 4.47-4.37 (m, 2H), 2.16-2.01 (m, 2H), 1.97-1.86 (m, 1H), 1.82-1.61 (m, 3H).

Example 301: N-((1R,2R)-2-Acrylamidocyclopentyl)-5-(*S)-(2-methyl-6-phenoxypyridin-3-yl)-4-oxo-4,5-dihydro-3H-1-thia-3,5,8-triazaacenaphthylene-2-carboxamide

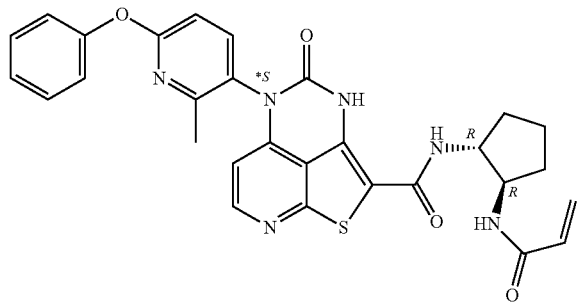

Step A. N-((1R,2R)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1R,2R)-2-aminocyclopentyl]carbamate, and substituting diisopropylethylamine for triethylamine. Step B. N-((1R,2R)-2-Acrylamidocyclopentyl)-5-(*S)-(2-methyl-6-phenoxypyridin-3-yl)-4-oxo-4,5-dihydro-3H-1-thia-3,5,8-triazaacenaphthylene-2-carboxamide. The title compound was prepared in a manner analogous to Example 337, using N-((1R,2R)-2-aminocyclopentyl)-5-(2-methyl-6-phenoxypyridin-3-yl)-4-oxo-4,5-dihydro-3H-1-thia-3,5,8-triazaacenaphthylene-2-carboxamide. MS (ESI): mass calcd. for $C_{29}H_{26}N_6O_4S$, 554.6; m/z found, 555.0 [M+H]$^+$. $^1$H NMR (500 MHz, CDCl$_3$): δ 9.55 (s, 1H), 8.37 (d, J=5.4 Hz, 1H), 7.53 (d, J=8.6 Hz, 1H), 7.48-7.38 (m, 2H), 7.26-7.10 (m, 3H), 6.93-6.73 (m, 2H), 6.45-6.26 (m, 2H), 1.72-1.70 (m, OH), 6.19-5.96 (m, 2H), 5.67 (dd, J=10.3, 1.4 Hz, 1H), 4.27-3.98 (m, 2H), 2.43-2.33 (m, 1H), 2.33-2.22 (m, 4H), 1.91-1.81 (m, 2H), 1.66-1.43 (m, 2H).

Example 302: N-((1R,2S)-2-Acrylamidocyclohexyl)-4-oxo-5-(2-phenoxypyrimidin-5-yl)-4,5-dihydro-3H-1-thia-3,5,8-triazaacenaphthylene-2-carboxamide

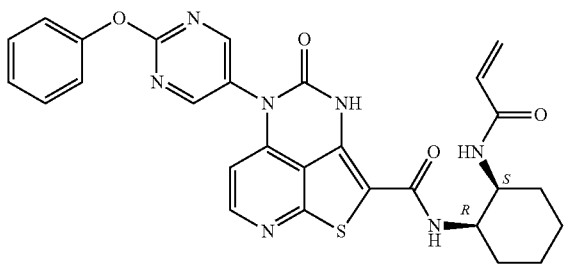

Step A. 5-Nitro-2-phenoxypyrimidine

The title compound was prepared in a manner analogous to Intermediate 24, Step A, using 2-chloro-5-nitropyrimidine and phenol, and substituting TEA or DIEA for Cs$_2$CO$_3$.

Step B. 4-Oxo-5-(2-phenoxypyrimidin-5-yl)-4,5-dihydro-3H-1-thia-3,5,8-triazaacenaphthylene-2-carboxylic acid The title compound was prepared in a manner analogous to Intermediate 16, steps B-C, using 5-nitro-2-phenoxypyrimidine in Step B.

Step C. N-((1R,2S)-2-Acrylamidocyclohexyl)-4-oxo-5-(2-phenoxypyrimidin-5-yl)-4,5-dihydro-3H-1-thia-3,5,8-triazaacenaphthylene-2-carboxamide The title compound was prepared in a manner analogous to Example 1, Step A, using N-[(1S,2R)-2-aminocyclohexyl]prop-2-enamide (Intermediate 40) and 4-oxo-5-(2-phenoxypyrimidin-5-yl)-4,5-dihydro-3H-1-thia-3,5,8-triazaacenaphthylene-2-carboxylic acid (no HCl/MeOH deprotection). MS (ESI): mass calcd. for $C_{28}H_{25}N_7O_4S$, 555.6; m/z found, 556.3 [M+H]$^+$. $^1$H NMR (400 MHz, DMSO-d$_6$): δ 10.12 (s, 1H), 8.76 (s, 2H), 8.37-8.32 (m, 1H), 7.90-7.81 (m, 2H), 7.50-7.42 (m, 2H), 7.31-7.24 (m, 3H), 6.44-6.33 (m, 2H), 6.16-6.07 (m, 1H), 5.62-5.56 (m, 1H), 4.24-4.17 (m, 1H), 4.05-3.97 (m, 1H), 1.74-1.52 (m, 6H), 1.45-1.31 (m, 2H).

Example 303: N-((1R,2S)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide

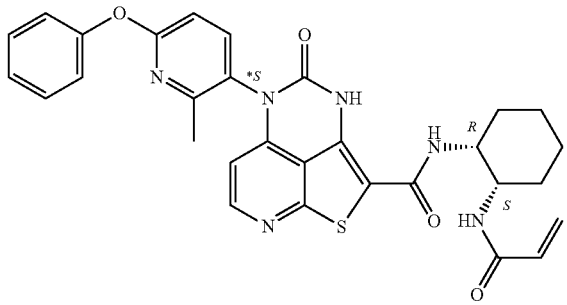

Step A. N-((1R,2S)-2-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1S,2R)-2-aminocyclohexyl]carbamate and diisopropylethylamine.

Step B. N-((1R,2S)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide The title compound was prepared in a manner analogous to Example 337. MS (ESI): mass calcd. for $C_{30}H_{28}N_6O_4S$, 568.7; m/z found, 569.1 [M+H]+. 1H NMR (500 MHz, CDCl3): δ 9.52 (s, 1H), 8.36 (d, J=5.4 Hz, 1H), 7.60-7.37 (m, 3H), 7.26-7.18 (m, 3H), 7.14-7.01 (m, 1H), 6.81 (dd, J=8.5, 0.8 Hz, 1H), 6.42 (dd, J=16.9, 1.4 Hz, 1H), 6.31 (s, 1H), 6.19 (dd, J=16.9, 10.3 Hz, 1H), 6.00 (d, J=5.5 Hz, 1H), 5.74 (dd, J=10.2, 1.4 Hz, 1H), 4.33-4.25 (m, 1H), 4.21-4.08 (m, 1H), 2.29 (s, 3H), 2.10-1.88 (m, 2H), 1.75-1.67 (m, 4H), 1.60-1.56 (m, 2H).

Example 304: N-((1R,2S)-2-Acrylamidocyclopentyl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide

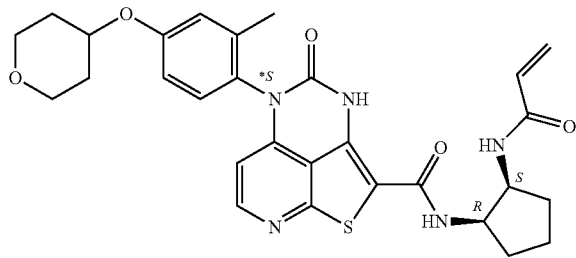

The title compound was prepared in a manner analogous to Example 1, using 5-(2-methyl-4-((tetrahydro-2H-pyran-4-yl)oxy)phenyl)-4-oxo-4,5-dihydro-3H-1-thia-3,5,8-triazaacenaphthylene-2-carboxylic acid (Intermediate 12) and tert-butyl N-[(1S,2R)-2-aminocyclopentyl]carbamate, and substituting diisopropylethylamine for triethylamine in Step A. Chiral SFC purification (Stationary phase: CHIRALCEL OD-H 5 μm 250×20 mm, Mobile phase: 65% CO2, 35% MeOH) afforded the title compound and N-((1R,2S)-2-Acrylamidocyclopentyl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide (Example 347). MS (ESI): mass calcd. for C29H31N5O5S, 561.7; m/z found, 562.3 [M+H]+. 1H NMR (400 MHz, CD3OD): δ 8.29-8.23 (m, 1H), 7.24-7.16 (m, 1H), 7.06-7.00 (m, 1H), 6.99-6.93 (m, 1H), 6.32-6.14 (m, 2H), 6.02-5.96 (m, 1H), 5.63-5.56 (m, 1H), 4.68-4.56 (m, 1H), 4.46-4.33 (m, 2H), 3.99-3.89 (m, 2H), 3.66-3.54 (m, 2H), 2.18-1.98 (m, 7H), 1.96-1.83 (m, 1H), 1.81-1.61 (m, 5H).

Example 305: N-((1R,2S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide

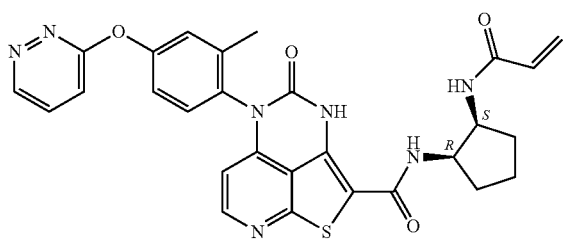

Step A. 5-(2-Methyl-4-(pyridazin-3-yloxy)phenyl)-4-oxo-4,5-dihydro-3H-1-thia-3,5,8-triazaacenaphthylene-2-carboxylic acid The title compound was prepared in a manner analogous to Intermediate 15, using 3,6-dichloropyridazine, 3-methyl-4-nitrophenol Step A, (no Cu).

Step B. N-((1R,2S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-(pyridazin-3-yloxy)phenyl)-4-oxo-4,5-dihydro-3H-1-thia-3,5,8-triazaacenaphthylene-2-carboxylic acid and N-[(1S,2R)-2-aminocyclopentyl]prop-2-enamide (Intermediate 36) (no HCl/MeOH deprotection). MS (ESI): mass calcd. for C28H25N7O4S, 555.6; m/z found, 556.1 [M+H]+. 1H NMR (400 MHz, CD3OD): δ 8.95 (d, J=4.0 Hz, 1H), 8.31 (d, J=5.5 Hz, 1H), 7.82-7.71 (m, 1H), 7.53-7.38 (m, 2H), 7.35-7.29 (m, 1H), 7.29-7.20 (m, 1H), 6.34-6.14 (m, 3H), 5.65-5.55 (m, 1H), 4.50-4.35 (m, 2H), 2.22-2.14 (m, 3H), 2.14-2.02 (m, 2H), 1.96-1.86 (m, 1H), 1.80-1.62 (m, 3H).

Example 306: N-((1*S,3*S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

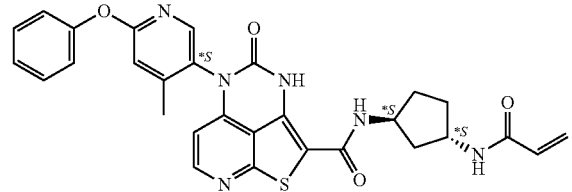

The title compound was prepared in a manner analogous to Example 166, Step C, using N-((1RS,3RS)-3-aminocyclopentyl)-5-(4-methyl-6-phenoxypyridin-3-yl)-4-oxo-4,5-dihydro-3H-1-thia-3,5,8-triazaacenaphthylene-2-carboxamide (Example 293); purification was performed via chiral SFC (Stationary phase: Chiralpak IA, 5 μm, 250×20 mm, Mobile phase: 50% CO2, 50% iPrOH). MS (ESI): mass calcd. for C29H26N6O4S, 554.6; m/z found, 555.3 [M+H]+. 1H NMR (400 MHz, CDCl3): δ 9.51 (s, 1H), 8.37 (d, J=5.4 Hz, 1H), 8.05 (s, 1H), 7.50-7.39 (m, 2H), 7.30-7.15 (m, 3H), 6.95 (d, J=1.1 Hz, 1H), 6.29 (dd, J=16.9, 1.5 Hz, 1H), 6.14-6.01 (m, 2H), 5.87 (d, J=7.2 Hz, 1H), 5.77 (d, J=7.4 Hz, 1H), 5.66 (dd, J=10.3, 1.4 Hz, 1H), 4.52 (dh, J=10.3, 7.2 Hz, 2H), 2.39-2.18 (m, 4H), 2.03 (qdd, J=13.9, 7.9, 6.6 Hz, 2H), 1.69-1.46 (m, 2H), 1.21 (d, J=6.1 Hz, 1H).

Example 307: N-((1R,2R)-2-Acrylamidocyclopentyl)-4-oxo-5-(5-phenoxypyrimidin-2-yl)-4,5-dihydro-3H-1-thia-3,5,8-triazaacenaphthylene-2-carboxamide

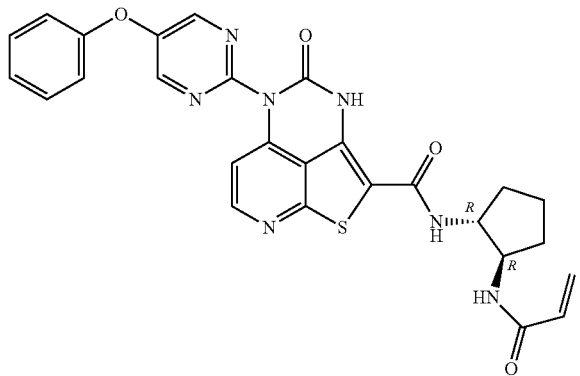

The title compound was prepared in a manner analogous to Example 1, Step A, using 4-oxo-5-(5-phenoxypyrimidin-2-yl)-4,5-dihydro-3H-1-thia-3,5,8-triazaacenaphthylene-2-carb oxy c acid (Intermediate 14) and N-[(1R,2R)-2-aminocyclopentyl]prop-2-enamide (Intermediate 46), no deprotection with MeOH/HCl. MS (ESI): mass calcd. for $C_{27}H_{23}N_7O_4S$, 541.6; m/z found, 542.1 [M+H]$^+$. $^1$H NMR (400 MHz, CD$_3$OD): δ 8.69 (s, 2H), 8.35-8.30 (m, 1H), 7.55-7.45 (m, 2H), 7.34-7.23 (m, 3H), 6.33-6.28 (m, 1H), 6.24-6.20 (m, 2H), 5.65-5.58 (m, 1H), 4.34-4.17 (m, 2H), 2.23-2.13 (m, 2H), 1.86-1.79 (m, 2H), 1.69-1.47 (m, 2H).

Example 308: N-((1*S,3*S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

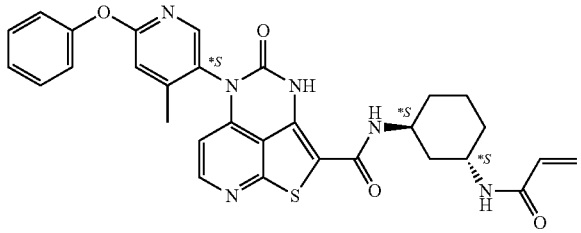

Step A. N-((1RS,3RS)-3-amino cyclohexyl)-5-(*S)-(4-methyl-6-phenoxypyridin-3-yl)-4-oxo-4,5-dihydro-3H-1-thia-3,5,8-triazaacenaphthylene-2-carboxamide The title compound was prepared in a manner analogous to Example 166, Step A-B, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl rac-[(1R,3R)-3-aminocyclohexyl]carbamate.

Step B. N-((1*S,3*S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide The title compound was prepared in a manner analogous to Example 166, Step C, using N-((1RS,3RS)-3-amino cyclohexyl)-5-(*S)-(4-methyl-6-phenoxypyridin-3-yl)-4-oxo-4,5-dihydro-3H-1-thia-3,5,8-triazaacenaphthylene-2-carboxamide; chiral SFC purification afforded the title compound and N-((1*R,3*R)-3-acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide (Example 332) (Stationary phase: CHIRALPAK AD-H, 5 μm, 250×20 mm, Mobile phase: 60% CO$_2$, 40% iPrOH) (387 mg). MS (ESI): mass calcd. for $C_{30}H_{28}N_6O_4S$, 568.7; m/z found, 569.3 [M+H]$^+$. $^1$H NMR (500 MHz, CDCl$_3$): δ 9.42 (s, 1H), 8.37 (d, J=5.5 Hz, 1H), 8.07 (s, 1H), 7.48-7.40 (m, 2H), 7.29-7.16 (m, 3H), 6.98-6.93 (m, 1H), 6.30 (dd, J=17.0, 1.5 Hz, 1H), 6.17-6.02 (m, 2H), 5.84 (d, J=7.8 Hz, 1H), 5.72 (d, J=7.5 Hz, 1H), 5.65 (dd, J=10.3, 1.5 Hz, 1H), 4.27 (dqt, J=19.9, 7.5, 3.9 Hz, 2H), 2.21 (d, J=0.8 Hz, 3H), 1.92-1.63 (m, 4H), 1.54 (dtd, J=12.2, 7.8, 4.0 Hz, 1H), 1.21 (d, J=6.1 Hz, 3H).

Example 309: N-((1R,2S)-2-Acrylamidocyclohexyl)-5-(*S)-(6-(cyclopentyloxy)-4-methylpyridin-3-yl)-4-oxo-4,5-dihydro-3H-1-thia-3,5,8-triazaacenaphthylene-2-carboxamide

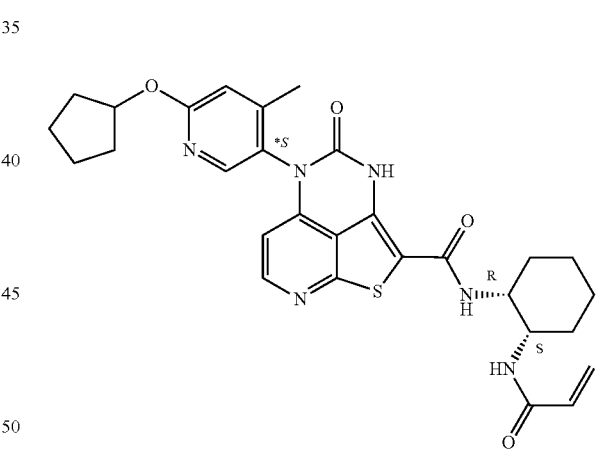

The title compound was prepared in a manner analogous to Example 166, Step A, using 5-(6-(cyclopentyloxy)-4-methylpyridin-3-yl)-4-oxo-4,5-dihydro-3H-1-thia-3,5,8-triazaacenaphthylene-2-carboxylic acid (Intermediate 25, including CHIRAL SEPARATION METHOD 1 to obtain the *S atropisomer) and using N-[(1S,2R)-2-aminocyclohexyl]prop-2-enamide (Intermediate 40). MS (ESI): mass calcd. for $C_{29}H_{32}N_6O_4S$, 560.7; m/z found, 561.2 [M+H]$^+$. $^1$H NMR (400 MHz, CD$_3$OD): δ 8.32 (d, J=5.5 Hz, 1H), 8.06 (s, 1H), 6.83 (s, 1H), 6.42 (dd, J=17.0, 10.2 Hz, 1H), 6.27 (dd, J=17.0, 1.8 Hz, 1H), 6.11 (d, J=5.6 Hz, 1H), 5.67 (dd, J=10.2, 1.9 Hz, 1H), 5.44-5.37 (m, 1H), 4.49-4.41 (m, 1H), 4.16 (d, J=10.3 Hz, 1H), 2.14 (s, 3H), 2.07-1.94 (m, 2H), 1.89-1.77 (m, 8H), 1.74-1.63 (m, 4H), 1.60-1.48 (m, 2H).

Example 310: N-((1R,2S)-2-Acrylamidocyclopentyl)-4-oxo-5-(2-phenoxypyrimidin-5-yl)-4,5-dihydro-3H-1-thia-3,5,8-triazaacenaphthylene-2-carboxamide

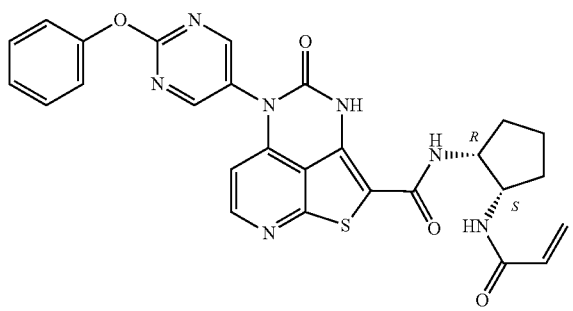

The title compound was prepared in a manner analogous to Example 1, Step A, using N-[(1S,2R)-2-aminocyclopentyl]prop-2-enamide (Intermediate 36) and N-[(1S,2R)-2-aminocyclohexyl]prop-2-enamide (Intermediate 40) and 4-oxo-5-(2-phenoxypyrimidin-5-yl)-4,5-dihydro-3H-1-thia-3,5,8-triazaacenaphthylene-2-carboxylic acid (Example 302, product from Step B) (no HCl/MeOH deprotection). MS (ESI): mass calcd. for $C_{27}H_{23}N_7O_4S$, 541.6; m/z found, 542.3 $[M+H]^+$. $^1$H NMR (400 MHz, a mixture of DMSO-$d_6$ and $CD_3OD$): δ 8.70 (s, 2H), 8.33-8.29 (m, 1H), 7.90-7.64 (m, 1H), 7.46-7.39 (m, 2H), 7.28-7.20 (m, 3H), 6.34-6.29 (m, 1H), 6.25-6.15 (m, 1H), 6.09-6.01 (m, 1H), 5.56-5.49 (m, 1H), 4.33-4.21 (m, 2H), 1.99-1.63 (m, 2H), 1.79-1.57 (m, 3H), 1.58-1.45 (m, 1H).

Example 311: N-((1R,2R)-2-Acrylamidocyclopentyl)-4-oxo-5-(5-phenoxypyrazin-2-yl)-4,5-dihydro-3H-1-thia-3,5,8-triazaacenaphthylene-2-carboxamide

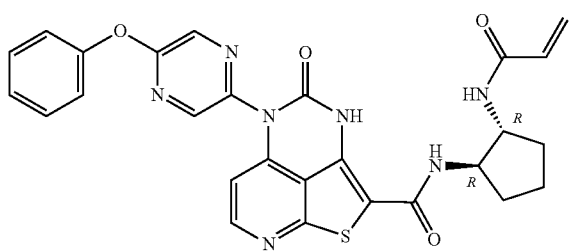

The title compound was prepared in a manner analogous to Example 1, Step A and 4-oxo-5-(5-phenoxypyrazin-2-yl)-4,5-dihydro-3H-1-thia-3,5,8-triazaacenaphthylene-2-carboxylic acid (Example 201, product from Step A) and N-[(1R,2R)-2-aminocyclopentyl]prop-2-enamide (Intermediate 46) (no HCl/MeOH deprotection). MS (ESI): mass calcd. for $C_{27}H_{23}N_7O_4S$, 541.6; m/z found, 542.2 $[M+H]^+$. $^1$H NMR (400 MHz, $CD_3OD$): δ 8.50-8.45 (m, 1H), 8.36-8.29 (m, 2H), 7.56-7.40 (m, 2H), 7.32-7.18 (m, 3H), 6.33 (d, J=5.6 Hz, 1H), 6.24-6.16 (m, 2H), 5.67-5.57 (m, 1H), 4.37-4.15 (m, 2H), 2.26-2.07 (m, 2H), 1.89-1.76 (m, 2H), 1.73-1.50 (m, 2H).

Example 312: N-((1R,2S)-2-Acrylamidocyclohexyl)-5-(*S)-(6-isobutoxy-4-methylpyridin-3-yl)-4-oxo-4,5-dihydro-3H-1-thia-3,5,8-triazaacenaphthylene-2-carboxamide

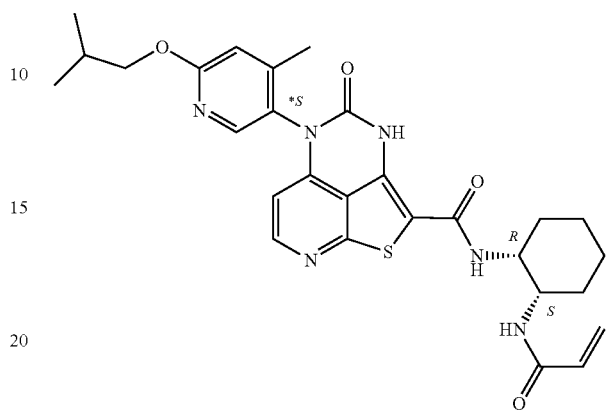

Chiral SFC (Stationary phase: Chiralpak AS-H 5 μm 250*20 mm, Mobile phase: 70% $CO_2$, 30% MeOH) of N-((1R,2S)-2-Acrylamidocyclohexyl)-5-(6-isobutoxy-4-methylpyridin-3-yl)-4-oxo-4,5-dihydro-3H-1-thia-3,5,8-triazaacenaphthylene-2-carboxamide (Example 225) afforded the title compound and N-((1R,2S)-2-acrylamidocyclohexyl)-5-(*R)-(6-isobutoxy-4-methylpyridin-3-yl)-4-oxo-4,5-dihydro-3H-1-thia-3,5,8-triazaacenaphthylene-2-carboxamide (Example 352). MS (ESI): mass calcd. for $C_{28}H_{32}N_6O_4S$, 548.7; m/z found, 549.2 $[M+H]^+$. $^1$H NMR (500 MHz, $CD_3OD$): δ 8.39-8.29 (m, 1H), 8.06 (s, 1H), 6.89 (s, 1H), 6.42 (dd, J=16.9, 10.1 Hz, 1H), 6.27 (d, J=18.0 Hz, 1H), 6.16-6.06 (m, 1H), 5.67 (d, J=11.0 Hz, 1H), 4.48-4.41 (m, 1H), 4.22-4.15 (m, 1H), 4.14-4.06 (m, 2H), 2.16 (s, 3H), 2.14-2.06 (m, 1H), 1.87-1.77 (m, 3H), 1.75-1.61 (m, 3H), 1.59-1.47 (m, 2H), 1.04 (d, J=6.7 Hz, 6H).

Example 313: N-((1S,3R)-3-Acrylamidocyclopentyl)-4-oxo-5-(5-phenoxypyridin-2-yl)-4,5-dihydro-3H-1-thia-3,5,8-triazaacenaphthylene-2-carboxamide

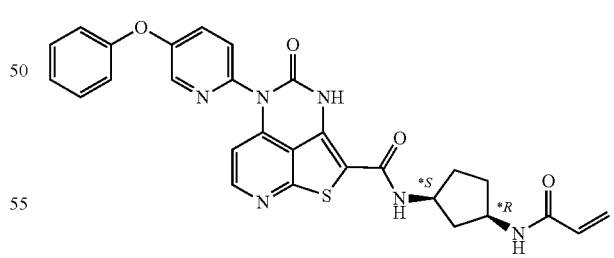

The title compound was isolated by Chiral SFC from Example 214. MS (ESI): mass calcd. for $C_{28}H_{24}N_6O_4S$, 540.6; m/z found, 541.3 $[M+H]^+$. $^1$H NMR (400 MHz, $CDCl_3$): δ 9.53 (s, 1H), 8.53-8.26 (m, 2H), 7.59-7.33 (m, 5H), 7.26-7.22 (m, 1H), 7.21-7.08 (m, 2H), 6.54-6.45 (m, 1H), 6.44-6.34 (m, 1H), 6.26-6.20 (m, 1H), 6.10 (dd, J=16.9, 10.3 Hz, 1H), 5.67 (dd, J=10.2, 1.5 Hz, 1H), 4.44-4.31 (m, 1H), 4.18-4.06 (m, 1H), 2.54-2.40 (m, 1H), 2.10-1.57 (m, 4H), 0.86-0.82 (m, 1H).

Example 314: N-((1R,2R)-2-Acrylamidocyclopentyl)-4-oxo-5-(2-phenoxypyrimidin-5-yl)-4,5-dihydro-3H-1-thia-3,5,8-triazaacenaphthylene-2-carboxamide

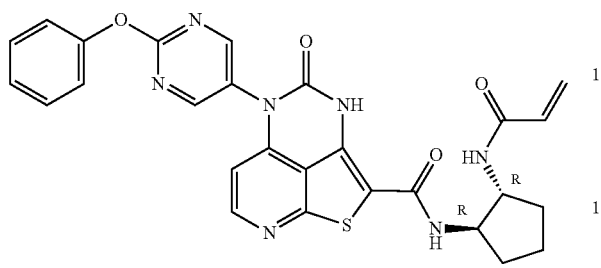

The title compound was prepared in a manner analogous to Example 1, Step A, using N-[(1R,2R)-2-aminocyclopentyl]prop-2-enamide (Intermediate 46) in place of tert-butyl ((1S,4S)-4-aminocyclohexyl)carbamate and N-[(1S,2R)-2-aminocyclohexyl]prop-2-enamide (Intermediate 40) and 4-oxo-5-(2-phenoxypyrimidin-5-yl)-4,5-dihydro-3H-1-thia-3,5,8-triazaacenaphthylene-2-carboxylic acid (Example 302, product from Step B) (no HCl/MeOH deprotection). MS (ESI): mass calcd. for $C_{27}H_{23}N_7O_4S$, 541.6; m/z found, 542.4 [M+H]$^+$. $^1$H NMR (400 MHz, DMSO-d$_6$): δ 10.28 (s, 1H), 8.75 (s, 2H), 8.44-8.00 (m, 3H), 7.53-7.36 (m, 2H), 7.36-7.18 (m, 3H), 6.34 (d, J=5.5 Hz, 1H), 6.23-6.10 (m, 1H), 6.09-5.97 (m, 1H), 5.60-5.50 (m, 1H), 4.27-4.17 (m, 1H), 4.17-4.06 (m, 1H), 2.08-1.90 (m, 2H), 1.76-1.37 (m, 4H).

Example 315: N-((1*S,3*S)-3-Acrylamidocyclohexyl)-4-oxo-5-(5-phenoxypyridin-2-yl)-4,5-dihydro-3H-1-thia-3,5,8-triazaacenaphthylene-2-carboxamide

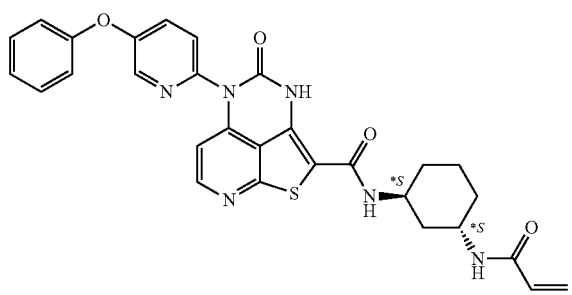 [SMILES: C=CC(=O)N[C@H]1CCC[C@H](NC(=O)c2sc3nccc4c3c2NC(=O)N4c2ccc(Oc3ccccc3)cn2)C1]

Chiral SFC Purification of N-((1RS,3RS)-3-Acrylamidocyclohexyl)-4-oxo-5-(5-phenoxypyridin-2-yl)-4,5-dihydro-3H-1-thia-3,5,8-triazaacenaphthylene-2-carboxamide (Example 216), (Stationary phase: Chiralpak IA, 5 µm, 250×20 mm, Mobile phase: 50% CO$_2$, 50% iPrOH) afforded the title compound and N-((1*R,3*R)-3-Acrylamidocyclohexyl)-4-oxo-5-(5-phenoxypyridin-2-yl)-4,5-dihydro-3H-1-thia-3,5,8-triazaacenaphthylene-2-carboxamide (Example 344). MS (ESI): mass calcd. for $C_{29}H_{26}N_6O_4S$, 554.6; m/z found, 555.3 [M+H]$^+$. $^1$H NMR (400 MHz, CDCl$_3$): δ 9.44 (s, 1H), 8.46-8.30 (m, 2H), 7.58-7.35 (m, 4H), 7.26-7.22 (m, 1H), 7.19-7.06 (m, 2H), 6.34-6.22 (m, 2H), 6.16-6.06 (m, 1H), 5.94-5.86 (m, 1H), 5.71 (d, J=7.5 Hz, 1H), 5.68-5.61 (m, 1H), 9.41-9.24 (m, OH), 4.35-4.19 (m, 2H), 1.97-1.88 (m, 2H), 1.85-1.77 (m, 5H), 1.59-1.49 (m, 1H).

Example 316: N-((1R,2R)-2-Acrylamidocyclopentyl)-5-(*S)-(4-isopropoxy-2-methylphenyl)-4-oxo-4,5-dihydro-3H-1-thia-3,5,8-triazaacenaphthylene-2-carboxamide

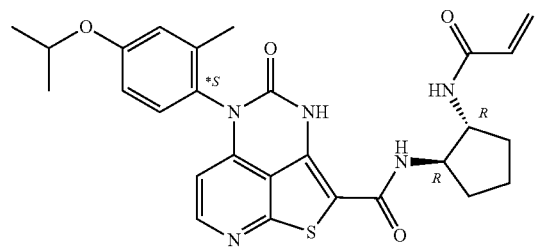

The title compound was prepared in a manner analogous to Example 1, Step A, using 5-(4-isopropoxy-2-methylphenyl)-4-oxo-4,5-dihydro-3H-1-thia-3,5,8-triazaacenaphthylene-2-carboxylic acid (Intermediate 31, including CHIRAL SEPARATION METHOD 1 to obtain the *S atropisomer) and N-[(1R,2R)-2-aminocyclopentyl]prop-2-enamide (Intermediate 46), no HCl/MeOH deprotection. MS (ESI): mass calcd. for $C_{27}H_{29}N_5O_4S$, 519.6; m/z found, 520.3 [M+H]$^+$. $^1$H NMR (400 MHz, DMSO-d$_6$): δ 10.13 (s, 1H), 8.32-8.23 (m, 2H), 8.22-8.12 (br, 1H), 7.20 (d, J=8.6 Hz, 1H), 6.97-6.91 (m, 1H), 6.89-6.82 (m, 1H), 6.22-6.11 (m, 1H), 6.08-6.01 (m, 1H), 5.86 (d, J=5.4 Hz, 1H), 5.60-5.50 (m, 1H), 4.67-4.56 (m, 1H), 4.27-4.08 (m, 2H), 2.07-1.90 (m, 5H), 1.72-1.61 (m, 2H), 1.61-1.50 (m, 1H), 1.49-1.36 (m, 1H), 1.26 (d, J=6.0 Hz, 6H).

Example 317: 5-([2,3'-Bipyridin]-4-yl)-N-((1R,2S)-2-acrylamidocyclopentyl)-4-oxo-4,5-dihydro-3H-1-thia-3,5,8-triazaacenaphthylene-2-carboxamide

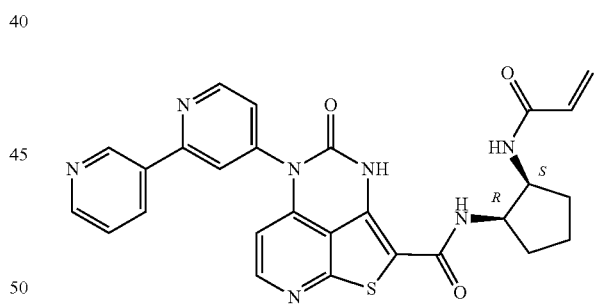

Step A. 5-([2,3'-Bipyridin]-4-yl)-4-oxo-4,5-dihydro-3H-1-thia-3,5,8-triazaacenaphthylene-2-carboxylic acid The title compound was prepared in a manner analogous to Intermediate 19, Method A, using pyridin-3-ylboronic acid and 2-chloropyridin-4-amine, and substituting PdCl$_2$(PPh$_3$)$_2$ for Pd(OAc)$_2$, in Step A.

Step B. 5-([2,3'-Bipyridin]-4-yl)-N-((1R,2S)-2-acrylamidocyclopentyl)-4-oxo-4,5-dihydro-3H-1-thia-3,5,8-triazaacenaphthylene-2-carboxamide The title compound was prepared in a manner analogous to Example 1, Step A, using 5-([2,3'-bipyridin]-4-yl)-4-oxo- 4,5-dihydro-3H-1-thia-3,5,8-triazaacenaphthylene-2-carboxylic acid and N-((1S,2R)-2-aminocyclopentyl)acrylamide (Intermediate 36), no HCl/MeOH deprotection. MS (ESI): mass calcd. for $C_{27}H_{23}N_7O_3S$, 525.6; m/z found, 526.2 $[M+H]^+$. $^1$H NMR (400 MHz, $CD_3OD$): δ 9.31-9.19 (m, 1H), 8.98-8.86 (m, 1H), 8.65-8.56 (m, 1H), 8.54-8.47 (m, 1H), 8.35-8.26 (m, 1H), 8.21-8.11 (m, 1H), 7.61-7.51 (m, 2H), 6.34-6.23 (m, 2H), 6.23-6.16 (m, 1H), 5.67-5.55 (m, 1H), 4.46-4.35 (m, 2H), 2.13-2.00 (m, 2H), 1.96-1.85 (m, 1H), 1.80-1.60 (m, 3H).

Example 318: N-((1*R,2*S)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide

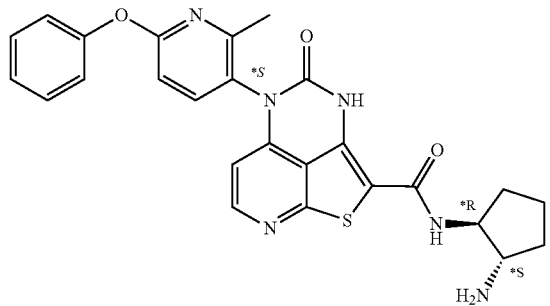

The title compound was prepared in a manner analogous to Example 1, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl ((1S,2R)-2-aminocyclopentyl)carbamate. MS (ESI): mass calcd. for $C_{26}H_{24}N_6O_3S$, 500.6; m/z found, 501.0 $[M+H]^+$. $^1$H NMR (500 MHz, $CDCl_3$): δ 9.53 (s, 1H), 8.36 (d, J=5.5 Hz, 1H), 7.52 (d, J=8.5 Hz, 1H), 7.46-7.36 (m, 2H), 7.28-7.16 (m, 2H), 6.97 (s, 1H), 6.84-6.76 (m, 1H), 6.00 (d, J=5.5 Hz, 1H), 4.69-4.60 (m, 1H), 4.27-4.14 (m, 1H), 4.12-4.04 (m, 1H), 2.29 (s, 3H), 2.12-2.01 (m, 1H), 1.91-1.55 (m, 5H), 1.49 (s, 9H).

Example 319: N-((1S,3R)-3-Acrylamidocyclopentyl)-4-oxo-5-(2-phenoxypyrimidin-5-yl)-4,5-dihydro-3H-1-thia-3,5,8-triazaacenaphthylene-2-carboxamide

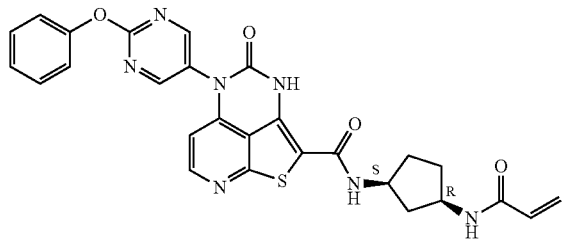

The title compound was prepared in a manner analogous to Example 337, using tert-butyl N-[(1R,3S)-3-aminocyclopentyl]carbamate and 4-oxo-5-(2-phenoxypyrimidin-5-yl)-4,5-dihydro-3H-1-thia-3,5,8-triazaacenaphthylene-2-carboxylic acid (Example 302, product from Step B). MS (ESI): mass calcd. for $C_{27}H_{23}N_7O_4S$, 541.6; m/z found, 542.3 $[M+H]^+$.

Example 320: N-((1R,2S)-2-Acrylamidocyclopentyl)-4-oxo-5-(5-phenylpyridazin-3-yl)-4,5-dihydro-3H-1-thia-3,5,8-triazaacenaphthylene-2-carboxamide

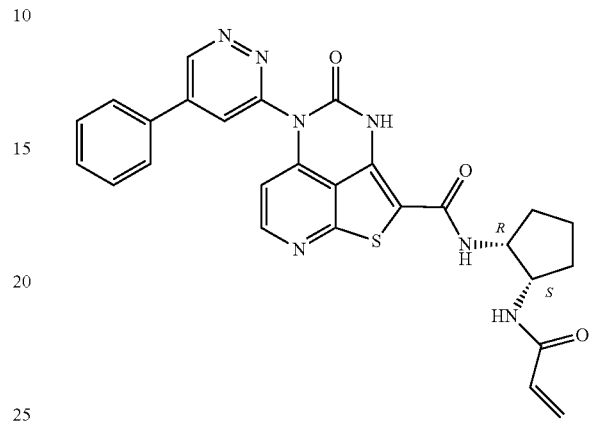

Step A: 3-Chloro-5-phenyl-pyridazine

A solution of 3,5-dichloropyridazine (2.00 g, 13.4 mmol), phenylboronic acid (1.64 g, 13.4 mmol), Pd(OAc)$_2$ (0.301 g, 1.34 mmol), 1,2,3,4,5-pentaphenyl-1'-(di-tert-butylphosphino)ferrocene (1.906 g, 2.685 mmol), KF (1.947 g, 33.56 mmol), dioxane (50 mL), and water (12 mL) was stirred at reflux for 15 h under N$_2$. The mixture was diluted with EtOAc, washed with brine, dried over anhydrous Na$_2$SO$_4$, and concentrated to dryness. The residue was purified by flash column chromatography to give the title compound (1.53 g, 59.8% yield) as white solid. MS (ESI): mass calcd. for $C_{10}H_7ClN_2$, 190.63; m/z found, 190.0 $[M+H]^+$.

Step B: tert-Butyl (5-phenylpyridazin-3-yl)carbamate

A mixture of 3-chloro-5-phenyl-pyridazine (1.53 g, 8.03 mmol), tert-butyl carbamate (1.88 g, 16.1 mmol), Pd(dppf) C12 (0.592 g, 0.803 mmol), Xphos (0.928 g, 1.61 mmol), and Cs$_2$CO$_3$ (6.54 g, 20.1 mmol) in dioxane (30 mL) was stirred at 100° C. for 16 hours. The mixture was diluted with EtOAc and filtered. The filtrate was partitioned between EtOAc and water, the organic layer was washed with water and brine, and dried over anhydrous Na$_2$SO$_4$, and concentrated to dryness. The residue was purified by flash column chromatography to give the title compound (0.96 g, 44% yield) as light yellow solid. MS (ESI): mass calcd. for $C_{15}H_7N_3O_2$, 271.31; m/z found, 272.0 $[M+H]^+$.

Step C: Methyl 3-amino-4-((tert-butoxycarbonyl)(5-phenylpyridazin-3-yl)amino)thieno[2,3-b]pyridine-2-carboxylate The title compound was prepared using analogous conditions described in Intermediate 1, steps C-D, and using tert-butyl (5-phenylpyridazin-3-yl)carbamate and Cs$_2$CO$_3$ in place of 5-fluoro-2-nitrotoluene and K$_2$CO$_3$ in step C (1.05 g). MS (ESI): mass calcd. for $C_{24}H_{23}N_5O_4S$, 477.54; m/z found, 478.3 $[M+H]^+$.

Step D: Methyl 3-amino-4-((5-phenylpyridazin-3-yl)amino)thieno[2,3-b]pyridine-2-carboxylate A solution of methyl 3-amino-4-((tert-butoxycarbonyl)(5-phenylpyridazin-3-yl)amino)thieno[2,3-b]pyridine-2-carboxylate (1.05 g, 2.20 mmol) in TFA (4 mL) and DCM (12 mL) was stirred at rt for 3 h. The mixture was concentrated to dryness to give the title compound (0.79 g, 95% yield) as yellow solid, which was used in the next step directly. MS (ESI): mass calcd. for $C_{19}H_{15}N_5O_2S$, 377.42; m/z found, 378.3 $[M+H]^+$.

Step E. 4-Oxo-5-(5-phenylpyridazin-3-yl)-4,5-dihydro-3H-1-thia-3,5,8-triazaacenaphthylene-2-carboxylic acid The title compound was prepared in a manner analogous to Intermediate 1, Steps E-F, using methyl 3-amino-4-((5-phenylpyridazin-3-yl)amino)thieno[2,3-b]pyridine-2-carboxylate.

Step F: N-((1R,2S)-2-Acrylamidocyclopentyl)-4-oxo-5-(5-phenylpyridazin-3-yl)-4,5-dihydro-3H-1-thia-3,5,8-triazaacenaphthylene-2-carboxamide The title compound was prepared in a manner analogous to Example 1, Step A, using 4-oxo-5-(5-phenylpyridazin-3-yl)-4,5-dihydro-3H-1-thia-3,5,8-triazaacenaphthylene-2-carboxylic acid and N-[(1S,2R)-2-aminocyclopentyl]prop-2-enamide (Intermediate 36) (no HCl/MeOH deprotection. MS (ESI): mass calcd. for $C_{27}H_{23}N_7O_3S$, 525.6; m/z found, 526.1 $[M+H]^+$. $^1$H NMR (400 MHz, DMSO-$d_6$): δ 10.27 (s, 1H), 9.86-9.83 (m, 1H), 8.40-8.33 (m, 2H), 7.99-7.93 (m, 2H), 7.90-7.85 (m, 1H), 7.82-7.77 (m, 1H), 7.62-7.55 (m, 3H), 6.34-6.28 (m, 1H), 6.28-6.18 (m, 1H), 6.11-6.02 (m, 1H), 5.58-5.52 (m, 1H), 4.34-4.19 (m, 2H), 2.00-1.84 (m, 2H), 1.82-1.67 (m, 2H), 1.67-1.47 (m, 2H).

Example 321: N-((1*S,3*S)-3-Acrylamidocyclopentyl)-4-oxo-5-(6-phenoxypyridin-3-yl)-4,5-dihydro-3H-1-thia-3,5,8-triazaacenaphthylene-2-carboxamide

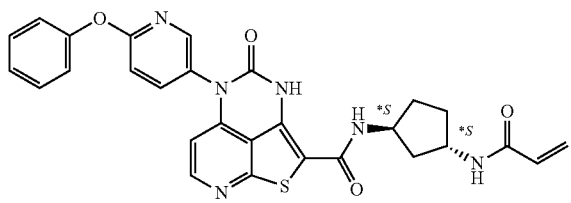 [SMILES: C=CC(=O)N[C@H]1CC[C@H](NC(=O)c2sc3nccc4c3c2NC(=O)N4c2ccc(Oc3ccccc3)nc2)C1]

The title compound was purified from N-((1RS,2RS)-2-Acrylamidocyclopentyl)-5-(2-methyl-6-phenoxypyridin-3-yl)-4-oxo-4,5-dihydro-3H-1-thia-3,5,8-triazaacenaphthylene-2-carboxamide (Example 292) chiral SFC (Stationary phase: Chiralpak IA, 5 μm, 250×20 mm, Mobile phase: 50% $CO_2$, 50% iPrOH) afforded the title compound and N-((1*R,3*R)-3-Acrylamidocyclopentyl)-4-oxo-5-(6-phenoxypyridin-3-yl)-4,5-dihydro-3H-1-thia-3,5,8-triazaacenaphthylene-2-carboxamide (Example 334). MS (ESI): mass calcd. for $C_{28}H_{24}N_6O_4S$, 540.6; m/z found, 541.2 $[M+H]^+$. $^1$H NMR (500 MHz, CDCl$_3$): δ 8.38-8.32 (m, 1H), 8.17 (t, J=2.2 Hz, 1H), 7.73-7.66 (m, 1H), 7.50-7.41 (m, 2H), 7.32-7.17 (m, 4H), 7.11 (dd, J=8.8, 1.7 Hz, 1H), 6.98 (p, J=5.3 Hz, 1H), 6.29 (dq, J=16.9, 1.4 Hz, 1H), 6.20-6.07 (m, 2H), 5.65 (dq, J=10.3, 1.4 Hz, 1H), 4.44 (dp, J=27.6, 6.8 Hz, 2H), 2.65 (d, J=5.1 Hz, 1H), 2.25 (tdd, J=12.2, 7.3, 3.5 Hz, 2H), 1.96 (dq, J=23.9, 6.7 Hz, 2H), 1.67-1.48 (m, 2H).

Example 322: N-((1R,2R)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide

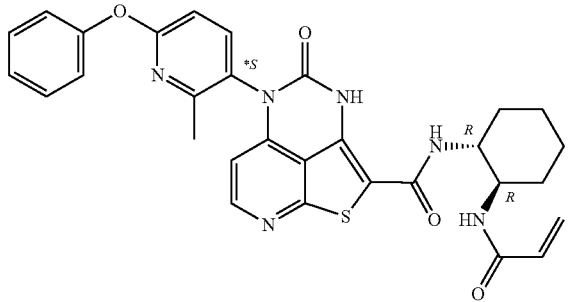

Step A. N-((1R,2R)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1R,2R)-2-aminocyclohexyl]carbamate and substituting diisopropylethylamine for triethylamine.

Step B. N-((1R,2R)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide The title compound was prepared in a manner analogous to Example 337, using N-((1R,2R)-2-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide. MS (ESI): mass calcd. for $C_{30}H_{28}N_6O_4S$, 568.7; m/z found, 569.0 $[M+H]^+$. $^1$H NMR (500 MHz, CDCl$_3$): δ 9.61 (s, 1H), 8.35 (d, J=5.4 Hz, 1H), 7.58-7.38 (m, 3H), 7.26-7.14 (m, 3H), 6.81 (d, J=8.5 Hz, 1H), 6.69 (d, J=7.2 Hz, 1H), 6.39-6.19 (m, 2H), 6.17-5.93 (m, 2H), 5.62 (dd, J=10.3, 1.4 Hz, 1H), 4.04-3.74 (m, 2H), 2.33-1.36 (m, 11H).

Example 323: N-((1S,3S)-3-Acrylamidocyclohexyl)-4-oxo-5-(6-phenoxypyridin-3-yl)-4,5-dihydro-3H-1-thia-3,5,8-triazaacenaphthylene-2-carboxamide

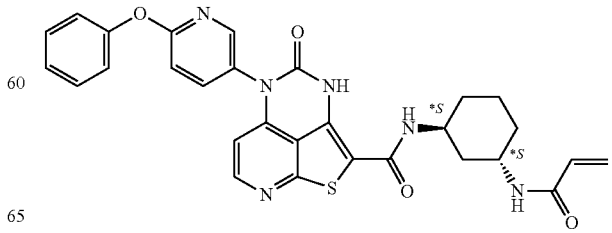

The title compound was prepared in a manner analogous to Example 166, using 4-oxo-5-(6-phenoxypyridin-3-yl)-4,5-dihydro-3H-1-thia-3,5,8-triazaacenaphthylene-2-carboxylic acid (Intermediate 28) and tert-butyl racemic-[(1R,3R)-3-aminocyclohexyl]carbamate in Step A. Chiral SFC purification of racemic N-((1RS,3RS)-3-acrylamidocyclohexyl)-4-oxo-5-(6-phenoxypyridin-3-yl)-4,5-dihydro-3H-1-thia-3,5,8-triazaacenaphthylene-2-carboxamide (Stationary phase: Chiralpak IA, 5 μm, 250×20 mm, Mobile phase: 50% $CO_2$, 50% iPrOH) afforded the title compound and N-((1*R,3*R)-3-Acrylamidocyclohexyl)-4-oxo-5-(6-phenoxypyridin-3-yl)-4,5-dihydro-3H-1-thia-3,5,8-triazaacenaphthylene-2-carboxamide (Example 331). MS (ESI): mass calcd. for $C_{29}H_{26}N_6O_4S$, 554.6; m/z found, 555.2 [M+H]+. 1H NMR (500 MHz, $CDCl_3$): δ 8.36 (tt, J=4.8, 1.8 Hz, 1H), 8.21-8.15 (m, 1H), 7.75-7.69 (m, 1H), 7.56-7.43 (m, 3H), 7.36 (dt, J=4.3, 1.8 Hz, 1H), 7.29 (dd, J=7.6, 3.8 Hz, 1H), 7.22 (t, J=5.8 Hz, 2H), 7.13 (ddd, J=9.0, 5.9, 2.7 Hz, 1H), 6.32-6.21 (m, 2H), 6.21 (ddt, J=7.0, 4.8, 2.1 Hz, 1H), 5.67 (ddd, J=9.6, 4.9, 2.2 Hz, 1H), 4.23 (dd, J=7.2, 3.5 Hz, 1H), 4.15 (dq, J=9.6, 4.8 Hz, 1H), 3.45-3.35 (m, 2H), 1.90 (td, J=13.7, 6.9 Hz, 2H), 1.77 (dd, J=9.4, 4.6 Hz, 2H), 1.66-1.59 (m, 2H), 1.54 (q, J=9.4 Hz, 1H).

Example 324: N-((1R,2R)-2-Acrylamidocyclopentyl)-4-oxo-5-(3-(pyridin-3-yl)phenyl)-4,5-dihydro-3H-1-thia-3,5,8-triazaacenaphthylene-2-carboxamide

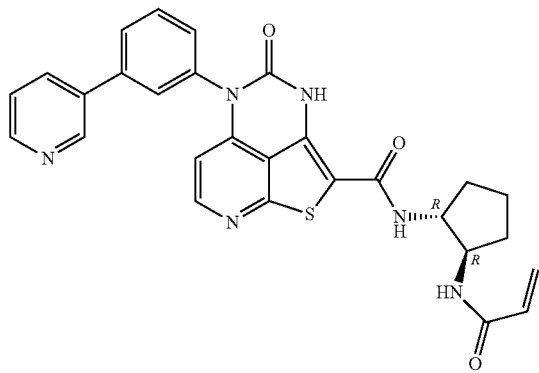

The title compound was prepared in a manner analogous to Example 1, Step A, using 4-oxo-5-(3-(pyridin-3-yl)phenyl)-4,5-dihydro-3H-1-thia-3,5,8-triazaacenaphthylene-2-carboxylic acid (Example 202, product from Step A) and N-[(1R,2R)-2-aminocyclopentyl]prop-2-enamide (Intermediate 46) (no HCl/MeOH deprotection). MS (ESI): mass calcd. for $C_{28}H_{24}N_6O_3S$, 524.6; m/z found, 525.1 [M+H]+. 1H NMR (400 MHz, $CD_3OD$): δ 8.94-8.79 (m, 1H), 8.60-8.49 (m, 1H), 8.33-8.24 (m, 1H), 8.20-8.09 (m, 1H), 7.92-7.80 (m, 2H), 7.76-7.68 (m, 1H), 7.56-7.46 (m, 2H), 6.25-6.12 (m, 3H), 5.66-5.56 (m, 1H), 4.33-4.13 (m, 2H), 2.23-2.04 (m, 2H), 1.86-1.72 (m, 2H), 1.72-1.47 (m, 2H).

Example 325: 5-([2,2'-Bipyridin]-4-yl)-N-((1R,2S)-2-acrylamidocyclopentyl)-4-oxo-4,5-dihydro-3H-1-thia-3,5,8-triazaacenaphthylene-2-carboxamide

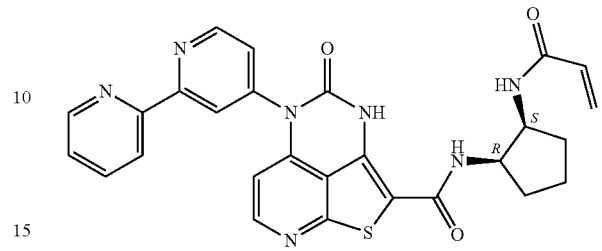

Step A. 4-Nitro-2,2'-bipyridine

The title compound was prepared in a manner analogous to Intermediate 20, Step A, using 2-(trimethylstannyl)pyridine and 2-chloro-4-nitropyridine, no base, and DMF as the solvent.

Step B. 5-([2,2'-Bipyridin]-4-yl)-4-oxo-4,5-dihydro-3H-1-thia-3,5,8-triazaacenaphthylene-2-carboxylic acid The title compound was prepared in a manner analogous to Intermediate 25, Steps B-C, using 4-nitro-2,2'-bipyridine in Step B.

Step C. 5-([2,2'-Bipyridin]-4-yl)-N-((1R,2S)-2-acrylamidocyclopentyl)-4-oxo-4,5-dihydro-3H-1-thia-3,5,8-triazaacenaphthylene-2-carboxamide The title compound was prepared in a manner analogous to Example 1, Step A, using 5-([2,2'-bipyridin]-4-yl)-4-oxo-4,5-dihydro-3H-1-thia-3,5,8-triazaacenaphthylene-2-carboxylic acid and N-[(1S,2R)-2-aminocyclopentyl]prop-2-enamide (Intermediate 36) (no HCl/MeOH deprotection). MS (ESI): mass calcd. for $C_{27}H_{23}N_7O_3S$, 525.6; m/z found, 526.1 [M+H]+. 1H NMR (400 MHz, $CD_3OD$): δ 8.92-8.82 (m, 1H), 8.64-8.59 (m, 1H), 8.49-8.44 (m, 1H), 8.44-8.39 (m, 1H), 8.30-8.23 (m, 1H), 7.97-7.91 (m, 1H), 7.57-7.50 (m, 1H), 7.45-7.40 (m, 1H), 6.33-6.24 (m, 2H), 6.23-6.18 (m, 1H), 5.64-5.60 (m, 1H), 4.46-4.39 (m, 2H), 2.15-2.01 (m, 2H), 1.96-1.86 (m, 1H), 1.83-1.61 (m, 3H).

Example 326: 5-([2,3'-Bipyridin]-4-yl)-N-((1R,2R)-2-acrylamidocyclopentyl)-4-oxo-4,5-dihydro-3H-1-thia-3,5,8-triazaacenaphthylene-2-carboxamide

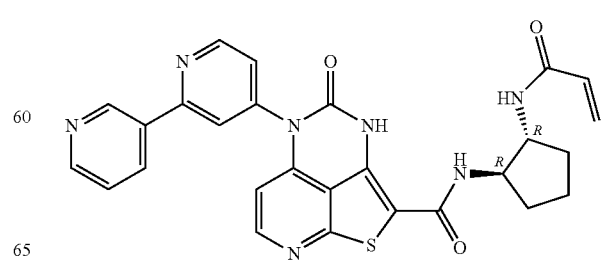

The title compound was prepared in a manner analogous to Example 1, Step A, using 5-([2,3'-bipyridin]-4-yl)-4-oxo-4,5-dihydro-3H-1-thia-3,5,8-triazaacenaphthylene-2-carboxylic acid (Example 317, product from Step A) and N-((1R,2R)-2-aminocyclopentyl)acrylamide (Intermediate 46) (no HCl/MeOH deprotection). MS (ESI): mass calcd. for $C_{27}H_{23}N_7O_3S$, 525.6; m/z found, 526.1 [M+H]$^+$. $^1$H NMR (400 MHz, CD$_3$OD): δ 9.27-9.22 (m, 1H), 8.94-8.88 (m, 1H), 8.62-8.57 (m, 1H), 8.53-8.47 (m, 1H), 8.32-8.27 (m, 1H), 8.21-8.15 (m, 1H), 7.59-7.52 (m, 2H), 6.31-6.26 (m, 1H), 6.22-6.16 (m, 2H), 5.63-5.56 (m, 1H), 4.29-4.17 (m, 2H), 2.19-2.09 (m, 2H), 1.84-1.73 (m, 2H), 1.70-1.60 (m, 1H), 1.60-1.51 (m, 1H).

Example 327: N-((1R,2R)-2-Acrylamidocyclopentyl)-4-oxo-5-(3-(pyridin-2-yl)phenyl)-4,5-dihydro-3H-1-thia-3,5,8-triazaacenaphthylene-2-carboxamide

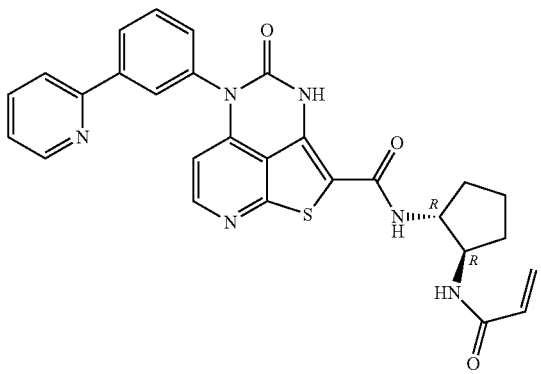

The title compound was prepared in a manner analogous to Example 1, Step A, using 4-oxo-5-(3-(pyridin-2-yl)phenyl)-4,5-dihydro-3H-1-thia-3,5,8-triazaacenaphthylene-2-carboxylic acid (Example 194, product from Step A) and N-[(1R,2R)-2-aminocyclopentyl]prop-2-enamide (Intermediate 46) in place of tert-butyl ((1S,4S)-4-aminocyclohexyl)carbamate in step G. MS (ESI): mass calcd. for $C_{28}H_{24}N_6O_3S$, 524.6; m/z found, 525.1 [M+H]$^+$. $^1$H NMR (400 MHz, CD$_3$OD): δ 8.65-8.56 (m, 1H), 8.30-8.25 (m, 1H), 8.18-8.12 (m, 1H), 8.08-8.04 (m, 1H), 7.94-7.85 (m, 2H), 7.75-7.69 (m, 1H), 7.54-7.45 (m, 1H), 7.40-7.33 (m, 1H), 6.24-6.20 (m, 2H), 6.19-6.15 (m, 1H), 5.65-5.58 (m, 1H), 4.31-4.16 (m, 2H), 2.25-2.05 (m, 2H), 1.90-1.76 (m, 2H), 1.72-1.50 (m, 2H).

Example 328: N-((1*R,3*S)-3-Acrylamidocyclopentyl)-4-oxo-5-(5-phenoxypyridin-2-yl)-4,5-dihydro-3H-1-thia-3,5,8-triazaacenaphthylene-2-carboxamide

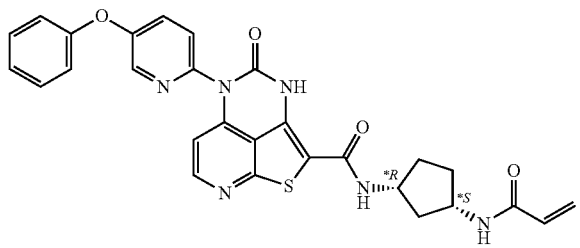

The title compound was isolated by Chiral SFC from Example 214. MS (ESI): mass calcd. for $C_{28}H_{24}N_6O_4S$, 540.6; m/z found, 541.0 [M+H]$^+$. $^1$H NMR (400 MHz, CDCl$_3$): δ 9.53 (s, 1H), 8.50-8.21 (m, 2H), 7.56-7.33 (m, 5H), 7.25-7.22 (m, 1H), 7.16-7.11 (m, 2H), 6.48-6.33 (m, 1H), 6.23 (d, J=5.5 Hz, 1H), 6.17-6.03 (m, 1H), 5.68 (dd, J=10.4, 1.4 Hz, 1H), 4.38 (s, 1H), 4.18-4.05 (m, 1H), 2.53-2.41 (m, 1H), 2.11-1.77 (m, 5H), 0.94-0.80 (m, 1H).

Example 329: N-((1*R,3*R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

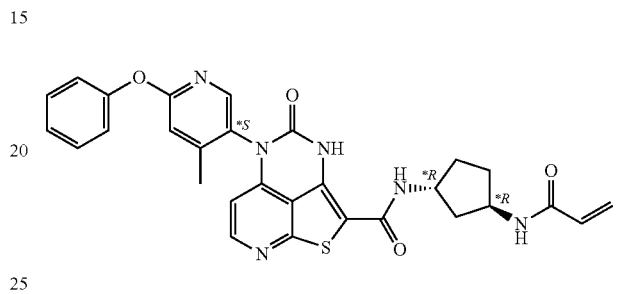

The title compound was prepared in a manner analogous to Example 166, Step C, using N-((1RS,3RS)-3-aminocyclopentyl)-5-(4-methyl-6-phenoxypyridin-3-yl)-4-oxo-4,5-dihydro-3H-1-thia-3,5,8-triazaacenaphthylene-2-carboxamide (Example 293); purification was performed via chiral SFC (Stationary phase: Chiralpak IA, 5 µm, 250×20 mm, Mobile phase: 50% CO$_2$, 50% iPrOH). MS (ESI): mass calcd. for $C_{29}H_{26}N_6O_4S$, 554.6; m/z found, 555.3 [M+H]$^+$. $^1$H NMR (400 MHz, CDCl$_3$): δ 9.51 (s, 1H), 8.37 (d, J=5.4 Hz, 1H), 8.05 (s, 1H), 7.50-7.39 (m, 2H), 7.30-7.15 (m, 3H), 6.95 (d, J=1.1 Hz, 1H), 6.29 (dd, J=16.9, 1.5 Hz, 1H), 6.14-6.01 (m, 2H), 5.87 (d, J=7.2 Hz, 1H), 5.77 (d, J=7.4 Hz, 1H), 5.66 (dd, J=10.3, 1.4 Hz, 1H), 4.52 (dh, J=10.3, 7.2 Hz, 2H), 2.39-2.18 (m, 4H), 2.03 (qdd, J=13.9, 7.9, 6.6 Hz, 2H), 1.69-1.46 (m, 2H), 1.21 (d, J=6.1 Hz, 1H).

Example 330: N-((1R,2S)-2-Acrylamidocyclopentyl)-5-(6-(isopropylamino)-4-methylpyridin-3-yl)-4-oxo-4,5-dihydro-3H-1-thia-3,5,8-triazaacenaphthylene-2-carboxamide

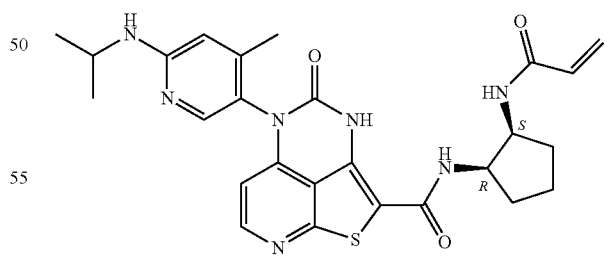

Step A. tert-Butyl isopropyl(4-methyl-5-nitropyridin-2-yl)carbamate

A solution of 2-chloro-4-methyl-5-nitropyridine (2.5 g, 14.5 mmol) and propan-2-amine (10 mL) was stirred at reflux overnight. The reaction mix was cooled and the solvent was removed under reduced pressure. THF (50 mL), DMAP (178 mg, 1.4 mmol), and di-tert-butyl dicarbonate (3.47 g, 15.9 mmol) were added to the crude mix and the reaction was stirred at reflux overnight. Purification by FCC afforded the title compound.

Step B. tert-Butyl (5-amino-4-methylpyridin-2-yl)(isopropyl)carbamate

The title compound was prepared in a manner analogous to Intermediate 16, Step B, using tert-Butyl isopropyl(4-methyl-5-nitropyridin-2-yl)carbamate.

Step C. 5-(6-(Isopropylamino)-4-methylpyridin-3-yl)-4-oxo-4,5-dihydro-3H-1-thia-3,5,8-triazaacenaphthylene-2-carboxylic acid The title compound was prepared in a manner analogous to Intermediate 1, Steps C-F, using 2-chloro-4-iodonicotinonitrile and tert-butyl (5-amino-4-methylpyridin-2-yl)(isopropyl)carbamate in Step C.

Step D. N-((1R,2S)-2-Acrylamidocyclopentyl)-5-(6-(isopropylamino)-4-methylpyridin-3-yl)-4-oxo-4,5-dihydro-3H-1-thia-3,5,8-triazaacenaphthylene-2-carboxamide The title compound was prepared in a manner analogous to Example 1, Step A, using 5-(6-(isopropylamino)-4-methylpyridin-3-yl)-4-oxo-4,5-dihydro-3H-1-thia-3,5,8-triazaacenaphthylene-2-carboxylic acid and N-[(1S,2R)-2-aminocyclopentyl]prop-2-enamide (Intermediate 36) (no HCl/MeOH deprotection). MS (ESI): mass calcd. for $C_{26}H_{29}N_7O_3S$, 519.6; m/z found, 520.2 [M+H]$^+$. $^1$H NMR (400 MHz, CD$_3$OD): δ 8.35-8.24 (m, 1H), 7.89-7.80 (m, 1H), 6.50 (s, 1H), 6.33-6.12 (m, 3H), 5.65-5.55 (m, 1H), 4.47-4.34 (m, 2H), 4.04-3.95 (m, 1H), 2.14-1.99 (m, 5H), 1.95-1.85 (m, 1H), 1.80-1.59 (m, 3H), 1.25-1.17 (m, 6H).

Example 331: N-((1*R,3*R)-3-Acrylamidocyclohexyl)-4-oxo-5-(6-phenoxypyridin-3-yl)-4,5-dihydro-3H-1-thia-3,5,8-triazaacenaphthylene-2-carboxamide

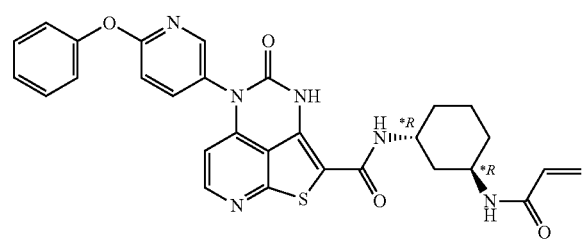 [SMILES: C=CC(=O)N[C@@H]1CCC[C@@H](NC(=O)c2sc3nccc4c3c2NC(=O)N4c2ccc(Oc3ccccc3)nc2)C1]

The title compound was isolated as a product from Example 323. MS (ESI): mass calcd. for $C_{29}H_{26}N_6O_4S$, 554.6; m/z found, 555.3 [M+H]$^+$. $^1$H NMR (500 MHz, CDCl$_3$): δ 8.35 (dd, J=5.5, 2.1 Hz, 1H), 8.18 (d, J=2.8 Hz, 1H), 7.71 (dd, J=8.6, 2.9 Hz, 1H), 7.51-7.37 (m, 3H), 7.37-7.18 (m, 4H), 7.12 (dd, J=8.8, 2.1 Hz, 1H), 6.35-6.17 (m, 3H), 5.66 (dt, J=9.9, 1.9 Hz, 1H), 4.27-4.20 (m, 1H), 3.21 (s, 1H), 1.89 (tt, J=13.2, 4.9 Hz, 2H), 1.80-1.59 (m, 6H), 1.52 (td, J=9.4, 3.6 Hz, 1H).

Example 332: N-((1*R,3*R)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

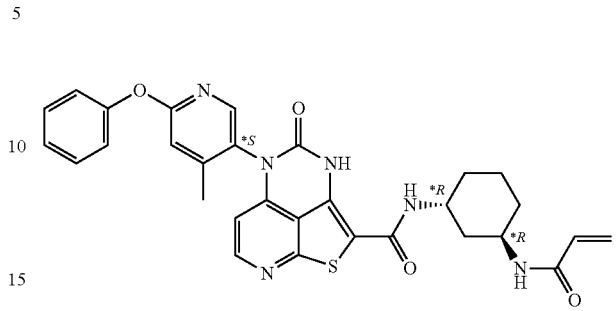

The title compound was prepared by chiral purification from Example 308. MS (ESI): mass calcd. for $C_{30}H_{28}N_6O_4S$, 568.7; m/z found, 569.3 [M+H]$^+$. $^1$H NMR (500 MHz, CDCl$_3$): δ 9.42 (s, 1H), 8.37 (d, J=5.5 Hz, 1H), 8.07 (s, 1H), 7.48-7.40 (m, 2H), 7.29-7.16 (m, 3H), 6.98-6.93 (m, 1H), 6.30 (dd, J=17.0, 1.5 Hz, 1H), 6.17-6.02 (m, 2H), 5.84 (d, J=7.8 Hz, 1H), 5.72 (d, J=7.5 Hz, 1H), 5.65 (dd, J=10.3, 1.5 Hz, 1H), 4.27 (dqt, J=19.9, 7.5, 3.9 Hz, 2H), 2.21 (d, J=0.8 Hz, 3H), 1.92-1.63 (m, 4H), 1.54 (dtd, J=12.2, 7.8, 4.0 Hz, 1H), 1.21 (d, J=6.1 Hz, 3H).

Example 333: N-((1R,2S)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide

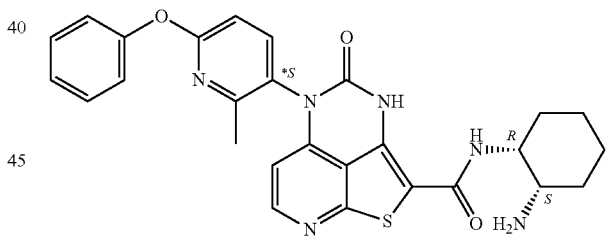

The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1S,2R)-2-aminocyclohexyl]carbamate, and substituting diisopropylethylamine for triethylamine. MS (ESI): mass calcd. for $C_{27}H_{26}N_6O_3S$, 514.6; m/z found, 515.0 [M+H]$^+$. $^1$H NMR (500 MHz, CD$_3$OD): δ 8.51 (dd, J=6.3, 2.1 Hz, 1H), 7.83 (d, J=8.5 Hz, 1H), 7.56-7.40 (m, 2H), 7.36-7.13 (m, 3H), 6.95 (dd, J=8.7, 1.1 Hz, 1H), 6.41 (d, J=7.1 Hz, 1H), 4.54-4.38 (m, 1H), 3.73-3.55 (m, 1H), 2.26 (s, 3H), 1.96-1.48 (m, 8H).

Example 334: N-((1*R,3*R)-3-Acrylamidocyclopentyl)-4-oxo-5-(6-phenoxypyridin-3-yl)-4,5-dihydro-3H-1-thia-3,5,8-triazaacenaphthylene-2-carboxamide

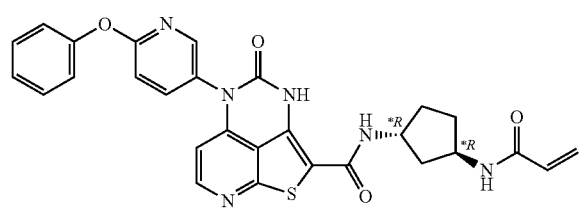

Isolated from chiral purification from Example 321. MS (ESI): mass calcd. for $C_{28}H_{24}N_6O_4S$, 540.6; m/z found, 541.2 $[M+H]^+$. $^1H$ NMR (500 MHz, CDCl$_3$): δ 8.35 (dd, J=5.6, 1.0 Hz, 1H), 8.20-8.15 (m, 1H), 7.70 (ddd, J=8.8, 2.8, 1.1 Hz, 1H), 7.46 (tt, J=7.5, 1.0 Hz, 2H), 7.33-7.18 (m, 4H), 7.15-7.02 (m, 2H), 6.29 (dt, J=17.0, 1.2 Hz, 1H), 6.21-6.08 (m, 2H), 5.66 (dt, J=10.3, 1.2 Hz, 1H), 4.51-4.36 (m, 2H), 2.74 (s, 1H), 2.30-2.19 (m, 2H), 2.04-1.87 (m, 2H), 1.67-1.48 (m, 2H).

Example 335: N-((1R,2S)-2-Aminocyclohexyl)-5-(*S)-(6-isobutyl-4-methylpyridin-3-yl)-4-oxo-4,5-dihydro-3H-1-thia-3,5,8-triazaacenaphthylene-2-carboxamide

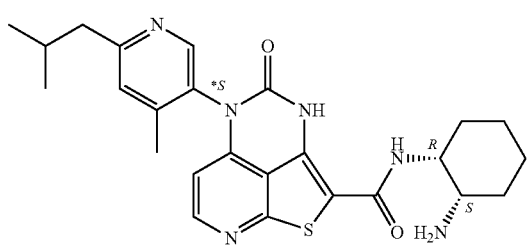

The title compound was prepared in a manner analogous to Example 1, Step A, using 5-(6-isobutyl-4-methylpyridin-3-yl)-4-oxo-4,5-dihydro-3H-1-thia-3,5,8-triazaacenaphthylene-2-carboxylic acid (Intermediate 18, including CHIRAL SEPARATION METHOD 1 to obtain the *S atropisomer) and tert-butyl N-[(1S,2R)-2-aminocyclohexyl]carbamate. MS (ESI): mass calcd. for $C_{25}H_{30}N_6O_2S$, 478.6; m/z found, 479.1 $[M+H]^+$. $^1H$ NMR (500 MHz, CDCl$_3$): δ 9.81 (s, 1H), 8.42 (s, 1H), 8.26 (d, J=5.5 Hz, 1H), 8.13 (s, 4H), 7.20 (s, 1H), 6.93 (s, 1H), 5.88 (d, J=5.5 Hz, 1H), 4.42 (dd, J=7.7, 4.1 Hz, 1H), 3.56 (s, 1H), 2.74-2.66 (m, 2H), 2.14 (s, 3H), 1.87-1.75 (m, 3H), 1.55-1.49 (m, 2H), 1.47-1.35 (m, 2H), 0.98 (dd, J=6.6, 2.4 Hz, 6H).

Example 336: N-((1R,2R)-2-Aminocyclopentyl)-5-(2-isopropylpyridin-4-yl)-4-oxo-4,5-dihydro-3H-1-thia-3,5,8-triazaacenaphthylene-2-carboxamide

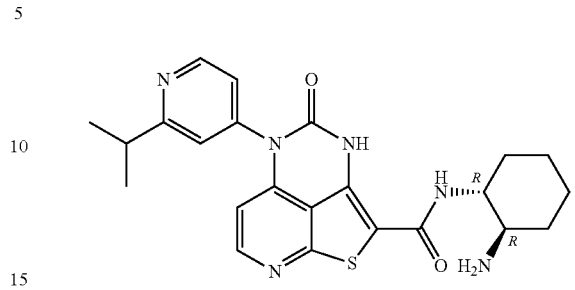

The title compound was prepared in a manner analogous to Example 1, Step A, using 5-(2-isopropylpyridin-4-yl)-4-oxo-4,5-dihydro-3H-1-thia-3,5,8-triazaacenaphthylene-2-carboxylic acid (Intermediate 16) and tert-butyl N-[(1R,2R)-2-aminocyclopentyl]carbamate. MS (ESI): mass calcd. for $C_{22}H_{24}N_6O_2S$, 436.5; m/z found, 437.2 $[M+H]^+$. $^1H$ NMR (400 MHz, CD$_3$OD): δ 8.62 (d, J=5.3 Hz, 1H), 8.13-8.03 (m, 1H), 7.37-7.32 (m, 1H), 7.30-7.23 (m, 1H), 5.97 (d, J=5.7 Hz, 1H), 4.05-3.91 (m, 1H), 3.28-3.19 (m, 1H), 3.18-3.06 (m, 1H), 2.22-2.12 (m, 1H), 2.11-1.99 (m, 1H), 1.84-1.63 (m, 3H), 1.51-1.41 (m, 1H), 1.34 (d, J=6.9 Hz, 6H).

Example 337: N-((1R,2R)-2-Acrylamidocyclopentyl)-5-(2-isopropylpyridin-4-yl)-4-oxo-4,5-dihydro-3H-1-thia-3,5,8-triazaacenaphthylene-2-carboxamide

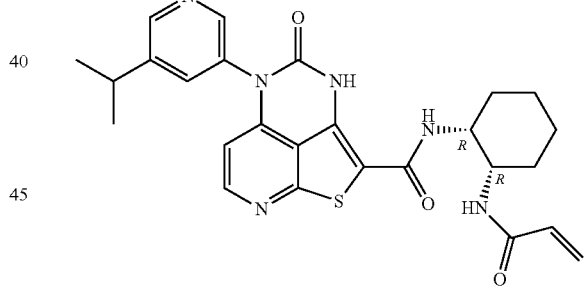

To a cooled (0° C.) solution of N-((1R,2R)-2-aminocyclopentyl)-5-(2-isopropylpyridin-4-yl)-4-oxo-4,5-dihydro-3H-1-thia-3,5,8-triazaacenaphthylene-2-carboxamide (Example 336, 270 mg, 0.62 mmol) and DIPEA (0.08 mL, 0.74 mmol) in DCM (5 mL) was added prop-2-enoyl prop-2-enoate (0.08 mL, 0.74 mmol). The reaction mix was stirred for 5 min. The solvent was removed under reduced pressure and the crude mix was purified (FCC, SiO$_2$, MeOH/H$_2$O) to afford the title compound (160 mg, 52%). MS (ESI): mass calcd. for $C_{25}H_{26}N_6O_3S$, 490.6; m/z found, 491.2 $[M+H]^+$. $^1H$ NMR (400 MHz, CD$_3$OD): δ 8.73-8.64 (m, 1H), 8.36-8.25 (m, 1H), 7.54-7.44 (m, 1H), 7.40-7.35 (m, 1H), 6.25-6.15 (m, 3H), 5.67-5.59 (m, 1H), 4.33-4.16 (m, 2H), 3.21-3.10 (m, 1H), 2.23-2.08 (m, 2H), 1.87-1.77 (m, 2H), 1.72-1.51 (m, 2H), 1.34 (d, J=6.9 Hz, 6H).

Example 338: N-((1R,2R)-2-Acrylamidocyclohexyl)-4-oxo-5-(2-phenoxypyrimidin-5-yl)-4,5-dihydro-3H-1-thia-3,5,8-triazaacenaphthylene-2-carboxamide

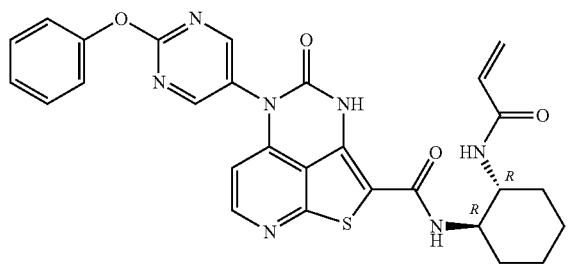

The title compound was prepared in a manner analogous to Example 1, using tert-butyl N-[(1R,2R)-2-aminocyclohexyl]carbamate and 4-oxo-5-(2-phenoxypyrimidin-5-yl)-4,5-dihydro-3H-1-thia-3,5,8-triazaacenaphthylene-2-carboxylic acid (Example 302, product from Step B). MS (ESI): mass calcd. for $C_{28}H_{25}N_7O_4S$, 555.6; m/z found, 556.3 [M+H]$^+$. $^1$H NMR (400 MHz, DMSO-d$_6$): δ 10.31 (s, 1H), 8.76 (s, 2H), 8.37-8.30 (m, 1H), 8.20-8.13 (m, 1H), 8.04-7.96 (m, 1H), 7.50-7.42 (m, 2H), 7.31-7.24 (m, 3H), 6.37-6.30 (m, 1H), 6.22-6.02 (m, 2H), 5.56-5.50 (m, 1H), 3.83-3.57 (m, 2H), 1.90-1.80 (m, 2H), 1.73-1.64 (m, 2H), 1.47-1.23 (m, 4H).

Example 339: N-((1R,2R)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide

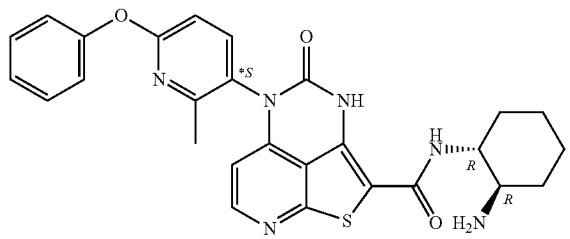

The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1R,2R)-2-aminocyclopentyl]carbamate and diisopropylethylamine. MS (ESI): mass calcd. for $C_{26}H_{24}N_6O_3S$, 500.6; m/z found, 501.1 [M+H]$^+$. $^1$H NMR (500 MHz, CD$_3$OD): δ 8.53 (d, J=6.2 Hz, 1H), 7.85 (d, J=8.6 Hz, 1H), 7.51-7.37 (m, 2H), 7.36-7.16 (m, 3H), 6.96 (d, J=8.6 Hz, 1H), 6.45 (d, J=6.2 Hz, 1H), 4.36-4.23 (m, 1H), 3.59-3.46 (m, 1H), 2.35-2.14 (m, 5H), 1.96-1.65 (m, 4H).

Example 340: N-((1R,2S)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide

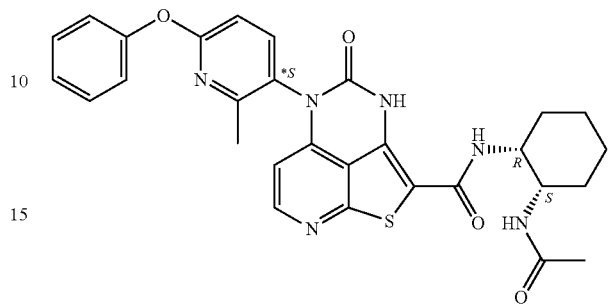

Step A. N-((1R,2S)-2-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide The title compound was prepared in a manner analogous to Example 1, Step A using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1S,2R)-2-aminocyclohexyl]carbamate and diisopropylethylamine in Step A.

Step B. N-((1R,2S)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide The title compound was prepared in a manner analogous to Example 1, Step B using and acetic anhydride. MS (ESI): mass calcd. for $C_{29}H_{28}N_6O_4S$, 556.6; m/z found, 557.0 [M+H]$^+$. $^1$H NMR (500 MHz, CDCl$_3$): δ 9.51 (s, 1H), 8.36 (d, J=5.5 Hz, 1H), 7.54 (d, J=8.6 Hz, 1H), 7.49-7.38 (m, 2H), 7.27-7.17 (m, 3H), 7.07 (s, 1H), 6.81 (d, J=8.6 Hz, 1H), 6.22-5.91 (m, 2H), 4.31-4.05 (m, 2H), 2.29 (s, 3H), 2.09 (s, 3H), 1.93-1.39 (m, 8H).

Example 341: N-((1R,2S)-2-Acrylamidocyclohexyl)-5-(*R)-(6-(cyclopentyloxy)-4-methylpyridin-3-yl)-4-oxo-4,5-dihydro-3H-1-thia-3,5,8-triazaacenaphthylene-2-carboxamide

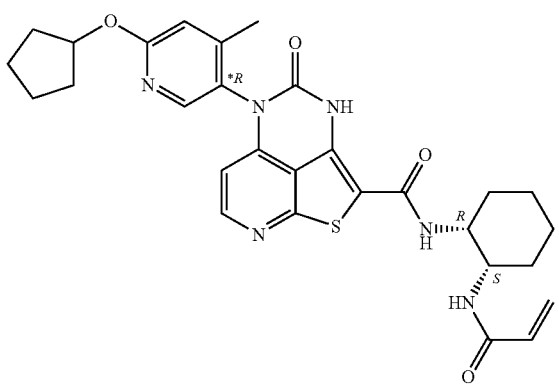

The title compound was prepared in a manner analogous to Example 166, Step A, using 5-(6-(cyclopentyloxy)-4-methylpyridin-3-yl)-4-oxo-4,5-dihydro-3H-1-thia-3,5,8-triazaacenaphthylene-2-carboxylic acid (Intermediate 25, including CHIRAL SEPARATION METHOD 1 to obtain the *R atropisomer) and N-[(1S,2R)-2-aminocyclohexyl] prop-2-enamide (Intermediate 40). MS (ESI): mass calcd. for $C_{29}H_{32}N_6O_4S$, 560.7; m/z found, 561.2 [M+H]$^+$. $^1$H NMR (400 MHz, CD$_3$OD): δ 8.33 (d, J=5.5 Hz, 1H), 8.05 (s, 1H), 6.83 (s, 1H), 6.42 (dd, J=17.0, 10.1 Hz, 1H), 6.28 (dd, J=17.0, 1.8 Hz, 1H), 6.11 (d, J=5.6 Hz, 1H), 5.68 (dd, J=10.1, 1.9 Hz, 1H), 5.45-5.37 (m, 1H), 4.43 (s, 1H), 4.24-4.12 (m, 1H), 2.14 (s, 3H), 2.06-1.94 (m, 2H), 1.88-1.77 (m, 8H), 1.74-1.63 (m, 4H), 1.60-1.48 (m, 2H).

Example 342: 5-([2,2'-Bipyridin]-4-yl)-N-((1R,2R)-2-acrylamidocyclopentyl)-4-oxo-4,5-dihydro-3H-1-thia-3,5,8-triazaacenaphthylene-2-carboxamide

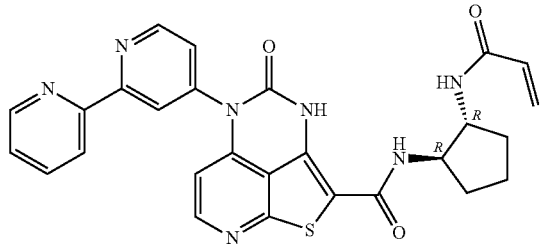

The title compound was prepared in a manner analogous to Example 1, Step A, using 5-([2,2'-bipyridin]-4-yl)-4-oxo-4,5-dihydro-3H-1-thia-3,5,8-triazaacenaphthylene-2-carboxylic acid (Example 325, product from Step B) and N-[(1R,2R)-2-aminocyclopentyl]prop-2-enamide (Intermediate 46) (no HCl/MeOH deprotection). MS (ESI): mass calcd. for $C_{27}H_{23}N_7O_3S$, 525.6; m/z found, 526.1 [M+H]$^+$. $^1$H NMR (400 MHz, CD$_3$OD): δ 8.90-8.85 (m, 1H), 8.63-8.59 (m, 1H), 8.48-8.44 (m, 1H), 8.43-8.39 (m, 1H), 8.30-8.23 (m, 1H), 7.96-7.91 (m, 1H), 7.56-7.51 (m, 1H), 7.45-7.40 (m, 1H), 6.30-6.20 (m, 3H), 5.66-5.59 (m, 1H), 4.32-4.21 (m, 2H), 2.22-2.11 (m, 2H), 1.89-1.77 (m, 2H), 1.75-1.65 (m, 1H), 1.63-1.52 (m, 1H).

Example 343: 5-(*S)-(2-Methyl-6-phenoxypyridin-3-yl)-4-oxo-N-((1R,2S)-2-propionamidocyclohexyl)-4,5-dihydro-3H-1-thia-3,5,8-triazaacenaphthylene-2-carboxamide

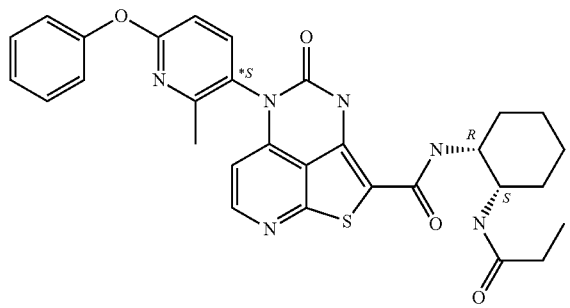

The title compound was prepared in a manner analogous to Example 1, Step B, using N-((1R,2S)-2-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide (Example 333), propanoyl propanoate, and substituting diisopropylethylamine for triethylamine. MS (ESI): mass calcd. for $C_{30}H_{30}N_6O_4S$, 570.7; m/z found, 571.1 [M+H]$^+$. $^1$H NMR (400 MHz, CDCl$_3$): δ 9.51 (s, 1H), 8.37 (d, J=5.5 Hz, 1H), 7.68-7.39 (m, 3H), 7.25-7.09 (m, 3H), 6.81 (d, J=8.5 Hz, 1H), 6.00 (dd, J=7.0, 2.1 Hz, 2H), 4.29-4.07 (m, 2H), 2.43-1.16 (m, 17H).

Example 344: N-((1*R,3*R)-3-Acrylamidocyclohexyl)-4-oxo-5-(5-phenoxypyridin-2-yl)-4,5-dihydro-3H-1-thia-3,5,8-triazaacenaphthylene-2-carboxamide

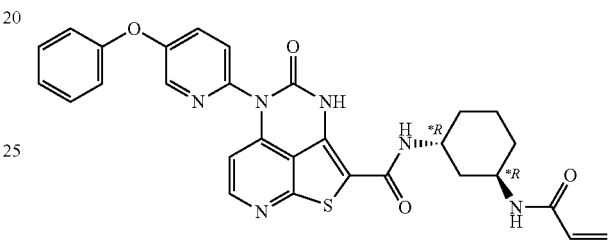

Chiral SFC Purification of N-((1RS,3RS)-3-Acrylamidocyclohexyl)-4-oxo-5-(5-phenoxypyridin-2-yl)-4,5-dihydro-3H-1-thia-3,5,8-triazaacenaphthylene-2-carboxamide (Example 216), (Stationary phase: Chiralpak IA, 5 μm, 250×20 mm, Mobile phase: 50% CO$_2$, 50% iPrOH) afforded the title compound. MS (ESI): mass calcd. for $C_{29}H_{26}N_6O_4S$, 554.6; m/z found, 555.3 [M+H]$^+$. $^1$H NMR (400 MHz, CDCl$_3$): δ 9.45 (s, 1H), 8.46-8.26 (m, 2H), 7.59-7.38 (m, 4H), 7.26-7.09 (m, 3H), 6.40-6.01 (m, 4H), 5.89 (d, J=7.4 Hz, 1H), 5.71-5.56 (m, 1H), 4.43-4.13 (m, 2H), 2.35-1.77 (m, 6H), 1.63-1.44 (m, 1H), 1.29-1.16 (m, 1H).

Example 345: N-((1R,2S)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide

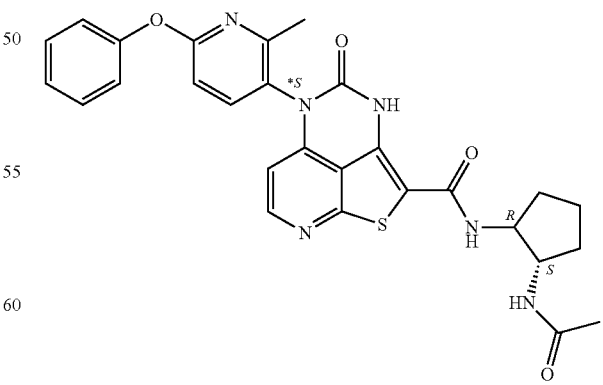

The title compound was prepared in a manner analogous to Example 1, Step B, using N-((1*R,2*S)-2-aminocyclopentyl)-5-(*S)-(2-methyl-6-phenoxypyridin-3-yl)-4-oxo-4, 5-dihydro-3H-1-thia-3,5,8-triazaacenaphthylene-2-carboxamide (Example 318) and substituting acetic anhydride and diisopropylethylamine for prop-2-enoyl chloride and triethylamine. MS (ESI): mass calcd. for $C_{28}H_{26}N_6O_4S$, 542.6; m/z found, 543.0 [M+H]$^+$. $^1$H NMR (500 MHz, CDCl$_3$): δ 9.53 (s, 1H), 8.37 (d, J=5.5 Hz, 1H), 7.61-7.36 (m, 3H), 7.27-7.14 (m, 3H), 6.86-6.70 (m, 2H), 6.27-5.90 (m, 2H), 4.37-4.00 (m, 2H), 2.28 (s, 3H), 2.20-1.62 (m, 9H).

Example 346: 5-(*S)-(2-Methyl-6-phenoxypyridin-3-yl)-4-oxo-N-((1R,2S)-2-propionamidocyclopentyl)-4,5-dihydro-3H-1-thia-3,5,8-triazaacenaphthylene-2-carboxamide

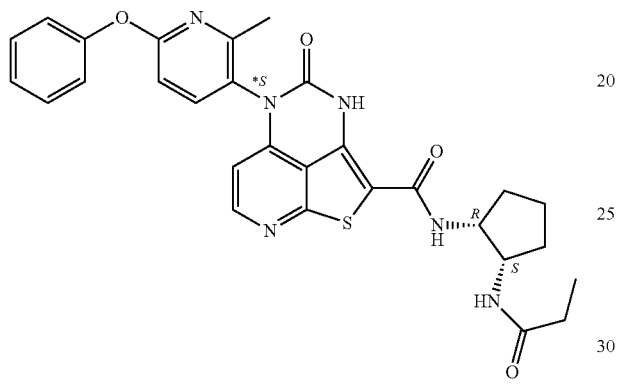

The title compound was prepared in a manner analogous to Example 1, Step B, using N-((1*R,2*S)-2-amino cyclopentyl)-5-(*S)-(2-methyl-6-phenoxypyridin-3-yl)-4-oxo-4,5-dihydro-3H-1-thia-3,5,8-triazaacenaphthylene-2-carboxamide (Example 318) and propanoyl propanoate and diisopropylethylamine for prop-2-enoyl chloride and triethylamine. MS (ESI): mass calcd. for $C_{29}H_{28}N_6O_4S$, 556.6; m/z found, 557.0 [M+H]$^+$. $^1$H NMR (500 MHz, Methanol-d4) δ 8.34 (d, J=5.6 Hz, 1H), 7.77 (d, J=8.6 Hz, 1H), 7.50-7.38 (m, 2H), 7.33-7.08 (m, 3H), 6.91 (d, J=8.6 Hz, 1H), 6.13 (d, J=5.5 Hz, 1H), 4.50-4.27 (m, 2H), 2.30-2.14 (m, 5H), 2.14-1.55 (m, 6H), 1.09 (t, J=7.6 Hz, 3H).

Example 347: N-((1R,2S)-2-Acrylamidocyclopentyl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide

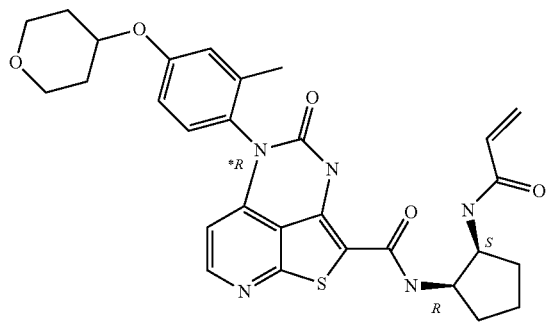

The title compound was prepared in a manner analogous to Example 1, using 5-(2-methyl-4-((tetrahydro-2H-pyran-4-yl)oxy)phenyl)-4-oxo-4,5-dihydro-3H-1-thia-3,5,8-triazaacenaphthylene-2-carboxylic acid (Intermediate 12) and tert-butyl N-[(1S,2R)-2-aminocyclopentyl]carbamate, and substituting diisopropylethylamine for triethylamine in Step A. Chiral SFC purification (Stationary phase: CHIRALCEL OD-H 5 µm 250×20 mm, Mobile phase: 65% CO$_2$, 35% MeOH) afforded the title compound and N-((1R,2S)-2-acrylamidocyclopentyl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide (Example 304) MS (ESI): mass calcd. for $C_{29}H_{31}N_5O_5S$, 561.7; m/z found, 562.3 [M+H]$^+$. $^1$H NMR (400 MHz, CD$_3$OD): δ 8.29-8.23 (m, 1H), 7.24-7.16 (m, 1H), 7.06-7.00 (m, 1H), 6.99-6.93 (m, 1H), 6.32-6.14 (m, 2H), 6.02-5.96 (m, 1H), 5.63-5.56 (m, 1H), 4.68-4.56 (m, 1H), 4.46-4.33 (m, 2H), 3.99-3.89 (m, 2H), 3.66-3.54 (m, 2H), 2.18-1.98 (m, 7H), 1.96-1.83 (m, 1H), 1.81-1.61 (m, 5H).

Example 348: N-((1R,2S)-2-Acrylamidocyclohexyl)-5-(*R)-(6-isopropoxy-4-methylpyridin-3-yl)-4-oxo-4,5-dihydro-3H-1-thia-3,5,8-triazaacenaphthylene-2-carboxamide

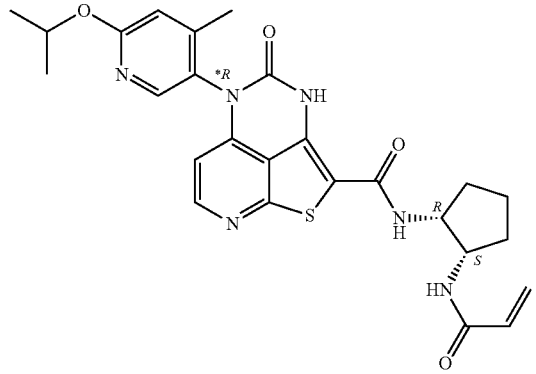

Chiral SFC purification of N-((1R,2S)-2-acrylamidocyclohexyl)-5-(6-isopropoxy-4-methylpyridin-3-yl)-4-oxo-4,5-dihydro-3H-1-thia-3,5,8-triazaacenaphthylene-2-carboxamide (Example 222) afforded the title compound (Stationary phase: Chiralpak AS-H 5 µm 250*20 mm, Mobile phase: 70% CO$_2$, 30% MeOH). MS (ESI): mass calcd. for $C_{27}H_{30}N_6O_4S$, 534.6; m/z found, 535.2 [M+H]$^+$. $^1$H NMR (500 MHz, CD$_3$OD): δ 8.32 (d, J=5.5 Hz, 1H), 8.05 (s, 1H), 6.81 (s, 1H), 6.42 (dd, J=17.0, 10.2 Hz, 1H), 6.28 (dd, J=17.0, 1.7 Hz, 1H), 6.10 (d, J=5.5 Hz, 1H), 5.67 (dd, J=10.2, 1.8 Hz, 1H), 5.35-5.25 (m, 1H), 4.42 (s, 1H), 4.18 (d, J=10.2 Hz, 1H), 2.14 (s, 3H), 1.88-1.61 (m, 6H), 1.59-1.46 (m, 2H), 1.36 (dd, J=6.1, 3.9 Hz, 6H).

Example 349: N-((1R,2S)-2-Aminocyclopentyl)-4-oxo-5-(5-phenylpyridazin-3-yl)-4,5-dihydro-3H-1-thia-3,5,8-triazaacenaphthylene-2-carboxamide

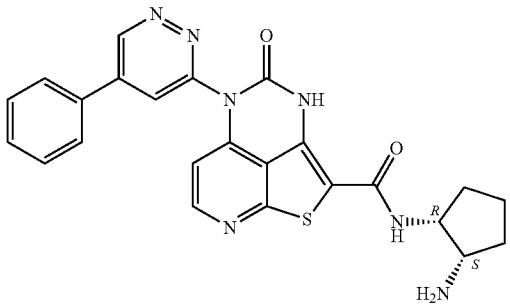

The title compound was prepared in a manner analogous to Example 1, Step A, using 4-oxo-5-(5-phenylpyridazin-3-yl)-4,5-dihydro-3H-1-thia-3,5,8-triazaacenaphthylene-2-carboxylic acid (Example 320, product from Step E) and tert-butyl N-[(1S,2R)-2-aminocyclopentyl]carbamate. MS (ESI): mass calcd. for $C_{24}H_{21}N_7O_2S$, 471.5; m/z found, 472.2 [M+H]$^+$. $^1$H NMR (400 MHz, a mixture of CD$_3$OD and DMSO-d$_6$): δ 9.66-9.61 (m, 1H), 8.38-8.34 (m, 1H), 8.24-8.16 (m, 2H), 7.90-7.83 (m, 2H), 7.55-7.45 (m, 3H), 6.26-6.19 (m, 1H), 4.40-4.34 (m, 1H), 3.67-3.58 (m, 1H), 2.12-1.97 (m, 2H), 1.90-1.77 (m, 2H), 1.74-1.52 (m, 2H).

Example 350: N-((1R,2R)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide

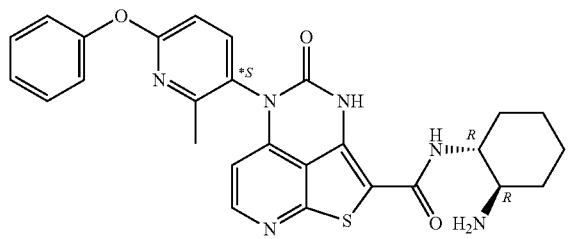

The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1R,2R)-2-aminocyclohexyl]carbamate and diisopropylethylamine. MS (ESI): mass calcd. for $C_{27}H_{26}N_6O_3S$, 514.6; m/z found, 515.1 [M+H]$^+$. $^1$H NMR (600 MHz, CD$_3$OD): δ 8.62 (d, J=6.6 Hz, 1H), 7.96 (d, J=8.7 Hz, 1H), 7.54-7.45 (m, 2H), 7.37-7.22 (m, 3H), 7.01 (d, J=8.8 Hz, 1H), 6.63 (d, J=6.6 Hz, 1H), 4.06 (ddd, J=12.0, 10.5, 4.3 Hz, 1H), 3.20 (td, J=11.3, 4.2 Hz, 1H), 2.34 (s, 3H), 2.21-2.15 (m, 1H), 1.94-1.31 (m, 7H).

Example 351: N-((1S,3R)-3-Acrylamidocyclohexyl)-4-oxo-5-(2-phenylpyridin-4-yl)-4,5-dihydro-3H-1-thia-3,5,8-triazaacenaphthylene-2-carboxamide

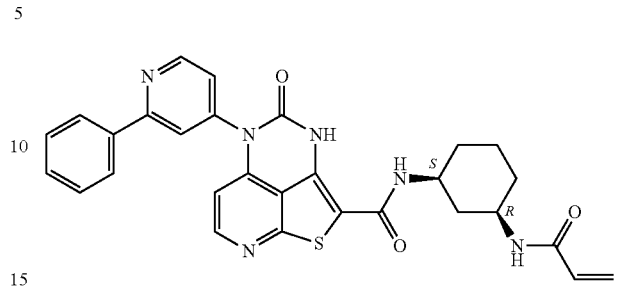

The title compound was prepared in a manner analogous to Example 1, Step A, using 4-oxo-5-(2-phenylpyridin-4-yl)-4,5-dihydro-3H-1-thia-3,5,8-triazaacenaphthylene-2-carboxylic acid (Intermediate 20) and N-[(1R,3S)-3-aminocyclohexyl]prop-2-enamide (no HCl/MeOH deprotection). MS (ESI): mass calcd. for $C_{29}H_{26}N_6O_3S$, 538.6; m/z found, 539.4 [M+H]$^+$. $^1$H NMR (400 MHz, DMSO-d$_6$): δ 8.88 (d, J=5.1 Hz, 1H), 8.35-7.98 (m, 6H), 7.59-7.37 (m, 4H), 6.29-5.99 (m, 3H), 5.62-5.48 (m, 1H), 3.93-3.79 (m, 1H), 3.74-3.62 (m, 1H), 2.08-1.95 (m, 1H), 1.87-1.68 (m, 3H), 1.47-1.19 (m, 3H), 1.15-1.02 (m, 1H).

Example 352: N-((1R,2S)-2-Acrylamidocyclohexyl)-5-(*R)-(6-isobutoxy-4-methylpyridin-3-yl)-4-oxo-4,5-dihydro-3H-1-thia-3,5,8-triazaacenaphthylene-2-carboxamide

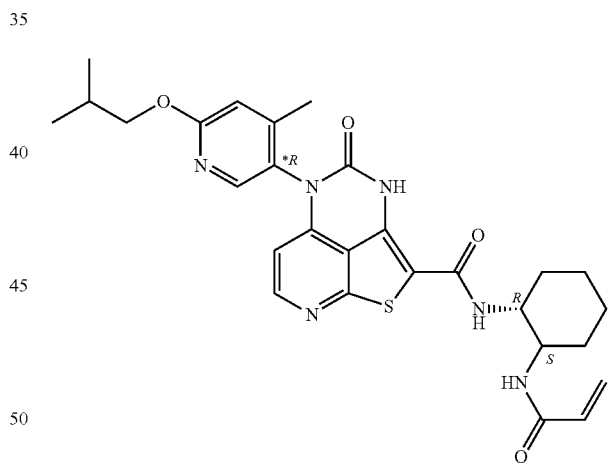

Chiral SFC (Stationary phase: Chiralpak AS-H 5 μm 250*20 mm, Mobile phase: 70% CO$_2$, 30% MeOH) of N-((1R,2S)-2-Acrylamidocyclohexyl)-5-(6-isobutoxy-4-methylpyridin-3-yl)-4-oxo-4,5-dihydro-3H-1-thia-3,5,8-triazaacenaphthylene-2-carboxamide (Example 225) afforded the title compound and N-((1R,2S)-2-Acrylamidocyclohexyl)-5-(*S)-(6-isobutoxy-4-methylpyridin-3-yl)-4-oxo-4,5-dihydro-3H-1-thia-3,5,8-triazaacenaphthylene-2-carboxamide (Example 312). MS (ESI): mass calcd. for $C_{28}H_{32}N_6O_4S$, 548.7; m/z found, 549.2 [M+H]$^+$. $^1$H NMR (500 MHz, CD$_3$OD): δ 8.38-8.27 (m, 1H), 8.05 (s, 1H), 6.89 (s, 1H), 6.42 (dd, J=17.0, 10.2 Hz, 1H), 6.28 (d, J=15.8 Hz, 1H), 6.14-6.07 (m, 1H), 5.72-5.64 (m, 1H), 4.43 (s, 1H), 4.25-4.15 (m, 1H), 4.13-4.07 (m, 2H), 2.16 (s, 3H), 2.13-

2.07 (m, 1H), 1.86-1.78 (m, 3H), 1.76-1.62 (m, 3H), 1.60-1.46 (m, 2H), 1.04 (d, J=6.7 Hz, 6H).

Example 353: 5-(*S)-(2-Methyl-6-phenoxypyridin-3-yl)-4-oxo-N-((1R,2R)-2-propionamidocyclopentyl)-4,5-dihydro-3H-1-thia-3,5,8-triazaacenaphthylene-2-carboxamide

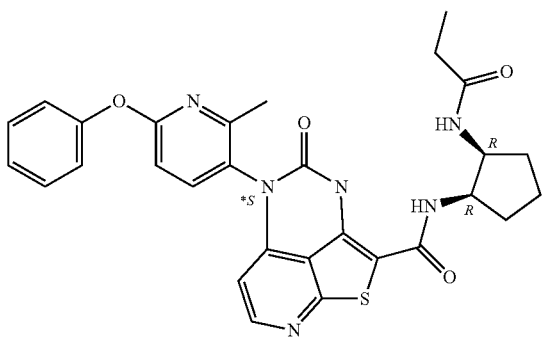

The title compound was prepared in a manner analogous to Example 1, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl N-[(1R,2R)-2-aminocyclopentyl]carbamate, and substituting diisopropylethylamine for triethylamine in Step A, and using propanoyl propanoate and diisopropylethylamine in place of prop-2-enoyl chloride and triethylamine in Step B. MS (ESI): mass calcd. for $C_{29}H_{28}N_6O_4S$, 556.6; m/z found, 557.0 [M+H]$^+$. $^1$H NMR (500 MHz, DMSO-d$_6$): δ 10.28 (s, 1H), 8.52-8.01 (m, 2H), 7.90 (d, J=8.0 Hz, 2H), 7.48-7.44 (m, 2H), 7.27-7.20 (m, 3H), 7.01 (d, J=8.7 Hz, 1H), 6.09 (s, 1H), 4.32-4.02 (m, 2H), 2.14 (s, 3H), 2.11-1.01 (m, 7H), 0.96 (t, J=7.6 Hz, 3H).

Example 354: N-((1R,2S)-2-Aminocyclopentyl)-5-(*S)-(6-isobutyl-4-methylpyridin-3-yl)-4-oxo-4,5-dihydro-3H-1-thia-3,5,8-triazaacenaphthylene-2-carboxamide

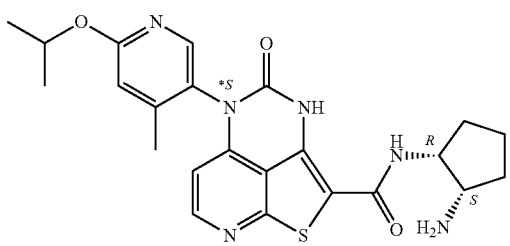

The title compound was prepared in a manner analogous to Example 1, Step A, using 5-(6-isobutyl-4-methylpyridin-3-yl)-4-oxo-4,5-dihydro-3H-1-thia-3,5,8-triazaacenaphthylene-2-carboxylic acid (Intermediate 18, including CHIRAL SEPARATION METHOD 1 to obtain the *S atropisomer) and tert-butyl ((1S,2R)-2-aminocyclopentyl)carbamate. MS (ESI): mass calcd. for $C_{24}H_{28}N_6O_2S$, 464.6; m/z found, 465.1 [M+H]$^+$. $^1$H NMR (500 MHz, CDCl$_3$): δ 8.36 (d, J=3.0 Hz, 1H), 8.29 (t, J=4.2 Hz, 1H), 7.26 (d, J=2.7 Hz, 1H), 5.92 (t, J=4.2 Hz, 1H), 5.11 (s, 1H), 3.66 (q, J=6.4 Hz, 1H), 3.43-3.38 (m, 6H), 2.72 (dd, J=7.4, 3.1 Hz, 2H), 2.22-2.07 (m, 4H), 1.98-1.78 (m, 2H), 1.74 (ddd, J=11.0, 7.8, 5.5 Hz, 1H), 1.64 (tt, J=11.3, 8.1 Hz, 1H), 1.00 (t, J=4.8 Hz, 6H).

Example 355: N-((1R,3S)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide

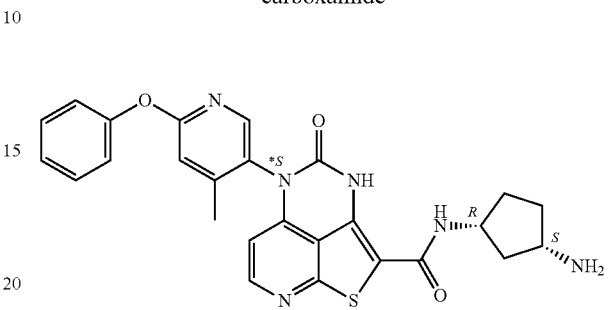

The title compound was prepared in a manner analogous to Example 166, Step A-B, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl N-[(1S,3R)-3-aminocyclopentyl]carbamate. MS (ESI): mass calcd. for $C_{26}H_{24}N_6O_3S$, 500.6; m/z found, 501.0 [M+H]$^+$. $^1$H NMR (400 MHz, CDCl$_3$): δ 8.34 (d, J=5.4 Hz, 1H), 8.04 (s, 1H), 7.92 (d, J=8.4 Hz, 1H), 7.49-7.39 (m, 2H), 7.29-7.15 (m, 3H), 6.95 (s, 1H), 6.01 (d, J=5.4 Hz, 1H), 4.60 (dt, J=9.1, 6.1 Hz, 1H), 3.75 (tt, J=5.3, 2.2 Hz, 1H), 3.48 (s, 1H), 2.83-2.64 (m, 5H), 2.11-1.86 (m, 4H), 1.59 (dp, J=13.6, 2.2 Hz, 2H).

Example 356: N-((1R,3S)-3-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide

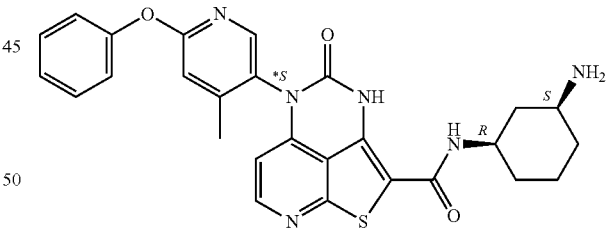

The title compound was prepared in a manner analogous to Example 166, Step A-B, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl N-[(1R,3S)-3-aminocyclohexyl]carbamate. MS (ESI): mass calcd. for $C_{27}H_{26}N_6O_3S$, 514.6; m/z found, 515.0 [M+H]$^+$. $^1$H NMR (400 MHz, CDCl$_3$): δ 8.35 (dd, J=5.4, 1.4 Hz, 1H), 8.05 (s, 1H), 7.49-7.39 (m, 2H), 7.92 (d, J=8.4 Hz, 1H), 7.30-7.15 (m, 3H), 6.95 (s, 1H), 6.03 (d, J=5.5 Hz, 1H), 4.60 (dt, J=9.1, 6.1 Hz, 1H), 3.75 (tt, J=5.3, 2.2 Hz, 1H), 3.14 (s, 1H), 2.83-2.64 (m, 5H), 2.11-1.86 (m, 4H), 1.88 (ddd, J=12.6, 6.3, 2.9 Hz, 1H), 1.50-1.29 (m, 3H).

Example 357: N-((1R,2S)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide

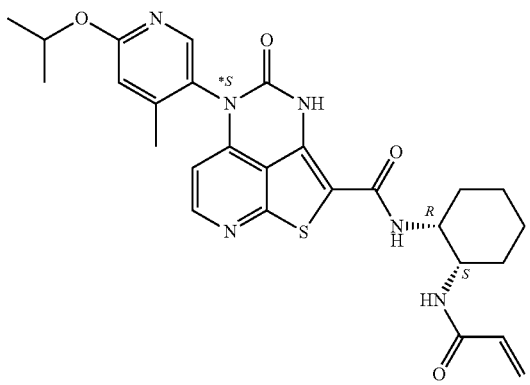

The title compound was prepared in a manner analogous to Example 337 using N-((1R,2S)-2-aminocyclohexyl)-5-(*S)-(6-isobutyl-4-methylpyridin-3-yl)-4-oxo-4,5-dihydro-3H-1-thia-3,5,8-triazaacenaphthylene-2-carboxamide (Example 335). MS (ESI): mass calcd. for $C_{28}H_{32}N_6O_3S$, 532.7; m/z found, 533.1 [M+H]$^+$. $^1$H NMR (500 MHz, CDCl$_3$): δ 9.53 (s, 1H), 8.40-8.31 (m, 2H), 7.19 (s, 1H), 7.07 (s, 1H), 6.45-6.37 (m, 2H), 6.21 (dd, J=16.9, 10.3 Hz, 1H), 5.94 (d, J=5.4 Hz, 1H), 5.76-5.70 (m, 1H), 4.32 (d, J=6.4 Hz, 1H), 4.12 (q, J=7.2 Hz, 1H), 2.71 (d, J=7.0 Hz, 2H), 2.04 (s, 3H), 1.96-1.84 (m, 3H), 1.58 (td, J=30.3, 28.1, 18.1 Hz, 2H), 1.26 (t, J=7.1 Hz, 4H), 0.99 (d, J=6.5 Hz, 6H).

Example 358: N-((1R,2R)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide

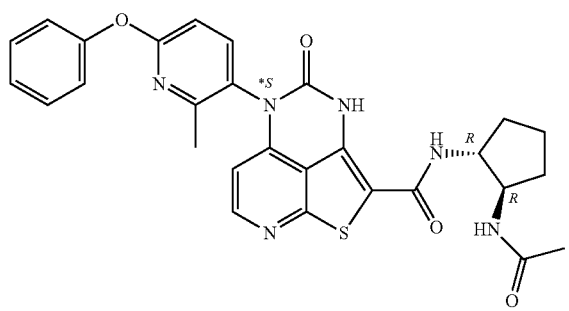

The title compound was prepared in a manner analogous to Example 1, Step B, using N-((1R,2R)-2-aminocyclopentyl)-5-(*S)-(2-methyl-6-phenoxypyridin-3-yl)-4-oxo-4,5-dihydro-3H-1-thia-3,5,8-triazaacenaphthylene-2-carboxamide (Example 301, product from Step A) and replacing acetic anhydride and diisopropylethylamine for prop-2-enoyl chloride and triethylamine. MS (ESI): mass calcd. for $C_{28}H_{26}N_6O_4S$, 542.6; m/z found, 543.0 [M+H]$^+$. $^1$H NMR (600 MHz, CDCl$_3$): δ 8.42-8.31 (m, 1H), 7.53 (d, J=8.6 Hz, 1H), 7.48-7.37 (m, 2H), 7.26-7.18 (m, 3H), 6.96 (d, J=5.8 Hz, 1H), 6.81 (dd, J=8.5, 0.8 Hz, 1H), 6.18 (d, J=6.6 Hz, 1H), 6.00 (d, J=5.3 Hz, 1H), 4.24-3.92 (m, 3H), 2.41-2.30 (m, 1H), 2.28 (s, 3H), 2.26-2.15 (m, 1H), 1.99 (s, 3H), 1.83 (tdd, J=9.2, 6.3, 4.7 Hz, 2H), 1.64-1.45 (m, 2H).

Example 359: N-((1R,3S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

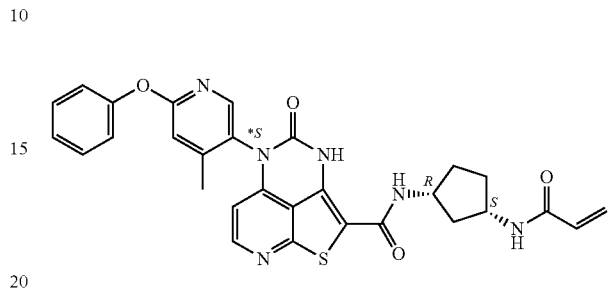

The title compound was prepared in a manner analogous to Example 337, using N-((1R,3S)-3-amino cyclopentyl)-5-(*S)-(4-methyl-6-phenoxypyridin-3-yl)-4-oxo-4,5-dihydro-3H-1-thia-3,5,8-triazaacenaphthylene-2-carboxamide (Example 355). MS (ESI): mass calcd. for $C_{29}H_{26}N_6O_4S$, 554.6; m/z found, 555.00 [M+H]$^+$. $^1$H NMR (400 MHz, CDCl$_3$): δ 8.31 (d, J=5.4 Hz, 1H), 8.06 (s, 1H), 7.79 (d, J=7.3 Hz, 1H), 7.48-7.38 (m, 2H), 7.32-7.14 (m, 4H), 6.95 (s, 1H), 6.37 (dd, J=17.0, 1.6 Hz, 1H), 6.12 (dd, J=16.9, 10.2 Hz, 1H), 6.01 (d, J=5.5 Hz, 1H), 5.63 (dd, J=10.1, 1.6 Hz, 1H), 4.39 (tq, J=8.8, 4.4 Hz, 1H), 2.44 (dt, J=14.2, 8.6 Hz, 1H), 2.10-1.83 (m, 9H), 1.17 (dd, J=10.1, 6.9 Hz, 1H).

Example 360: N-((1R,3S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

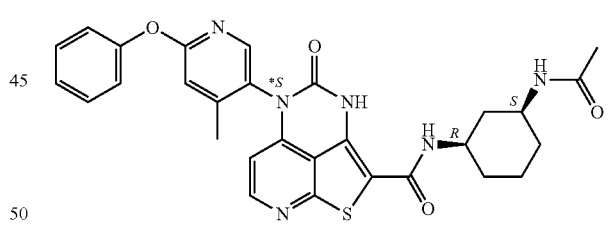

The title compound was prepared in a manner analogous to Example 1, step B, using N-((1R,3S)-3-amino cyclohexyl)-5-(*S)-(4-methyl-6-phenoxy pyridin-3-yl)-4-oxo-4,5-dihydro-3H-1-thia-3,5,8-triazaacenaphthylene-2-carboxamide (Example 356) and substituting acetic anhydride and diisopropylethylamine for prop-2-enoyl chloride and triethylamine. MS (ESI): mass calcd. for $C_{29}H_{28}N_6O_4S$, 556.6; m/z found, 557.00 [M+H]$^+$. $^1$H NMR (500 MHz, CDCl$_3$): δ 9.62 (s, 1H), 8.34 (d, J=5.4 Hz, 1H), 8.05 (s, 1H), 7.48-7.40 (m, 2H), 7.29-7.15 (m, 3H), 6.94 (s, 1H), 6.04 (d, J=5.4 Hz, 1H), 5.97 (d, J=7.7 Hz, 1H), 5.88 (d, J=7.8 Hz, 1H), 4.05-3.94 (m, 2H), 3.88 (dtd, J=12.4, 8.5, 8.0, 4.0 Hz, 1H), 3.54-347 (m, 2H), 2.35 (d, J=11.6 Hz, 1H), 2.19 (s, 3H), 2.11-1.95 (m, 5H), 1.89-1.81 (m, 1H), 1.47 (ddd, J=14.1, 10.3, 4.1 Hz, 1H).

Example 361: 5-(*S)-(4-Methyl-6-phenoxypyridin-3-yl)-4-oxo-N-((1R,3S)-3-propionamidocyclopentyl)-4,5-dihydro-3H-1-thia-3,5,8-triazaacenaphthylene-2-carboxamide

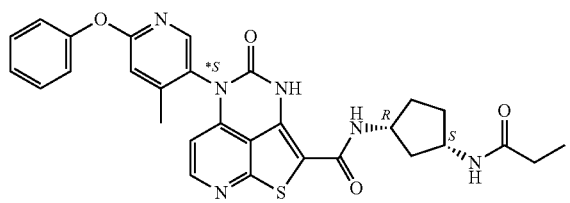

The title compound was prepared in a manner analogous to Example 35, using N-((1R,3S)-3-aminocyclopentyl)-5-(*S)-(4-methyl-6-phenoxypyridin-3-yl)-4-oxo-4,5-dihydro-3H-1-thia-3,5,8-triazaacenaphthylene-2-carboxamide (Example 355), and substituting diisopropylethylamine for triethylamine. MS (ESI): mass calcd. for $C_{29}H_{28}N_6O_4S$, 556.6; m/z found, 557.00 [M+H]$^+$. $^1$H NMR (500 MHz, CDCl$_3$): δ 9.64 (s, 1H), 8.33 (d, J=5.4 Hz, 1H), 8.06 (s, 1H), 7.63 (d, J=7.3 Hz, 1H), 7.47-7.39 (m, 2H), 7.29-7.15 (m, 3H), 6.95 (s, 1H), 6.66 (d, J=6.4 Hz, 1H), 6.02 (d, J=5.5 Hz, 1H), 5.29 (s, 1H), 4.37 (tt, J=7.7, 2.9 Hz, 1H), 4.16-3.99 (m, 1H), 2.47-2.30 (m, 1H), 2.26-2.15 (m, 3H), 2.04 (s, 2H), 1.98-1.85 (m, 4H), 1.26 (t, J=7.2 Hz, 3H).

Example 362: N-((1R,2R)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide

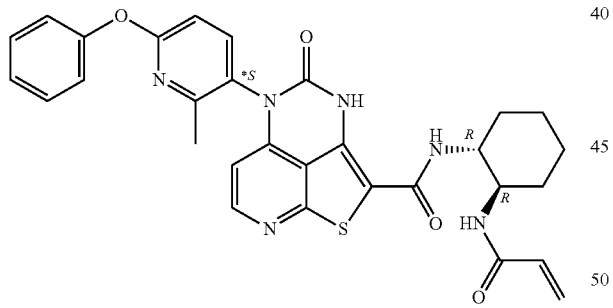

The title compound was prepared in a manner analogous to Example 1, Step B, using N-((1R,2R)-2-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide (Example 350), substituting acetic anhydride and diisopropylethylamine for prop-2-enoyl chloride and triethylamine. MS (ESI): mass calcd. for $C_{29}H_{28}N_6O_4S$, 556.6; m/z found, 557.0 [M+H]$^+$. $^1$H NMR (600 MHz, CDCl$_3$): δ 9.49 (s, 1H), 8.37 (d, J=5.4 Hz, 1H), 7.51 (d, J=8.5 Hz, 1H), 7.46-7.40 (m, 2H), 7.25-7.18 (m, 3H), 6.81 (d, J=8.6 Hz, 1H), 6.58 (d, J=7.1 Hz, 1H), 5.99 (d, J=5.4 Hz, 1H), 3.88-3.68 (m, 2H), 2.28 (s, 3H), 2.27-2.20 (m, 1H), 2.10-2.04 (m, 1H), 2.03-1.95 (m, 3H), 1.85-1.76 (m, 2H), 1.42-1.28 (m, 5H).

Example 363: N-((1R,3S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

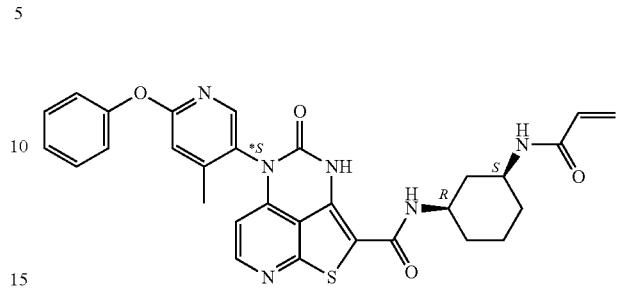

The title compound was prepared in a manner analogous to Example 337, using N-((1R,3S)-3-aminocyclohexyl)-5-(*S)-(4-methyl-6-phenoxypyridin-3-yl)-4-oxo-4,5-dihydro-3H-1-thia-3,5,8-triazaacenaphthylene-2-carboxamide (Example 356). MS (ESI): mass calcd. for $C_{30}H_{28}N_6O_4S$, 568.7; m/z found, 569.00 [M+H]$^+$. $^1$H NMR (500 MHz, CDCl$_3$): δ 9.54 (s, 1H), 8.34 (d, J=5.4 Hz, 1H), 8.04 (s, 1H), 7.48-7.39 (m, 2H), 7.28-7.15 (m, 3H), 6.94 (s, 1H), 6.27 (dd, J=16.9, 1.5 Hz, 1H), 6.12-6.01 (m, 2H), 5.80 (t, J=8.6 Hz, 2H), 5.63 (dd, J=10.2, 1.5 Hz, 1H), 5.30 (s, 2H), 3.48 (s, 1H), 2.45-2.38 (m, 1H), 2.06 (q, J=8.7, 5.5 Hz, 3H), 1.86 (dt, J=7.2, 3.6 Hz, 1H), 1.51 (qt, J=13.6, 3.6 Hz, 1H), 1.29-1.07 (m, 4H).

Example 364: 5-(*S)-(2-Methyl-6-phenoxypyridin-3-yl)-4-oxo-N-((1R,2R)-2-propionamidocyclohexyl)-4,5-dihydro-3H-1-thia-3,5,8-triazaacenaphthylene-2-carboxamide

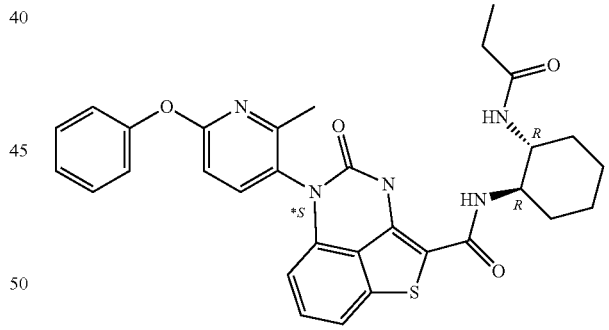

The title compound was prepared in a manner analogous to Example 35, using N-((1R,2R)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide (Example 350 Example 350: N-((1R,2R)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide. MS (ESI): mass calcd. for $C_{30}H_{30}N_6O_4S$, 570.7; m/z found, 571.0 [M+H]$^+$. $^1$H NMR (500 MHz, CDCl$_3$): δ 9.57 (s, 1H), 8.37 (d, J=5.5 Hz, 1H), 7.64-7.36 (m, 3H), 7.26-7.18 (m, 3H), 6.81 (dd, J=8.5, 0.7 Hz, 1H), 6.73 (d, J=7.2 Hz, 1H), 5.99 (d, J=5.4 Hz, 1H), 5.90 (d, J=8.0 Hz, 1H), 3.89-3.70 (m, 2H), 2.28 (s, 3H), 2.27-2.11 (m, 3H), 1.89-1.77 (m, 3H), 1.45-1.32 (m, 4H), 1.10 (t, J=7.6 Hz, 3H).

Example 365: N-((1R,3S)-3-Acrylamidocyclopentyl)-5-(6-isobutoxy-4-methylpyridin-3-yl)-4-oxo-4,5-dihydro-3H-1-thia-3,5,8-triazaacenaphthylene-2-carboxamide

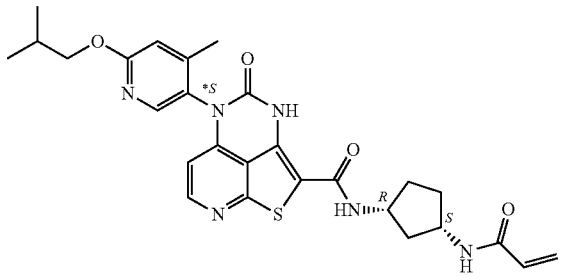

Step A. N-((1R,3S)-3-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide The title compound was prepared in a manner analogous to Example 166, Step A, using 5-(6-isobutoxy-4-methylpyridin-3-yl)-4-oxo-4,5-dihydro-3H-1-thia-3,5,8-triazaacenaphthylene-2-carboxylic acid (Intermediate 33, including CHIRAL SEPARATION METHOD 1 to obtain the *S atropisomer) and tert-butyl ((1S,3R)-3-aminocyclopentyl)carbamate (with a TFA/DCM deprotection).

Step B. N-((1R,3S)-3-Acrylamidocyclopentyl)-5-(6-isobutoxy-4-methylpyridin-3-yl)-4-oxo-4,5-dihydro-3H-1-thia-3,5,8-triazaacenaphthylene-2-carboxamide The title compound was prepared in a manner analogous to Example 1, Step B, using N-((1R,3S)-3-aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide, acrylic anhydride and diisopropylethylamine in place of prop-2-enoyl chloride and triethylamine in step B. MS (ESI): mass calcd. for $C_{27}H_{30}N_6O_4S$, 534.6; m/z found, 535.0 [M+H]$^+$. $^1$H NMR (500 MHz, CDCl$_3$): δ 9.63 (s, 1H), 8.33 (d, J=5.5 Hz, 1H), 8.02 (s, 1H), 7.58 (d, J=7.3 Hz, 1H), 6.87 (d, J=7.1 Hz, 1H), 6.83-6.78 (m, 1H), 6.39 (dd, J=17.0, 1.4 Hz, 1H), 6.11 (dd, J=16.9, 10.3 Hz, 1H), 6.02 (d, J=5.4 Hz, 1H), 5.66 (dd, J=10.3, 1.4 Hz, 1H), 4.40 (ddt, J=11.5, 7.7, 3.6 Hz, 1H), 4.18-4.04 (m, 3H), 2.51-2.40 (m, 1H), 2.16-1.82 (m, 9H), 1.03 (dd, J=6.8, 1.3 Hz, 6H).

Example 366: N-((1R,3S)-3-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide

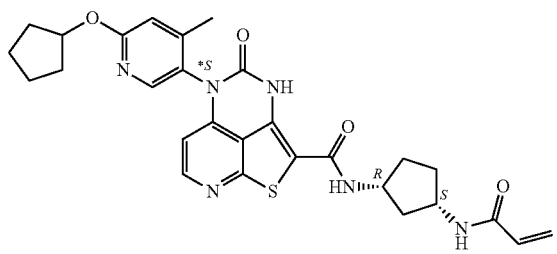

The title compound was prepared in a manner analogous to Example 1, Step B, using N-((1R,3S)-3-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide (Example 394), and acrylic anhydride and diisopropylethylamine in place of prop-2-enoyl chloride and triethylamine in step B. MS (ESI): mass calcd. for $C_{28}H_{30}N_6O_4S$, 546.7; m/z found, 547.0 [M+H]$^+$. $^1$H NMR (500 MHz, CDCl$_3$): δ 8.32 (d, J=5.4 Hz, 1H), 8.03 (s, 1H), 7.68 (d, J=7.3 Hz, 1H), 7.19 (d, J=7.2 Hz, 1H), 6.73 (s, 1H), 6.37 (dd, J=17.0, 1.5 Hz, 1H), 6.12 (dd, J=16.9, 10.3 Hz, 1H), 6.02 (d, J=5.4 Hz, 1H), 5.64 (dd, J=10.2, 1.5 Hz, 1H), 5.46-5.35 (m, 1H), 4.21-3.99 (m, 1H), 2.44 (s, OH), 2.13 (s, 3H), 2.54-2.37 (m, 1H), 2.13 (s, 3H), 2.04-1.95 (m, 3H), 1.94-1.86 (m, 5H), 1.64 (dq, J=7.0, 2.7, 2.2 Hz, 4H).

Example 367: N-((1R,2S)-2-Acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide

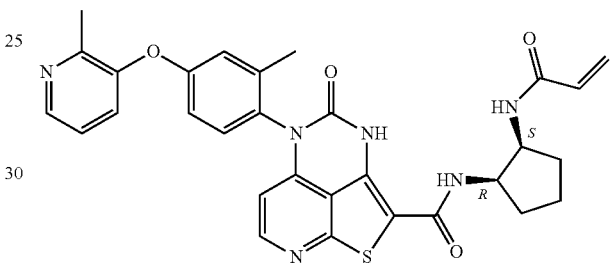

Step A.
2-Methyl-3-(3-methyl-4-nitrophenoxy)pyridine

The title compound was prepared in a manner analogous to Intermediate 1, Step A, using 4-fluoro-2-methyl-1-nitrobenzene and 2-methylpyridin-3-ol.

Step B. 5-(2-Methyl-4-((2-methylpyridin-3-yl)oxy)phenyl)-4-oxo-4,5-dihydro-3H-1-thia-3,5,8-triazaacenaphthylene-2-carboxylic acid The title compound was prepared in a manner analogous to Intermediate 25, Steps B-C, using 2-methyl-3-(3-methyl-4-nitrophenoxy)pyridine in Step B.

Step C: N-((1R,2S)-2-Acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-((2-methylpyridin-3-yl)oxy)phenyl)-4-oxo-4,5-dihydro-3H-1-thia-3,5,8-triazaacenaphthylene-2-carboxylic acid and N-((1S,2R)-2-aminocyclopentyl)acrylamide (Intermediate 36), no HCl/MeOH deprotection. MS (ESI): mass calcd. for $C_{30}H_{28}N_6O_4S$, 568.6; m/z found, 569.2 [M+H]$^+$. $^1$H NMR (400 MHz, CD$_3$OD): δ 8.35-8.28 (m, 1H), 8.28-8.22 (m, 1H), 7.50-7.43 (m, 1H), 7.36-7.28 (m, 2H), 7.10-7.02 (m, 1H), 6.99-6.93 (m, 1H), 6.32-6.16 (m, 2H), 6.09-6.01 (m, 1H), 5.64-5.58 (m, 1H), 4.46-4.36 (m, 2H), 2.50 (s, 3H), 2.13 (s, 3H), 2.11-2.01 (m, 2H), 1.96-1.86 (m, 1H), 1.81-1.61 (m, 3H).

Example 368: N-((1R,2S)-2-Acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide

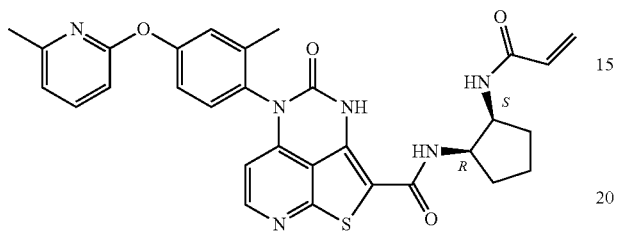

Step A.
2-Methyl-4-((6-methylpyridin-2-yl)oxy)aniline

The title compound was prepared in a manner analogous to Intermediate 1, Step A, using 4-amino-3-methylphenol and 2-fluoro-6-methylpyridine.

Step B. 5-(2-Methyl-4-((6-methylpyridin-2-yl)oxy)phenyl)-4-oxo-4,5-dihydro-3H-1-thia-3,5,8-triazaacenaphthylene-2-carboxylic acid The title compound was prepared in a manner analogous to Intermediate 1, Steps C-F, using 2-methyl-4-((6-methylpyridin-2-yl)oxy)aniline in Step C.

Step C. N-((1R,2S)-2-Acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide The title compound was prepared in a manner analogous to Example 1, Step A using 5-(2-methyl-4-((6-methylpyridin-2-yl)oxy)phenyl)-4-oxo-4,5-dihydro-3H-1-thia-3,5,8-triazaacenaphthylene-2-carboxylic acid and N-((1S,2R)-2-aminocyclopentyl)acrylamide (Intermediate 36), no HCl/MeOH deprotection. MS (ESI): mass calcd. for $C_{30}H_{28}N_6O_4S$, 568.6; m/z found, 569.2 [M+H]$^+$. $^1$H NMR (400 MHz, CD$_3$OD): δ 8.36-8.24 (m, 1H), 7.76-7.65 (m, 1H), 7.44-7.29 (m, 1H), 7.20-7.15 (m, 1H), 7.13-7.06 (m, 1H), 7.06-6.97 (m, 1H), 6.82-6.72 (m, 1H), 6.34-6.15 (m, 2H), 6.14-6.05 (m, 1H), 5.66-5.55 (m, 1H), 4.48-4.34 (m, 2H), 2.42 (s, 3H), 2.20-2.00 (m, 5H), 1.98-1.84 (m, 1H), 1.82-1.61 (m, 3H).

Example 369: N-((1R,2S)-2-Acrylamidocyclopentyl)-5-(4-((6-methylpyridin-2-yl)oxy)phenyl)-4-oxo-4,5-dihydro-3H-1-thia-3,5,8-triazaacenaphthylene-2-carboxamide

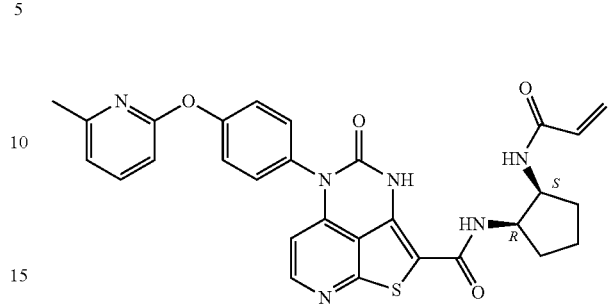

The title compound was prepared in a manner analogous to Example 368, using 4-aminophenol and 2-fluoro-6-methylpyridine in Step A. MS (ESI): mass calcd. for $C_{29}H_{26}N_6O_4S$, 554.6; m/z found, 555.1 [M+H]$^+$. $^1$H NMR (400 MHz, DMSO-d$_6$): δ 9.98 (s, 1H), 8.30 (d, J=5.5 Hz, 1H), 7.92-7.81 (m, 1H), 7.81-7.62 (m, 2H), 7.52-7.40 (m, 2H), 7.34-7.21 (m, 2H), 7.08-6.97 (m, 1H), 6.89-6.80 (m, 1H), 6.30-6.15 (m, 1H), 6.11-5.96 (m, 2H), 5.62-5.47 (m, 1H), 4.42-4.14 (m, 2H), 2.35 (s, 3H), 2.02-1.82 (m, 2H), 1.80-1.68 (m, 2H), 1.66-1.44 (m, 2H).

Example 370: N-((1R,2S)-2-Acrylamidocyclopentyl)-5-(4-((6-methylpyridin-3-yl)oxy)phenyl)-4-oxo-4,5-dihydro-3H-1-thia-3,5,8-triazaacenaphthylene-2-carboxamide

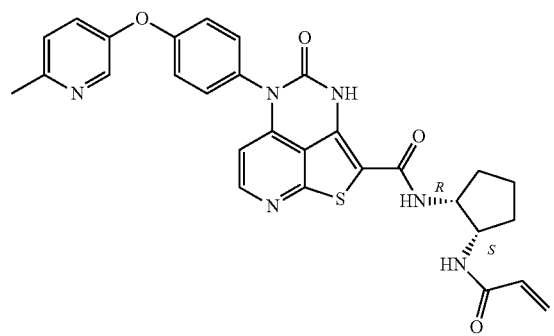

The title compound was prepared in a manner analogous to Example 1, using 5-(4-((6-methylpyridin-3-yl)oxy)phenyl)-4-oxo-4,5-dihydro-3H-1-thia-3,5,8-triazaacenaphthylene-2-carboxylic acid (Intermediate 32) and tert-butyl ((1S,2R)-2-aminocyclopentyl)carbamate in Step A, and using acrylic anhydride in place of prop-2-enoyl chloride in Step B. MS (ESI): mass calcd. for $C_{29}H_{26}N_6O_4S$, 554.6; m/z found, 555.1 [M+H]$^+$. $^1$H NMR (400 MHz, CD$_3$OD): δ 8.34-8.24 (m, 2H), 7.54-7.46 (m, 1H), 7.45-7.38 (m, 2H), 7.37-7.30 (m, 1H), 7.24-7.18 (m, 2H), 6.31-6.12 (m, 3H), 5.68-5.53 (m, 1H), 4.47-4.32 (m, 2H), 2.52 (s, 3H), 2.14-1.99 (m, 2H), 1.97-1.85 (m, 1H), 1.80-1.61 (m, 3H).

Example 371: N-((1R,2S)-2-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide

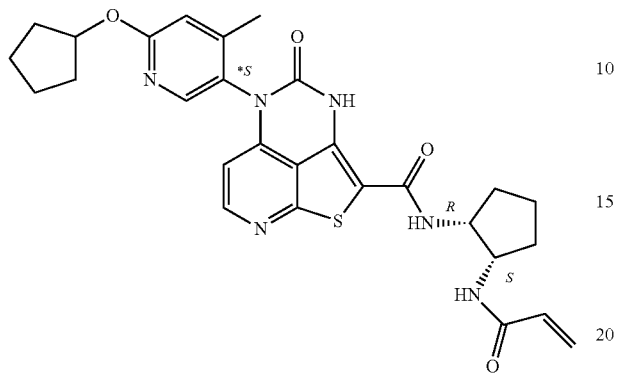

The title compound was prepared in manner analogous to Example 1, Step B, using N-((1R,2S)-2-aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide (Example 374) and acrylic anhydride and diisopropylethylamine in place of prop-2-enoyl chloride and triethylamine. MS (ESI): mass calcd. for $C_{28}H_{30}N_6O_4S$, 546.7; m/z found, 547.0 [M+H]$^+$. $^1$H NMR (500 MHz, CDCl$_3$): δ 9.48 (s, 1H), 8.33 (d, J=5.4 Hz, 1H), 8.02 (s, 1H), 6.86 (d, J=6.1 Hz, 1H), 6.80 (d, J=6.4 Hz, 1H), 6.72 (s, 1H), 6.33 (d, J=16.8 Hz, 1H), 6.16 (dd, J=16.9, 10.1 Hz, 1H), 6.02 (d, J=5.3 Hz, 1H), 5.65 (d, J=10.3 Hz, 1H), 5.41 (dq, J=6.5, 3.4, 3.0 Hz, 1H), 4.38 (dq, J=19.3, 6.8 Hz, 2H), 2.28-2.17 (m, 1H), 2.11 (s, 4H), 1.98 (dq, J=15.8, 7.9, 7.2 Hz, 2H), 1.92-1.65 (m, 10H).

Example 372: N-((1R,2S)-2-Acrylamidocyclopentyl)-5-(4-((2-methylpyridin-3-yl)oxy)phenyl)-4-oxo-4,5-dihydro-3H-1-thia-3,5,8-triazaacenaphthylene-2-carboxamide

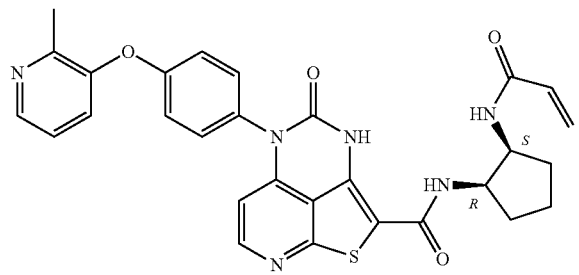

The title compound was prepared in a manner analogous to Example 368, using 4-fluoronitrobenzene and 2-methylpyridin-3-ol in Step A. MS (ESI): mass calcd. for $C_{29}H_{26}N_6O_4S$, 554.6; m/z found, 555.2 [M+H]$^+$. $^1$H NMR (400 MHz, CD$_3$OD) d 8.33-8.22 (m, 2H), 7.51-7.39 (m, 3H), 7.34-7.28 (m, 1H), 7.19-7.12 (m, 2H), 6.32-6.13 (m, 3H), 5.64-5.57 (m, 1H), 4.46-4.35 (m, 2H), 2.51 (s, 3H), 2.14-2.01 (m, 2H), 1.95-1.85 (m, 1H), 1.81-1.61 (m, 3H).

Example 373: N-((1R,2S)-2-Acrylamidocyclopentyl)-5-(*S)-(6-isobutoxy-4-methylpyridin-3-yl)-4-oxo-4,5-dihydro-3H-1-thia-3,5,8-triazaacenaphthylene-2-carboxamide

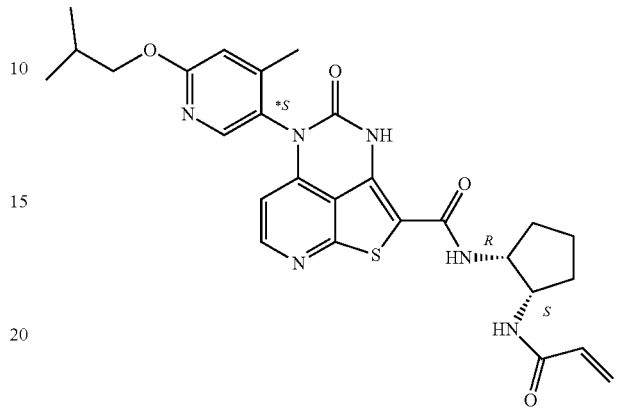

Step A. N-((1R,2S)-2-aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide The title compound was prepared in a manner analogous to Example 166, Step A, using 5-(6-isobutoxy-4-methylpyridin-3-yl)-4-oxo-4,5-dihydro-3H-1-thia-3,5,8-triazaacenaphthylene-2-carboxylic acid (Intermediate 33, including CHIRAL SEPARATION METHOD 1 to obtain the *S atropisomer) and tert-butyl ((1S,2R)-2-aminocyclopentyl)carbamate.

Step B. N-((1R,2S)-2-Acrylamidocyclopentyl)-5-(*S)-(6-isobutoxy-4-methylpyridin-3-yl)-4-oxo-4,5-dihydro-3H-1-thia-3,5,8-triazaacenaphthylene-2-carboxamide The title compound was prepared in a manner analogous to Example 1, Step B, using N-((1R,2S)-2-aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide, acrylic anhydride and diisopropylethylamine in place of prop-2-enoyl chloride and triethylamine in step B. MS (ESI): mass calcd. for $C_{27}H_{30}N_6O_4S$, 534.6; m/z found, 535.0 [M+H]$^+$. $^1$H NMR (400 MHz, CDCl$_3$): δ 9.49 (s, 1H), 8.33 (d, J=5.4 Hz, 1H), 8.02 (s, 1H), 6.94 (dd, J=22.5, 5.8 Hz, 2H), 6.79 (s, 1H), 6.33 (dd, J=17.1, 1.7 Hz, 1H), 6.17 (dd, J=16.9, 10.2 Hz, 1H), 6.02 (d, J=5.5 Hz, 1H), 5.63 (dd, J=10.2, 1.7 Hz, 1H), 4.40 (hept, J=6.5 Hz, 2H), 4.09 (dt, J=6.7, 3.7 Hz, 2H), 3.53-3.43 (m, 1H), 2.28-2.03 (m, 6H), 1.92-1.68 (m, 3H), 1.03 (d, J=6.7 Hz, 6H).

Example 374: N-((1R,2S)-2-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide

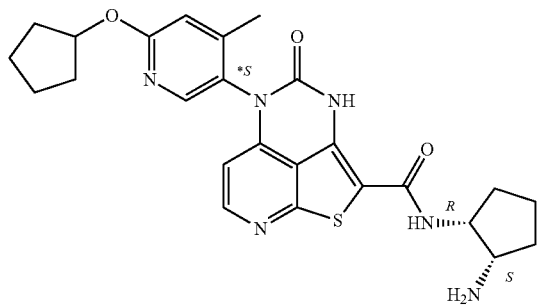

The title compound was prepared in a manner analogous to Example 166, using 5-(6-(cyclopentyloxy)-4-methylpyridin-3-yl)-4-oxo-4,5-dihydro-3H-1-thia-3,5,8-triazaacenaphthylene-2-carboxylic acid (Intermediate 25, including CHIRAL SEPARATION METHOD 1 to obtain the *S atropisomer) and tert-butyl ((1S,2R)-2-aminocyclopentyl)carbamate in Step A. MS (ESI): mass calcd. for $C_{25}H_{28}N_6O_3S$, 492.6; m/z found, 493.0 [M+H]$^+$. $^1$H NMR (500 MHz, CDCl$_3$): δ 8.34 (d, J=5.5 Hz, 1H), 8.01 (s, 1H), 6.77-6.71 (m, 2H), 6.03 (d, J=5.5 Hz, 1H), 5.42 (tt, J=6.2, 2.9 Hz, 1H), 4.15 (p, J=7.1 Hz, 1H), 3.48-3.26 (m, 5H), 2.81 (s, 3H), 2.20-2.09 (m, 2H), 2.10-1.91 (m, 3H), 1.91-1.74 (m, 4H), 1.72-1.46 (m, 4H).

Example 375: N-((1R,2S)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide

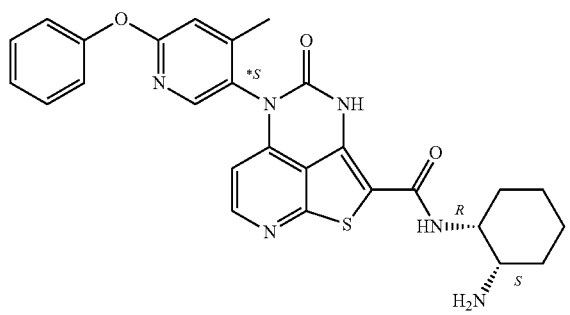

The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and (1S,2R)-(2-aminocyclohexyl)carbamic acid tert-butyl ester, and diisopropylethylamine. MS (ESI): mass calcd. for $C_{27}H_{26}N_6O_3S$, 514.6; m/z found, 515.0 [M+H]$^+$. $^1$H NMR (400 MHz, CD$_3$OD): δ 8.55 (s, 1H), 8.16 (s, 1H), 7.58-7.40 (m, 2H), 7.39-7.01 (m, 4H), 6.49 (d, J=6.3 Hz, 1H), 4.54-4.39 (m, 1H), 3.73-3.56 (m, 1H), 2.24 (s, 3H), 1.86-1.54 (m, 8H).

Example 376: N-((1R,2S)-2-Acrylamidocyclopentyl)-5-(2-cyclobutylpyridin-4-yl)-4-oxo-4,5-dihydro-3H-1-thia-3,5,8-triazaacenaphthylene-2-carboxamide

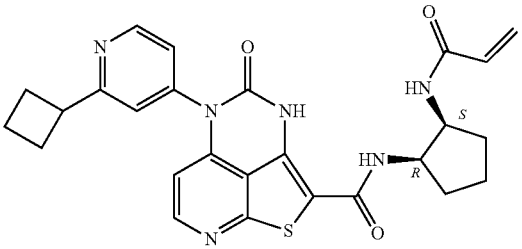

Step A. 2-Cyclobutylpyridin-4-amine

To a solution of 2-bromopyridin-4-amine (17.3 g, 100 mmol) and Pd(dppf)C12 (4.08 g, 5 mmol) in THF (600 mL), was added via syringe cyclobutylzinc(II) bromide (200 mL, 100 mmol). The reaction mixture was stirred at 60° C. for 18 h. The reaction mixture was treated with saturated aqueous sodium bicarbonate (300 mL), then extracted with EtOAc (2×300 mL). The combined organic layers were dried (Na$_2$SO$_4$) and concentrated under reduced pressure. Purification (FCC, SiO$_2$, PE/EA) afforded the title compound as a brown oil (4.4 g, 30%).

Step B. 5-(2-Cyclobutylpyridin-4-yl)-4-oxo-4,5-dihydro-3H-1-thia-3,5,8-triazaacenaphthylene-2-carboxylic acid The title compound was prepared in a manner analogous to Intermediate 1, Steps C-G, using 2-cyclobutylpyridin-4-amine.

Step C. N-((1R,2R)-2-Acrylamidocyclopentyl)-5-(2-cyclobutylpyridin-4-yl)-4-oxo-4,5-dihydro-3H-1-thia-3,5,8-triazaacenaphthylene-2-carboxamide The title compound was prepared in a manner analogous to Example 1, Step A, using 5-(2-cyclobutylpyridin-4-yl)-4-oxo-4,5-dihydro-3H-1-thia-3,5,8-triazaacenaphthylene-2-carboxylic acid and N-((1S,2R)-2-aminocyclopentyl)acrylamide (Intermediate 36), no HCl/MeOH deprotection step. MS (ESI): mass calcd. for $C_{26}H_{26}N_6O_3S$, 502.6; m/z found, 503.3 [M+H]$^+$. $^1$H NMR (400 MHz, CD$_3$OD): δ 8.70 (d, J=5.3 Hz, 1H), 8.30 (d, J=5.6 Hz, 1H), 7.46 (s, 1H), 7.38-7.32 (m, 1H), 6.33-6.15 (m, 3H), 5.65-5.58 (m, 1H), 4.50-4.33 (m, 2H), 3.88-3.71 (m, 1H), 2.46-2.28 (m, 4H), 2.17-1.99 (m, 3H), 1.97-1.84 (m, 2H), 1.81-1.57 (m, 3H).

Example 377: N-((1R,2S)-2-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

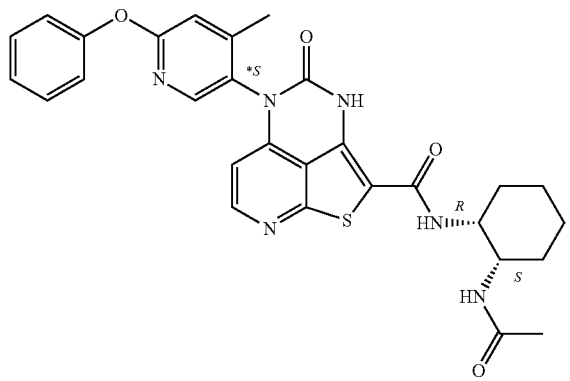

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and (1S,2R)-(2-aminocyclohexyl)carbamic acid tert-butyl ester and diisopropylethylamine in Step A, and using acetic anhydride and diisopropylethylamine in place of prop-2-enoyl chloride and triethylamine in Step B. MS (ESI): mass calcd. for $C_{29}H_{28}N_6O_4S$, 556.6; m/z found, 557.0 [M+H]$^+$. $^1$H NMR (500 MHz, CD$_3$OD): δ 8.39-8.31 (m, 1H), 8.09 (s, 1H), 7.53-7.36 (m, 2H), 7.33-7.11 (m, 3H), 7.05 (s, 1H), 6.29-6.00 (m, 1H), 4.35 (s, 1H), 4.11 (d, J=7.1 Hz, 1H), 2.21 (s, 3H), 2.02 (s, 3H), 1.82-1.45 (m, 8H).

Example 378: N-((1R,2S)-2-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

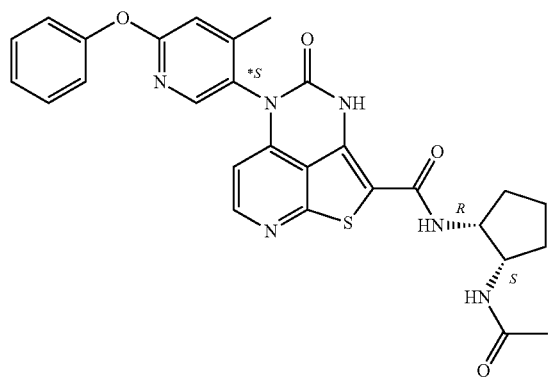

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,2R)-2-aminocyclopentyl)carbamate and diisopropylethylamine in Step A, and using acetic anhydride and diisopropylethylamine in place of prop-2-enoyl chloride and triethylamine in Step B. MS (ESI): mass calcd. for $C_{28}H_{26}N_6O_4S$, 542.6; m/z found, 543.0 [M+H]$^+$. $^1$H NMR (500 MHz, CDCl$_3$): δ 9.54 (s, 1H), 8.35 (d, J=5.5 Hz, 1H), 8.05 (s, 1H), 7.52-7.39 (m, 2H), 7.26-7.23 (m, 1H), 7.23-7.17 (m, 2H), 6.99-6.94 (m, 1H), 6.72 (d, J=6.0 Hz, 1H), 6.08 (d, J=6.6 Hz, 1H), 6.05-6.02 (m, 1H), 4.35-4.23 (m, 2H), 2.29-2.22 (m, 1H), 2.20 (d, J=0.8 Hz, 3H), 2.14-2.07 (m, 1H), 2.04 (s, 3H), 1.91-1.81 (m, 4H).

Example 379: N-((1R,2R)-2-Acrylamidocyclopentyl)-5-(2-cyclobutylpyridin-4-yl)-4-oxo-4,5-dihydro-3H-1-thia-3,5,8-triazaacenaphthylene-2-carboxamide

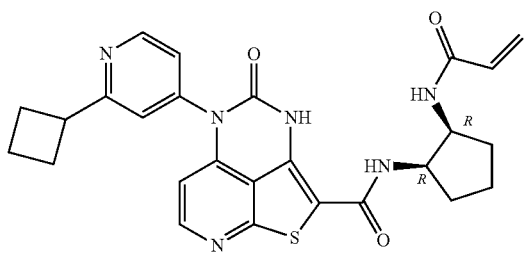

The title compound was prepared in a manner analogous to Example 1, Step A, using 5-(2-cyclobutylpyridin-4-yl)-4-oxo-4,5-dihydro-3H-1-thia-3,5,8-triazaacenaphthylene-2-carboxylic acid (Example 376, product from Step B) and N-((1R,2R)-2-aminocyclopentyl)acrylamide (Example 382, product from Step A), no HCl/MeOH deprotection step. MS (ESI): mass calcd. for $C_{26}H_{26}N_6O_3S$, 502.6; m/z found, 503.1 [M+H]$^+$. $^1$H NMR (400 MHz, CD$_3$OD): δ 8.69 (d, J=5.3 Hz, 1H), 8.26 (d, J=5.5 Hz, 1H), 7.49 (s, 1H), 7.38 (dd, J=5.2, 1.7 Hz, 1H), 6.24-6.10 (m, 3H), 5.61-5.54 (m, 1H), 4.29-4.15 (m, 2H), 3.84-3.69 (m, 1H), 2.44-2.29 (m, 4H), 2.20-2.02 (m, 3H), 1.95-1.86 (m, 1H), 1.83-1.72 (m, 2H), 1.68-1.49 (m, 2H).

Example 380: 5-(*S)-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide

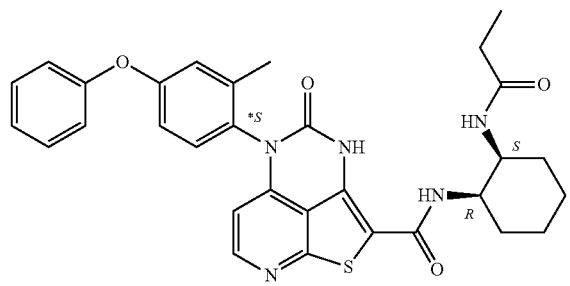

Step A. N-((1R,2S)-2-aminocyclohexyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 166, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1S,2R)-2-aminocyclohexyl)carbamate.

Step B. 5-(*S)-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide The title compound was prepared in manner analogous to Example 1, Step B, using propionic anhydride and diisopropylethylamine in place of prop-2-enoyl chloride and triethylamine. MS (ESI): mass calcd. for $C_{31}H_{31}N_5O_4S$, 569.7; m/z found, 570.0 [M+H]$^+$. $^1$H NMR (500 MHz, CD$_3$OD): δ 8.33 (d, J=5.6 Hz, 1H), 7.47-7.36 (m, 2H), 7.30 (d, J=8.6 Hz, 1H), 7.23-6.96 (m, 5H), 6.07 (d, J=5.6 Hz, 1H), 4.37-4.29 (m, 1H), 4.16-4.06 (m, 1H), 2.38-2.19 (m, 2H), 2.13 (s, 3H), 1.83-1.49 (m, 8H), 1.14 (t, J=7.6 Hz, 3H).

Example 381: 5-(*S)-(4-Methyl-6-phenoxypyridin-3-yl)-4-oxo-N-((1R,2S)-2-propionamidocyclohexyl)-4,5-dihydro-3H-1-thia-3,5,8-triazaacenaphthylene-2-carboxamide

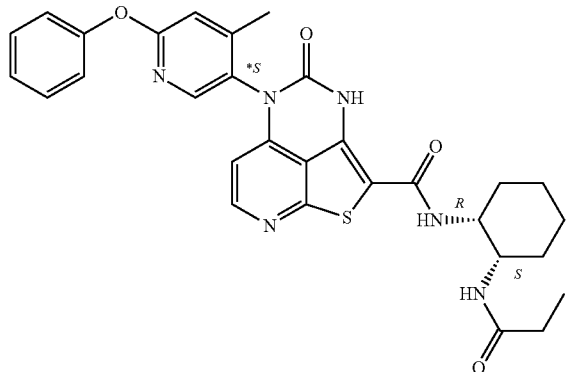

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,2R)-2-aminocyclohexyl)carbamate and diisopropylethylamine in Step A, and using propionic anhydride and diisopropylethylamine in place of prop-2-enoyl chloride and triethylamine in Step B. MS (ESI): mass calcd. for $C_{30}H_{30}N_6O_4S$, 570.7; m/z found, 571.0 [M+H]$^+$.

Example 382: N-((1R,2R)-2-Acrylamidocyclopentyl)-5-(*S)-(6-isobutyl-4-methylpyridin-3-yl)-4-oxo-4,5-dihydro-3H-1-thia-3,5,8-triazaacenaphthylene-2-carboxamide

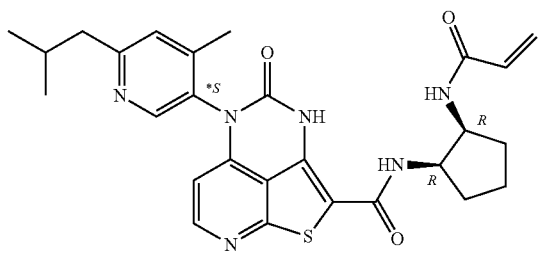

Step A. N-((1R,2R)-2-aminocyclopentyl)acrylamide

The title compound was prepared in a manner analogous to Intermediate 36, using tert-butyl ((1R,2R)-2-aminocyclopentyl)carbamate.

Step B. N-((1R,2R)-2-Acrylamidocyclopentyl)-5-(*S)-(6-isobutyl-4-methylpyridin-3-yl)-4-oxo-4,5-dihydro-3H-1-thia-3,5,8-triazaacenaphthylene-2-carboxamide The title compound was prepared in a manner analogous to Example 1, Step A, using 5-(6-isobutyl-4-methylpyridin-3-yl)-4-oxo-4,5-dihydro-3H-1-thia-3,5,8-triazaacenaphthylene-2-carboxylic acid (Intermediate 18, including CHIRAL SEPARATION METHOD 1 to obtain the *S atropisomer) and N-((1R,2R)-2-aminocyclopentyl)acrylamide, no HCl/MeOH deprotection step. MS (ESI): mass calcd. for $C_{27}H_{30}N_6O_3S$, 518.6; m/z found, 519 [M+H]$^+$. $^1$H NMR (400 MHz, CD$_3$OD): δ 8.39 (s, 1H), 8.33-8.28 (m, 1H), 7.39 (s, 1H), 6.27-6.16 (m, 2H), 6.03-5.97 (m, 1H), 5.67-5.55 (m, 1H), 4.30-4.18 (m, 2H), 2.73-2.67 (m, 2H), 2.20 (s, 3H), 2.18-2.06 (m, 3H), 1.87-1.75 (m, 2H), 1.71-1.51 (m, 2H), 0.97 (d, J=6.6 Hz, 6H).

Example 383: N-((1R,2S)-2-Acrylamidocyclopentyl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide

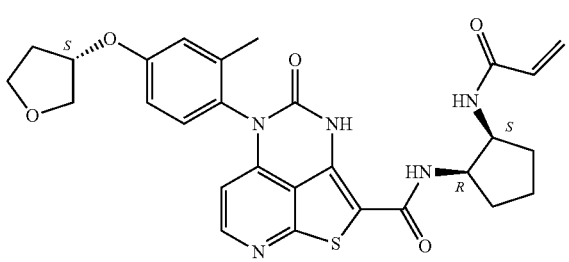

Step A. (S)-5-(2-methyl-4-((tetrahydrofuran-3-yl) oxy)phenyl)-4-oxo-4,5-dihydro-3H-1-thia-3,5,8-triazaacenaphthylene-2-carboxylic acid The title compound was prepared in a manner analogous to Intermediate 7, using 4-fluoro-2-methyl-1-nitrobenzene and (S)-tetrahydrofuran-3-ol Step A.

Step B. N-((1R,2S)-2-Acrylamidocyclopentyl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide The title compound was prepared in a manner analogous to Example 1, Step A, using N-((1S,2R)-2-aminocyclopentyl)acrylamide (Intermediate 36) and (S)-5-(2-methyl-4-((tetrahydrofuran-3-yl)oxy)phenyl)-4-oxo-4,5-dihydro-3H-1-thia-3,5,8-triazaacenaphthylene-2-carboxylic acid, no HCl/MeOH deprotection step. MS (ESI): mass calcd. for $C_{28}H_{29}N_5O_5S$, 547.6; m/z found, 548.2 [M+H]$^+$. $^1$H NMR (400 MHz, CD$_3$OD): δ 8.28 (d, J=5.6 Hz, 1H), 7.26-7.18 (m, 1H), 7.02-6.89 (m, 2H), 6.34-6.16 (m, 2H), 6.06-5.96 (m, 1H), 5.68-5.55 (m, 1H), 5.11-5.05 (m, 1H), 4.48-4.35 (m, 2H), 4.05-3.92 (m, 3H), 3.90-3.85 (m, 1H), 2.35-2.23 (m, 1H), 2.18-2.02 (m, 6H), 1.98-1.86 (m, 1H), 1.80-1.62 (m, 3H).

Example 384: N-((1R,2S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide

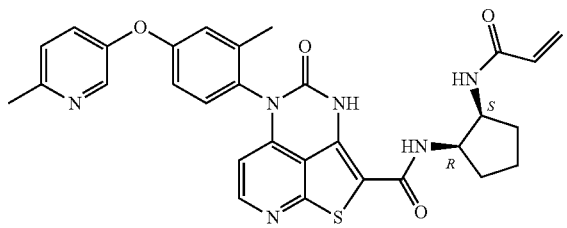

Step A. 5-(2-methyl-4-((6-methylpyridin-3-yl)oxy) phenyl)-4-oxo-4,5-dihydro-3H-1-thia-3,5,8-triazaacenaphthylene-2-carboxylic acid The title compound was prepared in a manner analogous to Intermediate 7, using 4-fluoro-2-methyl-1-nitrobenzene and 6-methylpyridin-3-ol Step A.

Step B. N-((1R,2S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide The title compound was prepared in a manner analogous to Example 1, Step A, using N-((1S,2R)-2-aminocyclopentyl)acrylamide (Intermediate 36) and 5-(2-methyl-4-((6-methylpyridin-3-yl)oxy)phenyl)-4-oxo-4,5-dihydro-3H-1-thia-3,5,8-triazaacenaphthylene-2-carboxylic acid, no HCl/MeOH deprotection step. MS (ESI): mass calcd. for $C_{30}H_{28}N_6O_4S$, 568.6; m/z found, 569.2 [M+H]$^+$. $^1$H NMR (400 MHz, DMSO-d$_6$ and CD$_3$OD): δ 8.25 (d, J=5.5 Hz, 1H), 8.23-8.17 (m, 1H), 7.46-7.36 (m, 1H), 7.33-7.22 (m, 2H), 7.07-7.00 (m, 1H), 6.97-6.91 (m, 1H), 6.26-6.05 (m, 2H), 5.96 (d, J=5.5 Hz, 1H), 5.56-5.48 (m, 1H), 4.30-4.26 (m, 1H), 4.10-4.03 (m, 1H), 2.44 (s, 3H), 2.04 (s, 3H), 2.00-1.91 (m, 2H), 1.84-1.75 (m, 1H), 1.72-1.61 (m, 2H), 1.60-1.50 (m, 1H).

Example 385: 5-(*S)-(4-Methyl-6-phenoxy pyridin-3-yl)-4-oxo-N-((1R,3S)-3-propionamidocyclohexyl)-4,5-dihydro-3H-1-thia-3,5,8-triazaacenaphthylene-2-carboxamide

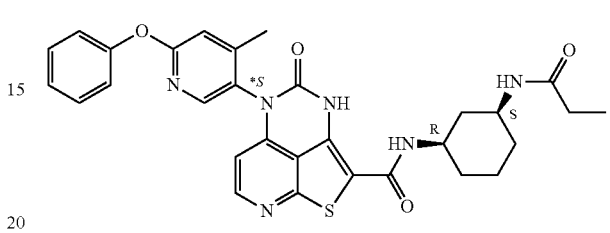

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,3R)-3-aminocyclohexyl)carbamate in Step A, and using propionic anhydride in place of prop-2-enoyl chloride in Step B. MS (ESI): mass calcd. for $C_{30}H_{30}N_6O_4S$, 570.7; m/z found, 571 [M+H]$^+$. $^1$H NMR (400 MHz, CD$_3$OD:DMSO-d$_6$=2:1): δ 8.30-8.24 (m, 1H), 8.04-8.02 (m, 1H), 7.40-7.32 (m, 2H), 7.21-7.09 (m, 3H), 7.02-6.98 (m, 1H), 6.07-6.01 (m, 1H), 3.90-3.78 (m, 1H), 3.70-3.55 (m, 1H), 2.11 (s, 3H), 2.09-2.02 (m, 2H), 2.01-1.96 (m, 1H), 1.83-1.71 (m, 3H), 1.39-1.19 (m, 3H), 1.12-1.03 (m, 1H), 1.01-0.97 (m, 3H).

Example 386: N-((1R,2S)-2-Acrylamidocyclopentyl)-5-(2-methyl-4-(((R)-tetrahydrofuran-3-yl)oxy) phenyl)-4-oxo-4,5-dihydro-3H-1-thia-3,5,8-triazaacenaphthylene-2-carboxamide

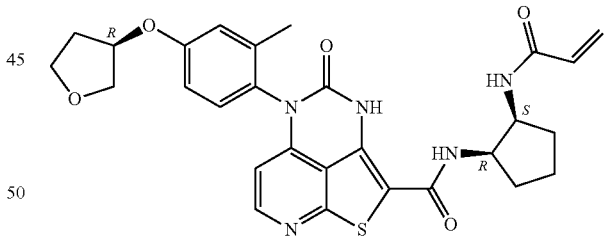

Step A. (R)-5-(2-methyl-4-((tetrahydrofuran-3-yl) oxy)phenyl)-4-oxo-4,5-dihydro-3H-1-thia-3,5,8-triazaacenaphthylene-2-carboxylic acid The title compound was prepared in a manner analogous to Intermediate 7, using 4-fluoro-2-methyl-1-nitrobenzene and (R)-tetrahydrofuran-3-ol Step A.

Step B. N-((1R,2S)-2-Acrylamidocyclopentyl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide The title compound was prepared in a manner analogous to Example 1, Step A, using N-((1S,2R)-2-aminocyclopentyl)acrylamide (Intermediate 36) and (R)-5-(2-methyl-4-((tetrahydrofuran-3-yl)oxy)phenyl)-4-oxo-4,5-dihydro-3H-1-thia-3,5,8-triazaacenaphthylene-2-carboxylic acid. MS (ESI): mass calcd. for $C_{28}H_{29}N_5O_5S$, 547.6; m/z found, 548.1 [M+H]$^+$. $^1$H NMR (400 MHz, CD$_3$OD): δ 8.28 (d, J=5.5 Hz, 1H), 7.29-7.16 (m, 1H), 7.05-6.97 (m, 1H), 6.95-6.88 (m, 1H), 6.36-6.14 (m, 2H), 6.06-5.93 (m, 1H), 5.71-5.57 (m, 1H), 5.15-5.04 (m, 1H), 4.51-4.34 (m, 2H), 4.05-3.79 (m, 4H), 2.39-2.24 (m, 1H), 2.20-2.01 (m, 6H), 1.9-1.86 (m, 1H), 1.84-1.56 (m, 3H).

Example 387: N-((1R,2S)-2-Acrylamidocyclopentyl)-4-oxo-5-(4-(pyridazin-3-yloxy)phenyl)-4,5-dihydro-3H-1-thia-3,5,8-triazaacenaphthylene-2-carboxamide

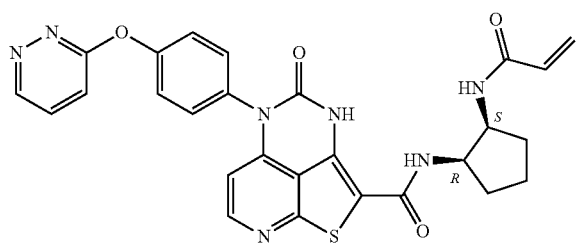

Step A. 4-Oxo-5-(4-(pyridazin-3-yloxy)phenyl)-4,5-dihydro-3H-1-thia-3,5,8-triazaacenaphthylene-2-carboxylic acid The title compound was prepared in a manner analogous to Intermediate 15, using 3,6-dichloropyridazine, 4-nitrophenol in Step A, (no Cu).

Step B. N-((1R,2S)-2-Acrylamidocyclopentyl)-4-oxo-5-(4-(pyridazin-3-yloxy)phenyl)-4,5-dihydro-3H-1-thia-3,5,8-triazaacenaphthylene-2-carboxamide The title compound was prepared in a manner analogous to Example 1, Step A, using N-((1S,2R)-2-aminocyclopentyl)acrylamide (Intermediate 36) and 4-oxo-5-(4-(pyridazin-3-yloxy)phenyl)-4,5-dihydro-3H-1-thia-3,5,8-triazaacenaphthylene-2-carboxylic acid, no HC/MeOH deprotection. MS (ESI): mass calcd. for $C_{27}H_{23}N_7O_4S$, 541.6; m/z found, 542.1 [M+H]$^+$. $^1$H NMR (400 MHz, DMSO-d$_6$): δ 10.01 (s, 1H), 9.06-9.01 (m, 1H), 8.35-8.30 (m, 1H), 7.88-7.83 (m, 1H), 7.82-7.76 (m, 1H), 7.74-7.68 (br, 1H), 7.55-7.48 (m, 3H), 7.45-7.37 (m, 2H), 6.27-6.17 (m, 1H), 6.10-6.02 (m, 2H), 5.57-5.51 (m, 1H), 4.33-4.22 (m, 2H), 1.98-1.85 (m, 2H), 1.81-1.70 (m, 2H), 1.65-1.50 (m, 2H).

Example 388: 5-(*S)-(4-Methyl-6-phenoxypyridin-3-yl)-4-oxo-N-((1R,3R)-3-propionamidocyclopentyl)-4,5-dihydro-3H-1-thia-3,5,8-triazaacenaphthylene-2-carboxamide

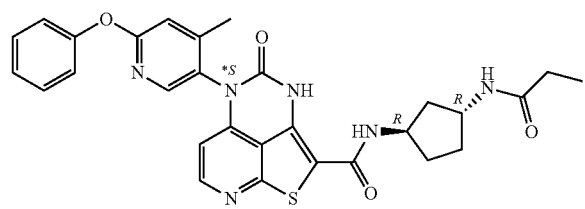

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1R,3R)-3-aminocyclopentyl)carbamate in Step A, and using propionic anhydride in place of prop-2-enoyl chloride Step B. MS (ESI): mass calcd. for $C_{29}H_{28}N_6O_4S$, 556.6; m/z found, 557 [M+H]$^+$. $^1$H NMR (400 MHz, CD$_3$OD): δ 8.30 (d, J=5.5 Hz, 1H), 8.09 (s, 1H), 7.49-7.37 (m, 2H), 7.29-7.19 (m, 1H), 7.18-7.11 (m, 2H), 7.01 (s, 1H), 6.12 (d, J=5.5 Hz, 1H), 4.54-4.39 (m, 1H), 4.36-4.21 (m, 1H), 2.22-2.10 (m, 7H), 2.06-1.84 (m, 2H), 1.73-1.41 (m, 2H), 1.19-1.02 (m, 3H).

Example 389: N-((1S,4S)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

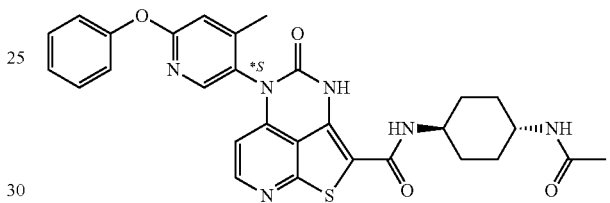

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1s,4s)-4-aminocyclohexyl)carbamate in Step A, and using acetic anhydride in place of prop-2-enoyl chloride in Step B. MS (ESI): mass calcd. for $C_{29}H_{28}N_6O_4S$, 556.6; m/z found, 557 [M+H]$^+$. $^1$H NMR (400 MHz, CD$_3$OD): δ 8.34 (d, J=5.3 Hz, 1H), 8.14 (s, 1H), 7.52-7.39 (m, 2H), 7.31-7.23 (m, 1H), 7.22-7.15 (m, 2H), 7.05 (s, 1H), 6.15 (d, J=5.5 Hz, 1H), 4.11-3.77 (m, 2H), 2.22 (s, 3H), 2.00 (s, 3H), 1.86-1.68 (m, 8H).

Example 390: 5-(*S)-(4-Methyl-6-phenoxypyridin-3-yl)-4-oxo-N-((1S,3R)-3-propionamidocyclopentyl)-4,5-dihydro-3H-1-thia-3,5,8-triazaacenaphthylene-2-carboxamide

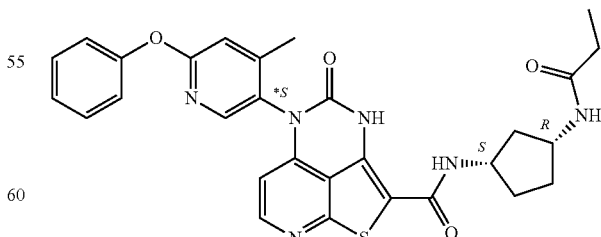

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPA- RATION METHOD 1 to obtain the *S atropisomer) and tert-butyl ((1R,3S)-3-aminocyclopentyl)carbamate in Step A, and using propionic anhydride in place of prop-2-enoyl chloride in Step B. MS (ESI): mass calcd. for $C_{29}H_{28}N_6O_4S$, 556.6; m/z found, 557.3 [M+H]$^+$. $^1$H NMR (400 MHz, CD$_3$OD): δ 8.34 (d, J=5.6 Hz, 1H), 8.08 (s, 1H), 7.51-7.36 (m, 2H), 7.27-7.13 (m, 1H), 7.19-7.12 (m, 2H), 7.03 (s, 1H), 6.15 (d, J=5.5 Hz, 1H), 4.41-4.23 (m, 1H), 4.18-4.00 (m, 1H), 2.51-2.34 (m, 1H), 2.24-2.13 (m, 5H), 2.09-1.91 (m, 2H), 1.82-1.63 (m, 2H), 1.60-1.48 (m, 1H), 1.12 (t, J=7.6 Hz, 3H).

Example 391: N-((1S,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

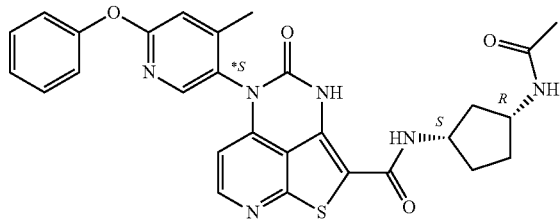

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1R,3S)-3-aminocyclopentyl)carbamate in Step A, and using acetic anhydride in place of prop-2-enoyl chloride in Step B. MS (ESI): mass calcd. for $C_{28}H_{26}N_6O_4S$, 542.6; m/z found, 543.2 [M+H]$^+$. $^1$H NMR (400 MHz, CD$_3$OD): δ 8.34 (d, J=5.5 Hz, 1H), 8.08 (s, 1H), 7.49-7.37 (m, 2H), 7.29-7.21 (m, 1H), 7.21-7.12 (m, 2H), 7.03 (s, 1H), 6.15 (d, J=5.6 Hz, 1H), 4.38-4.27 (m, 1H), 4.19-4.03 (m, 1H), 2.50-2.37 (m, 1H), 2.19 (s, 3H), 2.10-1.94 (m, 2H), 1.93 (s, 3H), 1.83-1.64 (m, 2H), 1.59-1.49 (m, 1H).

Example 392: N-((1R,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

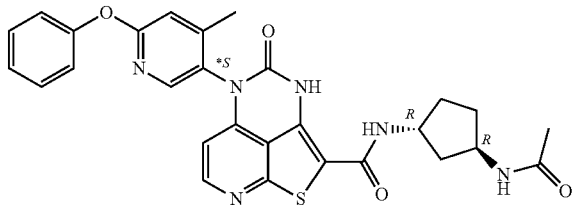

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1R,3R)-3-aminocyclopentyl)carbamate in Step A, and using acetic anhydride in place of prop-2-enoyl chloride Step B. MS (ESI): mass calcd. for $C_{28}H_{26}N_6O_4S$, 542.61; m/z found, 543.0 [M+H]$^+$. $^1$H NMR (400 MHz, CD$_3$OD): δ 8.37-8.31 (m, 1H), 8.11-8.04 (m, 1H), 7.45-7.38 (m, 2H), 7.27-7.20 (m, 1H), 7.19-7.12 (m, 2H), 7.05-6.99 (m, 1H), 6.18-6.11 (m, 1H), 4.55-4.39 (m, 1H), 4.33-4.20 (m, 1H), 2.20-2.10 (m, 5H), 2.01-1.84 (m, 5H), 1.70-1.58 (m, 1H), 1.53-1.41 (m, 1H).

Example 393: N-((1R,2R)-2-Hydroxycyclopentyl)-4-oxo-5-(4-phenoxyphenyl)-4,5-dihydro-3H-1-thia-3,5,8-triazaacenaphthylene-2-carboxamide

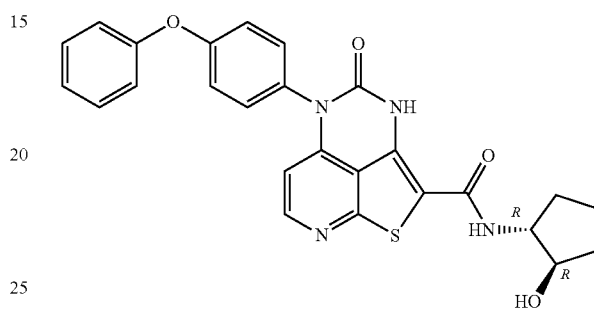

To a dry scintillation vial under Ar containing a stir bar were added (1R,2R)-trans-2-aminocyclopentanol hydrochloride (1.5 mmol), and diisopropylethylamine (0.525 mL, 3.00 mmol) in THF (4 mL). To this reaction solution was added slowly by syringe 4-oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol) at room temperature. The reaction was monitored by LCMS and when it had gone to completion, the reaction was concentrated to dryness, the residue dissolved in DMF, and was purified by basic reverse phase HPLC to give the title compound (91.4 mg, 18.8% yield). MS (ESI): mass calcd. for $C_{26}H_{22}N_4O_4S$, 486.6; m/z found, 487.1 [M+H]$^+$. $^1$H NMR (500 MHz, CD$_3$OD): δ 8.31 (d, J=5.6 Hz, 1H), 7.49-7.27 (m, 4H), 7.27-7.03 (m, 5H), 6.18 (d, J=5.6 Hz, 1H), 4.18-4.06 (m, 2H), 2.25-2.07 (m, 1H), 2.07-1.93 (m, 1H), 1.93-1.72 (m, 2H), 1.72-1.54 (m, 2H).

Example 394: N-((1R,3S)-3-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide

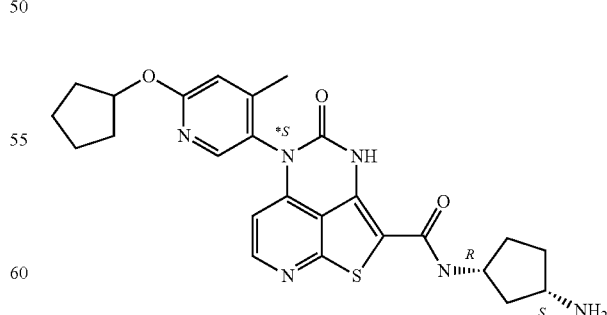

The title compound was prepared in a manner analogous to Example 166, using 5-(6-(cyclopentyloxy)-4-methylpyridin-3-yl)-4-oxo-4,5-dihydro-3H-1-thia-3,5,8-triazaacenaphthylene-2-carboxylic acid (Intermediate 25, including CHI- RAL SEPARATION METHOD 1 to obtain the *S atropisomer) and tert-butyl ((1S,3R)-3-aminocyclopentyl) carbamate in Step A. MS (ESI): mass calcd. for $C_{25}H_{28}N_6O_3S$, 492.6; m/z found, 493.0 [M+H]$^+$. $^1$H NMR (500 MHz, CDCl$_3$): δ 8.32 (d, J=5.5 Hz, 1H), 8.01 (s, 1H), 7.91 (d, J=8.3 Hz, 1H), 6.72 (t, J=0.8 Hz, 1H), 6.02 (d, J=5.4 Hz, 1H), 5.41 (td, J=6.0, 3.0 Hz, 1H), 4.59 (tdd, J=9.1, 6.3, 2.7 Hz, 1H), 3.73 (tt, J=5.5, 2.5 Hz, 1H), 3.48 (d, J=6.2 Hz, 4H), 3.37-3.29 (m, 5H), 2.13 (s, 3H), 2.10-1.88 (m, 2H), 1.90-1.74 (m, 3H), 1.70-1.54 (m, 3H).

Example 395: N-((1S,3S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

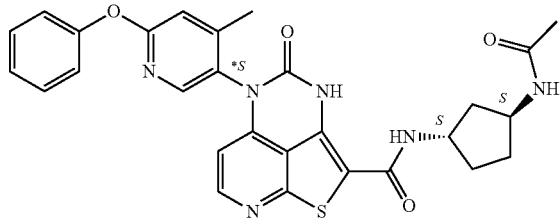

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,3S)-3-aminocyclopentyl)carbamate in Step A, and using acetic anhydride Step B. MS (ESI): mass calcd. for $C_{28}H_{26}N_6O_4S$, 542.6; m/z found, 543 [M+H]$^+$. $^1$H NMR (400 MHz, CD$_3$OD): δ 8.41-8.28 (m, 1H), 812-8.04 (m, 1H), 7.49-7.36 (m, 2H), 7.28-7.21 (m, 1H), 7.20-7.13 (m, 2H), 7.06-6.98 (m, 1H), 6.19-6.09 (m, 1H), 4.51-4.44 (m, 1H), 4.33-4.23 (m, 1H), 2.24-2.09 (m, 5H), 2.01-1.85 (m, 5H), 1.72-1.59 (m, 1H), 1.57-1.46 (m, 1H).

Example 396: N-((1R,2S)-2-Acetamidocyclopentyl)-4-oxo-5-(4-phenoxyphenyl)-4,5-dihydro-3H-1-thia-3,5,8-triazaacenaphthylene-2-carboxamide

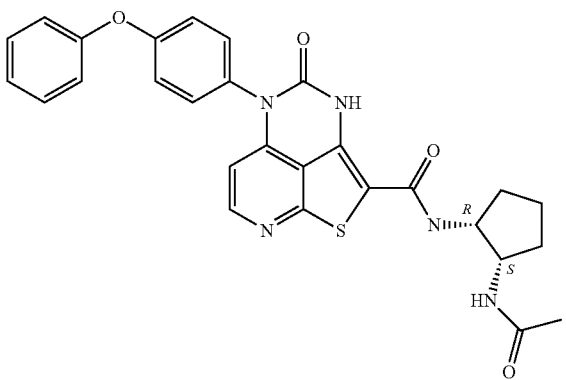

Step A: N-((1R,2S)-2-Aminocyclopentyl)-4-oxo-5-(4-phenoxyphenyl)-4,5-dihydro-3H-1-thia-3,5,8-triazaacenaphthylene-2-carboxamide To a dry scintillation vial under Ar containing a stir bar were added tert-butyl ((1S,2R)-2-aminocyclopentyl)carbamate (301 mg, 1.50 mmol), and diisopropylethylamine (0.525 mL, 3.00 mmol) in THF (4 mL). To this reaction solution was added slowly by syringe 4-oxo-5-(4-phenoxyphenyl)-4,5-dihydro-3H-1-thia-3,5,8-triazaacenaphthylene-2-carbonyl chloride (Intermediate 9, 10 mL, 0.1 M, 1 mmol) at room temperature. The reaction was monitored by LCMS and when it had gone to completion, the reaction was concentrated to dryness, the residue dissolved in DMF, and was purified by basic reverse phase HPLC to give the title compound (142.3 mg, 29.31% yield).

Step B: N-((1R,2S)-2-Acetamidocyclopentyl)-4-oxo-5-(4-phenoxyphenyl)-4,5-dihydro-3H-1-thia-3,5,8-triazaacenaphthylene-2-carboxamide The title compound in a manner analogous to Example 1, Step B, using N-((1R,2S)-2-aminocyclopentyl)-4-oxo-5-(4-phenoxyphenyl)-4,5-dihydro-3H-1-thia-3,5,8-triazaacenaphthylene-2-carboxamide, acetic anhydride and diisopropylethylamine. MS (ESI): mass calcd. for $C_{28}H_{25}N_5O_4S$, 527.6; m/z found, 528.0 [M+H]$^+$. $^1$H NMR (400 MHz, CDCl$_3$): δ 8.33 (d, J=5.5 Hz, 1H), 7.47-7.34 (m, 2H), 7.34-7.27 (m, 2H), 7.24-7.01 (m, 6H), 6.61 (d, J=5.6 Hz, 1H), 6.23-6.07 (m, 2H), 4.36-4.25 (m, 2H), 2.33-2.21 (m, 1H), 2.19-2.06 (m, 1H), 2.03 (s, 3H), 1.94-1.71 (m, 4H).

Example 397: N-((1R,2S)-2-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide

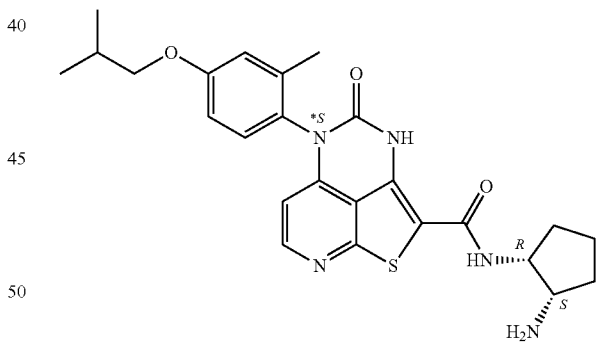

The title compound was prepared in a manner analogous to Example 166, Step A, using 5-(6-isobutoxy-4-methylpyridin-3-yl)-4-oxo-4,5-dihydro-3H-1-thia-3,5,8-triazaacenaphthylene-2-carboxylic acid (Intermediate 33, including CHIRAL SEPARATION METHOD 1 to obtain the *S atropisomer) and tert-butyl ((1S,2R)-2-aminocyclopentyl) carbamate (with a TFA/DCM deprotection). MS (ESI): mass calcd. for $C_{24}H_{28}N_6O_3S$, 480.6; m/z found, 481.0 [M+H]$^+$. $^1$H NMR (500 MHz, CDCl$_3$): δ 8.27 (d, J=5.4 Hz, 1H), 8.00 (s, 1H), 6.94 (s, 1H), 6.79 (d, J=0.9 Hz, 1H), 5.99 (d, J=5.5 Hz, 1H), 5.30 (s, 1H), 4.20 (p, J=7.1 Hz, 1H), 4.12-4.02 (m, 2H), 3.54-3.46 (m, 3H), 2.19-2.01 (m, 5H), 1.84 (dddd, J=13.2, 8.8, 6.1, 3.0 Hz, 1H), 1.74-1.50 (m, 4H), 1.03 (dd, J=6.7, 1.7 Hz, 6H).

Example 398: 4-Oxo-5-(4-phenoxyphenyl)-N-((1R, 2S)-2-propionamidocyclopentyl)-4,5-dihydro-3H-1-thia-3,5,8-triazaacenaphthylene-2-carboxamide

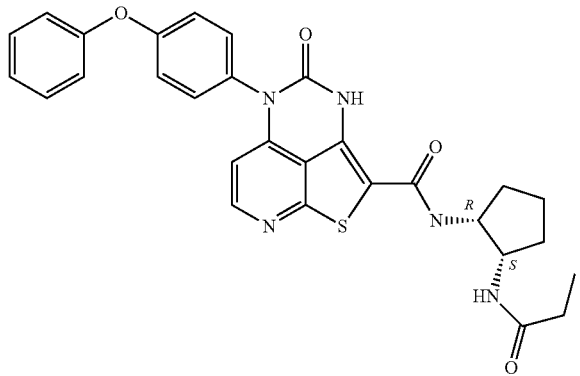

The title compound was prepared in a manner analogous to Example 1, Step B, using N-((1R,2S)-2-aminocyclopentyl)-4-oxo-5-(4-phenoxyphenyl)-4,5-dihydro-3H-1-thia-3,5, 8-triazaacenaphthylene-2-carboxamide (Example 396, product from Step A), propionic anhydride and diisopropylethylamine in place of prop-2-enoyl chloride and triethylamine. MS (ESI): mass calcd. for $C_{29}H_{27}N_5O_4S$, 541.62; m/z found, 542.0 [M+H]$^+$. $^1$H NMR (400 MHz, CDCl$_3$): δ 9.48 (s, 1H), 8.34 (d, J=5.5 Hz, 1H), 7.53-7.36 (m, 2H), 7.31-7.27 (m, 1H), 7.23-7.08 (m, 5H), 6.67 (d, J=5.6 Hz, 1H), 6.14 (d, J=5.5 Hz, 1H), 5.92 (d, J=6.2 Hz, 1H), 4.41-4.10 (m, 2H), 2.36-2.20 (m, 3H), 2.19-2.05 (m, 1H), 1.91-1.68 (m, 5H), 1.19 (t, J=7.6 Hz, 3H).

Example 399: 5-(*S)-(4-Methyl-6-phenoxypyridin-3-yl)-4-oxo-N-((1S,3S)-3-propionamidocyclopentyl)-4,5-dihydro-3H-1-thia-3,5,8-triazaacenaphthylene-2-carboxamide

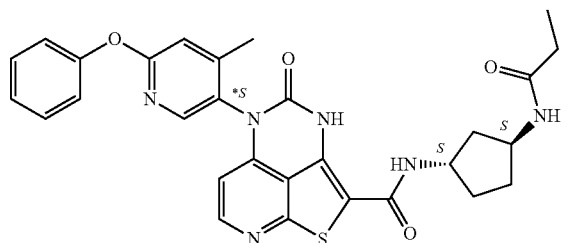

The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,3S)-3-aminocyclopentyl)carbamate in Step A, and using propionic anhydride in place of prop-2-enoyl chloride in Step B. MS (ESI): mass calcd. for $C_{29}H_{28}N_6O_4S$, 556.6; m/z found, 557 [M+H]$^+$. $^1$H NMR (400 MHz, CD$_3$OD): δ 8.33 (d, J=5.5 Hz, 1H), 8.08 (s, 1H), 7.48-7.37 (m, 2H), 7.27-7.20 (m, 1H), 7.19-7.13 (m, 2H), 7.02 (s, 1H), 6.14 (d, J=5.6 Hz, 1H), 4.53-4.41 (m, 1H), 4.36-4.22 (m, 2H), 2.24-2.10 (m, 7H), 2.05-1.83 (m, 2H), 1.71-1.59 (m, 1H), 1.56-1.43 (m, 1H), 1.15-1.05 (m, 3H).

Example 400: N-((1S,3S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

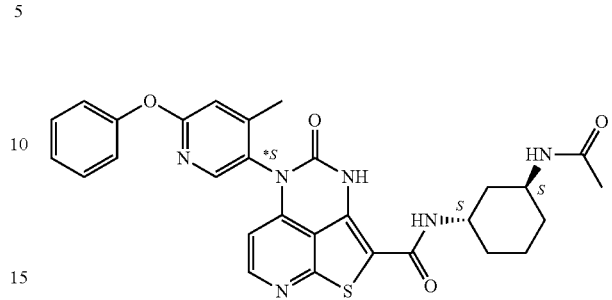

The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,3S)-3-aminocyclohexyl)carbamate in place of tert-butyl ((1S,4S)-4-aminocyclohexyl)carbamate Step A, and using acetic anhydride in place of prop-2-enoyl chloride in Step B. MS (ESI): mass calcd. for $C_{29}H_{28}N_6O_4S$, 556.6; m/z found, 557.0 [M+H]$^+$. $^1$H NMR (400 MHz, CD$_3$OD): δ 8.36-8.32 (m, 1H), 8.10-8.06 (m, 1H), 7.45-7.38 (m, 2H), 7.27-7.20 (m, 1H), 7.19-7.12 (m, 2H), 7.05-6.99 (m, 1H), 6.18-6.12 (m, 1H), 4.21-4.08 (m, 2H), 2.19 (s, 3H), 1.85 (s, 3H), 1.90-1.81 (m, 2H), 1.77-1.56 (m, 6H).

Example 401: N-((1R,2S)-2-Acrylamidocyclohexyl)-5-(2-methyl-4-(pyridin-2-yloxy)phenyl)-4-oxo-4,5-dihydro-3H-1-thia-3,5,8-triazaacenaphthylene-2-carboxamide

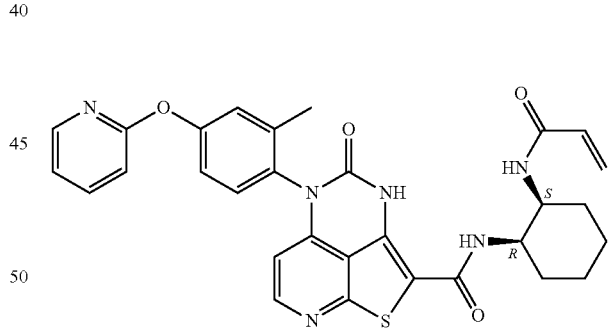

The title compound was prepared in a manner analogous to Example 1, Step A, using 5-(2-methyl-4-(pyridin-2-yloxy)phenyl)-4-oxo-4,5-dihydro-3H-1-thia-3,5,8-triazaacenaphthylene-2-carboxylic acid (Example 220, product from Step A) and N-((1S,2R)-2-aminocyclohexyl)acrylamide (Intermediate 40), no HCl/MeOH deprotection. MS (ESI): mass calcd. for $C_{30}H_{28}N_6O_4S$, 568.6; m/z found, 569.3 [M+H]$^+$. $^1$H NMR (400 MHz, CD$_3$OD): δ 8.36-8.26 (m, 1H), 8.19-8.10 (m, 1H), 7.92-7.80 (m, 1H), 7.39-7.32 (m, 1H), 7.24-7.17 (m, 1H), 7.17-7.09 (m, 2H), 7.08-7.01 (m, 1H), 6.45-6.35 (m, 1H), 6.30-6.17 (m, 2H), 5.70-5.59 (m, 1H), 4.47-4.35 (m, 1H), 4.20-4.05 (m, 1H), 2.15 (s, 3H), 1.83-1.60 (m, 6H), 1.58-1.45 (m, 2H).

Example 402: 5-(*S)-(4-Methyl-6-phenoxypyridin-3-yl)-4-oxo-N-((1S,3S)-3-propionamidocyclohexyl)-4,5-dihydro-3H-1-thia-3,5,8-triazaacenaphthylene-2-carboxamide

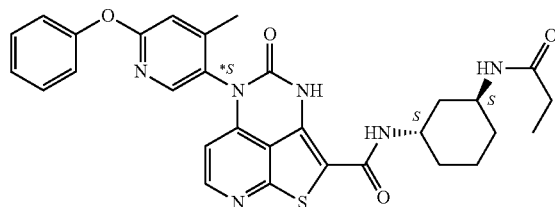

The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,3S)-3-aminocyclohexyl)carbamate in Step A, and using propionic anhydride in place of prop-2-enoyl chloride in Step B. MS (ESI): mass calcd. for $C_{30}H_{30}N_6O_4S$, 570.7; m/z found, 571.0 [M+H]$^+$. $^1$H NMR (400 MHz, CD$_3$OD): δ 8.36-8.32 (m, 1H), 8.10-8.06 (m, 1H), 7.45-7.38 (m, 2H), 7.27-7.20 (m, 1H), 7.19-7.12 (m, 2H), 7.05-6.99 (m, 1H), 6.18-6.12 (m, 1H), 4.22-4.05 (m, 2H), 2.27-2.20 (m, 2H), 2.19 (s, 3H), 1.91-1.79 (m, 2H), 1.78-1.55 (m, 6H), 1.15-1.08 (m, 3H).

Example 403: N-((1R,3S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

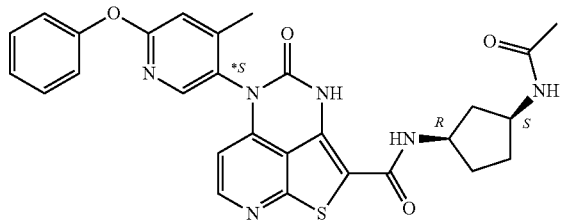

The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1S,3R)-3-aminocyclopentyl)carbamate in Step A, and using acetic anhydride in place of prop-2-enoyl chloride in Step B. MS (ESI): mass calcd. for $C_{28}H_{26}N_6O_4S$, 542.6; m/z found, 542.9 [M+H]$^+$. $^1$H NMR (400 MHz, DMSO-d$_6$ and CD$_3$OD): δ 8.26 (d, J=5.5 Hz, 1H), 8.02 (s, 1H), 7.42-7.31 (m, 2H), 7.19-7.13 (m, 1H), 7.12-7.07 (m, 2H), 7.00 (s, 1H), 6.04 (d, J=5.6 Hz, 1H), 4.30-4.18 (m, 1H), 4.05-3.91 (m, 1H), 2.35-2.23 (m, 1H), 2.11 (s, 3H), 1.98-1.83 (m, 2H), 1.81 (s, 3H), 1.74-1.53 (m, 2H), 1.52-1.40 (m, 1H).

Example 404: N-((1R,2R)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide

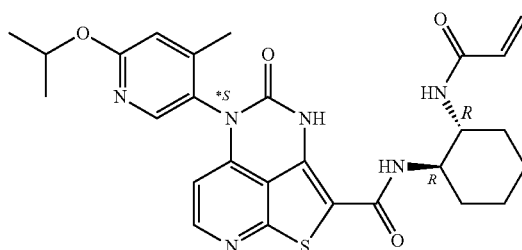

The title compound was prepared in a manner analogous to Example 1, Step A, using 5-(6-isobutyl-4-methylpyridin-3-yl)-4-oxo-4,5-dihydro-3H-1-thia-3,5,8-triazaacenaphthylene-2-carboxylic acid (Intermediate 18, including CHIRAL SEPARATION METHOD 1 to obtain the *S atropisomer) and N-((1R,2R)-2-aminocyclohexyl)acrylamide (Intermediate 41), no HCl/MeOH deprotection. MS (ESI): mass calcd. for $C_{28}H_{32}N_6O_3S$, 532.7; m/z found, 533.0 [M+H]$^+$. $^1$H NMR (400 MHz, CD$_3$OD): δ 8.38 (s, 1H), 8.32-8.24 (m, 1H), 7.38 (s, 1H), 6.24-6.09 (m, 2H), 6.04-5.93 (m, 1H), 5.66-5.48 (m, 1H), 3.93-3.77 (m, 2H), 2.75-2.65 (m, 2H), 2.19 (s, 3H), 2.12-1.94 (m, 3H), 1.85-1.73 (m, 2H), 1.51-1.32 (m, 4H), 0.96 (d, J=5.9 Hz, 6H).

Example 405: N-((1R,3S)-3-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide

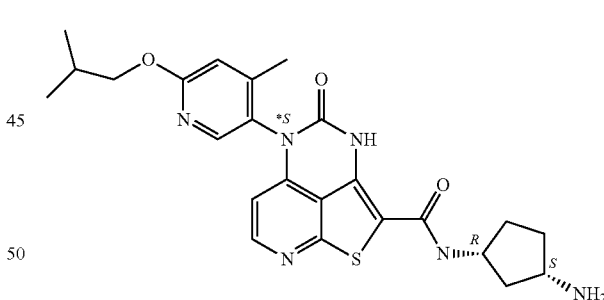

The title compound was prepared in a manner analogous to Example 1, Step A, using 5-(6-isobutoxy-4-methylpyridin-3-yl)-4-oxo-4,5-dihydro-3H-1-thia-3,5,8-triazaacenaphthylene-2-carboxylic acid (Intermediate 33, including CHIRAL SEPARATION METHOD 1 to obtain the *S atropisomer) and tert-butyl ((1S,3R)-3-aminocyclopentyl)carbamate. MS (ESI): mass calcd. for $C_{24}H_{28}N_6O_3S$, 480.6; m/z found, 481.0 [M+H]$^+$. $^1$H NMR (500 MHz, CDCl$_3$): δ 8.33 (d, J=5.5 Hz, 1H), 8.01 (s, 1H), 7.90 (d, J=8.4 Hz, 1H), 6.81-6.77 (m, 1H), 6.01 (d, J=5.5 Hz, 1H), 4.65-4.55 (m, 1H), 4.09 (qd, J=10.1, 6.6 Hz, 2H), 3.74 (tt, J=5.5, 2.4 Hz, 1H), 3.48 (s, 3H), 2.17-1.87 (m, 8H), 1.63-1.53 (m, 2H), 1.03 (dd, J=6.7, 1.4 Hz, 6H).

Example 406: N-((1R,2S)-2-Acrylamidocyclo-
hexyl)-5-(2-methyl-4-(pyridazin-3-yloxy)phenyl)-4-
oxo-4,5-dihydro-3H-1-thia-3,5,8-triazaacenaphthyl-
ene-2-carboxamide

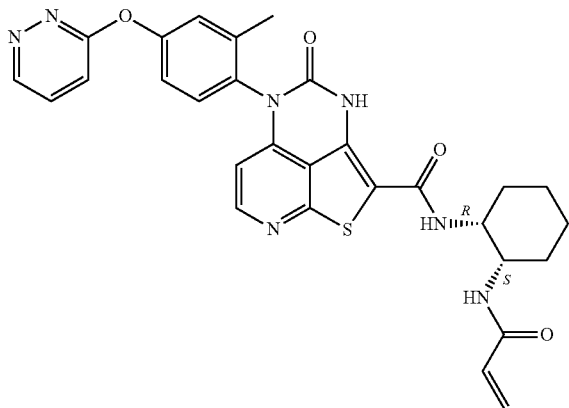

The title compound was prepared in a manner analogous to Example 1, Step A, using 5-(2-methyl-4-(pyridazin-3-yloxy)phenyl)-4-oxo-4,5-dihydro-3H-1-thia-3,5,8-triazaacenaphthylene-2-carboxylic acid (Example 305, product from Step A) and N-((1S,2R)-2-aminocyclohexyl)acrylamide (Intermediate 40), no HCl/MeOH deprotection. MS (ESI): mass calcd. for $C_{29}H_{27}N_7O_4S$, 569.6; m/z found, 570.2 [M+H]$^+$. $^1$H NMR (400 MHz, CD$_3$OD): δ 8.96-8.92 (m, 1H), 8.32-8.28 (m, 1H), 7.79-7.73 (m, 1H), 7.50-7.42 (m, 2H), 7.34-7.30 (m, 1H), 7.27-7.21 (m, 1H), 6.48-6.36 (m, 1H), 6.31-6.22 (m, 1H), 6.21-6.16 (m, 1H), 5.69-5.62 (m, 1H), 4.46-4.39 (m, 1H), 4.17-4.08 (m, 1H), 2.20-2.14 (m, 3H), 1.83-1.48 (m, 8H).

Example 407: N-((1S,3R)-3-Acetamidocyclohexyl)-
5-(*S)-(4-methyl-6-phenoxypyridin-3-yl)-4-oxo-4,5-
dihydro-3H-1-thia-3,5,8-triazaacenaphthylene-2-
carboxamide

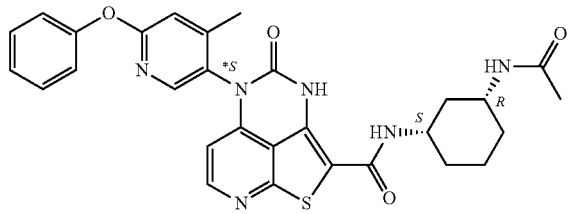

The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and N-((1R,3S)-3-aminocyclohexyl)acetamide, no deprotection with HCl/MeOH. MS (ESI): mass calcd. for $C_{29}H_{28}N_6O_4S$, 556.6; m/z found, 557.0 [M+H]$^+$. $^1$H NMR (400 MHz, CD$_3$OD): δ 8.36-8.31 (m, 1H), 8.10-8.06 (m, 1H), 7.46-7.38 (m, 2H), 7.27-7.20 (m, 1H), 7.19-7.12 (m, 2H), 7.05-6.99 (m, 1H), 6.16-6.12 (m, 1H), 4.03-3.88 (m, 1H), 3.78-3.68 (m, 1H), 2.19 (s, 3H), 2.15-2.06 (m, 1H), 1.96-1.80 (m, 6H), 1.47-1.25 (m, 3H), 1.20-1.09 (m, 1H).

Example 408: N-((1R,2S)-2-Acrylamidocyclo-
hexyl)-4-oxo-5-(4-(pyridazin-3-yloxy)phenyl)-4,5-
dihydro-3H-1-thia-3,5,8-triazaacenaphthylene-2-
carboxamide

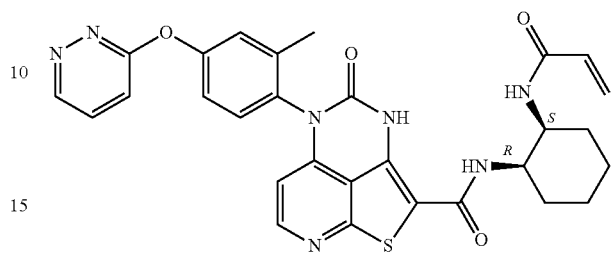

The title compound was prepared in a manner analogous to Example 1, Step A, using 4-oxo-5-(4-(pyridazin-3-yloxy)phenyl)-4,5-dihydro-3H-1-thia-3,5,8-triazaacenaphthylene-2-carboxylic acid (Example 387, product from Step A) and N-((1S,2R)-2-aminocyclohexyl)acrylamide (Intermediate 40), no HCl/MeOH deprotection. MS (ESI): mass calcd. for $C_{28}H_{25}N_7O_4S$, 555.6; m/z found, 556.1 [M+H]$^+$. $^1$H NMR (400 MHz, CD$_3$OD): δ 8.99-8.94 (m, 1H), 8.35-8.29 (m, 1H), 7.82-7.74 (m, 1H), 7.55-7.49 (m, 3H), 7.46-7.42 (m, 2H), 6.47-6.37 (m, 1H), 6.33-6.23 (m, 2H), 5.70-5.62 (m, 1H), 4.45-4.39 (m, 1H), 4.20-4.10 (m, 1H), 1.85-1.74 (m, 4H), 1.69-1.48 (m, 4H).

Example 409: 5-(*S)-(2-Methyl-6-phenoxypyridin-
3-yl)-4-oxo-N-((1S,3S)-3-propionamidocyclopen-
tyl)-4,5-dihydro-3H-1-thia-3,5,8-triazaacenaphthyl-
ene-2-carboxamide

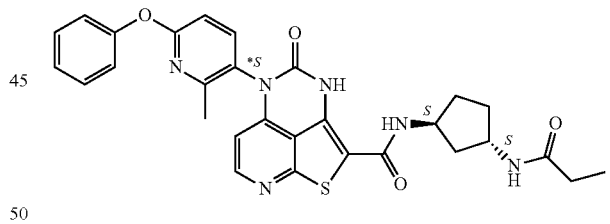

The title compound was prepared in a manner analogous to Example 1, using 5-(2-methyl-6-phenoxypyridin-3-yl)-4-oxo-4,5-dihydro-3H-1-thia-3,5,8-triazaacenaphthylene-2-carboxylic acid (Intermediate 29) and tert-butyl ((1S,3S)-3-aminocyclopentyl)carbamate and diisopropylethylamine in Step A, and propionic anhydride in place of prop-2-enoyl chloride in Step B. MS (ESI): mass calcd. for $C_{29}H_{28}N_6O_4S$, 556.6; m/z found, 557.0 [M+H]$^+$. $^1$H NMR (500 MHz, CDCl$_3$): δ 12.31 (d, J=5.5 Hz, 1H), 11.74 (d, J=8.6 Hz, 1H), 11.49-11.32 (m, 2H), 11.29-11.09 (m, 3H), 10.86 (d, J=8.6 Hz, 1H), 10.10 (d, J=5.5 Hz, 1H), 8.54-8.34 (m, 1H), 8.34-8.18 (m, 1H), 6.20 (s, 3H), 6.20-6.08 (m, 4H), 5.94-5.80 (m, 2H), 5.73-5.41 (m, 2H), 5.08 (t, J=7.6 Hz, 3H).

Example 410: N-((1S,3S)-3-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide

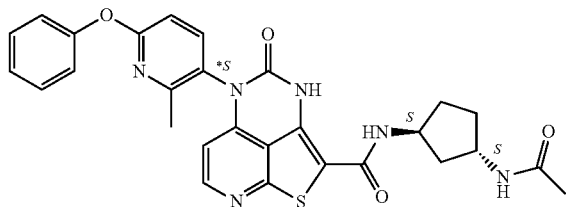

The title compound was prepared in a manner analogous to Example 1, Step B, using N-((1S,3S)-3-amino cyclopentyl)-5-(*S)-(2-methyl-6-phenoxypyridin-3-yl)-4-oxo-4,5-dihydro-3H-1-thia-3,5,8-triazaacenaphthylene-2-carboxamide (Example 415) and acetic anhydride in place of prop-2-enoyl chloride. MS (ESI): mass calcd. for $C_{28}H_{26}N_6O_4S$, 542.6; m/z found, 543.1 [M+H]$^+$. $^1$H NMR (400 MHz, CD$_3$OD): δ 8.35 (d, J=5.6 Hz, 1H), 7.78 (d, J=8.5 Hz, 1H), 7.52-7.38 (m, 2H), 7.31-7.15 (m, 3H), 6.90 (d, J=8.5 Hz, 1H), 6.20-6.08 (m, 1H), 4.58-4.39 (m, 1H), 4.35-4.11 (m, 2H), 2.38-1.43 (m, 12H).

Example 411: N-((1S,3R)-3-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide

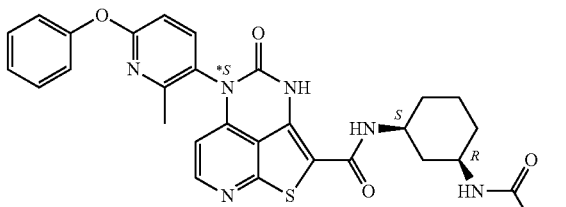

The title compound was prepared in a manner analogous to Example 1, Step B, using N-((1S,3R)-3-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide (Example 414), acrylic anhydride and diisopropylethylamine, in place of prop-2-enoyl chloride and trimethylamine. MS (ESI): mass calcd. for $C_{30}H_{28}N_6O_4S$, 568.7; m/z found, 569.0 [M+H]$^+$. $^1$H NMR (500 MHz, CD$_3$OD): δ 8.36 (d, J=5.6 Hz, 1H), 7.78 (d, J=8.6 Hz, 1H), 7.53-7.37 (m, 2H), 7.35-7.14 (m, 3H), 6.91 (d, J=8.6 Hz, 1H), 6.32-6.08 (m, 3H), 5.64 (dd, J=7.2, 4.8 Hz, 1H), 4.09-3.81 (m, 2H), 2.25 (s, 3H), 2.22-2.14 (m, 1H), 2.00-1.88 (m, 3H), 1.54-1.14 (m, 4H).

Example 412: 5-(*S)-(2-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide

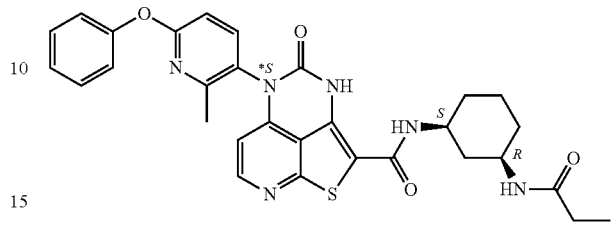

The title compound was prepared in a manner analogous to Example 1, Step B, using N-((1S,3R)-3-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide (Example 414), propionic anhydride and diisopropylethylamine in place of prop-2-enoyl chloride and triethylamine. MS (ESI): mass calcd. for $C_{30}H_{30}N_6O_4S$, 570.7; m/z found, 571.0 [M+H]$^+$. $^1$H NMR (500 MHz, CD$_3$OD): δ 8.36 (d, J=5.5 Hz, 1H), 7.78 (d, J=8.6 Hz, 1H), 7.55-7.37 (m, 2H), 7.32-7.12 (m, 3H), 6.91 (d, J=8.6 Hz, 1H), 6.15 (d, J=5.5 Hz, 1H), 4.03-3.67 (m, 2H), 2.25 (s, 3H), 2.23-2.09 (m, 3H), 1.97-1.82 (m, 3H), 1.53-1.41 (m, 1H), 1.39-1.27 (m, 2H), 1.23-1.14 (m, 1H), 1.12 (t, J=7.6 Hz, 3H).

Example 413: N-((1S,3R)-3-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide

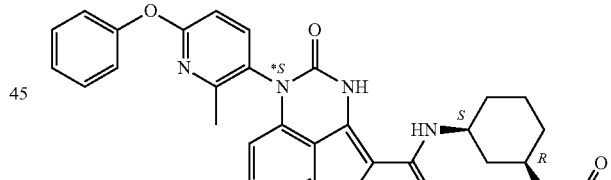

The title compound was prepared in a manner analogous to Example 1, Step B, using N-((1S,3R)-3-aminocyclohexyl)-5-(*S)-(2-methyl-6-phenoxypyridin-3-yl)-4-oxo-4,5-dihydro-3H-1-thia-3,5,8-triazaacenaphthylene-2-carboxamide (Example 414), acetic anhydride and diisopropylethylamine in place of prop-2-enoyl chloride and triethylamine. MS (ESI): mass calcd. for $C_{29}H_{28}N_6O_4S$, 556.6; m/z found, 557.0 [M+H]$^+$. $^1$H NMR (500 MHz, CD$_3$OD): δ 8.35 (d, J=5.6 Hz, 1H), 7.77 (d, J=8.6 Hz, 1H), 7.53-7.34 (m, 2H), 7.32-7.13 (m, 3H), 7.00-6.76 (m, 1H), 6.14 (d, J=5.5 Hz, 1H), 4.08-3.92 (m, 1H), 3.84-3.69 (m, 1H), 2.25 (s, 3H), 2.15 (d, J=12.1 Hz, 1H), 2.00-1.79 (m, 5H), 1.54-1.41 (m, 1H), 1.40-1.27 (m, 3H), 1.23-1.11 (m, 1H).

Example 414: N-((1S,3R)-3-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide

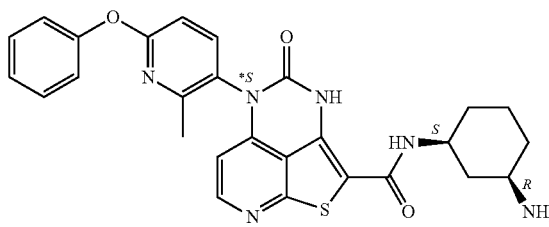

The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and tert-butyl ((1R,3S)-3-aminocyclohexyl)carbamate, and diisopropylethylamine. MS (ESI): mass calcd. for $C_{27}H_{26}N_6O_3S$, 514.6; m/z found, 515.1 [M+H]$^+$. $^1$H NMR (500 MHz, CD$_3$OD): δ 8.57 (d, J=6.2 Hz, 1H), 7.88 (d, J=8.6 Hz, 1H), 7.55-7.38 (m, 2H), 7.34-7.20 (m, 3H), 6.97 (d, J=8.4 Hz, 1H), 6.59-6.45 (m, 1H), 4.13-3.49 (m, 1H), 3.28-3.16 (m, 1H), 2.41-2.27 (m, 4H), 2.16-1.93 (m, 3H), 1.64-1.13 (m, 4H).

Example 415: N-((1S,3S)-3-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide

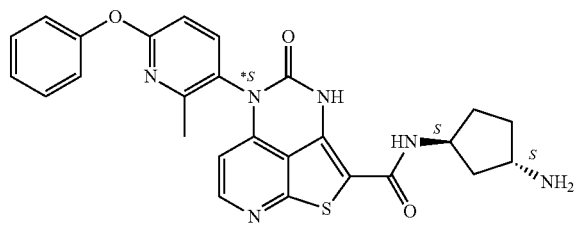

The title compound was prepared in a manner analogous to Example 1, Step A, using 5-(2-methyl-6-phenoxypyridin-3-yl)-4-oxo-4,5-dihydro-3H-1-thia-3,5,8-triazaacenaphthylene-2-carboxylic acid (Intermediate 29, including CHIRAL SEPARATION METHOD 1 to obtain the *S atropisomer) and using tert-butyl ((1S,3S)-3-aminocyclopentyl)carbamate. MS (ESI): mass calcd. for $C_{26}H_{24}N_6O_3S$, 500.6; m/z found, 501.0 [M+H]$^+$. $^1$H NMR (600 MHz, CDCl$_3$): δ 8.37 (d, J=5.5 Hz, 1H), 7.58-7.33 (m, 3H), 7.26-7.17 (m, 3H), 6.81 (d, J=8.5 Hz, 1H), 6.02 (d, J=5.4 Hz, 1H), 5.53 (d, J=7.2 Hz, 1H), 4.65-4.50 (m, 1H), 3.62-3.52 (m, 1H), 2.40-2.30 (m, 1H), 2.28 (s, 3H), 2.14-2.05 (m, 1H), 1.88-1.83 (m, 2H), 1.59-1.47 (m, 1H), 1.47-1.36 (m, 1H).

Example 416: 5-(*S)-(4-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide

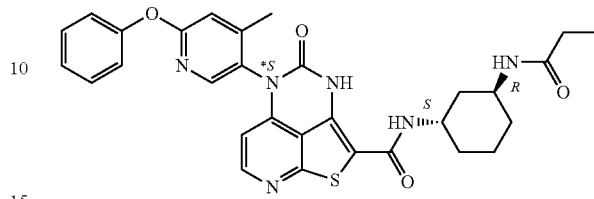

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and N-((1R,3S)-3-aminocyclohexyl)propionamide in Step A. MS (ESI): mass calcd. for $C_{30}H_{30}N_6O_4S$, 570.7; m/z found, 571.0 [M+H]$^+$. $^1$H NMR (400 MHz, CD$_3$OD): δ 8.35-8.30 (m, 1H), 8.10-8.07 (m, 1H), 7.45-7.38 (m, 2H), 7.27-7.20 (m, 1H), 7.19-7.12 (m, 2H), 7.05-6.99 (m, 1H), 6.15-6.11 (m, 1H), 4.01-3.87 (m, 1H), 3.79-3.66 (m, 1H), 2.19 (s, 3H), 2.18-2.08 (m, 3H), 1.94-1.80 (m, 3H), 1.51-1.38 (m, 1H), 1.37-1.26 (m, 2H), 1.21-1.12 (m, 1H), 1.11-1.06 (m, 3H).

Example 417: (S)-5-(2-Methyl-4-phenoxyphenyl)-2-(3-(methylamino)pyrrolidine-1-carbonyl)-3H-1-thia-3,5,8-triazaacenaphthylen-4(5H)-one

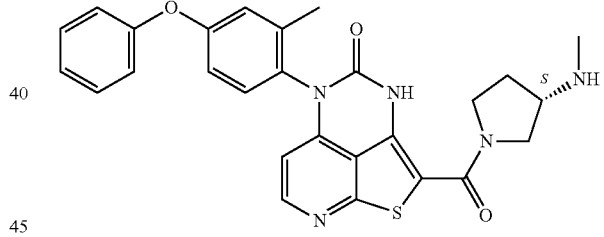

Step A: (R)-2-(3-Hydroxypyrrolidine-1-carbonyl)-5-(2-methyl-4-phenoxyphenyl)-3H-1-thia-3,5,8-triazaacenaphthylen-4(5H)-one The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (3R)-pyrrolidin-3-ol, no deprotection with HCl/MeOH.

Step B: (R)-1-(5-(2-Methyl-4-phenoxyphenyl)-4-oxo-4,5-dihydro-3H-1-thia-3,5,8-triazaacenaphthylene-2-carbonyl)pyrrolidin-3-yl 4-methylbenzenesulfonate To a round bottom flask were added (R)-2-(3-hydroxypyrrolidine-1-carbonyl)-5-(2-methyl-4-phenoxyphenyl)-3H-1-thia-3,5,8-triazaacenaphthylen-4(5H)-one (152 mg, 0.312 mmol), diisopropylethylamine (80 mg, 0.62 mmol), DCM (10 mL), and 4-methylbenzenesulfonyl chloride (77 mg, 0.41 mmol) sequentially and stirred at reflux for 3 h. The mixture was concentrated to dryness and used in the next step without purification (203 mg).

Step C: (S)-5-(2-Methyl-4-phenoxyphenyl)-2-(3-(methylamino)pyrrolidine-1-carbonyl)-3H-1-thia-3,5,8-triazaacenaphthylen-4(5H)-one A solution of (R)-1-(5-(2-methyl-4-phenoxyphenyl)-4-oxo-4,5-dihydro-3H-1-thia-3,5,8-triazaacenaphthylene-2-carbonyl)pyrrolidin-3-yl 4-methylbenzenesulfonate (203 mg, 0.317 mmol) and methyl amine (5 mL) was added to a sealed tube and stirred at 80° C. for 15 h. The mixture was concentrated to dryness and purified by flash column chromatography, then by prep-TLC to give the title compound as a light yellow solid (10 mg, 6.3% yield). MS (ESI): mass calcd. for $C_{27}H_{25}N_5O_3S$, 499.6; m/z found, 500.4 [M+H]$^+$. $^1$H NMR (400 MHz, CD$_3$OD): δ 8.35-8.31 (m, 1H), 7.43-7.36 (m, 2H), 7.32-7.25 (m, 1H), 7.20-7.13 (m, 1H), 7.13-7.03 (m, 3H), 7.02-6.95 (m, 1H), 6.09-6.05 (m, 1H), 4.10-3.87 (m, 3H), 3.84-3.76 (m, 1H), 2.87-2.82 (m, 1H), 2.73 (s, 3H), 2.52-2.40 (m, 1H), 2.10 (s, 3H), 2.08-1.91 (m, 1H).

Example 418: (S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)propionamide

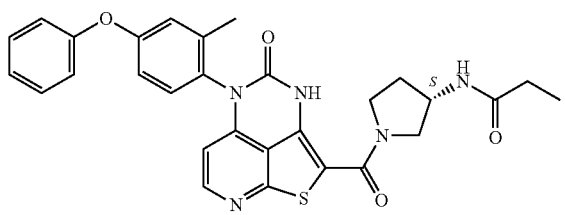

A solution of (S)-2-(3-aminopyrrolidine-1-carbonyl)-5-(2-methyl-4-phenoxyphenyl)-3H-1-thia-3,5,8-triazaacenaphthylen-4(5H)-one (Example 420, 150 mg, 0.31 mmol), propionic acid (46 mg, 0.62 mmol), HATU (153 mg, 0.402 mmol), and diisopropylethylamine (60 mg, 0.46 mmol) in DMF (5 mL) was stirred at rt for 2 h. The mixture was purified by HPLC to give the title compound as a light yellow solid (75 mg, 44% yield). MS (ESI): mass calcd. for $C_{29}H_{27}N_5O_4S$, 541.6; m/z found, 542.6 [M+H]$^+$. $^1$H NMR (400 MHz, CD$_3$OD): δ 8.32-8.27 (m, 1H), 7.42-7.35 (m, 3H), 7.19-7.12 (m, 1H), 7.10-7.01 (m, 3H), 6.99-6.93 (m, 1H), 6.06-6.01 (m, 1H), 4.49-4.37 (m, 1H), 4.00-3.53 (m, 4H), 2.28-2.15 (m, 3H), 2.13-2.09 (m, 3H), 2.06-1.94 (m, 1H), 1.11 (t, J=7.6 Hz, 3H).

Example 419: (S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acetamide

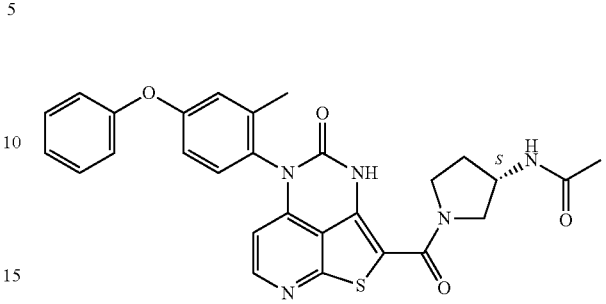

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(3S)-pyrrolidin-3-yl]carbamate in Step A, and acetyl chloride in place of prop-2-enoyl chloride in Step B. MS (ESI): mass calcd. for $C_{28}H_{25}N_5O_4S$, 527.6; m/z found, 528.1 [M+H]$^+$. $^1$H NMR (400 MHz, CD$_3$OD): δ 8.34-8.30 (m, 1H), 7.42-7.32 (m, 3H), 7.19-7.12 (m, 1H), 7.11-7.02 (m, 3H), 6.99-6.94 (m, 1H), 6.08-6.04 (m, 1H), 4.47-4.39 (m, 1H), 4.07-3.73 (m, 3H), 3.69-3.54 (m, 1H), 2.30-2.19 (m, 1H), 2.15-2.08 (m, 3H), 2.06-1.98 (m, 1H), 1.95 (s, 3H).

Example 420: (S)-2-(3-Aminopyrrolidine-1-carbonyl)-5-(2-methyl-4-phenoxyphenyl)-3H-1-thia-3,5,8-triazaacenaphthylen-4(5H)-one

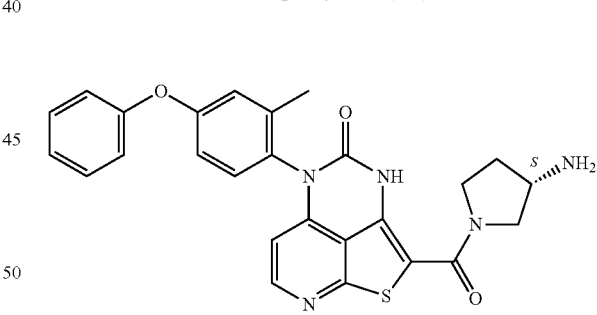

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl N-[(3S)-pyrrolidin-3-yl]carbamate. MS (ESI): mass calcd. for $C_{26}H_{23}N_5O_3S$, 485.6; m/z found, 486.0 [M+H]$^+$. $^1$H NMR (400 MHz, CD$_3$OD): δ 8.34-8.28 (m, 1H), 7.44-7.32 (m, 3H), 7.20-7.13 (m, 1H), 7.12-7.02 (m, 3H), 7.01-6.94 (m, 1H), 6.09-6.03 (m, 1H), 3.98-3.63 (m, 4H), 3.59-3.44 (m, 1H), 2.30-2.17 (m, 1H), 2.12 (s, 3H), 1.98-1.84 (m, 1H).

Example 421: (S)-2-(3-(Dimethylamino)pyrrolidine-1-carbonyl)-5-(2-methyl-4-phenoxyphenyl)-3H-1-thia-3,5,8-triazaacenaphthylen-4(5H)-one

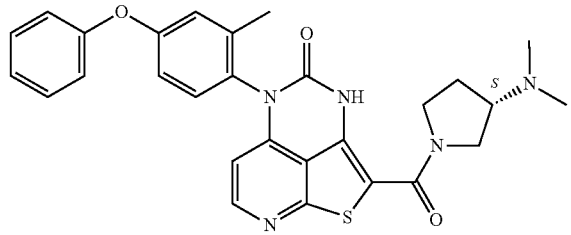

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and (3S)—N,N-dimethylpyrrolidin-3-amine, no deprotection step with HCl/MeOH. MS (ESI): mass calcd. for $C_{28}H_{27}N_5O_3S$, 513.6; m/z found, 514.1 [M+H]$^+$. $^1$H NMR (400 MHz, CD$_3$OD): δ 8.36-8.32 (m, 1H), 8.31 (s, 1H), 7.43-7.36 (m, 2H), 7.34-7.29 (m, 1H), 7.19-7.13 (m, 1H), 7.11-7.03 (m, 3H), 7.00-6.96 (m, 1H), 6.10-6.06 (m, 1H), 4.12-3.98 (m, 2H), 3.82-3.67 (m, 1H), 3.66-3.57 (m, 1H), 2.56 (s, 6H), 2.42-2.33 (m, 1H), 2.12 (s, 3H), 2.08-1.99 (m, 1H).

Example 422: N-((1R,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

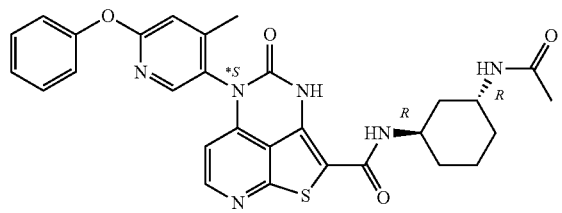

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1R,3R)-3-aminocyclohexyl)carbamate in Step A, and acetic anhydride in place of prop-2-enoyl chloride in Step B. MS (ESI): mass calcd. for $C_{29}H_{28}N_6O_4S$, 556.6; m/z found, 557.1 [M+H]$^+$. $^1$H NMR (400 MHz, CD$_3$OD): δ 8.36-8.31 (m, 1H), 8.11-8.06 (m, 1H), 7.48-7.39 (m, 2H), 7.27-7.20 (m, 1H), 7.19-7.14 (m, 2H), 7.06-7.00 (m, 1H), 6.17-6.10 (m, 1H), 4.19-4.04 (m, 2H), 2.20 (s, 3H), 1.97 (s, 3H), 1.88-1.58 (m, 8H).

Example 423: 5-(*S)-(4-Methyl-6-phenoxypyridin-3-yl)-4-oxo-N-((1R,3R)-3-propionamidocyclohexyl)-4,5-dihydro-3H-1-thia-3,5,8-triazaacenaphthylene-2-carboxamide

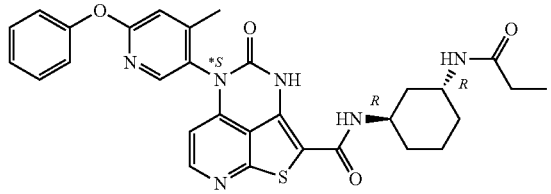

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1R,3R)-3-aminocyclohexyl)carbamate in Step A, and propionic anhydride in place of prop-2-enoyl chloride in Step B. MS (ESI): mass calcd. for $C_{30}H_{30}N_6O_4S$, 570.7; m/z found, 571.1 [M+H]$^+$. $^1$H NMR (400 MHz, CD$_3$OD): δ 8.42-8.32 (m, 1H), 8.15-8.06 (m, 1H), 7.50-7.37 (m, 2H), 7.29-7.10 (m, 3H), 7.07-7.00 (m, 1H), 6.24-6.15 (m, 1H), 4.21-4.06 (m, 2H), 2.17-2.06 (m, 5H), 1.86-1.57 (m, 8H), 1.19-1.05 (m, 3H).

Example 424: N-((1R,2S)-2-Acrylamidocyclopentyl)-5-(*S)-(2-methyl-4-(pyridazin-3-yloxy)phenyl)-4-oxo-4,5-dihydro-3H-1-thia-3,5,8-triazaacenaphthylene-2-carboxamide

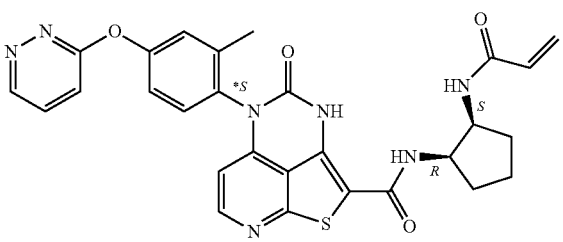

Chiral SFC purification (Stationary phase: CHIRALCEL AS-H, 5 μm, 250×20 mm, Mobile phase: 60% CO$_2$, 40% MeOH) of N-((1R,2S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide (Example 305) afforded the title compound. MS (ESI): mass calcd. for $C_{28}H_{25}N_7O_4S$, 555.6; m/z found, 556.2 [M+H]$^+$. $^1$H NMR (500 MHz, CDCl$_3$): δ 9.06-8.92 (m, 1H), 8.36 (d, J=5.5 Hz, 1H), 7.66-7.48 (m, 1H), 7.31-7.27 (m, 3H), 7.26-7.21 (m, 1H), 6.77-6.60 (m, 1H), 6.48-6.26 (m, 2H), 6.26-5.94 (m, 2H), 5.87-5.57 (m, 1H), 4.48-4.26 (m, 2H), 2.35-2.22 (m, 1H), 2.19 (s, 4H), 1.96-1.81 (m, 1H), 1.79-1.73 (m, 3H).

Example 425: N-((1R,2S)-2-Acrylamidocyclopentyl)-5-(*R)-(2-methyl-4-(pyridazin-3-yloxy)phenyl)-4-oxo-4,5-dihydro-3H-1-thia-3,5,8-triazaacenaphthylene-2-carboxamide

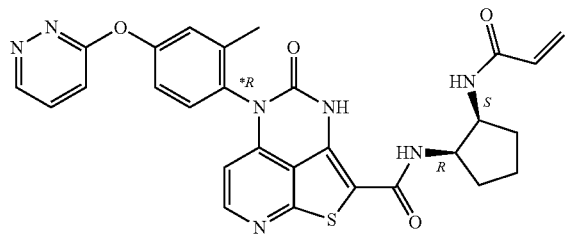

Chiral SFC purification (Stationary phase: CHIRALCEL AS-H, 5 μm, 250×20 mm, Mobile phase: 60% $CO_2$, 40% MeOH) of N-((1R,2S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide (Example 305) afforded the title compound. MS (ESI): mass calcd. for $C_{28}H_{25}N_7O_4S$, 555.6; m/z found, 556.2 $[M+H]^+$. $^1H$ NMR (500 MHz, $CDCl_3$): δ 9.50 (s, 1H), 9.00 (dd, J=4.5, 1.4 Hz, 1H), 8.45-8.27 (m, 1H), 7.66-7.44 (m, 1H), 7.31-7.27 (m, 3H), 7.26-7.22 (m, 1H), 6.80-6.63 (m, 1H), 6.50-6.33 (m, 1H), 6.33-5.95 (m, 3H), 5.84-5.56 (m, 1H), 4.50-4.19 (m, 2H), 2.35-2.22 (m, 1H), 2.18 (s, 3H), 2.04-1.83 (m, 1H), 1.78-1.68 (m, 4H).

Example 426: N-((1R,2S)-2-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide

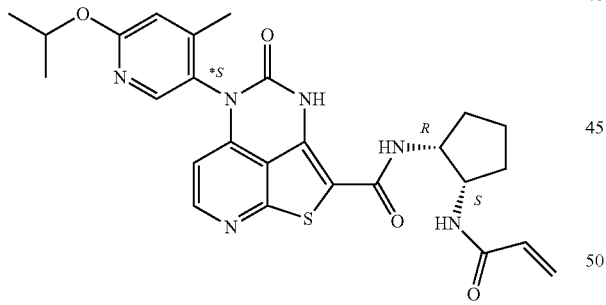

The title compound was prepared in a manner analogous to Example 1, Step B, using acrylic anhydride and N-((1R,2S)-2-aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide (Example 428). MS (ESI): mass calcd. for $C_{26}H_{28}N_6O_4S$, 520.6; m/z found, 521.2 $[M+H]^+$. $^1H$ NMR (500 MHz, $CDCl_3$): δ 8.34 (d, J=5.5 Hz, 1H), 8.01 (s, 1H), 6.79 (d, J=6.2 Hz, 1H), 6.72 (s, 1H), 6.64 (d, J=6.5 Hz, 1H), 6.38-6.31 (m, 1H), 6.15 (dd, J=16.9, 10.2 Hz, 1H), 6.04 (d, J=5.4 Hz, 1H), 5.66 (d, J=10.4 Hz, 1H), 5.32 (hept, J=6.1 Hz, 1H), 4.36 (tt, J=13.3, 6.5 Hz, 2H), 2.30-2.06 (m, 6H), 1.87 (qd, J=8.4, 7.8, 4.1 Hz, 1H), 1.73 (dtd, J=19.7, 10.4, 9.1, 4.8 Hz, 3H), 1.37 (dd, J=13.1, 6.1 Hz, 6H).

Example 427: N-((1R,3S)-3-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide

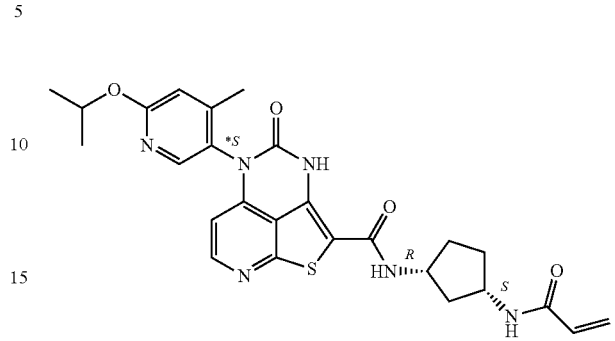

The title compound was prepared in a manner analogous to Example 1, Step B, using acrylic anhydride and N-((1R,3S)-3-aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide (Example 429). MS (ESI): mass calcd. for $C_{26}H_{28}N_6O_4S$, 520.6; m/z found, 521.2 $[M+H]^+$. $^1H$ NMR (400 MHz, $CDCl_3$): δ 8.32 (d, J=5.6 Hz, 1H), 8.03 (s, 1H), 7.70 (d, J=7.3 Hz, 1H), 7.24 (s, 1H), 6.72 (s, 1H), 6.37 (d, J=16.9 Hz, 1H), 6.12 (dd, J=17.0, 10.2 Hz, 1H), 6.03 (d, J=5.5 Hz, 1H), 5.64 (d, J=10.4 Hz, 1H), 5.31 (d, J=4.6 Hz, 2H), 4.39 (p, J=5.4, 4.8 Hz, 1H), 4.14 (dq, J=14.4, 6.9 Hz, 2H), 2.45 (dt, J=14.4, 8.8 Hz, 1H), 2.13 (s, 3H), 2.07-1.79 (m, 6H), 1.40-1.32 (m, 4H).

Example 428: N-((1R,2S)-2-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide

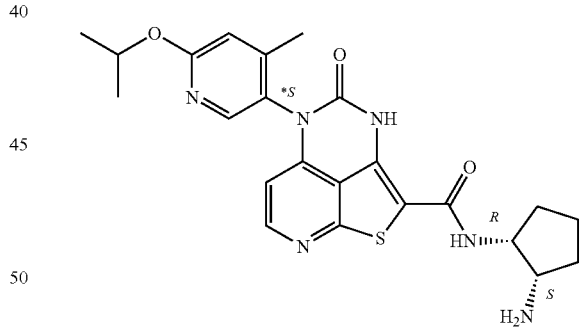

The title compound was prepared in a manner analogous to Example 166, using 5-(6-isopropoxy-4-methylpyridin-3-yl)-4-oxo-4,5-dihydro-3H-1-thia-3,5,8-triazaacenaphthylene-2-carboxylic acid (Intermediate 30, including CHIRAL SEPARATION METHOD 1 to obtain the *S atropisomer) and tert-butyl ((1S,2R)-2-aminocyclopentyl)carbamate in Step A, and TFA/DCM deprotection in Step B. MS (ESI): mass calcd. for $C_{23}H_{26}N_6O_3S$, 466.6; m/z found, 467.2 $[M+H]^+$. $^1H$ NMR (400 MHz, $CDCl_3$): δ 7.93 (d, J=16.3 Hz, 3H), 6.65 (s, 1H), 5.84 (d, J=5.5 Hz, 1H), 5.19-4.95 (m, 1H), 4.78-4.45 (m, 1H), 3.70 (q, J=6.7, 6.2 Hz, 1H), 2.25 (d, J=28.5 Hz, 4H), 2.16-1.97 (m, 1H), 1.96-1.70 (m, 3H), 1.53 (d, J=9.2 Hz, 1H), 1.31 (d, J=6.1 Hz, 3H), 1.27 (dd, J=27.9, 6.1 Hz, 6H).

Example 429: N-((1R,3S)-3-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide

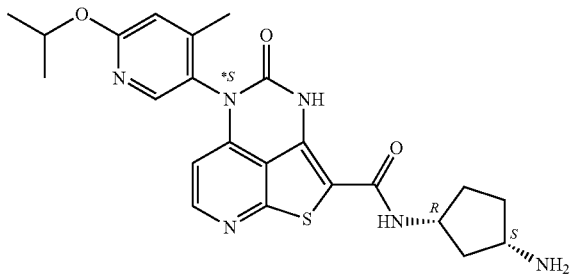

The title compound was prepared in a manner analogous to Example 166, using 5-(6-isopropoxy-4-methylpyridin-3-yl)-4-oxo-4,5-dihydro-3H-1-thia-3,5,8-triazaacenaphthylene-2-carboxylic acid (Intermediate 30, including CHIRAL SEPARATION METHOD 1 to obtain the *S atropisomer) and tert-butyl ((1S,3R)-3-aminocyclopentyl)carbamate in Step A, and TFA/DCM deprotection in Step B. MS (ESI): mass calcd. for $C_{23}H_{26}N_6O_3S$, 466.6; m/z found, 467.2 [M+H]$^+$. $^1$H NMR (400 MHz, CDCl$_3$): δ 8.30 (d, J=5.5 Hz, 1H), 8.00 (d, J=25.9 Hz, 2H), 6.71 (d, J=1.0 Hz, 1H), 6.01 (d, J=5.5 Hz, 1H), 5.39-5.25 (m, 1H), 4.59 (dtt, J=8.7, 6.3, 2.5 Hz, 1H), 4.07 (s, 3H), 3.73 (tt, J=5.2, 2.2 Hz, 1H), 2.14 (d, J=0.9 Hz, 3H), 2.12-1.87 (m, 4H), 1.66-1.56 (m, 2H), 1.37 (dd, J=10.5, 6.2 Hz, 6H).

Example 430: N-((1S,3R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide

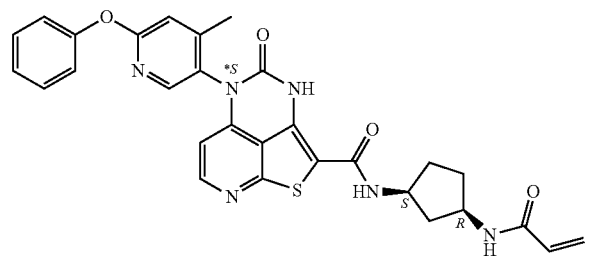

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and in Step A and acrylic anhydride in place of prop-2-enoyl chloride in Step B. MS (ESI): mass calcd. for $C_{29}H_{26}N_6O_4S$, 554.6; m/z found, 555.3 [M+H]$^+$. $^1$H NMR (400 MHz, CD$_3$OD): δ 8.33 (d, J=5.5 Hz, 1H), 8.08 (s, 1H), 7.50-7.37 (m, 2H), 7.27-7.20 (m, 1H), 7.19-7.13 (m, 2H), 7.02 (s, 1H), 6.27-6.20 (m, 2H), 6.14 (d, J=5.5 Hz, 1H), 5.68-5.57 (m, 1H), 4.41-4.29 (m, 1H), 4.25-4.12 (m, 1H), 2.55-2.40 (m, 1H), 2.19 (s, 3H), 2.10-1.95 (m, 2H), 1.89-1.71 (m, 2H), 1.67-1.53 (m, 1H).

Example 431: N-((1S,3R)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide

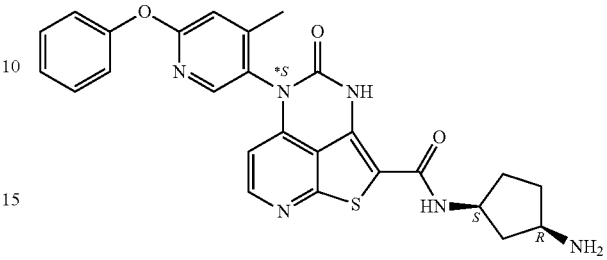

The title compound was prepared in a manner analogous to Example 1, Step A, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1R,3S)-3-aminocyclopentyl)carbamate. MS (ESI): mass calcd. for $C_{26}H_{24}N_6O_3S$, 500.6; m/z found, 501.2 [M+H]$^+$. $^1$H NMR (400 MHz, CD$_3$OD): δ 8.13 (d, J=5.6 Hz, 1H), 7.98 (s, 1H), 7.46-7.38 (m, 2H), 7.25-7.14 (m, 3H), 7.02-6.97 (m, 1H), 5.91 (d, J=5.6 Hz, 1H), 4.43-4.28 (m, 1H), 3.65-3.55 (m, 1H), 2.59-2.48 (m, 1H), 2.17 (s, 3H), 2.13-2.03 (m, 2H), 2.02-1.93 (m, 1H), 1.91-1.82 (m, 1H), 1.75-1.67 (m, 1H).

Example 432: N-((1r,4r)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide

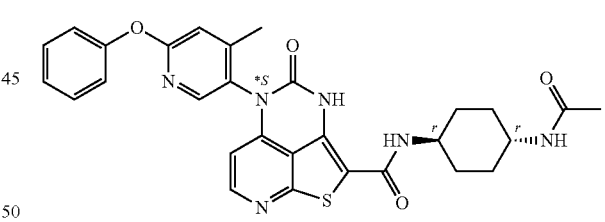

The title compound was prepared in a manner analogous to Example 1, using 5-(4-methyl-6-phenoxypyridin-3-yl)-4-oxo-4,5-dihydro-3H-1-thia-3,5,8-triazaacenaphthylene-2-carboxylic acid (Intermediate 27, including CHIRAL SEPARATION METHOD 1 to obtain the *S atropisomer) and tert-butyl ((1r,4r)-4-aminocyclohexyl)carbamate in Step A, and acetic anhydride in place of prop-2-enoyl chloride in Step B. MS (ESI): mass calcd. for $C_{29}H_{28}N_6O_4S$, 556.6; m/z found, 557.0 [M+H]$^+$. $^1$H NMR (400 MHz, CD$_3$OD): δ 8.33 (d, J=5.6 Hz, 1H), 8.08 (s, 1H), 7.46-7.39 (m, 2H), 7.26-7.20 (m, 1H), 7.19-7.14 (m, 2H), 7.04-7.00 (m, 1H), 6.13 (d, J=5.6 Hz, 1H), 3.95-3.79 (m, 1H), 3.69-3.58 (m, 1H), 2.19 (s, 3H), 2.01-1.93 (m, 4H), 1.90 (s, 3H), 1.58-1.44 (m, 2H), 1.41-1.28 (m, 2H).

Example 433: (S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide

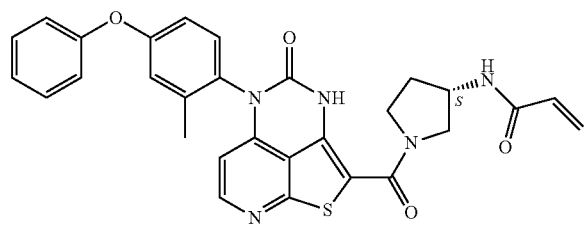

The title compound was prepared in a manner analogous to Example 1 using tert-butyl (S)-pyrrolidin-3-ylcarbamate and 5-(2-methyl-4-phenoxyphenyl)-4-oxo-4,5-dihydro-3H-1-thia-3,5,8-triazaacenaphthylene-2-carboxylic acid (Intermediate 1) in Step A. MS (ESI): mass calcd. for $C_{29}H_{25}N_5O_4S$, 539.6; m/z found, 540.4 $[M+H]^+$. $^1H$ NMR (400 MHz, a mixture of DMSO-$d_6$ and CD$_3$OD): δ 8.35-8.28 (m, 1H), 7.44-7.33 (m, 3H), 7.21-7.02 (m, 4H), 6.99-6.91 (m, 1H), 6.27-6.06 (m, 2H), 6.02-5.97 (m, 1H), 5.62-5.55 (m, 1H), 4.48-4.38 (m, 1H), 3.85-3.70 (m, 2H), 3.65-3.51 (m, 2H), 2.26-2.15 (m, 1H), 2.07 (s, 3H), 2.01-1.91 (m, 1H).

Example 434: (R)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide

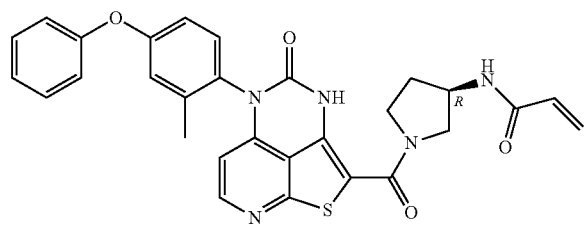

The title compound was prepared in a manner analogous to Example 1, using tert-butyl (R)-pyrrolidin-3-ylcarbamate and 5-(2-methyl-4-phenoxyphenyl)-4-oxo-4,5-dihydro-3H-1-thia-3,5,8-triazaacenaphthylene-2-carboxylic acid (Intermediate 1) in Step A. MS (ESI): mass calcd. for $C_{29}H_{25}N_5O_4S$, 539.6; m/z found, 540.4 $[M+H]^+$. $^1H$ NMR (400 MHz, a mixture of DMSO-$d_6$ and CD$_3$OD): δ 8.37-8.32 (m, 1H), 7.45-7.38 (m, 2H), 7.38-7.32 (m, 1H), 7.21-7.14 (m, 1H), 7.13-7.05 (m, 3H), 7.00-6.94 (m, 1H), 6.27-6.08 (m, 2H), 6.02-5.98 (m, 1H), 5.64-5.57 (m, 1H), 4.47-4.37 (m, 1H), 3.86-3.71 (m, 2H), 3.58-3.51 (m, 2H), 2.26-2.16 (m, 1H), 2.07 (s, 3H), 2.00-1.90 (m, 1H).

Example 435: (S,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide

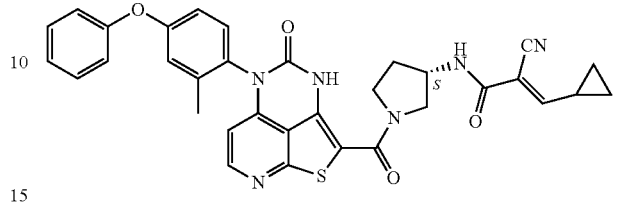

Step A: tert-butyl (S)-(1-(5-(2-methyl-4-phenoxyphenyl)-4-oxo-4,5-dihydro-3H-1-thia-3,5,8-triazaacenaphthylene-2-carbonyl)pyrrolidin-3-yl)carbamate A mixture of 5-(2-Methyl-4-phenoxyphenyl)-4-oxo-4,5-dihydro-3H-1-thia-3,5,8-triazaacenaphthylene-2-carboxylic acid (Intermediate 1, 500 mg, 1.2 mmol), tert-butyl (S)-pyrrolidin-3-ylcarbamate (0.43 g, 2.4 mmol), HATU (0.59 g, 1.56 mmol), DIEA (0.23 g, 1.8 mmol) in DMF (5 mL) was stirred at room temperature for one hour. The mixture was quenched with water, the solid was filtered and dried to afford the title compound.

Step B: (S)-2-(3-Aminopyrrolidine-1-carbonyl)-5-(2-methyl-4-phenoxyphenyl)-3H-1-thia-3,5,8-triazaacenaphthylen-4(5H)-one Tert-butyl (S)-(1-(5-(2-methyl-4-phenoxyphenyl)-4-oxo-4,5-dihydro-3H-1-thia-3,5,8-triazaacenaphthylene-2-carbonyl)pyrrolidin-3-yl)carbamate was dissolved in a solution of 10 mL con HCl in MeOH (10 mL), stirred at room temperature for one hour. The mixture was concentrated to give the title compound (0.29 g, 50% yield).

Step C: (S,E)-2-cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide A mixture of (S)-2-(3-aminopyrrolidine-1-carbonyl)-5-(2-methyl-4-phenoxyphenyl)-3H-1-thia-3,5,8-triazaacenaphthylen-4(5H)-one (200 mg, 0.41 mmol), (E)-2-cyano-3-cyclopropylacrylic acid (Intermediate 44, 113 mg, 0.82 mmol), HATU (201 mg, 0.53 mmol), DIEA (132 mg, 1.03 mmol) in DMF (5 mL) was stirred at room temperature for two hours. The mixture was purified by flash column chromatography (MeOH/water) to afford the title compound (85 mg, 34% yield). MS (ESI): mass calcd. for $C_{33}H_{28}N_6O_4S$, 604.7; m/z found, 605.4 $[M+H]^+$. $^1H$ NMR (400 MHz, a mixture of DMSO-$d_6$ and CD$_3$OD) δ 8.34-8.31 (m, 1H), 7.43-7.36 (m, 2H), 7.34-7.30 (m, 1H), 7.18-7.12 (m, 1H), 7.11-7.03 (m, 3H), 6.98-6.92 (m, 1H), 6.90-6.84 (m, 1H), 6.03-5.98 (m, 1H), 4.48-4.39 (m, 1H), 3.98-3.86 (m, 1H), 3.86-3.75 (m, 2H), 3.66-3.56 (m, 1H), 2.25-2.15 (m, 1H), 2.02 (s, 3H), 2.04-1.98 (m, 1H), 1.97-1.87 (m, 1H), 1.23-1.17 (m, 2H), 0.95-0.87 (m, 2H).

Example 436: (R,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide

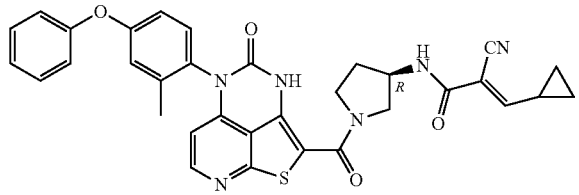

The title compound was prepared in a manner analogous to Example 435, using tert-butyl (R)-pyrrolidin-3-ylcarbamate in place of tert-butyl (S)-pyrrolidin-3-ylcarbamate in Step A. MS (ESI): mass calcd. for $C_{33}H_{28}N_6O_4S$, 604.7; m/z found, 605.4 [M+H]⁺. ¹H NMR (400 MHz, a mixture of DMSO-d₆ and CD₃OD) δ 8.34-8.31 (m, 1H), 7.43-7.36 (m, 2H), 7.34-7.30 (m, 1H), 7.18-7.12 (m, 1H), 7.11-7.03 (m, 3H), 6.98-6.92 (m, 1H), 6.90-6.84 (m, 1H), 6.03-5.98 (m, 1H), 4.48-4.39 (m, 1H), 3.98-3.86 (m, 1H), 3.86-3.75 (m, 2H), 3.66-3.56 (m, 1H), 2.25-2.15 (m, 1H), 2.02 (s, 3H), 2.04-1.98 (m, 1H), 1.97-1.87 (m, 1H), 1.23-1.17 (m, 2H), 0.95-0.87 (m, 2H).

Example 437: N-((1R,2S)-2-Acrylamidocyclopentyl)-4-oxo-5-(4-(pyridin-2-yloxy)phenyl)-4,5-dihydro-3H-1-thia-3,5,8-triazaacenaphthylene-2-carboxamide

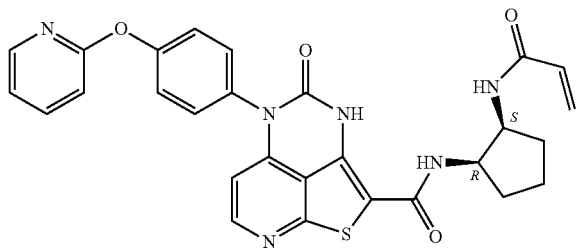

Step A. 4-Oxo-5-(4-(pyridin-2-yloxy)phenyl)-4,5-dihydro-3H-1-thia-3,5,8-triazaacenaphthylene-2-carboxylic acid The title compound was prepared in a manner analogous to Intermediate 15, Step A and C, using 2-fluoropyridine and 4-aminophenol, in Step A, (no Cu).

Step B: N-((1R,2S)-2-Acrylamidocyclopentyl)-4-oxo-5-(4-(pyridin-2-yloxy)phenyl)-4,5-dihydro-3H-1-thia-3,5,8-triazaacenaphthylene-2-carboxamide The title compound was prepared in a manner analogous to Example 1, Step A, using 4-oxo-5-(4-(pyridin-2-yloxy)phenyl)-4,5-dihydro-3H-1-thia-3,5,8-triazaacenaphthylene-2-carboxylic acid and N-((1S,2R)-2-aminocyclopentyl)acrylamide (Intermediate 36), no HCl/MeOH deprotection step. MS (ESI): mass calcd. for $C_{28}H_{24}N_6O_4S$, 540.6; m/z found, 541.1 [M+H]⁺. ¹H NMR (400 MHz, DMSO-d₆): δ 10.00 (s, 1H), 8.34-8.26 (m, 1H), 8.23-8.14 (m, 1H), 7.93-7.83 (m, 2H), 7.76-7.63 (m, 1H), 7.50-7.39 (m, 2H), 7.35-7.27 (m, 2H), 7.20-7.15 (m, 1H), 7.14-7.06 (m, 1H), 6.26-6.14 (m, 1H), 6.10-6.01 (m, 2H), 5.58-5.50 (m, 1H), 4.36-4.18 (m, 2H), 1.99-1.83 (m, 2H), 1.80-1.68 (m, 2H), 1.63-1.47 (m, 2H).

Example 438: N-((1R,2S)-2-Acrylamidocyclopentyl)-5-(3-isopropylphenyl)-4-oxo-4,5-dihydro-3H-1-thia-3,5,8-triazaacenaphthylene-2-carboxamide

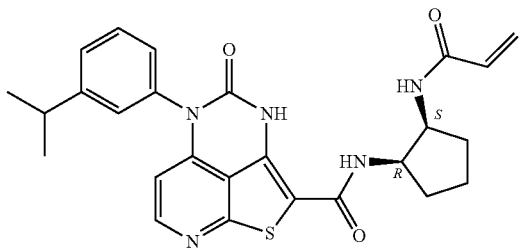

Step A. 5-(3-Isopropylphenyl)-4-oxo-4,5-dihydro-3H-1-thia-3,5,8-triazaacenaphthylene-2-carboxylic acid The title compound was prepared in a manner analogous to Intermediate 1, Steps C-F, using 3-isopropylaniline in Step C.

Step B. N-((1R,2S)-2-Acrylamidocyclopentyl)-5-(3-isopropylphenyl)-4-oxo-4,5-dihydro-3H-1-thia-3,5,8-triazaacenaphthylene-2-carboxamide The title compound was prepared in a manner analogous to Example 1, using 5-(3-isopropylphenyl)-4-oxo-4,5-dihydro-3H-1-thia-3,5,8-triazaacenaphthylene-2-carboxylic acid and tert-butyl ((1S,2R)-2-aminocyclopentyl)carbamate. MS (ESI): mass calcd. for $C_{26}H_{27}N_5O_3S$, 489.6; m/z found, 490.5 [M+H]⁺. ¹H NMR (400 MHz, CD₃OD): δ 8.26 (d, J=5.6 Hz, 1H), 7.57-7.49 (m, 1H), 7.46-7.39 (m, 1H), 7.32-7.26 (m, 1H), 7.24-7.16 (m, 1H), 6.33-6.16 (m, 2H), 6.06 (d, J=5.6 Hz, 1H), 5.66-5.57 (m, 1H), 4.48-4.35 (m, 2H), 3.04-2.95 (m, 1H), 2.14-2.03 (m, 2H), 1.95-1.87 (m, 1H), 1.81-1.62 (m, 3H), 1.30-1.27 (m, 6H).

Example 439: N-((1R,2R)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide

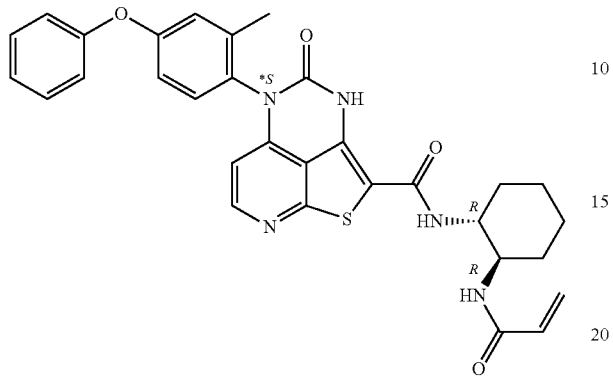

The title compound was prepared in a manner analogous to Example 1, Step B, using N-((1R,2R)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 440). MS (ESI): mass calcd. for $C_{31}H_{29}N_5O_4S$, 567.7; m/z found, 568.2 [M+H]$^+$. $^1$H NMR (400 MHz, CD$_3$OD): δ 8.32-8.26 (m, 1H), 7.43-7.33 (m, 2H), 7.29-7.24 (m, 1H), 7.19-7.12 (m, 1H), 7.10-7.03 (m, 3H), 6.98-6.93 (m, 1H), 6.22-6.15 (m, 2H), 6.05-6.01 (m, 1H), 5.62-5.54 (m, 1H), 3.91-3.76 (m, 2H), 2.10 (s, 3H), 2.08-1.98 (m, 2H), 1.83-1.75 (m, 2H), 1.50-1.36 (m, 4H).

Example 440: N-((1R,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide

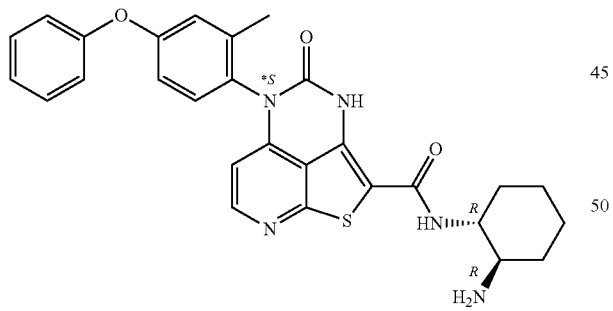

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2R)-2-aminocyclohexyl)carbamate. MS (ESI): mass calcd. for $C_{28}H_{27}N_5O_3S$, 513.6; m/z found, 514.2 [M+H]$^+$. $^1$H NMR (400 MHz, CD$_3$OD): δ 8.19-8.14 (m, 1H), 7.42-7.33 (m, 2H), 7.24-7.18 (m, 1H), 7.16-7.11 (m, 1H), 7.08-7.01 (m, 3H), 6.98-6.93 (m, 1H), 5.92-5.88 (m, 1H), 3.92-3.82 (m, 1H), 3.09-2.98 (m, 1H), 2.13-1.98 (m, 5H), 1.87-1.75 (m, 2H), 1.52-1.39 (m, 4H).

Example 441: N-((1R,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide

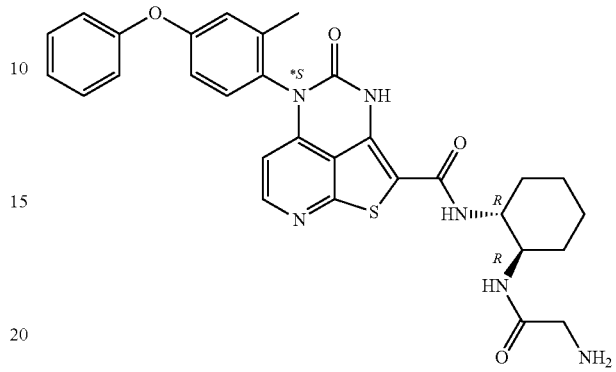

Step A: tert-Butyl (2-(((1R,2R)-2-(5-(*S)-(2-methyl-4-phenoxyphenyl)-4-oxo-4,5-dihydro-3H-1-thia-3,5,8-triazaacenaphthylene-2-carboxamido)cyclohexyl)amino)-2-oxoethyl)carbamate A solution of N-((1R,2R)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 440, 65.0 mg, 0.127 mmol), 2-((tert-butoxycarbonyl)amino)acetic acid (50 mg, 0.28 mmol), triethylamine (50 mg, 0.50 mmol), and HATU (95 mg, 0.25 mmol) in DMF (5 mL) was reacted at room temperature for 2 h. The reaction was quenched with 10 mL of H$_2$O, extracted with DCM, dried over anhydrous Na$_2$SO$_4$, filtered, and concentrated to dryness. The residue was purified by flash column chromatography to yield the title compound (80 mg, 94% yield) as a yellow solid. MS (ESI): mass calcd. for $C_{35}H_{38}N_6O_6S$. 670.78; m/z found, 671.2 [M+H]$^+$.

Step B: N-((1R,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide To a solution of tert-butyl (2-(((1R,2R)-2-(5-(*S)-(2-methyl-4-phenoxyphenyl)-4-oxo-4,5-dihydro-3H-1-thia-3,5,8-triazaacenaphthylene-2-carboxamido)cyclohexyl)amino)-2-oxoethyl)carbamate (80 mg, 0.12 mmol) in MeOH (2.0 mL) was added HCl (1.0 mL) and was reacted at 60° C. for 30 minutes. The reaction was concentrated to dryness and the residue was purified by flash column chromatography and preparative TLC to yield the title compound (51 mg) as a yellow solid. MS (ESI): mass calcd. for $C_{30}H_{30}N_6O_4S$, 570.7; m/z found, 571.2 [M+H]$^+$. $^1$H NMR (400 MHz, CD$_3$OD): δ 8.31-8.26 (m, 1H), 7.44-7.34 (m, 2H), 7.28-7.21 (m, 1H), 7.16-7.11 (m, 1H), 7.10-7.01 (m, 3H), 6.98-6.93 (m, 1H), 6.05-5.98 (m, 1H), 3.89-3.77 (m, 2H), 3.24 (s, 2H), 2.11 (s, 3H), 2.08-1.93 (m, 2H), 1.85-1.73 (m, 2H), 1.52-1.36 (m, 4H).

Example 442: N-((1R,2S)-2-Acrylamidocyclohexyl)-4-oxo-5-(4-(pyridin-2-yloxy)phenyl)-4,5-dihydro-3H-1-thia-3,5,8-triazaacenaphthylene-2-carboxamide

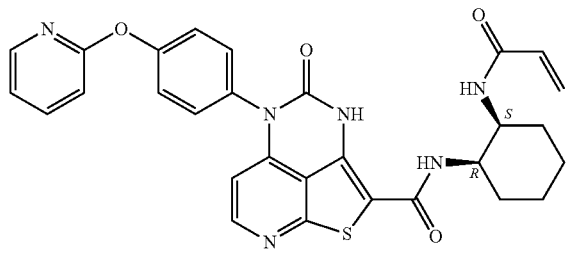

The title compound was prepared in a manner analogous to Example 1, Step A, using 4-oxo-5-(4-(pyridin-2-yloxy)phenyl)-4,5-dihydro-3H-1-thia-3,5,8-triazaacenaphthylene-2-carboxylic acid (Example 437, product from Step A) and N-((1S,2R)-2-aminocyclohexyl)acrylamide (Intermediate 40), no HCl/MeOH deprotection. MS (ESI): mass calcd. for $C_{29}H_{26}N_6O_4S$, 554.6; m/z found, 555.2 [M+H]$^+$. $^1$H NMR (400 MHz, CD$_3$OD): δ 8.33-8.28 (m, 1H), 8.19-8.13 (m, 1H), 7.90-7.83 (m, 1H), 7.50-7.43 (m, 2H), 7.36-7.30 (m, 2H), 7.19-7.12 (m, 1H), 7.10-7.04 (m, 1H), 6.46-6.36 (m, 1H), 6.33-6.23 (m, 2H), 5.69-5.63 (m, 1H), 4.45-4.35 (m, 1H), 4.20-4.10 (m, 1H), 1.85-1.64 (m, 6H), 1.60-1.48 (m, 2H).

Example 443: 5-(*S)-(2-Methyl-4-phenoxyphenyl)-N-((1S,2R)-2-(2-(methylamino)acetamido)cyclohexyl)-4-oxo-4,5-dihydro-3H-1-thia-3,5,8-triazaacenaphthylene-2-carboxamide

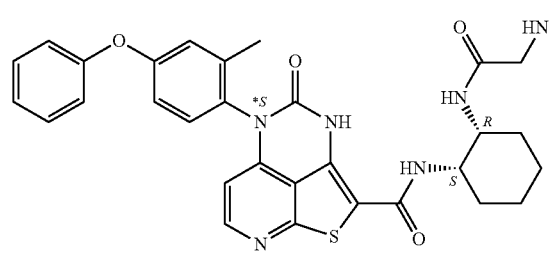

Step A: N-((1S,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2S)-2-aminocyclohexyl). MS (ESI): mass calcd. for $C_{28}H_{27}N_5O_3S$, 513.61; m/z found, 514.2 [M+H]$^+$. $^1$H NMR (400 MHz, CD$_3$OD): δ 8.53 (d, J=6.2 Hz, 1H), 7.47-7.38 (m, 2H), 7.38-7.31 (m, 1H), 7.24-7.16 (m, 1H), 7.15-7.07 (m, 3H), 7.05-6.97 (m, 1H), 6.40 (d, J=6.2 Hz, 1H), 4.51-4.43 (m, 1H), 3.70-3.59 (m, 1H), 2.16 (s, 3H), 1.97-1.74 (m, 6H), 1.66-1.53 (m, 2H).

Step B: 5-(*S)-(2-Methyl-4-phenoxyphenyl)-N-((1S,2R)-2-(2-(methylamino)acetamido)cyclohexyl)-4-oxo-4,5-dihydro-3H-1-thia-3,5,8-triazaacenaphthylene-2-carboxamide To a solution of N-((1S,2R)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (150 mg, 0.292 mmol) and Boc-sarcosine (207 mg, 0.438 mmol) in anhydrous DMF (3 mL) were added HATU (166 mg, 0.438 mmol) and DIPEA (76 mg, 0.58 mmol) and was stirred overnight at rt. The reaction was purified by flash column chromatography to get 120 mg of a yellow solid. The solid was dissolved in MeOH (2 mL) and concentrated HCl (1 mL) and was stirred at room temperature for 2 h. The reaction was concentrated to dryness and was purified by preparative TLC (DCM/MeOH; 20/1) to give the title compound (51 mg, 30% yield) as a yellow solid. MS (ESI): mass calcd. for $C_{31}H_{32}N_6O_4S$, 584.7; m/z found, 585.2 [M+H]$^+$. $^1$H NMR (400 MHz, CD$_3$OD): δ 8.17 (d, J=5.6 Hz, 1H), 7.42-7.33 (m, 2H), 7.24-7.19 (m, 1H), 7.18-7.11 (m, 1H), 7.11-7.00 (m, 3H), 6.99-6.91 (m, 1H), 5.90 (d, J=5.6 Hz, 1H), 4.38-4.28 (m, 1H), 4.26-4.15 (m, 1H), 3.67-3.57 (m, 1H), 3.56-3.46 (m, 1H), 2.51 (s, 3H), 2.10 (s, 3H), 1.83-1.67 (m, 5H), 1.61-1.47 (m, 3H).

Example 444: N-((1S,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide

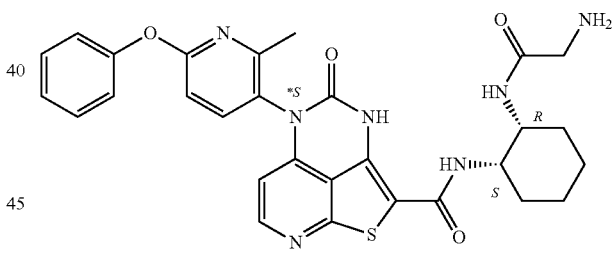

Step A: N-((1S,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2S)-2-aminocyclohexyl)carbamate. MS (ESI): mass calcd. for $C_{28}H_{27}N_5O_3S$, 513.61; m/z found, 514.2 [M+H]$^+$. $^1$H NMR (400 MHz, CD$_3$OD): δ 8.53 (d, J=6.2 Hz, 1H), 7.47-7.38 (m, 2H), 7.38-7.31 (m, 1H), 7.24-7.16 (m, 1H), 7.15-7.07 (m, 3H), 7.05-6.97 (m, 1H), 6.40 (d, J=6.2 Hz, 1H), 4.51-4.43 (m, 1H), 3.70-3.59 (m, 1H), 2.16 (s, 3H), 1.97-1.74 (m, 6H), 1.66-1.53 (m, 2H).

Step B: N-((1S,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide To a solution of N-((1S,2R)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (150 mg, 0.292 mmol) and Boc-glycine (192 mg, 0.438 mmol) in anhydrous DMF (3 mL) were added HATU (166 mg, 0.438 mmol) and DIPEA (76 mg, 0.58 mmol) and was stirred overnight at rt. The reaction was purified by flash column chromatography to get 130 mg of a yellow solid. The solid was dissolved in MeOH (2 mL) and concentrated HCl (1 mL) and was stirred at room temperature for 2 h. The reaction was concentrated to dryness and was purified by preparative TLC (DCM/MeOH; 20/1) to give the title compound (82 mg, 49% yield) as a yellow solid. MS (ESI): mass calcd. for $C_{30}H_{30}N_6O_4S$, 570.7; m/z found, 571.2 [M+H]$^+$. $^1$H NMR (400 MHz, CD$_3$OD): δ 8.14 (d, J=5.6 Hz, 1H), 7.42-7.35 (m, 2H), 7.24-7.18 (m, 1H), 7.18-7.11 (m, 1H), 7.10-7.05 (m, 2H), 7.05-7.00 (m, 1H), 6.98-6.91 (m, 1H), 5.87 (d, J=5.6 Hz, 1H), 4.35-4.28 (m, 1H), 4.26-4.17 (m, 1H), 3.69-3.61 (m, 1H), 3.56-3.47 (m, 1H), 2.10 (s, 3H), 1.87-1.64 (m, 5H), 1.64-1.42 (m, 3H).

Example 445: N-((1R,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide

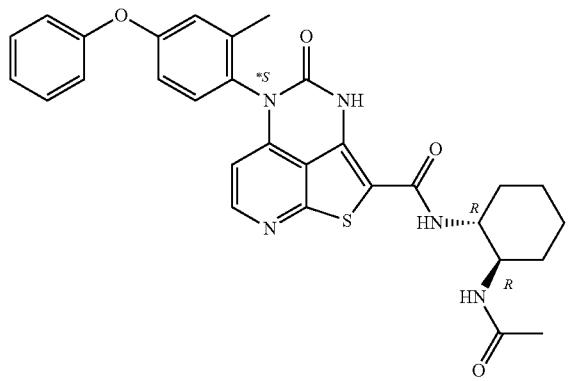

To a solution of N-((1R,2R)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 440, 120 mg, 0.234 mmol) in DCM (2 mL), were added acetic anhydride (24 mg, 0.23 mmol) and triethylamine (36 mg, 0.35 mmol) and was reacted at room temperature for 20 minutes. The reaction was concentrated to dryness and the residue was purified by flash column chromatography to get the title compound (100 mg, 77% yield) as a gray solid. MS (ESI): mass calcd. for $C_{30}H_{29}N_5O_4S$, 555.6; m/z found, 556.2 [M+H]$^+$. $^1$H NMR (400 MHz, CD$_3$OD): δ 8.34-8.27 (m, 1H), 7.44-7.35 (m, 2H), 7.31-7.24 (m, 1H), 7.19-7.12 (m, 1H), 7.11-7.02 (m, 3H), 6.98-6.93 (m, 1H), 6.08-6.02 (m, 1H), 3.85-3.74 (m, 2H), 2.11 (s, 3H), 2.06-1.98 (m, 1H), 1.97-1.90 (m, 1H), 1.88 (s, 3H), 1.82-1.75 (m, 2H), 1.50-1.33 (m, 4H).

Example 446: N-((1S,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide

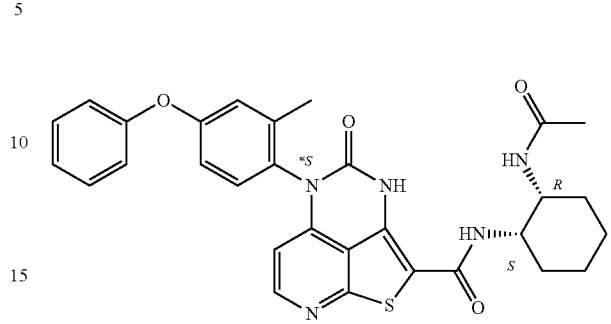

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2S)-2-aminocyclohexyl)carbamate, in Step A, and acetyl chloride in Step B. MS (ESI): mass calcd. for $C_{30}H_{29}N_5O_4S$, 555.6; m/z found, 556.2 [M+H]$^+$. $^1$H NMR (400 MHz, CD$_3$OD): δ 8.31 (d, J=5.5 Hz, 1H), 7.44-7.34 (m, 2H), 7.31-7.23 (m, 1H), 7.20-7.12 (m, 1H), 7.11-7.01 (m, 3H), 7.00-6.91 (m, 1H), 6.05 (d, J=5.5 Hz, 1H), 4.36-4.26 (m, 1H), 4.17-4.08 (m, 1H), 2.11 (s, 3H), 2.00 (s, 3H), 1.79-1.45 (m, 8H).

Example 447: N-((1R,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide

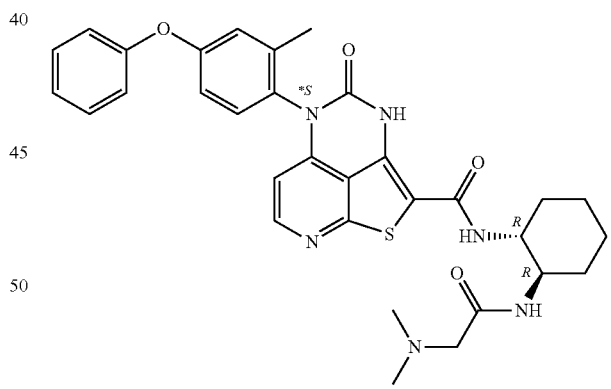

The title compound was prepared in a manner analogous to Example 1, Step A, using N-((1R,2R)-2-amino cyclohexyl)-5-(*S)-(2-methyl-4-phenoxyphenyl)-4-oxo-4,5-dihydro-3H-1-thia-3,5,8-triazaacenaphthylene-2-carboxamide (Example 440) and 2-(dimethylamino)acetic acid, no MeOH/HCl deprotection step necessary. MS (ESI): mass calcd. for $C_{32}H_{34}N_6O_4S$, 598.7; m/z found, 599.2 [M+H]$^+$. $^1$H NMR (400 MHz, CD$_3$OD): δ 8.35-8.29 (m, 2H), 7.42-7.38 (m, 2H), 7.31-7.24 (m, 1H), 7.19-7.12 (m, 1H), 7.11-7.02 (m, 3H), 6.98-6.93 (m, 1H), 6.09-6.04 (m, 1H), 3.95-3.77 (m, 2H), 3.35 (s, 2H), 2.48 (s, 6H), 2.10 (s, 3H), 2.04-1.98 (m, 2H), 1.85-1.74 (m, 2H), 1.58-1.36 (m, 4H).

Example 448: 5-(*S)-(2-Methyl-4-phenoxyphenyl)-N-((1R,2R)-2-(2-(methylamino)acetamido)cyclohexyl)-4-oxo-4,5-dihydro-3H-1-thia-3,5,8-triazaacenaphthylene-2-carboxamide

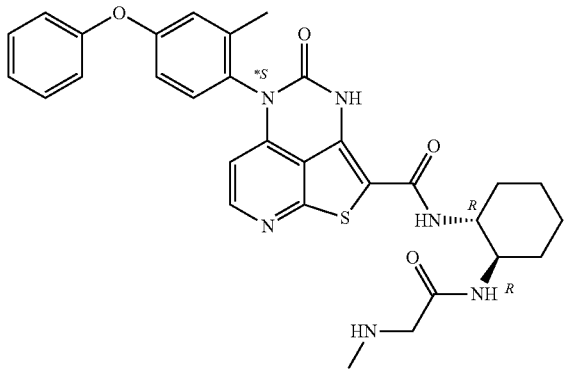

Step A: tert-Butyl methyl(2-(((1R,2R)-2-(5-(*S)-(2-methyl-4-phenoxyphenyl)-4-oxo-4,5-dihydro-3H-1-thia-3,5,8-triazaacenaphthylene-2-carboxamido)cyclohexyl)amino)-2-oxoethyl)carbamate A solution of N-((1R,2R)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (Example 440, 120 mg, 0.234 mmol), 2-((tert-butoxycarbonyl)(methyl)amino)acetic acid (65 mg, 0.34 mmol), triethylamine (50 mg, 0.50 mmol), and HATU (95 mg, 0.25 mmol) in DMF (5 mL) was reacted at room temperature for 2 h. The reaction was quenched with H$_2$O (10 mL), extracted with DCM, dried over anhydrous Na$_2$SO$_4$, filtered, and concentrated to dryness. The residue was purified by flash column chromatography to yield the title compound (120 mg, 75% yield) as a yellow solid. MS (ESI): mass calcd. for C$_{36}$H$_{40}$N$_6$O$_6$S. 684.80; m/z found, 685.2 [M+H]$^+$.

Step B: 5-(*S)-(2-Methyl-4-phenoxyphenyl)-N-((1R,2R)-2-(2-(methylamino)acetamido)cyclohexyl)-4-oxo-4,5-dihydro-3H-1-thia-3,5,8-triazaacenaphthylene-2-carboxamide A solution of tert-butyl methyl(2-(((1R,2R)-2-(5-(*S)-(2-methyl-4-phenoxyphenyl)-4-oxo-4,5-dihydro-3H-1-thia-3,5,8-triazaacenaphthylene-2-carboxamido)cyclohexyl)amino)-2-oxoethyl)carbamate (120 mg, 0.175 mmol) in HCl (1 mL) and MeOH (2 mL) was reacted at 60° C. for 30 minutes. The reaction was concentrated to dryness and the residue was purified by flash column chromatography and preparative TLC to yield the title compound (95 mg, 93% yield) as a yellow solid. MS (ESI): mass calcd. for C$_{31}$H$_{32}$N$_6$O$_4$S, 584.7; m/z found, 585.2 [M+H]$^+$. $^1$H NMR (400 MHz, CD$_3$OD): δ 8.05-7.99 (m, 1H), 7.40-7.33 (m, 2H), 7.18-7.10 (m, 2H), 7.09-7.05 (m, 2H), 7.03-6.99 (m, 1H), 6.96-6.91 (m, 1H), 5.77-5.73 (m, 1H), 3.97-3.85 (m, 1H), 3.84-3.72 (m, 1H), 3.16-3.02 (m, 2H), 2.21 (s, 3H), 2.09 (s, 3H), 2.07-2.01 (m, 2H), 1.81-1.66 (m, 2H), 1.47-1.25 (m, 4H).

Example 449: N-((1S,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide

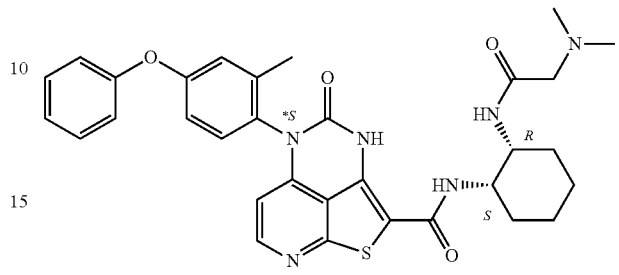

Step A: N-((1S,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2S)-2-aminocyclohexyl)carbamate in place of tert-butyl ((1s,4s)-4-aminocyclohexyl)carbamate in step G (1100 mg). MS (ESI): mass calcd. for C$_{28}$H$_{27}$N$_5$O$_3$S, 513.6; m/z found, 514.2 [M+H]$^+$. $^1$H NMR (400 MHz, CD$_3$OD): δ 8.12 (d, J=5.6 Hz, 1H), 7.42-7.33 (m, 2H), 7.23-7.18 (m, 1H), 7.16-7.11 (m, 1H), 7.10-7.04 (m, 2H), 7.04-7.01 (m, 1H), 6.98-6.93 (m, 1H), 5.85 (d, J=5.6 Hz, 1H), 4.44-4.38 (m, 1H), 3.40-3.34 (m, 1H), 2.09 (s, 3H), 1.90-1.68 (m, 6H), 1.60-1.43 (m, 2H).

Step B: N-((1S,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide To a solution of N-((1S,2R)-2-aminocyclohexyl)-5-(*S)-(2-methyl-4-phenoxyphenyl)-4-oxo-4,5-dihydro-3H-1-thia-3,5,8-triazaacenaphthylene-2-carboxamide (80 mg, 0.16 mmol) and 2-(dimethylamino)acetic acid (60 mg, 0.23 mmol) in anhydrous DMF (2 mL) was added HATU (89 mg, 0.23 mmol) and DIPEA (40 mg, 0.31 mmol) and the reaction was stirred overnight at rt. The reaction was purified by flash column chromatography to yield the title compound (66 mg, 71% yield) as a yellow solid. MS (ESI): mass calcd. for C$_{32}$H$_{34}$N$_6$O$_4$S, 598.7; m/z found, 599.2 [M+H]$^+$. $^1$H NMR (400 MHz, CD$_3$OD): δ 8.32-8.26 (m, 1H), 7.43-7.34 (m, 2H), 7.29-7.23 (m, 1H), 7.19-7.12 (m, 1H), 7.11-7.02 (m, 3H), 6.99-6.93 (m, 1H), 6.05-6.00 (m, 1H), 4.39-4.29 (m, 1H), 4.23-4.13 (m, 1H), 3.11 (s, 2H), 2.36 (s, 6H), 2.11 (s, 3H), 1.83-1.67 (m, 5H), 1.60-1.47 (m, 3H).

Example 450: N-((1S,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide

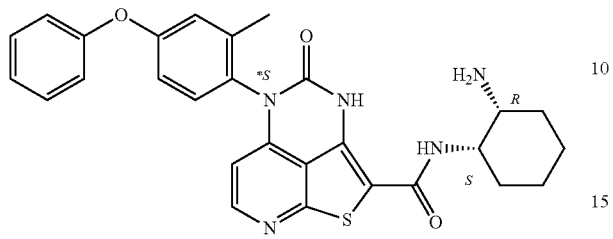

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2S)-2-aminocyclohexyl)carbamate. MS (ESI): mass calcd. for $C_{28}H_{27}N_5O_3S$, 513.6; m/z found, 514.2 [M+H]$^+$. $^1$H NMR (400 MHz, CD$_3$OD): δ 8.12 (d, J=5.6 Hz, 1H), 7.42-7.33 (m, 2H), 7.23-7.18 (m, 1H), 7.16-7.11 (m, 1H), 7.10-7.04 (m, 2H), 7.04-7.01 (m, 1H), 6.98-6.93 (m, 1H), 5.85 (d, J=5.6 Hz, 1H), 4.44-4.38 (m, 1H), 3.40-3.34 (m, 1H), 2.09 (s, 3H), 1.90-1.68 (m, 6H), 1.60-1.43 (m, 2H).

Example 451: N-((1S,2R)-2-Acrylamidocyclohexyl)-5-(2-methyl-4-phenoxyphenyl)-4-oxo-4,5-dihydro-3H-1-thia-3,5,8-triazaacenaphthylene-2-carboxamide

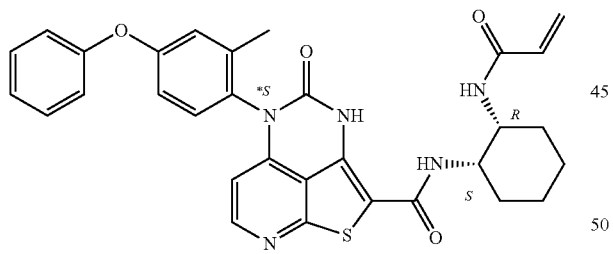

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2S)-2-aminocyclohexyl)carbamate. MS (ESI): mass calcd. for $C_{31}H_{29}N_5O_4S$, 567.7; m/z found, 568.5 [M+H]$^+$. $^1$H NMR (400 MHz, CD$_3$OD): δ 8.30 (d, J=5.5 Hz, 1H), 7.44-7.34 (m, 2H), 7.30-7.23 (m, 1H), 7.19-7.12 (m, 1H), 7.11-7.02 (m, 3H), 6.99-6.92 (m, 1H), 6.47-6.34 (m, 1H), 6.31-6.21 (m, 1H), 6.05 (d, J=5.5 Hz, 1H), 5.69-5.60 (m, 1H), 4.46-4.35 (m, 1H), 4.21-4.10 (m, 1H), 2.11 (s, 3H), 1.84-1.47 (m, 8H).

Example 452: N-((1S,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide

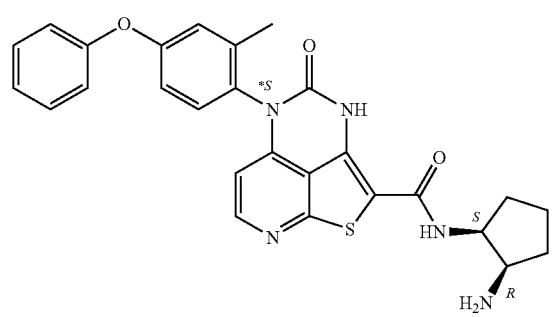

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1, including CHIRAL SEPARATION METHOD 1 to obtain the *S atropisomer) and tert-butyl ((1R,2S)-2-aminocyclopentyl)carbamate. MS (ESI): mass calcd. for $C_{27}H_{25}N_5O_3S$, 499.6; m/z found, 500.4 [M+H]$^+$. $^1$H NMR (400 MHz, CD$_3$OD): δ 8.33 (d, J=5.9 Hz, 1H), 7.45-7.33 (m, 2H), 7.28-7.23 (m, 1H), 7.20-7.13 (m, 1H), 7.10-7.04 (m, 3H), 7.00-6.93 (m, 1H), 6.07 (d, J=5.8 Hz, 1H), 4.52-4.42 (m, 1H), 3.80-3.68 (m, 1H), 2.24-2.13 (m, 2H), 2.11 (s, 3H), 2.00-1.85 (m, 2H), 1.80-1.64 (m, 2H).

Example 453: N-((1R,2S)-2-Aminocyclopentyl)-5-(4-isopropoxy-2-methylphenyl)-4-oxo-4,5-dihydro-3H-1-thia-3,5,8-triazaacenaphthylene-2-carboxamide

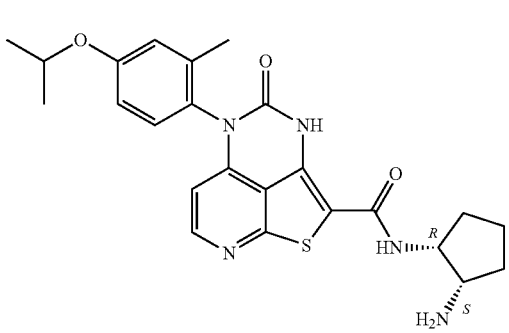

The title compound was prepared in a manner analogous to Example 1, Step A, using 5-(4-isopropoxy-2-methylphenyl)-4-oxo-4,5-dihydro-3H-1-thia-3,5,8-triazaacenaphthylene-2-carboxylic acid (Intermediate 31) and tert-butyl ((1S,2R)-2-aminocyclopentyl)carbamate. MS (ESI): mass calcd. for $C_{24}H_{27}N_5O_3S$, 465.6; m/z found, 466.2 [M+H]$^+$. $^1$H NMR (400 MHz, CD$_3$OD): δ 8.19-8.06 (m, 1H), 7.16-7.06 (m, 1H), 6.98-6.84 (m, 2H), 5.89-5.79 (m, 1H), 4.69-4.59 (m, 1H), 4.53-4.43 (m, 1H), 3.65-3.52 (m, 1H), 2.20-2.03 (m, 5H), 1.97-1.81 (m, 2H), 1.78-1.60 (m, 2H), 1.38-1.28 (m, 6H).

Example 454: N-((1S,3R)-3-Acetamidocyclopentyl)-5-(4-isopropoxy-2-methylphenyl)-4-oxo-4,5-dihydro-3H-1-thia-3,5,8-triazaacenaphthylene-2-carboxamide

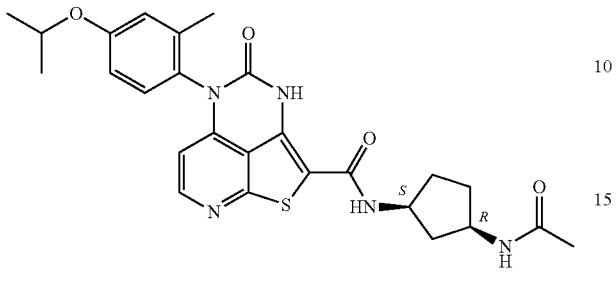

The title compound was prepared in a manner analogous to Example 1, using 5-(4-isopropoxy-2-methylphenyl)-4-oxo-4,5-dihydro-3H-1-thia-3,5,8-triazaacenaphthylene-2-carboxylic acid (Intermediate 31) and using tert-butyl ((1R,3S)-3-aminocyclopentyl)carbamate in Step A, and acetyl chloride in Step B. MS (ESI): mass calcd. for $C_{26}H_{29}N_5O_4S$, 507.6; m/z found, 508.2 $[M+H]^+$. $^1H$ NMR (400 MHz, $CD_3OD$): δ 8.30 (d, J=5.6 Hz, 1H), 7.22-7.15 (m, 1H), 6.99-6.95 (m, 1H), 6.94-6.88 (m, 1H), 6.02 (d, J=5.6 Hz, 1H), 4.70-4.61 (m, 1H), 4.39-4.26 (m, 1H), 4.17-4.05 (m, 1H), 2.48-2.38 (m, 1H), 2.10 (s, 3H), 2.08-1.88 (m, 5H), 1.81-1.64 (m, 2H), 1.62-1.48 (m, 1H), 1.35-1.32 (m, 6H).

Example 455: N-((1R,2S)-2-Aminocyclopentyl)-5-(3-isopropylphenyl)-4-oxo-4,5-dihydro-3H-1-thia-3,5,8-triazaacenaphthylene-2-carboxamide

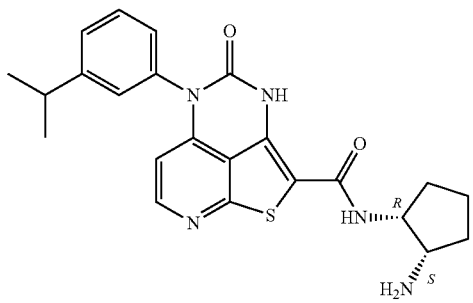

The title compound was prepared in a manner analogous to Example 1, using 5-(3-isopropylphenyl)-4-oxo-4,5-dihydro-3H-1-thia-3,5,8-triazaacenaphthylene-2-carboxylic acid (Example 428, product from Step A, tert-butyl ((1S,2R)-2-aminocyclopentyl)carbamate. MS (ESI): mass calcd. for $C_{23}H_{25}N_5O_2S$, 435.17; m/z found, 436.2 $[M+H]^+$. $^1H$ NMR (400 MHz, $CD_3OD$): δ 8.17 (d, J=5.6 Hz, 1H), 7.54-7.46 (m, 1H), 7.42-7.36 (m, 1H), 7.25-7.19 (m, 1H), 7.20-7.11 (m, 1H), 5.97 (d, J=5.6 Hz, 1H), 4.52-4.44 (m, 1H), 3.71-3.54 (m, 1H), 3.03-2.94 (m, 1H), 2.19-2.09 (m, 2H), 1.98-1.82 (m, 2H), 1.78-1.64 (m, 2H), 1.30-1.27 (m, 6H).

Example 456: N-((1R,2R)-2-Hydroxycyclopentyl)-5-(4-isopropoxy-2-methylphenyl)-4-oxo-4,5-dihydro-3H-1-thia-3,5,8-triazaacenaphthylene-2-carboxamide

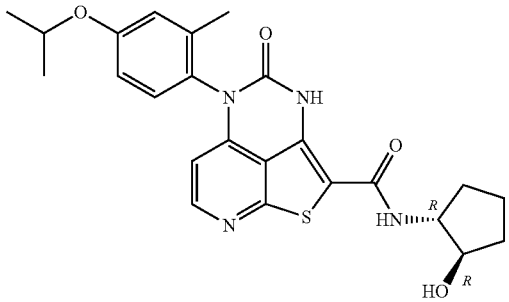

The title compound was prepared in a manner analogous to Example 1, Step A, using 5-(4-isopropoxy-2-methylphenyl)-4-oxo-4,5-dihydro-3H-1-thia-3,5,8-triazaacenaphthylene-2-carboxylic acid (Intermediate 31) and (1R,2R)-2-aminocyclopentanol, no MeOH/HCl deprotection. MS (ESI): mass calcd. for $C_{24}H_{26}N_4O_4S$, 466.6; m/z found, 467.1 $[M+H]^+$. $^1H$ NMR (400 MHz, $CD_3OD$): δ 8.29 (d, J=5.6 Hz, 1H), 7.22-7.15 (m, 1H), 7.00-6.94 (m, 1H), 6.94-6.87 (m, 1H), 6.02 (d, J=5.6 Hz, 1H), 4.70-4.61 (m, 1H), 4.18-4.01 (m, 2H), 2.18-2.08 (m, 4H), 2.04-1.95 (m, 1H), 1.83-1.72 (m, 2H), 1.65-1.55 (m, 2H), 1.37-1.30 (m, 6H).

Example 457: N-((1S,2R)-2-Aminocyclohexyl)-4-oxo-5-(4-phenoxyphenyl)-4,5-dihydro-3H-1-thia-3,5,8-triazaacenaphthylene-2-carboxamide

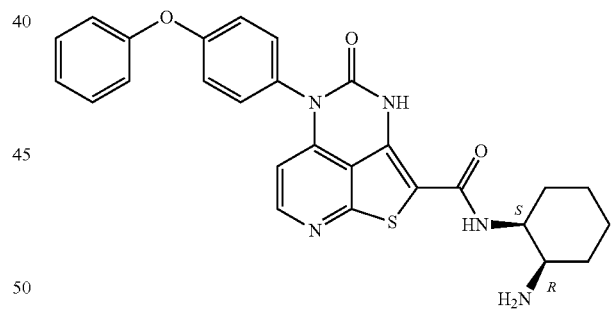

To a dry scintillation vial under Ar were added tert-butyl (1R,2S)-2-aminocyclohexylcarbamate (191 mg, 0.891 mmol), THF (2.097 mL), and DIPEA (0.262 mL, 1.50 mmol). To this solution was added dropwise slowly over 10 min was 4-oxo-5-(4-phenoxyphenyl)-4,5-dihydro-3H-1-thia-3,5,8-triazaacenaphthylene-2-carbonyl chloride (Intermediate 9, 13.11 mL, 0.04 M, 0.5240 mmol) and was stirred for 2 hours. The reaction was quenched with water, which caused a precipitate to form. The solution was filtered to isolate the solid and the solid was treated with DCM (5 mL) and HCl (5 mL, in ether, 2M). The reaction was warmed to 60° C. for 10 min, and then stirred at room temperature overnight. The reaction was concentrated to dryness and dissolved in methanol and purified by Gilson reverse phase HPLC to give the title compound (8.3 mg, 2.9% yield). MS (ESI): mass calcd. for $C_{27}H_{25}N_5O_3S$, 499.6; m/z found, 500.0 [M+H]$^+$. $^1$H NMR (400 MHz, CD$_3$OD): δ 8.21 (d, J=5.6 Hz, 1H), 7.49-7.25 (m, 4H), 7.25-7.02 (m, 5H), 6.08 (d, J=5.7 Hz, 1H), 4.48-4.31 (m, 1H), 3.53 (q, J=6.6, 5.4 Hz, 1H), 2.01-1.41 (m, 8H).

Example 458: N-((1S,2S)-2-Acrylamidocyclopentyl)-5-(2-methyl-4-phenoxyphenyl)-4-oxo-4,5-dihydro-3H-1-thia-3,5,8-triazaacenaphthylene-2-carboxamide

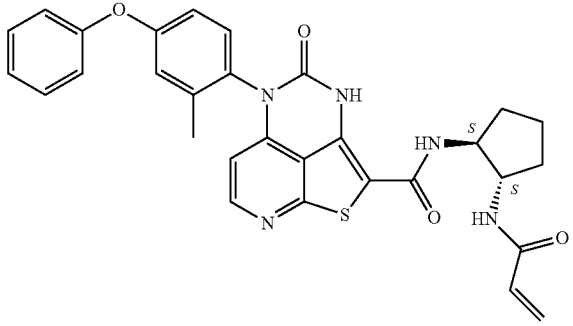

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl ((1S,2S)-2-aminocyclopentyl)carbamate in step A. MS (ESI): mass calcd. for $C_{30}H_{27}N_5O_4S$, 553.6; m/z found, 554.2 [M+H]$^+$. $^1$H NMR (400 MHz, a mixture of DMSO-d$_6$ and CD$_3$OD): δ 8.26 (d, J=5.3 Hz, 1H), 7.42-7.32 (m, 2H), 7.31-7.24 (m, 1H), 7.16-7.08 (m, 1H), 7.08-6.98 (m, 3H), 6.95-6.87 (m, 1H), 6.20-6.11 (m, 1H), 6.10-6.01 (m, 1H), 5.93 (d, J=5.4 Hz, 1H), 5.56-5.44 (m, 1H), 4.26-4.16 (m, 1H), 4.16-4.12 (m, 1H), 2.10-1.86 (m, 5H), 1.73-1.60 (m, 2H), 1.60-1.50 (m, 1H), 1.48-1.40 (m, 1H).

Example 459: N-((1S,2R)-2-Acrylamidocyclopentyl)-5-(2-methyl-4-phenoxyphenyl)-4-oxo-4,5-dihydro-3H-1-thia-3,5,8-triazaacenaphthylene-2-carboxamide

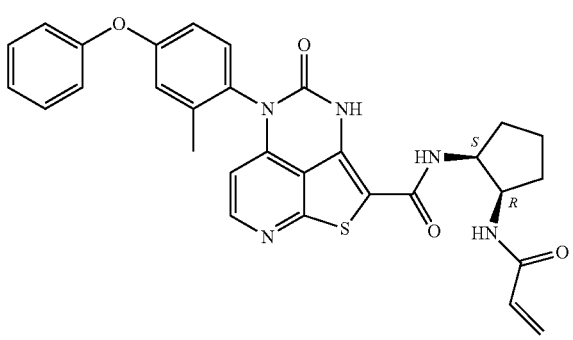

The title compound was prepared in a manner analogous to Example 1, using 5-(2-methyl-4-phenoxyphenyl)-4-oxo-4,5-dihydro-3H-1-thia-3,5,8-triazaacenaphthylene-2-carboxylic acid (Intermediate 1) and tert-butyl ((1R,2S)-2-aminocyclopentyl)carbamate in Step A. MS (ESI): mass calcd. for $C_{30}H_{27}N_5O_4S$, 553.6; m/z found, 554.2 [M+H]$^+$. $^1$H NMR (400 MHz, DMSO-d$_6$): δ 10.03 (s, 1H), 8.30 (d, J=5.5 Hz, 1H), 7.92-7.81 (m, 1H), 7.79-7.67 (m, 1H), 7.48-7.39 (m, 2H), 7.39-7.30 (m, 1H), 7.22-7.14 (m, 1H), 7.13-7.04 (m, 3H), 6.99-6.92 (m, 1H), 6.27-6.16 (m, 1H), 6.09-6.02 (m, 1H), 5.94 (d, J=5.4 Hz, 1H), 5.60-5.49 (m, 1H), 4.33-4.19 (m, 2H), 2.03 (s, 3H), 1.97-1.82 (m, 2H), 1.78-1.68 (m, 2H), 1.66-1.46 (m, 2H).

Example 460: 5-(4-(3-((2-Cyanophenoxy)methyl)phenoxy)-2-methylphenyl)-N-cyclohexyl-4-oxo-4,5-dihydro-3H-1-thia-3,5,8-triazaacenaphthylene-2-carboxamide

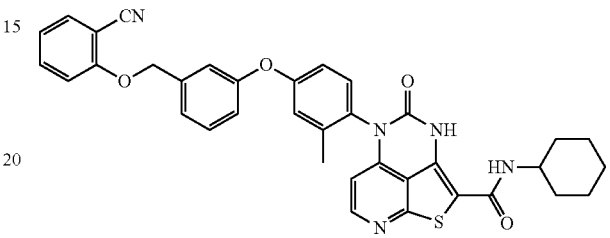

To a mixture of cyclohexanamine (67 mg, 0.67 mmol) in 10 mL of dry THF was added 1M Me$_3$Al (2 mL, 2.0 mmol) at room temperature and stirred at room temperature for 30 minutes, then was added methyl 5-(4-(3-((2-cyanophenoxy)methyl)phenoxy)-2-methylphenyl)-4-oxo-4,5-dihydro-3H-1-thia-3,5,8-triazaacenaphthylene-2-carboxylate (Intermediate 43, 187 mg, 0.33 mmol) and stirred under N$_2$ at reflux for 16 hours. The reaction was quenched by adding MeOH (3 mL), diluted with CH$_2$Cl$_2$, filtered through Celite®. The filtrate was condensed, purified by preparative TLC (MeOH/DCM=1/50). (69 mg, 33% yield). MS (ESI): mass calcd. for $C_{36}H_{31}N_5O_4S$, 629.7; m/z found, 630.3 [M+H]$^+$. $^1$H NMR (400 MHz, DMSO-d$_6$): δ 8.31-8.20 (m, 1H), 8.20-8.15 (m, 1H), 7.74-7.69 (m, 1H), 7.68-7.61 (m, 1H), 7.50-7.42 (m, 1H), 7.34-7.29 (m, 1H), 7.29-7.24 (m, 2H), 7.24-7.20 (m, 1H), 7.12-7.04 (m, 3H), 6.98-6.92 (m, 1H), 5.84-5.79 (m, 1H), 5.32 (s, 2H), 3.80-3.69 (m, 1H), 2.03 (s, 3H), 1.87-1.78 (m, 2H), 1.76-1.67 (m, 2H), 1.63-1.53 (m, 1H), 1.37-1.23 (m, 5H).

Example 461: N-(5-(4-(3-((2-Cyanophenoxy)methyl)phenoxy)-2-methylphenyl)-4-oxo-4,5-dihydro-3H-1-thia-3,5,8-triazaacenaphthylen-2-yl)cyclopropanecarboxamide

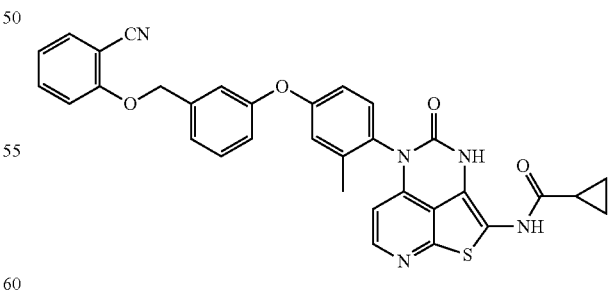

Step A: 5-(4-(3-((2-cyanophenoxy)methyl)phenoxy)-2-methylphenyl)-4-oxo-4,5-dihydro-3H-1-thia-3,5,8-triazaacenaphthylene-2-carboxylic acid The title compound was prepared in a manner analogous to Intermediate 1, Step F, using methyl 5-(4-(3-((2-cyanophenoxy)methyl)phenoxy)-2-methylphenyl)-4-oxo-4,5-di-hydro-3H-1-thia-3,5,8-triazaacenaphthylene-2-carboxylate (Intermediate 43).

Step B: tert-butyl (5-(4-(3-((2-cyanophenoxy) methyl)phenoxy)-2-methylphenyl)-4-oxo-4,5-di-hydro-3H-1-thia-3,5,8-triazaacenaphthylen-2-yl) carbamate To the suspension of 5-(4-(3-((2-cyanophenoxy)methyl) phenoxy)-2-methylphenyl)-4-oxo-4,5-dihydro-3H-1-thia-3, 5,8-triazaacenaphthylene-2-carboxylic acid (1.7 g, 3.1 mmol) in 60 ml of $CH_2Cl_2$ was added oxalyl chloride and one drop of DMF, then was stirred at room temperature for 3 hours. then concentrated, acetone was added and cooled to 0° C. under ice bath, a solution of $NaN_3$ in water was added and stirred for 30 minutes, diluted in EtOAc, washed with water, brine, dried and concentrated. The residue was diluted in toluene and reflux for one hour, then n-BuOH was added and reflux for two hours, then concentrated, and purified by flash chromatography with DCM/MeOH to get a yellow solid. (950 mg, 49% yield).

Step C: 2-((3-(4-(2-amino-4-oxo-3,4-dihydro-5H-1-thia-3,5,8-triazaacenaphthylen-5-yl)-3-methylphe-noxy)benzyl)oxy)benzonitrile To a solution of tert-butyl (5-(4-(3-((2-cyanophenoxy) methyl)phenoxy)-2-methylphenyl)-4-oxo-4,5-dihydro-3H-1-thia-3,5,8-triazaacenaphthylen-2-yl)carbamate (750 mg, 1.21 mmol) in 2,2,2-trifluoroethanol (50 mL) was heated in microwave at 120° C. for one hour, then concentrated and purified by purified by flash chromatography with DCM/MeOH to get a yellow solid. (450 mg, 72% yield).

Step D: N-(5-(4-(3-((2-cyanophenoxy)methyl)phe-noxy)-2-methylphenyl)-4-oxo-4,5-dihydro-3H-1-thia-3,5,8-triazaacenaphthylen-2-yl)cyclopropan-ecarboxamide To a solution of 2-((3-(4-(2-amino-4-oxo-3,4-dihydro-5H-1-thia-3,5,8-triazaacenaphthylen-5-yl)-3-methylphe-noxy)benzyl)oxy)benzonitrile (35.0 mg, 0.0673 mmol) and 4-methylmorpholine (6.8 mg, 0.0673 mmol) in $CH_2Cl_2$ (20 mL) was added cyclopropanecarbonyl chloride (7.0 mg, 0.0673 mmol). The reaction was stirred at room temperature for 30 minutes, then concentrated and purified by flash column chromatography (MeOH/water) to afford the title compound (15 mg, 38% yield). MS (ESI): mass calcd. for $C_{33}H_{25}N_5O_4S$, 587.6; m/z found, 588.1 [M+H]$^+$. $^1$H NMR (400 MHz, DMSO-d$_6$): δ 10.45 (s, 1H), 10.12 (s, 1H), 8.08 (d, J=5.4 Hz, 1H), 7.73-7.68 (m, 1H), 7.67-7.60 (m, 1H), 7.50-7.40 (m, 1H), 7.36-7.24 (m, 3H), 7.23-7.17 (m, 1H), 7.11-7.02 (m, 3H), 6.98-6.92 (m, 1H), 5.80 (d, J=5.4 Hz, 1H), 5.30 (s, 2H), 2.04 (s, 3H), 1.73-1.65 (m, 1H), 0.87-0.81 (m, 4H).

Example 462: N-Cyclohexyl-5-(2-methyl-4-phe-noxyphenyl)-4-oxo-4,5-dihydro-3H-1-thia-3,5,8-triazaacenaphthylene-2-carboxamide

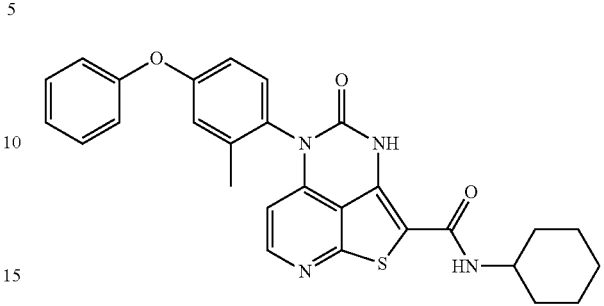

The title compound was prepared in a manner analogous to Example 1, Step A, using 5-(2-methyl-4-phenoxyphenyl)-4-oxo-4,5-dihydro-3H-1-thia-3,5,8-triazaacenaphthylene-2-carboxylic acid (Intermediate 1) and cyclohexanamine, no HCl/MeOH deprotection. MS (ESI): mass calcd. for $C_{28}H_{26}N_4O_3S$, 498.6; m/z found, 499.2 [M+H]$^+$. $^1$H NMR (400 MHz, DMSO-d$_6$): δ 10.14 (s, 1H), 8.36-8.32 (m, 1H), 7.95-7.89 (m, 1H), 7.49-7.41 (m, 2H), 7.41-7.36 (m, 1H), 7.24-7.17 (m, 1H), 7.17-7.08 (m, 3H), 7.02-6.97 (m, 1H), 6.00-5.96 (m, 1H), 3.80-3.76 (m, 1H), 2.07 (s, 3H), 1.86-1.78 (m, 2H), 1.78-1.70 (m, 2H), 1.66-1.57 (m, 1H), 1.42-1.21 (m, 4H), 1.14-1.03 (m, 1H).

Example 463: N-Cyclohexyl-4-oxo-5-(4-phenoxy-phenyl)-4,5-dihydro-3H-1-thia-3,5,8-triazaacenaph-thylene-2-carboxamide

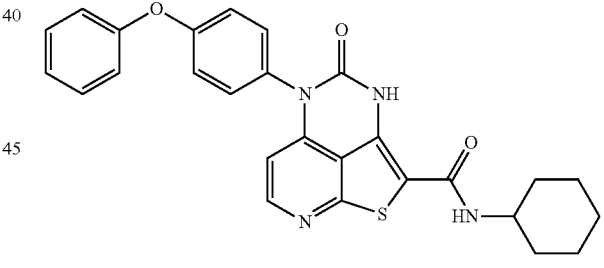

To the suspension of 4-oxo-5-(4-phenoxyphenyl)-4,5-di-hydro-3H-1-thia-3,5,8-triazaacenaphthylene-2-carboxylic acid (Intermediate 2, 109 mg, 0.27 mmol) in 10 mL of $CH_2Cl_2$ was added oxalyl chloride (70 mg, 0.54 mmol) and one drop of DMF, then was stirred at 40° C. for 2 hours. After concentration under vacuo to dryness, the residue was dissolved in 10 mL of $CH_2Cl_2$ and was added a solution of cyclohexanamine (55 mg, 0.54 mmol) in 5 mL of $CH_2Cl2$, stirred at room temperature for 5 minutes. The mixture was concentrated and purified by ISCO using MeOH/$H_2O$ as eluent to get the title compound as yellow solid. (46 mg, 35% yield). MS (ESI): mass calcd. for $C_{27}H_{24}N_4O_3S$, 484.6; m/z found, 485.2 [M+H]$^+$. $^1$H NMR (400 MHz, DMSO-d$_6$): δ 8.29 (d, J=5.1 Hz, 1H), 7.94-7.92 (m, 1H), 7.42-7.40 (m, 4H), 7.30-7.04 (m, 5H), 6.04 (d, J=5.2 Hz, 1H), 3.78-3.68 (m, 1H), 1.85-1.52 (m, 5H), 1.34-1.08 (m, 5H).

Example 464: N1-((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3 aS,4S,6aR)-2-oxohexahydro-1H-thieno[3,4-d]imidazol-4-yl)-4,7,10-trioxa-14-azanonadecyl) glutaramide

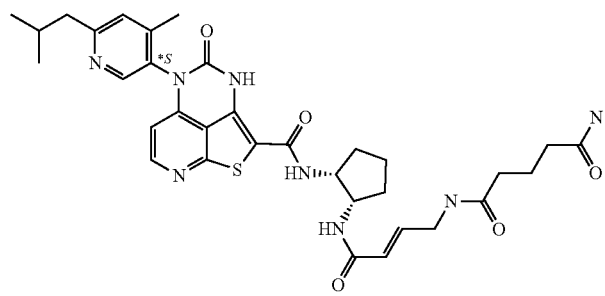
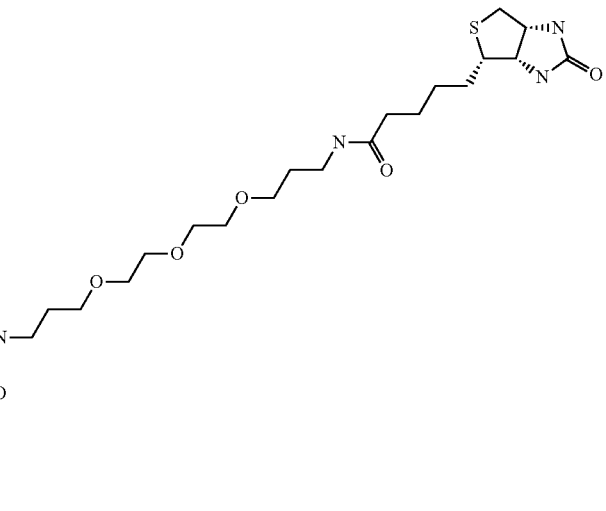

Step A: tert-Butyl ((E)-4-(((1S,2R)-2-(5-(*S)-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl) carbamate The mixture of (E)-4-((tert-butoxycarbonyl)amino)but-2-enoic acid (Intermediate 23, 333.5 mg, 1.657 mmol), N-((1R,2S)-2-aminocyclopentyl)-5-(6-isobutyl-4-methylpyridin-3-yl)-4-oxo-4,5-dihydro-3H-1-thia-3,5,8-triazaacenaphthylene-2-carboxamide (Example 298, product from Step A, 700.0 mg, 1.507 mmol), HATU (744.6 mg, 1.959 mmol), triethylamine (456.5 mg, 4.52 mmol) in DMF (10.0 mL) was stirred at room temperature for 15 minutes and TLC showed reaction completed. The mixture was purified by column chromatography eluting with water/methanol to get target compound as a light yellow solid (500 mg, 60% yield).

Step B: N1-((E)-4-(((1S,2R)-2-(5-(*S)-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl) glutaramide Tert-butyl ((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)carbamate (500 mg, 0.772 mmol) was dissolved in 4 N HCl in methanol (10.0 mL), then stirred at room temperature for one hour, concentrated to give de-Boc product. The mixture of 5,21-dioxo-25-((3aS,4S,6aR)-2-oxohexahydro-1H-thieno[3,4-d]imidazol-4-yl)-10,13,16-trioxa-6,20-diazapentacosanoic acid (432.8 mg, 0.772 mmol), HATU (440.1 mg, 1.158 mmol), triethylamine (312.2 mg, 3.087 mmol) in DMF (5.0 mL) was stirred at room temperature for 5 minutes to give activated-ester solution. De-Boc product was dissolved in DMF (5.0 mL), then to it was added activated-ester solution. The mixture was stirred at room temperature for 10 minutes and TLC showed reaction was completed. Then, the mixture was purified by column chromatography eluting with water/methanol to get target compound as a white solid. (350 mg, 41.5% yield). MS (ESI): mass calcd. for $C_{53}H_{75}N_{11}O_{10}S_2$, 1090.4; m/z found, 1090.5 [M+H]$^+$. $^1$H NMR (400 MHz, CD$_3$OD): δ 8.41 (s, 1H), 8.33 (d, J=5.5 Hz, 1H), 7.42 (s, 1H), 6.75-6.66 (m, 1H), 6.12-6.00 (m, 1H), 6.03 (d, J=5.5 Hz, 1H), 4.52-4.37 (m, 3H), 4.32-4.26 (m, 1H), 3.92-3.87 (m, 2H), 3.64-3.59 (m, 4H), 3.59-3.54 (m, 4H), 3.53-3.47 (m, 4H), 3.27-3.15 (m, 5H), 2.94-2.87 (m, 1H), 2.75-2.65 (m, 3H), 2.25-2.16 (m, 9H), 2.15-2.01 (m, 3H), 1.96-1.83 (m, 3H), 1.82-1.67 (m, 8H), 1.66-1.53 (m, 3H), 1.46-1.36 (m, 2H), 1.03-0.96 (m, 6H).

Example 465: N-((1R,2S)-2-Acrylamidocyclopentyl)-5-(4-methyl-6-(pyrimidin-2-yloxy)pyridin-3-yl)-4-oxo-4,5-dihydro-3H-1-thia-3,5,8-triazaacenaphthylene-2-carboxamide

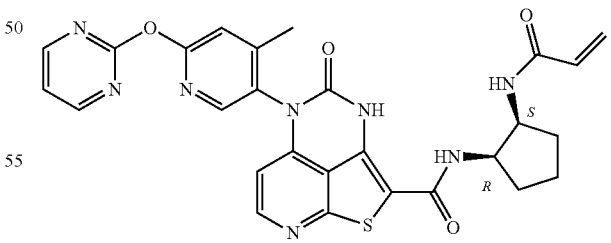

Step A. 5-(4-Methyl-6-(pyrimidin-2-yloxy)pyridin-3-yl)-4-oxo-4,5-dihydro-3H-1-thia-3,5,8-triazaacenaphthylene-2-carboxylic acid The title compound was prepared in a manner analogous to Intermediate 1 Steps A, and C-F, using amino-4-methylpyridin-2-ol and 2-chloropyrimidine Step A.

Step B: N-((1R,2S)-2-Acrylamidocyclopentyl)-5-(4-methyl-6-(pyrimidin-2-yloxy)pyridin-3-yl)-4-oxo-4,5-dihydro-3H-1-thia-3,5,8-triazaacenaphthylene-2-carboxamide The title compound was prepared in a manner analogous to Example 1, Step A, using 5-(4-methyl-6-(pyrimidin-2-yloxy)pyridin-3-yl)-4-oxo-4,5-dihydro-3H-1-thia-3,5,8-triazaacenaphthylene-2-carboxylic acid and N-((1S,2R)-2-aminocyclopentyl)acrylamide (Intermediate 36), no HCl/MeOH deprotection. MS (ESI): mass calcd. for $C_{27}H_{24}H_8O_4S$, 556.6; m/z found, 557.1 [M+H]$^+$. $^1$H NMR (400 MHz, CD$_3$OD): δ 8.73-8.66 (m, 2H), 8.39-8.34 (m, 1H), 8.32-8.28 (m, 1H), 7.42-7.28 (m, 2H), 6.34-6.17 (m, 3H), 5.67-5.58 (m, 1H), 4.50-4.37 (m, 2H), 2.30-2.24 (m, 3H), 2.15-2.02 (m, 2H), 1.97-1.86 (m, 1H), 1.81-1.63 (m, 3H).

Example 466: N-((1R,2S)-2-((E)-2-Cyano-3-cyclopropylacrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide

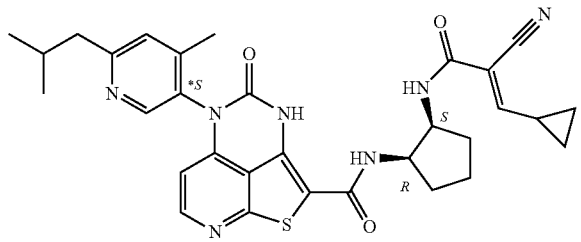

To a solution of (E)-2-cyano-3-cyclopropylacrylic acid (25 mg, 0.18 mmol), HATU (68 mg, 0.18 mmol), and triethylamine (46 mg, 0.45 mmol) in DMF (1 mL) was added a solution of N-((1R,2S)-2-aminocyclopentyl)-5-(*S)-(6-isobutyl-4-methylpyridin-3-yl)-4-oxo-4,5-dihydro-3H-1-thia-3,5,8-triazaacenaphthylene-2-carboxamide (Example 298, product from Step A, 70 mg, 0.15 mmol) in DMF (1 mL) and was stirred at room temperature for 10 minutes. The mixture was purified by flash column chromatography and then by preparative TLC (MeOH/DCM=1/20) to yield the title compound (31 mg, 34% yield) as yellow solid. MS (ESI): mass calcd. for $C_{31}H_{33}N_7O_3S$, 583.70; m/z found, 584.2 [M+H]$^+$. $^1$H NMR (400 MHz, DMSO-d$_6$): δ 10.31-9.98 (br, 1H), 8.45-8.26 (m, 2H), 8.10-7.81 (m, 2H), 7.34 (s, 1H), 6.96-6.86 (m, 1H), 5.96-5.82 (m, 1H), 4.41-4.22 (m, 2H), 2.66-2.61 (m, 2H), 2.15-2.05 (m, 4H), 1.97-1.88 (m, 2H), 1.84-1.72 (m, 3H), 1.71-1.62 (m, 1H), 1.52-1.42 (m, 1H), 1.16-1.07 (m, 2H), 0.92 (d, J=6.6 Hz, 6H), 0.85-0.75 (m, 2H).

Example 467: N-((1R,2S)-2-Acrylamidocyclohexyl)-5-(4-methyl-6-(pyridazin-3-yloxy)pyridin-3-yl)-4-oxo-4,5-dihydro-3H-1-thia-3,5,8-triazaacenaphthylene-2-carboxamide

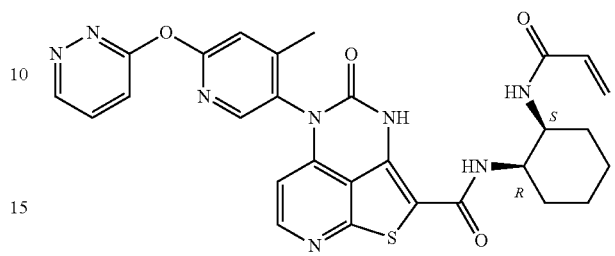

Step A. 5-(4-Methyl-6-(pyridazin-3-yloxy)pyridin-3-yl)-4-oxo-4,5-dihydro-3H-1-thia-3,5,8-triazaacenaphthylene-2-carboxylic acid The title compound was prepared in a manner analogous to Intermediate 25, using 3,6-dichloropyridazine and 5-amino-4-methylpyridin-2-ol in Step A.

Step B: N-((1R,2S)-2-Acrylamidocyclohexyl)-5-(4-methyl-6-(pyridazin-3-yloxy)pyridin-3-yl)-4-oxo-4,5-dihydro-3H-1-thia-3,5,8-triazaacenaphthylene-2-carboxamide The title compound was prepared in a manner analogous to Example 1, Step A, using 5-(4-methyl-6-(pyridazin-3-yloxy)pyridin-3-yl)-4-oxo-4,5-dihydro-3H-1-thia-3,5,8-triazaacenaphthylene-2-carboxylic acid and N-((1S,2R)-2-aminocyclohexyl)acrylamide (Intermediate 40), no HCl/MeOH deprotection. MS (ESI): mass calcd. for $C_{28}H_{26}N_8O_4S$, 570.6; m/z found, 571.2 [M+H]$^+$. $^1$H NMR (400 MHz, CD$_3$OD): δ 9.12-8.95 (m, 1H), 8.33-8.19 (m, 2H), 7.87-7.76 (m, 1H), 7.67-7.56 (m, 1H), 7.35 (s, 1H), 6.47-6.34 (m, 1H), 6.28-6.12 (m, 2H), 5.69-5.57 (m, 1H), 4.46-4.33 (m, 1H), 4.16-4.01 (m, 1H), 2.26 (d, J=7.6 Hz, 3H), 1.85-1.38 (m, 8H).

Example 468: N-((1R,2S)-2-Acrylamidocyclopentyl)-5-(2-methyl-6-(pyrimidin-2-yloxy)pyridin-3-yl)-4-oxo-4,5-dihydro-3H-1-thia-3,5,8-triazaacenaphthylene-2-carboxamide

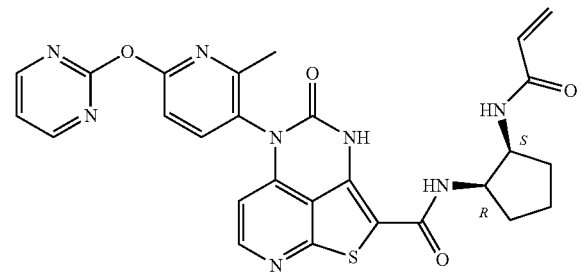

Step A. 5-(2-Methyl-6-(pyrimidin-2-yloxy)pyridin-3-yl)-4-oxo-4,5-dihydro-3H-1-thia-3,5,8-triazaacenaphthylene-2-carboxylic acid The title compound was prepared in a manner analogous to Intermediate 1 Steps A, and C-F, using 5-amino-6-methylpyridin-2-ol and 2-chloropyrimidine in Step A.

Step C: N-((1R,2S)-2-Acrylamidocyclopentyl)-5-(2-methyl-6-(pyrimidin-2-yloxy)pyridin-3-yl)-4-oxo-4,5-dihydro-3H-1-thia-3,5,8-triazaacenaphthylene-2-carboxamide The title compound was prepared in a manner analogous to Example 1, Step A, using 5-(2-methyl-6-(pyrimidin-2-yloxy)pyridin-3-yl)-4-oxo-4,5-dihydro-3H-1-thia-3,5,8-triazaacenaphthylene-2-carboxylic acid and N-((1S,2R)-2-aminocyclopentyl)acrylamide (Intermediate 36), no HCl/MeOH deprotection. MS (ESI): mass calcd. for $C_{27}H_{24}N_8O_4S$, 556.6; m/z found, 557.0 [M+H]$^+$. $^1$H NMR (400 MHz, CD$_3$OD): δ 8.72-8.67 (m, 2H), 8.36-8.32 (m, 1H), 8.02-7.92 (m, 1H), 7.37-7.32 (m, 1H), 7.31-7.25 (m, 1H), 6.33-6.16 (m, 3H), 5.66-5.60 (m, 1H), 4.48-4.35 (m, 2H), 2.34-2.27 (m, 3H), 2.18-2.02 (m, 2H), 1.97-1.86 (m, 1H), 1.84-1.63 (m, 3H).

Example 469: N-((1R,2S)-2-Acrylamidocyclopentyl)-5-(*S)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide

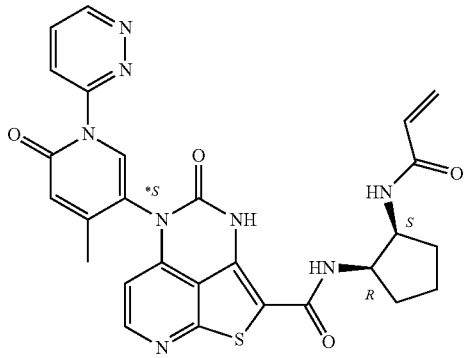

Step A. N-((1S,2R)-2-aminocyclopentyl)acrylamide

A solution of tert-butyl ((1R,2S)-2-acrylamidocyclopentyl)carbamate (363 mg, 1.42 mmol) in 4.0 N HCl/MeOH was stirred at room temperature for 1 hr. The reaction mixture was concentrated under reduced pressure and used crude in Step C without further purification.

Step B. 5-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxylic acid The title compound was prepared in a manner analogous to Intermediate 25, using 3,6-dichloropyridazine and 5-amino-4-methylpyridin-2-ol in Step A.

Step C. N-((1R,2S)-2-Acrylamidocyclopentyl)-5-(*S)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide The title compound was prepared in a manner analogous to Example 1, Step A, using 5-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxylic acid and N-((1S,2R)-2-aminocyclopentyl)acrylamide (Step A), no HCl/MeOH deprotection, purification using flash column chromatography afforded the title compound as the *S atropisomer. MS (ESI): mass calcd. for $C_{27}H_{24}N_8O_4S$, 556.6; m/z found, 557.2 [M+H]$^+$. $^1$H NMR (400 MHz, CD$_3$OD): δ 9.25 (d, J=4.6 Hz, 1H), 8.44-8.39 (m, 1H), 8.31 (s, 1H), 8.25 (d, J=9.0 Hz, 1H), 7.95-7.83 (m, 1H), 6.72 (s, 1H), 6.61-6.55 (m, 1H), 6.34-6.09 (m, 2H), 5.61 (d, J=9.7 Hz, 1H), 4.50-4.35 (m, 2H), 2.14 (s, 3H), 2.11-2.00 (m, 2H), 1.98-1.84 (m, 1H), 1.81-1.59 (m, 3H).

Example 470: N-((1R,2S)-2-Acrylamidocyclopentyl)-5-(*R)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide

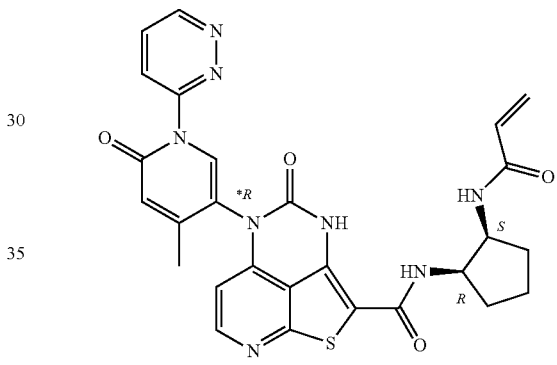

Flash column chromatography of Example 469, Step B afforded the *R atropisomer. MS (ESI): mass calcd. for $C_{27}H_{24}N_8O_4S$, 556.6; m/z found, 557.2 [M+H]$^+$. $^1$H NMR (400 MHz, CD$_3$OD): δ 9.24 (d, J=4.6 Hz, 1H), 8.40 (d, J=5.5 Hz, 1H), 8.36 (s, 1H), 8.25 (d, J=8.8 Hz, 1H), 7.93-7.86 (m, 1H), 6.71 (s, 1H), 6.56 (d, J=5.5 Hz, 1H), 6.32-6.12 (m, 2H), 5.61 (d, J=9.7 Hz, 1H), 4.48-4.29 (m, 2H), 2.13 (s, 3H), 2.11-2.00 (m, 2H), 1.98-1.83 (m, 1H), 1.81-1.58 (m, 3H).

Example 471: N-((1R,2S)-2-Acrylamidocyclopentyl)-5-(4-methyl-6-(pyridazin-3-yloxy)pyridin-3-yl)-4-oxo-4,5-dihydro-3H-1-thia-3,5,8-triazaacenaphthylene-2-carboxamide

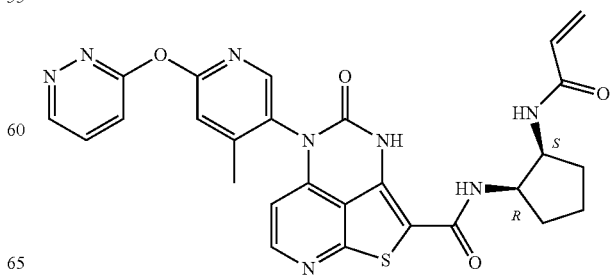

Step A. N-((1S,2R)-2-Aminocyclopentyl)acrylamide

A solution of tert-butyl ((1R,2S)-2-acrylamidocyclohexyl)carbamate (800 mg, 1.90 mmol) in 4 M HCl in MeOH (2 mL) was stirred at room temperature for 60 minutes. The reaction was concentrated to dryness to give N-((1S,2R)-2-aminocyclopentyl)acrylamide, which was used without further purification.

Step B: 5-(4-Methyl-6-(pyridazin-3-yloxy)pyridin-3-yl)-4-oxo-4,5-dihydro-3H-1-thia-3,5,8-triazaacenaphthylene-2-carboxylic acid The title compound was prepared in a manner analogous to Intermediate 25, Step A and C, using 3,6-dichloropyridazine and 5-amino-4-methylpyridin-2-ol in Step A. MS (ESI): mass calcd. for $C_{19}H_{12}N_6O_4S$, 420.40; m/z found, 421.0 [M+H]+.

Step C: N-((1R,2S)-2-Acrylamidocyclopentyl)-5-(4-methyl-6-(pyridazin-3-yloxy)pyridin-3-yl)-4-oxo-4,5-dihydro-3H-1-thia-3,5,8-triazaacenaphthylene-2-carboxamide A solution of 5-(4-methyl-6-(pyridazin-3-yloxy)pyridin-3-yl)-4-oxo-4,5-dihydro-3H-1-thia-3,5,8-triazaacenaphthylene-2-carboxylic acid (800 mg, 1.90 mmol), triethylamine (384 mg, 3.80 mmol), and HATU (940 mg, 2.47 mmol) in DMF was stirred at room temperature for 15 minutes to give activated-ester solution. N-((1S,2R)-2-aminocyclopentyl)acrylamide from Step A, was dissolved in DMF and triethylamine (384 mg, 3.80 mmol) and was added to the activated-ester solution. The reaction was stirred at room temperature for 10 minutes. The reaction was purified by flash column chromatography to give the title compound (441 mg, 41.5% yield) as a light yellow solid. MS (ESI): mass calcd. for $C_{27}H_{24}H_8O_4S$, 556.6; m/z found, 557.2 [M+H]+. 1H NMR (400 MHz, CD3OD): δ 9.07 (d, J=4.6 Hz, 1H), 8.35 (d, J=5.6 Hz, 1H), 8.21 (d, J=4.0 Hz, 1H), 7.88-7.80 (m, 1H), 7.65 (d, J=8.9 Hz, 1H), 7.39 (s, 1H), 6.35-6.14 (m, 3H), 5.62 (d, J=9.6 Hz, 1H), 4.52-4.31 (m, 2H), 2.29 (s, 3H), 2.17-2.00 (m, 2H), 1.97-1.82 (m, 1H), 1.83-1.60 (m, 3H).

Example 472: N-((1R,2S)-2-Acrylamidocyclohexyl)-5-(2-methyl-6-(pyridazin-3-yloxy)pyridin-3-yl)-4-oxo-4,5-dihydro-3H-1-thia-3,5,8-triazaacenaphthylene-2-carboxamide

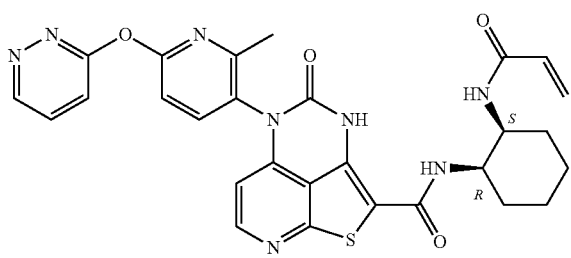

Step A. 5-(2-Methyl-6-(pyridazin-3-yloxy)pyridin-3-yl)-4-oxo-4,5-dihydro-3H-1-thia-3,5,8-triazaacenaphthylene-2-carboxylic acid The title compound was prepared in a manner analogous to Intermediate 25, using 5-amino-6-methylpyridin-2-ol and 3,6-dichloropyridazine in Step A.

Step B: N-((1R,2S)-2-Acrylamidocyclohexyl)-5-(2-methyl-6-(pyridazin-3-yloxy)pyridin-3-yl)-4-oxo-4,5-dihydro-3H-1-thia-3,5,8-triazaacenaphthylene-2-carboxamide The title compound was prepared in a manner analogous to Example 1, Step A, using 5-(2-methyl-6-(pyridazin-3-yloxy)pyridin-3-yl)-4-oxo-4,5-dihydro-3H-1-thia-3,5,8-triazaacenaphthylene-2-carboxylic acid and N-((1S,2R)-2-aminocyclohexyl)acrylamide (Intermediate 40), no HCl/MeOH deprotection. MS (ESI): mass calcd. for $C_{28}H_{26}N_8O_4S$, 570.6; m/z found, 571.2 [M+H]+. 1H NMR (400 MHz, CD3OD): δ 9.11-9.04 (m, 1H), 8.38-8.35 (m, 1H), 7.98-7.91 (m, 1H), 7.90-7.82 (m, 1H), 7.70-7.63 (m, 1H), 7.32-7.25 (m, 1H), 6.47-6.38 (m, 1H), 6.32-6.22 (m, 2H), 5.73-5.63 (m, 1H), 4.50-4.40 (m, 1H), 4.20-4.14 (m, 1H), 2.29-2.24 (m, 3H), 1.85-1.59 (m, 8H).

Example 473: N-((1R,2S)-2-Acrylamidocyclopentyl)-5-(2-methyl-6-(pyridazin-3-yloxy)pyridin-3-yl)-4-oxo-4,5-dihydro-3H-1-thia-3,5,8-triazaacenaphthylene-2-carboxamide

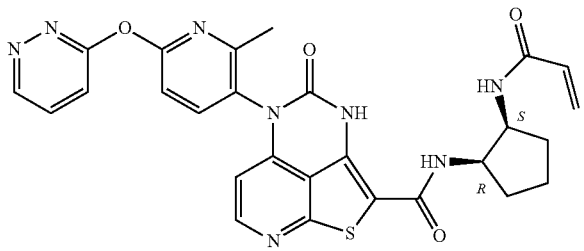

The title compound was prepared in a manner analogous to Example 1, Step A, using 5-(2-methyl-6-(pyridazin-3-yloxy)pyridin-3-yl)-4-oxo-4,5-dihydro-3H-1-thia-3,5,8-triazaacenaphthylene-2-carboxylic acid (Example 472, product from Step A) and N-((1S,2R)-2-aminocyclopentyl)acrylamide (Intermediate 36), no HCl/MeOH deprotection. MS (ESI): mass calcd. for $C_{27}H_{24}H_8O_4S$, 556.6; m/z found, 557.1 [M+H]+. 1H NMR (400 MHz, CD3OD): δ 9.08-9.04 (m, 1H), 8.36-8.32 (m, 1H), 7.97-7.92 (m, 1H), 7.87-7.82 (m, 1H), 7.68-7.63 (m, 1H), 7.31-7.25 (m, 1H), 6.32-6.15 (m, 3H), 5.65-5.56 (m, 1H), 4.53-4.34 (m, 2H), 2.27-2.21 (m, 3H), 2.15-2.02 (m, 2H), 1.97-1.86 (m, 1H), 1.80-1.63 (m, 3H).

Example 474: N-((1R,2S)-2-Acrylamidocyclopentyl)-5-(2-methyl-6-((2-methylpyridin-3-yl)oxy)pyridin-3-yl)-4-oxo-4,5-dihydro-3H-1-thia-3,5,8-triazaacenaphthylene-2-carboxamide

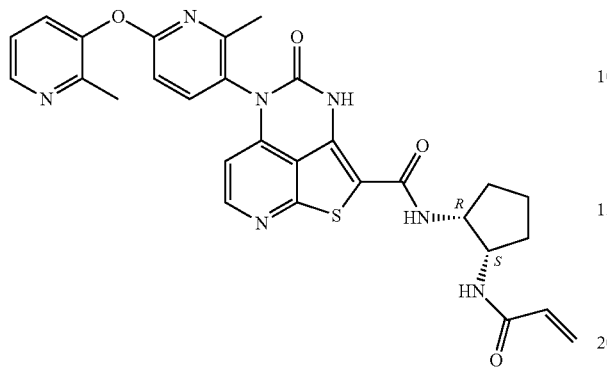

Example 475: N-((1R,2S)-2-Acrylamidocyclohexyl)-4-oxo-5-(5-(pyridazin-3-yloxy)pyridin-2-yl)-4,5-dihydro-3H-1-thia-3,5,8-triazaacenaphthylene-2-carboxamide

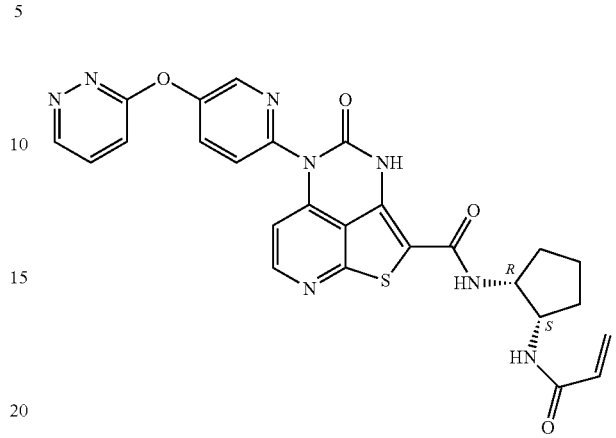

Step A. N-((1S,2R)-2-aminocyclopentyl)acrylamide

To a solution of tert-butyl ((1R,2S)-2-acrylamidocyclohexyl)carbamate (500 mg, 1.97 mmol) in DCM (3 mL) was added methanesulfonic acid (0.387 mL) and was stirred at room temperature for 2 h. The reaction was concentrated to dryness to give N-((1S,2R)-2-aminocyclopentyl)acrylamide, which was used without further purification.

Step B: 5-(2-Methyl-6-((2-methylpyridin-3-yl)oxy)pyridin-3-yl)-4-oxo-4,5-dihydro-3H-1-thia-3,5,8-triazaacenaphthylene-2-carboxylic acid The title compound was prepared in a manner analogous to Intermediate 15, using 6-chloro-2-methyl-3-nitropyridine and 2-methylpyridin-3-ol in Step A, no Cu. MS (ESI): mass calcd. for $C_{21}H_{15}N_5O_4S$, 433.44; m/z found, 434.0 [M+H]$^+$.

Step C: N-((1R,2S)-2-Acrylamidocyclopentyl)-5-(2-methyl-6-((2-methylpyridin-3-yl)oxy)pyridin-3-yl)-4-oxo-4,5-dihydro-3H-1-thia-3,5,8-triazaacenaphthylene-2-carboxamide A solution of 5-(2-methyl-6-((2-methylpyridin-3-yl)oxy)pyridin-3-yl)-4-oxo-4,5-dihydro-3H-1-thia-3,5,8-triazaacenaphthylene-2-carboxylic acid (736 mg, 1.34 mmol), triethylamine (0.474 mL, 3.40 mmol), and HATU (742 mg, 1.95 mmol) in DMF (3 mL) was stirred at room temperature for 15 minutes to give activated-ester solution. N-((1S,2R)-2-aminocyclopentyl)acrylamide (From Step A), was dissolved in DMF (3 mL) and triethylamine (0.474 mL, 3.40 mmol) and was added to the activated-ester solution. The reaction was stirred at room temperature for 2 h. The reaction was purified by flash column chromatography to give the title compound (580 mg, 99.1% yield) as a grey solid. MS (ESI): mass calcd. for $C_{29}H_{27}N_7O_4S$, 569.6; m/z found, 570.1 [M+H]$^+$. $^1$H NMR (400 MHz, CD$_3$OD): δ 8.40-8.25 (m, 2H), 7.99-7.77 (m, 1H), 7.70-7.51 (m, 1H), 7.44-7.22 (m, 1H), 7.17-6.99 (m, 1H), 6.36-6.15 (m, 2H), 6.15-6.04 (m, 1H), 5.69-5.54 (m, 1H), 4.50-4.29 (m, 2H), 2.43 (s, 3H), 2.25-2.12 (m, 3H), 2.11-1.99 (m, 2H), 1.98-1.85 (m, 1H), 1.80-1.58 (m, 3H).

Step A. 4-Oxo-5-(5-(pyridazin-3-yloxy)pyridin-2-yl)-4,5-dihydro-3H-1-thia-3,5,8-triazaacenaphthylene-2-carboxylic acid The title compound was prepared in a manner analogous to Intermediate 1, Steps A, and C-F, using 6-aminopyridin-3-ol and 3,6-dichloropyridazine in place of phenol and 5-fluoro-2-nitrotoluene in step A.

Step B: N-((1R,2S)-2-Acrylamidocyclohexyl)-4-oxo-5-(5-(pyridazin-3-yloxy)pyridin-2-yl)-4,5-dihydro-3H-1-thia-3,5,8-triazaacenaphthylene-2-carboxamide The title compound was prepared in a manner analogous to Example 1, Step A, using 4-oxo-5-(5-(pyridazin-3-yloxy)pyridin-2-yl)-4,5-dihydro-3H-1-thia-3,5,8-triazaacenaphthylene-2-carboxylic acid and N-((1S,2R)-2-aminocyclohexyl)acrylamide (Intermediate 40), no HCl/MeOH deprotection. MS (ESI): mass calcd. for $C_{27}H_{24}H_8O_4S$, 556.6; m/z found, 557.2 [M+H]$^+$. $^1$H NMR (400 MHz, DMSO-d$_6$): δ 10.10 (s, 1H), 9.09-9.05 (m, 1H), 8.64 (s, 1H), 8.36-8.30 (m, 1H), 8.10-8.02 (m, 1H), 7.90-7.80 (m, 3H), 7.76-7.69 (m, 1H), 7.68-7.62 (m, 1H), 6.46-6.34 (m, 1H), 6.21-6.08 (m, 2H), 5.64-5.54 (m, 1H), 4.25-4.18 (m, 1H), 4.07-3.96 (m, 1H), 1.78-1.60 (m, 4H), 1.60-1.48 (m, 2H), 1.46-1.29 (m, 2H).

Example 476: N-((1R,2S)-2-Acrylamidocyclopentyl)-4-oxo-5-(5-(pyridazin-3-yloxy)pyridin-2-yl)-4,5-dihydro-3H-1-thia-3,5,8-triazaacenaphthylene-2-carboxamide

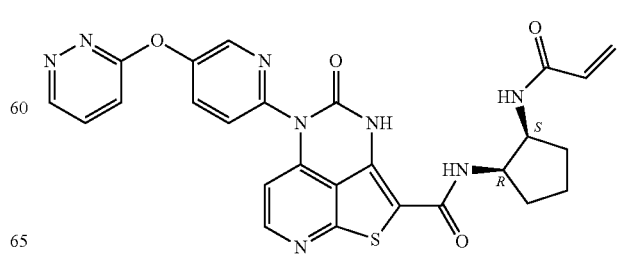

The title compound was prepared in a manner analogous to Example 1, Step A, using 4-oxo-5-(5-(pyridazin-3-yloxy)pyridin-2-yl)-4,5-dihydro-3H-1-thia-3,5,8-triazaacenaphthylene-2-carboxylic acid and N-((1S,2R)-2-aminocyclopentyl)acrylamide (Intermediate 36), (no HCl/MeOH deprotection). MS (ESI): mass calcd. for $C_{26}H_{22}N_8O_4S$, 542.6; m/z found, 543.2 [M+H]$^+$. $^1$H NMR (400 MHz, CD$_3$OD): δ 9.03-8.98 (m, 1H), 8.68-8.61 (m, 1H), 8.37-8.30 (m, 1H), 8.07-8.00 (m, 1H), 7.86-7.79 (m, 1H), 7.75-7.68 (m, 1H), 7.64-7.57 (m, 1H), 6.40-6.33 (m, 1H), 6.32-6.19 (m, 2H), 5.67-5.59 (m, 1H), 4.46-4.40 (m, 2H), 2.15-2.03 (m, 2H), 1.98-1.85 (m, 1H), 1.82-1.65 (m, 3H).

Example 477: N-((1R,2S)-2-Acrylamidocyclopentyl)-5-(6'-methyl-2-oxo-2H-[1,2'-bipyridin]-5'-yl)-4-oxo-4,5-dihydro-3H-1-thia-3,5,8-triazaacenaphthylene-2-carboxamide

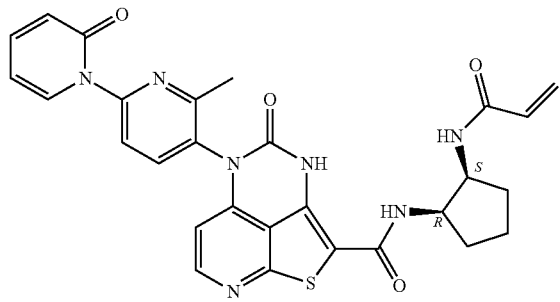

Step A. N-((1S,2R)-2-aminocyclopentyl)acrylamide

A solution of tert-butyl ((1R,2S)-2-acrylamidocyclopentyl)carbamate (582 mg, 2.29 mmol) in 4 M HCl in dioxane was stirred at room temperature for 60 minutes. The reaction was concentrated to dryness to give N-((1S,2R)-2-aminocyclopentyl)acrylamide, which was used without further purification.

Step B. 5-(6'-Methyl-2-oxo-2H-[1,2'-bipyridin]-5'-yl)-4-oxo-4,5-dihydro-3H-1-thia-3,5,8-triazaacenaphthylene-2-carboxylic acid The title compound was prepared in a manner analogous to Intermediate 1, using 6-fluoro-2-methyl-3-nitropyridine and pyridin-2-ol in place of 5-fluoro-2-nitrotoluene and phenol in step A. MS (ESI): mass calcd. for $C_{20}H_{13}N_5O_4S$, 419.41; m/z found, 420.1 [M+H]$^+$.

Step C: N-((1R,2S)-2-Acrylamidocyclopentyl)-5-(6'-methyl-2-oxo-2H-[1,2'-bipyridin]-5'-yl)-4-oxo-4,5-dihydro-3H-1-thia-3,5,8-triazaacenaphthylene-2-carboxamide A solution of 5-(6'-methyl-2-oxo-2H-[1,2'-bipyridin]-5'-yl)-4-oxo-4,5-dihydro-3H-1-thia-3,5,8-triazaacenaphthylene-2-carboxylic acid (686 mg, 1.64 mmol), triethylamine (0.456 mL, 3.26 mmol), and HATU (808 mg, 2.13 mmol) in DMF (4 mL) was stirred at room temperature for 15 minutes to give activated-ester solution. N-((1S,2R)-2-Aminocyclopentyl)acrylamide (From Step A), was dissolved in DMF (4 mL) and triethylamine (0.456 mL, 3.26 mmol) and was added to the activated-ester solution. The reaction was stirred at room temperature for 10 minutes. The reaction was purified by flash column chromatography to give the title compound (370 mg, 98.5% yield) as a white solid. MS (ESI): mass calcd. for $C_{28}H_{25}N_7O_4S$, 555.6; m/z found, 556.2 [M+H]$^+$. $^1$H NMR (400 MHz, CD$_3$OD): δ 8.34 (d, J=5.6 Hz, 1H), 8.07-7.93 (m, 2H), 7.87-7.80 (m, 1H), 7.69-7.59 (m, 1H), 6.66 (d, J=9.2 Hz, 1H), 6.58-6.47 (m, 1H), 6.33-6.16 (m, 3H), 5.62 (d, J=9.7 Hz, 1H), 4.49-4.34 (m, 2H), 2.44 (s, 3H), 2.17-2.00 (m, 2H), 1.99-1.85 (m, 1H), 1.82-1.57 (m, 3H).

Example 478: N-((1R,2S)-2-Acrylamidocyclopentyl)-5-(2-methyl-6-(pyridin-2-yloxy)pyridin-3-yl)-4-oxo-4,5-dihydro-3H-1-thia-3,5,8-triazaacenaphthylene-2-carboxamide

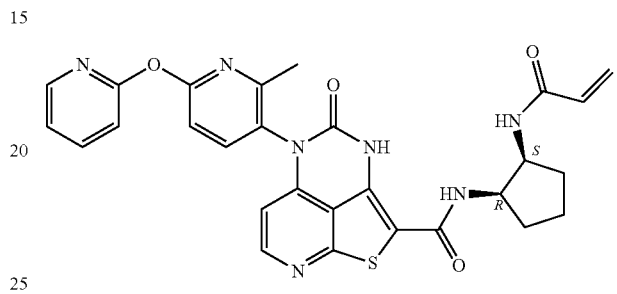

Step A. N-((1S,2R)-2-aminocyclopentyl)acrylamide

A solution of tert-butyl ((1R,2S)-2-acrylamidocyclopentyl)carbamate (497 mg, 1.95 mmol) in 4 M HCl in dioxane was stirred at room temperature for 60 minutes. The reaction was concentrated to dryness to give N-((1S,2R)-2-aminocyclopentyl)acrylamide, which was used without further purification.

Step B: 5-(2-Methyl-6-(pyridin-2-yloxy)pyridin-3-yl)-4-oxo-4,5-dihydro-3H-1-thia-3,5,8-triazaacenaphthylene-2-carboxylic acid The title compound was prepared in a manner analogous to Intermediate 15, using 6-fluoro-2-methyl-3-nitropyridine and pyridin-2-ol Step A, no Cu. MS (ESI): mass calcd. for $C_{20}H_{13}N_5O_4S$, 419.41; m/z found, 420.1 [M+H]$^+$.

Step C: N-((1R,2S)-2-Acrylamidocyclopentyl)-5-(2-methyl-6-(pyridin-2-yloxy)pyridin-3-yl)-4-oxo-4,5-dihydro-3H-1-thia-3,5,8-triazaacenaphthylene-2-carboxamide A solution of 5-(2-methyl-6-(pyridin-2-yloxy)pyridin-3-yl)-4-oxo-4,5-dihydro-3H-1-thia-3,5,8-triazaacenaphthylene-2-carboxylic acid (630 mg, 1.50 mmol), triethylamine (304 mg, 3.00 mmol), and HATU (742 mg, 1.95 mmol) in DMF (2.5 mL) was stirred at room temperature for 15 minutes to give activated-ester solution. N-((1S,2R)-2-aminocyclopentyl)acrylamide (From Step A), was dissolved in DMF (2.5 mL) and triethylamine (304 mg, 3.00 mmol) and was added to the activated-ester solution. The reaction was stirred at room temperature for 10 minutes. The reaction was purified by flash column chromatography to give the title compound (450 mg, 53.9% yield) as a white solid. MS (ESI): mass calcd. for $C_{28}H_{25}N_7O_4S$, 555.6; m/z found, 556.2 [M+H]$^+$. $^1$H NMR (400 MHz, CD$_3$OD): δ 8.35 (d, J=5.5 Hz, 1H), 8.30-8.23 (m, 1H), 7.97-7.91 (m, 1H), 7.90-7.84 (m, 1H), 7.31-7.24 (m, 1H), 7.21 (d, J=8.3 Hz, 1H), 7.14 (d, J=8.5 Hz, 1H), 6.36-6.13 (m, 3H), 5.61 (d, J=9.5 Hz, 1H), 4.48-4.35 (m, 2H), 2.25 (s, 3H), 2.15-1.99 (m, 2H), 1.96-1.85 (m, 1H), 1.82-1.57 (m, 3H).

Example 479: N-((1R,2S)-2-Acrylamidocyclopentyl)-5-(5-((6-methylpyridin-2-yl)oxy)pyridin-2-yl)-4-oxo-4,5-dihydro-3H-1-thia-3,5,8-triazaacenaphthylene-2-carboxamide

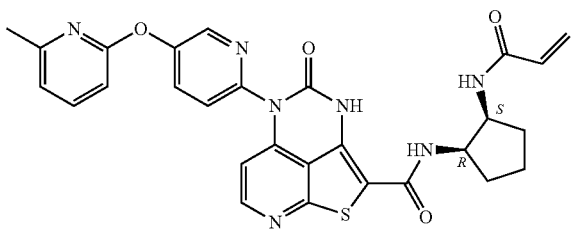

Step A. N-((1S,2R)-2-aminocyclopentyl)acrylamide

To a solution of tert-butyl ((1R,2S)-2-acrylamidocyclopentyl)carbamate (958 mg, 3.78 mmol) in DCM (15 mL) was added methanesulfonic acid (402 mg, 4.19 mmol) and was stirred at room temperature for 1 h. The reaction was concentrated to dryness to give N-((1S,2R)-2-aminocyclopentyl)acrylamide, which was used without further purification.

Step B: 5-(5-((6-Methylpyridin-2-yl)oxy)pyridin-2-yl)-4-oxo-4,5-dihydro-3H-1-thia-3,5,8-triazaacenaphthylene-2-carboxylic acid The title compound was prepared in a manner analogous to Intermediate 1, using Steps A, C-F, and using 2-fluoro-6-methylpyridine and 6-aminopyridin-3-ol in place of 5-fluoro-2-nitrotoluene and phenol in Step A. MS (ESI): mass calcd. for $C_{20}H_{13}N_5O_4S$, 419.41; m/z found, 420.1 $[M+H]^+$.

Step C: N-((1R,2S)-2-Acrylamidocyclopentyl)-5-(5-((6-methylpyridin-2-yl)oxy)pyridin-2-yl)-4-oxo-4,5-dihydro-3H-1-thia-3,5,8-triazaacenaphthylene-2-carboxamide A solution of 5-(5-((6-methylpyridin-2-yl)oxy)pyridin-2-yl)-4-oxo-4,5-dihydro-3H-1-thia-3,5,8-triazaacenaphthylene-2-carboxylic acid (1000 mg, 1.88 mmol), triethylamine (483 mg, 4.78 mmol), and HATU (1.43 g, 3.77 mmol) in DMF (5 mL) was stirred at room temperature for 15 minutes to give activated-ester solution. N-((1S,2R)-2-aminocyclopentyl)acrylamide (From Step A), was dissolved in DMF (5 mL) and triethylamine (483 mg, 4.78 mmol) and was added to the activated-ester solution. The reaction was stirred at room temperature for 30 minutes. The reaction was purified by flash column chromatography to give the title compound (532 mg, 48.4% yield) as a yellow solid. MS (ESI): mass calcd. for $C_{28}H_{25}N_7O_4S$, 555.6; m/z found, 556.1 $[M+H]^+$. $^1$H NMR (400 MHz, DMSO-$d_6$): δ10.10 (s, 1H), 8.58-8.48 (m, 1H), 8.33 (d, J=5.2 Hz, 1H), 8.00-7.73 (m, 4H), 7.69-7.59 (m, 1H), 7.13-7.04 (m, 1H), 7.00-6.92 (m, 1H), 6.30-5.99 (m, 3H), 5.61-5.48 (m, 1H), 4.42-4.17 (m, 2H), 2.35 (s, 3H), 2.03-1.82 (m, 2H), 1.80-1.47 (m, 4H).

Example 480: N-((1R,2S)-2-Acrylamidocyclopentyl)-4-oxo-5-(5-(pyridin-2-yloxy)pyridin-2-yl)-4,5-dihydro-3H-1-thia-3,5,8-triazaacenaphthylene-2-carboxamide

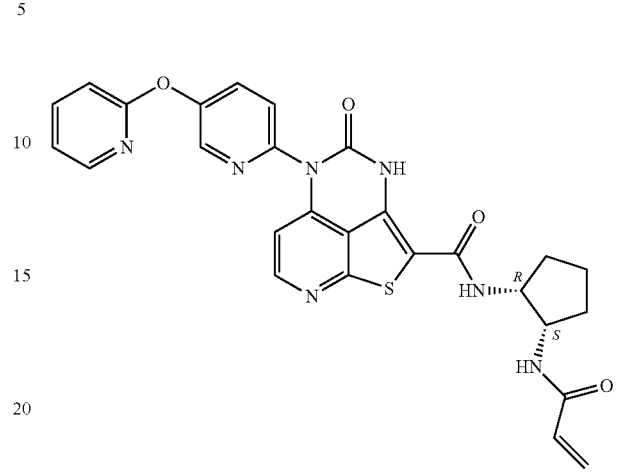

Step A. N-((1S,2R)-2-aminocyclopentyl)acrylamide

To a solution of tert-butyl ((1R,2S)-2-acrylamidocyclopentyl)carbamate (504 mg, 1.98 mmol) in DCM (15 mL) was added methanesulfonic acid (381 mg, 3.97 mmol) and was stirred at room temperature for 2 h. The reaction was concentrated to dryness to give N-((1S,2R)-2-aminocyclopentyl)acrylamide, which was dissolved in DMF (2.5 mL) and used without further purification.

Step B: 4-Oxo-5-(5-(pyridin-2-yloxy)pyridin-2-yl)-4,5-dihydro-3H-1-thia-3,5,8-triazaacenaphthylene-2-carboxylic acid The title compound was prepared in a manner analogous to Intermediate 1, using Steps A, C-F, and using 2-fluoropyridine and 6-aminopyridin-3-ol in place of 5-fluoro-2-nitrotoluene and phenol in Step A. MS (ESI): mass calcd. for $C_{19}H_{11}N_5O_4S$, 405.39; m/z found, 406.0 $[M+H]^+$.

Step C: N-((1R,2S)-2-Acrylamidocyclopentyl)-4-oxo-5-(5-(pyridin-2-yloxy)pyridin-2-yl)-4,5-dihydro-3H-1-thia-3,5,8-triazaacenaphthylene-2-carboxamide To a solution of 4-oxo-5-(5-(pyridin-2-yloxy)pyridin-2-yl)-4,5-dihydro-3H-1-thia-3,5,8-triazaacenaphthylene-2-carboxylic acid (670 mg, 1.65 mmol), triethylamine, and HATU (817 mg, 2.15 mmol) in DMF (2.5 mL) was added N-((1S,2R)-2-aminocyclopentyl)acrylamide (From Step A). The reaction mixture was stirred at room temperature until LCMS showed the reaction had gone to completion. The reaction was poured into water and the precipitate that formed was collected by filtration. The solid was purified by flash column chromatography to give the title compound (190 mg, 21.2% yield) as a grey solid. MS (ESI): mass calcd. for $C_{27}H_{23}N_7O_4S$, 541.6; m/z found, 542.0 $[M+H]^+$. $^1$H NMR (400 MHz, DMSO-$d_6$): δ 10.28 (br, 1H), 8.58-8.48 (m, 1H), 8.35-8.28 (m, 1H), 8.23-8.16 (m, 1H), 7.98-7.84 (m, 3H), 7.82-7.73 (m, 1H), 7.69-7.62 (m, 1H), 7.26-7.14 (m, 2H), 6.29-6.00 (m, 3H), 5.60-5.49 (m, 1H), 4.35-4.19 (m, 2H), 2.01-1.83 (m, 2H), 1.81-1.68 (m, 2H), 1.67-1.48 (m, 2H).

Example 481: N-((1R,2S)-2-Acrylamidocyclopentyl)-5-(5-((6-methylpyridin-3-yl)oxy)pyridin-2-yl)-4-oxo-4,5-dihydro-3H-1-thia-3,5,8-triazaacenaphthylene-2-carboxamide

Example 482: N-((1R,2S)-2-Acrylamidocyclopentyl)-5-(2-methyl-4-(pyrimidin-5-yloxy)phenyl)-4-oxo-4,5-dihydro-3H-1-thia-3,5,8-triazaacenaphthylene-2-carboxamide

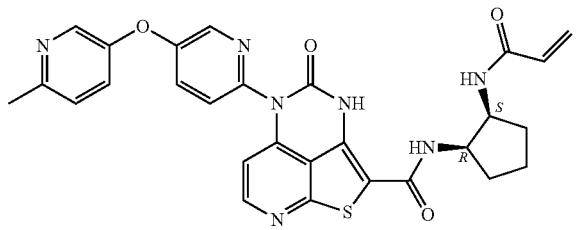

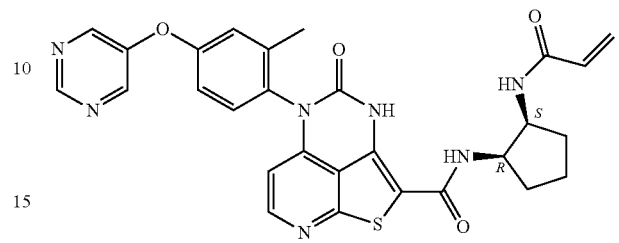

Step A. N-(1S,2R)-2-aminocyclopentyl)acrylamide

To a solution of tert-butyl ((1R,2S)-2-acrylamidocyclopentyl)carbamate (554 mg, 2.19 mmol) in DCM (3 mL) was added methanesulfonic acid (837 mg, 8.71 mmol) and was stirred at room temperature for 1 h. The reaction was concentrated to dryness to give N-((1S,2R)-2-aminocyclopentyl)acrylamide, which was dissolved in DMF (2.0 mL) and used without further purification.

Step B: 5-(5-((6-Methylpyridin-3-yl)oxy)pyridin-2-yl)-4-oxo-4,5-dihydro-3H-1-thia-3,5,8-triazaacenaphthylene-2-carboxylic acid The title compound was prepared in a manner analogous to Intermediate 15, using 5-bromopyrimidine and 6-methylpyridin-3-ol in Step A, no Cu. MS (ESI): mass calcd. for $C_{20}H_{13}N_5O_4S$, 419.41; m/z found, 420.0 [M+H]$^+$.

Step C: N-((1R,2S)-2-Acrylamidocyclopentyl)-5-(5-((6-methylpyridin-3-yl)oxy)pyridin-2-yl)-4-oxo-4,5-dihydro-3H-1-thia-3,5,8-triazaacenaphthylene-2-carboxamide A solution of 5-(5-((6-methylpyridin-3-yl)oxy)pyridin-2-yl)-4-oxo-4,5-dihydro-3H-1-thia-3,5,8-triazaacenaphthylene-2-carboxylic acid (1.096 g, 2.614 mmol), triethylamine (1.168 g, 11.54 mmol), and HATU (1.077 g, 2.83 mmol) in DMF (3.0 mL) was stirred at room temperature for 15 minutes to form the activated ester. To this solution was added N-((1S,2R)-2-aminocyclopentyl)acrylamide (From Step A) in DMF (2.5 mL) and was stirred at room for 30 minutes. The reaction was purified by flash column chromatography (MeOH/H$_2$O) and again by flash column chromatography (DCM/MeOH) to give the title compound (420 mg, 34.1% yield) as a yellow solid. MS (ESI): mass calcd. for $C_{28}H_{25}N_7O_4S$, 555.6; m/z found, 556.1 [M+H]$^+$. $^1$H NMR (400 MHz, CD$_3$OD): δ 8.49-8.38 (m, 1H), 8.38-8.30 (m, 1H), 8.30-8.21 (m, 1H), 7.75-7.64 (m, 1H), 7.64-7.50 (m, 2H), 7.42-7.32 (m, 1H), 6.32-6.12 (m, 3H), 5.69-5.52 (m, 1H), 4.47-4.34 (m, 2H), 2.54 (s, 3H), 2.13-2.00 (m, 2H), 1.95-1.85 (m, 1H), 1.81-1.62 (m, 3H).

Step A: N-((1S,2R)-2-aminocyclopentyl)acrylamide

To a solution of tert-butyl ((1R,2S)-2-acrylamidocyclopentyl)carbamate (479 mg, 1.88 mmol) in DCM (15 mL) was added methanesulfonic acid (201 mg, 2.09 mmol) and was stirred at room temperature for 1 h. The reaction was concentrated to dryness to give N-((1S,2R)-2-aminocyclopentyl)acrylamide, which was used without further purification.

Step B: 5-(2-Methyl-4-(pyrimidin-5-yloxy)phenyl)-4-oxo-4,5-dihydro-3H-1-thia-3,5,8-triazaacenaphthylene-2-carboxylic acid The title compound was prepared in a manner analogous to Intermediate 1, using Steps A-F, using 4-fluoro-2-methyl-1-nitrobenzene and pyrimidin-5-ol in Step A. MS (ESI): mass calcd. for $C_{20}H_{13}N_5O_4S$, 419.41; m/z found, 420.0 [M+H]$^+$.

Step C: N-((1R,2S)-2-Acrylamidocyclopentyl)-5-(2-methyl-4-(pyrimidin-5-yloxy)phenyl)-4-oxo-4,5-dihydro-3H-1-thia-3,5,8-triazaacenaphthylene-2-carboxamide A solution of 5-(2-methyl-4-(pyrimidin-5-yloxy)phenyl)-4-oxo-4,5-dihydro-3H-1-thia-3,5,8-triazaacenaphthylene-2-carboxylic acid (500 mg, 0.942 mmol), triethylamine (242 mg, 2.39 mmol), and HATU (716 mg, 1.88 mmol) in DMF (3.0 mL) was stirred at room temperature for 15 minutes to form the activated ester. To this solution was added N-((1S,2R)-2-aminocyclopentyl)acrylamide (From Step A), triethylamine (242 mg, 2.39 mmol) in DMF (3.0 mL). The reaction mixture was stirred at room temperature until LCMS showed the reaction had gone to completion. The reaction was purified by flash column chromatography to give the title compound (189 mg, 34.8% yield) as a white solid. MS (ESI): mass calcd. for $C_{28}H_{25}N_7O_4S$, 555.6; m/z found, 556.1 [M+H]$^+$. $^1$H NMR (400 MHz, CD$_3$OD): δ 8.95 (s, 1H), 8.70-8.61 (m, 2H), 8.32 (d, J=4.7 Hz, 1H), 7.51-7.34 (m, 1H), 7.26 (s, 1H), 7.21-7.11 (m, 1H), 6.37-6.16 (m, 2H), 6.13-6.05 (m, 1H), 5.68-5.57 (m, 1H), 4.50-4.35 (m, 2H), 2.17 (s, 3H), 2.13-2.01 (m, 2H), 1.96-1.85 (m, 1H), 1.84-1.60 (m, 3H).

Example 483: N-((1R,2S)-2-Acrylamidocyclopentyl)-5-(4-methyl-6-((6-methylpyridin-2-yl)oxy)pyridin-3-yl)-4-oxo-4,5-dihydro-3H-1-thia-3,5,8-triazaacenaphthylene-2-carboxamide

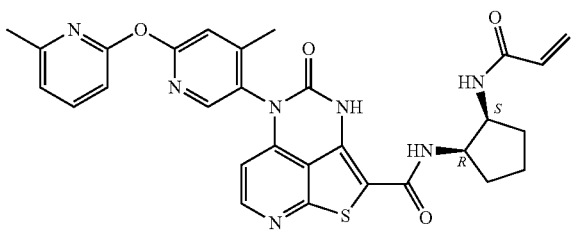

Step A. N-((1S,2R)-2-aminocyclopentyl)acrylamide

To a solution of tert-butyl ((1R,2S)-2-acrylamidocyclopentyl)carbamate (417 mg, 1.64 mmol) in DCM (15 mL) was added methanesulfonic acid (233 mg, 2.43 mmol) and was stirred at room temperature for 1 h. The reaction was concentrated to dryness to give N-((1S,2R)-2-aminocyclopentyl)acrylamide, which was used without further purification.

Step B: 5-(4-Methyl-6-((6-methylpyridin-2-yl)oxy)pyridin-3-yl)-4-oxo-4,5-dihydro-3H-1-thia-3,5,8-triazaacenaphthylene-2-carboxylic acid The title compound was prepared in a manner analogous to Intermediate 15, using 2-fluoro-4-methyl-5-nitropyridine and 6-methylpyridin-2-ol in place of 5-fluoro-2-nitrotoluene and phenol in Step A, and no Cu. MS (ESI): mass calcd. for $C_{21}H_{15}N_5O_4S$, 433.44; m/z found, 434.0 [M+H]$^+$.

Step C: N-((1R,2S)-2-Acrylamidocyclopentyl)-5-(4-methyl-6-((6-methylpyridin-2-yl)oxy)pyridin-3-yl)-4-oxo-4,5-dihydro-3H-1-thia-3,5,8-triazaacenaphthylene-2-carboxamide A solution of 5-(4-methyl-6-((6-methylpyridin-2-yl)oxy)pyridin-3-yl)-4-oxo-4,5-dihydro-3H-1-thia-3,5,8-triazaacenaphthylene-2-carboxylic acid (600 mg, 1.09 mmol), triethylamine (280 mg, 1.22 mmol), and HATU (748 mg, 1.97 mmol) in DMF (3.0 mL) was stirred at room temperature for 15 minutes to form the activated ester. To this solution was added the N-((1S,2R)-2-aminocyclopentyl)acrylamide (from Step A) in DMF (3.0 mL) and triethylamine (280 mg, 1.22 mmol). The reaction mixture was stirred at room temperature for 30 minutes. The reaction was purified by flash column chromatography to give the title compound (525 mg, 82.0% yield) as a yellow solid. MS (ESI): mass calcd. for $C_{29}H_{27}N_7O_4S$, 569.6; m/z found, 570.1 [M+H]$^+$. $^1$H NMR (400 MHz, CD$_3$OD): δ 8.34 (d, J=5.4 Hz, 1H), 8.22-8.12 (m, 1H), 7.88-7.75 (m, 1H), 7.21 (s, 1H), 7.18-7.12 (m, 1H), 7.04-6.95 (m, 1H), 6.3-6.13 (m, 3H), 5.68-5.57 (m, 1H), 4.5-4.37 (m, 2H), 2.48 (s, 3H), 2.30-2.20 (m, 3H), 2.16-2.03 (m, 2H), 1.99-1.87 (m, 1H), 1.83-1.62 (m, 3H).

Example 484: N-((1R,2S)-2-Acrylamidocyclopentyl)-4-oxo-5-(5-(pyrimidin-2-yloxy)pyridin-2-yl)-4,5-dihydro-3H-1-thia-3,5,8-triazaacenaphthylene-2-carboxamide

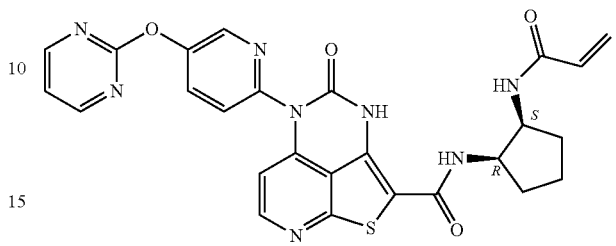

Step A. N-((1S,2R)-2-aminocyclopentyl)acrylamide

A solution of tert-butyl ((1R,2S)-2-acrylamidocyclopentyl)carbamate (407 mg, 1.60 mmol) in 4.0 M HCl in dioxane (50 mL) was stirred at room temperature for 1 h. The reaction was concentrated to dryness to give N-((1S,2R)-2-aminocyclopentyl)acrylamide, which was used without further purification.

Step B: 4-Oxo-5-(5-(pyrimidin-2-yloxy)pyridin-2-yl)-4,5-dihydro-3H-1-thia-3,5,8-triazaacenaphthylene-2-carboxylic acid The title compound was prepared in a manner analogous to Intermediate 1, using Steps A, C-F, and using 2-chloropyrimidine and 6-aminopyridin-3-ol in place of 5-fluoro-2-nitrotoluene and phenol in Step A. MS (ESI): mass calcd. for $C_{18}H_{10}N_6O_4S$, 406.38; m/z found, 407.0 [M+H]$^+$.

Step C: N-((1R,2S)-2-Acrylamidocyclopentyl)-4-oxo-5-(5-(pyrimidin-2-yloxy)pyridin-2-yl)-4,5-dihydro-3H-1-thia-3,5,8-triazaacenaphthylene-2-carboxamide A solution of 4-oxo-5-(5-(pyrimidin-2-yloxy)pyridin-2-yl)-4,5-dihydro-3H-1-thia-3,5,8-triazaacenaphthylene-2-carboxylic acid (500 mg, 1.23 mmol), triethylamine (257 mL, 1.84 mmol), and HATU (608 mg, 1.60 mmol) in DMF (100 mL) was stirred at room temperature for 15 minutes to form the activated ester. To this solution was added the N-((1S,2R)-2-aminocyclopentyl)acrylamide (from Step A) in DMF (50 mL) and triethylamine (257 mL, 1.84 mmol). The reaction mixture was stirred at room temperature for 10 minutes. The reaction was purified by flash column chromatography to give the title compound (365 mg, 54.8% yield) as a white solid. MS (ESI): mass calcd. for $C_{26}H_{22}N_8O_4S$, 542.6; m/z found, 543.1 [M+H]$^+$. $^1$H NMR (400 MHz, DMSO-d$_6$): δ 10.13 (s, 1H), 8.77-8.67 (m, 2H), 8.66-8.58 (m, 1H), 8.38-8.30 (m, 1H), 8.08-7.99 (m, 1H), 7.93-7.84 (m, 1H), 7.81-7.73 (s, 1H), 7.73-7.65 (m, 1H), 7.44-7.28 (m, 1H), 6.29-5.97 (m, 3H), 5.62-5.47 (m, 1H), 4.36-4.17 (m, 2H), 2.01-1.82 (m, 2H), 1.80-1.45 (m, 4H).

Example 485: N-((1R,2S)-2-Acrylamidocyclopentyl)-4-oxo-5-(5-(pyrimidin-5-yloxy)pyridin-2-yl)-4,5-dihydro-3H-1-thia-3,5,8-triazaacenaphthylene-2-carboxamide

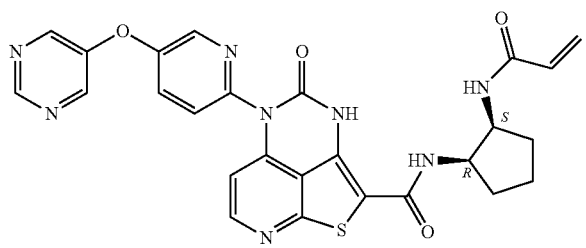

Step A: 4-Oxo-5-(5-(pyrimidin-5-yloxy)pyridin-2-yl)-4,5-dihydro-3H-1-thia-3,5,8-triazaacenaphthylene-2-carboxylic acid The title compound was prepared in a manner analogous to Intermediate 1, using Steps A-F, using 5-chloro-2-nitropyridine and pyrimidin-5-ol in place of 5-fluoro-2-nitrotoluene and phenol in Step A. MS (ESI): mass calcd. for $C_{18}H_{10}N_6O_4S$, 406.38; m/z found, 407.0 [M+H]$^+$.

Step B: N-((1R,2S)-2-Acrylamidocyclopentyl)-4-oxo-5-(5-(pyrimidin-5-yloxy)pyridin-2-yl)-4,5-dihydro-3H-1-thia-3,5,8-triazaacenaphthylene-2-carboxamide A solution of 4-oxo-5-(5-(pyrimidin-5-yloxy)pyridin-2-yl)-4,5-dihydro-3H-1-thia-3,5,8-triazaacenaphthylene-2-carboxylic acid (400 mg, 0.984 mmol), triethylamine (149 mg, 1.48 mmol), and HATU (486 mg, 1.28 mmol) in DMF (4 mL) was stirred at room temperature for 10 minutes to form the activated ester. To this solution was added a solution of N-((1S,2R)-2-aminocyclopentyl)acrylamide (Intermediate 36, 197 mg, 1.28 mmol) in DMF (1 mL) and triethylamine (248 mg, 2.46 mmol) and was stirred at room temperature for 30 minutes. The reaction was purified by reverse phase HPLC to give the title compound (266 mg, 49.8% yield). MS (ESI): mass calcd. for $C_{26}H_{22}N_8O_4S$, 542.6; m/z found, 543.1 [M+H]$^+$. $^1$H NMR (400 MHz, DMSO-d$_6$): δ 10.08 (s, 1H), 9.07 (s, 1H), 8.82 (s, 2H), 8.60-8.55 (m, 1H), 8.35-8.30 (m, 1H), 7.92-7.84 (m, 2H), 7.78-7.70 (m, 1H), 7.68-7.62 (m, 1H), 6.31-6.16 (m, 2H), 6.11-5.99 (m, 1H), 5.59-5.50 (m, 1H), 4.34-4.19 (m, 2H), 2.01-1.83 (m, 2H), 1.82-1.68 (m, 2H), 1.67-1.58 (m, 1H), 1.57-1.46 (m, 1H).

Example 486: N-((1R,2S)-2-Acrylamidocyclopentyl)-5-(4-methyl-6-(pyrimidin-5-yloxy)pyridin-3-yl)-4-oxo-4,5-dihydro-3H-1-thia-3,5,8-triazaacenaphthylene-2-carboxamide

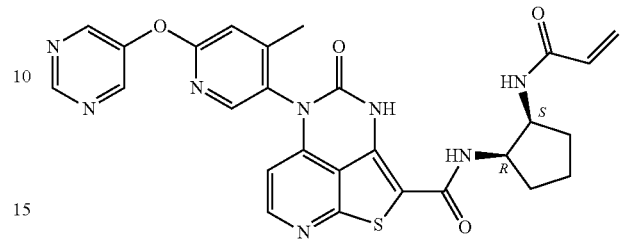

Step A: 5-(4-Methyl-6-(pyrimidin-5-yloxy)pyridin-3-yl)-4-oxo-4,5-dihydro-3H-1-thia-3,5,8-triazaacenaphthylene-2-carboxylic acid The title compound was prepared in a manner analogous to Intermediate 15, using 2-chloro-4-methyl-5-nitropyridine and pyrimidin-5-ol in Step A, no Cu. MS (ESI): mass calcd. for $C_{19}H_{12}N_6O_4S$, 420.40; m/z found, 421.1 [M+H]$^+$.

Step B: N-((1R,2S)-2-Acrylamidocyclopentyl)-5-(4-methyl-6-(pyrimidin-5-yloxy)pyridin-3-yl)-4-oxo-4,5-dihydro-3H-1-thia-3,5,8-triazaacenaphthylene-2-carboxamide A solution of 5-(4-methyl-6-(pyrimidin-5-yloxy)pyridin-3-yl)-4-oxo-4,5-dihydro-3H-1-thia-3,5,8-triazaacenaphthylene-2-carboxylic acid (800 mg, 1.90 mmol), triethylamine (289 mg, 2.85 mmol), and HATU (9.41 mg, 2.47 mmol) in DMF (8 mL) was stirred at room temperature for 10 minutes to form the activated ester. To this solution was added a solution of N-((1S,2R)-2-aminocyclopentyl)acrylamide (Intermediate 36, 382 mg, 2.47 mmol) in DMF (2 mL) and triethylamine (481 mg, 4.76 mmol) and was stirred at room temperature for 30 minutes. The reaction was purified by reverse phase HPLC to give the title compound (551 mg, 52.0% yield). MS (ESI): mass calcd. for $C_{27}H_{24}N_8O_4S$, 556.6; m/z found, 557.2 [M+H]$^+$. $^1$H NMR (400 MHz, DMSO-d$_6$): δ 10.15 (s, 1H), 9.06 (s, 1H), 8.84 (s, 2H), 8.34-8.28 (m, 1H), 8.18-8.12 (m, 1H), 7.90-7.83 (m, 1H), 7.80-7.70 (m, 1H), 7.36 (s, 1H), 6.27-6.15 (m, 1H), 6.13-6.01 (m, 2H), 5.59-5.50 (m, 1H), 4.33-4.20 (m, 2H), 2.17 (s, 3H), 1.98-1.82 (m, 2H), 1.82-1.67 (m, 2H), 1.67-1.56 (m, 1H), 1.56-1.44 (m, 1H).

Example 487: N-((1R,2S)-2-Acrylamidocyclopentyl)-5-(4-methyl-6-((6-methylpyridin-3-yl)oxy)pyridin-3-yl)-4-oxo-4,5-dihydro-3H-1-thia-3,5,8-triazaacenaphthylene-2-carboxamide

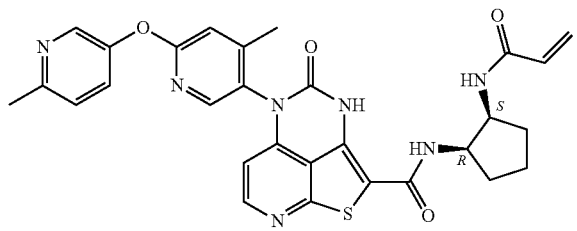

Step A. N-((1S,2R)-2-aminocyclopentyl)acrylamide

To a solution of tert-butyl ((1R,2S)-2-acrylamidocyclopentyl)carbamate (700 mg, 2.75 mmol) in DCM (4 mL) was added methanesulfonic acid (1.058 g, 11.01 mmol) and was stirred at room temperature for 1 h. The reaction was concentrated to dryness to give N-((1S,2R)-2-aminocyclopentyl)acrylamide, which was used without further purification.

Step B: 5-(4-Methyl-6-((6-methylpyridin-3-yl)oxy)pyridin-3-yl)-4-oxo-4,5-dihydro-3H-1-thia-3,5,8-triazaacenaphthylene-2-carboxylic acid The title compound was prepared in a manner analogous to Intermediate 15, using 2-bromo-4-methyl-5-nitropyridine and 6-methylpyridin-3-ol in Step A, no Cu. MS (ESI): mass calcd. for $C_{21}H_{15}N_5O_4S$, 433.44; m/z found, 434.0 [M+H]$^+$.

Step C: N-((1R,2S)-2-Acrylamidocyclopentyl)-5-(4-methyl-6-((6-methylpyridin-3-yl)oxy)pyridin-3-yl)-4-oxo-4,5-dihydro-3H-1-thia-3,5,8-triazaacenaphthylene-2-carboxamide A solution of 4-oxo-5-(5-(pyrimidin-2-yloxy)pyridin-2-yl)-4,5-dihydro-3H-1-thia-3,5,8-triazaacenaphthylene-2-carboxylic acid (1.432 g, 3.303 mmol), triethylamine (1.476 g, 14.59 mmol), and HATU (1.361 g, 3.578 mmol) in DMF (5 mL) was stirred at room temperature for 15 minutes to form the activated ester. To this solution was added N-((1S,2R)-2-aminocyclopentyl)acrylamide (from Step A) in DMF (3 mL). The reaction mixture was stirred at room temperature for 30 minutes. The reaction was purified by flash column chromatography to give the title compound (600 mg, 37.9% yield) as a yellow solid. MS (ESI): mass calcd. for $C_{29}H_{27}N_7O_4S$, 569.6; m/z found, 570.1 [M+H]$^+$. $^1$H NMR (400 MHz, CD$_3$OD): δ 8.37-8.26 (m, 2H), 8.10-8.01 (m, 1H), 7.63-7.56 (m, 1H), 7.39-7.32 (m, 1H), 7.20-7.14 (m, 1H), 6.33-6.09 (m, 3H), 5.65-5.56 (m, 1H), 4.47-4.35 (m, 2H), 2.54 (s, 3H), 2.22 (s, 3H), 2.13-2.01 (m, 2H), 1.95-1.85 (m, 1H), 1.81-1.60 (m, 3H).

Example 488: N-((1R,2S)-2-Acrylamidocyclopentyl)-5-(4-methyl-6-(pyridin-2-yloxy)pyridin-3-yl)-4-oxo-4,5-dihydro-3H-1-thia-3,5,8-triazaacenaphthylene-2-carboxamide

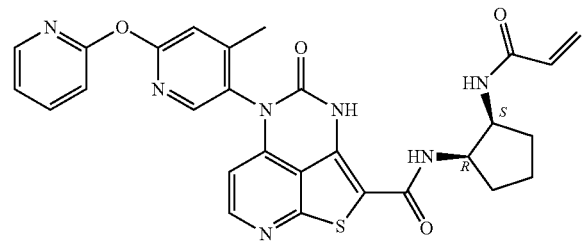

Step A: N-((1S,2R)-2-aminocyclopentyl)acrylamide

To a solution of tert-butyl ((1R,2S)-2-acrylamidocyclopentyl)carbamate (509 mg, 2.00 mmol) in DCM (10 mL) was added methanesulfonic acid (385 mg, 4.01 mmol) and was stirred at room temperature for 2 h. The reaction was concentrated to dryness to give N-((1S,2R)-2-aminocyclopentyl)acrylamide, which was dissolved in DMF (2 mL).

Step B: 5-(4-Methyl-6-(pyridin-2-yloxy)pyridin-3-yl)-4-oxo-4,5-dihydro-3H-1-thia-3,5,8-triazaacenaphthylene-2-carboxylic acid The title compound was prepared in a manner analogous to Intermediate 15, using 2-fluoro-4-methyl-5-nitropyridine and pyridin-2-ol in Step A, no Cu. MS (ESI): mass calcd. for $C_{20}H_{13}N_5O_4S$, 419.41; m/z found, 420.1 [M+H]$^+$.

Step C: N-((1R,2S)-2-Acrylamidocyclopentyl)-5-(4-methyl-6-(pyridin-2-yloxy)pyridin-3-yl)-4-oxo-4,5-dihydro-3H-1-thia-3,5,8-triazaacenaphthylene-2-carboxamide A solution of 5-(4-methyl-6-(pyridin-2-yloxy)pyridin-3-yl)-4-oxo-4,5-dihydro-3H-1-thia-3,5,8-triazaacenaphthylene-2-carboxylic acid (700 mg, 1.67 mmol), triethylamine, and HATU (825 mg, 2.17 mmol) in DMF (3 mL) was stirred at room temperature for 15 minutes to form the activated ester. To this solution was added the N-((1S,2R)-2-aminocyclopentyl)acrylamide (From Step A) and was stirred at room temperature until LCMS showed the reaction had gone to completion. The reaction was poured into H$_2$O and the precipitate that formed was collected by filtration. The residue was purified by flash column chromatography to give the title compound (380 mg, 41% yield) as a yellow solid. MS (ESI): mass calcd. for $C_{28}H_{25}N_7O_4S$, 555.6; m/z found, 556.1 [M+H]$^+$. $^1$H NMR (400 MHz, DMSO-d$_6$): δ10.22 (br, 1H), 8.40-8.19 (m, 3H), 7.95-7.84 (m, 2H), 7.82-7.69 (m, 1H), 7.29-7.23 (m, 2H), 7.22-7.16 (m, 1H), 6.28-6.14 (m, 1H), 6.11-6.02 (m, 2H), 5.60-5.46 (m, 1H), 4.34-4.19 (m, 2H), 2.15 (s, 3H), 1.98-1.83 (m, 2H), 1.82-1.68 (m, 2H), 1.67-1.48 (m, 2H).

Example 489: N-((1R,2S)-2-Acrylamidocyclopentyl)-5-(4-methyl-6-((2-methylpyridin-3-yl)oxy)pyridin-3-yl)-4-oxo-4,5-dihydro-3H-1-thia-3,5,8-triazaacenaphthylene-2-carboxamide

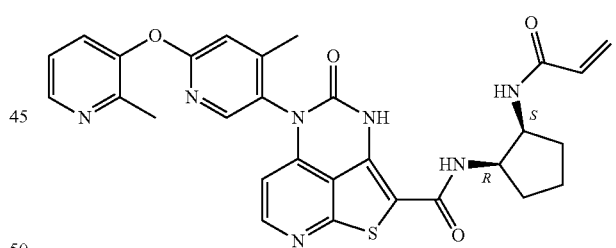

Step A: 5-(4-Methyl-6-((2-methylpyridin-3-yl)oxy)pyridin-3-yl)-4-oxo-4,5-dihydro-3H-1-thia-3,5,8-triazaacenaphthylene-2-carboxylic acid The title compound was prepared in a manner analogous to Intermediate 15, using 2-fluoro-4-methyl-5-nitropyridine and 2-methylpyridin-3-ol in Step A, no Cu. MS (ESI): mass calcd. for $C_{21}H_{15}N_5O_4S$, 433.44; m/z found, 434.0 [M+H]$^+$.

Step B: N-((1R,2S)-2-Acrylamidocyclopentyl)-5-(4-methyl-6-((2-methylpyridin-3-yl)oxy)pyridin-3-yl)-4-oxo-4,5-dihydro-3H-1-thia-3,5,8-triazaacenaphthylene-2-carboxamide To a solution of tert-butyl ((1R,2S)-2-acrylamidocyclopentyl)carbamate (500 mg, 1.97 mmol) in DCM (3 mL) was added methanesulfonic acid (0.387 g, 5.96 mmol) and was stirred at room temperature for 2 h. The reaction was concentrated to dryness to give N-((1S,2R)-2-aminocyclopentyl)acrylamide, which was dissolved in DMF (2 mL) and triethylamine (0.474 mL, 3.40 mmol). A solution of 5-(4-methyl-6-((2-methylpyridin-3-yl)oxy)pyridin-3-yl)-4-oxo-4,5-dihydro-3H-1-thia-3,5,8-triazaacenaphthylene-2-carboxylic acid (736 mg, 1.34 mmol), triethylamine (0.474 mL, 3.40 mmol), and HATU (742 mg, 1.95 mmol) in DMF (4 mL) was stirred at room temperature for 15 minutes to form the activated ester. To this solution was added the N-((1S,2R)-2-aminocyclopentyl)acrylamide solution from above and was stirred at room temperature for 2 h. The reaction was purified by flash column chromatography (MeOH/H$_2$O) and again using flash column chromatography (DCM/MeOH) to give the title compound (636 mg, 99.5% yield) as a white solid. MS (ESI): mass calcd. for C$_{29}$H$_{27}$N$_7$O$_4$S, 569.6; m/z found, 570.2 [M+H]$^+$. $^1$H NMR (400 MHz, CD$_3$OD): δ 8.29 (s, 2H), 8.15-8.04 (m, 1H), 7.59 (d, J=7.9 Hz, 1H), 7.40-7.28 (m, 1H), 7.19 (s, 1H), 6.32-6.14 (m, 2H), 6.13-6.05 (m, 1H), 5.59 (d, J=9.7 Hz, 1H), 4.47-4.28 (m, 2H), 2.41 (s, 3H), 2.26-2.18 (m, 3H), 2.11-1.98 (m, 2H), 1.94-1.82 (m, 1H), 1.76-1.55 (m, 3H).

Example 490: N-((1R,2S)-2-Acrylamidocyclopentyl)-5-(4-methyl-6-(pyridin-3-yloxy)pyridin-3-yl)-4-oxo-4,5-dihydro-3H-1-thia-3,5,8-triazaacenaphthylene-2-carboxamide

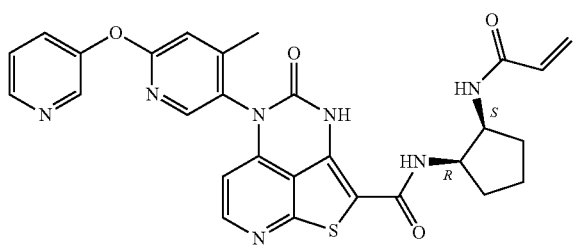

Step A: 5-(4-Methyl-6-(pyridin-3-yloxy)pyridin-3-yl)-4-oxo-4,5-dihydro-3H-1-thia-3,5,8-triazaacenaphthylene-2-carboxylic acid The title compound was prepared in a manner analogous to Intermediate 15, using 2-fluoro-4-methyl-5-nitropyridine and pyridin-3-ol in Step A, no Cu. MS (ESI): mass calcd. for C$_{20}$H$_{13}$N$_5$O$_4$S, 419.41; m/z found, 420.0 [M+H]$^+$.

Step B: N-((1R,2S)-2-Acrylamidocyclopentyl)-5-(4-methyl-6-(pyridin-3-yloxy)pyridin-3-yl)-4-oxo-4,5-dihydro-3H-1-thia-3,5,8-triazaacenaphthylene-2-carboxamide To a solution of tert-butyl ((1R,2S)-2-acrylamidocyclopentyl)carbamate (500 mg, 1.97 mmol) in DCM (3 mL) was added methanesulfonic acid (0.387 g, 5.96 mmol) and was stirred at room temperature for 2 h. The reaction was concentrated to dryness to give N-((1S,2R)-2-aminocyclopentyl)acrylamide, which was dissolved in DMF (2 mL) and triethylamine (0.474 mL, 3.40 mmol). A solution of 5-(4-methyl-6-((2-methylpyridin-3-yl)oxy)pyridin-3-yl)-4-oxo-4,5-dihydro-3H-1-thia-3,5,8-triazaacenaphthylene-2-carboxylic acid (712 mg, 1.34 mmol), triethylamine (0.474 mL, 3.40 mmol), and HATU (742 mg, 1.95 mmol) in DMF (4 mL) was stirred at room temperature for 15 minutes to form the activated ester. To this solution was added the N-((1S,2R)-2-aminocyclopentyl)acrylamide solution from above and was stirred at room temperature for 2 h. The reaction was purified by flash column chromatography (MeOH/H$_2$O) and again using flash column chromatography (DCM/MeOH) to give the title compound (742 mg, 99.6% yield) as a yellow solid. MS (ESI): mass calcd. for C$_{28}$H$_{25}$N$_7$O$_4$S, 555.6; m/z found, 556.1 [M+H]$^+$. $^1$H NMR (400 MHz, CD$_3$OD): δ 8.46 (s, 1H), 8.43-8.35 (m, 1H), 8.32-8.23 (m, 1H), 8.16-8.04 (m, 1H), 7.71 (d, J=8.0 Hz, 1H), 7.56-7.41 (m, 1H), 7.18 (s, 1H), 6.31-6.15 (m, 2H), 6.14-6.06 (m, 1H), 5.58 (d, J=9.6 Hz, 1H), 4.48-4.29 (m, 2H), 2.26-2.16 (m, 3H), 2.11-1.96 (m, 2H), 1.95-1.82 (m, 1H), 1.78-1.58 (m, 3H).

Example 491: N-((1R,2S)-2-Acrylamidocyclopentyl)-4-oxo-5-(5-(pyridin-3-yloxy)pyridin-2-yl)-4,5-dihydro-3H-1-thia-3,5,8-triazaacenaphthylene-2-carboxamide

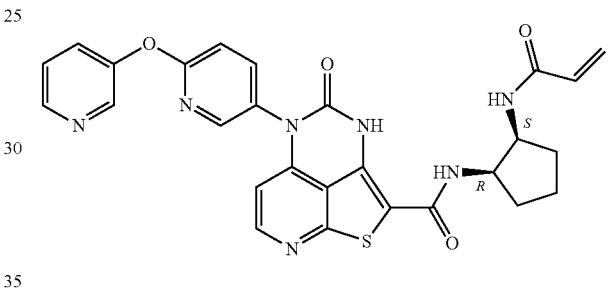

Step A: 4-Oxo-5-(5-(pyridin-3-yloxy)pyridin-2-yl)-4,5-dihydro-3H-1-thia-3,5,8-triazaacenaphthylene-2-carboxylic acid The title compound was prepared in a manner analogous to Intermediate 15, using 5-bromo-2-nitropyridine and pyridin-3-ol in Step A, no Cu. MS (ESI): mass calcd. for C$_{19}$H$_{11}$N$_5$O$_4$S, 405.39; m/z found, 406.0 [M+H]$^+$.

Step B: N-((1R,2S)-2-Acrylamidocyclopentyl)-4-oxo-5-(5-(pyridin-3-yloxy)pyridin-2-yl)-4,5-dihydro-3H-1-thia-3,5,8-triazaacenaphthylene-2-carboxamide To a solution of tert-butyl ((1R,2S)-2-acrylamidocyclopentyl)carbamate (350 mg, 1.38 mmol) in DCM (2 mL) was added methanesulfonic acid (0.271 mL, 4.17 mmol) and was stirred at room temperature for 2 h. The reaction was concentrated to dryness to give N-((1S,2R)-2-aminocyclopentyl)acrylamide, which was dissolved in DMF (2 mL) and triethylamine (0.332 mL, 2.38 mmol). A solution of 4-oxo-5-(5-(pyridin-3-yloxy)pyridin-2-yl)-4,5-dihydro-3H-1-thia-3,5,8-triazaacenaphthylene-2-carboxylic acid (482 mg, 0.939 mmol), triethylamine (0.332 mL, 2.38 mmol), and HATU (520 mg, 1.37 mmol) in DMF (2 mL) was stirred at room temperature for 15 minutes to form the activated ester. To this solution was added the N-((1S,2R)-2-aminocyclopentyl)acrylamide solution from above and was stirred at room temperature for 30 minutes. The reaction was purified by flash column chromatography (MeOH/H$_2$O) and again using flash column chromatography (DCM/MeOH) to give the title compound (210 mg, 40.6% yield) as a yellow solid. MS (ESI): mass calcd. for $C_{27}H_{23}N_7O_4S$, 541.6; m/z found, 542.1 $[M+H]^+$. $^1H$ NMR (400 MHz, DMSO-$d_6$): δ 10.09 (s, 1H), 8.58-8.52 (m, 1H), 8.52-8.40 (m, 2H), 8.37-8.27 (m, 1H), 7.95-7.83 (m, 1H), 7.83-7.71 (m, 2H), 7.69-7.59 (m, 2H), 7.54-7.39 (m, 1H), 6.27-6.13 (m, 2H), 6.13-5.96 (m, 1H), 5.60-5.48 (m, 1H), 4.33-4.20 (m, 2H), 2.00-1.86 (m, 2H), 1.80-1.68 (m, 2H), 1.65-1.46 (m, 2H).

Example 492: N-((1R,2S)-2-Acrylamidocyclopentyl)-5-(2-methyl-6-(pyrimidin-5-yloxy)pyridin-3-yl)-4-oxo-4,5-dihydro-3H-1-thia-3,5,8-triazaacenaphthylene-2-carboxamide

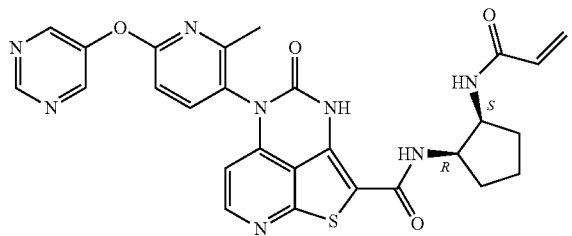

Step A: 5-(2-Methyl-6-(pyrimidin-5-yloxy)pyridin-3-yl)-4-oxo-4,5-dihydro-3H-1-thia-3,5,8-triazaacenaphthylene-2-carboxylic acid The title compound was prepared in a manner analogous to Intermediate 15, using 6-chloro-2-methyl-3-nitropyridine and 2-chloropyrimidin-5-ol in Step A, no Cu. MS (ESI): mass calcd. for $C_{19}H_{12}N_6O_4S$, 420.40; m/z found, 421.0 $[M+H]^+$.

Step B: N-((1R,2S)-2-Acrylamidocyclopentyl)-5-(2-methyl-6-(pyrimidin-5-yloxy)pyridin-3-yl)-4-oxo-4,5-dihydro-3H-1-thia-3,5,8-triazaacenaphthylene-2-carboxamide To a solution of 5-(2-methyl-6-(pyrimidin-5-yloxy)pyridin-3-yl)-4-oxo-4,5-dihydro-3H-1-thia-3,5,8-triazaacenaphthylene-2-carboxylic acid (800 mg, 1.90 mmol), triethylamine (289 mg, 2.85 mmol), and HATU (941 mg, 2.47 mmol) in DMF (8 mL) was stirred at room temperature for 15 minutes to form the activated ester. To this solution was added a solution of N-((1S,2R)-2-aminocyclopentyl)acrylamide (376 mg, 2.44 mmol) and triethylamine (481 mg, 4.76 mmol) in DMF (2 mL) and was stirred at room temperature for 30 minutes. The reaction was purified by flash column chromatography (MeOH/$H_2O$) to give the title compound (560 mg, 52.9% yield). MS (ESI): mass calcd. for $C_{27}H_{24}N_8O_4S$, 556.6; m/z found, 557.1 $[M+H]^+$. $^1H$ NMR (400 MHz, $CD_3OD$): δ 9.01 (s, 1H), 8.80 (s, 2H), 8.34-8.28 (m, 1H), 7.95-7.85 (m, 1H), 7.23-7.16 (m, 1H), 6.31-6.10 (m, 3H), 5.64-5.54 (m, 1H), 4.47-4.32 (m, 2H), 2.23-2.16 (m, 3H), 2.13-2.01 (m, 2H), 1.96-1.84 (m, 1H), 1.80-1.59 (m, 3H).

Example 493: N-((1R,2S)-2-Acrylamidocyclopentyl)-5-(5-((2-methylpyridin-3-yl)oxy)pyridin-2-yl)-4-oxo-4,5-dihydro-3H-1-thia-3,5,8-triazaacenaphthylene-2-carboxamide

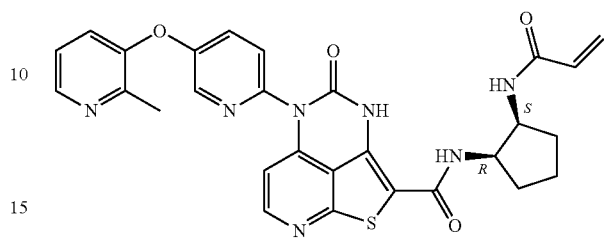

Step A: 5-(5-((2-Methylpyridin-3-yl)oxy)pyridin-2-yl)-4-oxo-4,5-dihydro-3H-1-thia-3,5,8-triazaacenaphthylene-2-carboxylic acid The title compound was prepared in a manner analogous to Intermediate 15, using 5-bromo-2-nitropyridine and 2-methylpyridin-3-ol in Step A, no Cu. MS (ESI): mass calcd. for $C_{20}H_{13}N_5O_4S$, 419.41; m/z found, 420.0 $[M+H]^+$.

Step B: N-((1R,2S)-2-Acrylamidocyclopentyl)-5-(5-((2-methylpyridin-3-yl)oxy)pyridin-2-yl)-4-oxo-4,5-dihydro-3H-1-thia-3,5,8-triazaacenaphthylene-2-carboxamide To a solution of tert-butyl ((1R,2S)-2-acrylamidocyclopentyl)carbamate (300 mg, 1.18 mmol) in DCM (2 mL) was added methanesulfonic acid (0.232 mL, 3.58 mmol) and was stirred at room temperature for 2 h. The reaction was concentrated to dryness to give N-((1S,2R)-2-aminocyclopentyl)acrylamide, which was dissolved in DMF (2 mL) and triethylamine (0.284 mL, 2.04 mmol). A solution of 5-(5-((2-methylpyridin-3-yl)oxy)pyridin-2-yl)-4-oxo-4,5-dihydro-3H-1-thia-3,5,8-triazaacenaphthylene-2-carboxylic acid (428 mg, 0.805 mmol), triethylamine (0.284 mL, 2.04 mmol), and HATU (445 mg, 1.17 mmol) in DMF (2 mL) was stirred at room temperature for 15 minutes to form the activated ester. To this solution was added the N-((1S,2R)-2-aminocyclopentyl)acrylamide solution from above and was stirred at room temperature for 2 h. The reaction was purified by flash column chromatography (MeOH/$H_2O$) and again using flash column chromatography (DCM/MeOH) to give the title compound (400 mg, 87.9% yield) as a white solid. MS (ESI): mass calcd. for $C_{28}H_{25}N_7O_4S$, 555.6; m/z found, 556.1 $[M+H]^+$. $^1H$ NMR (400 MHz, a mixture of DMSO-$d_6$ and $CD_3OD$): δ 8.40-8.33 (m, 1H), 8.33-8.26 (m, 2H), 7.60-7.53 (m, 2H), 7.51-7.46 (m, 1H), 7.32-7.25 (m, 1H), 6.26-6.15 (m, 2H), 6.12-6.06 (m, 1H), 5.56-5.51 (m, 1H), 4.32-4.28 (m, 2H), 2.45 (s, 3H), 2.01-1.88 (m, 2H), 1.84-1.74 (m, 1H), 1.73-1.60 (m, 2H), 1.59-1.48 (m, 1H).

Example 494: N-((1R,2S)-2-Acrylamidocyclopentyl)-5-(2-methyl-6-(pyridin-3-yloxy)pyridin-3-yl)-4-oxo-4,5-dihydro-3H-1-thia-3,5,8-triazaacenaphthylene-2-carboxamide

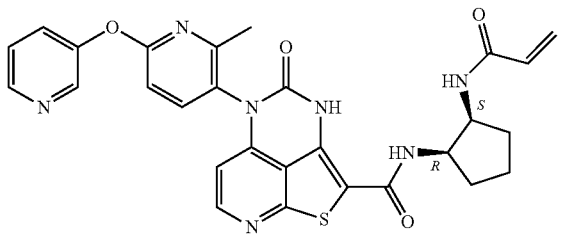

Step A: 5-(2-Methyl-6-(pyridin-3-yloxy)pyridin-3-yl)-4-oxo-4,5-dihydro-3H-1-thia-3,5,8-triazaacenaphthylene-2-carboxylic acid The title compound was prepared in a manner analogous to Intermediate 15, using 6-chloro-2-methyl-3-nitropyridine and pyridin-3-ol in Step A, no Cu. MS (ESI): mass calcd. for $C_{20}H_{13}N_5O_4S$, 419.41; m/z found, 420.1 [M+H]$^+$.

Step B: N-((1R,2S)-2-Acrylamidocyclopentyl)-5-(2-methyl-6-(pyridin-3-yloxy)pyridin-3-yl)-4-oxo-4,5-dihydro-3H-1-thia-3,5,8-triazaacenaphthylene-2-carboxamide To a solution of 5-(2-methyl-6-(pyridin-3-yloxy)pyridin-3-yl)-4-oxo-4,5-dihydro-3H-1-thia-3,5,8-triazaacenaphthylene-2-carboxylic acid (650 mg, 1.55 mmol), triethylamine (313 mg, 3.10 mmol), and HATU (331 mg, 0.870 mmol) in DMF (5 mL) was stirred at room temperature for 15 minutes to form the activated ester. To this solution was added a solution of N-((1S,2R)-2-aminocyclopentyl)acrylamide (303 mg, 1.97 mmol) and triethylamine (894 mg, 8.85 mmol) in DMF (5 mL) and was stirred at room temperature for 10 minutes. The reaction was purified by flash column chromatography (MeOH/H$_2$O) and again by flash column chromatography (DCM/MeOH) to give the title compound (480 mg, 55.7% yield) as a yellow solid. MS (ESI): mass calcd. for $C_{28}H_{25}N_7O_4S$, 555.6; m/z found, 556.1 [M+H]$^+$. $^1$H NMR (400 MHz, CD$_3$OD): δ 8.52-8.45 (m, 1H), 8.43-8.37 (m, 1H), 8.36-8.30 (m, 1H), 7.85-7.79 (m, 1H), 7.78-7.70 (m, 1H), 7.54-7.46 (m, 1H), 7.15-7.06 (m, 1H), 6.31-6.10 (m, 3H), 5.65-5.56 (m, 1H), 4.50-4.27 (m, 2H), 2.18 (s, 3H), 2.10-1.88 (m, 3H), 1.78-1.60 (m, 3H).

Example 495: N-((1R,2S)-2-Acrylamidocyclopentyl)-5-(2-methyl-6-((6-methylpyridin-3-yl)oxy)pyridin-3-yl)-4-oxo-4,5-dihydro-3H-1-thia-3,5,8-triazaacenaphthylene-2-carboxamide

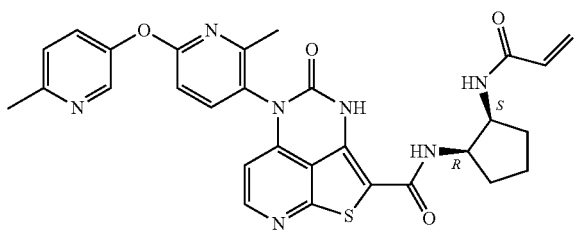

Step A: 5-(2-Methyl-6-((6-methylpyridin-3-yl)oxy)pyridin-3-yl)-4-oxo-4,5-dihydro-3H-1-thia-3,5,8-triazaacenaphthylene-2-carboxylic acid The title compound was prepared in a manner analogous to Intermediate 15, using 6-chloro-2-methyl-3-nitropyridine and 6-methylpyridin-3-ol in Step A, no Cu. MS (ESI): mass calcd. for $C_{20}H_{13}N_5O_4S$, 419.41; m/z found, 420.1 [M+H]$^+$.

Step B: N-((1R,2S)-2-Acrylamidocyclopentyl)-5-(2-methyl-6-((6-methylpyridin-3-yl)oxy)pyridin-3-yl)-4-oxo-4,5-dihydro-3H-1-thia-3,5,8-triazaacenaphthylene-2-carboxamide To a solution of 5-(2-methyl-6-((6-methylpyridin-3-yl)oxy)pyridin-3-yl)-4-oxo-4,5-dihydro-3H-1-thia-3,5,8-triazaacenaphthylene-2-carboxylic acid (1000 mg, 2.31 mmol), triethylamine (466 mg, 4.61 mmol), and HATU (1315 mg, 3.460 mmol) in DMF (5 mL) was stirred at room temperature for 15 minutes to form the activated ester. To this solution was added a solution of N-((1S,2R)-2-aminocyclopentyl)acrylamide (485 mg, 3.15 mmol) and triethylamine (1472 mg, 14.57 mmol) in DMF (5 mL) and was stirred at room temperature for 10 minutes. The reaction was purified by flash column chromatography (MeOH/H$_2$O) and again by flash column chromatography (DCM/MeOH) to give the title compound (781 mg, 59.4% yield) as a yellow solid. MS (ESI): mass calcd. for $C_{29}H_{27}N_7O_4S$, 569.6; m/z found, 570.1 [M+H]$^+$. $^1$H NMR (400 MHz, CD$_3$OD): δ 8.36-8.29 (m, 2H), 7.86-7.78 (m, 1H), 7.65-7.58 (m, 1H), 7.40-7.33 (m, 1H), 7.10-7.01 (m, 1H), 6.33-6.15 (m, 2H), 6.13-6.08 (m, 1H), 5.65-5.56 (m, 1H), 4.53-4.32 (m, 2H), 2.55 (s, 3H), 2.22-2.16 (m, 3H), 2.15-2.00 (m, 2H), 1.96-1.83 (m, 1H), 1.81-1.59 (m, 3H).

Example 496: N-((1R,2S)-2-Acrylamidocyclopentyl)-5-(*S)-(2-methyl-4-((6-methylpyridin-2-yl)oxy)phenyl)-4-oxo-4,5-dihydro-3H-1-thia-3,5,8-triazaacenaphthylene-2-carboxamide

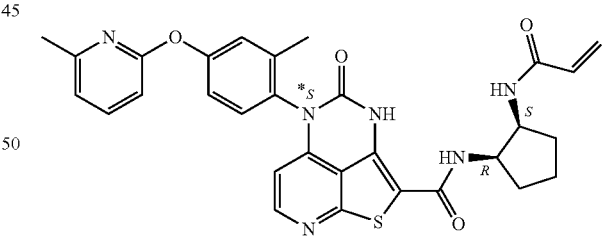

Chiral SFC purification (Stationary phase: CHIRALCEL AS-H, 5 μm, 250×20 mm, Mobile phase: 60% CO$_2$, 40% MeOH) of N-((1R,2S)-2-acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide (Example 368) afforded the *S atropisomer. MS (ESI): mass calcd. for $C_{30}H_{28}N_6O_4S$, 568.7; m/z found, 569.3 [M+H]$^+$. $^1$H NMR (400 MHz, CDCl$_3$): δ 9.52 (s, 1H), 8.34 (d, J=5.5 Hz, 1H), 7.67-7.56 (m, 1H), 7.27-7.08 (m, 3H), 6.95 (d, J=7.4 Hz, 1H), 6.80-6.63 (m, 2H), 6.49-6.28 (m, 2H), 6.20-6.01 (m, 2H), 5.67 (dd, J=10.2, 1.4 Hz, 1H), 4.47-4.26 (m, 2H), 2.49 (s, 3H), 2.34-2.09 (m, 5H), 1.92-1.73 (m, 4H).

Example 497: N-((1R,2S)-2-Acrylamidocyclopentyl)-5-(*R)-(2-methyl-4-((6-methylpyridin-2-yl)oxy)phenyl)-4-oxo-4,5-dihydro-3H-1-thia-3,5,8-triazaacenaphthylene-2-carboxamide

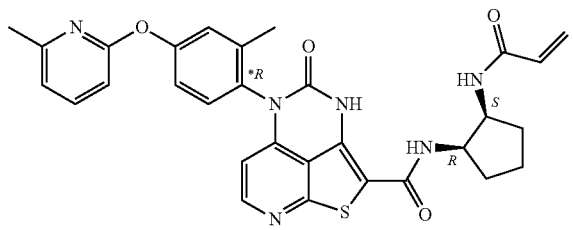

Chiral SFC purification (Stationary phase: CHIRALCEL AS-H, 5 μm, 250×20 mm, Mobile phase: 60% CO$_2$, 40% MeOH) of N-((1R,2S)-2-acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide (Example 368) afforded the *R atropisomer. MS (ESI): mass calcd. for C$_{30}$H$_{28}$N$_6$O$_4$S, 568.7; m/z found, 569.3 [M+H]$^+$. $^1$H NMR (400 MHz, CDCl$_3$): δ 9.51 (s, 1H), 8.42-8.28 (m, 1H), 7.70-7.55 (m, 1H), 7.25-7.02 (m, 4H), 6.94 (d, J=7.2 Hz, 2H), 6.81-6.65 (m, 3H), 6.46-6.29 (m, 3H), 6.26-5.99 (m, 3H), 5.79-5.60 (m, 1H), 4.45-4.24 (m, 3H), 2.49 (s, 3H), 2.40-1.82 (m, 9H).

Example 498: N-((1R,2S)-2-Acrylamidocyclopentyl)-5-(*S)-(2-methyl-4-((6-methylpyridin-3-yl)oxy)phenyl)-4-oxo-4,5-dihydro-3H-1-thia-3,5,8-triazaacenaphthylene-2-carboxamide

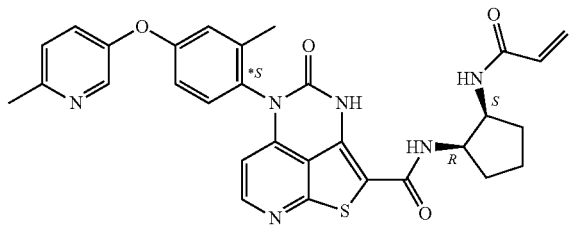

Chiral SFC column (Stationary phase: CHIRALCEL AS-H, 5 μm, 250×20 mm, Mobile phase: 60% CO$_2$, 40% MeOH) of N-((1R,2S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide (Example 384) affords the title compound as the *S atropisomer. MS (ESI): mass calcd. for C$_{30}$H$_{28}$N$_6$O$_4$S, 568.7; m/z found, 569.3 [M+H]$^+$. $^1$H NMR (400 MHz, CDCl$_3$): δ 9.49 (s, 1H), 8.36 (dd, J=13.0, 4.2 Hz, 2H), 7.39-7.30 (m, 1H), 7.24-7.12 (m, 2H), 7.07-6.86 (m, 2H), 6.73-6.62 (m, 1H), 6.47-6.24 (m, 2H), 6.14 (dd, J=16.8, 10.3 Hz, 1H), 5.98 (d, J=5.4 Hz, 1H), 5.68 (d, J=10.1 Hz, 1H), 4.46-4.24 (m, 2H), 2.58 (s, 3H), 2.37-1.58 (m, 9H).

Example 499: N-((1R,2S)-2-Acrylamidocyclopentyl)-5-(*R)-(2-methyl-4-((6-methylpyridin-3-yl)oxy)phenyl)-4-oxo-4,5-dihydro-3H-1-thia-3,5,8-triazaacenaphthylene-2-carboxamide

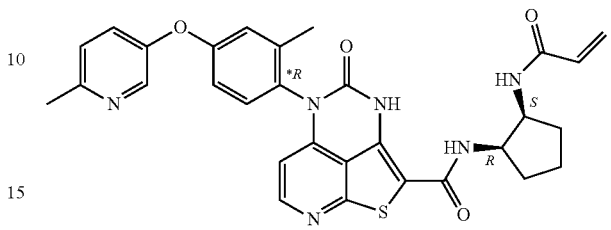

Chiral SFC column (Stationary phase: CHIRALCEL AS-H, 5 μm, 250×20 mm, Mobile phase: 60% CO$_2$, 40% MeOH) of N-((1R,2S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide (Example 384) affords the title compound as the *R atropisomer. MS (ESI): mass calcd. for C$_{30}$H$_{28}$N$_6$O$_4$S, 568.7; m/z found, 569.3 [M+H]$^+$. $^1$H NMR (400 MHz, CDCl$_3$): δ 9.50 (s, 1H), 8.44-8.21 (m, 2H), 7.33 (dd, J=8.4, 2.8 Hz, 1H), 7.19 (d, J=8.5 Hz, 2H), 7.03-6.85 (m, 2H), 6.74 (d, J=5.8 Hz, 1H), 6.45-6.33 (m, 1H), 6.31-6.08 (m, 2H), 6.02-5.93 (m, 1H), 5.69 (d, J=10.2 Hz, 1H), 4.42-4.22 (m, 2H), 2.58 (s, 3H), 2.37-1.73 (m, 9H).

Example 500: N-((1R,2S)-2-Acrylamidocyclopentyl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide

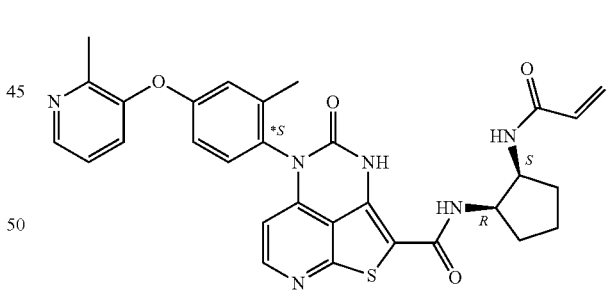

Chiral SFC purification (Stationary phase: CHIRALCEL AS-H, 5 μm, 250×20 mm, Mobile phase: 60% CO$_2$, 40% MeOH) of N-((1R,2S)-2-acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide (Example 367) afforded the *S atropisomer. MS (ESI): mass calcd. for C$_{30}$H$_{28}$N$_6$O$_4$S, 568.7; m/z found, 569.3 [M+H]$^+$. $^1$H NMR (400 MHz, CDCl$_3$): δ 9.54 (s, OH), 8.42-8.27 (m, 2H), 7.39-7.11 (m, 4H), 6.99-6.49 (m, 3H), 6.46-5.90 (m, 3H), 5.66 (d, J=10.2 Hz, 1H), 5.30 (d, J=2.1 Hz, 1H), 4.45-4.24 (m, 2H), 2.71-1.23 (m, 11H).

Example 501: N-((1R,2S)-2-Acrylamidocyclopentyl)-5-(*R)-(2-methyl-4-((2-methylpyridin-3-yl)oxy)phenyl)-4-oxo-4,5-dihydro-3H-1-thia-3,5,8-triazaacenaphthylene-2-carboxamide

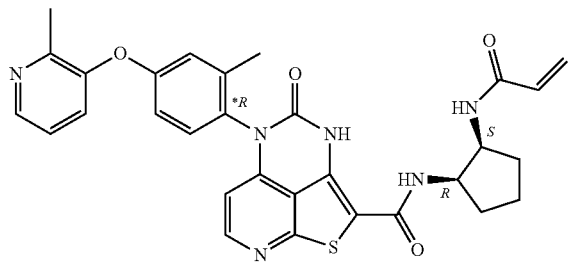

Chiral SFC purification (Stationary phase: CHIRALCEL AS-H, 5 μm, 250×20 mm, Mobile phase: 60% $CO_2$, 40% MeOH) of N-((1R,2S)-2-acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide (Example 367) afforded the *R atropisomer. MS (ESI): mass calcd. for $C_{30}H_{28}N_6O_4S$, 568.7; m/z found, 569.3 $[M+H]^+$. $^1$H NMR (400 MHz, $CDCl_3$): δ 9.64-5.57 (m, 13H), 5.36-5.23 (m, 1H), 4.46-4.22 (m, 2H), 2.54 (s, 3H), 2.34-2.04 (m, 5H), 1.95-1.60 (m, 4H).

Example 502: N-((1R,2S)-2-Acrylamidocyclopentyl)-5-(*S)-(2-methyl-4-(pyrimidin-2-yloxy)phenyl)-4-oxo-4,5-dihydro-3H-1-thia-3,5,8-triazaacenaphthylene-2-carboxamide

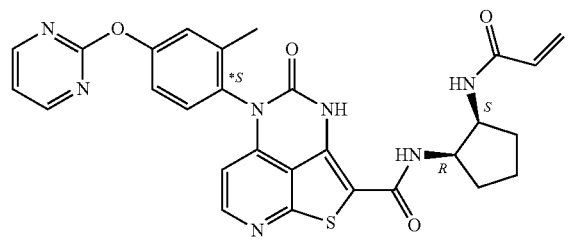

Chiral separation of N-((1R,2S)-2-acrylamidocyclopentyl)-5-(2-methyl-4-(pyrimidin-2-yloxy)phenyl)-4-oxo-4,5-dihydro-3H-1-thia-3,5,8-triazaacenaphthylene-2-carboxamide (Example 224) using chiral SFC column (Stationary phase: CHIRALCEL AS-H, 5 μm, 250×20 mm, Mobile phase: 60% $CO_2$, 40% MeOH) to give the *S atropisomer. MS (ESI): mass calcd. for $C_{28}H_{25}N_7O_4S$, 555.6; m/z found, 556.2 $[M+H]^+$. $^1$H NMR (400 MHz, $CDCl_3$): δ 8.60 (d, J=4.7 Hz, 2H), 8.36 (d, J=5.5 Hz, 1H), 7.38-7.19 (m, 5H), 7.12-7.05 (m, 1H), 6.72-6.61 (m, 1H), 6.44-6.31 (m, 1H), 6.26-6.00 (m, 2H), 5.69 (d, J=10.3 Hz, 1H), 4.41-4.26 (m, 2H), 2.37-2.25 (m, 1H), 2.20 (s, 3H), 1.97-1.81 (m, 1H), 1.81-1.68 (m, 4H).

Example 503: N-((1R,2S)-2-Acrylamidocyclopentyl)-5-(*R)-(2-methyl-4-(pyrimidin-2-yloxy)phenyl)-4-oxo-4,5-dihydro-3H-1-thia-3,5,8-triazaacenaphthylene-2-carboxamide

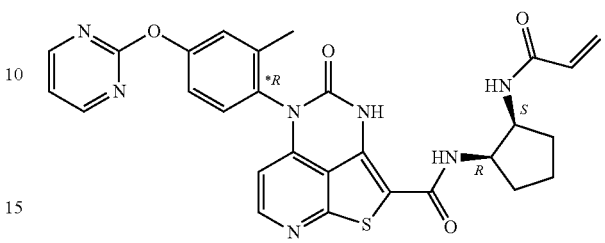

Chiral separation of N-((1R,2S)-2-acrylamidocyclopentyl)-5-(2-methyl-4-(pyrimidin-2-yloxy)phenyl)-4-oxo-4,5-dihydro-3H-1-thia-3,5,8-triazaacenaphthylene-2-carboxamide (Example 224) using chiral SFC column (Stationary phase: CHIRALCEL AS-H, 5 μm, 250×20 mm, Mobile phase: 60% $CO_2$, 40% MeOH) to give the *R atropisomer. MS (ESI): mass calcd. for $C_{28}H_{25}N_7O_4S$, 555.6; m/z found, 556.2 $[M+H]^+$. $^1$H NMR (400 MHz, $CDCl_3$): δ 9.50 (s, 1H), 8.60 (d, J=4.7 Hz, 2H), 8.36 (d, J=5.6 Hz, 1H), 7.33-7.18 (m, 3H), 7.15-7.02 (m, 1H), 6.72 (d, J=5.3 Hz, 1H), 6.42-6.34 (m, 1H), 6.25-6.19 (m, 1H), 6.19-6.09 (m, 1H), 6.07 (d, J=5.4 Hz, 1H), 5.70 (dd, J=10.4, 1.5 Hz, 1H), 4.38-4.27 (m, 2H), 2.35-2.23 (m, 1H), 2.20 (s, 3H), 1.93-1.84 (m, 1H), 1.81-1.66 (m, 4H).

Example 504: N-((1R,2S)-2-Acrylamidocyclopentyl)-5-(*S)-(2-methyl-4-(pyridin-2-yloxy)phenyl)-4-oxo-4,5-dihydro-3H-1-thia-3,5,8-triazaacenaphthylene-2-carboxamide

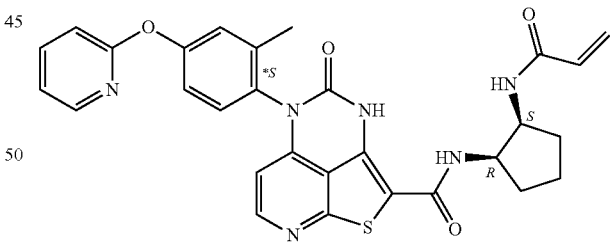

Chiral SFC column purification (Stationary phase: CHIRALCEL AS-H, 5 μm, 250×20 mm, Mobile phase: 60% $CO_2$, 40% MeOH) of N-((1R,2S)-2-acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide (Example 220) provides the title compound. MS (ESI): mass calcd. for $C_{29}H_{26}N_6O_4S$, 554.6; m/z found, 555.3 $[M+H]^+$. $^1$H NMR (400 MHz, $CDCl_3$): δ 9.69-9.42 (m, 1H), 8.45-8.17 (m, 2H), 7.86-7.64 (m, 1H), 7.22-6.92 (m, 5H), 6.82-6.63 (m, 1H), 6.63-6.47 (m, 1H), 6.40-6.30 (m, 1H), 6.20-6.00 (m, 2H), 5.66 (d, J=10.0 Hz, 1H), 4.50-4.24 (m, 2H), 2.33-1.75 (m, 9H).

Example 505: N-((1R,2S)-2-Acrylamidocyclopentyl)-5-(*R)-(2-methyl-4-(pyridin-2-yloxy)phenyl)-4-oxo-4,5-dihydro-3H-1-thia-3,5,8-triazaacenaphthylene-2-carboxamide

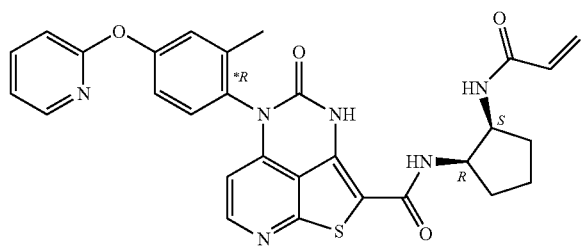

Chiral SFC column purification (Stationary phase: CHIRALCEL AS-H, 5 μm, 250×20 mm, Mobile phase: 60% CO$_2$, 40% MeOH) of N-((1R,2S)-2-acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide (Example 220) provides the title compound. MS (ESI): mass calcd. for C$_{29}$H$_{26}$N$_6$O$_4$S, 554.6; m/z found, 555.3 [M+H]$^+$. $^1$H NMR (400 MHz, CDCl$_3$): δ 9.60-9.48 (m, 1H), 8.41-8.18 (m, 2H), 7.85-7.65 (m, 1H), 7.24-6.93 (m, 5H), 6.80-6.43 (m, 1H), 6.41-6.31 (m, 1H), 6.20-6.03 (m, 2H), 5.67 (d, J=10.1 Hz, 1H), 4.35 (d, J=6.6 Hz, 2H), 2.40-1.65 (m, 10H).

Example 506: N-((1R,2S)-2-((E)-2-Cyano-3-(3-methyloxetan-3-yl)acrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide

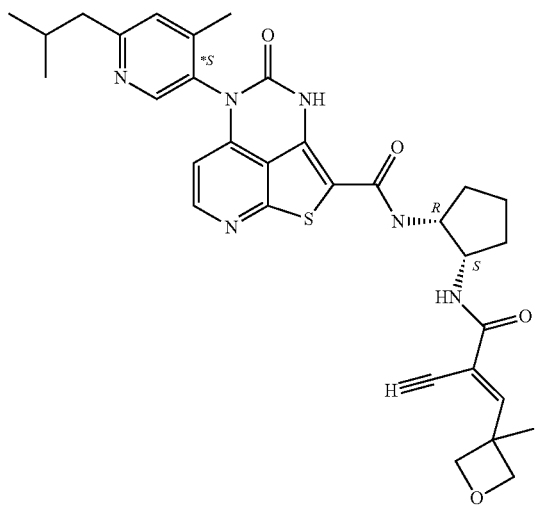

Step A: N-((1R,2S)-2-(2-Cyanoacetamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide A solution of N-((1R,2S)-2-aminocyclopentyl)-5-(*S)-(6-isobutyl-4-methylpyridin-3-yl)-4-oxo-4,5-dihydro-3H-1-thia-3,5,8-triazaacenaphthylene-2-carboxamide (Example 298, product from Step A, 500 mg, 0.998 mmol), 2,5-dioxopyrrolidin-1-yl 2-cyanoacetate (273 mg, 1.50 mmol), triethylamine (202 mg, 2.00 mmol), and DCM (20 mL) was stirred at room temperature for 2 h. The reaction was concentrated to dryness and purified by flash column chromatography to yield the title compound (359 mg, 67.7% yield) as light yellow solid. MS (ESI): mass calcd. for C$_{27}$H$_{29}$N$_7$O$_3$S, 531.63; m/z found, 532.3 [M+H]$^+$.

Step B: N-((1R,2S)-2-((E)-2-Cyano-3-(3-methyloxetan-3-yl)acrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide A solution of N-((1R,2S)-2-(2-cyanoacetamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide (120 mg, 0.226 mmol), 3-methyloxetane-3-carbaldehyde (68 mg, 0.68 mmol), piperidine (0.3 mL), acetic acid (0.1 mL), 4 A molecular sieves (0.5 g), and dioxane (5 mL) was stirred at reflux for 1 h. The reaction was filtered and the filtrate was concentrated to dryness. The residue was purified by flash column chromatography to yield the title compound (99 mg, 71% yield) as white solid. MS (ESI): mass calcd. for C$_{32}$H$_{35}$N$_7$O$_4$S, 613.73; m/z found, 614.3 [M+H]$^+$. $^1$H NMR (400 MHz, CD$_3$OD): δ 8.42-8.36 (m, 1H), 8.35-8.31 (m, 1H), 7.56 (s, 1H), 7.41 (s, 1H), 6.05-6.00 (m, 1H), 4.80-4.57 (m, 2H), 4.53-4.32 (m, 4H), 2.76-2.70 (m, 2H), 2.25-2.19 (m, 3H), 2.19-2.03 (m, 3H), 2.01-1.75 (m, 3H), 1.71-1.54 (m, 4H), 1.03-0.94 (m, 6H).

Example 507: N-((1R,2S)-2-((E)-2-Cyano-4-ethoxy-4-methylpent-2-enamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide

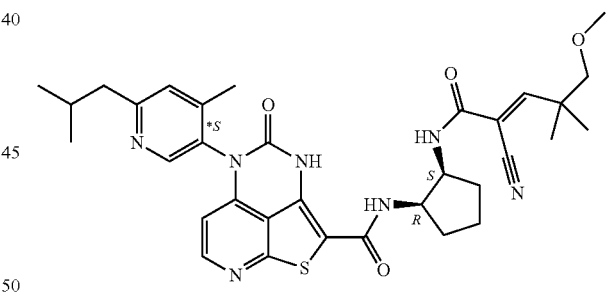

To a solution of N-((1R,2S)-2-(2-cyanoacetamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide (Example 506, product from Step A, 250 mg, 0.470 mmol), 2-ethoxy-2-methylpropanal (109 mg, 0.941 mmol), and acetic acid (504) in dioxane (5 mL) was added piperidine (1504) and heated at reflux for 1 h. The reaction was concentrated to dryness and purified by flash column chromatography to yield the title compound (71 mg, 23% yield) as pale yellow solid. $^1$H NMR (400 MHz, CD$_3$OD): d 8.42 (s, 1H), 8.32 (d, J=5.5 Hz, 1H), 7.41 (s, 1H), 7.31 (s, 1H), 6.02 (d, J=5.5 Hz, 1H), 4.54-4.44 (m, 1H), 4.40-4.32 (m, 1H), 3.35 (q, J=7.0 Hz, 2H), 2.72 (d, J=7.3 Hz, 2H), 2.21 (s, 3H), 2.16-2.06 (m, 3H), 1.97-1.73 (m, 3H), 1.68-1.58 (m, 1H), 1.34 (s, 3H), 1.34 (s, 3H), 1.09 (t, J=7.0 Hz, 3H), 1.01-0.96 (m, 6H).

Example 508: N-((1R,2S)-2-acrylamidocyclopentyl)-4-oxo-5-(4-(pyrimidin-5-yloxy)phenyl)-4,5-dihydro-3H-1-thia-3,5,8-triazaacenaphthylene-2-carboxamide

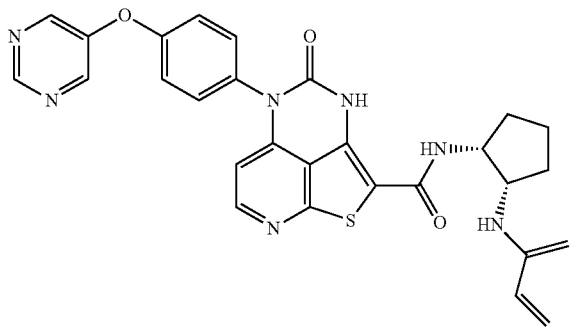 [SMILES: C=CC(=C)N[C@H]1CCC[C@H]1NC(=O)c1sc2nccc3c2c1NC(=O)N3c1ccc(Oc2cncnc2)cc1]

Step A. 4-Oxo-5-(4-(pyrimidin-5-yloxy)phenyl)-4,5-dihydro-3H-1-thia-3,5,8-triazaacenaphthylene-2-carboxylic acid The title compound was prepared in a manner analogous to Intermediate 1 Steps A, C-F, using 5-bromopyrimidine and 4-aminophenol in Step A.

Step B. N-((1R,2S)-2-acrylamidocyclopentyl)-4-oxo-5-(4-(pyrimidin-5-yloxy)phenyl)-4,5-dihydro-3H-1-thia-3,5,8-triazaacenaphthylene-2-carboxamide tert-Butyl ((1R,2S)-2-acrylamidocyclopentyl)carbamate (Intermediate 36, product from Step A, 301 mg, 1.18 mmol) was dissolved in $CH_2Cl_2$, MsOH (227.6 mg, 2.37 mmol) was added and the mixture was stirred for two hours, then the solvent was removed in vacuum, the residue was dissolved in DMF, it was added into the solvent of 4-oxo-5-(4-(pyrimidin-5-yloxy)phenyl)-4,5-dihydro-3H-1-thia-3,5,8-triazaacenaphthylene-2-carboxylic acid (400 mg, 0.98 mmol) and HATU (488 mg, 1.28 mmol) and triethylamine in DMF, after LCMS show the reaction was finished, it was poured into water, the solid formed was filtered and purified by silica gel column (DCM/EA/MeOH=2000/1000/20) to afford the title compound as brown solid. (310 mg, 58%). MS (ESI): mass calcd. for $C_{27}H_{23}N_7O_4S$, 541.6; m/z found, 542.1 $[M+H]^+$. $^1H$ NMR (400 MHz, DMSO-$d_6$): δ 9.06 (s, 1H), 8.76 (s, 2H), 8.35-8.26 (m, 1H), 7.93-7.86 (m, 1H), 7.86-7.77 (m, 1H), 7.57-7.44 (m, 2H), 7.40-7.30 (m, 2H), 6.31-6.19 (m, 1H), 6.15-6.04 (m, 2H), 5.61-5.50 (m, 1H), 4.35-4.23 (m, 2H), 2.00-1.86 (m, 2H), 1.84-1.70 (m, 2H), 1.70-1.51 (m, 2H).

BTK Kinase Lanthascreen Binding Assay:

A BTK kinase lanthascreen binding assay monitors compound binding to unphosphorylated-BTK kinase domain (UP-BTK), by competing with a fluorescent labeled tracer. UP-BTK, consisting of the kinase domain of non-phosphorylated BTK protein (389-659aa), was produced in a Baculovirus/insect cell expression system. Into a 384-well plate, 2 ng of GST-tagged human BTK (389-659aa) was incubated with compound, 50 nM of Tracer 236 and 2 nM anti-GST antibody for 60 minutes using an optimized Lanthascreen™ assay. After 60 minutes, plates were read at 340 nM and 615/665 nM in an Infinite F500 (Tecan). Data were analyzed using Xlfit™ version 5.3 from ID Business Solutions (Guildford), Microsoft Excel add-in. $pIC_{50}$ refers to the negative log of the $IC_{50}$ in molar.

| Ex # | Compound Name | BTK_I_binding pIC50 |
|---|---|---|
| 1 | N-((1S,4S)-4-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.61 |
| 2 | N-((1R,3S)-3-Acrylamidocyclohexyl)-5-(2-methyl-4-phenoxyphenyl)-4-oxo-4,5-dihydro-3H-1-thia-3,5,8-triazaacenaphthylene-2-carboxamide; | 7.36 |
| 3 | N-((1S,4S)-4-Acrylamidocyclohexyl)-5-(2-methyl-4-phenoxyphenyl)-4-oxo-4,5-dihydro-3H-1-thia-3,5,8-triazaacenaphthylene-2-carboxamide; | 7.42 |
| 4 | N-((1R,2R)-2-Hydroxycyclopentyl)-5-(S)-(2-methyl-4-phenoxyphenyl)-4-oxo-4,5-dihydro-3H-1-thia-3,5,8-triazaacenaphthylene-2-carboxamide; | 7.73 |
| 5 | N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide; | 7.69 |
| 6 | N-((1R,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide; | 7.48 |
| 7 | N-((1R,2S)-2-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide; | 7.31 |
| 8 | N-((1R,2S)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide; | 7.95 |
| 9 | N-((1R,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide; | 7.41 |
| 10 | N-((1R,2S)-2-Aminocyclohexyl)-5-(2-methyl-4-phenoxyphenyl)-4-oxo-4,5-dihydro-3H-1-thia-3,5,8-triazaacenaphthylene-2-carboxamide; | 7.35 |
| 11 | N-((1R,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide; | 7.24 |

-continued

| Ex # | Compound Name | BTK_I_binding pIC50 |
|---|---|---|
| 12 | N-((1R,2S)-2-Aminocyclopentyl)-5-(2-methyl-4-phenoxyphenyl)-4-oxo-4,5-dihydro-3H-1-thia-3,5,8-triazaacenaphthylene-2-carboxamide; | 7.03 |
| 13 | N-((1R,4R)-4-Acrylamidocyclohexyl)-5-(2-methyl-4-phenoxyphenyl)-4-oxo-4,5-dihydro-3H-1-thia-3,5,8-triazaacenaphthylene-2-carboxamide; | 6.94 |
| 14 | N-((1R,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide; | 7.30 |
| 15 | N-((1R,4R)-4-Hydroxycyclohexyl)-5-(2-methyl-4-phenoxyphenyl)-4-oxo-4,5-dihydro-3H-1-thia-3,5,8-triazaacenaphthylene-2-carboxamide; | 7.21 |
| 16 | N-((1S,4S)-4-Hydroxycyclohexyl)-5-(2-methyl-4-phenoxyphenyl)-4-oxo-4,5-dihydro-3H-1-thia-3,5,8-triazaacenaphthylene-2-carboxamide; | 7.14 |
| 17 | N-((1R,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide; | 6.92 |
| 18 | N-((1R,4R)-4-Methoxycyclohexyl)-5-(2-methyl-4-phenoxyphenyl)-4-oxo-4,5-dihydro-3H-1-thia-3,5,8-triazaacenaphthylene-2-carboxamide; | 6.99 |
| 19 | N-((1S,4S)-4-((E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide; | 6.63 |
| 20 | N-((1S,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide; | 7.02 |
| 21 | 5-(2-Methyl-4-phenoxyphenyl)-N-((1R,2R)-2-(methylamino)cyclopentyl)-4-oxo-4,5-dihydro-3H-1-thia-3,5,8-triazaacenaphthylene-2-carboxamide; | 6.85 |
| 22 | N-((1R,2R)-2-Aminocyclopentyl)-5-(2-methyl-4-phenoxyphenyl)-4-oxo-4,5-dihydro-3H-1-thia-3,5,8-triazaacenaphthylene-2-carboxamide; | 7.13 |
| 23 | N-((1S,4S)-4-Cyanamidocyclohexyl)-5-(2-methyl-4-phenoxyphenyl)-4-oxo-4,5-dihydro-3H-1-thia-3,5,8-triazaacenaphthylene-2-carboxamide; | 6.77 |
| 24 | N-((1R,3S)-3-(Dimethylamino)cyclohexyl)-5-(2-methyl-4-phenoxyphenyl)-4-oxo-4,5-dihydro-3H-1-thia-3,5,8-triazaacenaphthylene-2-carboxamide; | 6.59 |
| 25 | N-((1S,4S)-4-Aminocyclohexyl)-5-(2-methyl-4-phenoxyphenyl)-4-oxo-4,5-dihydro-3H-1-thia-3,5,8-triazaacenaphthylene-2-carboxamide; | 6.66 |
| 26 | 5-(2-Methyl-4-phenoxyphenyl)-4-oxo-N-((1R,2R)-2-propionamidocyclopentyl)-4,5-dihydro-3H-1-thia-3,5,8-triazaacenaphthylene-2-carboxamide; | 6.69 |
| 27 | N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide; | 6.96 |
| 28 | N-Cyclopentyl-5-(2-methyl-4-phenoxyphenyl)-4-oxo-4,5-dihydro-3H-1-thia-3,5,8-triazaacenaphthylene-2-carboxamide; | 6.67 |
| 29 | N-((1R,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide; | 6.81 |
| 30 | N-((1r,3s,5R,7S)-3-Hydroxyadamantan-1-yl)-5-(2-methyl-4-phenoxyphenyl)-4-oxo-4,5-dihydro-3H-1-thia-3,5,8-triazaacenaphthylene-2-carboxamide; | 6.36 |
| 31 | 5-(2-Methyl-4-phenoxyphenyl)-N-(2-(methylamino)cyclohexyl)-4-oxo-4,5-dihydro-3H-1-thia-3,5,8-triazaacenaphthylene-2-carboxamide; | 6.66 |
| 32 | N-((1S,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide; | 7.12 |
| 33 | N-((1R,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide; | 6.98 |
| 34 | 5-(2-Methyl-4-phenoxyphenyl)-4-oxo-N-((1R,2S)-2-propionamidocyclopentyl)-4,5-dihydro-3H-1-thia-3,5,8-triazaacenaphthylene-2-carboxamide; | 6.91 |
| 35 | 5-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide; | 6.87 |
| 36 | N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide; | 6.72 |

| Ex # | Compound Name | BTK_I_binding pIC50 |
|---|---|---|
| 37 | N-((1R,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide; | 6.68 |
| 38 | N-((1R,2R)-2-Aminocyclohexyl)-5-(2-methyl-4-phenoxyphenyl)-4-oxo-4,5-dihydro-3H-1-thia-3,5,8-triazaacenaphthylene-2-carboxamide; | 6.68 |
| 39 | N-((1S,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide; | 6.51 |
| 40 | N-((1S,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide; | 6.40 |
| 41 | N-((1S,2S)-2-Aminocyclopentyl)-5-(2-methyl-4-phenoxyphenyl)-4-oxo-4,5-dihydro-3H-1-thia-3,5,8-triazaacenaphthylene-2-carboxamide; | 6.37 |
| 42 | 5-(2-Methyl-4-phenoxyphenyl)-4-oxo-N-((1S,2R)-2-propionamidocyclohexyl)-4,5-dihydro-3H-1-thia-3,5,8-triazaacenaphthylene-2-carboxamide; | 6.24 |
| 43 | N-((1R,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide; | 6.23 |
| 44 | N-((1S,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide; | 6.17 |
| 45 | 5-(2-Methyl-4-phenoxyphenyl)-4-oxo-N-((1S,2S)-2-propionamidocyclopentyl)-4,5-dihydro-3H-1-thia-3,5,8-triazaacenaphthylene-2-carboxamide; | 6.14 |
| 46 | 5-(2-Methyl-4-phenoxyphenyl)-N-((1S,2S)-2-(methylamino)cyclopentyl)-4-oxo-4,5-dihydro-3H-1-thia-3,5,8-triazaacenaphthylene-2-carboxamide; | 6.14 |
| 47 | N-((1R,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide; | 6.12 |
| 48 | N-((1S,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide; | 6.12 |
| 49 | N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide; | 6.12 |
| 50 | 5-(2-Methyl-4-phenoxyphenyl)-N-((1S,2R)-2-(methylamino)cyclohexyl)-4-oxo-4,5-dihydro-3H-1-thia-3,5,8-triazaacenaphthylene-2-carboxamide; | 6.07 |
| 51 | N-((1S,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide; | 6.01 |
| 52 | 5-(2-Methyl-4-phenoxyphenyl)-4-oxo-N-((1R,2R)-2-propionamidocyclohexyl)-4,5-dihydro-3H-1-thia-3,5,8-triazaacenaphthylene-2-carboxamide; | 6.01 |
| 53 | N-((1S,2R)-2-Aminocyclopentyl)-5-(2-methyl-4-phenoxyphenyl)-4-oxo-4,5-dihydro-3H-1-thia-3,5,8-triazaacenaphthylene-2-carboxamide; | 5.95 |
| 54 | N-((1S,2S)-2-Formamidocyclohexyl)-5-(2-methyl-4-phenoxyphenyl)-4-oxo-4,5-dihydro-3H-1-thia-3,5,8-triazaacenaphthylene-2-carboxamide; | 5.90 |
| 55 | N-((1S,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide; | 5.88 |
| 56 | N-((1S,2S)-2-Acrylamidocyclopentyl)-5-(*R)-(2-methyl-4-phenoxyphenyl)-4-oxo-4,5-dihydro-3H-1-thia-3,5,8-triazaacenaphthylene-2-carboxamide; | 5.77 |
| 57 | N-((1S,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide; | 5.65 |
| 58 | N-((1S,2S)-2-Aminocyclohexyl)-5-(2-methyl-4-phenoxyphenyl)-4-oxo-4,5-dihydro-3H-1-thia-3,5,8-triazaacenaphthylene-2-carboxamide; | 5.51 |
| 59 | 5-(2-Methyl-4-phenoxyphenyl)-4-oxo-N-((1S,2R)-2-propionamidocyclopentyl)-4,5-dihydro-3H-1-thia-3,5,8-triazaacenaphthylene-2-carboxamide; | 5.46 |
| 60 | 5-(2-Methyl-4-phenoxyphenyl)-4-oxo-N-((1S,2S)-2-propionamidocyclohexyl)-4,5-dihydro-3H-1-thia-3,5,8-triazaacenaphthylene-2-carboxamide; | 5.40 |
| 61 | N-((1R,2R)-2-Hydroxycyclopentyl)-5-(*R)-(2-methyl-4-phenoxyphenyl)-4-oxo-4,5-dihydro-3H-1-thia-3,5,8-triazaacenaphthylene-2-carboxamide; | 5.36 |

-continued

| Ex # | Compound Name | BTK_I_binding pIC50 |
|---|---|---|
| 62 | N-((1S,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide; | 5.29 |
| 63 | 5-(2-Methyl-4-phenoxyphenyl)-N-(4-(methylamino)cyclohexyl)-4-oxo-4,5-dihydro-3H-1-thia-3,5,8-triazaacenaphthylene-2-carboxamide; | 6.85 |
| 64 | N-((1S,4S)-4-Acetamidocyclohexyl)-5-(2-methyl-4-phenoxyphenyl)-4-oxo-4,5-dihydro-3H-1-thia-3,5,8-triazaacenaphthylene-2-carboxamide; | 7.28 |
| 65 | 5-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide; | 7.20 |
| 66 | N-((1S,4S)-4-(Dimethylamino)cyclohexyl)-5-(2-methyl-4-phenoxyphenyl)-4-oxo-4,5-dihydro-3H-1-thia-3,5,8-triazaacenaphthylene-2-carboxamide; | 6.56 |
| 67 | N-((1R,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide; | 7.41 |
| 68 | N-((1S,3R)-3-acrylamidocyclopentyl)-5-(2-methyl-4-phenoxyphenyl)-4-oxo-4,5-dihydro-3H-1-thia-3,5,8-triazaacenaphthylene-2-carboxamide; | 7.78 |
| 69 | 5-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide; | 7.73 |
| 70 | N-((1S,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide; | 7.69 |
| 71 | N-((1S,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide; | 7.38 |
| 72 | 5-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide; | 7.02 |
| 73 | N-((1S,3R)-3-(Dimethylamino)cyclopentyl)-5-(2-methyl-4-phenoxyphenyl)-4-oxo-4,5-dihydro-3H-1-thia-3,5,8-triazaacenaphthylene-2-carboxamide; | 7.00 |
| 74 | N-((1S,3R)-3-Hydroxycyclopentyl)-5-(2-methyl-4-phenoxyphenyl)-4-oxo-4,5-dihydro-3H-1-thia-3,5,8-triazaacenaphthylene-2-carboxamide; | 7.07 |
| 75 | N-((1S,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide; | 7.30 |
| 76 | N-((1S,3R)-3-Aminocyclopentyl)-5-(2-methyl-4-phenoxyphenyl)-4-oxo-4,5-dihydro-3H-1-thia-3,5,8-triazaacenaphthylene-2-carboxamide; | 6.88 |
| 77 | N-((1S,4S)-4-((E)-4-(Dimethylamino)but-2-enamido)cyclohexyl)-5-(2-methyl-4-phenoxyphenyl)-4-oxo-4,5-dihydro-3H-1-thia-3,5,8-triazaacenaphthylene-2-carboxamide; | 6.61 |
| 78 | 5-(2-Methyl-4-phenoxyphenyl)-N-((1S,4S)-4-((E)-4-(methylamino)but-2-enamido)cyclohexyl)-4-oxo-4,5-dihydro-3H-1-thia-3,5,8-triazaacenaphthylene-2-carboxamide; | 6.55 |
| 79 | N-((1S,4S)-4-((E)-4-Aminobut-2-enamido)cyclohexyl)-5-(2-methyl-4-phenoxyphenyl)-4-oxo-4,5-dihydro-3H-1-thia-3,5,8-triazaacenaphthylene-2-carboxamide; | 6.47 |
| 80 | 5-(2-Methyl-4-phenoxyphenyl)-N-((1S)-3-(methylamino)cyclopentyl)-4-oxo-4,5-dihydro-3H-1-thia-3,5,8-triazaacenaphthylene-2-carboxamide; | 6.42 |
| 81 | N-Cyclopentyl-5-(*S)-(2-methyl-4-phenoxyphenyl)-4-oxo-4,5-dihydro-3H-1-thia-3,5,8-triazaacenaphthylene-2-carboxamide; | 7.03 |
| 82 | N-Cyclopentyl-5-(*R)-(2-methyl-4-phenoxyphenyl)-4-oxo-4,5-dihydro-3H-1-thia-3,5,8-triazaacenaphthylene-2-carboxamide; | 5.35 |
| 83 | N-((1S,4S)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide; | 7.60 |
| 84 | N-((1S,4S)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide; | 6.21 |
| 85 | N-((1R,4R)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide; | 7.67 |
| 86 | N-((1R,4R)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide; | 6.64 |
| 87 | 5-(*S)-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide; | 7.87 |

-continued

| Ex # | Compound Name | BTK_I_binding pIC50 |
|---|---|---|
| 88 | N-((1S,3R)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide; | 7.89 |
| 91 | N-((1R,2R)-2-Aminocyclopentyl)-4-oxo-5-(4-phenoxyphenyl)-4,5-dihydro-3H-1-thia-3,5,8-triazaacenaphthylene-2-carboxamide; | 7.31 |
| 92 | 5-(*S)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide; | 6.91 |
| 93 | 5-(*R)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide; | 6.99 |
| 94 | N-((1S,4S)-4-Acetamidocyclohexyl)-5-(*R)-(2-methyl-4-phenoxyphenyl)-4-oxo-4,5-dihydro-3H-1-thia-3,5,8-triazaacenaphthylene-2-carboxamide; | 7.59 |
| 95 | N-((1S,4S)-4-Acetamidocyclohexyl)-5-(*R)-(2-methyl-4-phenoxyphenyl)-4-oxo-4,5-dihydro-3H-1-thia-3,5,8-triazaacenaphthylene-2-carboxamide; | 6.14 |
| 96 | N-(rac-(1,3-cis)-3-Aminocyclopentyl)-4-oxo-5-(4-phenoxyphenyl)-4,5-dihydro-3H-1-thia-3,5,8-triazaacenaphthylene-2-carboxamide; | 7.11 |
| 97 | N-((1R,2S)-2-Aminocyclopentyl)-4-oxo-5-(4-phenoxyphenyl)-4,5-dihydro-3H-1-thia-3,5,8-triazaacenaphthylene-2-carboxamide; | 7.70 |
| 98 | N-((1S,2R)-2-Aminocyclopentyl)-4-oxo-5-(4-phenoxyphenyl)-4,5-dihydro-3H-1-thia-3,5,8-triazaacenaphthylene-2-carboxamide; | 6.10 |
| 99 | N-((1S,4S)-4-(Dimethylamino)cyclohexyl)-5-(*R)-(2-methyl-4-phenoxyphenyl)-4-oxo-4,5-dihydro-3H-1-thia-3,5,8-triazaacenaphthylene-2-carboxamide; | 7.03 |
| 100 | N-((1S,4S)-4-(Dimethylamino)cyclohexyl)-5-(*R)-(2-methyl-4-phenoxyphenyl)-4-oxo-4,5-dihydro-3H-1-thia-3,5,8-triazaacenaphthylene-2-carboxamide; | 5.86 |
| 101 | N-((1S,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 7.95 |
| 102 | N-((1S,3R)-3-(2-(dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 7.50 |
| 103 | 5-(*S)-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide; | 7.40 |
| 104 | N-((1R,2S)-2-acrylamidocyclopentyl)-4-oxo-5-(4-phenoxyphenyl)-4,5-dihydro-3H-1-thia-3,5,8-triazaacenaphthylene-2-carboxamide; | 8.37 |
| 105 | N-((1R,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 8.11 |
| 106 | 5-([1,1'-Biphenyl]-3-yl)-N-((1R,2S)-2-acrylamidocyclohexyl)-4-oxo-4,5-dihydro-3H-1-thia-3,5,8-triazaacenaphthylene-2-carboxamide; | 8.06 |
| 107 | N-((1R,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 8.25 |
| 108 | N-((1R,2S)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.56 |
| 109 | N-((1RS,3RS)-3-Acrylamidocyclopentyl)-4-oxo-5-(4-phenoxyphenyl)-4,5-dihydro-3H-1-thia-3,5,8-triazaacenaphthylene-2-carboxamide; | 7.85 |
| 110 | N-((1S,3R)-3-Acrylamidocyclopentyl)-5-(4-isopropoxy-2-methylphenyl)-4-oxo-4,5-dihydro-3H-1-thia-3,5,8-triazaacenaphthylene-2-carboxamide; | 7.23 |
| 111 | N-((1R,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 7.68 |
| 112 | 5-(*S)-(2-Methyl-4-phenoxyphenyl)-N-((1R,2R)-2-(2-(methylamino)acetamido)cyclopentyl)-4-oxo-4,5-dihydro-3H-1-thia-3,5,8-triazaacenaphthylene-2-carboxamide; | 8.04 |
| 113 | N-((1R,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 7.88 |
| 114 | N-((1S,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 6.81 |
| 115 | N-((1R,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide; | 7.57 |
| 116 | N-((1S,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 7.30 |

| Ex # | Compound Name | BTK_I_binding pIC50 |
|---|---|---|
| 117 | N-((1S,3R)-3-Acrylamidocyclopentyl)-4-oxo-5-(4-phenoxyphenyl)-4,5-dihydro-3H-1-thia-3,5,8-triazaacenaphthylene-2-carboxamide; | 7.80 |
| 118 | N-((1R,2S)-2-Acrylamidocyclohexyl)-4-oxo-5-(4-phenoxyphenyl)-4,5-dihydro-3H-1-thia-3,5,8-triazaacenaphthylene-2-carboxamide; | 8.12 |
| 119 | N-((1S,4S)-4-Acrylamidocyclohexyl)-4-oxo-5-(4-phenoxyphenyl)-4,5-dihydro-3H-1-thia-3,5,8-triazaacenaphthylene-2-carboxamide; | 7.61 |
| 120 | N-((1R,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide; | 7.54 |
| 121 | N-((1R,3S)-3-Acrylamidocyclopentyl)-4-oxo-5-(4-phenoxyphenyl)-4,5-dihydro-3H-1-thia-3,5,8-triazaacenaphthylene-2-carboxamide; | 6.57 |
| 122 | 5-(*S)-(2-Methyl-4-phenoxyphenyl)-N-((1R,2S)-2-(2-(methylamino)acetamido)cyclopentyl)-4-oxo-4,5-dihydro-3H-1-thia-3,5,8-triazaacenaphthylene-2-carboxamide; | 7.18 |
| 123 | N-((1S,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 7.07 |
| 124 | N-((1S,2R)-Acrylamidocyclohexyl)-4-oxo-5-(4-phenoxyphenyl)-4,5-dihydro-3H-1-thia-3,5,8-triazaacenaphthylene-2-carboxamide; | 6.71 |
| 125 | 5-(*S)-(2-Methyl-4-phenoxyphenyl)-N-((1R,2S)-2-(2-(methylamino)acetamido)cyclohexyl)-4-oxo-4,5-dihydro-3H-1-thia-3,5,8-triazaacenaphthylene-2-carboxamide; | 7.11 |
| 126 | N-((1R,2S)-2-Aminocyclohexyl)-4-oxo-5-(4-phenoxyphenyl)-4,5-dihydro-3H-1-thia-3,5,8-triazaacenaphthylene-2-carboxamide; | 7.13 |
| 127 | N-((1S,2R)-Acrylamidocyclopentyl)-4-oxo-5-(4-phenoxyphenyl)-4,5-dihydro-3H-1-thia-3,5,8-triazaacenaphthylene-2-carboxamide; | 6.56 |
| 128 | N-((1R,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 7.10 |
| 129 | N-((1R,2S)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 7.39 |
| 130 | N-((1S,2S)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 7.17 |
| 131 | N-((1R,2S)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 7.40 |
| 132 | N-((1R,2S)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 7.27 |
| 133 | 5-(*S)-(2-Methyl-4-phenoxyphenyl)-N-((1S,2S)-2-(2-(methylamino)acetamido)cyclopentyl)-4-oxo-4,5-dihydro-3H-1-thia-3,5,8-triazaacenaphthylene-2-carboxamide; | 7.13 |
| 134 | N-((1S,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide; | 6.76 |
| 135 | N-((1S,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide; | 6.82 |
| 136 | N-((1R,2S)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.52 |
| 137 | N-((1R,2S)-2-Aminocyclohexyl)-5-(3-chloro-4-phenoxyphenyl)-4-oxo-4,5-dihydro-3H-1-thia-3,5,8-triazaacenaphthylene-2-carboxamide; | 7.49 |
| 138 | N-((1R,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide; | 7.49 |
| 139 | N-((1R,3R)-3-Hydroxycyclohexyl)-4-oxo-5-(4-phenoxyphenyl)-4,5-dihydro-3H-1-thia-3,5,8-triazaacenaphthylene-2-carboxamide; | 7.23 |
| 140 | N-((1R,2S)-2-Hydroxycyclopentyl)-4-oxo-5-(4-phenoxyphenyl)-4,5-dihydro-3H-1-thia-3,5,8-triazaacenaphthylene-2-carboxamide; | 7.15 |
| 141 | 5-([1,1'-Biphenyl]-3-yl)-N-((1R,2S)-2-aminocyclohexyl)-4-oxo-4,5-dihydro-3H-1-thia-3,5,8-triazaacenaphthylene-2-carboxamide; | 7.01 |
| 142 | N-((1R,3S)-3-Hydroxycyclohexyl)-4-oxo-5-(4-phenoxyphenyl)-4,5-dihydro-3H-1-thia-3,5,8-triazaacenaphthylene-2-carboxamide; | 6.87 |
| 143 | N-((1S,3S)-3-Hydroxycyclohexyl)-4-oxo-5-(4-phenoxyphenyl)-4,5-dihydro-3H-1-thia-3,5,8-triazaacenaphthylene-2-carboxamide; | 6.75 |
| 144 | 5-([1,1'-Biphenyl]-3-yl)-N-((1R,2R)-2-hydroxycyclopentyl)-4-oxo-4,5-dihydro-3H-1-thia-3,5,8-triazaacenaphthylene-2-carboxamide; | 6.69 |
| 145 | N-((1S,4S)-4-Aminocyclohexyl)-4-oxo-5-(4-phenoxyphenyl)-4,5-dihydro-3H-1-thia-3,5,8-triazaacenaphthylene-2-carboxamide; | 6.69 |
| 146 | N-(trans-(1R,4R)-4-Aminocyclohexyl)-4-oxo-5-(4-phenoxyphenyl)-4,5-dihydro-3H-1-thia-3,5,8-triazaacenaphthylene-2-carboxamide; | 6.66 |

| Ex # | Compound Name | BTK_I_binding pIC50 |
|---|---|---|
| 147 | trans-N-((1RS,3RS)-3-Aminocyclopentyl)-4-oxo-5-(4-phenoxyphenyl)-4,5-dihydro-3H-1-thia-3,5,8-triazaacenaphthylene-2-carboxamide; | 6.63 |
| 148 | N-((1S,2S)-2-Aminocyclopentyl)-4-oxo-5-(4-phenoxyphenyl)-4,5-dihydro-3H-1-thia-3,5,8-triazaacenaphthylene-2-carboxamide; | 6.47 |
| 149 | N-((1R,2R)-2-Aminocyclohexyl)-4-oxo-5-(4-phenoxyphenyl)-4,5-dihydro-3H-1-thia-3,5,8-triazaacenaphthylene-2-carboxamide; | 6.45 |
| 150 | tert-Butyl ((1R,3S)-3-(4-oxo-5-(4-phenoxyphenyl)-4,5-dihydro-3H-1-thia-3,5,8-triazaacenaphthylene-2-carboxamido)cyclopentyl)carbamate; | 6.40 |
| 151 | tert-Butyl trans-((1R,4R)-4-(4-oxo-5-(4-phenoxyphenyl)-4,5-dihydro-3H-1-thia-3,5,8-triazaacenaphthylene-2-carboxamido)cyclohexyl)carbamate; | 6.33 |
| 152 | N-((1-Hydroxycyclohexyl)methyl)-4-oxo-5-(4-phenoxyphenyl)-4,5-dihydro-3H-1-thia-3,5,8-triazaacenaphthylene-2-carboxamide; | 6.25 |
| 153 | N-((1S,3R)-3-((E)-4-(Dimethylamino)but-2-enamido)cyclopentyl)-5-(4-isopropoxy-2-methylphenyl)-4-oxo-4,5-dihydro-3H-1-thia-3,5,8-triazaacenaphthylene-2-carboxamide; | 6.44 |
| 154 | N-((1S,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 6.36 |
| 155 | N-((1S,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide; | 6.35 |
| 156 | 5-(*S)-(2-Methyl-4-phenoxyphenyl)-N-((1S,2R)-2-(2-(methylamino)acetamido)cyclopentyl)-4-oxo-4,5-dihydro-3H-1-thia-3,5,8-triazaacenaphthylene-2-carboxamide; | 6.26 |
| 157 | N-((1S,3R)-3-Hydroxycyclohexyl)-4-oxo-5-(4-phenoxyphenyl)-4,5-dihydro-3H-1-thia-3,5,8-triazaacenaphthylene-2-carboxamide; | 6.19 |
| 158 | N-((1S,3R)-3-(2-(Dimethylamino)acetamido)cyclopentyl)-5-(4-isopropoxy-2-methylphenyl)-4-oxo-4,5-dihydro-3H-1-thia-3,5,8-triazaacenaphthylene-2-carboxamide; | 6.11 |
| 159 | 4-Oxo-5-(2-phenylpyridin-4-yl)-N-((1S,2R)-2-propionamidocyclopentyl)-4,5-dihydro-3H-1-thia-3,5,8-triazaacenaphthylene-2-carboxamide; | <6 |
| 160 | N-((1R,2S)-2-Aminocyclohexyl)-5-(4-isopropoxy-2-methylphenyl)-4-oxo-4,5-dihydro-3H-1-thia-3,5,8-triazaacenaphthylene-2-carboxamide; | <6 |
| 161 | 5-(4-Isopropoxy-2-methylphenyl)-N-((1S,3R)-3-(2-(methylamino)acetamido)cyclopentyl)-4-oxo-4,5-dihydro-3H-1-thia-3,5,8-triazaacenaphthylene-2-carboxamide; | <6 |
| 162 | N-((1S,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide; | <6 |
| 163 | tert-Butyl ((1S,4S)-4-(4-oxo-5-(4-phenoxyphenyl)-4,5-dihydro-3H-1-thia-3,5,8-triazaacenaphthylene-2-carboxamido)cyclohexyl)carbamate; | 5.43 |
| 164 | N-((1S,3R)-3-Aminocyclopentyl)-4-oxo-5-(4-phenoxyphenyl)-4,5-dihydro-3H-1-thia-3,5,8-triazaacenaphthylene-2-carboxamide; | 5.19 |
| 165 | N-((1R,2S)-2-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide; | 8.30 |
| 166 | N-((1R,2S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide; | 8.13 |
| 167 | N-((1R,2S)-2-Acrylamidocyclopentyl)-4-oxo-5-(6-phenylpyrimidin-4-yl)-4,5-dihydro-3H-1-thia-3,5,8-triazaacenaphthylene-2-carboxamide; | 8.34 |
| 168 | N-((1R,2S)-2-Acrylamidocyclohexyl)-4-oxo-5-(2-phenylpyridin-4-yl)-4,5-dihydro-3H-1-thia-3,5,8-triazaacenaphthylene-2-carboxamide; | 8.10 |
| 169 | N-((1R,2S)-2-Acrylamidocyclopentyl)-4-oxo-5-(2-phenylpyridin-4-yl)-4,5-dihydro-3H-1-thia-3,5,8-triazaacenaphthylene-2-carboxamide; | 8.26 |
| 170 | N-((1R,2S)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 7.02 |
| 171 | N-((1R,2S)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 8.19 |
| 172 | N-((1R,2S)-2-Acrylamidocyclohexyl)-4-oxo-5-(6-phenoxypyridin-3-yl)-4,5-dihydro-3H-1-thia-3,5,8-triazaacenaphthylene-2-carboxamide; | 8.35 |
| 173 | N-((1R,2S)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 8.02 |

-continued

| Ex # | Compound Name | BTK_I_binding pIC50 |
|---|---|---|
| 174 | N-((1R,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide; | 8.28 |
| 175 | N-((1R,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 8.05 |
| 176 | N-((1S,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.78 |
| 177 | N-((1R,2R)-2-Acrylamidocyclopentyl)-4-oxo-5-(6-phenoxypyridin-3-yl)-4,5-dihydro-3H-1-thia-3,5,8-triazaacenaphthylene-2-carboxamide; | 7.49 |
| 178 | N-((1R,2S)-2-Acrylamidocyclopentyl)-4-oxo-5-(6-phenoxypyridin-3-yl)-4,5-dihydro-3H-1-thia-3,5,8-triazaacenaphthylene-2-carboxamide; | 8.28 |
| 179 | N-((1R,2S)-2-Acrylamidocyclopentyl)-4-oxo-5-(5-phenoxypyridin-2-yl)-4,5-dihydro-3H-1-thia-3,5,8-triazaacenaphthylene-2-carboxamide; | 8.37 |
| 180 | N-((1S,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.94 |
| 181 | N-((1R,3R)-3-Aminocyclohexyl)-5-(2-methyl-4-phenoxyphenyl)-4-oxo-4,5-dihydro-3H-1-thia-3,5,8-triazaacenaphthylene-2-carboxamide; | 7.33 |
| 182 | N-((1R,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.66 |
| 183 | N-((1R,2S)-2-Acrylamidocyclohexyl)-5-(6-cyclobutoxy-4-methylpyridin-3-yl)-4-oxo-4,5-dihydro-3H-1-thia-3,5,8-triazaacenaphthylene-2-carboxamide; | 7.58 |
| 184 | N-((1R,3R)-3-Acrylamidocyclopentyl)-5-(2-methyl-4-phenoxyphenyl)-4-oxo-4,5-dihydro-3H-1-thia-3,5,8-triazaacenaphthylene-2-carboxamide; | 7.55 |
| 185 | N-((1R,2R)-2-Acrylamidocyclopentyl)-4-oxo-5-(5-phenoxypyridin-2-yl)-4,5-dihydro-3H-1-thia-3,5,8-triazaacenaphthylene-2-carboxamide; | 7.56 |
| 186 | N-((1S,3R)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide; | 7.62 |
| 187 | N-((1R,2S)-2-Acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide; | 7.30 |
| 188 | N-((1RS,3RS)-3-Acrylamidocyclopentyl)-4-oxo-5-(6-phenoxypyridin-3-yl)-4,5-dihydro-3H-1-thia-3,5,8-triazaacenaphthylene-2-carboxamide; | 7.11 |
| 189 | N-((1R,2S)-2-Acrylamidocyclopentyl)-4-oxo-5-(4-phenylpyridin-2-yl)-4,5-dihydro-3H-1-thia-3,5,8-triazaacenaphthylene-2-carboxamide; | 8.23 |
| 190 | N-((1S,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide; | 7.10 |
| 191 | N-((1S,3R)-3-Acrylamidocyclopentyl)-5-(3-chloro-4-phenoxyphenyl)-4-oxo-4,5-dihydro-3H-1-thia-3,5,8-triazaacenaphthylene-2-carboxamide; | 7.95 |
| 192 | N-((1R,2S)-2-Acrylamidocyclopentyl)-4-oxo-5-(5-phenylpyridin-3-yl)-4,5-dihydro-3H-1-thia-3,5,8-triazaacenaphthylene-2-carboxamide; | 7.92 |
| 193 | 5-([1,1'-Biphenyl]-3-yl)-N-((1R,2S)-2-acrylamidocyclopentyl)-4-oxo-4,5-dihydro-3H-1-thia-3,5,8-triazaacenaphthylene-2-carboxamide; | 8.09 |
| 194 | N-((1R,2S)-2-Acrylamidocyclopentyl)-4-oxo-5-(3-(pyridin-2-yl)phenyl)-4,5-dihydro-3H-1-thia-3,5,8-triazaacenaphthylene-2-carboxamide; | 7.89 |
| 195 | N-((1R,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.55 |
| 196 | N-((1R,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 7.12 |
| 197 | N-((1R,2R)-2-Acrylamidocyclopentyl)-4-oxo-5-(2-phenylpyridin-4-yl)-4,5-dihydro-3H-1-thia-3,5,8-triazaacenaphthylene-2-carboxamide; | 7.48 |
| 198 | N-((1S,3R)-3-Acrylamidocyclopentyl)-4-oxo-5-(2-phenylpyridin-4-yl)-4,5-dihydro-3H-1-thia-3,5,8-triazaacenaphthylene-2-carboxamide; | 7.98 |

-continued

| Ex # | Compound Name | BTK_I_binding pIC50 |
|---|---|---|
| 199 | N-((1R,2S)-2-Acrylamidocyclopentyl)-5-(2-methyl-4-(pyridin-3-yloxy)phenyl)-4-oxo-4,5-dihydro-3H-1-thia-3,5,8-triazaacenaphthylene-2-carboxamide; | 8.13 |
| 200 | N-((1R,2R)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 8.18 |
| 201 | N-((1R,2S)-2-Acrylamidocyclopentyl)-4-oxo-5-(5-phenoxypyrazin-2-yl)-4,5-dihydro-3H-1-thia-3,5,8-triazaacenaphthylene-2-carboxamide; | 8.32 |
| 202 | N-((1R,2S)-2-Acrylamidocyclopentyl)-4-oxo-5-(3-(pyridin-3-yl)phenyl)-4,5-dihydro-3H-1-thia-3,5,8-triazaacenaphthylene-2-carboxamide; | 7.90 |
| 203 | N-((1R,2S)-2-Acrylamidocyclopentyl)-4-oxo-5-(6-phenylpyridazin-4-yl)-4,5-dihydro-3H-1-thia-3,5,8-triazaacenaphthylene-2-carboxamide; | 8.06 |
| 204 | N-((1R,2S)-2-Acrylamidocyclohexyl)-5-(*S)-(6-cyclobutoxy-2-methylpyridin-3-yl)-4-oxo-4,5-dihydro-3H-1-thia-3,5,8-triazaacenaphthylene-2-carboxamide; | 8.03 |
| 205 | N-((1R,2S)-2-Acrylamidocyclopentyl)-5-(4-isopropoxyphenyl)-4-oxo-4,5-dihydro-3H-1-thia-3,5,8-triazaacenaphthylene-2-carboxamide; | 7.62 |
| 206 | N-((1R,2S)-2-Acrylamidocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 7.33 |
| 207 | N-((1R,2S)-2-Acrylamidocyclopentyl)-5-(2-isopropylpyridin-4-yl)-4-oxo-4,5-dihydro-3H-1-thia-3,5,8-triazaacenaphthylene-2-carboxamide; | 7.53 |
| 208 | N-((1R,3S)-3-Acrylamidocyclopentyl)-4-oxo-5-(2-phenylpyridin-4-yl)-4,5-dihydro-3H-1-thia-3,5,8-triazaacenaphthylene-2-carboxamide; | <6 |
| 209 | N-((1R,2S)-2-Acrylamidocyclohexyl)-5-(*S)-(6-isopropoxy-2-methylpyridin-3-yl)-4-oxo-4,5-dihydro-3H-1-thia-3,5,8-triazaacenaphthylene-2-carboxamide; | 7.31 |
| 210 | N-((1R,2S)-2-(3-Chloropropanamido)cyclopentyl)-5-(*S)-(4-methyl-6-phenoxypyridin-3-yl)-4-oxo-4,5-dihydro-3H-1-thia-3,5,8-triazaacenaphthylene-2-carboxamide; | 7.19 |
| 211 | N-((1R,2S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide; | 6.92 |
| 212 | N-((1R,3R)-3-Acrylamidocyclopentyl)-4-oxo-5-(2-phenylpyridin-4-yl)-4,5-dihydro-3H-1-thia-3,5,8-triazaacenaphthylene-2-carboxamide; | 7.49 |
| 213 | N-((1R,2R)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 7.30 |
| 214 | N-((1RS,3RS)-3-Acrylamidocyclopentyl)-4-oxo-5-(5-phenoxypyridin-2-yl)-4,5-dihydro-3H-1-thia-3,5,8-triazaacenaphthylene-2-carboxamide; | 7.85 |
| 215 | N-((1R,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide; | 7.13 |
| 216 | N-((1RS,3RS)-3-Acrylamidocyclohexyl)-4-oxo-5-(5-phenoxypyridin-2-yl)-4,5-dihydro-3H-1-thia-3,5,8-triazaacenaphthylene-2-carboxamide; | 7.44 |
| 217 | N-((1R,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide; | 7.44 |
| 218 | N-((1R,2R)-2-Acrylamidocyclohexyl)-4-oxo-5-(5-phenoxypyridin-2-yl)-4,5-dihydro-3H-1-thia-3,5,8-triazaacenaphthylene-2-carboxamide; | 6.76 |
| 219 | N-((1R,2R)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide; | 7.94 |
| 220 | N-((1R,2S)-2-Acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide; | 8.16 |
| 221 | N-((1R,2S)-2-Acrylamidocyclohexyl)-5-(*S)-(6-cyclobutoxy-4-methylpyridin-3-yl)-4-oxo-4,5-dihydro-3H-1-thia-3,5,8-triazaacenaphthylene-2-carboxamide; | 8.29 |
| 222 | N-((1R,2S)-2-Acrylamidocyclohexyl)-5-(6-isopropoxy-4-methylpyridin-3-yl)-4-oxo-4,5-dihydro-3H-1-thia-3,5,8-triazaacenaphthylene-2-carboxamide; | 7.91 |
| 223 | N-((1R,2S)-2-Acrylamidocyclohexyl)-5-(6-(cyclopentyloxy)-4-methylpyridin-3-yl)-4-oxo-4,5-dihydro-3H-1-thia-3,5,8-triazaacenaphthylene-2-carboxamide; | 7.81 |

| Ex # | Compound Name | BTK_I_binding pIC50 |
|---|---|---|
| 224 | N-((1R,2S)-2-Acrylamidocyclopentyl)-5-(2-methyl-4-(pyrimidin-2-yloxy)phenyl)-4-oxo-4,5-dihydro-3H-1-thia-3,5,8-triazaacenaphthylene-2-carboxamide; | 7.46 |
| 225 | N-((1R,2S)-2-Acrylamidocyclohexyl)-5-(6-isobutoxy-4-methylpyridin-3-yl)-4-oxo-4,5-dihydro-3H-1-thia-3,5,8-triazaacenaphthylene-2-carboxamide; | 7.66 |
| 226 | N-((1S,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide; | 6.85 |
| 227 | N-((1R,2R)-2-Acrylamidocyclohexyl)-4-oxo-5-(2-phenylpyridin-4-yl)-4,5-dihydro-3H-1-thia-3,5,8-triazaacenaphthylene-2-carboxamide; | 6.76 |
| 228 | N-((1R,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide; | 7.34 |
| 229 | 5-(2-Methyl-4-phenoxyphenyl)-N-((1R,3R)-3-(2-(methylamino)acetamido)cyclopentyl)-4-oxo-4,5-dihydro-3H-1-thia-3,5,8-triazaacenaphthylene-2-carboxamide; | 7.29 |
| 230 | N-((1S,3R)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide; | 7.24 |
| 231 | N-((1S,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide; | 6.56 |
| 232 | N-((1R,3R)-3-Acrylamidocyclohexyl)-4-oxo-5-(2-phenylpyridin-4-yl)-4,5-dihydro-3H-1-thia-3,5,8-triazaacenaphthylene-2-carboxamide; | 7.05 |
| 233 | N-((1R,2R)-2-Aminocyclopentyl)-5-(4-methyl-6-phenoxypyridin-3-yl)-4-oxo-4,5-dihydro-3H-1-thia-3,5,8-triazaacenaphthylene-2-carboxamide; | 6.85 |
| 234 | N-((1R,2S)-2-Acrylamidocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide; | 6.76 |
| 235 | N-((1R,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide; | 7.44 |
| 236 | N-((1R,3R)-3-Aminocyclopentyl)-5-(2-methyl-4-phenoxyphenyl)-4-oxo-4,5-dihydro-3H-1-thia-3,5,8-triazaacenaphthylene-2-carboxamide; | 7.00 |
| 237 | N-((1R,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide; | 6.56 |
| 238 | N-((1R,2S)-2-Acrylamidocyclohexyl)-5-(*R)-(6-isopropoxy-2-methylpyridin-3-yl)-4-oxo-4,5-dihydro-3H-1-thia-3,5,8-triazaacenaphthylene-2-carboxamide; | 6.95 |
| 239 | N-((1R,2R)-2-Acrylamidocyclohexyl)-4-oxo-5-(6-phenoxypyridin-3-yl)-4,5-dihydro-3H-1-thia-3,5,8-triazaacenaphthylene-2-carboxamide; | 6.47 |
| 240 | N-((1R,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide; | 6.72 |
| 241 | N-((1S,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide; | 7.26 |
| 242 | N-((1R,2S)-2-Acrylamidocyclohexyl)-5-(*R)-(6-cyclobutoxy-2-methylpyridin-3-yl)-4-oxo-4,5-dihydro-3H-1-thia-3,5,8-triazaacenaphthylene-2-carboxamide; | 7.04 |
| 243 | N-((1S,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide; | 6.85 |
| 244 | N-((1R,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide; | 6.66 |
| 245 | N-((1S,3S)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide; | 6.73 |
| 246 | 5-(2-Methyl-4-phenoxyphenyl)-N-((1S,3S)-3-(2-(methylamino)acetamido)cyclopentyl)-4-oxo-4,5-dihydro-3H-1-thia-3,5,8-triazaacenaphthylene-2-carboxamide; | 6.84 |
| 247 | N-((1S,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide; | 6.66 |
| 248 | 5-(3-Chloro-4-phenoxyphenyl)-N-((1S,3R)-3-((E)-4-(dimethylamino)but-2-enamido)cyclopentyl)-4-oxo-4,5-dihydro-3H-1-thia-3,5,8-triazaacenaphthylene-2-carboxamide; | 6.98 |

| Ex # | Compound Name | BTK_I_binding pIC50 |
|---|---|---|
| 249 | 5-([1,1'-Biphenyl]-3-yl)-N-((1R,2S)-2-aminocyclopentyl)-4-oxo-4,5-dihydro-3H-1-thia-3,5,8-triazaacenaphthylene-2-carboxamide; | 6.90 |
| 250 | 5-(*S)-(2-Methyl-4-phenoxyphenyl)-N-((1R,3S)-3-(2-(methylamino)acetamido)cyclohexyl)-4-oxo-4,5-dihydro-3H-1-thia-3,5,8-triazaacenaphthylene-2-carboxamide; | 6.75 |
| 251 | N-((1R,3S)-3-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 6.71 |
| 252 | N-((1R,3S)-3-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 6.63 |
| 253 | N-((1R,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide; | 6.63 |
| 254 | N-((1R,2S)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide; | 6.55 |
| 255 | N-((1R,2R)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.51 |
| 256 | N-((1R,2R)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide; | 6.48 |
| 257 | N-((1R,2S)-2-Aminocyclohexyl)-4-oxo-5-(6-phenoxypyridin-3-yl)-4,5-dihydro-3H-1-thia-3,5,8-triazaacenaphthylene-2-carboxamide; | 6.47 |
| 258 | N-((1S,2R)-2-Acetamidocyclopentyl)-4-oxo-5-(2-phenylpyridin-4-yl)-4,5-dihydro-3H-1-thia-3,5,8-triazaacenaphthylene-2-carboxamide; | <6 |
| 259 | N-((1S,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide; | 6.45 |
| 260 | N-((1R,2S)-2-Aminocyclohexyl)-4-oxo-5-(2-phenylpyridin-4-yl)-4,5-dihydro-3H-1-thia-3,5,8-triazaacenaphthylene-2-carboxamide; | 6.45 |
| 261 | N-((1R,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide; | 6.42 |
| 262 | N-((1R,2S)-2-Aminocyclopentyl)-5-(*R)-(4-isopropoxy-2-methylphenyl)-4-oxo-4,5-dihydro-3H-1-thia-3,5,8-triazaacenaphthylene-2-carboxamide; | 6.39 |
| 263 | N-((1R,2S)-2-Aminocyclopentyl)-4-oxo-5-(2-phenylpyridin-4-yl)-4,5-dihydro-3H-1-thia-3,5,8-triazaacenaphthylene-2-carboxamide; | 6.38 |
| 264 | N-((1R,2R)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide; | 6.26 |
| 265 | N-((1R,2S)-2-Aminocyclopentyl)-4-oxo-5-(6-phenoxypyridin-3-yl)-4,5-dihydro-3H-1-thia-3,5,8-triazaacenaphthylene-2-carboxamide; | 6.24 |
| 266 | N-((1R,2S)-2-Acrylamidocyclohexyl)-5-(*R)-(6-cyclobutoxy-4-methylpyridin-3-yl)-4-oxo-4,5-dihydro-3H-1-thia-3,5,8-triazaacenaphthylene-2-carboxamide; | 6.21 |
| 267 | N-((1R,2S)-2-Aminocyclopentyl)-4-oxo-5-(4-phenylpyridin-2-yl)-4,5-dihydro-3H-1-thia-3,5,8-triazaacenaphthylene-2-carboxamide; | 6.21 |
| 268 | N-((1R,2R)-2-Hydroxycyclopentyl)-4-oxo-5-(2-phenylpyridin-4-yl)-4,5-dihydro-3H-1-thia-3,5,8-triazaacenaphthylene-2-carboxamide; | 6.20 |
| 269 | N-((1R,2R)-2-Aminocyclopentyl)-4-oxo-5-(6-phenoxypyridin-3-yl)-4,5-dihydro-3H-1-thia-3,5,8-triazaacenaphthylene-2-carboxamide; | 6.00 |
| 270 | N-((1R,2S)-2-Aminocyclopentyl)-5-(2-isopropylpyridin-4-yl)-4-oxo-4,5-dihydro-3H-1-thia-3,5,8-triazaacenaphthylene-2-carboxamide; | <6 |
| 271 | N-((1R,2S)-2-Aminocyclopentyl)-5-(4-isopropoxyphenyl)-4-oxo-4,5-dihydro-3H-1-thia-3,5,8-triazaacenaphthylene-2-carboxamide; | <6 |
| 272 | N-((1S,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide; | <6 |
| 273 | N-((1R,2R)-2-Acrylamidocyclohexyl)-5-(*S)-(4-isopropoxy-2-methylphenyl)-4-oxo-4,5-dihydro-3H-1-thia-3,5,8-triazaacenaphthylene-2-carboxamide; | <6 |
| 274 | N-((1S,S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide; | <6 |
| 275 | N-((1R,3S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide; | <6 |
| 276 | N-((1R,3S)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide; | <6 |

| Ex # | Compound Name | BTK_I_binding pIC50 |
|---|---|---|
| 277 | N-((1R,2R)-2-Aminocyclohexyl)-4-oxo-5-(6-phenoxypyridin-3-yl)-4,5-dihydro-3H-1-thia-3,5,8-triazaacenaphthylene-2-carboxamide; | <6 |
| 278 | N-((1R,2S)-2-Aminocyclopentyl)-4-oxo-5-(6-phenylpyridazin-4-yl)-4,5-dihydro-3H-1-thia-3,5,8-triazaacenaphthylene-2-carboxamide; | <6 |
| 279 | N-((1S,3S)-3-Acrylamidocyclohexyl)-4-oxo-5-(2-phenylpyridin-4-yl)-4,5-dihydro-3H-1-thia-3,5,8-triazaacenaphthylene-2-carboxamide; | <6 |
| 280 | N-((1R,2S)-2-Acetamidocyclopentyl)-4-oxo-5-(2-phenylpyridin-4-yl)-4,5-dihydro-3H-1-thia-3,5,8-triazaacenaphthylene-2-carboxamide; | <6 |
| 281 | N-((1R,2S)-2-Aminocyclopentyl)-4-oxo-5-(6-phenylpyrimidin-4-yl)-4,5-dihydro-3H-1-thia-3,5,8-triazaacenaphthylene-2-carboxamide; | <6 |
| 282 | N-((1S,3S)-3-Acrylamidocyclopentyl)-4-oxo-5-(2-phenylpyridin-4-yl)-4,5-dihydro-3H-1-thia-3,5,8-triazaacenaphthylene-2-carboxamide; | <6 |
| 283 | N-((1R,3S)-3-Acrylamidocyclohexyl)-4-oxo-5-(2-phenylpyridin-4-yl)-4,5-dihydro-3H-1-thia-3,5,8-triazaacenaphthylene-2-carboxamide; | <6 |
| 284 | N-((1R,2S)-2-Aminocyclopentyl)-4-oxo-5-(5-phenylpyridin-3-yl)-4,5-dihydro-3H-1-thia-3,5,8-triazaacenaphthylene-2-carboxamide; | <6 |
| 285 | N-((1R,2S)-2-Aminocyclopentyl)-4-oxo-5-(3-(pyridin-2-yl)phenyl)-4,5-dihydro-3H-1-thia-3,5,8-triazaacenaphthylene-2-carboxamide; | <6 |
| 286 | N-((1S,2R)-2-(2-(Methylamino)acetamido)cyclopentyl)-4-oxo-5-(2-phenylpyridin-4-yl)-4,5-dihydro-3H-1-thia-3,5,8-triazaacenaphthylene-2-carboxamide; | <6 |
| 287 | N-((1R,2S)-2-Aminocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide; | <6 |
| 288 | N-((1R,2S)-2-Aminocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide; | <6 |
| 289 | racemic cis N-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide; | 5.77 |
| 290 | racemic trans N-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide; | 5.65 |
| 291 | N-((1R,2S)-2-Acrylamidocyclohexyl)-4-oxo-5-(5-phenoxypyridin-2-yl)-4,5-dihydro-3H-1-thia-3,5,8-triazaacenaphthylene-2-carboxamide; | 8.60 |
| 292 | N-((1RS,2RS)-2-Acrylamidocyclopentyl)-5-(2-methyl-6-phenoxypyridin-3-yl)-4-oxo-4,5-dihydro-3H-1-thia-3,5,8-triazaacenaphthylene-2-carboxamide; | 8.38 |
| 295 | N-((1R,2S)-2-Acrylamidocyclohexyl)-4-oxo-5-(5-phenoxypyrazin-2-yl)-4,5-dihydro-3H-1-thia-3,5,8-triazaacenaphthylene-2-carboxamide; | 8.39 |
| 296 | N-((1R,2S)-2-acrylamidocyclopentyl)-4-oxo-5-(5-phenoxypyrimidin-2-yl)-4,5-dihydro-3H-1-thia-3,5,8-triazaacenaphthylene-2-carboxamide; | 8.39 |
| 297 | N-((1R,2S)-2-Acrylamidocyclohexyl)-4-oxo-5-(5-phenoxypyrimidin-2-yl)-4,5-dihydro-3H-1-thia-3,5,8-triazaacenaphthylene-2-carboxamide; | 8.53 |
| 298 | N-((1R,2S)-2-Acrylamidocyclopentyl)-5-(S)-(6-isobutyl-4-methylpyridin-3-yl)-4-oxo-4,5-dihydro-3H-1-thia-3,5,8-triazaacenaphthylene-2-carboxamide; | 8.09 |
| 299 | N-((1R,2S)-2-Acrylamidocyclohexyl)-5-(*S)-(6-isopropoxy-4-methylpyridin-3-yl)-4-oxo-4,5-dihydro-3H-1-thia-3,5,8-triazaacenaphthylene-2-carboxamide; | 8.19 |
| 300 | N-((1R,2S)-2-Acrylamidocyclopentyl)-4-oxo-5-(*S)-(4-(pyridin-3-yloxy)phenyl)-4,5-dihydro-3H-1-thia-3,5,8-triazaacenaphthylene-2-carboxamide; | 8.27 |
| 301 | N-((1R,2R)-2-Acrylamidocyclopentyl)-5-(*S)-(2-methyl-6-phenoxypyridin-3-yl)-4-oxo-4,5-dihydro-3H-1-thia-3,5,8-triazaacenaphthylene-2-carboxamide; | 7.97 |
| 302 | N-((1R,2S)-2-Acrylamidocyclohexyl)-4-oxo-5-(2-phenoxypyrimidin-5-yl)-4,5-dihydro-3H-1-thia-3,5,8-triazaacenaphthylene-2-carboxamide; | 8.23 |
| 303 | N-((1R,2S)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide; | 8.40 |
| 304 | N-((1R,2S)-2-Acrylamidocyclopentyl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 7.48 |

-continued

| Ex # | Compound Name | BTK_I_binding pIC50 |
|---|---|---|
| 305 | N-((1R,2S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide; | 7.84 |
| 306 | N-((1*S,3*S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 8.04 |
| 307 | N-((1R,2R)-2-Acrylamidocyclopentyl)-4-oxo-5-(5-phenoxypyrimidin-2-yl)-4,5-dihydro-3H-1-thia-3,5,8-triazaacenaphthylene-2-carboxamide; | 7.58 |
| 308 | N-((1*S,3*S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 7.78 |
| 309 | N-((1R,2S)-2-Acrylamidocyclohexyl)-5-(*S)-(6-(cyclopentyloxy)-4-methylpyridin-3-yl)-4-oxo-4,5-dihydro-3H-1-thia-3,5,8-triazaacenaphthylene-2-carboxamide; | 7.91 |
| 310 | N-((1R,2S)-2-Acrylamidocyclopentyl)-4-oxo-5-(2-phenoxypyrimidin-5-yl)-4,5-dihydro-3H-1-thia-3,5,8-triazaacenaphthylene-2-carboxamide; | 8.04 |
| 311 | N-((1R,2R)-2-Acrylamidocyclopentyl)-4-oxo-5-(5-phenoxypyrazin-2-yl)-4,5-dihydro-3H-1-thia-3,5,8-triazaacenaphthylene-2-carboxamide; | 7.57 |
| 312 | N-((1R,2S)-2-Acrylamidocyclohexyl)-5-(*S)-(6-isobutoxy-4-methylpyridin-3-yl)-4-oxo-4,5-dihydro-3H-1-thia-3,5,8-triazaacenaphthylene-2-carboxamide; | 8.01 |
| 313 | N-((1S,3R)-3-Acrylamidocyclopentyl)-4-oxo-5-(5-phenoxypyridin-2-yl)-4,5-dihydro-3H-1-thia-3,5,8-triazaacenaphthylene-2-carboxamide; | 7.83 |
| 314 | N-((1R,2R)-2-Acrylamidocyclopentyl)-4-oxo-5-(2-phenoxypyrimidin-5-yl)-4,5-dihydro-3H-1-thia-3,5,8-triazaacenaphthylene-2-carboxamide; | 7.14 |
| 315 | N-((1*S,3*S)-3-Acrylamidocyclohexyl)-4-oxo-5-(5-phenoxypyridin-2-yl)-4,5-dihydro-3H-1-thia-3,5,8-triazaacenaphthylene-2-carboxamide; | 7.50 |
| 316 | N-((1R,2R)-2-Acrylamidocyclopentyl)-5-(*S)-(4-isopropoxy-2-methylphenyl)-4-oxo-4,5-dihydro-3H-1-thia-3,5,8-triazaacenaphthylene-2-carboxamide; | 7.33 |
| 317 | 5-([2,3'-Bipyridin]-4-yl)-N-((1R,2S)-2-acrylamidocyclopentyl)-4-oxo-4,5-dihydro-3H-1-thia-3,5,8-triazaacenaphthylene-2-carboxamide; | 7.74 |
| 318 | N-((1*R,2*S)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide; | 6.46 |
| 319 | N-((1S,3R)-3-Acrylamidocyclopentyl)-4-oxo-5-(2-phenoxypyrimidin-5-yl)-4,5-dihydro-3H-1-thia-3,5,8-triazaacenaphthylene-2-carboxamide; | 7.21 |
| 320 | N-((1R,2S)-2-Acrylamidocyclopentyl)-4-oxo-5-(5-phenylpyridazin-3-yl)-4,5-dihydro-3H-1-thia-3,5,8-triazaacenaphthylene-2-carboxamide; | 7.23 |
| 321 | N-((1*S,3*S)-3-Acrylamidocyclopentyl)-4-oxo-5-(6-phenoxypyridin-3-yl)-4,5-dihydro-3H-1-thia-3,5,8-triazaacenaphthylene-2-carboxamide; | 7.71 |
| 322 | N-((1R,2R)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide; | 6.81 |
| 323 | N-((1S,3S)-3-Acrylamidocyclohexyl)-4-oxo-5-(6-phenoxypyridin-3-yl)-4,5-dihydro-3H-1-thia-3,5,8-triazaacenaphthylene-2-carboxamide; | 7.13 |
| 324 | N-((1R,2R)-2-Acrylamidocyclopentyl)-4-oxo-5-(3-(pyridin-3-yl)phenyl)-4,5-dihydro-3H-1-thia-3,5,8-triazaacenaphthylene-2-carboxamide; | 6.90 |
| 325 | 5-([2,2'-Bipyridin]-4-yl)-N-((1R,2S)-2-acrylamidocyclopentyl)-4-oxo-4,5-dihydro-3H-1-thia-3,5,8-triazaacenaphthylene-2-carboxamide; | 7.07 |
| 326 | 5-([2,3'-Bipyridin]-4-yl)-N-((1R,2R)-2-acrylamidocyclopentyl)-4-oxo-4,5-dihydro-3H-1-thia-3,5,8-triazaacenaphthylene-2-carboxamide; | 6.72 |
| 327 | N-((1R,2R)-2-Acrylamidocyclopentyl)-4-oxo-5-(3-(pyridin-2-yl)phenyl)-4,5-dihydro-3H-1-thia-3,5,8-triazaacenaphthylene-2-carboxamide; | 6.98 |
| 328 | N-((1*R,3*S)-3-Acrylamidocyclopentyl)-4-oxo-5-(5-phenoxypyridin-2-yl)-4,5-dihydro-3H-1-thia-3,5,8-triazaacenaphthylene-2-carboxamide; | 6.58 |
| 329 | N-((1*R,3*R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 6.85 |

| Ex # | Compound Name | BTK_I_binding pIC50 |
|---|---|---|
| 330 | N-((1R,2S)-2-Acrylamidocyclopentyl)-5-(6-(isopropylamino)-4-methylpyridin-3-yl)-4-oxo-4,5-dihydro-3H-1-thia-3,5,8-triazaacenaphthylene-2-carboxamide; | 6.69 |
| 331 | N-((1*R,3*R)-3-Acrylamidocyclohexyl)-4-oxo-5-(6-phenoxypyridin-3-yl)-4,5-dihydro-3H-1-thia-3,5,8-triazaacenaphthylene-2-carboxamide; | 6.66 |
| 332 | N-((1*R,3*R)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.60 |
| 333 | N-((1R,2S)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide; | 6.50 |
| 334 | N-((1*R,3*R)-3-Acrylamidocyclopentyl)-4-oxo-5-(6-phenoxypyridin-3-yl)-4,5-dihydro-3H-1-thia-3,5,8-triazaacenaphthylene-2-carboxamide; | 6.81 |
| 335 | N-((1R,2S)-2-Aminocyclohexyl)-5-(*S)-(6-isobutyl-4-methylpyridin-3-yl)-4-oxo-4,5-dihydro-3H-1-thia-3,5,8-triazaacenaphthylene-2-carboxamide; | 6.38 |
| 336 | N-((1R,2R)-2-Aminocyclopentyl)-5-(2-isopropylpyridin-4-yl)-4-oxo-4,5-dihydro-3H-1-thia-3,5,8-triazaacenaphthylene-2-carboxamide; | 6.01 |
| 337 | N-((1R,2R)-2-Acrylamidocyclopentyl)-5-(2-isopropylpyridin-4-yl)-4-oxo-4,5-dihydro-3H-1-thia-3,5,8-triazaacenaphthylene-2-carboxamide; | 6.42 |
| 338 | N-((1R,2R)-2-Acrylamidocyclohexyl)-4-oxo-5-(2-phenoxypyrimidin-5-yl)-4,5-dihydro-3H-1-thia-3,5,8-triazaacenaphthylene-2-carboxamide; | 6.39 |
| 339 | N-((1R,2R)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide; | 6.28 |
| 340 | N-((1R,2S)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide; | 6.26 |
| 341 | N-((1R,2S)-2-Acrylamidocyclohexyl)-5-(*R)-(6-(cyclopentyloxy)-4-methylpyridin-3-yl)-4-oxo-4,5-dihydro-3H-1-thia-3,5,8-triazaacenaphthylene-2-carboxamide; | 6.23 |
| 342 | 5-([2,2'-Bipyridin]-4-yl)-N-((1R,2R)-2-acrylamidocyclopentyl)-4-oxo-4,5-dihydro-3H-1-thia-3,5,8-triazaacenaphthylene-2-carboxamide; | 6.12 |
| 343 | 5-(*S)-(2-Methyl-6-phenoxypyridin-3-yl)-4-oxo-N-((1R,2S)-2-propionamidocyclohexyl)-4,5-dihydro-3H-1-thia-3,5,8-triazaacenaphthylene-2-carboxamide; | 6.11 |
| 344 | N-((1*R,3*R)-3-Acrylamidocyclohexyl)-4-oxo-5-(5-phenoxypyridin-2-yl)-4,5-dihydro-3H-1-thia-3,5,8-triazaacenaphthylene-2-carboxamide; | 6.11 |
| 345 | N-((1R,2S)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide; | 6.09 |
| 346 | 5-(*S)-(2-Methyl-6-phenoxypyridin-3-yl)-4-oxo-N-((1R,2S)-2-propionamidocyclopentyl)-4,5-dihydro-3H-1-thia-3,5,8-triazaacenaphthylene-2-carboxamide; | 6.07 |
| 347 | N-((1R,2S)-2-Acrylamidocyclopentyl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 6.06 |
| 348 | N-((1R,2S)-2-Acrylamidocyclohexyl)-5-(*R)-(6-isopropoxy-4-methylpyridin-3-yl)-4-oxo-4,5-dihydro-3H-1-thia-3,5,8-triazaacenaphthylene-2-carboxamide; | 6.00 |
| 349 | N-((1R,2S)-2-Aminocyclopentyl)-4-oxo-5-(5-phenylpyridazin-3-yl)-4,5-dihydro-3H-1-thia-3,5,8-triazaacenaphthylene-2-carboxamide; | <6 |
| 350 | N-((1R,2R)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide; | <6 |
| 351 | N-((1S,3R)-3-Acrylamidocyclohexyl)-4-oxo-5-(2-phenylpyridin-4-yl)-4,5-dihydro-3H-1-thia-3,5,8-triazaacenaphthylene-2-carboxamide; | <6 |
| 352 | N-((1R,2S)-2-Acrylamidocyclohexyl)-5-(*R)-(6-isobutoxy-4-methylpyridin-3-yl)-4-oxo-4,5-dihydro-3H-1-thia-3,5,8-triazaacenaphthylene-2-carboxamide; | <6 |
| 353 | 5-(*S)-(2-Methyl-6-phenoxypyridin-3-yl)-4-oxo-N-((1R,2R)-2-propionamidocyclopentyl)-4,5-dihydro-3H-1-thia-3,5,8-triazaacenaphthylene-2-carboxamide; | <6 |
| 354 | N-((1R,2S)-2-Aminocyclopentyl)-5-(*S)-(6-isobutyl-4-methylpyridin-3-yl)-4-oxo-4,5-dihydro-3H-1-thia-3,5,8-triazaacenaphthylene-2-carboxamide; | |

| Ex # | Compound Name | BTK_I_binding pIC50 |
|---|---|---|
| 355 | N-((1R,3S)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 6.61 |
| 356 | N-((1R,3S)-3-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide; | <6 |
| 357 | N-((1R,2S)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide; | 7.98 |
| 358 | N-((1R,2R)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide; | 6.44 |
| 359 | N-((1R,3S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 8.05 |
| 360 | N-((1R,3S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.26 |
| 361 | 5-(*S)-(4-Methyl-6-phenoxypyridin-3-yl)-4-oxo-N-((1R,3S)-3-propionamidocyclopentyl)-4,5-dihydro-3H-1-thia-3,5,8-triazaacenaphthylene-2-carboxamide; | 7.94 |
| 362 | N-((1R,2R)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide; | <6 |
| 363 | N-((1R,3S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.31 |
| 364 | 5-(*S)-(2-Methyl-6-phenoxypyridin-3-yl)-4-oxo-N-((1R,2R)-2-propionamidocyclohexyl)-4,5-dihydro-3H-1-thia-3,5,8-triazaacenaphthylene-2-carboxamide; | <6 |
| 365 | N-((1R,3S)-3-Acrylamidocyclopentyl)-5-(6-isobutoxy-4-methylpyridin-3-yl)-4-oxo-4,5-dihydro-3H-1-thia-3,5,8-triazaacenaphthylene-2-carboxamide; | 7.93 |
| 366 | N-((1R,3S)-3-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide; | 8.07 |
| 367 | N-((1R,2S)-2-Acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide; | 7.54 |
| 368 | N-((1R,2S)-2-Acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide; | 8.13 |
| 369 | N-((1R,2S)-2-Acrylamidocyclopentyl)-5-(4-((6-methylpyridin-2-yl)oxy)phenyl)-4-oxo-4,5-dihydro-3H-1-thia-3,5,8-triazaacenaphthylene-2-carboxamide; | 8.06 |
| 370 | N-((1R,2S)-2-Acrylamidocyclopentyl)-5-(4-((6-methylpyridin-3-yl)oxy)phenyl)-4-oxo-4,5-dihydro-3H-1-thia-3,5,8-triazaacenaphthylene-2-carboxamide; | 7.79 |
| 371 | N-((1R,2S)-2-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide; | 8.23 |
| 372 | N-((1R,2S)-2-Acrylamidocyclopentyl)-5-(4-((2-methylpyridin-3-yl)oxy)phenyl)-4-oxo-4,5-dihydro-3H-1-thia-3,5,8-triazaacenaphthylene-2-carboxamide; | 7.93 |
| 373 | N-((1R,2S)-2-Acrylamidocyclopentyl)-5-(*S)-(6-isobutoxy-4-methylpyridin-3-yl)-4-oxo-4,5-dihydro-3H-1-thia-3,5,8-triazaacenaphthylene-2-carboxamide; | 8.25 |
| 374 | N-((1R,2S)-2-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide; | 6.82 |
| 375 | N-((1R,2S)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.92 |
| 376 | N-((1R,2S)-2-Acrylamidocyclopentyl)-5-(2-cyclobutylpyridin-4-yl)-4-oxo-4,5-dihydro-3H-1-thia-3,5,8-triazaacenaphthylene-2-carboxamide; | 7.81 |
| 377 | N-((1R,2S)-2-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.83 |
| 378 | N-((1R,2S)-2-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 6.39 |
| 379 | N-((1R,2R)-2-Acrylamidocyclopentyl)-5-(2-cyclobutylpyridin-4-yl)-4-oxo-4,5-dihydro-3H-1-thia-3,5,8-triazaacenaphthylene-2-carboxamide; | 6.80 |

| Ex # | Compound Name | BTK_I_binding pIC50 |
|---|---|---|
| 380 | 5-(*S)-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide; | 7.20 |
| 381 | 5-(*S)-(4-Methyl-6-phenoxypyridin-3-yl)-4-oxo-N-((1R,2S)-2-propionamidocyclohexyl)-4,5-dihydro-3H-1-thia-3,5,8-triazaacenaphthylene-2-carboxamide; | 6.75 |
| 382 | N-((1R,2R)-2-Acrylamidocyclopentyl)-5-(*S)-(6-isobutyl-4-methylpyridin-3-yl)-4-oxo-4,5-dihydro-3H-1-thia-3,5,8-triazaacenaphthylene-2-carboxamide; | 7.68 |
| 383 | N-((1R,2S)-2-Acrylamidocyclopentyl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide; | 7.45 |
| 384 | N-((1R,2S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide; | 7.54 |
| 385 | 5-(*S)-(4-Methyl-6-phenoxypyridin-3-yl)-4-oxo-N-((1R,3S)-3-propionamidocyclohexyl)-4,5-dihydro-3H-1-thia-3,5,8-triazaacenaphthylene-2-carboxamide; | 7.98 |
| 386 | N-((1R,2S)-2-Acrylamidocyclopentyl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide; | 7.09 |
| 387 | N-((1R,2S)-2-Acrylamidocyclopentyl)-4-oxo-5-(4-(pyridazin-3-yloxy)phenyl)-4,5-dihydro-3H-1-thia-3,5,8-triazaacenaphthylene-2-carboxamide; | 7.16 |
| 388 | 5-(*S)-(4-Methyl-6-phenoxypyridin-3-yl)-4-oxo-N-((1R,3R)-3-propionamidocyclopentyl)-4,5-dihydro-3H-1-thia-3,5,8-triazaacenaphthylene-2-carboxamide; | 7.64 |
| 389 | N-((1S,4S)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 7.30 |
| 390 | 5-(*S)-(4-Methyl-6-phenoxypyridin-3-yl)-4-oxo-N-((1S,3R)-3-propionamidocyclopentyl)-4,5-dihydro-3H-1-thia-3,5,8-triazaacenaphthylene-2-carboxamide; | 8.04 |
| 391 | N-((1S,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 7.86 |
| 392 | N-((1R,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 7.34 |
| 393 | N-((1R,2R)-2-Hydroxycyclopentyl)-4-oxo-5-(4-phenoxyphenyl)-4,5-dihydro-3H-1-thia-3,5,8-triazaacenaphthylene-2-carboxamide; | 6.74 |
| 394 | N-((1R,3S)-3-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide; | 6.70 |
| 395 | N-((1S,3S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 6.66 |
| 396 | N-((1R,2S)-2-Acetamidocyclopentyl)-4-oxo-5-(4-phenoxyphenyl)-4,5-dihydro-3H-1-thia-3,5,8-triazaacenaphthylene-2-carboxamide; | 6.66 |
| 397 | N-((1R,2S)-2-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide; | 6.62 |
| 398 | 4-Oxo-5-(4-phenoxyphenyl)-N-((1R,2S)-2-propionamidocyclopentyl)-4,5-dihydro-3H-1-thia-3,5,8-triazaacenaphthylene-2-carboxamide; | 6.56 |
| 399 | 5-(*S)-(4-Methyl-6-phenoxypyridin-3-yl)-4-oxo-N-((1S,3S)-3-propionamidocyclopentyl)-4,5-dihydro-3H-1-thia-3,5,8-triazaacenaphthylene-2-carboxamide; | 6.51 |
| 400 | N-((1S,3S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.46 |
| 401 | N-((1R,2S)-2-Acrylamidocyclohexyl)-5-(2-methyl-4-(pyridin-2-yloxy)phenyl)-4-oxo-4,5-dihydro-3H-1-thia-3,5,8-triazaacenaphthylene-2-carboxamide; | 6.39 |
| 402 | 5-(*S)-(4-Methyl-6-phenoxypyridin-3-yl)-4-oxo-N-((1S,3S)-3-propionamidocyclohexyl)-4,5-dihydro-3H-1-thia-3,5,8-triazaacenaphthylene-2-carboxamide; | 6.38 |
| 403 | N-((1R,3S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 6.26 |
| 404 | N-((1R,2R)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide; | 6.21 |
| 405 | N-((1R,3S)-3-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide; | 6.16 |

-continued

| Ex # | Compound Name | BTK_I_binding pIC50 |
|---|---|---|
| 406 | N-((1R,2S)-2-Acrylamidocyclohexyl)-5-(2-methyl-4-(pyridazin-3-yloxy)phenyl)-4-oxo-4,5-dihydro-3H-1-thia-3,5,8-triazaacenaphthylene-2-carboxamide; | 6.13 |
| 407 | N-((1S,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 6.05 |
| 408 | N-((1R,2S)-2-Acrylamidocyclohexyl)-4-oxo-5-(4-(pyridazin-3-yloxy)phenyl)-4,5-dihydro-3H-1-thia-3,5,8-triazaacenaphthylene-2-carboxamide; | <6 |
| 409 | 5-(*S)-(2-Methyl-6-phenoxypyridin-3-yl)-4-oxo-N-((1S,3S)-3-propionamidocyclopentyl)-4,5-dihydro-3H-1-thia-3,5,8-triazaacenaphthylene-2-carboxamide; | <6 |
| 410 | N-((1S,3S)-3-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide; | <6 |
| 411 | N-((1S,3R)-3-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide; | <6 |
| 412 | 5-(*S)-(2-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide; | <6 |
| 413 | N-((1S,3R)-3-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide; | <6 |
| 414 | N-((1S,3R)-3-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide; | <6 |
| 415 | N-((1S,3S)-3-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide; | <6 |
| 416 | 5-(*S)-(4-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide; | <6 |
| 417 | (S)-5-(2-Methyl-4-phenoxyphenyl)-2-(3-(methylamino)pyrrolidine-1-carbonyl)-3H-1-thia-3,5,8-triazaacenaphthylen-4(5H)-one; | 5.89 |
| 418 | (S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)propionamide; | 5.80 |
| 419 | (S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acetamide; | 5.79 |
| 420 | (S)-2-(3-Aminopyrrolidine-1-carbonyl)-5-(2-methyl-4-phenoxyphenyl)-3H-1-thia-3,5,8-triazaacenaphthylen-4(5H)-one; | 5.73 |
| 421 | (S)-2-(3-(Dimethylamino)pyrrolidine-1-carbonyl)-5-(2-methyl-4-phenoxyphenyl)-3H-1-thia-3,5,8-triazaacenaphthylen-4(5H)-one; | 5.66 |
| 422 | N-((1R,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 7.72 |
| 423 | 5-(*S)-(4-Methyl-6-phenoxypyridin-3-yl)-4-oxo-N-((1R,3R)-3-propionamidocyclohexyl)-4,5-dihydro-3H-1-thia-3,5,8-triazaacenaphthylene-2-carboxamide; | 7.75 |
| 424 | N-((1R,2S)-2-Acrylamidocyclopentyl)-5-(*S)-(2-methyl-4-(pyridazin-3-yloxy)phenyl)-4-oxo-4,5-dihydro-3H-1-thia-3,5,8-triazaacenaphthylene-2-carboxamide; | 7.76 |
| 425 | N-((1R,2S)-2-Acrylamidocyclopentyl)-5-(*R)-(2-methyl-4-(pyridazin-3-yloxy)phenyl)-4-oxo-4,5-dihydro-3H-1-thia-3,5,8-triazaacenaphthylene-2-carboxamide; | 6.67 |
| 426 | N-((1R,2S)-2-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide; | 8.20 |
| 427 | N-((1R,3S)-3-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide; | 7.88 |
| 428 | N-((1R,2S)-2-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide; | 6.67 |
| 429 | N-((1R,3S)-3-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide; | <6 |
| 430 | N-((1S,3R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 8.17 |
| 431 | N-((1S,3R)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 6.68 |

| Ex # | Compound Name | BTK_I_binding pIC50 |
|---|---|---|
| 432 | N-((1r,4r)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide; | 7.45 |
| 433 | (S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide; | 7.01 |
| 434 | (R)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide; | 6.29 |
| 435 | (R,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide; | 6.15 |
| 436 | (S,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide; | 6.09 |
| 437 | N-((1R,2S)-2-Acrylamidocyclopentyl)-4-oxo-5-(4-(pyridin-2-yloxy)phenyl)-4,5-dihydro-3H-1-thia-3,5,8-triazaacenaphthylene-2-carboxamide; | 8.38 |
| 438 | N-((1R,2S)-2-Acrylamidocyclopentyl)-5-(3-isopropylphenyl)-4-oxo-4,5-dihydro-3H-1-thia-3,5,8-triazaacenaphthylene-2-carboxamide; | 8.02 |
| 439 | N-((1R,2R)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide; | 7.53 |
| 440 | N-((1R,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide; | 7.07 |
| 441 | N-((1R,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 7.01 |
| 442 | N-((1R,2S)-2-Acrylamidocyclohexyl)-4-oxo-5-(4-(pyridin-2-yloxy)phenyl)-4,5-dihydro-3H-1-thia-3,5,8-triazaacenaphthylene-2-carboxamide; | 6.84 |
| 443 | 5-(*S)-(2-Methyl-4-phenoxyphenyl)-N-((1S,2R)-2-(2-(methylamino)acetamido)cyclohexyl)-4-oxo-4,5-dihydro-3H-1-thia-3,5,8-triazaacenaphthylene-2-carboxamide; | 6.74 |
| 444 | N-((1S,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 6.73 |
| 445 | N-((1R,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide; | 6.73 |
| 446 | N-((1S,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide; | 6.72 |
| 447 | N-((1R,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 6.67 |
| 448 | 5-(*S)-(2-Methyl-4-phenoxyphenyl)-N-((1R,2R)-2-(2-(methylamino)acetamido)cyclohexyl)-4-oxo-4,5-dihydro-3H-1-thia-3,5,8-triazaacenaphthylene-2-carboxamide; | 6.66 |
| 449 | N-((1S,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide; | 6.51 |
| 450 | N-((1S,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide; | 6.47 |
| 451 | N-((1S,2R)-2-Acrylamidocyclohexyl)-5-(2-methyl-4-phenoxyphenyl)-4-oxo-4,5-dihydro-3H-1-thia-3,5,8-triazaacenaphthylene-2-carboxamide; | 6.40 |
| 452 | N-((1S,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide; | 6.38 |
| 453 | N-((1R,2S)-2-Aminocyclopentyl)-5-(4-isopropoxy-2-methylphenyl)-4-oxo-4,5-dihydro-3H-1-thia-3,5,8-triazaacenaphthylene-2-carboxamide; | 6.32 |
| 454 | N-((1S,3R)-3-Acetamidocyclopentyl)-5-(4-isopropoxy-2-methylphenyl)-4-oxo-4,5-dihydro-3H-1-thia-3,5,8-triazaacenaphthylene-2-carboxamide; | 6.21 |
| 455 | N-((1R,2S)-2-Aminocyclopentyl)-5-(3-isopropylphenyl)-4-oxo-4,5-dihydro-3H-1-thia-3,5,8-triazaacenaphthylene-2-carboxamide; | <6 |
| 456 | N-((1R,2R)-2-Hydroxycyclopentyl)-5-(4-isopropoxy-2-methylphenyl)-4-oxo-4,5-dihydro-3H-1-thia-3,5,8-triazaacenaphthylene-2-carboxamide; | <6 |

| Ex # | Compound Name | BTK_I_binding pIC50 |
|---|---|---|
| 457 | N-((1S,2R)-2-Aminocyclohexyl)-4-oxo-5-(4-phenoxyphenyl)-4,5-dihydro-3H-1-thia-3,5,8-triazaacenaphthylene-2-carboxamide; | 5.81 |
| 458 | N-((1S,2S)-2-Acrylamidocyclopentyl)-5-(2-methyl-4-phenoxyphenyl)-4-oxo-4,5-dihydro-3H-1-thia-3,5,8-triazaacenaphthylene-2-carboxamide; | 7.53 |
| 459 | N-((1S,2R)-2-Acrylamidocyclopentyl)-5-(2-methyl-4-phenoxyphenyl)-4-oxo-4,5-dihydro-3H-1-thia-3,5,8-triazaacenaphthylene-2-carboxamide; | 7.13 |
| 460 | 5-(4-(3-((2-Cyanophenoxy)methyl)phenoxy)-2-methylphenyl)-N-cyclohexyl-4-oxo-4,5-dihydro-3H-1-thia-3,5,8-triazaacenaphthylene-2-carboxamide; | 6.78 |
| 461 | N-(5-(4-(3-((2-Cyanophenoxy)methyl)phenoxy)-2-methylphenyl)-4-oxo-4,5-dihydro-3H-1-thia-3,5,8-triazaacenaphthylen-2-yl)cyclopropanecarboxamide; | 6.46 |
| 462 | N-Cyclohexyl-5-(2-methyl-4-phenoxyphenyl)-4-oxo-4,5-dihydro-3H-1-thia-3,5,8-triazaacenaphthylene-2-carboxamide; | 6.33 |
| 463 | N-Cyclohexyl-4-oxo-5-(4-phenoxyphenyl)-4,5-dihydro-3H-1-thia-3,5,8-triazaacenaphthylene-2-carboxamide; | 6.22 |
| 464 | N1-((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide; | 6.64 |
| 465 | N-((1R,2S)-2-Acrylamidocyclopentyl)-5-(4-methyl-6-(pyrimidin-2-yloxy)pyridin-3-yl)-4-oxo-4,5-dihydro-3H-1-thia-3,5,8-triazaacenaphthylene-2-carboxamide; | 7.25 |
| 466 | N-((1R,2S)-2-((E)-2-Cyano-3-cyclopropylacrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide; | 7.63 |
| 467 | N-((1R,2S)-2-Acrylamidocyclohexyl)-5-(4-methyl-6-(pyridazin-3-yloxy)pyridin-3-yl)-4-oxo-4,5-dihydro-3H-1-thia-3,5,8-triazaacenaphthylene-2-carboxamide; | <6 |
| 468 | N-((1R,2S)-2-Acrylamidocyclopentyl)-5-(2-methyl-6-(pyrimidin-2-yloxy)pyridin-3-yl)-4-oxo-4,5-dihydro-3H-1-thia-3,5,8-triazaacenaphthylene-2-carboxamide; | 6.52 |
| 476 | N-((1R,2S)-2-Acrylamidocyclopentyl)-4-oxo-5-(5-(pyridazin-3-yloxy)pyridin-2-yl)-4,5-dihydro-3H-1-thia-3,5,8-triazaacenaphthylene-2-carboxamide; | 6.20 |
| 477 | N-((1R,2S)-2-Acrylamidocyclopentyl)-5-(6'-methyl-2-oxo-2H-[1,2'-bipyridin]-5'-yl)-4-oxo-4,5-dihydro-3H-1-thia-3,5,8-triazaacenaphthylene-2-carboxamide; | 6.85 |
| 478 | N-((1R,2S)-2-Acrylamidocyclopentyl)-5-(2-methyl-6-(pyridin-2-yloxy)pyridin-3-yl)-4-oxo-4,5-dihydro-3H-1-thia-3,5,8-triazaacenaphthylene-2-carboxamide; | 7.64 |
| 479 | N-((1R,2S)-2-Acrylamidocyclopentyl)-5-(5-((6-methylpyridin-2-yl)oxy)pyridin-2-yl)-4-oxo-4,5-dihydro-3H-1-thia-3,5,8-triazaacenaphthylene-2-carboxamide; | 7.54 |
| 480 | N-((1R,2S)-2-Acrylamidocyclopentyl)-4-oxo-5-(5-(pyridin-2-yloxy)pyridin-2-yl)-4,5-dihydro-3H-1-thia-3,5,8-triazaacenaphthylene-2-carboxamide; | 7.59 |
| 481 | N-((1R,2S)-2-Acrylamidocyclopentyl)-5-(5-((6-methylpyridin-3-yl)oxy)pyridin-2-yl)-4-oxo-4,5-dihydro-3H-1-thia-3,5,8-triazaacenaphthylene-2-carboxamide; | 7.33 |
| 482 | N-((1R,2S)-2-Acrylamidocyclopentyl)-5-(2-methyl-4-(pyrimidin-5-yloxy)phenyl)-4-oxo-4,5-dihydro-3H-1-thia-3,5,8-triazaacenaphthylene-2-carboxamide; | 7.79 |
| 483 | N-((1R,2S)-2-Acrylamidocyclopentyl)-5-(4-methyl-6-((6-methylpyridin-2-yl)oxy)pyridin-3-yl)-4-oxo-4,5-dihydro-3H-1-thia-3,5,8-triazaacenaphthylene-2-carboxamide; | 7.49 |
| 484 | N-((1R,2S)-2-Acrylamidocyclopentyl)-4-oxo-5-(5-(pyrimidin-2-yloxy)pyridin-2-yl)-4,5-dihydro-3H-1-thia-3,5,8-triazaacenaphthylene-2-carboxamide; | 6.93 |
| 485 | N-((1R,2S)-2-Acrylamidocyclopentyl)-4-oxo-5-(5-(pyrimidin-5-yloxy)pyridin-2-yl)-4,5-dihydro-3H-1-thia-3,5,8-triazaacenaphthylene-2-carboxamide; | 6.59 |
| 486 | N-((1R,2S)-2-Acrylamidocyclopentyl)-5-(4-methyl-6-(pyrimidin-5-yloxy)pyridin-3-yl)-4-oxo-4,5-dihydro-3H-1-thia-3,5,8-triazaacenaphthylene-2-carboxamide; | 7.39 |
| 487 | N-((1R,2S)-2-Acrylamidocyclopentyl)-5-(4-methyl-6-((6-methylpyridin-3-yl)oxy)pyridin-3-yl)-4-oxo-4,5-dihydro-3H-1-thia-3,5,8-triazaacenaphthylene-2-carboxamide; | 6.87 |
| 488 | N-((1R,2S)-2-Acrylamidocyclopentyl)-5-(4-methyl-6-(pyridin-2-yloxy)pyridin-3-yl)-4-oxo-4,5-dihydro-3H-1-thia-3,5,8-triazaacenaphthylene-2-carboxamide; | 7.62 |

-continued

| Ex # | Compound Name | BTK_I_binding pIC50 |
|---|---|---|
| 489 | N-((1R,2S)-2-Acrylamidocyclopentyl)-5-(4-methyl-6-((2-methylpyridin-3-yl)oxy)pyridin-3-yl)-4-oxo-4,5-dihydro-3H-1-thia-3,5,8-triazaacenaphthylene-2-carboxamide; | 7.03 |
| 490 | N-((1R,2S)-2-Acrylamidocyclopentyl)-5-(4-methyl-6-(pyridin-3-yloxy)pyridin-3-yl)-4-oxo-4,5-dihydro-3H-1-thia-3,5,8-triazaacenaphthylene-2-carboxamide; | 7.40 |
| 491 | N-((1R,2S)-2-Acrylamidocyclopentyl)-4-oxo-5-(5-(pyridin-3-yloxy)pyridin-2-yl)-4,5-dihydro-3H-1-thia-3,5,8-triazaacenaphthylene-2-carboxamide; | 7.43 |
| 492 | N-((1R,2S)-2-Acrylamidocyclopentyl)-5-(2-methyl-6-(pyrimidin-5-yloxy)pyridin-3-yl)-4-oxo-4,5-dihydro-3H-1-thia-3,5,8-triazaacenaphthylene-2-carboxamide; | 6.66 |
| 493 | N-((1R,2S)-2-Acrylamidocyclopentyl)-5-(5-((2-methylpyridin-3-yl)oxy)pyridin-2-yl)-4-oxo-4,5-dihydro-3H-1-thia-3,5,8-triazaacenaphthylene-2-carboxamide; | 7.32 |
| 494 | N-((1R,2S)-2-Acrylamidocyclopentyl)-5-(2-methyl-6-(pyridin-3-yloxy)pyridin-3-yl)-4-oxo-4,5-dihydro-3H-1-thia-3,5,8-triazaacenaphthylene-2-carboxamide; | 7.37 |
| 495 | N-((1R,2S)-2-Acrylamidocyclopentyl)-5-(2-methyl-6-((6-methylpyridin-3-yl)oxy)pyridin-3-yl)-4-oxo-4,5-dihydro-3H-1-thia-3,5,8-triazaacenaphthylene-2-carboxamide; and | 6.63 |
| 508 | N-((1R,2S)-2-acrylamidocyclopentyl)-4-oxo-5-(4-(pyrimidin-5-yloxy)phenyl)-4,5-dihydro-3H-1-thia-3,5,8-triazaacenaphthylene-2-carboxamide. | 7.48 |

Aspects

The disclosure is also directed to the following aspects:

Aspect 1. A compound of formula I:

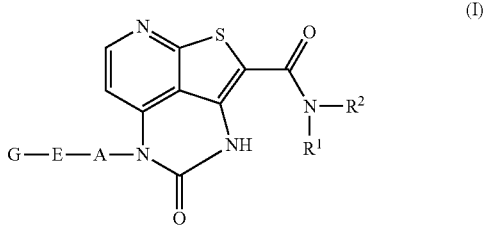

(I)

wherein
$R^1$ is H or $C_{1-6}$alkyl;
$R^2$—$C_{0-6}$alk-cycloalkyl optionally substituted with 1, 2, or 3 substituents selected from the group consisting of $NR^8$—C(O)—C($R^3$)=C$R^4$($R^5$); —$NR^6R^7$; —OH; —CN; oxo; —O—$C_{1-6}$alkyl; halogen; —$C_{1-6}$alkyl; $C_{1-6}$haloalkyl; —$C_{1-6}$alk-OH; —$C_{3-6}$cycloalkyl; —$C_{1-6}$alkaryl; —SO$_2$$C_{1-6}$alkyl; —SO$_2$$C_{2-6}$alkenyl; —$NR^8$—C(O)—$C_{1-6}$ alk-$NR^6R^7$; —$NR^8$—C(O)—$C_{1-6}$alkyl; —$NR^8$—C(O)—O—$C_{1-6}$alkyl; —$NR^8$—C(O)—$C_{3-6}$cycloalkyl; —$NR^8$—C(O)H; —$NR^8$—C(O)—$C_{3-6}$cycloalkyl; —$NR^8$—C(O)—$C_{1-6}$haloalkyl; —$NR^8$—C(O)-alkynyl; —$NR^8$—C(O)—$C_{6-10}$aryl; —$NR^8$—C(O)-heteroaryl; —$NR^8$—C(O)—$C_{1-6}$alk-CN; —$NR^8$—C(O)—$C_{1-6}$alk-OH; —$NR^8$—C(O)—$C_{1-6}$alk-SO$_2$—$C_{1-6}$alkyl; —$NR^8$—C(O)—$C_{1-6}$alk-$NR^6R^7$; —$NR^8$—C(O)—$C_{1-6}$alk-O—$C_{1-6}$ alkyl wherein the $C_{1-6}$alk- is optionally substituted with OH, —O$C_{1-6}$alkyl, or —$NR^6R^7$; and —$NR^8$—C(O)—$C_{0-6}$alk-heterocycloalkyl wherein the —$C_{0-6}$alk- is optionally substituted with oxo and the heterocycloalkyl is optionally substituted with —$C_{1-6}$alkyl;
wherein $R^6$ and $R^7$ are each independently H; —$C_{1-6}$alkyl; —$C_{3-6}$cycloalkyl, —C(O)H, —CN;
$R^3$ is H, —CN; halogen; —$C_{1-6}$haloalkyl; or —$C_{1-6}$alkyl;

$R^4$ and $R^5$ each independently H, —$C_{0-6}$alk-$NR^6R^7$; —$C_{1-6}$alk-OH;
—$C_{0-6}$alk-$C_{3-6}$cycloalkyl optionally substituted with $C_{1-6}$alkyl; halogen;
—$C_{1-6}$alkyl; —O$C_{1-6}$alkyl; —$C_{1-6}$alk-O—$C_{1-6}$alkyl;
—$C_{1-6}$alk-NH—$C_{0-6}$alk-O—$C_{1-6}$alkyl; —$C_{0-6}$alk-heterocycloalkyl optionally substituted with C(O)$C_{1-6}$alkyl or $C_{1-6}$alkyl; —$C_{1-6}$alk-NHSO$_2$—$C_{1-6}$alkyl;
—$C_{1-6}$alk-SO$_2$—$C_{1-6}$alkyl; —NHC(O)—$C_{1-6}$alkyl; or -linker-PEG-Biotin;
$R^8$ is H or $C_{1-6}$alkyl;
A is a bond; pyridyl; phenyl; napthalenyl; pyrimidinyl; pyrazinyl; pyridazinyl; benzo[d][1,3]dioxolyl optionally substituted with halogen; benzothiophenyl; or pyrazolyl; wherein the A is optionally substituted with 1, 2, or 3 substituents independently selected from the group consisting of —$C_{1-6}$alkyl; halogen; —SF$_5$; —O$C_{1-6}$alkyl; —C(O)—$C_{1-6}$alkyl; and —$C_{1-6}$haloalkyl;
E is O—; a bond; —C(O)—NH—; —CH$_2$—; or —CH$_2$—O—;
G is H; —$C_{3-6}$cycloalkyl; -phenyl; -thiophenyl; —$C_{1-6}$alkyl; -pyrimidinyl; -pyridyl; -pyridazinyl; -benzofuranyl; —$C_{1-6}$haloalkyl; -heterocycloalkyl that contains an oxygen heteroatom; -phenyl-CH$_2$—O-phenyl; —$C_{1-6}$alk-O—$C_{1-6}$alkyl; —$NR^6R^7$; —SO$_2$$C_{1-6}$alkyl; or OH; wherein the phenyl; pyridyl; pyridazinyl; benzofuranyl; or thiophenyl is optionally substituted with 1, 2, or 3 substituents independently selected from the group consisting of halogen; —$C_{1-6}$alkyl; —$C_{1-6}$haloalkyl; —O$C_{1-6}$ haloalkyl; —$C_{3-6}$cycloalkyl; —O$C_{1-6}$alkyl; —CN; —OH; —$C_{1-6}$alk-O—$C_{1-6}$alkyl; —C(O)—$NR^6R^7$; or —C(O)—$C_{1-6}$alkyl;
or a stereoisomer or isotopic variant thereof;
or a pharmaceutically acceptable salt thereof.
Aspect 2. The compound of aspect 1, wherein $R^1$ is H.
Aspect 3. The compound of any one of the preceding aspects, wherein $R^2$ is cyclopentyl.
Aspect 4. The compound of any one of the preceding aspects, wherein $R^2$ is substituted with 1 or 2 substituents, preferably $R^2$ is substituted with 1 substituent.

Aspect 5. The compound of aspect 4, wherein $R^2$ is substituted with oxo.

Aspect 6. The compound of aspect 4 or aspect 5, wherein $R^2$ is substituted with halogen; —CN; —OH; —CN; —$C_{1-6}$alkyl; —$C_{1-6}$alk-OH; —$OC_{1-6}$alkyl; —$C_{3-6}$cycloalkyl; or —$C_{1-6}$alkaryl.

Aspect 7. The compound of any one of aspects 4 to 6, wherein $R^2$ is substituted with $NR^8$—C(O)H; —$NR^8$—C(O)—$C_{1-6}$alkyl; —$NR^8$—C(O)—$C_{3-6}$cycloalkyl; —$NR^8$—C(O)—$C_{1-6}$haloalkyl; —$NR^8$—C(O)-alkynyl; —$NR^8$—C(O)—$C_{6-10}$aryl; —$NR^8$—C(O)—$C_{1-6}$alk-CN; —$NR^8$—C(O)—$C_{1-6}$alk-OH; —$NR^8$—C(O)—$C_{1-6}$alk-SO$_2$—$C_{1-6}$alkyl; —$NR^8$—C(O)—O—$C_{1-6}$alkyl; —$NR^8$—C(O)—$C_{1-6}$alk-$NR^6R^7$; or —$NR^8$—C(O)—$C_{1-6}$alk-O—$C_{1-6}$alkyl wherein the $C_{1-6}$alk- is optionally substituted with OH, —$OC_{1-6}$alkyl, or —$NR^6R^7$.

Aspect 8. The compound of any one of aspects 4 to 7, wherein $R^2$ is substituted with —$NR^8$—C(O)-heteroaryl or $NR^8$—C(O)—$C_{0-6}$alk-heterocycloalkyl wherein the heterocycloalkyl is optionally substituted with —$C_{1-6}$alkyl.

Aspect 9. The compound of any one of aspects 4 to 8, wherein $R^2$ is substituted with —$SO_2C_{1-6}$alkyl; —$NR^8$—C(O)—$C_{1-6}$alk-SO$_2$—$C_{1-6}$alkyl; or —$SO_2C_{2-6}$alkenyl.

Aspect 10. The compound of any one of aspects 4 to 9, wherein $R^2$ is substituted with —$NR^8$—C(O)—C($R^3$)=CR$^4$($R^5$).

Aspect 11. The compound of aspect 10, wherein $R^8$ is H.

Aspect 12. The compound of aspect 10 or aspect 11, wherein $R^3$ is H.

Aspect 13. The compound of aspect 10 or aspect 11, wherein $R^3$ is CN.

Aspect 14. The compound of aspect 10 or aspect 11, wherein $R^3$ is F or Cl.

Aspect 15. The compound of any one of aspects 10 to 14, wherein one of $R^4$ and $R^5$ is H.

Aspect 16. The compound of any one of aspect 10 to 15, wherein $R^4$ is H and $R^5$ is H.

Aspect 17. The compound of any one of aspect 10 to 14, wherein one of $R^4$ and $R^5$ is halogen; —$C_{1-6}$alkyl; —$OC_{1-6}$ alkyl; —$C_{0-6}$alk-$C_{3-6}$cycloalkyl optionally substituted with $C_{1-6}$ alkyl; or —$C_{1-6}$alk-OH.

Aspect 18. The compound of any one of aspects 10 to 14, wherein one of $R^4$ and $R^5$ is $C_{0-6}$ alk-$NR^6R^7$, —$C_{1-6}$alk-$NR^6R^7$, or —$C_{1-6}$alk-NH—O—$C_{1-6}$alkyl.

Aspect 19. The compound of any one of aspects 10 to 14, wherein one of $R^4$ and $R^5$ is —$C_{0-6}$alk-heterocycloalkyl optionally substituted with C(O)$C_{1-6}$alkyl or C(O)$C_{1-6}$alkyl; or —$C_{1-6}$alk-O—$C_{1-6}$alkyl.

Aspect 20. The compound of any one of aspects 10 to 14, wherein one of $R^4$ and $R^5$ is —NHC(O)—$C_{1-6}$alkyl.

Aspect 21. The compound of any one of aspects 10 to 14, wherein one of $R^4$ and $R^5$ is —$C_{1-6}$alk-NHSO$_2$—$C_{1-6}$alkyl or —$C_{1-6}$alk-SO$_2$—$C_{1-6}$alkyl.

Aspect 22. The compound of any one of the preceding aspects, wherein A is phenyl.

Aspect 23. The compound of any one of aspects 1-21, wherein A is pyridyl.

Aspect 24. The compound of any one of aspects 1-21, wherein A is pyrimidinyl.

Aspect 25. The compound of any one of aspects 1-21, wherein A is pyrazinyl.

Aspect 26. The compound of any one of aspects 1-21, wherein A is pyridazinyl.

Aspect 27. The compound of any one of aspects 22 to 26, wherein A is substituted with 1 or 2 substitutents.

Aspect 28. The compound of aspect 27, wherein A is substituted with —$C_{1-6}$alkyl, preferably $CH_3$.

Aspect 29. The compound of any one of the preceding aspects, wherein E is O.

Aspect 30. The compound of any one of aspects 1-28, wherein E is a bond.

Aspect 31. The compound of any one of aspects 1-30, wherein G is —$C_{1-6}$alkyl; —$C_{1-6}$haloalkyl; —$C_{1-6}$alk-O—$C_{1-6}$alkyl; or —$C_{3-6}$cycloalkyl.

Aspect 32. The compound of any one of aspects 1-30, wherein G is —$C_{1-6}$alkyl or —$C_{3-6}$-cycloalkyl.

Aspect 33. The compound of any one of aspects 1-30, wherein G is —$NR^6R^7$ or OH.

Aspect 34. The compound of any one of aspects 1-30, wherein G is -heterocycloalkyl that contains an oxygen heteroatom.

Aspect 35. The compound of any one of aspects 1-30, wherein G is —$SO_2C_{1-6}$alkyl.

Aspect 36. The compound of any one of aspects 1-30, wherein G is phenyl.

Aspect 37. The compound of any one of aspects 1-30, wherein G is pyridyl.

Aspect 38. The compound of any one of aspects 1-30, wherein G is pyrimidinyl or pyridazinyl.

Aspect 39. The compound of any one of aspects 1-30, wherein G is benzofuranyl or thiophenyl.

Aspect 40. The compound of any one of aspects 1-30, wherein G is -phenyl-$CH_2$—O-phenyl.

Aspect 41. The compound of any one of aspects 36-40, wherein G is substituted with 1 or 2 substitutents.

Aspect 42. The compound of aspect 41, wherein G is substituted with halogen.

Aspect 43. The compound of aspect 41 or 42, wherein G is substituted with —$C_{1-6}$alkyl; —$C_{1-6}$ haloalkyl; —$OC_{1-6}$haloalkyl; —$C_{3-6}$cycloalkyl; —$OC_{1-6}$alkyl; —$C_{1-6}$alk-O—$C_{1-6}$alkyl; or —C(O)—$C_{1-6}$ alkyl.

Aspect 44. The compound of any one of aspects 41-43, wherein G is substituted with CN.

Aspect 45. The compound of any one of aspects 41-44, wherein G is substituted with OH.

Aspect 46. The compound of any one of aspects 41-45, wherein G is substituted with —C(O)—$NR^6R^7$.

Aspect 47. The compound of any one of aspects 1-21, wherein A-E-G is

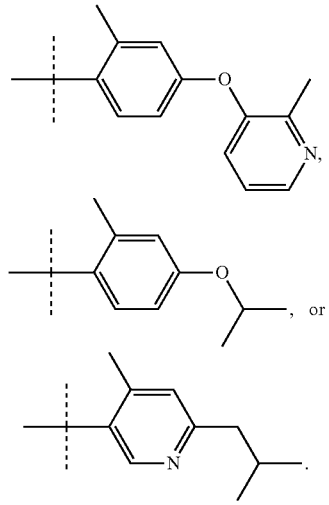

Aspect 48. The compound of aspect 1, wherein R¹ is H; R² is C₀alk-cyclopentyl substituted with 1 or 2 substituents wherein one of the substituents is —NR⁸—C(O)—C(R³)=CR⁴(R⁵), wherein R³, R⁴, and R⁵ are each H; A is phenyl or pyridyl substituted with CH₃, E is O or a bond; and G is phenyl or C₁₋₆ alkyl.

Aspect 49. The compound of aspect 48, wherein R² is substituted with 1 substituent that is —NR⁸—C(O)—C(R³)=CR⁴(R⁵).

Aspect 50. The compound of aspect 48 or 49, wherein A-E-G is

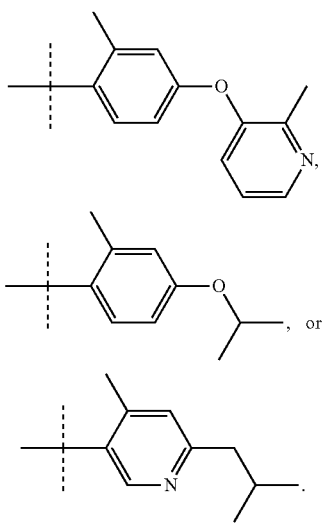

Aspect 51. The compound of any one of aspects 48, 49, or 50, wherein the compound of formula I is

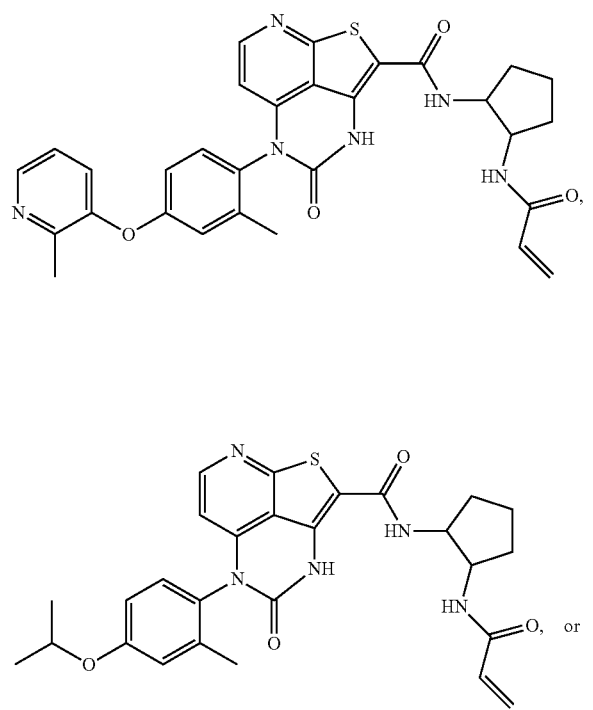

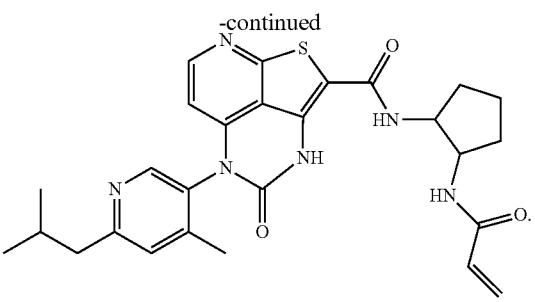

Aspect 52. The compound of any one of the preceding aspects that is a pharmaceutically acceptable salt.

Aspect 53. A pharmaceutical composition comprising a compound of any one of aspects 1-51, or a pharmaceutically acceptable salt thereof, and a pharmaceutically acceptable excipient.

Aspect 54. A method of inhibiting Bruton's tyrosine kinase comprising contacting the kinase with a compound of any one of aspects 1-51.

Aspect 55. A method of treating cancer in a patient comprising administering to the patient a compound of any one of aspects 1-51, or a pharmaceutically acceptable salt thereof.

Aspect 56. The method of aspect 55, wherein the cancer is mantle cell lymphoma, chronic lymphocytic leukemia, macroglobulinemia, or multiple myeloma.

Aspect 57. A method of treating systemic lupus erythematosus in a patient comprising administering to the patient a compound of any one of aspects 1-51, or a pharmaceutically acceptable salt thereof.

Aspect 58. A method of treating a pemphigus disorder or a pemphigoid disorder in a patient comprising administering to the patient a compound of any one of aspects 1-51, or a pharmaceutically acceptable salt thereof Aspect 59. A method of treating rheumatoid arthritis in a patient comprising administering to the patient a compound of any one of aspects 1-51, or a pharmaceutically acceptable salt thereof.

Aspect 60. A method of making a compound of any one of claims 1-51, or a pharmaceutically acceptable salt thereof.

Aspect 61. A compound as depicted in this disclosure.

What is claimed is:
1. A compound of Formula (I):

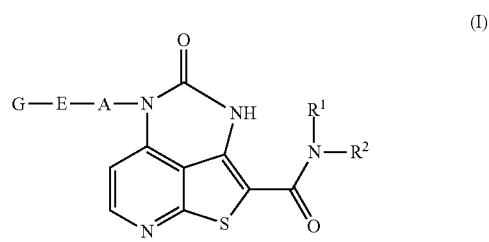

wherein
R¹ is H;
R² is selected from the group consisting of: CH₂-cyclohexyl, wherein the cyclohexyl is optionally substituted with OH; 3-hydroxyadamantan-1-yl; and C₃₋₆cycloalkyl optionally substituted with 1, 2, or 3 substituents each independently selected from the group consisting of: OH, halogen, C₁₋₆alkyl, C₁₋₆haloalkyl, OC₁₋₆ alkyl, CN, NR⁶R⁷, NR⁸—C(O)H, NR⁸—C (O)—C$_{1-6}$alkyl, NR$^8$—C(O)—C$_{1-6}$haloalkyl, NR$^8$—C(O)—O—C$_{1-6}$alkyl, NR$^8$—C(O)—C$_{1-6}$alk-OH, NR$^8$—C(O)—C$_{1-6}$alk-NR$^6$R$^7$, and NR$^8$—C(O)—C(R$^3$)=CR$^4$(R$^5$); wherein R$^3$ is selected from the group consisting of: H, CN, halogen, C$_{1-6}$haloalkyl, and C$_{1-6}$alkyl;

R$^4$ and R$^5$ are each independently selected from the group consisting of: H; C$_{0-6}$alk-NR$^6$R$^7$; C$_{1-6}$alk-O—C$_{1-6}$alkyl; C$_{3-6}$cycloalkyl; heterocycloalkyl optionally substituted with C$_{1-6}$alkyl; and -linker-PEG-Biotin;

R$^6$ and R$^7$ are each independently selected from the group consisting of: H, C$_{1-6}$alkyl, C(O)H, and CN; and R$^8$ is H;

or R$^1$ and R$^2$, together with the nitrogen atom to which they are attached, form a pyrrolidinyl ring optionally substituted with NR$^6$R$^7$, wherein R$^6$ and R$^7$ are each independently selected from the group consisting of H; C$_{1-6}$alkyl; NR$^8$—C(O)—C$_{1-6}$alkyl; and NR$^8$—C(O)—C(R$^3$)=CR$^4$(R$^5$), wherein R$^3$ is H or CN; R$^4$ is H; and R$^5$ is H or cyclopropyl;

A is selected from the group consisting of: pyridyl; phenyl; pyrimidinyl; pyrazinyl; pyridin-2(1H)-one; and pyridazinyl; wherein the A is optionally substituted with 1, 2, or 3 substituents each independently selected from the group consisting of: halogen, C$_{1-6}$alkyl, C$_{1-6}$haloalkyl, and OC$_{1-6}$alkyl;

E is selected from the group consisting of: O, a bond, and CH$_2$;

G is selected from the group consisting of: H; halogen; C$_{1-6}$alkyl; C$_{1-6}$haloalkyl; NH(C$_{1-6}$alkyl); C$_{3-6}$cycloalkyl; phenyl; pyrimidinyl; pyridyl; pyridazinyl; pyridin-2(1H)-one; heterocycloalkyl that contains an oxygen heteroatom; and phenyl-CH$_2$—O-phenyl, wherein the —O-phenyl is substituted with CN; wherein the phenyl; pyridyl; pyridazinyl; and pyridin-2(1H)-one is optionally substituted with 1, 2, or 3 substituents each independently selected from the group consisting of: halogen, C$_{1-6}$alkyl, C$_{1-6}$haloalkyl, OC$_{1-6}$haloalkyl, and OC$_{1-6}$alkyl;

a stereoisomer thereof; an isotopic variant thereof; or a pharmaceutically acceptable salt thereof.

2. The compound of claim 1, wherein R$^1$ is H.

3. The compound of claim 1, wherein R$^2$ is cyclopentyl.

4. The compound of claim 1, wherein R$^2$ is substituted with NR$^8$—C(O)—C(R$^3$)=CR$^4$(R$^5$).

5. The compound of claim 1, wherein R$^8$ is H.

6. The compound of claim 1, wherein R$^3$ is H.

7. The compound of claim 1, wherein R$^4$ is H and R$^5$ is H.

8. The compound of claim 1, wherein A is phenyl.

9. The compound of claim 1, wherein A is pyridyl.

10. The compound of claim 1, wherein A is substituted with C$_{1-6}$alkyl.

11. The compound of claim 1, wherein E is O.

12. The compound of claim 1, wherein E is a bond.

13. The compound of claim 1, wherein G is phenyl.

14. The compound of claim 1, wherein G is pyridyl.

15. The compound of claim 1, wherein G is substituted with C$_{1-6}$alkyl.

16. The compound of claim 1, wherein A-E-G is

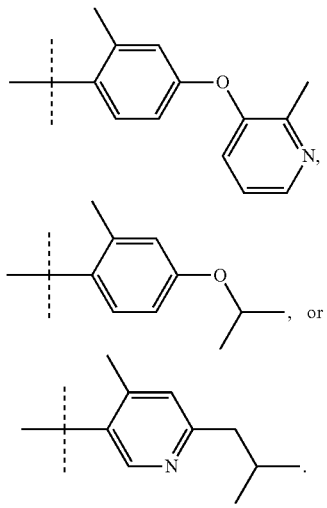

17. The compound of claim 1, wherein R$^1$ is H; R$^2$ is cyclopentyl substituted with 1 or 2 substituents wherein one of the substituents is NR$^8$—C(O)—C(R$^3$)=CR$^4$(R$^5$), wherein R$^3$, R$^4$, and R$^5$ are each H; A is phenyl or pyridyl, wherein the phenyl or pyridyl is substituted with CH$_3$, E is O or a bond; and G is phenyl or C$_{1-6}$alkyl.

18. A compound selected from the group consisting of:
N-((1S,4S)-4-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;
N-((1R,3  S)-3-Acrylamidocyclohexyl)-5-(2-methyl-4-phenoxyphenyl)-4-oxo-4,5-dihydro-3H-1-thia-3,5,8-triazaacenaphthylene-2-carboxamide;
N-((1S,4S)-4-Acrylamidocyclohexyl)-5-(2-methyl-4-phenoxyphenyl)-4-oxo-4,5-dihydro-3H-1-thia-3,5,8-triazaacenaphthylene-2-carboxamide;
N-((1R,2R)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide;
N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;
N-((1R,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide;
N-((1R,2S)-2-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide;
N-((1R,2S)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide;
N-((1R,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide;
N-((1R,2S)-2-Aminocyclohexyl)-5-(2-methyl-4-phenoxyphenyl)-4-oxo-4,5-dihydro-3H-1-thia-3,5,8-triazaacenaphthylene-2-carboxamide;
N-((1R,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide;
N-((1R,2S)-2-Aminocyclopentyl)-5-(2-methyl-4-phenoxyphenyl)-4-oxo-4,5-dihydro-3H-1-thia-3,5,8-triazaacenaphthylene-2-carboxamide;
N-((1R,4R)-4-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1R,4R)-4-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1R,4R)-4-Methoxycyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-((E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide;

N-((1S,2 S)-2-Hydroxycyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1R,2R)-2-(methylamino)cyclopentyl)-4-oxo-4,5-dihydro-3H-1-thia-3,5,8-triazaacenaphthylene-2-carboxamide;

N-((1R,2R)-2-Aminocyclopentyl)-5-(2-methyl-4-phenoxyphenyl)-4-oxo-4,5-dihydro-3H-1-thia-3,5,8-triazaacenaphthylene-2-carboxamide;

N-((1S,4S)-4-Cyanamidocyclohexyl)-5-(2-methyl-4-phenoxyphenyl)-4-oxo-4,5-dihydro-3H-1-thia-3,5,8-triazaacenaphthylene-2-carboxamide;

N-((1R,3 S)-3-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,4 S)-4-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2R)-2-propionamidocyclopentyl)-4,5-dihydro-3H-1-thia-3,5,8-triazaacenaphthylene-2-carboxamide;

N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide;

N-Cyclopentyl-5-(2-methyl-4-phenoxyphenyl)-4-oxo-4,5-dihydro-3H-1-thia-3,5,8-triazaacenaphthylene-2-carboxamide;

N-((1R,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1r,3 s,5R,7S)-3-Hydroxyadamantan-1-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(2-(methylamino)cyclohexyl)-4-oxo-4,5-dihydro-3H-1-thia-3,5,8-triazaacenaphthylene-2-carboxamide;

N-((1S,2 S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1R,2 S)-2-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2S)-2-propionamidocyclopentyl)-4,5-dihydro-3H-1-thia-3,5,8-triazaacenaphthylene-2-carboxamide;

5-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide;

N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Aminocyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Aminocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2R)-2-propionamidocyclohexyl)-4,5-dihydro-3H-1-thia-3,5,8-triazaacenaphthylene-2-carboxamide;

N-((1R,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2S)-2-propionamidocyclopentyl)-4,5-dihydro-3H-1-thia-3,5,8-triazaacenaphthylene-2-carboxamide;

5-(2-Methyl-4-phenoxyphenyl)-N-((1S,2S)-2-(methylamino)cyclopentyl)-4-oxo-4,5-dihydro-3H-1-thia-3,5,8-triazaacenaphthylene-2-carboxamide;

N-((1R,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,2R)-2-(methylamino)cyclohexyl)-4-oxo-4,5-dihydro-3H-1-thia-3,5,8-triazaacenaphthylene-2-carboxamide;

N-((1S,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2R)-2-propionamidocyclohexyl)-4,5-dihydro-3H-1-thia-3,5,8-triazaacenaphthylene-2-carboxamide;

N-((1S,2R)-2-Aminocyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Formamidocyclohexyl)-5-(2-methyl-4-phenoxyphenyl)-4-oxo-4,5-dihydro-3H-1-thia-3,5,8-triazaacenaphthylene-2-carboxamide;

N-((1S,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide;

N-((1S,2S)-2-Acrylamidocyclopentyl)-5-(*R)-(2-methyl-4-phenoxyphenyl)-4-oxo-4,5-dihydro-3H-1-thia-3,5,8-triazaacenaphthylene-2-carboxamide;

N-((1S,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2R)-2-propionamidocyclopentyl)-4,5-dihydro-3H-1-thia-3,5,8-triazaacenaphthylene-2-carboxamide;

5-(2-Methyl-4-phenoxyphenyl)-4-oxo-N-((1S,2S)-2-propionamidocyclohexyl)-4,5-dihydro-3H-1-thia-3,5,8-triazaacenaphthylene-2-carboxamide;

N-((1R,2R)-2-Hydroxycyclopentyl)-5-(*R)-(2-methyl-4-phenoxyphenyl)-4-oxo-4,5-dihydro-3H-1-thia-3,5,8-triazaacenaphthylene-2-carboxamide;

N-((1S,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(4-(methylamino)cyclohexyl)-4-oxo-4,5-dihydro-3H-1-thia-3,5,8-triazaacenaphthylene-2-carboxamide;

N-((1S,4S)-4-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;

N-((1S,4S)-4-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1R,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-acrylamidocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide;

N-((1S,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1S,3R)-3-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide;

N-((1S,3R)-3-Aminocyclopentyl)-5-(2-methyl-4-phenoxyphenyl)-4-oxo-4,5-dihydro-3H-1-thia-3,5,8-triazaacenaphthylene-2-carboxamide;

N-((1S,4S)-4-((E)-4-(Dimethylamino)but-2-enamido)cyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,4S)-4-((E)-4-(methylamino)but-2-enamido)cyclohexyl)-4-oxo-4,5-dihydro-3H-1-thia-3,5,8-triazaacenaphthylene-2-carboxamide;

N-((1S,4S)-4-((E)-4-Aminobut-2-enamido)cyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S)-3-(methylamino)cyclopentyl)-4-oxo-4,5-dihydro-3H-1-thia-3,5,8-triazaacenaphthylene-2-carboxamide;

N-Cyclopentyl-5-(*S)-(2-methyl-4-phenoxyphenyl)-4-oxo-4,5-dihydro-3H-1-thia-3,5,8-triazaacenaphthylene-2-carboxamide;

N-Cyclopentyl-5-(*R)-(2-methyl-4-phenoxyphenyl)-4-oxo-4,5-dihydro-3H-1-thia-3,5,8-triazaacenaphthylene-2-carboxamide;

N-((1S,4S)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide;

N-((1R,4R)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,4R)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide;

N-((1S,3R)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-((*E)-2-Cyano-3-cyclopropylacrylamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-((*E)-2-Cyano-3-cyclopropylacrylamido)cyclohexyl)-5-(*R)-(2-methyl-4-phenoxyphenyl)-4-oxo-4,5-dihydro-3H-1-thia-3,5,8-triazaacenaphthylene-2-carboxamide;

N-((1R,2R)-2-Aminocyclopentyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;

5-(*R)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;

N-((1S,4S)-4-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-Acetamidocyclohexyl)-5-(*R)-(2-methyl-4-phenoxyphenyl)-4-oxo-4,5-dihydro-3H-1-thia-3,5,8-triazaacenaphthylene-2-carboxamide;

N-(rac-(1,3-cis)-3-Aminocyclopentyl)-4-oxo-5-(4-phenoxyphenyl)-4,5-dihydro-3H-1-thia-3,5,8-triazaacenaphthylene-2-carboxamide;

N-((1R,2S)-2-Aminocyclopentyl)-4-oxo-5-(4-phenoxyphenyl)-4,5-dihydro-3H-1-thia-3,5,8-triazaacenaphthylene-2-carboxamide;

N-((1S,2R)-2-Aminocyclopentyl)-4-oxo-5-(4-phenoxyphenyl)-4,5-dihydro-3H-1-thia-3,5,8-triazaacenaphthylene-2-carboxamide;

N-((1S,4S)-4-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-(Dimethylamino)cyclohexyl)-5-(*R)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-(2-(dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1R,2S)-2-acrylamidocyclopentyl)-4-oxo-5-(4-phenoxyphenyl)-4,5-dihydro-3H-1-thia-3,5,8-triazaacenaphthylene-2-carboxamide;

N-((1R,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

5-([1,1'-Biphenyl]-3-yl)-N-((1R,2 S)-2-acrylamidocyclohexyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(4-phenoxyphenyl)-4,5-dihydro-3H-1-thia-3,5,8-triazaacenaphthylene-2-carboxamide;

N-((1S,3R)-3-Acrylamidocyclopentyl)-5-(4-isopropoxy-2-methylphenyl)-4-oxo-4,5-dihydro-3H-1-thia-3,5,8-triazaacenaphthylene-2-carboxamide;

N-((1R,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1R,2R)-2-(2-(methylamino)acetamido)cyclopentyl)-4-oxo-4,5-dihydro-3H-1-thia-3,5,8-triazaacenaphthylene-2-carboxamide;

N-((1R,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclopentyl)-4-oxo-5-(4-phenoxyphenyl)-4,5-dihydro-3H-1-thia-3,5,8-triazaacenaphthylene-2-carboxamide;

N-((1R,2S)-2-Acrylamidocyclohexyl)-4-oxo-5-(4-phenoxyphenyl)-4,5-dihydro-3H-1-thia-3,5,8-triazaacenaphthylene-2-carboxamide;

N-((1S,4S)-4-Acrylamidocyclohexyl)-4-oxo-5-(4-phenoxyphenyl)-4,5-dihydro-3H-1-thia-3,5,8-triazaacenaphthylene-2-carboxamide;

N-((1R,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclopentyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-N-((1R,2S)-2-(2-(methylamino)acetamido)cyclopentyl)-4-oxo-4,5-dihydro-3H-1-thia-3,5,8-triazaacenaphthylene-2-carboxamide;

N-((1S,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclohexyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-N-((1R,2S)-2-(2-(methylamino)acetamido)cyclohexyl)-4-oxo-4,5-dihydro-3H-1-thia-3,5,8-triazaacenaphthylene-2-carboxamide;

N-((1R,2S)-2-Aminocyclohexyl)-4-oxo-5-(4-phenoxyphenyl)-4,5-dihydro-3H-1-thia-3,5,8-triazaacenaphthylene-2-carboxamide;

N-((1S,2R)-2-Acrylamidocyclopentyl)-4-oxo-5-(4-phenoxyphenyl)-4,5-dihydro-3H-1-thia-3,5,8-triazaacenaphthylene-2-carboxamide;

N-((1R,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2S)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1S,2S)-2-(2-(methylamino)acetamido)cyclopentyl)-4-oxo-4,5-dihydro-3H-1-thia-3,5,8-triazaacenaphthylene-2-carboxamide;

N-((1S,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-5-(3-chloro-4-phenoxyphenyl)-4-oxo-4,5-dihydro-3H-1-thia-3,5,8-triazaacenaphthylene-2-carboxamide;

N-((1R,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Hydroxycyclohexyl)-4-oxo-5-(4-phenoxyphenyl)-4,5-dihydro-3H-1-thia-3,5,8-triazaacenaphthylene-2-carboxamide;

N-((1R,2S)-2-Hydroxycyclopentyl)-4-oxo-5-(4-phenoxyphenyl)-4,5-dihydro-3H-1-thia-3,5,8-triazaacenaphthylene-2-carboxamide;

5-([1,1'-Biphenyl]-3-yl)-N-((1R,2S)-2-aminocyclohexyl)-4-oxo-4,5-dihydro-3H-1-thia-3,5,8-triazaacenaphthylene-2-carboxamide;

N-((1R,3 S)-3-Hydroxycyclohexyl)-4-oxo-5-(4-phenoxyphenyl)-4,5-dihydro-3H-1-thia-3,5,8-triazaacenaphthylene-2-carboxamide;

N-((1S,3 S)-3-Hydroxycyclohexyl)-4-oxo-5-(4-phenoxyphenyl)-4,5-dihydro-3H-1-thia-3,5,8-triazaacenaphthylene-2-carboxamide;

5-([1,1'-Biphenyl]-3-yl)-N-((1R,2R)-2-hydroxycyclopentyl)-4-oxo-4,5-dihydro-3H-1-thia-3,5,8-triazaacenaphthylene-2-carboxamide;

N-((1S,4 S)-4-Aminocyclohexyl)-4-oxo-5-(4-phenoxyphenyl)-4,5-dihydro-3H-1-thia-3,5,8-triazaacenaphthylene-2-carboxamide;

N-(trans-(1R,4R)-4-Aminocyclohexyl)-4-oxo-5-(4-phenoxyphenyl)-4,5-dihydro-3H-1-thia-3,5,8-triazaacenaphthylene-2-carboxamide;

trans-N-((1RS,3RS)-3-Aminocyclopentyl)-4-oxo-5-(4-phenoxyphenyl)-4,5-dihydro-3H-1-thia-3,5,8-triazaacenaphthylene-2-carboxamide;

N-((1S,2 S)-2-Aminocyclopentyl)-4-oxo-5-(4-phenoxyphenyl)-4,5-dihydro-3H-1-thia-3,5,8-triazaacenaphthylene-2-carboxamide;

N-((1R,2R)-2-Aminocyclohexyl)-4-oxo-5-(4-phenoxyphenyl)-4,5-dihydro-3H-1-thia-3,5,8-triazaacenaphthylene-2-carboxamide;

1 tert-Butyl ((1R,3 S)-3-(4-oxo-5-(4-phenoxyphenyl)-4,5-dihydro-3H-1-thia-3,5,8-triazaacenaphthylene-2-carboxamido)cyclopentyl)carbamate;

1 tert-Butyl trans-((1R,4R)-4-(4-oxo-5-(4-phenoxyphenyl)-4,5-dihydro-3H-1-thia-3,5,8-triazaacenaphthylene-2-carboxamido)cyclohexyl)carbamate;

N-((1-Hydroxycyclohexyl)methyl)-4-oxo-5-(4-phenoxyphenyl)-4,5-dihydro-3H-1-thia-3,5,8-triazaacenaphthylene-2-carboxamide;

N-((1S,3R)-3-((E)-4-(Dimethylamino)but-2-enamido)cyclopentyl)-5-(4-isopropoxy-2-methylphenyl)-4-oxo-4,5-dihydro-3H-1-thia-3,5,8-triazaacenaphthylene-2-carboxamide;

N-((1S,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1S,2R)-2-(2-(methylamino)acetamido)cyclopentyl)-4-oxo-4,5-dihydro-3H-1-thia-3,5,8-triazaacenaphthylene-2-carboxamide;

N-((1S,3R)-3-Hydroxycyclohexyl)-4-oxo-5-(4-phenoxyphenyl)-4,5-dihydro-3H-1-thia-3,5,8-triazaacenaphthylene-2-carboxamide;

N-((1S,3R)-3-(2-(Dimethylamino)acetamido)cyclopentyl)-5-(4-isopropoxy-2-methylphenyl)-4-oxo-4,5-dihydro-3H-1-thia-3,5,8-triazaacenaphthylene-2-carboxamide;

4-Oxo-5-(2-phenylpyridin-4-yl)-N-((1S,2R)-2-propionamidocyclopentyl)-4,5-dihydro-3H-1-thia-3,5,8-triazaacenaphthylene-2-carboxamide;

N-((1R,2 S)-2-Aminocyclohexyl)-5-(4-isopropoxy-2-methylphenyl)-4-oxo-4,5-dihydro-3H-1-thia-3,5,8-triazaacenaphthylene-2-carboxamide;

5-(4-Isopropoxy-2-methylphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1S,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

1 tert-Butyl ((1S,4S)-4-(4-oxo-5-(4-phenoxyphenyl)-4,5-dihydro-3H-1-thia-3,5,8-triazaacenaphthylene-2-carboxamido)cyclohexyl)carbamate;

N-((1S,3R)-3-Aminocyclopentyl)-4-oxo-5-(4-phenoxyphenyl)-4,5-dihydro-3H-1-thia-3,5,8-triazaacenaphthylene-2-carboxamide;

N-((1R,2 S)-2-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2 S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(6-phenylpyrimidin-4-yl)-4,5-dihydro-3H-1-thia-3,5,8-triazaacenaphthylene-2-carboxamide;

N-((1R,2 S)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2 S)-2-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2 S)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,2 S)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2 S)-2-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2 S)-2-Acrylamidocyclopentyl)-4-oxo-5-(5-phenoxypyridin-2-yl)-4,5-dihydro-3H-1-thia-3,5,8-triazaacenaphthylene-2-carboxamide;

N-((1S,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Aminocyclohexyl)-5-(2-methyl-4-phenoxyphenyl)-4-oxo-4,5-dihydro-3H-1-thia-3,5,8-triazaacenaphthylene-2-carboxamide;

N-((1R,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(6-cyclobutoxy-4-methylpyridin-3-yl)-4-oxo-4,5-dihydro-3H-1-thia-3,5,8-triazaacenaphthylene-2-carboxamide;

N-((1R,3R)-3-Acrylamidocyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(5-phenoxypyridin-2-yl)-4,5-dihydro-3H-1-thia-3,5,8-triazaacenaphthylene-2-carboxamide;

N-((1S,3R)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide;

N-((1R,3 S)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2 S)-2-Acrylamidocyclopentyl)-4-oxo-5-(4-phenylpyridin-2-yl)-4,5-dihydro-3H-1-thia-3,5,8-triazaacenaphthylene-2-carboxamide;

N-((1S,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1S,3R)-3-Acrylamidocyclopentyl)-5-(3-chloro-4-phenoxyphenyl)-4-oxo-4,5-dihydro-3H-1-thia-3,5,8-triazaacenaphthylene-2-carboxamide;

N-((1R,2 S)-2-Acrylamidocyclopentyl)-4-oxo-5-(5-phenylpyridin-3-yl)-4,5-dihydro-3H-1-thia-3,5,8-triazaacenaphthylene-2-carboxamide;

5-([1,1'-Biphenyl]-3-yl)-N-((1R,2S)-2-acrylamidocyclopentyl)-4-oxo-4,5-dihydro-3H-1-thia-3,5,8-triazaacenaphthylene-2-carboxamide;

N-((1R,2 S)-2-Acrylamidocyclopentyl)-4-oxo-5-(3-(pyridin-2-yl)phenyl)-4,5-dihydro-3H-1-thia-3,5,8-triazaacenaphthylene-2-carboxamide;

N-((1R,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3 S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(2-phenylpyridin-4-yl)-4,5-dihydro-3H-1-thia-3,5,8-triazaacenaphthylene-2-carboxamide;

N-((1S,3R)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2 S)-2-Acrylamidocyclopentyl)-5-(2-methyl-4-(pyridin-3-yloxy)phenyl)-4-oxo-4,5-dihydro-3H-1-thia-3,5,8-triazaacenaphthylene-2-carboxamide;

N-((1R,2R)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(5-phenoxypyrazin-2-yl)-4,5-dihydro-3H-1-thia-3,5,8-triazaacenaphthylene-2-carboxamide;

N-((1R,2 S)-2-Acrylamidocyclopentyl)-4-oxo-5-(3-(pyridin-3-yl)phenyl)-4,5-dihydro-3H-1-thia-3,5,8-triazaacenaphthylene-2-carboxamide;

N-((1R,2 S)-2-Acrylamidocyclopentyl)-4-oxo-5-(6-phenylpyridazin-4-yl)-4,5-dihydro-3H-1-thia-3,5,8-triazaacenaphthylene-2-carboxamide;

N-((1R,2 S)-2-Acrylamidocyclohexyl)-5-(*S)-(6-cyclobutoxy-2-methylpyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(4-isopropoxyphenyl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(2-isopropylpyridin-4-yl)-4-oxo-4,5-dihydro-3H-1-thia-3,5,8-triazaacenaphthylene-2-carboxamide;

N-((1R,3 S)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2 S)-2-Acrylamidocyclohexyl)-5-(*S)-(6-isopropoxy-2-methylpyridin-3-yl)-4-oxo-4,5-dihydro-3H-1-thia-3,5,8-triazaacenaphthylene-2-carboxamide;

N-((1R,2 S)-2-(3-Chloropropanamido)cyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide;

N-((1R,3R)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2R)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(5-phenoxypyridin-2-yl)-4,5-dihydro-3H-1-thia-3,5,8-triazaacenaphthylene-2-carboxamide;

N-((1R,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1RS,3RS)-3-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,2R)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide;

N-((1R,2 S)-2-Acrylamidocyclohexyl)-5-(*S)-(6-cyclobutoxy-4-methylpyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(6-isopropoxy-4-methylpyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(6-(cyclopentyloxy)-4-methylpyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-(pyrimidin-2-yloxy)phenyl)-4-oxo-4,5-dihydro-3H-1-thia-3,5,8-triazaacenaphthylene-2-carboxamide;

N-((1R,2 S)-2-Acrylamidocyclohexyl)-5-(6-isobutoxy-4-methylpyridin-3-yl)-4-oxo-4,5-dihydro-3H-1-thia-3,5,8-triazaacenaphthylene-2-carboxamide;

N-((1S,3 S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1R,3R)-3-(2-(methylamino)acetamido)cyclopentyl)-4-oxo-4,5-dihydro-3H-1-thia-3,5,8-triazaacenaphthylene-2-carboxamide;

N-((1S,3R)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,3 S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2R)-2-Aminocyclopentyl)-5-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide;

N-((1R,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide;

N-((1R,3R)-3-Aminocyclopentyl)-5-(2-methyl-4-phenoxyphenyl)-4-oxo-4,5-dihydro-3H-1-thia-3,5,8-triazaacenaphthylene-2-carboxamide;

N-((1R,3 S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2 S)-2-Acrylamidocyclohexyl)-5-(*R)-(6-isopropoxy-2-methylpyridin-3-yl)-4-oxo-4,5-dihydro-3H-1-thia-3,5,8-triazaacenaphthylene-2-carboxamide;

N-((1R,2R)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,3 S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3 S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2 S)-2-Acrylamidocyclohexyl)-5-(*R)-(6-cyclobutoxy-2-methylpyridin-3-yl)-4-oxo-4,5-dihydro-3H-1-thia-3,5,8-triazaacenaphthylene-2-carboxamide;

N-((1S,3 S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3 S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3 S)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,3 S)-3-(2-(methylamino)acetamido)cyclopentyl)-4-oxo-4,5-dihydro-3H-1-thia-3,5,8-triazaacenaphthylene-2-carboxamide;

N-((1S,3 S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

5-(3-Chloro-4-phenoxyphenyl)-N-((1S,3R)-3-((E)-4-(dimethylamino)but-2-enamido)cyclopentyl)-4-oxo-4,5-dihydro-3H-1-thia-3,5,8-triazaacenaphthylene-2-carboxamide;

5-([1,1'-Biphenyl]-3-yl)-N-((1R,2S)-2-aminocyclopentyl)-4-oxo-4,5-dihydro-3H-1-thia-3,5,8-triazaacenaphthylene-2-carboxamide;

5-(*S)-(2-Methyl-4-phenoxyphenyl)-N-((1R,3 S)-3-(2-(methylamino)acetamido)cyclohexyl)-4-oxo-4,5-dihydro-3H-1-thia-3,5,8-triazaacenaphthylene-2-carboxamide;

N-((1R,3 S)-3-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3 S)-3-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3 S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2 S)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2R)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2 S)-2-Aminocyclohexyl)-4-oxo-5-(6-phenoxypyridin-3-yl)-4,5-dihydro-3H-1-thia-3,5,8-triazaacenaphthylene-2-carboxamide;

N-((1S,2R)-2-Acetamidocyclopentyl)-4-oxo-5-(2-phenylpyridin-4-yl)-4,5-dihydro-3H-1-thia-3,5,8-triazaacenaphthylene-2-carboxamide;

N-((1S,3 S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2 S)-2-Aminocyclohexyl)-4-oxo-5-(2-phenylpyridin-4-yl)-4,5-dihydro-3H-1-thia-3,5,8-triazaacenaphthylene-2-carboxamide;

N-((1R,3 S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2 S)-2-Aminocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2 S)-2-Aminocyclopentyl)-4-oxo-5-(2-phenylpyridin-4-yl)-4,5-dihydro-3H-1-thia-3,5,8-triazaacenaphthylene-2-carboxamide;

N-((1R,2R)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,2 S)-2-Aminocyclopentyl)-4-oxo-5-(6-phenoxypyridin-3-yl)-4,5-dihydro-3H-1-thia-3,5,8-triazaacenaphthylene-2-carboxamide;

N-((1R,2 S)-2-Acrylamidocyclohexyl)-5-(*R)-(6-cyclobutoxy-4-methylpyridin-3-yl)-4-oxo-4,5-dihydro-3H-1-thia-3,5,8-triazaacenaphthylene-2-carboxamide;

N-((1R,2 S)-2-Aminocyclopentyl)-4-oxo-5-(4-phenylpyridin-2-yl)-4,5-dihydro-3H-1-thia-3,5,8-triazaacenaphthylene-2-carboxamide;

N-((1R,2R)-2-Hydroxycyclopentyl)-4-oxo-5-(2-phenylpyridin-4-yl)-4,5-dihydro-3H-1-thia-3,5,8-triazaacenaphthylene-2-carboxamide;

N-((1R,2R)-2-Aminocyclopentyl)-4-oxo-5-(6-phenoxy-pyridin-3-yl)-4,5-dihydro-3H-1-thia-3,5,8-triazaacenaphthylene-2-carboxamide;

N-((1R,2 S)-2-Aminocyclopentyl)-5-(2-isopropylpyridin-4-yl)-4-oxo-4,5-dihydro-3H-1-thia-3,5,8-triazaacenaphthylene-2-carboxamide;

N-((1R,2 S)-2-Aminocyclopentyl)-5-(4-isopropoxyphenyl)-4-oxo-4,5-dihydro-3H-1-thia-3,5,8-triazaacenaphthylene-2-carboxamide;

N-((1S,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,2R)-2-Acrylamidocyclohexyl)-5-(*S)-(4-isopropoxy-2-methylphenyl)-4-oxo-4,5-dihydro-3H-1-thia-3,5,8-triazaacenaphthylene-2-carboxamide;

N-((1 S, S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,3 S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,3 S)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2R)-2-Aminocyclohexyl)-4-oxo-5-(6-phenoxy-pyridin-3-yl)-4,5-dihydro-3H-1-thia-3,5,8-triazaacenaphthylene-2-carboxamide;

N-((1R,2 S)-2-Aminocyclopentyl)-4-oxo-5-(6-phenylpyridazin-4-yl)-4,5-dihydro-3H-1-thia-3,5,8-triazaacenaphthylene-2-carboxamide;

N-((1S,3 S)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2 S)-2-Acetamidocyclopentyl)-4-oxo-5-(2-phenylpyridin-4-yl)-4,5-dihydro-3H-1-thia-3,5,8-triazaacenaphthylene-2-carboxamide;

N-((1R,2 S)-2-Aminocyclopentyl)-4-oxo-5-(6-phenylpyrimidin-4-yl)-4,5-dihydro-3H-1-thia-3,5,8-triazaacenaphthylene-2-carboxamide;

N-((1S,3 S)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,3 S)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2 S)-2-Aminocyclopentyl)-4-oxo-5-(5-phenylpyridin-3-yl)-4,5-dihydro-3H-1-thia-3,5,8-triazaacenaphthylene-2-carboxamide;

N-((1R,2 S)-2-Aminocyclopentyl)-4-oxo-5-(3-(pyridin-2-yl)phenyl)-4,5-dihydro-3H-1-thia-3,5,8-triazaacenaphthylene-2-carboxamide;

N-((1S,2R)-2-(2-(Methylamino)acetamido)cyclopentyl)-4-oxo-5-(2-phenylpyridin-4-yl)-4,5-dihydro-3H-1-thia-3,5,8-triazaacenaphthylene-2-carboxamide;

N-((1R,2 S)-2-Aminocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2 S)-2-Aminocyclopentyl)-5-(4-((tetrahydro-2H-pyran-4-yl)oxy)phenyl)-4,5-dihydro-3H-1-thia-3,5,8-triazaacenaphthylene-2-carboxamide;

racemic cisN-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide;

racemic transN-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide;

N-((1R,2 S)-2-Acrylamidocyclohexyl)-4-oxo-5-(5-phenoxypyridin-2-yl)-4,5-dihydro-3H-1-thia-3,5,8-triazaacenaphthylene-2-carboxamide;

N-((1RS,2RS)-2-Acrylamidocyclopentyl)-5-(2-methyl-6-phenoxypyridin-3-yl)-4-oxo-4,5-dihydro-3H-1-thia-3,5,8-triazaacenaphthylene-2-carboxamide;

N-((1RS,3RS)-3-Aminocyclopentyl)-5-(4-methyl-6-phenoxypyridin-3-yl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2 S)-2-Acrylamidocyclohexyl)-5-(5-phenoxypyrazin-2-yl)-4,5-dihydro-3H-1-thia-3,5,8-triazaacenaphthylene-2-carboxamide;

N-((1R,2 S)-2-acrylamidocyclopentyl)-4-oxo-5-(5-phenoxypyrimidin-2-yl)-4,5-dihydro-3H-1-thia-3,5,8-triazaacenaphthylene-2-carboxamide;

N-((1R,2 S)-2-Acrylamidocyclohexyl)-4-oxo-5-(5-phenoxypyrimidin-2-yl)-4,5-dihydro-3H-1-thia-3,5,8-triazaacenaphthylene-2-carboxamide;

N-((1R,2 S)-2-Acrylamidocyclopentyl)-5-(S)-(6-isobutyl-4-methylpyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(*S)-(4-(pyridin-3-yloxy)phenyl)-4,5-dihydro-3H-1-thia-3,5,8-triazaacenaphthylene-2-carboxamide;

N-((1R,2R)-2-Acrylamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-4-oxo-5-(2-phenoxypyrimidin-5-yl)-4,5-dihydro-3H-1-thia-3,5,8-triazaacenaphthylene-2-carboxamide;

N-((1R,2 S)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide;

N-((1*S,3*S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Acrylamidocyclopentyl)-4-oxo-5-(5-phenoxypyrimidin-2-yl)-4,5-dihydro-3H-1-thia-3,5,8-triazaacenaphthylene-2-carboxamide;

N-((1*S,3*S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(2-phenoxypyrimidin-5-yl)-4,5-dihydro-3H-1-thia-3,5,8-triazaacenaphthylene-2-carboxamide;

N-((1R,2R)-2-Acrylamidocyclopentyl)-4-oxo-5-(5-phenoxypyrazin-2-yl)-4,5-dihydro-3H-1-thia-3,5,8-triazaacenaphthylene-2-carboxamide;

N-((1R,2 S)-2-Acrylamidocyclohexyl)-5-(*S)-(6-isobutoxy-4-methylpyridin-3-yl)-4-oxo-4,5-dihydro-3H-1-thia-3,5,8-triazaacenaphthylene-2-carboxamide;

N-((1S,3R)-3-Acrylamidocyclopentyl)-4-oxo-5-(5-phenoxypyridin-2-yl)-4,5-dihydro-3H-1-thia-3,5,8-triazaacenaphthylene-2-carboxamide;

N-((1R,2R)-2-Acrylamidocyclopentyl)-4-oxo-5-(2-phenoxypyrimidin-5-yl)-4,5-dihydro-3H-1-thia-3,5,8-triazaacenaphthylene-2-carboxamide;

N-((1*S,3*S)-3-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,2R)-2-Acrylamidocyclopentyl)-5-(*S)-(4-isopropoxy-2-methylphenyl)-4-oxo-4,5-dihydro-3H-1-thia-3,5,8-triazaacenaphthylene-2-carboxamide;

5-([2,3'-Bipyridin]-4-yl)-N-((1R,2 S)-2-acrylamidocyclopentyl)-4-oxo-4,5-dihydro-3H-1-thia-3,5,8-triazaacenaphthylene-2-carboxamide;

N-((1*R,2*S)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3R)-3-Acrylamidocyclopentyl)-4-oxo-5-(2-phenoxypyrimidin-5-yl)-4,5-dihydro-3H-1-thia-3,5,8-triazaacenaphthylene-2-carboxamide;

N-((1R,2 S)-2-Acrylamidocyclopentyl)-4-oxo-5-(5-phenylpyridazin-3-yl)-4,5-dihydro-3H-1-thia-3,5,8-triazaacenaphthylene-2-carboxamide;

N-((1*S,3*S)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2R)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3 S)-3-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,2R)-2-Acrylamidocyclopentyl)-4-oxo-5-(3-(pyridin-3-yl)phenyl)-4,5-dihydro-3H-1-thia-3,5,8-triazaacenaphthylene-2-carboxamide;

5-([2,2'-Bipyridin]-4-yl)-N-((1R,2 S)-2-acrylamidocyclopentyl)-4-oxo-4,5-dihydro-3H-1-thia-3,5,8-triazaacenaphthylene-2-carboxamide;

5-([2,3'-Bipyridin]-4-yl)-N-((1R,2R)-2-acrylamidocyclopentyl)-4-oxo-4,5-dihydro-3H-1-thia-3,5,8-triazaacenaphthylene-2-carboxamide;

N-((1R,2R)-2-Acrylamidocyclopentyl)-4-oxo-5-(3-(pyridin-2-yl)phenyl)-4,5-dihydro-3H-1-thia-3,5,8-triazaacenaphthylene-2-carboxamide;

N-((1*R,3*S)-3-Acrylamidocyclopentyl)-4-oxo-5-(5-phenoxypyridin-2-yl)-4,5-dihydro-3H-1-thia-3,5,8-triazaacenaphthylene-2-carboxamide;

N-((1*R, 3*R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(6-(isopropylamino)-4-methylpyridin-3-yl)-4-oxo-4,5-dihydro-3H-1-thia-3,5,8-triazaacenaphthylene-2-carboxamide;

N-((1*R,3*R)-3-Acrylamidocyclohexyl)-4-oxo-5-(6-phenoxypyridin-3-yl)-4,5-dihydro-3H-1-thia-3,5,8-triazaacenaphthylene-2-carboxamide;

N-((1*R,3*R)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1*R,3*R)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2 S)-2-Aminocyclohexyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2R)-2-Aminocyclopentyl)-5-(2-isopropylpyridin-4-yl)-4-oxo-4,5-dihydro-3H-1-thia-3,5,8-triazaacenaphthylene-2-carboxamide;

N-((1R,2R)-2-Acrylamidocyclopentyl)-5-(2-isopropylpyridin-4-yl)-4-oxo-4,5-dihydro-3H-1-thia-3,5,8-triazaacenaphthylene-2-carboxamide;

N-((1R,2R)-2-Acrylamidocyclohexyl)-4-oxo-5-(2-phenoxypyrimidin-5-yl)-4,5-dihydro-3H-1-thia-3,5,8-triazaacenaphthylene-2-carboxamide;

N-((1R,2R)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2 S)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(*R)-(6-(cyclopentyloxy)-4-methylpyridin-3-yl)-4-oxo-4,5-dihydro-3H-1-thia-3,5,8-triazaacenaphthylene-2-carboxamide;

5-([2,2'-Bipyridin]-4-yl)-N-((1R,2R)-2-acrylamidocyclopentyl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1R,2 S)-2-propionamidocyclohexyl)-4,5-dihydro-3H-1-thia-3,5,8-triazaacenaphthylene-2-carboxamide;

N-((1*R,3*R)-3-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,2 S)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1R,2S)-2-propionamidocyclopentyl)-4,5-dihydro-3H-1-thia-3,5,8-triazaacenaphthylene-2-carboxamide;

N-((1R,2S)-2-Acrylamidocyclopentyl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2 S)-2-Acrylamidocyclohexyl)-5-(*R)-(6-isopropoxy-4-methylpyridin-3-yl)-4-oxo-4,5-dihydro-3H-1-thia-3,5,8-triazaacenaphthylene-2-carboxamide;

N-((1R,2 S)-2-Aminocyclopentyl)-4-oxo-5-(5-phenylpyridazin-3-yl)-4,5-dihydro-3H-1-thia-3,5,8-triazaacenaphthylene-2-carboxamide;

N-((1R,2R)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3R)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2 S)-2-Acrylamidocyclohexyl)-5-(*R)-(6-isobutoxy-4-methylpyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1R,2R)-2-propionamidocyclopentyl)-4,5-dihydro-3H-1-thia-3,5,8-triazaacenaphthylene-2-carboxamide;

N-((1R,2 S)-2-Aminocyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,3 S)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,3 S)-3-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2R)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,3 S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,3 S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1R,3 S)-3-propionamidocyclopentyl)-4,5-dihydro-3H-1-thia-3,5,8-triazaacenaphthylene-2-carboxamide;

N-((1R,2R)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,3 S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1R,2R)-2-propionamidocyclohexyl)-4,5-dihydro-3H-1-thia-3,5,8-triazaacenaphthylene-2-carboxamide;

N-((1R,3 S)-3-Acrylamidocyclopentyl)-5-(6-isobutoxy-4-methylpyridin-3-yl)-4-oxo-4,5-dihydro-3H-1-thia-3,5,8-triazaacenaphthylene-2-carboxamide;

N-((1R,3 S)-3-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(4-((6-methylpyridin-2-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(4-((6-methylpyridin-2-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(4-((2-methylpyridin-3-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*S)-(6-isobutoxy-4-methylpyridin-3-yl)-4-oxo-4,5-dihydro-3H-1-thia-3,5,8-triazaacenaphthylene-2-carboxamide;

N-((1R,2 S)-2-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2 S)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-cyclobutylpyridin-4-yl)-4-oxo-4,5-dihydro-3H-1-thia-3,5,8-triazaacenaphthylene-2-carboxamide;

N-((1R,2 S)-2-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Acrylamidocyclopentyl)-5-(2-cyclobutylpyridin-4-yl)-4-oxo-4,5-dihydro-3H-1-thia-3,5,8-triazaacenaphthylene-2-carboxamide;

5-(*S)-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide;

5-(*S)-(4-Methyl-6-phenoxypyridin-3-yl)-4-oxo-N-((1R,2 S)-2-propionamidocyclohexyl)-4,5-dihydro-3H-1-thia-3,5,8-triazaacenaphthylene-2-carboxamide;

N-((1R,2R)-2-Acrylamidocyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1R,3 S)-3-propionamidocyclohexyl)-4,5-dihydro-3H-1-thia-3,5,8-triazaacenaphthylene-2-carboxamide;

N-((1R,2 S)-2-Acrylamidocyclopentyl)-5-(2-methyl-4-4(R)-tetrahydrofuran-3-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-4-oxo-5-(4-(pyridazin-3-yloxy)phenyl)-4,5-dihydro-3H-1-thia-3,5,8-triazaacenaphthylene-2-carboxamide;

5-(*S)-(4-Methyl-6-phenoxypyridin-3-yl)-4-oxo-N-((1R,3R)-3-propionamidocyclopentyl)-4,5-dihydro-3H-1-thia-3,5,8-triazaacenaphthylene-2-carboxamide;

N-((1S,4S)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1S,3R)-3-propionamidocyclopentyl)-4,5-dihydro-3H-1-thia-3,5,8-triazaacenaphthylene-2-carboxamide;

N-((1S,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Hydroxycyclopentyl)-4-oxo-5-(4-phenoxyphenyl)-4,5-dihydro-3H-1-thia-3,5,8-triazaacenaphthylene-2-carboxamide;

N-((1R,3 S)-3-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1S,3 S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acetamidocyclopentyl)-4-oxo-5-(4-phenoxyphenyl)-4,5-dihydro-3H-1-thia-3,5,8-triazaacenaphthylene-2-carboxamide;

N-((1R,2 S)-2-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide;

4-Oxo-5-(4-phenoxyphenyl)-N-((1R,2S)-2-propionamidocyclopentyl)-4,5-dihydro-3H-1-thia-3,5,8-triazaacenaphthylene-2-carboxamide;

5-(*S)-(4-Methyl-6-phenoxypyridin-3-yl)-4-oxo-N-((1S,3 S)-3-propionamidocyclopentyl)-4,5-dihydro-3H-1-thia-3,5,8-triazaacenaphthylene-2-carboxamide;

N-((1S,3 S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(2-methyl-4-(pyridin-2-yloxy)phenyl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1S,3 S)-3-propionamidocyclohexyl)-4,5-dihydro-3H-1-thia-3,5,8-triazaacenaphthylene-2-carboxamide;

N-((1R,3 S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,3 S)-3-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(2-methyl-4-(pyridazin-3-yloxy)phenyl)-4-oxo-4,5-dihydro-3H-1-thia-3,5,8-triazaacenaphthylene-2-carboxamide;

N-((1S,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2 S)-2-Acrylamidocyclohexyl)-4-oxo-5-(4-(pyridazin-3-yloxy)phenyl)-4,5-dihydro-3H-1-thia-3,5,8-triazaacenaphthylene-2-carboxamide;

5-(*S)-(2-Methyl-6-phenoxypyridin-3-yl)-4-oxo-N-((1S,3 S)-3-propionamidocyclopentyl)-4,5-dihydro-3H-1-thia-3,5,8-triazaacenaphthylene-2-carboxamide;

N-((1S,3 S)-3-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3R)-3-Acrylamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide;

N-((1S,3R)-3-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3R)-3-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3 S)-3-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide;

(S)-5-(2-Methyl-4-phenoxyphenyl)-2-(3-(methylamino)pyrrolidine-1-carbonyl)-3H-1-thia-3,5,8-triazaacenaphthylen-4(5H)-one;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)propionamide;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acetamide;

(S)-2-(3-Aminopyrrolidine-1-carbonyl)-5-(2-methyl-4-phenoxyphenyl)-3H-1-thia-3,5,8-triazaacenaphthylen-4(5H)-one;

(S)-2-(3-(Dimethylamino)pyrrolidine-1-carbonyl)-5-(2-methyl-4-phenoxyphenyl)-3H-1-thia-3,5,8-triazaacenaphthylen-4(5H)-one;

N-((1R,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1R,3R)-3-propionamidocyclohexyl)-4,5-dihydro-3H-1-thia-3,5,8-triazaacenaphthylene-2-carboxamide;

N-((1R,2 S)-2-Acrylamidocyclopentyl)-5-(*S)-(2-methyl-4-(pyridazin-3-yloxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*R)-(2-methyl-4-(pyridazin-3-yloxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,3 S)-3-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,2 S)-2-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,3 S)-3-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1S,3R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1S,3R)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1r,4r)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide;

(R)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide;

(S,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide;

(R,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide;

N-((1R,2 S)-2-Acrylamidocyclopentyl)-4-oxo-5-(4-(pyridin-2-yloxy)phenyl)-4,5-dihydro-3H-1-thia-3,5,8-triazaacenaphthylene-2-carboxamide;

N-((1R,2 S)-2-Acrylamidocyclopentyl)-5-(3-isopropylphenyl)-4-oxo-4,5-dihydro-3H-1-thia-3,5,8-triazaacenaphthylene-2-carboxamide;

N-((1R,2R)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2 S)-2-Acrylamidocyclohexyl)-4-oxo-5-(4-(pyridin-2-yloxy)phenyl)-4,5-dihydro-3H-1-thia-3,5,8-triazaacenaphthylene-2-carboxamide;

5-(*S)-(2-Methyl-4-phenoxyphenyl)-N-((1S,2R)-2-(2-(methylamino)acetamido)cyclohexyl)-4-oxo-4,5-dihydro-3H-1-thia-3,5,8-triazaacenaphthylene-2-carboxamide;

N-((1S,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1R,2R)-2-(2-(methylamino)acetamido)cyclohexyl)-4-oxo-4,5-dihydro-3H-1-thia-3,5,8-triazaacenaphthylene-2-carboxamide;

N-((1S,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2 S)-2-Aminocyclopentyl)-5-(4-isopropoxy-2-methylphenyl)-4-oxo-4,5-dihydro-3H-1-thia-3,5,8-triazaacenaphthylene-2-carboxamide;

N-((1S,3R)-3-Acetamidocyclopentyl)-5-(4-isopropoxy-2-methylphenyl)-4-oxo-4,5-dihydro-3H-1-thia-3,5,8-triazaacenaphthylene-2-carboxamide;

N-((1R,2 S)-2-Aminocyclopentyl)-5-(3-isopropylphenyl)-4-oxo-4,5-dihydro-3H-1-thia-3,5,8-triazaacenaphthylene-2-carboxamide;

N-((1R,2R)-2-Hydroxycyclopentyl)-5-(4-isopropoxy-2-methylphenyl)-4-oxo-4,5-dihydro-3H-1-thia-3,5,8-triazaacenaphthylene-2-carboxamide;

N-((1S,2R)-2-Aminocyclohexyl)-4-oxo-5-(4-phenoxyphenyl)-4,5-dihydro-3H-1-thia-3,5,8-triazaacenaphthylene-2-carboxamide;

N-((1S,2 S)-2-Acrylamidocyclopentyl)-5-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclopentyl)-5-(2-methyl-4-phenoxyphenyl)-4-oxo-4,5-dihydro-3H-1-thia-3,5,8-triazaacenaphthylene-2-carboxamide;

5-(4-(3-((2-Cyanophenoxy)methyl)phenoxy)-2-methylphenyl)-N-cyclohexyl-4-oxo-4,5-dihydro-3H-1-thia-3,5,8-triazaacenaphthylene-2-carboxamide;

N-(5-(4-(3-((2-Cyanophenoxy)methyl)phenoxy)-2-methylphenyl)-4-oxo-4,5-dihydro-3H-1-thia-3,5,8-triazaacenaphthylen-2-yl)cyclopropanecarboxamide;

N-Cyclohexyl-5-(2-methyl-4-phenoxyphenyl)-4-oxo-4,5-dihydro-3H-1-thia-3,5,8-triazaacenaphthylene-2-carboxamide;

N-Cyclohexyl-4-oxo-5-(4-phenoxyphenyl)-4,5-dihydro-3H-1-thia-3,5,8-triazaacenaphthylene-2-carboxamide;

N1-((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide;

N-((1R,2 S)-2-Acrylamidocyclopentyl)-5-(4-methyl-6-(pyrimidin-2-yloxy)pyridin-3-yl)-4-oxo-4,5-dihydro-3H-1-thia-3,5,8-triazaacenaphthylene-2-carboxamide;

N-((1R,2 S)-2-((E)-2-Cyano-3-cyclopropylacrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(4-methyl-6-(pyridazin-3-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-6-(pyrimidin-2-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(*S)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*R)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(4-methyl-6-(pyridazin-3-yloxy)pyridin-3-yl)-4-oxo-4,5-dihydro-3H-1-thia-3,5,8-triazaacenaphthylene-2-carboxamide;

N-((1R,2 S)-2-Acrylamidocyclohexyl)-5-(2-methyl-6-(pyridazin-3-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-6-(pyridazin-3-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-6-((2-methylpyridin-3-yl)oxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(5-(pyridazin-3-yloxy)pyridin-2-yl)-4,5-dihydro-3H-1-thia-3,5,8-triazaacenaphthylene-2-carboxamide;

N-((1R,2 S)-2-Acrylamidocyclopentyl)-5-(6'-methyl-2-oxo-2H-[1,2'-bipyridin]-5'-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-6-(pyridin-2-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(5-((6-methylpyridin-3-yl)oxy)pyridin-2-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(5-(pyridin-2-yloxy)pyridin-2-yl)-4,5-dihydro-3H-1-thia-3,5,8-triazaacenaphthylene-2-carboxamide;

N-((1R,2 S)-2-Acrylamidocyclopentyl)-5-(5-((6-methylpyridin-3-yl)oxy)pyridin-2-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-4-(pyrimidin-5-yloxy)phenyl)-4-oxo-4,5-dihydro-3H-1-thia-3,5,8-triazaacenaphthylene-2-carboxamide;

N-((1R,2 S)-2-Acrylamidocyclopentyl)-5-(4-methyl-6-((6-methylpyridin-2-yl)oxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(5-(pyrimidin-2-yloxy)pyridin-2-yl)-4,5-dihydro-3H-1-thia-3,5,8-triazaacenaphthylene-2-carboxamide;

N-((1R,2 S)-2-Acrylamidocyclopentyl)-4-oxo-5-(5-(pyrimidin-5-yloxy)pyridin-2-yl)-4,5-dihydro-3H-1-thia-3,5,8-triazaacenaphthylene-2-carboxamide;

N-((1R,2 S)-2-Acrylamidocyclopentyl)-5-(4-methyl-6-(pyrimidin-5-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(4-methyl-6-((6-methylpyridin-3-yl)oxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(4-methyl-6-(pyridin-2-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(4-methyl-6-((2-methylpyridin-3-yl)oxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(4-methyl-6-(pyridin-3-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-4-oxo-5-(5-(pyridin-3-yloxy)pyridin-2-yl)-4,5-dihydro-3H-1-thia-3,5,8-triazaacenaphthylene-2-carboxamide;

N-((1R,2 S)-2-Acrylamidocyclopentyl)-5-(2-methyl-6-(pyrimidin-5-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(5-((2-methylpyridin-3-yl)oxy)pyridin-2-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-6-(pyridin-3-yloxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(2-methyl-6-((6-methylpyridin-3-yl)oxy)pyridin-3-yl)-4-oxo-4,5-dihydro-3H-1-thia-3,5,8-triazaacenaphthylene-2-carboxamide;

N-((1R,2 S)-2-Acrylamidocyclopentyl)-5-(*S)-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*R)-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*S)-(2-methyl-4-((6-methylpyridin-3-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*R)-(2-methyl-4-((methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2 S)-2-Acrylamidocyclopentyl)-5-(*R)-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-((E)-2-Cyano-3-(3-methyloxetan-3-yl)acrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2S)-2-((E)-2-Cyano-4-ethoxy-4-methylpent-2-enamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N1-((E)-4-((((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide;

N-((1R,2 S)-2-acrylamidocyclopentyl)-4-oxo-5-(4-(pyrimidin-5-yloxy)phenyl)-4,5-dihydro-3H-1-thia-3,5,8-triazaacenaphthylene-2-carboxamide;

an isotopic variant thereof; and a pharmaceutically acceptable salt thereof.

19. A pharmaceutical composition comprising: an effective amount of at least one compound of claim 1 and at least one pharmaceutically acceptable excipient.

20. A method of treating a subject suffering from or diagnosed with a disease, disorder, or medical condition mediated by Bruton's tyrosine kinase activity, comprising administering to a subject in need of such treatment an effective amount of at least one compound of claim 1.

21. The method of claim 19, wherein the disease, disorder, or medical condition mediated by Bruton's tyrosine kinase activity is rheumatoid arthritis.

22. A method of making a compound of claim 1, or a pharmaceutically acceptable salt thereof.

23. A compound of claim 1 having the structure of Formula (IIa), or a pharmaceutically acceptable salt thereof,

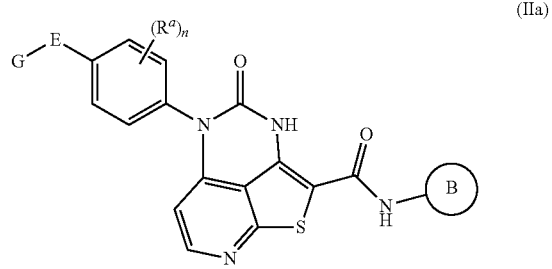

(IIa)

wherein $R^a$ is selected from the group consisting of: H, Cl and $CH_3$;

n is 0 or 1;

E is O;

G is selected from the group consisting of: $C_{1-6}$alkyl, phenyl, pyridyl, pyridyl substituted with $CH_3$, pyrimidinyl, pyridazinyl, tetrahydrofuranyl, tetrahydropyranyl, and

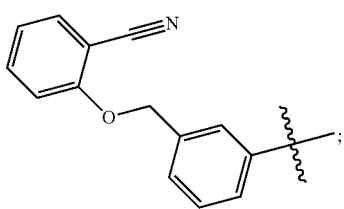 [SMILES: *c1cccc(COc2ccccc2C#N)c1]

Ring B is selected from the group consisting of:

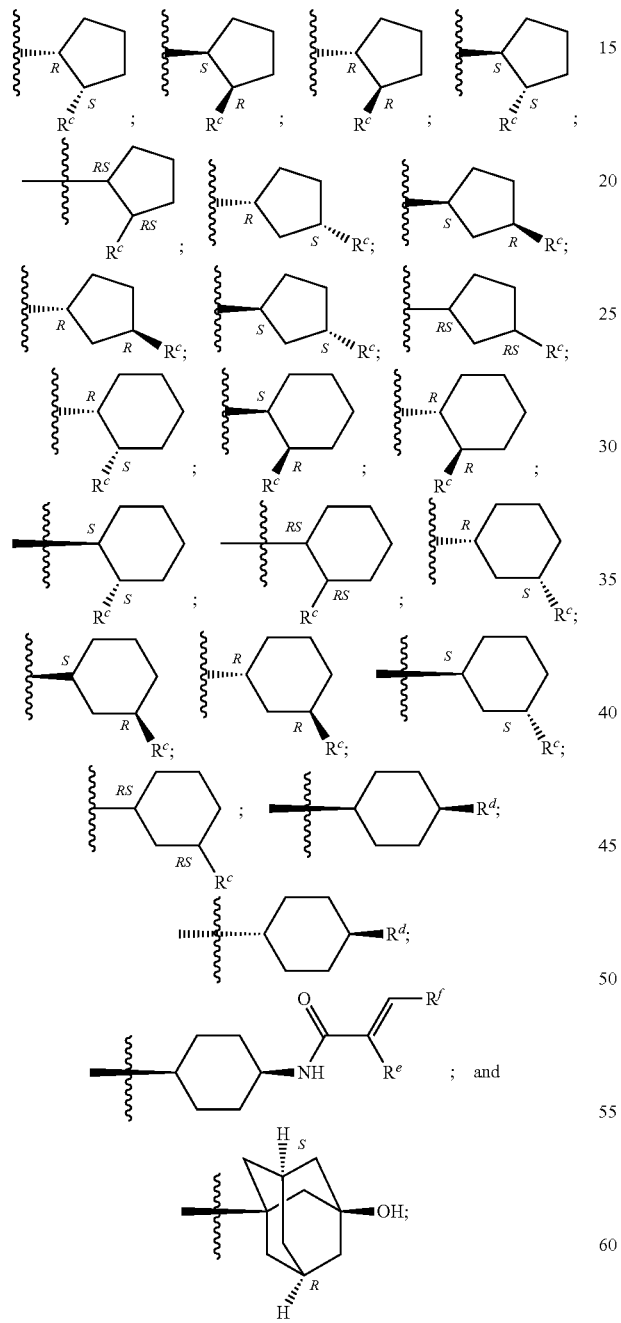

$R^c$ is selected from the group consisting of: OH, OCH$_3$, NH$_2$, NH(CH$_3$), N(CH$_3$)$_2$, NH(CO$_2$-tert-butyl), NH(C=O)C$_{1-3}$alkyl, NH(C=O)CH=CH$_2$, NH(C=O)CH$_2$NH$_2$, NH(C=O)CH$_2$NH(CH$_3$), NH(C=O)CH$_2$N(CH$_3$)$_2$, and NH(C=O)CH=CHCH$_2$N(CH$_3$)$_2$;

$R^d$ is selected from the group consisting of: OH, OCH$_3$, CN, NH$_2$, NH(CH$_3$), N(CH$_3$)$_2$, NH(CO$_2$-tert-butyl), NH(C=O)C$_{1-3}$alkyl, and NH(C=O)CH=CH$_2$;

$R^e$ is H or CN; and $R^f$ is selected from the group consisting of: CH$_2$NH$_2$, CH$_2$NH(CH$_3$), CH$_2$N(CH$_3$)$_2$, and cyclopropyl.

24. A compound of claim 1 having the structure of Formula (IIb), or a pharmaceutically acceptable salt thereof, (IIb)

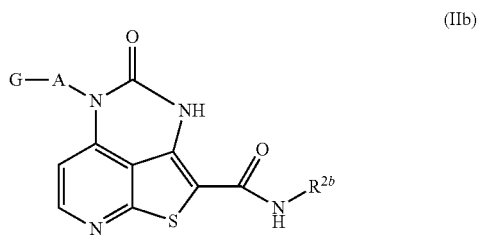

wherein

G-A is selected from the group consisting of:

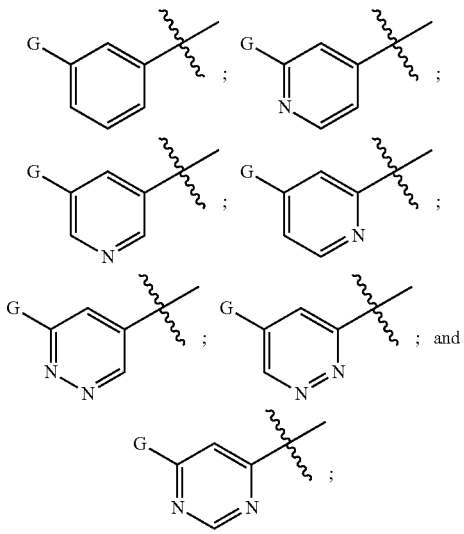

G is selected from the group consisting of: C$_{1-6}$alkyl, C$_{3-6}$cycloalkyl, phenyl, and pyridyl;

$R^{2b}$ is selected from the group consisting of:

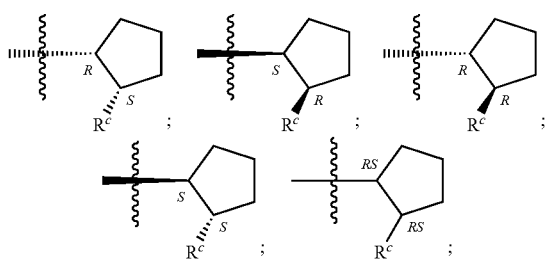

-continued

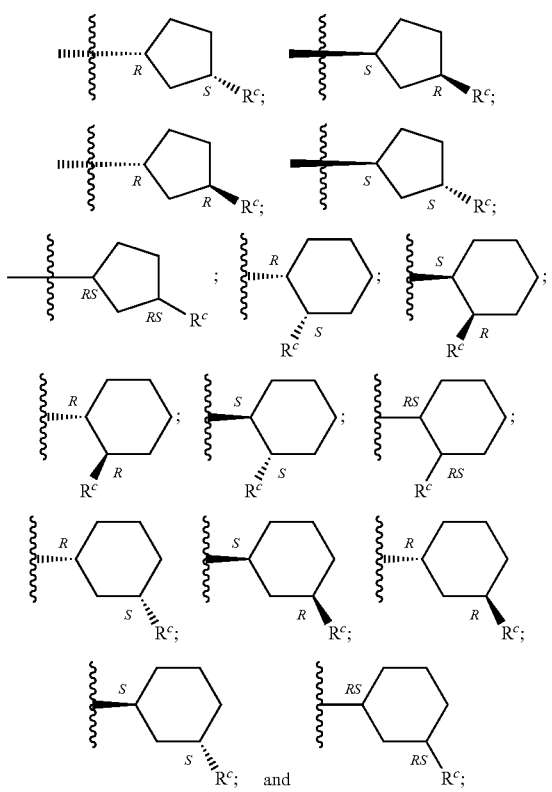

and $R^c$ is selected from the group consisting of: OH, OCH$_3$, NH$_2$, NH(CH$_3$), N(CH$_3$)$_2$, NH(CO$_2$-tert-butyl), NH(C=O)C$_{1-3}$alkyl, NH(C=O)CH=CH$_2$, NH(C=O)CH$_2$NH$_2$, NH(C=O)CH$_2$NH(CH$_3$), NH(C=O)CH$_2$N(CH$_3$)$_2$, and NH(C=O)CH=CHCH$_2$N(CH$_3$)$_2$.

25. A compound of claim 1 having the structure of Formula (IIc), a stereoisomer thereof, an isotopic variant thereof, or a pharmaceutically acceptable salt thereof,

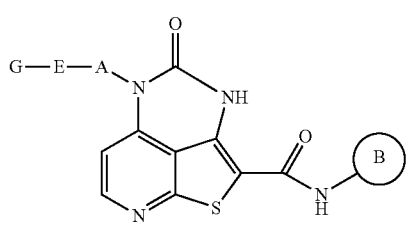
(IIc)

wherein

G-E-A is selected from the group consisting of:

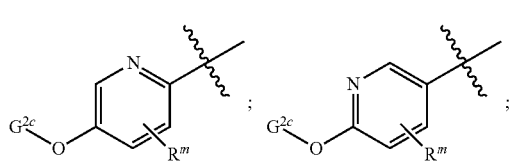

-continued

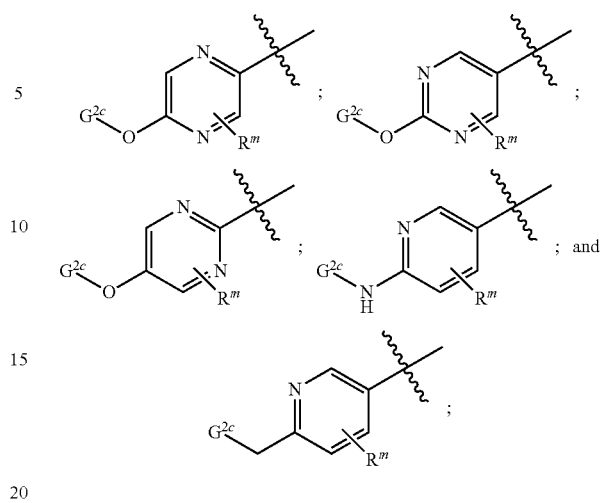

where $G^{2c}$ is selected from the group consisting of: C$_{1-6}$alkyl, phenyl, pyrimidinyl, pyridyl, pyridyl substituted with CH$_3$, and C$_{3-6}$cycloalkyl; and $R^m$ is H or CH$_3$;

Ring B is selected from the group consisting of:

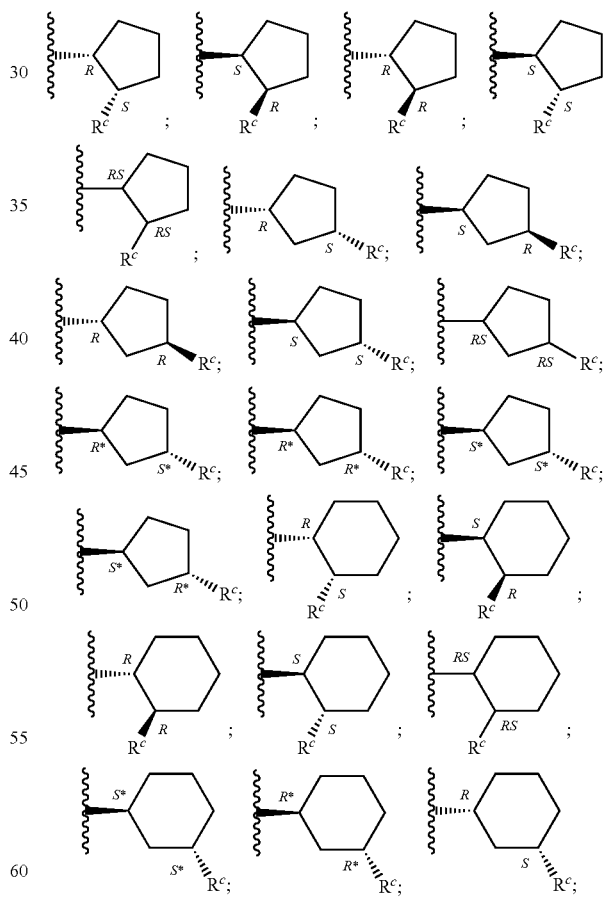

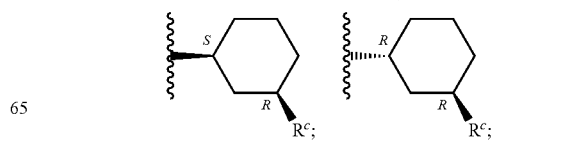

-continued

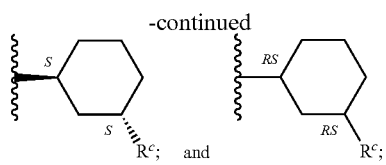

and $R^c$ is selected from the group consisting of: OH, OCH$_3$, NH$_2$, NH(CH$_3$), N(CH$_3$)$_2$, NH(CO$_2$-tert-butyl), NH(C=O)C$_{1-3}$alkyl, NH(C=O)CH=CH$_2$, NH(C=O)CH$_2$NH$_2$, NH(C=O)CH$_2$NH(CH$_3$), NH(C=O)CH$_2$N(CH$_3$)$_2$, and NH(C=O)CH=CHCH$_2$N(CH$_3$)$_2$.

26. A compound as claimed in claim 18, wherein said compound is selected from
N-((1R,2S)-2-Acrylamidocylcopentyl)-5-(4-methyl-6-(pyrimidin-2-yloxy) pyridin-3-yl)4-oxo-4,5-dihydro-3H-1-thia-3,5,8-triazaacenaphthylene-2-carboxamide;
N-((1R,2S)-2-Acrylamidocylcopentyl)-5-(S)-(6-isbobutyl-4-methylpyridin-3-yl) -4-oxo-4,5-dihydro-3H-1-thia-3,5,8-triazaacenaphthylene-2-carboxamide;
N-((1R,2S)-2-Acrylamidocyclopentyl)-5-(*S)-(-2-methyl-4-(pyridin-2-yloxy) phenyl)-4-oxo-4,5-dihydro-3H-1-thia-3,5,8-triazaacenaphthylene-2-carboxamide; and
N-((1R,2S)-2-Acrylamidocyclopentyl)-5-(*R)-(2-methyl-4-(pryidin-2-yloxy) phenyl)-4-oxo-4,5-dihydro-3H-1-thia-3,5,8-triazaacenaphthylene-2-carboximide.

* * * * *